(12) United States Patent
Rehberger et al.

(10) Patent No.: US 10,835,561 B2
(45) Date of Patent: Nov. 17, 2020

(54) BACILLUS COMPOSITIONS AND METHODS OF USE WITH RUMINANTS

(71) Applicant: Church & Dwight Co., Inc., Ewing, NJ (US)

(72) Inventors: Thomas Rehberger, Wauwatosa, WI (US); John O'Neill, Ponca City, OK (US); Alexandra Smith, Greendale, WI (US); Mari Ellen Davis, Waukesha, WI (US); Jesse Thompson, Menomonee Falls, WI (US); Jennifer Schissel, Milwaukee, WI (US)

(73) Assignee: Church & Dwight Co., Inc., Ewing, NJ (US)

( * ) Notice: Subject to any disclaimer, the term of this patent is extended or adjusted under 35 U.S.C. 154(b) by 0 days.

(21) Appl. No.: 15/605,484

(22) Filed: May 25, 2017

(65) Prior Publication Data

US 2017/0340682 A1 Nov. 30, 2017

Related U.S. Application Data

(60) Provisional application No. 62/341,332, filed on May 25, 2016.

(51) Int. Cl.

| | | |
|---|---|---|
| *A61K 39/00* | (2006.01) | |
| *A61K 39/02* | (2006.01) | |
| *A61K 39/07* | (2006.01) | |
| *A61K 35/742* | (2015.01) | |
| *C12R 1/125* | (2006.01) | |
| *A23K 10/18* | (2016.01) | |
| *A23K 50/10* | (2016.01) | |
| *A23K 20/10* | (2016.01) | |
| *A61K 9/00* | (2006.01) | |
| *A61K 9/19* | (2006.01) | |
| *A61K 35/00* | (2006.01) | |

(52) U.S. Cl.
CPC ............ *A61K 35/742* (2013.01); *A23K 10/18* (2016.05); *A23K 20/10* (2016.05); *A23K 50/10* (2016.05); *A61K 9/0056* (2013.01); *A61K 9/19* (2013.01); *C12R 1/125* (2013.01); *A61K 2035/115* (2013.01)

(58) Field of Classification Search
CPC ......... A61K 39/00; A61K 39/02; A61K 39/07
USPC .................................. 424/93.1, 93.4, 93.46
See application file for complete search history.

(56) References Cited

U.S. PATENT DOCUMENTS

| | | |
|---|---|---|
| 6,051,219 A | 4/2000 | Kubota |
| 6,140,106 A | 10/2000 | Lawler et al. |
| 6,162,634 A | 12/2000 | Lawler et al. |
| 6,162,635 A | 12/2000 | Lawler et al. |
| 6,422,174 B1 | 7/2002 | Horikawa et al. |
| 6,660,294 B2 | 12/2003 | Maruta et al. |
| 6,812,022 B1 | 11/2004 | Aonuma |
| 6,989,370 B2 | 1/2006 | Fahrlander et al. |
| 7,247,299 B2 | 7/2007 | Lin et al. |
| 7,618,640 B2 | 11/2009 | Rehberger et al. |
| 7,754,469 B2 | 7/2010 | Baltzley et al. |
| 8,021,654 B2 | 9/2011 | Rehberger et al. |
| 8,420,138 B2 | 4/2013 | Knap et al. |
| 8,455,238 B2 | 6/2013 | Baltzley et al. |
| 8,506,951 B2 | 8/2013 | Rehberger et al. |
| 8,540,981 B1 | 9/2013 | Wehnes et al. |
| 8,642,317 B2 | 2/2014 | Zhou et al. |
| 8,722,058 B2 | 5/2014 | Rehberger et al. |
| 8,741,280 B2 | 6/2014 | Cantor et al. |
| 8,802,079 B2 | 8/2014 | Knapp et al. |
| 9,005,601 B2 | 4/2015 | Hargis et al. |
| 9,011,836 B2 | 4/2015 | Rehberger et al. |
| 9,089,151 B2 | 7/2015 | Davis et al. |
| 9,144,588 B2 | 9/2015 | Rubio et al. |
| 9,247,757 B2 | 2/2016 | Schmidt et al. |
| 2010/0092428 A1* | 4/2010 | Schmidt ................. A23K 50/75 424/93.2 |
| 2014/0037582 A1 | 2/2014 | Romero et al. |
| 2015/0079058 A1 | 3/2015 | Nielsen et al. |
| 2015/0118203 A1 | 4/2015 | Boyette et al. |
| 2015/0216915 A1 | 8/2015 | Frouel et al. |
| 2015/0230498 A1 | 8/2015 | Davis et al. |
| 2015/0250831 A1 | 9/2015 | Rehberger et al. |
| 2015/0257400 A1 | 9/2015 | Reuter et al. |
| 2015/0290254 A1 | 10/2015 | Remus et al. |
| 2015/0306154 A1 | 10/2015 | Davis et al. |
| 2016/0007614 A1 | 1/2016 | Rubio et al. |
| 2016/0120919 A1 | 5/2016 | Ashida et al. |

FOREIGN PATENT DOCUMENTS

| | | | |
|---|---|---|---|
| WO | WO2010065625 A1 * | 6/2010 | ................ C12P 1/04 |
| WO | 2015160960 A1 | 10/2015 | |
| WO | 2015175667 A1 | 11/2015 | |

(Continued)

OTHER PUBLICATIONS

Fascella, S., et al. Acta Horticulturae (2015) No. 1099, pp. 291-295.*

Pranto et al., "Enhancing antimicrobial activity of chitosan films by incorporating garlic oil, potassium sorbate and nisin", LWT—Food Science and Technology, Academic Press, United Kingdom, vol. 38, No. 8, Dec. 1, 2005, pp. 859-865.

(Continued)

*Primary Examiner* — Rodney P Swartz

(74) *Attorney, Agent, or Firm* — Womble Bond Dickinson (US) LLP

(57) ABSTRACT

*Bacillus* strains, compositions and methods are disclosed for reducing growth of microorganisms in a feed. *Bacillus* strains, compositions and methods are disclosed for providing beneficial effects to animals, including but not limited to increasing performance of the animal.

6 Claims, 101 Drawing Sheets

Specification includes a Sequence Listing.

(56) References Cited

FOREIGN PATENT DOCUMENTS

| WO | 2016022779 A1 | 2/2016 |
| WO | 2016030441 A1 | 3/2016 |
| WO | 2016060934 A1 | 4/2016 |
| WO | 2016060935 A2 | 4/2016 |
| WO | 2016118840 A1 | 7/2016 |
| WO | 2016118850 A1 | 7/2016 |
| WO | 2016118864 A1 | 7/2016 |

OTHER PUBLICATIONS

Veerapandian et al., "Analytical and biological characterization of quinazoline semicarbazone derivatives", Med. Chem. Res, vol. 19, No. 3, Apr. 23, 2009, pp. 283-298.
PCT/US2017/034512, International Search Report and Written Opinion, dated Sep. 20, 2017, 16 pages.

* cited by examiner

| ID | Description | Location |
|---|---|---|
| S55.9.1 | Dry Cow TMR | New York |
| S120.4.6 | | Texas |
| S91.3.5 | Pre Fresh TMR | Vermont |
| S63.5.3 | TMR 5 | Wisconsin |
| S60.7.5 | Whey | Wisconsin |
| S60.7.6 | Whey | Wisconsin |
| S60.7.8 | Whey | Wisconsin |
| S60.7.3 | Whey | Wisconsin |
| S89.13.4 | WOM #1058 (Calf Pellet) | Pennsylvania |
| S89.20.9 | WOM #1550 | Pennsylvania |
| S143.8.1 | | |
| S81.11.1 | Bird Seed Screening | Ohio |
| HN-1 | Haylage | Wisconsin |
| DL-1 | Haylage | Wisconsin |
| DL-5 | Haylage | Wisconsin |
| S102.8.8 | Close Up Cow TMR | Iowa |
| S42.3.3 | Face Haylage | Texas |
| S81.10.4 | Wheat Midds | Ohio |
| S42.3.4 | Face Haylage | Texas |
| S42.3.5 | Face Haylage | Texas |
| S114.7.3 | | Texas |
| S117.2.6 | Canola | Colorado |
| 20.1.2 | Corn Silage | Wisconsin |
| S127.2.2 | Fresh Cow TMR Pen 10 | Texas |
| 21.2.4 | Haylage | Wisconsin |
| 27.2.4 | Haylage | Wisconsin |
| S110.3.2 | Pen 1 Breeding 2+ TMR | |
| S120.7.1 | | Texas |
| S128.46.8 | Straw | GA |
| S120.3.3 | | Texas |
| S128.18.1 | Cotton Hulls | GA |
| S81.10.3 | Wheat Midds | Ohio |
| S128.5.7 | Dry Close TMR | GA |
| 27.2.3 | Haylage | Wisconsin |
| S98.6.1 | High Cow TMR | |
| S98.6.5 | High Cow TMR | |
| S102.9.8 | High Cow TMR | Iowa |
| S127.7.7 | Late Lac Cow TMR Pen 32 | Texas |
| S128.39.4 | Oat Silage | GA |
| S75.9.2 | Soy Hulls | Indiana |
| S128.12.2 | Straw | GA |
| S36.1.6 | Face Wheatlage | Texas |
| 26.1.3 | Corn Silage | Wisconsin |
| 28.1.2 | Ryelage | Wisconsin |
| S135.9.3 | Dry Cows TMR | Texas |
| S63.2.2 | Alfalfa Haylage B3 2016 | Wisconsin |
| S81.11.7 | Bird Seed Screening | Ohio |
| S60.4.3 | Ryelage | Wisconsin |
| S59.8.3 | TMR (close up) | Texas |
| S135.10.5 | Canola Gluten Pellets | Texas |
| S71.15.3 | Corn Gluten | Texas |
| S71.18.5 | Dry Hay | Texas |

FIG. 3 (Cont)

| ID | Description | Location |
|---|---|---|
| S71.15.3 | Corn Gluten | Texas |
| S71.18.5 | Dry Hay | Texas |
| S128.11.2 | Gin Trash | GA |
| 15.2.1 | Haylage | Wisconsin |
| 15.2.3 | Haylage | Wisconsin |
| 15.2.4 | Haylage | Wisconsin |
| S127.7.2 | Late Lac Cow TMR Pen 32 | Texas |
| S51.5.1 | Low/High Ration | New York |
| S71.13.1 | Soybean Meal | Texas |
| S54.1.1 | Wet Brewers Grain | New York |
| S82.9.7 | Low TMR | Virginia |
| S143.6.1 | | |
| S115.12.1 | Whey | Wisconsin |
| S115.12.2 | Whey | Wisconsin |
| S115.12.3 | Whey | Wisconsin |
| S70.1.1 | Corn Silage | Texas |
| S91.2.5 | Grass Haylage | Vermont |
| S76.3.8 | Baylage 4th Home | Iowa |
| S59.10.2 | TMR (High Cow) | Texas |
| S86.2.8 | Alfalfa Haylage | Pennsylvania |
| S126.1.2 | Corn Silage | WI |
| S76.3.5 | Baylage 4th Home | Iowa |
| S102.1.5 | Baylage Mark | Iowa |
| DL-2 | Haylage | Wisconsin |
| S49.5.3 | Natural Start Feed (Pen 146) | Texas |
| S54.18.3 | High Cow TMR | New York |
| S54.19.4 | Far Off Dry TMR | New York |
| S42.3.6 | Face Haylage | Texas |
| S135.4.7 | Fresh Heifer TMR | Texas |
| ROS-3 | Haylage | Wisconsin |
| S120.5.5 | | Texas |
| S58.9.3 | Cotton | Texas |
| S58.9.4 | Cotton | Texas |
| S135.5.2 | Early Lac TMR | Texas |
| S50.6.3 | High Cow TMR | New York |
| S102.14.6 | Late Cow TMR | Iowa |
| S82.9.8 | Low TMR | Virginia |
| S135.7.4 | Mid Lac B TMR | Texas |
| S135.7.10 | Mid Lac B TMR | Texas |
| S60.5.1 | Milk Cow TMR | Wisconsin |
| S110.1.2 | Corn Silage | |
| S63.5.10 | TMR 5 | Wisconsin |
| S41.8.1 | Cotton | Wisconsin |
| S135.4.9 | Fresh Heifer TMR | Texas |
| 15.4.2 | Haylage | Wisconsin |
| 15.4.3 | Haylage | Wisconsin |
| 15.4.4 | Haylage | Wisconsin |
| 27.2.11 | Haylage | Wisconsin |
| 32.1.1 | Haylage 2nd Crop | Wisconsin |
| S111.4.9 | Lac 1 TMR | |
| 27.3.2 | Oatlage | Wisconsin |
| 27.3.3 | Oatlage | Wisconsin |

FIG. 3 (Cont.)

| | | |
|---|---|---|
| ROL-3 | Haylage | Wisconsin |
| S52.10.4 | 1st Lactation TMR | New York |
| S102.1.3 | Baylage Mark | Iowa |
| 26.1.2 | Corn Silage | Wisconsin |
| S71.10.10 | Dry Cow Ration | Texas |
| S53.5.8 | Dry Cow Straw | New York |
| S89.20.8 | WOM #1550 | Pennsylvania |
| S102.1.8 | Baylage Mark | Iowa |
| S43.6.1 | HMC | Texas |
| S114.6.1 | | Texas |
| S63.3.3 | Alfalfa Haylage B4 2nd 2018 | Wisconsin |
| S115.6.8 | Alley Cake High | Wisconsin |
| S75.10.7 | Amino Shot | Indiana |
| 20.1.4 | Corn Silage | Wisconsin |
| 22.1.1 | Corn Silage | Wisconsin |
| 22.1.2 | Corn Silage | Wisconsin |
| 30.4.2 | Corn Silage | Wisconsin |
| HC-1 | Corn Silage | Wisconsin |
| S58.9.1 | Cotton | Texas |
| S63.6.7 | Dry Corn | Wisconsin |
| S98.4.7 | Dry Cow TMR | |
| S127.8.6 | Dry Cow TMR | Texas |
| S127.3.3 | Fresh Heifer TMR Pen 40 | Texas |
| S53.7.2 | Ground Corn | New York |
| 20.4.6 | Haylage | Wisconsin |
| 21.1.1 | Haylage | Wisconsin |
| 21.2.7 | Haylage | Wisconsin |
| 21.2.8 | Haylage | Wisconsin |
| 27.2.5 | Haylage | Wisconsin |
| HN-2 | Haylage | Wisconsin |
| S102.9.9 | High Cow TMR | Iowa |
| S102.12.3 | High Cow TMR | Iowa |
| S102.14.5 | Late Cow TMR | Iowa |
| S127.7.8 | Late Lac Cow TMR Pen 32 | Texas |
| S41.12.1 | Molasses | Wisconsin |
| S110.5.4 | Pen 3 TMR 1st Lac Breeding | |
| S41.10.1 | Protein Mix + Clostat | Wisconsin |
| S42.10.1 | Protein Pellets | Texas |
| Silage 1-1 | Silage | Wisconsin |
| Silage 1-2 | Silage | Wisconsin |
| Silage 3-5 | Silage | Wisconsin |
| Silage 8-1 | Silage | Wisconsin |
| 23.1.4 | Sorghum | Wisconsin |
| 24.1.3 | Sorghum | Wisconsin |
| S41.13.1 | Water | Wisconsin |
| S81.10.6 | Wheat Midds | Ohio |
| S89.20.1 | WOM #1550 | Pennsylvania |
| S59.8.2 | TMR (close up) | Texas |
| S135.12.5 | Cotton Seed | Texas |
| S98.4.5 | Dry Cow TMR | |
| S102.10.6 | Heifer TMR | Iowa |
| S120.1.6 | | Texas |

FIG. 3 (Cont.)

| | | |
|---|---|---|
| S53.7.3 | Ground Corn | New York |
| S52.6.1 | Haylage Deep | New York |
| S102.12.5 | High Cow TMR | Iowa |
| S50.6.2 | High Cow TMR | New York |
| S108.11.8 | CU Pen 12 | |
| S102.7.2 | Fresh Heifer TMR | Iowa |
| S74.2.1 | Haylage Deep | Michigan |
| S102.10.4 | Heifer TMR | Iowa |
| S102.9.10 | High Cow TMR | Iowa |
| S89.13.6 | WOM #1058 (Calf Pellet) | Pennsylvania |
| S35.1.4 | Texture Feed #1 | Texas |
| S102.8.7 | Close Up Cow TMR | Iowa |
| S53.7.7 | Ground Corn | New York |
| S53.11.1 | Fresh TMR | New York |
| S63.9.2 | Protein Blend with Bacillus | Wisconsin |
| S52.9.4 | Close Up Diet | New York |
| S70.1.6 | Corn Silage | Texas |
| S56.1.3 | Pellets | New York |
| S52.5.2 | Haylage Face | New York |
| S70.8.2 | Calf Premix | Texas |
| S102.12.1 | High Cow TMR | Iowa |
| S120.1.1 | | Texas |
| S120.1.8 | | Texas |
| S120.4.7 | | Texas |
| S114.7.10 | | Texas |
| S110.4.5 | 2 Preg TMR | |
| S97.12.9 | Alfalfa Hay | Minnesota |
| S111.3.10 | Close up TMR | |
| S110.1.3 | Corn Silage | |
| S102.2.1 | Corn Silage Pile | Iowa |
| S69.7.5 | Cow TMR | Texas |
| S97.13.3 | Dried Beet Shreds | Minnesota |
| S109.9.1 | Dry Corn 2016 | Wisconsin |
| S110.6.10 | Dry Cow TMR | |
| S127.2.7 | Fresh Cow TMR Pen 10 | Texas |
| S102.7.4 | Fresh Heifer TMR | Iowa |
| S102.11.5 | Fresh TMR | Iowa |
| S97.16.2 | Grass Hay | Minnesota |
| S97.16.4 | Grass Hay | Minnesota |
| S53.7.10 | Ground Corn | New York |
| S102.10.1 | Heifer TMR | Iowa |
| S102.10.2 | Heifer TMR | Iowa |
| S102.9.2 | High Cow TMR | Iowa |
| S102.9.6 | High Cow TMR | Iowa |
| S102.14.1 | Late Cow TMR | Iowa |
| S102.14.2 | Late Cow TMR | Iowa |
| S107.5.4 | Pen 4, 5 TMR | South Dakota |
| S109.2.1 | Vita Plus Inoc Alf Haylage 4th 2016 | Wisconsin |
| S102.12.6 | High Cow TMR | Iowa |
| S108.4.8 | Baleage | |
| S60.4.4 | Ryelage | Wisconsin |
| S102.10.5 | Heifer TMR | Iowa |

FIG. 3 (Cont.)

| Sample | Description | State |
|---|---|---|
| S60.4.4 | Ryelage | Wisconsin |
| S102.10.5 | Heifer TMR | Iowa |
| S63.3.2 | Alfalfa Haylage B4 2nd 2017 | Wisconsin |
| S63.1.2 | Corn Silage B1 2016 | Wisconsin |
| S113.2.1 | | |
| S97.3.3 | 2 Yr TMR | Minnesota |
| S97.13.4 | Dried Beet Shreds | Minnesota |
| S97.16.5 | Grass Hay | Minnesota |
| S97.4.7 | NDSV Haylage | Minnesota |
| S63.1.1 | Corn Silage B1 2015 | Wisconsin |
| S76.2.10 | Haylage 2nd 15 | Iowa |
| S114.4.1 | | Texas |
| S87.7.7 | Calves Hay from Bunk | Pennsylvania |
| S74.11.3 | Close up TMR | Michigan |
| S74.11.9 | Close up TMR | Michigan |
| S81.4.7 | Dry TMR | Ohio |
| S102.11.7 | Fresh TMR | Iowa |
| S102.11.8 | Fresh TMR | Iowa |
| S36.5.2 | Ground Corn | Texas |
| S36.5.4 | Ground Corn | Texas |
| S102.10.8 | Heifer TMR | Iowa |
| S102.9.4 | High Cow TMR | Iowa |
| S102.9.7 | High Cow TMR | Iowa |
| S74.10.4 | High TMR | Michigan |
| S102.14.4 | Late Cow TMR | Iowa |
| S83.1.7 | Pen 9 Low Ration | Texas |
| CSS-4 | Haylage | Wisconsin |
| S102.9.3 | High Cow TMR | Iowa |
| ROS-4 | Haylage | Wisconsin |
| S102.11.9 | Fresh TMR | Iowa |
| S102.13.1 | Late Cow TMR | Iowa |
| S109.8.7 | Grain Premix-Straw, Corn,Cotton,C. | Wisconsin |
| S63.9.1 | Protein Blend with Bacillus | Wisconsin |
| S60.7.9 | Whey | Wisconsin |
| DN-4 | Haylage | Wisconsin |
| S102.13.2 | Late Cow TMR | Iowa |
| S50.5.5 | Prefresh TMR | New York |
| S75.8.7 | Calf Pellets | Indiana |
| S102.11.10 | Fresh TMR | Iowa |
| S102.9.1 | High Cow TMR | Iowa |
| S58.4.2 | TMR (Early Lactating Cows) | Texas |
| S58.9.2 | Cotton | Texas |
| S58.9.6 | Cotton | Texas |
| S58.9.5 | Cotton | Texas |
| DL-3 | Haylage | Wisconsin |
| S41.3.1 | Corn Silage 2014 | Wisconsin |
| S53.5.6 | Dry Cow Straw | New York |
| S41.2.2 | Alfalfa Haylage 3rd | Wisconsin |
| S127.3.4 | Fresh Heifer TMR Pen 40 | Texas |
| S127.7.4 | Late Lac Cow TMR Pen 32 | Texas |
| S127.7.5 | Late Lac Cow TMR Pen 32 | Texas |
| S50.5.6 | Prefresh TMR | New York |

FIG. 3 (Cont)

| ID | Description | State |
|---|---|---|
| S127.7.5 | Late Lac Cow TMR Pen 32 | Texas |
| S50.5.6 | Prefresh TMR | New York |
| 23.1.3 | Sorghum | Wisconsin |
| 23.1.5 | Sorghum | Wisconsin |
| S58.5.1 | TMR (Mid Lactating Cows) | Texas |
| S81.10.8 | Wheat Midds | Ohio |
| S71.18.3 | Dry Hay | Texas |
| S59.10.3 | TMR (High Cow) | Texas |
| S63.6.8 | Dry Corn | Wisconsin |
| S69.6.5 | Dry Cow TMR | Texas |
| S59.11.1 | TMR (Dry Cow) | Texas |
| S59.10.1 | TMR (High Cow) | Texas |
| S57.6.4 | TMR (Lacating Cows) | Texas |
| HN-3 | Haylage | Wisconsin |
| 26.1.4 | Corn Silage | Wisconsin |
| 26.1.5 | Corn Silage | Wisconsin |
| 23.1.2 | Sorghum | Wisconsin |
| S133.1.1 | Calf Starter | WI |
| S36.1.7 | Face Wheatlage | Texas |
| S63.6.9 | Dry Corn | Wisconsin |
| S58.4.1 | TMR (Early Lactating Cows) | Texas |
| S102.8.6 | Close Up Cow TMR | Iowa |
| S42.4.6 | Deep Haylage | Texas |
| S53.11.2 | Fresh TMR | New York |
| S128.12.3 | Straw | GA |
| S47.2.6 | Triticale 2016 | Wisconsin |
| S63.3.1 | Alfalfa Haylage B4 2nd 2016 | Wisconsin |
| Silage 3-3 | Silage | Wisconsin |
| S89.20.10 | WOM #1550 | Pennsylvania |
| 20.1.5 | Corn Silage | Wisconsin |
| S89.20.7 | WOM #1550 | Pennsylvania |
| S109.9.2 | Dry Corn 2016 | Wisconsin |
| S58.4.10 | TMR (Early Lactating Cows) | Texas |
| CSS-1 | Haylage | Wisconsin |
| S128.21.1 | Soy Hulls | GA |
| S87.7.4 | Calves Hay from Bunk | Pennsylvania |
| S89.16.1 | WOM #1500 | Pennsylvania |
| S35.2.2 | Texture Feed #2 | Texas |
| S128.25.2 | Soy Hulls | GA |
| S59.9.2 | TMR (Medium Cow) | Texas |
| S71.17.1 | Burrs | Texas |
| S120.5.6 | | Texas |
| S76.3.9 | Baylage 4th Home | Iowa |
| S126.2.1 | Haylage | WI |
| S143.10.1 | | |
| F1.3.6 | Haylage | Wisconsin |
| S89.4.2 | Close up TMR | Pennsylvania |
| S135.5.7 | Early Lac TMR | Texas |
| S135.4.3 | Fresh Heifer TMR | Texas |
| S135.4.10 | Fresh Heifer TMR | Texas |
| S135.7.5 | Mid Lac B TMR | Texas |

FIG. 3 (Cont.)

| ID | Description | Location |
|---|---|---|
| S135.7.5 | Mid Lac B TMR | Texas |
| S135.7.6 | Mid Lac B TMR | Texas |
| S114.7.7 | | Texas |
| S114.7.9 | | Texas |
| S143.4.3 | | |
| S143.10.2 | | |
| S143.10.4 | | |
| S128.38.1 | 1st TMR | GA |
| S129.1.4 | 3rd Haylage | Iowa |
| S63.2.1 | Alfalfa Haylage B3 2015 | Wisconsin |
| S115.6.5 | Alley Cake High | Wisconsin |
| S115.6.7 | Alley Cake High | Wisconsin |
| S115.6.9 | Alley Cake High | Wisconsin |
| S137.2.2 | Calf Feed 21 | |
| S137.4.10 | Calf Feed 24 | |
| S111.3.2 | Close up TMR | |
| 20.1.1 | Corn Silage | Wisconsin |
| PS3-6 | Corn Silage | Wisconsin |
| S91.5.4 | Cow TMR | Vermont |
| S42.4.5 | Deep Haylage | Texas |
| 12.4.5 | Haylage | Wisconsin |
| F1.1.5 | Haylage | Wisconsin |
| S115.5.4 | Hensen Corn Silage | Wisconsin |
| S135.7.2 | Mid Lac B TMR | Texas |
| S135.7.3 | Mid Lac B TMR | Texas |
| 28.1.5 | Ryelage | Wisconsin |
| 18.2.3 | Sorghum | Wisconsin |
| S81.10.7 | Wheat Midds | Ohio |
| S89.3.1 | Ryegrass Haylage | Pennsylvania |
| S42.3.2 | Face Haylage | Texas |
| 20.3.1 | Haylage | Wisconsin |
| 31.2.1 | Haylage | Wisconsin |
| S102.7.3 | Fresh Heifer TMR | Iowa |
| 21.2.3 | Haylage | Wisconsin |
| S135.4.1 | Fresh Heifer TMR | Texas |
| 21.2.1 | Haylage | Wisconsin |
| 21.2.6 | Haylage | Wisconsin |
| S41.12.2 | Molasses | Wisconsin |
| S59.8.1 | TMR (close up) | Texas |
| S143.9.1 | | |
| S60.4.10 | Ryelage | Wisconsin |
| S60.7.7 | Whey | Wisconsin |
| S42.4.1 | Deep Haylage | Texas |
| S59.6.3 | Haylage | Texas |

FIG. 38 (Cont.)

| | | | | | |
|---|---|---|---|---|---|
| Farm WB | BT36-3 | - - - + | Unidentified | Cow Fecal | Wisconsin |
| Farm ME | D7-5 | + - - - | Type A | Milk Cow fecal | Wisconsin |
| Farm ME | D9-10 | + - - - | Type A | Milk Cow fecal | Wisconsin |
| Farm CR | G3-2 | + - - - | Type A | Pre-Fresh fecal | Wisconsin |
| Farm MC | F8-19 | + - - - | Type A | Calf fecal | Wisconsin |
| Farm CR | G10-3 | + - - - | Type A | Cow Fecal | Wisconsin |
| Farm MC | F8-20 | + - - - | Type A | Calf fecal | Wisconsin |
| Farm CR | G3-3 | + - - - | Type A | Pre-Fresh fecal | Wisconsin |
| Farm CR | G3-4 | + - - - | Type A | Pre-Fresh fecal | Wisconsin |
| Farm G | I8-7 | + - - - | Type A | Calf Fecal | Wisconsin |
| Farm GR | PA50-16 | + - - - | Type A | Calf Fecal | Wisconsin |
| Farm MI | 3.1.5 | + - - - | Type A | Haylage | Wisconsin |
| Farm ME | D8-17 | + - - - | Type A | Milk Cow fecal | Wisconsin |
| Farm GR | A2-13 | + - - - | Type A | Calf fecal | Wisconsin |
| Farm MV | PA84-6 | + - - - | Type A | Cow Fecal | Wisconsin |
| Farm MV | 27.2.3 | + - - - | Type A | Haylage | Wisconsin |
| Farm W | C1-11 | + - - - | Type A | Calf fecal | Wisconsin |
| Farm WB | BT42-5 | + - - - | A | Cow Fecal | Wisconsin |
| Farm G | I8-3 | + - - - | Type A | Calf Fecal | Wisconsin |
| Farm G | I8-6 | + - - - | Type A | Calf Fecal | Wisconsin |
| Farm CR | G10-4 | + - - - | Type A | Cow Fecal | Wisconsin |
| Farm DE | H9-4 | + - - - | Type A | Cow Fecal | Wisconsin |
| Farm G | I10-5 | + - - - | Type A | Cow Fecal | Wisconsin |
| Farm GR | A7-11 | + - - - | Type A | Calf fecal | Wisconsin |
| Farm AL | PA5-3 | + - - - | Type A | Calf Fecal | Wisconsin |
| Farm AL | PA7-2 | + - - - | Type A | Cow Fecal | Wisconsin |
| Farm ME | D8-18 | + - - - | Type A | Milk Cow fecal | Wisconsin |
| Farm AD | PA68-16 | + - - - | Type A | Cow Fecal | Wisconsin |
| Farm WB | BT47-3 | + - - - | A | Cow Fecal | Wisconsin |
| Farm WB | BT46-2 | - + - - | Unidentified | Cow Fecal | Wisconsin |
| Farm CR | G6-14 | + - - - | Type A | Calf Fecal | Wisconsin |
| Farm CR | G6-20 | + - - - | Type A | Calf Fecal | Wisconsin |
| Farm G | I8-5 | + - - - | Type A | Calf Fecal | Wisconsin |
| Farm G | I8-13 | + - - - | Type A | Calf Fecal | Wisconsin |
| Farm HN | HSS-1 | + - - - | Type A | Haylage | Wisconsin |
| Farm ME | D5-18 | + - - - | Type A | Calf fecal | Wisconsin |
| Farm ME | D9-15 | + - - - | Type A | Milk Cow fecal | Wisconsin |
| Farm Z | E9-4 | + - - - | Type A | Milk Cow fecal | Wisconsin |
| Farm ME | D6-15 | + - - - | Type A | Milk Cow fecal | Wisconsin |
| Farm MC | F11-20 | + - - - | Type A | Milk Cow fecal | Wisconsin |
| Farm ME | D9-11 | + - - - | Type A | Milk Cow fecal | Wisconsin |
| Farm ME | D9-19 | + - - - | Type A | Milk Cow fecal | Wisconsin |
| Farm Z | E7-2 | + - - - | Type A | Milk Cow fecal | Wisconsin |
| Farm CR | G5-5 | + - - - | Type A | Milk Cow fecal | Wisconsin |
| Farm CR | G5-12 | + - - - | Type A | Cow Fecal | Wisconsin |
| Farm CR | G9-17 | + - - - | Type A | Fresh Cow Fecal | Wisconsin |
| Farm CR | G10-17 | + - - - | Type A | Cow Fecal | Wisconsin |
| Farm AL | PA3-7 | + - - - | Type A | Calf Fecal | Wisconsin |
| Farm ME | D7-13 | + - - - | Type A | Milk Cow fecal | Wisconsin |
| Farm CR | G5-14 | + - - - | Type A | Cow Fecal | Wisconsin |
| Farm WB | BT10-1 | + - - - | A | Cow Fecal | Wisconsin |
| Farm Z | E9-17 | + - - - | Type A | Milk Cow fecal | Wisconsin |

FIG. 38 (Cont.)

| | | | | | |
|---|---|---|---|---|---|
| Farm AD | PA66-15 | + - - - | Type A | Calf Fecal | Wisconsin |
| Farm AD | PA66-17 | + - - - | Type A | Calf Fecal | Wisconsin |
| Farm HN | 28.1.2 | + - - - | Type A | Ryelage | Wisconsin |
| Farm CR | G8-8 | + - - - | Type A | Fresh Cow Fecal | Wisconsin |
| Farm CR | G8-14 | + - - - | Type A | Fresh Cow Fecal | Wisconsin |
| Farm CR | G8-16 | + - - - | Type A | Fresh Cow Fecal | Wisconsin |
| Farm CR | G8-15 | + - - - | Type A | Fresh Cow Fecal | Wisconsin |
| Farm WB | BT9-6 | + - - - | A | Cow Fecal | Wisconsin |
| Farm AL | PA5-14 | + - - - | Type A | Calf Fecal | Wisconsin |
| Farm S | PA57-7 | + - - - | Type A | Calf Fecal | Wisconsin |
| Farm S | PA57-13 | + - - - | Type A | Calf Fecal | Wisconsin |
| Farm MV | PA84-5 | + - - - | Type A | Cow Fecal | Wisconsin |
| Farm WB | BT7-9 | + - - - | A | Cow Fecal | Wisconsin |
| Farm G | I1-1 | + - - - | Type A | Cow Fecal | Wisconsin |
| Farm WB | BT24-3 | + - - - | A | Cow Fecal | Wisconsin |
| Farm MC | F9-5 | + - - - | Type A | Milk Cow fecal | Wisconsin |
| Farm MV | PA78-2 | + - - - | Type A | Calf Fecal | Wisconsin |
| Farm WB | PA21-2 | + - - - | Type A | Cow Fecal | Wisconsin |
| Farm WB | PA23-18 | + - - - | Type A | Cow Fecal | Wisconsin |
| Farm WB | PA23-9 | + - - - | Type A | Cow Fecal | Wisconsin |
| Farm G | I8-15 | + - - - | Type A | Calf Fecal | Wisconsin |
| Farm BA | PA47-1 | + - - - | Type A | Cow Fecal | Wisconsin |
| Farm BE | PA14-2 | + - - - | Type A | Fresh Cow Fecal | Wisconsin |
| Farm WB | PA23-5 | + - - - | Type A | Cow Fecal | Wisconsin |
| Farm MI | PA31-20 | + - - - | Type A | Cow Fecal | Wisconsin |
| Farm LP | PA35-6 | + - - - | Type A | Calf Fecal | Wisconsin |
| Farm GR | A7-14 | + - - - | Type A | Calf fecal | Wisconsin |
| Farm WB | PA23-10 | + - - - | Type A | Cow Fecal | Wisconsin |
| Farm ME | D7-15 | + - - - | Type A | Milk Cow fecal | Wisconsin |
| Farm HA | J1-1 | + - - - | Type A | Cow Fecal | Wisconsin |
| Farm ME | D7-19 | + - - - | Type A | Milk Cow fecal | Wisconsin |
| Farm AL | PA3-2 | + - - - | Type A | Calf Fecal | Wisconsin |
| Farm AL | PA6-1 | + - - - | Type A | Cow Fecal | Wisconsin |
| Farm BE | PA11-13 | + - - - | Type A | Heifer Fecal | Wisconsin |
| Farm AL | PA7-1 | + - - - | Type A | Cow Fecal | Wisconsin |
| Farm AL | PA7-9 | + - - - | Type A | Cow Fecal | Wisconsin |
| Farm WB | BT40-4 | + - - - | A | Cow Fecal | Wisconsin |
| Farm CR | G3-15 | + - - - | Type A | Pre-Fresh fecal | Wisconsin |
| Farm BE | PA14-14 | + - - - | Type A | Fresh Cow Fecal | Wisconsin |
| Farm WB | BT37-3 | + - - - | A | Cow Fecal | Wisconsin |
| Farm AL | PA3-4 | + - - - | Type A | Calf Fecal | Wisconsin |
| Farm AL | PA4-5 | + - - - | Type A | Calf Fecal | Wisconsin |
| Farm GR | A2-5 | + - - - | Type A | Calf fecal | Wisconsin |
| Farm ME | D7-1 | + - - - | Type A | Milk Cow fecal | Wisconsin |
| Farm MV | PA80-2 | + - - - | Type A | Calf Fecal | Wisconsin |
| Farm MV | PA80-19 | + - - - | Type A | Calf Fecal | Wisconsin |
| Farm WB | BT37-5 | + - - - | A | Cow Fecal | Wisconsin |
| Farm ME | D8-5 | + - - - | Type A | Milk Cow fecal | Wisconsin |
| Farm WB | BT7-4 | + - - - | A | Cow Fecal | Wisconsin |
| Farm CR | G8-18 | + - - - | Type A | Fresh Cow Fecal | Wisconsin |
| Farm CR | G8-10 | + - - - | Type A | Fresh Cow Fecal | Wisconsin |
| Farm WB | BT35-4 | + - - - | A | Cow Fecal | Wisconsin |

FIG. 38 (Cont.)

| | | | | | |
|---|---|---|---|---|---|
| Farm WB | BT42-3 | +--- | A | Cow Fecal | Wisconsin |
| Farm CR | G9-12 | +--- | Type A | Fresh Cow Fecal | Wisconsin |
| Farm CR | G9-18 | +--- | Type A | Fresh Cow Fecal | Wisconsin |
| Farm W | C3-18 | +--- | Type A | Calf fecal | Wisconsin |
| Farm WB | BT1-2 | +--- | A | Cow Fecal | Wisconsin |
| Farm CR | G5-6 | +--- | Type A | Cow Fecal | Wisconsin |
| Farm CR | G5-8 | +--- | Type A | Cow Fecal | Wisconsin |
| Farm CR | G9-4 | +--- | Type A | Fresh Cow Fecal | Wisconsin |
| Farm CR | G9-5 | +--- | Type A | Fresh Cow Fecal | Wisconsin |
| Farm CR | G9-6 | +--- | Type A | Fresh Cow Fecal | Wisconsin |
| Farm CR | G10-15 | +--- | Type A | Cow Fecal | Wisconsin |
| Farm BE | PA11-2 | +--- | Type A | Heifer Fecal | Wisconsin |
| Farm ME | D7-3 | +--- | Type A | Milk Cow fecal | Wisconsin |
| Farm WB | BT43-10 | +--- | A | Cow Fecal | Wisconsin |
| Farm CR | G9-7 | +--- | Type A | Fresh Cow Fecal | Wisconsin |
| Farm CR | G5-9 | +--- | Type A | Cow Fecal | Wisconsin |
| Farm G | I9-6 | +--- | Type A | Cow Fecal | Wisconsin |
| Farm WB | BT2-6 | +--- | A | Cow Fecal | Wisconsin |
| Farm S | 20.3.3 | +--- | Type A | Haylage | Wisconsin |
| Farm MC | F9-16 | +--- | Type A | Milk Cow fecal | Wisconsin |
| Farm MC | F10-9 | +--- | Type A | Milk Cow fecal | Wisconsin |
| Farm MC | F10-17 | ++-- | Type C | Milk Cow fecal | Wisconsin |
| Farm MC | F11-8 | +--- | Type A | Milk Cow fecal | Wisconsin |
| Farm WB | BT1-1 | +--- | A | Cow Fecal | Wisconsin |
| Farm WB | BT1-3 | +--- | A | Cow Fecal | Wisconsin |
| Farm WB | BT9-5 | +--- | A | Cow Fecal | Wisconsin |
| Farm WB | BT50-5 | +--- | A | Cow Fecal | Wisconsin |
| Farm BE | PA10-5 | +--- | Type A | Calf Fecal | Wisconsin |
| Farm CR | G5-7 | +--- | Type A | Cow Fecal | Wisconsin |
| Farm WB | BT1-9 | +--- | A | Cow Fecal | Wisconsin |
| Farm AD | PA67-12 | +--- | Type A | Prefresh Cow Fecal | Wisconsin |
| Farm MC | F8-14 | +--- | Type A | Calf fecal | Wisconsin |
| Farm WB | BT1-4 | +--- | A | Cow Fecal | Wisconsin |
| Farm WB | BT1-6 | +--- | A | Cow Fecal | Wisconsin |
| Farm WB | BT1-7 | +--- | A | Cow Fecal | Wisconsin |
| Farm WB | BT1-8 | +--- | A | Cow Fecal | Wisconsin |
| Farm WB | BT1-10 | +--- | A | Cow Fecal | Wisconsin |
| Farm CR | G10-8 | +--- | Type A | Cow Fecal | Wisconsin |
| Farm CR | G10-9 | +--- | Type A | Cow Fecal | Wisconsin |
| Farm CR | G5-2 | +--- | Type A | Milk Cow fecal | Wisconsin |
| Farm CR | G8-11 | +--- | Type A | Fresh Cow Fecal | Wisconsin |
| Farm Z | E9-12 | +--- | Type A | Milk Cow fecal | Wisconsin |
| Farm CR | G2-6 | +--- | Type A | Calf fecal | Wisconsin |
| Farm CR | G3-17 | +--- | Type A | Pre-Fresh fecal | Wisconsin |
| Farm CR | G5-15 | +--- | Type A | Cow Fecal | Wisconsin |
| Farm WB | BT17-4 | +--- | A | Cow Fecal | Wisconsin |
| Farm CR | G9-9 | +--- | Type A | Fresh Cow Fecal | Wisconsin |
| Farm CR | G8-19 | +--- | Type A | Fresh Cow Fecal | Wisconsin |
| Farm CR | G9-3 | +--- | Type A | Fresh Cow Fecal | Wisconsin |
| Farm GR | A1-11 | +--- | Type A | Calf fecal | Wisconsin |
| Farm OO | B1-1 | +--- | Type A | Calf fecal | Wisconsin |
| Farm CR | G4-8 | +--- | Type A | Milk Cow fecal | Wisconsin |
| Farm R | PA1-3 | +--- | Type A | Calf fecal | Wisconsin |

FIG. 38 (Cont.)

| Farm | ID | | Type | Source | State |
|---|---|---|---|---|---|
| Farm OO | B1-1 | +--- | Type A | Calf fecal | Wisconsin |
| Farm CR | G4-8 | +--- | Type A | Milk Cow fecal | Wisconsin |
| Farm R | PA1-3 | +--- | Type A | Calf fecal | Wisconsin |
| Farm GR | A1-17 | +--- | Type A | Calf fecal | Wisconsin |
| Farm WB | BT10-5 | +--- | A | Cow Fecal | Wisconsin |
| Farm DE | H9-10 | +--- | Type A | Cow Fecal | Wisconsin |
| Farm BE | PA11-19 | +--- | Type A | Heifer Fecal | Wisconsin |
| Farm G | I9-11 | +--- | Type A | Cow Fecal | Wisconsin |
| Farm HA | J1-3 | +--- | Type A | Cow Fecal | Wisconsin |
| Farm ME | D5-14 | +--- | Type A | Calf fecal | Wisconsin |
| Farm Z | E9-1 | +--- | Type A | Milk Cow fecal | Wisconsin |
| Farm G | I4-6 | +--- | Type A | Cow Fecal | Wisconsin |
| Farm G | I9-1 | +--- | Type A | Cow Fecal | Wisconsin |
| Farm MC | F11-13 | +--- | Type A | Milk Cow fecal | Wisconsin |
| Farm S | PA59-11 | +--- | Type A | Calf Fecal | Wisconsin |
| Farm HA | 4.2.1 | +--- | Type A | Corn Silage | Wisconsin |
| Farm S | 20.1.3 | +--- | Type A | Corn Silage | Wisconsin |
| Farm S | 20.3.6 | +--- | Type A | Haylage | Wisconsin |
| Farm HN | PA76-11 | +--- | Type A | Cow Fecal | Wisconsin |
| Farm HN | PA76-19 | +--- | Type A | Cow Fecal | Wisconsin |
| Farm HN | PA76-20 | +--- | Type A | Cow Fecal | Wisconsin |
| Farm MC | F9-20 | +--- | Type A | Milk Cow fecal | Wisconsin |
| Farm MV | PA83-7 | +--- | Type A | Cow Fecal | Wisconsin |
| Farm MC | F10-10 | +--- | Type A | Milk Cow fecal | Wisconsin |
| Farm MC | F10-11 | +--- | Type A | Milk Cow fecal | Wisconsin |
| Farm MC | F10-13 | +--- | Type A | Milk Cow fecal | Wisconsin |
| Farm MC | F10-14 | +--- | Type A | Milk Cow fecal | Wisconsin |
| Farm MC | F10-16 | +--- | Type A | Milk Cow fecal | Wisconsin |
| Farm MC | F11-2 | +--- | Type A | Milk Cow fecal | Wisconsin |
| Farm MC | F11-10 | +--- | Type A | Milk Cow fecal | Wisconsin |
| Farm MC | F11-12 | +--- | Type A | Milk Cow fecal | Wisconsin |
| Farm ME | D5-6 | +--- | Type A | Calf fecal | Wisconsin |
| Farm Z | E5-5 | +--- | Type A | Calf fecal | Wisconsin |
| Farm OO | B4-6 | +--- | Type A | Calf fecal | Wisconsin |
| Farm CR | G5-3 | +--- | Type A | Milk Cow fecal | Wisconsin |
| Farm R | PA1-4 | +--- | Type A | Calf fecal | Wisconsin |
| Farm R | ROS-1 | +--- | Type A | Haylage | Wisconsin |
| Farm DE | H3-1 | +--- | Type A | Cow Fecal | Wisconsin |
| Farm WB | BT3-3 | +--- | A | Cow Fecal | Wisconsin |
| Farm WB | BT4-2 | +--- | A | Cow Fecal | Wisconsin |
| Farm WB | BT4-10 | +--- | A | Cow Fecal | Wisconsin |
| Farm WB | BT6-3 | +--- | A | Cow Fecal | Wisconsin |
| Farm WB | BT10-8 | +--- | A | Cow Fecal | Wisconsin |
| Farm WB | BT10-9 | +--- | A | Cow Fecal | Wisconsin |
| Farm WB | BT10-10 | +--- | A | Cow Fecal | Wisconsin |
| Farm WB | BT13-4 | +--- | A | Cow Fecal | Wisconsin |
| Farm WB | BT29-3 | +--- | A | Cow Fecal | Wisconsin |
| Farm WB | BT36-7 | +--- | A | Cow Fecal | Wisconsin |
| Farm WB | BT10-6 | +--- | A | Cow Fecal | Wisconsin |
| Farm WB | BT10-7 | +--- | A | Cow Fecal | Wisconsin |
| Farm WB | BT32-8 | +--- | A | Cow Fecal | Wisconsin |
| Farm WB | BT17-6 | +--- | A | Cow Fecal | Wisconsin |

FIG. 38 (Cont.)

| | | | | | |
|---|---|---|---|---|---|
| Farm WB | BT32-8 | +- - - | A | Cow Fecal | Wisconsin |
| Farm WB | BT17-6 | +- - - | A | Cow Fecal | Wisconsin |
| Farm WB | BT19-1 | +- - - | A | Cow Fecal | Wisconsin |
| Farm WB | BT20-6 | +- - - | A | Cow Fecal | Wisconsin |
| Farm WB | BT22-9 | +- - - | A | Cow Fecal | Wisconsin |
| Farm WB | BT23-1 | +- - - | A | Cow Fecal | Wisconsin |
| Farm WB | BT23-3 | +- - - | A | Cow Fecal | Wisconsin |
| Farm WB | BT24-9 | +- - - | A | Cow Fecal | Wisconsin |
| Farm WB | BT27-5 | +- - - | A | Cow Fecal | Wisconsin |
| Farm WB | BT41-9 | +- - - | A | Cow Fecal | Wisconsin |
| Farm WB | BT43-6 | +- - - | A | Cow Fecal | Wisconsin |
| Farm CR | G9-1 | +- - - | Type A | Fresh Cow Fecal | Wisconsin |
| Farm CR | G9-11 | +- - - | Type A | Fresh Cow Fecal | Wisconsin |
| Farm CR | G9-16 | +- - - | Type A | Fresh Cow Fecal | Wisconsin |
| Farm CR | G10-1 | +- - - | Type A | Cow Fecal | Wisconsin |
| Farm CR | G10-2 | +- - - | Type A | Cow Fecal | Wisconsin |
| Farm CR | G10-12 | +- - - | Type A | Cow Fecal | Wisconsin |
| Farm DE | H9-2 | +- - - | Type A | Cow Fecal | Wisconsin |
| Farm G | I10-4 | +- - - | Type A | Cow Fecal | Wisconsin |
| Farm DE | DS-1 | +- - - | Type A | Haylage | Wisconsin |
| Farm AL | PA2-18 | +- - - | Type A | Calf Fecal | Wisconsin |
| Farm AL | PA2-19 | +- - - | Type A | Calf Fecal | Wisconsin |
| Farm AL | PA5-1 | +- - - | Type A | Calf Fecal | Wisconsin |
| Farm BE | PA10-1 | +- - - | Type A | Calf Fecal | Wisconsin |
| Farm BE | PA11-11 | +- - - | Type A | Heifer Fecal | Wisconsin |
| Farm HA | J1-4 | +- - - | Type A | Cow Fecal | Wisconsin |
| Farm HA | J1-5 | +- - - | Type A | Cow Fecal | Wisconsin |
| Farm DE | H5-2 | +- - - | Type A | Cow Fecal | Wisconsin |
| Farm AL | PA5-4 | +- - - | Type A | Calf Fecal | Wisconsin |
| Farm R | PA1-10 | +- - - | Type A | Calf fecal | Wisconsin |
| Farm AL | PA5-2 | +- - - | Type A | Calf Fecal | Wisconsin |
| Farm CR | G4-17 | +- - - | Type A | Milk Cow fecal | Wisconsin |
| Farm DE | H5-3 | +- - - | Type A | Cow Fecal | Wisconsin |
| Farm WB | BT42-4 | +- - - | A | Cow Fecal | Wisconsin |
| Farm MV | PA77-1 | +- - + | Type E | Calf Fecal | Wisconsin |
| Farm MV | PA77-4 | - - - + | Unidentified | Calf Fecal | Wisconsin |
| Farm CR | G5-1 | +- - - | Type A | Milk Cow fecal | Wisconsin |
| Farm DE | H1-7 | +- - - | Type A | Calf Fecal | Wisconsin |
| Farm WB | BT7-1 | +- - - | A | Cow Fecal | Wisconsin |
| Farm WB | BT8-8 | +- - - | A | Cow Fecal | Wisconsin |
| Farm ME | D6-8 | +- - - | Type A | Calf fecal | Wisconsin |
| Farm WB | BT3-4 | +- - - | A | Cow Fecal | Wisconsin |
| Farm WB | BT8-2 | +- - - | A | Cow Fecal | Wisconsin |
| Farm WB | BT21-3 | +- - - | A | Cow Fecal | Wisconsin |
| Farm WB | BT40-5 | +- - - | A | Cow Fecal | Wisconsin |
| Farm W | C4-19 | ++- - | Type C | Calf fecal | Wisconsin |
| Farm MI | PA31-6 | +- - - | Type A | Cow Fecal | Wisconsin |
| Farm CR | G8-12 | +- - - | Type A | Fresh Cow Fecal | Wisconsin |
| Farm WB | BT36-6 | +- - - | A | Cow Fecal | Wisconsin |
| Farm WB | BT45-4 | +- - - | A | Cow Fecal | Wisconsin |
| Farm WB | BT4-9 | +- - - | A | Cow Fecal | Wisconsin |
| Farm WB | BT2-3 | +- - - | A | Cow Fecal | Wisconsin |

FIG. 38 (Cont.)

| | | | | |
|---|---|---|---|---|
| Farm WB | BT4-9 | +- - - A | Cow Fecal | Wisconsin |
| Farm WB | BT2-3 | +- - - A | Cow Fecal | Wisconsin |
| Farm WB | BT31-2 | +- - - A | Cow Fecal | Wisconsin |
| Farm WB | BT37-1 | +- - - A | Cow Fecal | Wisconsin |
| Farm CR | G8-6 | +- - - Type A | Fresh Cow Fecal | Wisconsin |
| Farm WB | BT41-5 | +- - - A | Cow Fecal | Wisconsin |
| Farm LP | PA37-5 | +- - - Type A | Cow Fecal | Wisconsin |
| Farm LP | PA37-8 | +- - - Type A | Cow Fecal | Wisconsin |
| Farm ME | D8-3 | +- - - Type A | Milk Cow fecal | Wisconsin |
| Farm S | PA57-12 | +- - - Type A | Calf Fecal | Wisconsin |
| Farm S | PA58-11 | +- - - Type A | Calf Fecal | Wisconsin |
| Farm MC | F9-9 | +- - - Type A | Milk Cow fecal | Wisconsin |
| Farm MC | F9-10 | +- - - Type A | Milk Cow fecal | Wisconsin |
| Farm MC | F9-13 | +- - - Type A | Milk Cow fecal | Wisconsin |
| Farm MC | F9-14 | +- - - Type A | Milk Cow fecal | Wisconsin |
| Farm MC | F9-15 | +- - - Type A | Milk Cow fecal | Wisconsin |
| Farm MV | PA80-5 | +- - - Type A | Calf Fecal | Wisconsin |
| Farm MC | F9-18 | +- - - Type A | Milk Cow fecal | Wisconsin |
| Farm MC | F9-19 | +- - - Type A | Milk Cow fecal | Wisconsin |
| Farm MV | PA81-18 | +- - - Type A | Fresh Cow Fecal | Wisconsin |
| Farm MV | PA82-2 | +- - - Type A | Fresh Cow Fecal | Wisconsin |
| Farm MC | F10-1 | +- - - Type A | Milk Cow fecal | Wisconsin |
| Farm MC | F10-2 | +- - - Type A | Milk Cow fecal | Wisconsin |
| Farm MV | PA83-10 | +- - - Type A | Cow Fecal | Wisconsin |
| Farm MV | PA83-13 | +- - - Type A | Cow Fecal | Wisconsin |
| Farm MC | F10-3 | +- - - Type A | Milk Cow fecal | Wisconsin |
| Farm MC | F10-4 | +- - - Type A | Milk Cow fecal | Wisconsin |
| Farm MV | PA84-18 | +- - - Type A | Cow Fecal | Wisconsin |
| Farm MV | 27.2.11 | +- - - Type A | Haylage | Wisconsin |
| Farm MV | 27.3.2 | +- - - Type A | Oatlage | Wisconsin |
| Farm MV | 27.3.3 | +- - - Type A | Oatlage | Wisconsin |
| Farm MC | F10-6 | +- - - Type A | Milk Cow fecal | Wisconsin |
| Farm MC | F10-7 | +- - - Type A | Milk Cow fecal | Wisconsin |
| Farm MC | F10-19 | +- - - Type A | Milk Cow fecal | Wisconsin |
| Farm MC | F11-5 | +- - - Type A | Milk Cow fecal | Wisconsin |
| Farm MC | F8-6 | +- - - Type A | Calf fecal | Wisconsin |
| Farm CR | G3-13 | +- - - Type A | Pre-Fresh fecal | Wisconsin |
| Farm CR | G4-10 | +- - - Type A | Milk Cow fecal | Wisconsin |
| Farm CR | G4-11 | +- - - Type A | Milk Cow fecal | Wisconsin |
| Farm CR | G5-19 | +- - - Type A | Cow Fecal | Wisconsin |
| Farm DE | H2-3 | +- - - Type A | Calf Fecal | Wisconsin |
| Farm DE | H2-4 | +- - - Type A | Calf Fecal | Wisconsin |
| Farm DE | H2-5 | +- - - Type A | Calf Fecal | Wisconsin |
| Farm DE | H2-6 | +- - - Type A | Calf Fecal | Wisconsin |
| Farm DE | H2-10 | +- - - Type A | Calf Fecal | Wisconsin |
| Farm DE | H2-11 | +- - - Type A | Calf Fecal | Wisconsin |
| Farm DE | H2-12 | +- - - Type A | Calf Fecal | Wisconsin |
| Farm DE | H2-13 | +- - - Type A | Calf Fecal | Wisconsin |
| Farm DE | H2-14 | +- - - Type A | Calf Fecal | Wisconsin |
| Farm DE | H2-15 | +- - - Type A | Calf Fecal | Wisconsin |
| Farm DE | H2-18 | +- - - Type A | Calf Fecal | Wisconsin |
| Farm DE | H2-19 | +- - - Type A | Calf Fecal | Wisconsin |

FIG. 38 (Cont.)

| | | | | |
|---|---|---|---|---|
| Farm DE | H2-15 | +--- Type A | Calf Fecal | Wisconsin |
| Farm DE | H2-18 | +--- Type A | Calf Fecal | Wisconsin |
| Farm DE | H2-19 | +--- Type A | Calf Fecal | Wisconsin |
| Farm WB | BT7-2 | +--- A | Cow Fecal | Wisconsin |
| Farm WB | BT12-6 | +--- A | Cow Fecal | Wisconsin |
| Farm WB | BT49-2 | +--- A | Cow Fecal | Wisconsin |
| Farm WB | BT39-7 | +--- A | Cow Fecal | Wisconsin |
| Farm WB | BT16-7 | +--- A | Cow Fecal | Wisconsin |
| Farm WB | BT18-6 | +--- A | Cow Fecal | Wisconsin |
| Farm WB | BT18-9 | +--- A | Cow Fecal | Wisconsin |
| Farm WB | BT20-7 | +--- A | Cow Fecal | Wisconsin |
| Farm WB | BT22-10 | +--- A | Cow Fecal | Wisconsin |
| Farm WB | BT43-5 | +--- A | Cow Fecal | Wisconsin |
| Farm W | C3-7 | +--- Type A | Calf fecal | Wisconsin |
| Farm CR | G10-13 | +--- Type A | Cow Fecal | Wisconsin |
| Farm CR | G10-14 | +--- Type A | Cow Fecal | Wisconsin |
| Farm DE | H9-7 | +--- Type A | Cow Fecal | Wisconsin |
| Farm DE | H9-12 | +--- Type A | Cow Fecal | Wisconsin |
| Farm GR | A2-4 | +--- Type A | Calf fecal | Wisconsin |
| Farm DE | H10-17 | +--- Type A | Cow Fecal | Wisconsin |
| Farm G | I10-10 | +--- Type A | Cow Fecal | Wisconsin |
| Farm BE | PA11-6 | +--- Type A | Heifer Fecal | Wisconsin |
| Farm ME | D7-4 | +--- Type A | Milk Cow fecal | Wisconsin |
| Farm HA | J1-17 | +--- Type A | Cow Fecal | Wisconsin |
| Farm AL | PA2-10 | +--- Type A | Calf Fecal | Wisconsin |
| Farm WB | BT48-8 | +--- A | Cow Fecal | Wisconsin |
| Farm WB | BT16-5 | +--- A | Cow Fecal | Wisconsin |
| Farm WB | BT48-10 | +--- A | Cow Fecal | Wisconsin |
| Farm MC | F11-4 | +--- Type A | Milk Cow fecal | Wisconsin |
| Farm R | PA1-2 | +--- Type A | Calf fecal | Wisconsin |
| Farm DE | H2-8 | +--- Type A | Calf Fecal | Wisconsin |
| Farm CR | G6-18 | +--- Type A | Calf Fecal | Wisconsin |
| Farm CR | G8-17 | +--- Type A | Fresh Cow Fecal | Wisconsin |
| Farm HA | 4.2.4 | +--- Type A | Corn Silage | Wisconsin |
| Farm HA | 4.3.2 | +--- Type A | Sorghum | Wisconsin |
| Farm HA | 4.3.3 | +--- Type A | Sorghum | Wisconsin |
| Farm HN | PA76-3 | +--- Type A | Cow Fecal | Wisconsin |
| Farm CR | G4-2 | +--- Type A | Milk Cow fecal | Wisconsin |
| Farm WB | BT21-5 | +--- A | Cow Fecal | Wisconsin |
| Farm WB | BT18-5 | +--- A | Cow Fecal | Wisconsin |
| Farm DE | H10-20 | +--- Type A | Cow Fecal | Wisconsin |
| Farm BE | PA11-3 | +--- Type A | Heifer Fecal | Wisconsin |
| Farm MV | PA83-16 | +--- Type A | Cow Fecal | Wisconsin |
| Farm DE | H1-1 | +--- Type A | Calf Fecal | Wisconsin |
| Farm G | I7-11 | +--- Type A | Calf Fecal | Wisconsin |
| Farm G | I9-8 | +--- Type A | Cow Fecal | Wisconsin |
| Farm DE | H10-12 | +--- Type A | Cow Fecal | Wisconsin |
| Farm DE | H10-15 | +--- Type A | Cow Fecal | Wisconsin |
| Farm DE | H10-16 | +--- Type A | Cow Fecal | Wisconsin |
| Farm G | I9-15 | +--- Type A | Cow Fecal | Wisconsin |
| Farm MC | F10-5 | +--- Type A | Milk Cow fecal | Wisconsin |
| Farm MC | F10-18 | +--- Type A | Milk Cow fecal | Wisconsin |

FIG. 38 (Cont.)

| | | | | | |
|---|---|---|---|---|---|
| Farm GR | PA55-19 | +--- | Type A | Fresh Cow Fecal | Wisconsin |
| Farm GR | PA55-20 | +--- | Type A | Fresh Cow Fecal | Wisconsin |
| Farm S | PA57-14 | +--- | Type A | Calf Fecal | Wisconsin |
| Farm S | PA60-3 | +--- | Type A | Calf Fecal | Wisconsin |
| Farm S | PA63-5 | +--- | Type A | Cow Fecal | Wisconsin |
| Farm S | 20.1.4 | +--- | Type A | Corn Silage | Wisconsin |
| Farm S | 20.4.6 | +--- | Type A | Haylage | Wisconsin |
| Farm GR | 21.1.1 | +--- | Type A | Haylage | Wisconsin |
| Farm GR | 21.2.7 | +--- | Type A | Haylage | Wisconsin |
| Farm GR | 21.2.8 | ++-- | Type C | Haylage | Wisconsin |
| Farm AD | PA66-1 | +--- | Type A | Calf Fecal | Wisconsin |
| Farm AD | PA66-2 | +--- | Type A | Calf Fecal | Wisconsin |
| Farm AD | PA66-3 | +--- | Type A | Calf Fecal | Wisconsin |
| Farm AD | PA66-5 | +--- | Type A | Calf Fecal | Wisconsin |
| Farm AD | PA66-6 | +--- | Type A | Calf Fecal | Wisconsin |
| Farm AD | PA66-8 | +--- | Type A | Calf Fecal | Wisconsin |
| Farm HN | PA76-17 | +--- | Type A | Cow Fecal | Wisconsin |
| Farm MV | 27.2.5 | +--- | Type A | Haylage | Wisconsin |
| Farm CW | PA89-7 | +--- | Type A | Cow Fecal | Wisconsin |
| Farm CW | PA89-13 | +--- | Type A | Cow Fecal | Wisconsin |
| Farm CW | PA89-16 | +--- | Type A | Cow Fecal | Wisconsin |
| Farm CW | 30.4.2 | +--- | Type A | Corn Silage | Wisconsin |
| Farm HN | R4.1.3 | +--- | A | Cow Fecal | Wisconsin |
| Farm HN | R4.1.8 | +--- | A | Cow Fecal | Wisconsin |
| Farm HN | R4.1.9 | +--- | A | Cow Fecal | Wisconsin |
| Farm ME | D9-18 | +--- | Type A | Milk Cow fecal | Wisconsin |
| Farm Z | E9-18 | +--- | Type A | Milk Cow fecal | Wisconsin |
| Farm CR | G1-5 | +--- | Type A | Calf fecal | Wisconsin |
| Farm CR | G3-5 | +--- | Type A | Pre-Fresh fecal | Wisconsin |
| Farm CR | G5-18 | +--- | Type A | Cow Fecal | Wisconsin |
| Farm DE | H4-1 | +--- | Type A | Cow Fecal | Wisconsin |
| Farm W | C2-2 | +--- | Type A | Calf fecal | Wisconsin |
| Farm WB | BT8-1 | +--- | A | Cow Fecal | Wisconsin |
| Farm W | C2-18 | +--- | Type A | Calf fecal | Wisconsin |
| Farm WB | BT12-1 | +--- | A | Cow Fecal | Wisconsin |
| Farm WB | BT12-2 | +--- | A | Cow Fecal | Wisconsin |
| Farm WB | BT13-1 | +--- | A | Cow Fecal | Wisconsin |
| Farm WB | BT31-4 | +--- | A | Cow Fecal | Wisconsin |
| Farm WB | BT20-3 | +--- | A | Cow Fecal | Wisconsin |
| Farm WB | BT45-9 | +--- | A | Cow Fecal | Wisconsin |
| Farm WB | BT46-10 | +--- | A | Cow Fecal | Wisconsin |
| Farm WB | BT48-1 | +--- | A | Cow Fecal | Wisconsin |
| Farm WB | BT48-3 | +--- | A | Cow Fecal | Wisconsin |
| Farm WB | BT32-1 | +--- | A | Cow Fecal | Wisconsin |
| Farm WB | BT33-1 | +-+- | D | Cow Fecal | Wisconsin |
| Farm WB | BT39-1 | +--- | A | Cow Fecal | Wisconsin |
| Farm WB | BT15-10 | +--- | A | Cow Fecal | Wisconsin |
| Farm WB | BT18-3 | +--- | A | Cow Fecal | Wisconsin |
| Farm WB | BT18-4 | +--- | A | Cow Fecal | Wisconsin |
| Farm WB | BT19-5 | +--- | A | Cow Fecal | Wisconsin |
| Farm WB | BT20-1 | +--- | A | Cow Fecal | Wisconsin |
| Farm WB | BT20-9 | +--- | A | Cow Fecal | Wisconsin |

FIG. 38 (Cont.)

| | Farm | ID | Code | Type | Sample | State |
|---|---|---|---|---|---|---|
| | Farm WB | BT20-1 | +- - - | A | Cow Fecal | Wisconsin |
| | Farm WB | BT20-9 | +- - - | A | Cow Fecal | Wisconsin |
| | Farm WB | BT22-3 | +- - - | A | Cow Fecal | Wisconsin |
| | Farm WB | BT24-8 | +- - - | A | Cow Fecal | Wisconsin |
| | Farm WB | BT25-3 | +- - - | A | Cow Fecal | Wisconsin |
| | Farm WB | BT28-5 | +- - - | A | Cow Fecal | Wisconsin |
| | Farm WB | BT28-8 | +- - - | A | Cow Fecal | Wisconsin |
| | Farm WB | BT43-3 | +- - - | A | Cow Fecal | Wisconsin |
| | Farm WB | BT43-7 | +- - - | A | Cow Fecal | Wisconsin |
| | Farm WB | BT49-10 | +- - - | A | Cow Fecal | Wisconsin |
| | Farm WB | BT50-8 | +- - - | A | Cow Fecal | Wisconsin |
| | Farm CR | G6-19 | +- - - | Type A | Calf Fecal | Wisconsin |
| | Farm CR | G8-3 | +- - - | Type A | Fresh Cow Fecal | Wisconsin |
| | Farm CR | G8-4 | +- - - | Type A | Fresh Cow Fecal | Wisconsin |
| | Farm CR | G8-5 | +- - - | Type A | Fresh Cow Fecal | Wisconsin |
| | Farm CR | G8-7 | +- - - | Type A | Fresh Cow Fecal | Wisconsin |
| | Farm CR | G8-13 | +- - - | Type A | Fresh Cow Fecal | Wisconsin |
| | Farm W | C3-10 | +- - - | Type A | Calf fecal | Wisconsin |
| | Farm CR | G8-20 | +- - - | Type A | Fresh Cow Fecal | Wisconsin |
| | Farm G | I9-18 | +- - - | Type A | Cow Fecal | Wisconsin |
| | Farm G | I10-16 | +- - - | Type A | Cow Fecal | Wisconsin |
| | Farm HN | HN-2 | +- - - | Type A | Haylage | Wisconsin |
| | Farm HN | HC-1 | +- - - | Type A | Corn Silage | Wisconsin |
| | Farm HA | J1-20 | +- - - | Type A | Cow Fecal | Wisconsin |
| | Farm HA | J3-8 | +- - - | Type A | Cow Fecal | Wisconsin |
| | Farm HA | 4.2.3 | +- - - | Type A | Corn Silage | Wisconsin |
| | Farm MI | 3.1.3 | +- - - | Type A | Haylage | Wisconsin |
| | Farm LP | PA33-1 | +- - - | Type A | Calf Fecal | Wisconsin |
| | Farm LP | PA33-2 | ++- - | Type C | Calf Fecal | Wisconsin |
| | Farm LP | PA33-3 | +- - - | Type A | Calf Fecal | Wisconsin |
| | Farm LP | PA33-4 | +- - - | Type A | Calf Fecal | Wisconsin |
| | Farm LP | PA33-5 | +- - - | Type A | Calf Fecal | Wisconsin |
| | Farm LP | PA33-8 | +- - - | Type A | Calf Fecal | Wisconsin |
| | Farm LP | PA33-10 | +- - - | Type A | Calf Fecal | Wisconsin |
| | Farm LP | PA33-11 | +- - - | Type A | Calf Fecal | Wisconsin |
| | Farm LP | PA34-1 | +- - - | Type A | Calf Fecal | Wisconsin |
| | Farm LP | PA34-2 | +- - - | Type A | Calf Fecal | Wisconsin |
| | Farm LP | PA34-3 | +- - - | Type A | Calf Fecal | Wisconsin |
| | Farm LP | PA34-4 | +- - - | Type A | Calf Fecal | Wisconsin |
| | Farm LP | PA34-6 | +- +- | Type D | Calf Fecal | Wisconsin |
| | Farm LP | PA34-7 | +- - - | Type A | Calf Fecal | Wisconsin |
| | Farm LP | PA34-8 | +- - - | Type A | Calf Fecal | Wisconsin |
| | Farm LP | PA34-9 | +- - - | Type A | Calf Fecal | Wisconsin |
| | Farm LP | PA34-10 | +- - - | Type A | Calf Fecal | Wisconsin |
| | Farm LP | PA35-2 | +- - - | Type A | Calf Fecal | Wisconsin |
| | Farm LP | PA35-3 | +- - - | Type A | Calf Fecal | Wisconsin |
| | Farm Z | E9-19 | +- - - | Type A | Milk Cow fecal | Wisconsin |
| | Farm W | C3-17 | ++- - | Type C | Calf fecal | Wisconsin |
| | Farm R | PA1-20 | +- +- | Type D | Calf fecal | Wisconsin |
| | Farm WB | BT8-9 | +- - - | A | Cow Fecal | Wisconsin |
| | Farm WB | BT35-8 | +- - - | A | Cow Fecal | Wisconsin |

FIG. 38 (Cont.)

| | | | | | |
|---|---|---|---|---|---|
| Farm WB | BT8-9 | +- - - A | | Cow Fecal | Wisconsin |
| Farm WB | BT35-8 | +- - - A | | Cow Fecal | Wisconsin |
| Farm G | I8-18 | +- - - Type A | | Calf Fecal | Wisconsin |
| Farm MV | PA83-2 | +- - - Type A | | Cow Fecal | Wisconsin |
| Farm WB | BT31-2 | +- - - A | | Cow Fecal | Wisconsin |
| Farm S | PA63-19 | +- - - Type A | | Cow Fecal | Wisconsin |
| Farm HN | PA76-4 | +- - - Type A | | Cow Fecal | Wisconsin |
| Farm MI | PA32-17 | +- - - Type A | | Cow Fecal | Wisconsin |
| Farm MI | PA30-10 | +- - - Type A | | Cow Fecal | Wisconsin |
| Farm AD | PA66-19 | +- - - Type A | | Calf Fecal | Wisconsin |
| Farm MI | PA30-6 | +- - - Type A | | Cow Fecal | Wisconsin |
| Farm BA | PA41-11 | +- - - Type A | | Calf Fecal | Wisconsin |
| Farm MI | PA30-3 | +- - - Type A | | Cow Fecal | Wisconsin |
| Farm LP | PA37-9 | +- - - Type A | | Cow Fecal | Wisconsin |
| Farm BA | PA42-3 | +- +- Type D | | Calf Fecal | Wisconsin |
| Farm GR | PA49-18 | +- - - Type A | | Calf Fecal | Wisconsin |
| Farm GR | PA50-15 | +- - - Type A | | Calf Fecal | Wisconsin |
| Farm S | PA57-6 | +- - - Type A | | Calf Fecal | Wisconsin |
| Farm S | PA63-16 | +- - - Type A | | Cow Fecal | Wisconsin |
| Farm HN | PA74-2 | +- - - Type A | | Fresh Cow Fecal | Wisconsin |
| Farm HN | PA74-5 | +- - - Type A | | Fresh Cow Fecal | Wisconsin |
| Farm HN | PA74-12 | +- - - Type A | | Fresh Cow Fecal | Wisconsin |
| Farm HN | PA74-14 | +- - - Type A | | Fresh Cow Fecal | Wisconsin |
| Farm HN | PA76-8 | +- - - Type A | | Cow Fecal | Wisconsin |
| Farm HN | PA76-14 | +- - - Type A | | Cow Fecal | Wisconsin |
| Farm HN | PA76-16 | +- - - Type A | | Cow Fecal | Wisconsin |
| Farm MV | PA81-3 | +- - - Type A | | Fresh Cow Fecal | Wisconsin |
| Farm MV | PA83-9 | +- - - Type A | | Cow Fecal | Wisconsin |
| Farm MV | PA84-3 | +- - - Type A | | Cow Fecal | Wisconsin |
| Farm WB | PA22-3 | +- - - Type A | | Cow Fecal | Wisconsin |
| Farm MI | PA32-18 | +- - - Type A | | Cow Fecal | Wisconsin |
| Farm HA | J1-13 | +- - - Type A | | Cow Fecal | Wisconsin |
| Farm WB | BT50-2 | +- - - A | | Cow Fecal | Wisconsin |
| Farm AL | PA5-9 | +- - - Type A | | Calf Fecal | Wisconsin |
| Farm WB | BT8-10 | +- - - A | | Cow Fecal | Wisconsin |
| Farm WB | BT45-7 | +- - - A | | Cow Fecal | Wisconsin |
| Farm WB | BT9-4 | +- - - A | | Cow Fecal | Wisconsin |
| Farm G | I7-9 | +- - - Type A | | Calf Fecal | Wisconsin |
| Farm CR | G9-19 | +- - - Type A | | Fresh Cow Fecal | Wisconsin |
| Farm WB | BT9-3 | +- - - A | | Cow Fecal | Wisconsin |
| Farm WB | BT9-7 | +- - - A | | Cow Fecal | Wisconsin |
| Farm AD | PA65-3 | +- - - Type A | | Calf Fecal | Wisconsin |
| Farm AD | PA65-5 | +- - - Type A | | Calf Fecal | Wisconsin |
| Farm WB | BT2-1 | +- - - A | | Cow Fecal | Wisconsin |
| Farm CR | G8-2 | +- - - Type A | | Fresh Cow Fecal | Wisconsin |
| Farm DE | H7-3 | +- - - Type A | | Dry Cow Fecal | Wisconsin |
| Farm WB | BT16-3 | +- - - A | | Cow Fecal | Wisconsin |
| Farm WB | BT18-7 | +- - - A | | Cow Fecal | Wisconsin |
| Farm Z | E5-9 | +- - - Type A | | Calf fecal | Wisconsin |
| Farm Z | E5-10 | +- - - Type A | | Calf fecal | Wisconsin |
| Farm Z | E5-11 | +- - - Type A | | Calf fecal | Wisconsin |
| Farm Z | E5-12 | +- - - Type A | | Calf fecal | Wisconsin |

FIG. 38 (Cont.)

| | | | | |
|---|---|---|---|---|
| Farm MC | F8-8 | +--- Type A | Calf fecal | Wisconsin |
| Farm R | PA1-6 | +--- Type A | Calf fecal | Wisconsin |
| Farm G | I8-11 | +--- Type A | Calf Fecal | Wisconsin |
| Farm G | I10-1 | +--- Type A | Cow Fecal | Wisconsin |
| Farm MC | F11-18 | +--- Type A | Milk Cow fecal | Wisconsin |
| Farm AL | PA7-15 | +--- Type A | Cow Fecal | Wisconsin |
| Farm ME | D5-3 | +--- Type A | Calf fecal | Wisconsin |
| Farm Z | E5-8 | +--- Type A | Calf fecal | Wisconsin |
| Farm MC | F8-4 | +--- Type A | Calf fecal | Wisconsin |
| Farm MC | F8-18 | +--- Type A | Calf fecal | Wisconsin |
| Farm WB | BT16-4 | +--- A | Cow Fecal | Wisconsin |
| Farm Z | E6-11 | +--- Type A | Milk Cow fecal | Wisconsin |
| Farm WB | PA23-3 | +--- Type A | Cow Fecal | Wisconsin |
| Farm G | I2-18 | +--- Type A | Cow Fecal | Wisconsin |
| Farm W | C3-16 | ++-- Type C | Calf fecal | Wisconsin |
| Farm CR | G9-15 | +--- Type A | Fresh Cow Fecal | Wisconsin |
| Farm OO | B1-7 | +--- Type A | Calf fecal | Wisconsin |
| Farm WB | BT40-1 | +--- A | Cow Fecal | Wisconsin |
| Farm OO | B1-14 | +--- Type A | Calf fecal | Wisconsin |
| Farm OO | B1-15 | +--- Type A | Calf fecal | Wisconsin |
| Farm OO | B4-8 | +--- Type A | Calf fecal | Wisconsin |
| Farm ME | D9-9 | +--- Type A | Milk Cow fecal | Wisconsin |
| Farm CR | G5-11 | +--- Type A | Cow Fecal | Wisconsin |
| Farm WB | BT42-7 | +--- A | Cow Fecal | Wisconsin |
| Farm CR | G5-20 | +--- Type A | Cow Fecal | Wisconsin |
| Farm WB | BT41-3 | +--- A | Cow Fecal | Wisconsin |
| Farm ME | D9-1 | +--- Type A | Milk Cow fecal | Wisconsin |
| Farm HN | PA74-15 | +--- Type A | Fresh Cow Fecal | Wisconsin |
| Farm HN | PA71-15 | -+-- Unidentified | Calf Fecal | Wisconsin |
| Farm WB | BT40-6 | +--- A | Cow Fecal | Wisconsin |
| Farm AL | PA4-1 | +--- Type A | Calf Fecal | Wisconsin |
| Farm R | ROS-4 | +--- Type A | Haylage | Wisconsin |
| Farm Z | E6-16 | +--- Type A | Milk Cow fecal | Wisconsin |
| Farm WB | BT7-7 | +--- A | Cow Fecal | Wisconsin |
| Farm WB | BT27-10 | +--- A | Cow Fecal | Wisconsin |
| Farm MC | F3-2 | +--- Type A | Calf fecal | Wisconsin |
| Farm Z | E6-20 | +--- Type A | Milk Cow fecal | Wisconsin |
| Farm AL | PA2-11 | +--- Type A | Calf Fecal | Wisconsin |
| Farm AL | PA2-12 | +--- Type A | Calf Fecal | Wisconsin |
| Farm ME | D9-6 | +--- Type A | Milk Cow fecal | Wisconsin |
| Farm WB | BT6-4 | +--- A | Cow Fecal | Wisconsin |
| Farm WB | BT41-2 | +--- A | Cow Fecal | Wisconsin |
| Farm G | I3-8 | +--- Type A | Cow Fecal | Wisconsin |
| Farm WB | BT6-5 | +--- A | Cow Fecal | Wisconsin |
| Farm Z | E7-1 | +--- Type A | Milk Cow fecal | Wisconsin |
| Farm DE | H4-3 | +--- Type A | Cow Fecal | Wisconsin |
| Farm WB | BT8-6 | +--- A | Cow Fecal | Wisconsin |
| Farm G | I5-10 | +--- Type A | Cow Fecal | Wisconsin |
| Farm WB | BT41-10 | +--- A | Cow Fecal | Wisconsin |
| Farm MI | PA32-11 | +--- Type A | Cow Fecal | Wisconsin |
| Farm WB | BT38-3 | ---+ Unidentified | Cow Fecal | Wisconsin |
| Farm AL | PA2-13 | +--- Type A | Calf Fecal | Wisconsin |

FIG. 38 (Cont.)

| | Farm | ID | Type | Source | State |
|---|---|---|---|---|---|
| | Farm AL | PA2-17 | +- - - Type A | Calf Fecal | Wisconsin |
| | Farm AL | PA3-3 | +- - - Type A | Calf Fecal | Wisconsin |
| | Farm AL | PA2-7 | +- - - Type A | Calf Fecal | Wisconsin |
| | Farm AL | PA2-16 | +- - - Type A | Calf Fecal | Wisconsin |
| | Farm WB | BT22-5 | +- - - A | Cow Fecal | Wisconsin |
| | Farm AL | PA5-8 | +- - - Type A | Calf Fecal | Wisconsin |
| | Farm AL | PA5-10 | +- - - Type A | Calf Fecal | Wisconsin |
| | Farm AL | PA5-18 | +- - - Type A | Calf Fecal | Wisconsin |
| | Farm AL | PA5-20 | +- - - Type A | Calf Fecal | Wisconsin |
| | Farm AL | PA2-8 | +- - - Type A | Calf Fecal | Wisconsin |
| | Farm AL | PA4-6 | +- - - Type A | Calf Fecal | Wisconsin |
| | Farm AL | PA5-13 | +- - - Type A | Calf Fecal | Wisconsin |
| | Farm AL | PA5-16 | +- - - Type A | Calf Fecal | Wisconsin |
| | Farm ME | D8-11 | +- - - Type A | Milk Cow fecal | Wisconsin |
| | Farm AL | PA3-5 | +- - - Type A | Calf Fecal | Wisconsin |
| | Farm AL | PA5-17 | +- - - Type A | Calf Fecal | Wisconsin |
| | Farm BE | PA9-9 | - - - +Unidentified | Calf Fecal | Wisconsin |
| | Farm BE | PA11-1 | +- - - Type A | Heifer Fecal | Wisconsin |
| | Farm ME | D7-17 | +- - - Type A | Milk Cow fecal | Wisconsin |
| | Farm BE | PA10-4 | +- - - Type A | Calf Fecal | Wisconsin |
| | Farm ME | D7-9 | +- - - Type A | Milk Cow fecal | Wisconsin |
| | Farm MC | F11-6 | +- - - Type A | Milk Cow fecal | Wisconsin |
| | Farm MC | F8-17 | +- - - Type A | Calf fecal | Wisconsin |
| | Farm ME | D7-10 | +- - - Type A | Milk Cow fecal | Wisconsin |
| | Farm WB | BT2-7 | +- - - A | Cow Fecal | Wisconsin |
| | Farm WB | BT8-3 | +- - - A | Cow Fecal | Wisconsin |
| | Farm WB | BT9-1 | +- - - A | Cow Fecal | Wisconsin |
| | Farm WB | BT45-8 | +- - - A | Cow Fecal | Wisconsin |
| | Farm WB | BT50-6 | +- - - A | Cow Fecal | Wisconsin |
| | Farm DE | H4-2 | +- - - Type A | Cow Fecal | Wisconsin |
| | Farm DE | H10-18 | +- - - Type A | Cow Fecal | Wisconsin |
| | Farm WB | BT49-6 | +- - - A | Cow Fecal | Wisconsin |
| | Farm Z | E6-18 | +- - - Type A | Milk Cow fecal | Wisconsin |
| | Farm WB | BT45-2 | +- - - A | Cow Fecal | Wisconsin |
| | Farm HN | PA69-2 | +- - - Type A | Calf Fecal | Wisconsin |
| | Farm HN | PA69-8 | +- - - Type A | Calf Fecal | Wisconsin |
| | Farm DE | DN-4 | - +- - Unidentified | Haylage | Wisconsin |
| | Farm ME | D6-3 | +- - - Type A | Calf fecal | Wisconsin |
| | Farm S | 20.3.1 | +- - - Type A | Haylage | Wisconsin |
| | Farm MI | 31.2.1 | +- - +Type E | Haylage | Wisconsin |
| | Farm Z | E9-5 | +- - - Type A | Milk Cow fecal | Wisconsin |
| | Farm CW | PA87-1 | +- - - Type A | Cow Fecal | Wisconsin |
| | Farm AL | PA8-1 | +- - - Type A | Cow Fecal | Wisconsin |
| | Farm W | C2-7 | +- - - Type A | Calf fecal | Wisconsin |
| | Farm WB | BT36-1 | +- - - A | Cow Fecal | Wisconsin |
| | Farm AL | PA7-19 | +- - - Type A | Cow Fecal | Wisconsin |
| | Farm MV | PA84-7 | +- - - Type A | Cow Fecal | Wisconsin |
| | Farm CW | PA85-3 | +- - - Type A | Cow Fecal | Wisconsin |
| | Farm LP | PA35-20 | +- - - Type A | Calf Fecal | Wisconsin |
| | Farm LP | PA36-1 | +- - - Type A | Calf Fecal | Wisconsin |
| | Farm LP | PA36-4 | +- - - Type A | Calf Fecal | Wisconsin |
| | Farm LP | PA36-6 | +- - - Type A | Calf Fecal | Wisconsin |
| | Farm LP | PA36-7 | +- - - Type A | Calf Fecal | Wisconsin |

FIG. 38 (Cont.)

| | | | | | |
|---|---|---|---|---|---|
| Farm LP | PA36-4 | +- - - Type A | Calf Fecal | Wisconsin |
| Farm LP | PA36-6 | +- - - Type A | Calf Fecal | Wisconsin |
| Farm LP | PA36-7 | +- - - Type A | Calf Fecal | Wisconsin |
| Farm LP | PA36-12 | +- - - Type A | Calf Fecal | Wisconsin |
| Farm LP | PA36-13 | +- - - Type A | Calf Fecal | Wisconsin |
| Farm LP | PA36-14 | +- - - Type A | Calf Fecal | Wisconsin |
| Farm BA | PA42-2 | +- - - Type A | Calf Fecal | Wisconsin |
| Farm BA | PA42-11 | +- - - Type A | Calf Fecal | Wisconsin |
| Farm S | 20.1.2 | +- - - Type A | Corn Silage | Wisconsin |
| Farm GR | 21.2.4 | +- - - Type A | Haylage | Wisconsin |
| Farm MV | 27.2.4 | +- - - Type A | Haylage | Wisconsin |
| Farm ME | D5-12 | +- - - Type A | Calf fecal | Wisconsin |
| Farm ME | D5-17 | +- - - Type A | Calf fecal | Wisconsin |
| Farm ME | D5-20 | +- - - Type A | Calf fecal | Wisconsin |
| Farm ME | D6-5 | +- - +Type E | Calf fecal | Wisconsin |
| Farm ME | D6-6 | +- - - Type A | Calf fecal | Wisconsin |
| Farm Z | E9-2 | +- - - Type A | Milk Cow fecal | Wisconsin |
| Farm Z | E9-9 | +- - - Type A | Milk Cow fecal | Wisconsin |
| Farm WB | BT45-1 | +- - - A | Cow Fecal | Wisconsin |
| Farm WB | BT45-5 | +- - - A | Cow Fecal | Wisconsin |
| Farm WB | BT46-3 | +- - - A | Cow Fecal | Wisconsin |
| Farm WB | BT46-4 | +- - - A | Cow Fecal | Wisconsin |
| Farm WB | BT35-9 | +- - - A | Cow Fecal | Wisconsin |
| Farm WB | BT27-9 | +- - - A | Cow Fecal | Wisconsin |
| Farm WB | BT50-10 | +- - - A | Cow Fecal | Wisconsin |
| Farm W | C5-18 | +- - - Type A | Calf fecal | Wisconsin |
| Farm BE | PA11-14 | +- - - Type A | Heifer Fecal | Wisconsin |
| Farm BE | PA11-15 | +- - - Type A | Heifer Fecal | Wisconsin |
| Farm LP | PA33-9 | +- - - Type A | Calf Fecal | Wisconsin |
| Farm LP | PA35-7 | +- - - Type A | Calf Fecal | Wisconsin |
| Farm LP | PA35-8 | +- - - Type A | Calf Fecal | Wisconsin |
| Farm LP | PA35-9 | +- - - Type A | Calf Fecal | Wisconsin |
| Farm LP | PA35-11 | +- - - Type A | Calf Fecal | Wisconsin |
| Farm LP | PA35-12 | +- - - Type A | Calf Fecal | Wisconsin |
| Farm LP | PA35-13 | +- - - Type A | Calf Fecal | Wisconsin |
| Farm LP | PA35-15 | +- - - Type A | Calf Fecal | Wisconsin |
| Farm LP | PA35-16 | +- - - Type A | Calf Fecal | Wisconsin |
| Farm LP | PA35-17 | +- - - Type A | Calf Fecal | Wisconsin |
| Farm LP | PA35-18 | +- - - Type A | Calf Fecal | Wisconsin |
| Farm LP | PA35-19 | +- - - Type A | Calf Fecal | Wisconsin |
| Farm OO | B3-6 | +- - - Type A | Calf fecal | Wisconsin |
| Farm HN | HN-1 | +- - - Type A | Haylage | Wisconsin |
| Farm DE | DL-5 | +- - - Type A | Haylage | Wisconsin |
| Farm DE | DL-1 | +- - - Type A | Haylage | Wisconsin |
| Farm ME | D5-7 | +- - - Type A | Calf fecal | Wisconsin |
| Farm ME | D5-9 | +- - - Type A | Calf fecal | Wisconsin |
| Farm Z | E9-3 | +- - - Type A | Milk Cow fecal | Wisconsin |
| Farm DE | H1-6 | +- - - Type A | Calf Fecal | Wisconsin |
| Farm G | I7-12 | +- - - Type A | Calf Fecal | Wisconsin |
| Farm AL | PA4-4 | +- - - Type A | Calf Fecal | Wisconsin |
| Farm HN | PA69-12 | +- - - Type A | Calf Fecal | Wisconsin |
| Farm WB | BT6-2 | +- - - A | Cow Fecal | Wisconsin |

FIG. 38 (Cont.)

| | Farm | Sample | Toxin | Type | Source | State |
|---|---|---|---|---|---|---|
| | Farm HN | .PA69-12 | +- - - | Type A | Calf Fecal | Wisconsin |
| | Farm WB | .BT6-2 | +- - - | A | Cow Fecal | Wisconsin |
| | Farm AD | .PA66-11 | +- - - | Type A | Calf Fecal | Wisconsin |
| | Farm HN | .PA74-4 | +- - - | Type A | Fresh Cow Fecal | Wisconsin |
| | Farm WB | .BT18-2 | +- - - | A | Cow Fecal | Wisconsin |
| | Farm WB | .BT23-9 | +- - - | A | Cow Fecal | Wisconsin |
| | Farm WB | .BT42-2 | +- - - | A | Cow Fecal | Wisconsin |
| | Farm BE | .PA13-19 | +- - - | Type A | Fresh Cow Fecal | Wisconsin |
| | Farm WB | .PA24-9 | +- - - | Type A | Cow Fecal | Wisconsin |
| | Farm GR | .PA50-8 | +- - - | Type A | Calf Fecal | Wisconsin |
| | Farm BE | .PA13-13 | +- - - | Type A | Fresh Cow Fecal | Wisconsin |
| | Farm S | .PA61-3 | +- - - | Type A | Fresh Cow Fecal | Wisconsin |
| | Farm LP | .PA36-2 | +- - - | Type A | Calf Fecal | Wisconsin |
| | Farm LP | .PA36-15 | +- - - | Type A | Calf Fecal | Wisconsin |
| | Farm LP | .PA38-5 | +- - - | Type A | Cow Fecal | Wisconsin |
| | Farm LP | .PA38-12 | +- - - | Type A | Cow Fecal | Wisconsin |
| | Farm LP | .PA38-14 | +- - - | Type A | Cow Fecal | Wisconsin |
| | Farm LP | .PA38-18 | +- - - | Type A | Cow Fecal | Wisconsin |
| | Farm LP | .PA38-19 | +- - - | Type A | Cow Fecal | Wisconsin |
| | Farm LP | .PA38-20 | +- - - | Type A | Cow Fecal | Wisconsin |
| | Farm LP | .PA40-2 | +- - - | Type A | Cow Fecal | Wisconsin |
| | Farm LP | .PA40-6 | +- - - | Type A | Cow Fecal | Wisconsin |
| | Farm BA | .PA41-1 | +- - - | Type A | Calf Fecal | Wisconsin |
| | Farm BA | .PA41-2 | +- - - | Type A | Calf Fecal | Wisconsin |
| | Farm BA | .PA41-15 | +- - - | Type A | Calf Fecal | Wisconsin |
| | Farm BA | .PA41-17 | +- - - | Type A | Calf Fecal | Wisconsin |
| | Farm BA | .PA41-19 | +- - - | Type A | Calf Fecal | Wisconsin |
| | Farm BA | .PA46-7 | +- - - | Type A | Cow Fecal | Wisconsin |
| | Farm BA | .PA47-2 | +- - - | Type A | Cow Fecal | Wisconsin |
| | Farm GR | .PA50-1 | +- - - | Type A | Calf Fecal | Wisconsin |
| | Farm GR | .PA50-5 | +- - - | Type A | Calf Fecal | Wisconsin |
| | Farm GR | .PA50-9 | +- - - | Type A | Calf Fecal | Wisconsin |
| | Farm GR | .PA50-10 | +- - - | Type A | Calf Fecal | Wisconsin |
| | Farm GR | .PA50-11 | +- - - | Type A | Calf Fecal | Wisconsin |
| | Farm GR | .PA50-17 | +- - - | Type A | Calf Fecal | Wisconsin |
| | Farm GR | .PA51-20 | +- +- | Type D | Calf Fecal | Wisconsin |
| | Farm GR | .PA53-3 | +- - - | Type A | Cow Fecal | Wisconsin |
| | Farm GR | .PA53-4 | +- - - | Type A | Cow Fecal | Wisconsin |
| | Farm GR | .PA53-5 | +- - - | Type A | Cow Fecal | Wisconsin |
| | Farm GR | .PA53-7 | +- - - | Type A | Cow Fecal | Wisconsin |
| | Farm GR | .PA53-10 | +- - - | Type A | Cow Fecal | Wisconsin |
| | Farm GR | .PA53-11 | +- - - | Type A | Cow Fecal | Wisconsin |
| | Farm GR | .PA53-12 | +- - - | Type A | Cow Fecal | Wisconsin |
| | Farm GR | .PA53-13 | +- - - | Type A | Cow Fecal | Wisconsin |
| | Farm GR | .PA53-20 | +- - - | Type A | Cow Fecal | Wisconsin |
| | Farm GR | .PA54-2 | +- - - | Type A | Cow Fecal | Wisconsin |
| | Farm GR | .PA54-8 | +- - - | Type A | Cow Fecal | Wisconsin |
| | Farm GR | .PA54-10 | +- - - | Type A | Cow Fecal | Wisconsin |
| | Farm GR | .PA56-1 | +- - - | Type A | Fresh Cow Fecal | Wisconsin |
| | Farm GR | .PA56-2 | +- - - | Type A | Fresh Cow Fecal | Wisconsin |
| | Farm GR | .PA56-5 | +- +- | Type D | Fresh Cow Fecal | Wisconsin |
| | Farm GR | .PA56-9 | +- - - | Type A | Fresh Cow Fecal | Wisconsin |

FIG. 38 (Cont.)

| | | | | | |
|---|---|---|---|---|---|
| Farm GR | PA56-5 | +- +- | Type D | Fresh Cow Fecal | Wisconsin |
| Farm GR | PA56-9 | +- -- | Type A | Fresh Cow Fecal | Wisconsin |
| Farm S | PA57-9 | +- -- | Type A | Calf Fecal | Wisconsin |
| Farm S | PA57-15 | +- -- | Type A | Calf Fecal | Wisconsin |
| Farm S | PA57-16 | +- -- | Type A | Calf Fecal | Wisconsin |
| Farm S | PA57-17 | +- -- | Type A | Calf Fecal | Wisconsin |
| Farm S | PA57-18 | +- -- | Type A | Calf Fecal | Wisconsin |
| Farm S | PA57-19 | +- -- | Type A | Calf Fecal | Wisconsin |
| Farm S | PA57-20 | +- -- | Type A | Calf Fecal | Wisconsin |
| Farm S | PA58-2 | +- -  | Type A | Calf Fecal | Wisconsin |
| Farm S | PA58-3 | +- -- | Type A | Calf Fecal | Wisconsin |
| Farm S | PA58-4 | +- -- | Type A | Calf Fecal | Wisconsin |
| Farm S | PA58-16 | +- -- | Type A | Calf Fecal | Wisconsin |
| Farm S | PA58-17 | +- -- | Type A | Calf Fecal | Wisconsin |
| Farm S | PA58-18 | +- -- | Type A | Calf Fecal | Wisconsin |
| Farm S | PA58-19 | +- -- | Type A | Calf Fecal | Wisconsin |
| Farm S | PA58-20 | +- -- | Type A | Calf Fecal | Wisconsin |
| Farm S | PA59-15 | +- -- | Type A | Calf Fecal | Wisconsin |
| Farm S | PA59-16 | +- -- | Type A | Calf Fecal | Wisconsin |
| Farm S | PA59-17 | +- -- | Type A | Calf Fecal | Wisconsin |
| Farm S | PA59-18 | +- -- | Type A | Calf Fecal | Wisconsin |
| Farm S | PA59-19 | +- -- | Type A | Calf Fecal | Wisconsin |
| Farm S | PA60-1 | +- -- | Type A | Calf Fecal | Wisconsin |
| Farm S | PA60-4 | +- -- | Type A | Calf Fecal | Wisconsin |
| Farm S | PA60-5 | +- -- | Type A | Calf Fecal | Wisconsin |
| Farm S | PA61-1 | +- -- | Type A | Fresh Cow Fecal | Wisconsin |
| Farm S | PA61-2 | +- -- | Type A | Fresh Cow Fecal | Wisconsin |
| Farm S | PA61-4 | +- -- | Type A | Fresh Cow Fecal | Wisconsin |
| Farm S | PA61-10 | +- -- | Type A | Fresh Cow Fecal | Wisconsin |
| Farm S | PA62-6 | +- -- | Type A | Fresh Cow Fecal | Wisconsin |
| Farm S | PA62-12 | +- -- | Type A | Fresh Cow Fecal | Wisconsin |
| Farm S | PA62-15 | +- -- | Type A | Fresh Cow Fecal | Wisconsin |
| Farm S | PA62-16 | +- -- | Type A | Fresh Cow Fecal | Wisconsin |
| Farm S | PA62-17 | +- -- | Type A | Fresh Cow Fecal | Wisconsin |
| Farm S | PA62-18 | +- -- | Type A | Fresh Cow Fecal | Wisconsin |
| Farm S | PA62-19 | +- -- | Type A | Fresh Cow Fecal | Wisconsin |
| Farm S | PA63-1 | +- -- | Type A | Cow Fecal | Wisconsin |
| Farm S | PA63-2 | +- -- | Type A | Cow Fecal | Wisconsin |
| Farm S | PA63-3 | +- -- | Type A | Cow Fecal | Wisconsin |
| Farm S | PA63-4 | +- -- | Type A | Cow Fecal | Wisconsin |
| Farm S | PA63-6 | +- -- | Type A | Cow Fecal | Wisconsin |
| Farm S | PA63-7 | +- -- | Type A | Cow Fecal | Wisconsin |
| Farm S | PA63-8 | +- -- | Type A | Cow Fecal | Wisconsin |
| Farm S | PA63-9 | +- -- | Type A | Cow Fecal | Wisconsin |
| Farm S | PA63-11 | +- -- | Type A | Cow Fecal | Wisconsin |
| Farm S | PA63-12 | +- -- | Type A | Cow Fecal | Wisconsin |
| Farm S | PA63-14 | +- -- | Type A | Cow Fecal | Wisconsin |
| Farm S | PA63-15 | +- -- | Type A | Cow Fecal | Wisconsin |
| Farm S | PA63-20 | +- -- | Type A | Cow Fecal | Wisconsin |
| Farm S | 20.1.1 | +- -- | Type A | Corn Silage | Wisconsin |
| Farm HN | PA74-6 | +- -- | Type A | Fresh Cow Fecal | Wisconsin |

FIG. 38 (Cont.)

| Farm | ID | Type | Source | State |
|---|---|---|---|---|
| Farm S | 20.1.1 | +- - - Type A | Corn Silage | Wisconsin |
| Farm HN | PA74-6 | +- - - Type A | Fresh Cow Fecal | Wisconsin |
| Farm HN | PA74-13 | +- - - Type A | Fresh Cow Fecal | Wisconsin |
| Farm HN | PA74-19 | +- - - Type A | Fresh Cow Fecal | Wisconsin |
| Farm HN | PA76-1 | +- - - Type A | Cow Fecal | Wisconsin |
| Farm HN | PA76-5 | +- - - Type A | Cow Fecal | Wisconsin |
| Farm HN | PA76-15 | +- - - Type A | Cow Fecal | Wisconsin |
| Farm MV | PA80-17 | +- - - Type A | Calf Fecal | Wisconsin |
| Farm MV | PA81-6 | +- - - Type A | Fresh Cow Fecal | Wisconsin |
| Farm MV | PA81-7 | +- - - Type A | Fresh Cow Fecal | Wisconsin |
| Farm MV | PA84-2 | +- - - Type A | Cow Fecal | Wisconsin |
| Farm MV | PA84-4 | +- - - Type A | Cow Fecal | Wisconsin |
| Farm MV | PA84-10 | +- - - Type A | Cow Fecal | Wisconsin |
| Farm MV | PA84-13 | +- - - Type A | Cow Fecal | Wisconsin |
| Farm HN | 28.1.5 | +- - - Type A | Ryelage | Wisconsin |
| Farm WB | BT7-3 | +- - - A | Cow Fecal | Wisconsin |
| Farm WB | BT48-9 | +- - - A | Cow Fecal | Wisconsin |
| Farm WB | BT21-4 | +- - - A | Cow Fecal | Wisconsin |
| Farm BE | PA12-4 | +- - - Type A | Heifer Fecal | Wisconsin |
| Farm BE | PA12-5 | +- - - Type A | Heifer Fecal | Wisconsin |
| Farm BE | PA12-6 | +- - - Type A | Heifer Fecal | Wisconsin |
| Farm BE | PA12-7 | +- - - Type A | Heifer Fecal | Wisconsin |
| Farm BE | PA13-2 | +- - - Type A | Fresh Cow Fecal | Wisconsin |
| Farm BE | PA13-5 | +- - - Type A | Fresh Cow Fecal | Wisconsin |
| Farm BE | PA13-7 | +- - - Type A | Fresh Cow Fecal | Wisconsin |
| Farm BE | PA13-8 | +- - - Type A | Fresh Cow Fecal | Wisconsin |
| Farm BE | PA13-16 | +- - - Type A | Fresh Cow Fecal | Wisconsin |
| Farm BE | PA13-17 | +- - - Type A | Fresh Cow Fecal | Wisconsin |
| Farm BE | PA14-5 | +- - - Type A | Fresh Cow Fecal | Wisconsin |
| Farm BE | PA14-11 | +- - - Type A | Fresh Cow Fecal | Wisconsin |
| Farm BE | PA14-13 | +- - - Type A | Fresh Cow Fecal | Wisconsin |
| Farm BE | PA14-17 | +- - - Type A | Fresh Cow Fecal | Wisconsin |
| Farm BE | PA14-19 | +- - - Type A | Fresh Cow Fecal | Wisconsin |
| Farm BE | PA15-2 | +- - - Type A | Cow Fecal | Wisconsin |
| Farm BE | PA15-6 | +- - - Type A | Cow Fecal | Wisconsin |
| Farm BE | PA15-12 | +- - - Type A | Cow Fecal | Wisconsin |
| Farm WB | PA21-4 | +- - - Type A | Cow Fecal | Wisconsin |
| Farm WB | PA21-6 | +- - - Type A | Cow Fecal | Wisconsin |
| Farm WB | PA21-7 | +- - - Type A | Cow Fecal | Wisconsin |
| Farm WB | PA21-8 | +- - - Type A | Cow Fecal | Wisconsin |
| Farm WB | PA21-12 | +- - - Type A | Cow Fecal | Wisconsin |
| Farm WB | PA21-14 | +- - - Type A | Cow Fecal | Wisconsin |
| Farm WB | PA21-16 | +- - - Type A | Cow Fecal | Wisconsin |
| Farm WB | PA21-17 | +- - - Type A | Cow Fecal | Wisconsin |
| Farm WB | PA21-20 | +- - - Type A | Cow Fecal | Wisconsin |
| Farm WB | PA22-2 | +- - - Type A | Cow Fecal | Wisconsin |
| Farm WB | PA24-1 | +- - - Type A | Cow Fecal | Wisconsin |
| Farm WB | PA24-2 | +- - - Type A | Cow Fecal | Wisconsin |
| Farm WB | PA24-3 | +- - - Type A | Cow Fecal | Wisconsin |
| Farm WB | PA24-4 | +- - - Type A | Cow Fecal | Wisconsin |
| Farm WB | PA24-5 | +- - - Type A | Cow Fecal | Wisconsin |
| Farm WB | PA24-12 | +- - - Type A | Cow Fecal | Wisconsin |
| Farm WB | PA24-18 | +- - - Type A | Cow Fecal | Wisconsin |

FIG. 38 (Cont.)

| | | | | |
|---|---|---|---|---|
| Farm BE | PA14-6 | +--- Type A | Fresh Cow Fecal | Wisconsin |
| Farm BE | PA14-7 | +--- Type A | Fresh Cow Fecal | Wisconsin |
| Farm BE | PA14-16 | +--- Type A | Fresh Cow Fecal | Wisconsin |
| Farm HA | J1-16 | +--- Type A | Cow Fecal | Wisconsin |
| Farm LP | PA38-15 | +--- Type A | Cow Fecal | Wisconsin |
| Farm BA | PA41-14 | +--- Type A | Calf Fecal | Wisconsin |
| Farm GR | PA50-12 | +--- Type A | Calf Fecal | Wisconsin |
| Farm GR | PA50-18 | +--- Type A | Calf Fecal | Wisconsin |
| Farm GR | PA50-19 | +--- Type A | Calf Fecal | Wisconsin |
| Farm GR | PA56-11 | +--- Type A | Fresh Cow Fecal | Wisconsin |
| Farm GR | PA56-12 | +--- Type A | Fresh Cow Fecal | Wisconsin |
| Farm GR | PA56-20 | +--- Type A | Fresh Cow Fecal | Wisconsin |
| Farm S | PA60-2 | +--- Type A | Calf Fecal | Wisconsin |
| Farm S | PA61-5 | +--- Type A | Fresh Cow Fecal | Wisconsin |
| Farm S | PA61-6 | +--- Type A | Fresh Cow Fecal | Wisconsin |
| Farm S | PA61-7 | +--- Type A | Fresh Cow Fecal | Wisconsin |
| Farm S | PA61-8 | +--- Type A | Fresh Cow Fecal | Wisconsin |
| Farm S | 20.3.5 | +--+Type E | Haylage | Wisconsin |
| Farm AD | PA66-10 | +--- Type A | Calf Fecal | Wisconsin |
| Farm HN | PA76-2 | +--- Type A | Cow Fecal | Wisconsin |
| Farm HN | PA76-9 | +--- Type A | Cow Fecal | Wisconsin |
| Farm HN | PA76-10 | +--- Type A | Cow Fecal | Wisconsin |
| Farm WB | BT43-9 | +--- A | Cow Fecal | Wisconsin |
| Farm BE | PA13-3 | +--- Type A | Fresh Cow Fecal | Wisconsin |
| Farm BE | PA13-4 | +--- Type A | Fresh Cow Fecal | Wisconsin |
| Farm BE | PA14-18 | +--- Type A | Fresh Cow Fecal | Wisconsin |
| Farm BE | PA15-3 | +--- Type A | Cow Fecal | Wisconsin |
| Farm BE | PA15-8 | +--- Type A | Cow Fecal | Wisconsin |
| Farm BE | PA15-16 | +--- Type A | Cow Fecal | Wisconsin |
| Farm WB | PA21-3 | +--- Type A | Cow Fecal | Wisconsin |
| Farm WB | PA21-10 | +--- Type A | Cow Fecal | Wisconsin |
| Farm WB | PA21-11 | +--- Type A | Cow Fecal | Wisconsin |
| Farm WB | PA21-18 | +--- Type A | Cow Fecal | Wisconsin |
| Farm WB | PA21-19 | +--- Type A | Cow Fecal | Wisconsin |
| Farm WB | PA22-4 | +--- Type A | Cow Fecal | Wisconsin |
| Farm WB | PA23-7 | +--- Type A | Cow Fecal | Wisconsin |
| Farm WB | PA23-8 | +--- Type A | Cow Fecal | Wisconsin |
| Farm WB | PA23-12 | +--- Type A | Cow Fecal | Wisconsin |
| Farm WB | PA23-15 | +--- Type A | Cow Fecal | Wisconsin |
| Farm WB | PA24-6 | +--- Type A | Cow Fecal | Wisconsin |
| Farm WB | PA24-15 | +--- Type A | Cow Fecal | Wisconsin |
| Farm WB | PA24-7 | +--- Type A | Cow Fecal | Wisconsin |
| Farm CR | G9-13 | +--- Type A | Fresh Cow Fecal | Wisconsin |
| Farm BE | PA14-9 | +--- Type A | Fresh Cow Fecal | Wisconsin |
| Farm BE | PA13-15 | +--- Type A | Fresh Cow Fecal | Wisconsin |
| Farm HA | J3-2 | +--- Type A | Cow Fecal | Wisconsin |
| Farm LP | PA38-17 | +--- Type A | Cow Fecal | Wisconsin |
| Farm G | I8-14 | +--- Type A | Calf Fecal | Wisconsin |
| Farm WB | PA21-1 | +--- Type A | Cow Fecal | Wisconsin |
| Farm WB | PA23-2 | +--- Type A | Cow Fecal | Wisconsin |
| Farm WB | PA23-6 | +--- Type A | Cow Fecal | Wisconsin |
| Farm WB | PA23-11 | +--- Type A | Cow Fecal | Wisconsin |

FIG. 38 (Cont.)

| | | | | |
|---|---|---|---|---|
| Farm WB | PA23-13 | +- - - Type A | Cow Fecal | Wisconsin |
| Farm MI | PA31-5 | +- - - Type A | Cow Fecal | Wisconsin |
| Farm HA | J2-3 | +- - - Type A | Cow Fecal | Wisconsin |
| Farm HA | J2-6 | +- - - Type A | Cow Fecal | Wisconsin |
| Farm MV | PA81-8 | +- - - Type A | Fresh Cow Fecal | Wisconsin |
| Farm MV | PA82-4 | +- - - Type A | Fresh Cow Fecal | Wisconsin |
| Farm HA | J1-8 | +- - - Type A | Cow Fecal | Wisconsin |
| Farm S | PA62-5 | +- - - Type A | Fresh Cow Fecal | Wisconsin |
| Farm MV | PA81-11 | +- - - Type A | Fresh Cow Fecal | Wisconsin |
| Farm MV | PA82-1 | +- - - Type A | Fresh Cow Fecal | Wisconsin |
| Farm MV | PA82-9 | +- - - Type A | Fresh Cow Fecal | Wisconsin |
| Farm MV | PA82-11 | +- - - Type A | Fresh Cow Fecal | Wisconsin |
| Farm MC | F11-19 | +- - - Type A | Milk Cow fecal | Wisconsin |
| Farm Z | E5-4 | +- - - Type A | Calf fecal | Wisconsin |
| Farm Z | E6-19 | +- - - Type A | Milk Cow fecal | Wisconsin |
| Farm CR | G4-6 | +- - - Type A | Milk Cow fecal | Wisconsin |
| Farm CR | G4-15 | +- - - Type A | Milk Cow fecal | Wisconsin |
| Farm R | ROL-3 | +- - - Type A | Haylage | Wisconsin |
| Farm CR | G5-13 | +- - - Type A | Cow Fecal | Wisconsin |
| Farm DE | H1-2 | +- - - Type A | Calf Fecal | Wisconsin |
| Farm DE | H1-4 | +- - - Type A | Calf Fecal | Wisconsin |
| Farm G | I1-9 | +- - - Type A | Cow Fecal | Wisconsin |
| Farm WB | BT11-1 | +- - - A | Cow Fecal | Wisconsin |
| Farm WB | BT11-7 | +- - - A | Cow Fecal | Wisconsin |
| Farm WB | BT11-9 | +- - - A | Cow Fecal | Wisconsin |
| Farm WB | BT13-5 | +- - - A | Cow Fecal | Wisconsin |
| Farm WB | BT13-6 | +- - - A | Cow Fecal | Wisconsin |
| Farm WB | BT14-6 | +- - - A | Cow Fecal | Wisconsin |
| Farm WB | BT15-3 | +- - - A | Cow Fecal | Wisconsin |
| Farm G | I3-19 | +- - - Type A | Cow Fecal | Wisconsin |
| Farm G | I4-9 | +- - - Type A | Cow Fecal | Wisconsin |
| Farm WB | BT15-9 | +- - - A | Cow Fecal | Wisconsin |
| Farm WB | BT19-3 | +- - - A | Cow Fecal | Wisconsin |
| Farm WB | BT19-4 | +- - - A | Cow Fecal | Wisconsin |
| Farm G | I5-15 | +- - - Type A | Cow Fecal | Wisconsin |
| Farm G | I9-2 | +- - - Type A | Cow Fecal | Wisconsin |
| Farm G | I9-3 | +- - - Type A | Cow Fecal | Wisconsin |
| Farm G | I9-5 | +- - - Type A | Cow Fecal | Wisconsin |
| Farm G | I9-7 | +- - - Type A | Cow Fecal | Wisconsin |
| Farm G | I9-9 | +- - - Type A | Cow Fecal | Wisconsin |
| Farm G | I9-10 | +- - - Type A | Cow Fecal | Wisconsin |
| Farm CR | G9-20 | +- - - Type A | Fresh Cow Fecal | Wisconsin |
| Farm DE | H7-10 | +- - - Type A | Dry Cow Fecal | Wisconsin |
| Farm DE | H10-9 | +- - - Type A | Cow Fecal | Wisconsin |
| Farm DE | H10-10 | +- - - Type A | Cow Fecal | Wisconsin |
| Farm DE | H10-19 | +- - - Type A | Cow Fecal | Wisconsin |
| Farm G | I7-4 | +- - - Type A | Calf Fecal | Wisconsin |
| Farm G | I9-12 | +- - - Type A | Cow Fecal | Wisconsin |
| Farm G | I9-13 | +- - - Type A | Cow Fecal | Wisconsin |
| Farm G | I9-14 | +- - - Type A | Cow Fecal | Wisconsin |
| Farm G | I9-20 | +- - - Type A | Cow Fecal | Wisconsin |
| Farm BE | PA11-7 | +- - - Type A | Heifer Fecal | Wisconsin |
| Farm BE | PA11-9 | +- - - Type A | Heifer Fecal | Wisconsin |

FIG. 38 (Cont.)

| Farm | ID | Type | Source | State |
|---|---|---|---|---|
| Farm G | I9-20 | + - - - Type A | Cow Fecal | Wisconsin |
| Farm BE | PA11-7 | + - - - Type A | Heifer Fecal | Wisconsin |
| Farm BE | PA11-9 | + - - - Type A | Heifer Fecal | Wisconsin |
| Farm BE | PA11-16 | + - - - Type A | Heifer Fecal | Wisconsin |
| Farm WB | PA22-1 | + - - - Type A | Cow Fecal | Wisconsin |
| Farm MI | PA31-14 | + - - - Type A | Cow Fecal | Wisconsin |
| Farm MI | PA31-15 | + - - - Type A | Cow Fecal | Wisconsin |
| Farm MI | PA32-9 | + - - - Type A | Cow Fecal | Wisconsin |
| Farm HA | J1-14 | - - - + Unidentified | Cow Fecal | Wisconsin |
| Farm HA | J2-4 | + - - - Type A | Cow Fecal | Wisconsin |
| Farm WB | BT31-2 | + - - - A | Cow Fecal | Wisconsin |
| Farm WB | BT18-10 | + - - - A | Cow Fecal | Wisconsin |
| Farm WB | BT21-1 | + - - - A | Cow Fecal | Wisconsin |
| Farm WB | BT14-1 | + - - - A | Cow Fecal | Wisconsin |
| Farm WB | BT18-1 | + - - - A | Cow Fecal | Wisconsin |
| Farm WB | BT19-6 | + - - - A | Cow Fecal | Wisconsin |
| Farm WB | BT31-1 | + - - - A | Cow Fecal | Wisconsin |
| Farm MC | F11-15 | + - - - Type A | Milk Cow fecal | Wisconsin |
| Farm AL | PA3-1 | + - - - Type A | Calf Fecal | Wisconsin |
| Farm DE | H10-4 | + - - - Type A | Cow Fecal | Wisconsin |
| Farm DE | H10-5 | + - - - Type A | Cow Fecal | Wisconsin |
| Farm DE | H7-1 | + - - - Type A | Dry Cow Fecal | Wisconsin |
| Farm DE | H7-5 | + - - - Type A | Dry Cow Fecal | Wisconsin |
| Farm G | I1-10 | + - - - Type A | Cow Fecal | Wisconsin |
| Farm G | I2-2 | + - - - Type A | Cow Fecal | Wisconsin |
| Farm G | I2-5 | + - - - Type A | Cow Fecal | Wisconsin |
| Farm G | I2-6 | + - - - Type A | Cow Fecal | Wisconsin |
| Farm G | I2-8 | + - - - Type A | Cow Fecal | Wisconsin |
| Farm G | I2-13 | + - - - Type A | Cow Fecal | Wisconsin |
| Farm G | I2-15 | + - - - Type A | Cow Fecal | Wisconsin |
| Farm G | I2-20 | + - - - Type A | Cow Fecal | Wisconsin |
| Farm WB | BT11-5 | + - - - A | Cow Fecal | Wisconsin |
| Farm WB | BT14-8 | + - - - A | Cow Fecal | Wisconsin |
| Farm WB | BT36-5 | + - - - A | Cow Fecal | Wisconsin |
| Farm WB | BT35-6 | + - - - A | Cow Fecal | Wisconsin |
| Farm G | I5-19 | + - - - Type A | Cow Fecal | Wisconsin |
| Farm AL | PA3-6 | + - - - Type A | Calf Fecal | Wisconsin |
| Farm MC | F11-7 | + - - - Type A | Milk Cow fecal | Wisconsin |
| Farm ME | D5-11 | + - - - Type A | Calf fecal | Wisconsin |
| Farm ME | D9-16 | + - - - Type A | Milk Cow fecal | Wisconsin |
| Farm WB | BT7-10 | + - - - A | Cow Fecal | Wisconsin |
| Farm WB | BT11-2 | + - - - A | Cow Fecal | Wisconsin |
| Farm WB | BT11-3 | + - - - A | Cow Fecal | Wisconsin |
| Farm WB | BT11-6 | + - - - A | Cow Fecal | Wisconsin |
| Farm WB | BT11-10 | + - - - A | Cow Fecal | Wisconsin |
| Farm WB | BT14-3 | + - - - A | Cow Fecal | Wisconsin |
| Farm WB | BT14-7 | + - - - A | Cow Fecal | Wisconsin |
| Farm WB | BT15-2 | + - - - A | Cow Fecal | Wisconsin |
| Farm WB | BT31-3 | + - - - A | Cow Fecal | Wisconsin |
| Farm G | I4-5 | + - - - Type A | Cow Fecal | Wisconsin |
| Farm WB | BT17-10 | + - - - A | Cow Fecal | Wisconsin |
| Farm G | I5-3 | + - - - Type A | Cow Fecal | Wisconsin |

FIG. 39

| | | | |
|---|---|---|---|
| | | Clostridium botulinum ATCC 25763(T) | Clostridium sporogenes group |
| | | Clostridium sporogenes DSM 795(T) | Clostridium sporogenes group |
| | | Clostridium cochlearium ATCC 17787(T) | Clostridium cochlearium |
| | | Clostridium subterminale ATCC 25774(T) | Clostridium subterminale group |
| | | Clostridium thiosulfatireducens LUP 21(T) | Clostridium subterminale group |
| | | Clostridium subterminale DSM 6970(T) | Clostridium subterminale group |
| Farm MI | C134-27F | Clostridium subterminale group | Calf Fecal |
| | | Clostridium sulfidigenes SGB2(T) | Clostridium subterminale group |
| Farm MV | C174-27F | Clostridium subterminale group | Calf Fecal |
| Farm MV | PA80-1-27F | <Undetermined> | Calf Fecal |
| Farm MV | PA80-20-27F | <Undetermined> | Calf Fecal |
| | | Clostridium vulturis YMB-57(T) | Clostridium vulturis |
| | | Clostridium argentinense ATCC 27322(T) | Clostridium argentinense |
| Farm HN | C171-27F | Clostridium senegalense | Cow Fecal |
| | | Clostridium senegalense JC122(T) | Clostridium senegalense |
| Farm WB | BT5-5-27F | Clostridium senegalense | Cow Fecal |
| | | Clostridium aciditolerans JW/YJL-B3(T) | Clostridium aciditolerans group |
| | | Clostridium nitrophenolicum 1D(T) | Clostridium aciditolerans group |
| | | Clostridium magnum DSM 2767(T) | Clostridium magnum |
| Farm GR | C157-27F | Clostridium cadaveris | Calf Fecal |
| Farm CH | PA91-6-27F | Clostridium cadaveris | Calf Fecal |
| Farm CR | G2-1-27F | Clostridium cadaveris | Calf Fecal |
| Farm CR | G2-3-27F | Clostridium cadaveris | Calf Fecal |
| Farm AD | PA65-4-27F | Clostridium cadaveris | Calf Fecal |
| | | Clostridium cadaveris JCM 1392(T) | Clostridium cadaveris |
| Farm GR | C155-27F | Clostridium cadaveris | Calf Fecal |
| Farm GR | PA51-19-27F | Clostridium cadaveris | Calf Fecal |
| Farm CR | G2-4-27F | Clostridium cadaveris | Calf Fecal |
| Farm GR | PA49-20-27F | Clostridium cadaveris | Calf Fecal |
| Farm LP | PA36-11-27F | Clostridium paraputrificum | Calf Fecal |
| Farm LP | PA36-5-27F | Clostridium paraputrificum | Calf Fecal |
| Farm LP | PA36-6-27F | Clostridium paraputrificum | Calf Fecal |
| Farm BA | PA41-10-27F | Clostridium paraputrificum | Calf Fecal |
| Farm WB | BT12-8-27F | Clostridium paraputrificum | Cow Fecal |
| Farm BA | PA41-18-27F | Clostridium paraputrificum | Calf Fecal |
| Farm R | C116-27F | Clostridium paraputrificum | Calf Fecal |
| | | Clostridium paraputrificum DSM 2630(T) | Clostridium paraputrificum |
| Farm HN | C166-27F | Clostridium paraputrificum | Calf Fecal |
| | | Clostridium vincentii DSM 10228(T) | Clostridium vincentii |
| | | Clostridium aurantibutyricum NCIMB 1065 | Clostridium aurantibutyricum |
| | | Clostridium baratii ATCC 27638(T) | Clostridium sardiniense group |
| | | Clostridium sardiniense DSM 2632(T) | Clostridium sardiniense group |
| | | Eubacterium multiforme JCM 6484(T) | Clostridium sardiniense group |
| | | Eubacterium moniliforme ATCC 25546(T) | Eubacterium moniliforme |
| Farm S | C-49 | Clostridium celatum group | Haylage |
| | | Clostridium disporicum DSM 5521(T) | Clostridium celatum group |
| | | Clostridium celatum SJTU_D_05_03 | Clostridium celatum group |
| Farm G | I5-17-27F | Clostridium celatum group | Cow Fecal |
| Farm G | I5-18-27F | Clostridium celatum group | Cow Fecal |
| Farm WB | BT43-1-27F | Clostridium celatum group | Cow Fecal |

16S scale: 85, 90, 95, 100

FIG. 39 (Cont.)

| | | |
|---|---|---|
| Farm G    I5-18-27F | Clostridium celatum group | Cow Fecal |
| Farm WB   BT43-1-27F | Clostridium celatum group | Cow Fecal |
| Farm LP   C144-27F | Clostridium celatum group | Cow Fecal |
| Farm LP   PA38-7-27F | Clostridium celatum group | Cow Fecal |
| Farm Z    C104-27F | Clostridium tertium group | Cow Fecal |
| Farm HN   PA71-16-27F | Clostridium tertium group | Calf Fecal |
| Farm AD   PA68-17-27F | Clostridium tertium group | Cow Fecal |
| Farm MI   C136-27F | Clostridium tertium group | Cow Fecal |
| Farm HN   C164-27F | Clostridium tertium group | Calf Fecal |
| Farm MI   PA29-6-27F | Clostridium tertium group | Cow Fecal |
| Farm G    I4-2-27F | Clostridium tertium group | Cow Fecal |
| Clostridium sartagoforme DSM 1292(T) | Clostridium tertium group | |
| Farm MI   C137-27F | Clostridium tertium group | Cow Fecal |
| Farm MV   C-63 | Clostridium tertium group | Haylage |
| Clostridium tertium DSM 2485(T) | Clostridium tertium group | |
| Farm BA   PA42-20-27F | Clostridium tertium group | Calf Fecal |
| Farm BA   C148-27F | Clostridium tertium group | Calf Fecal |
| Farm AD   PA66-12-27F | Clostridium tertium group | Calf Fecal |
| Farm CW   C178-27F | Clostridium tertium group | Cow Fecal |
| Farm WB   C-1 | Clostridium tertium group | Haylage |
| Farm MV   C-62 | Clostridium tertium group | Haylage |
| Farm MV   PA78-5-27F | Clostridium tertium group | Calf Fecal |
| Farm MV   C-71 | Clostridium tertium group | Oatlage |
| Farm MV   C173-27F | <Undetermined> | Calf Fecal |
| Farm HN   C-76 | <Undetermined> | Ryelage |
| Farm AD   PA67-15-27F | Clostridium tertium group | Cow Fecal |
| Clostridium septicum ATCC 12464(T) | Clostridium septicum | |
| Clostridium carnis ATCC 25777(T) | Clostridium carnis | |
| Clostridium quinii DSM 6736(T) | Clostridium quinii | |
| Clostridium isatidis WV6(T) | Clostridium isatidis | |
| Clostridium intestinale Catt39 | Clostridium intestinale | |
| Clostridium frigidicarnis SPL77A(T) | Clostridium frigidicarnis | |
| Farm CW   C-88 | <Undetermined> | Corn Silage. |
| Farm CW   C-92 | Clostridium butyricum | Corn Silage. |
| Farm CW   C-91 | <Undetermined> | Corn Silage. |
| Farm CW   C-90 | Clostridium butyricum | Corn Silage. |
| Farm CW   C-86 | Clostridium butyricum | Corn Silage. |
| Farm WB   BT31-5-27F | <Undetermined> | Cow Fecal |
| Clostridium puniceum DSM 2619(T) | Clostridium beijerinckii group | |
| Clostridium saccharoperbutylacetonicum N. | Clostridium beijerinckii group | |
| Clostridium saccharobutylicum DSM 13864. | Clostridium beijerinckii group | |
| Clostridium chromiireducens GCAF-1(T) | Clostridium beijerinckii group | |
| Farm MC   F8-12-27F | Clostridium butyricum | Calf Fecal |
| Farm BE   PA9-17-27F | Clostridium butyricum | Calf Fecal |
| Farm BA   C147-27F | Clostridium butyricum | Calf Fecal |
|

FIG. 39 (Cont.)

| | | | |
|---|---|---|---|
| Farm LP | C141-27F | Clostridium butyricum | Calf Fecal |
| Farm GR | PA52-9-27F | Clostridium butyricum | Calf Fecal |
| Farm LP | PA33-6-27F | Clostridium butyricum | Calf Fecal |
| Farm BA | PA42-5-27F | Clostridium butyricum | Calf Fecal |
| Farm WB | BT28-10-27F | Clostridium butyricum | Cow Fecal |
| Farm DE | H9-5-27F | Clostridium butyricum | Cow Fecal |
| Farm ME | D5-19-27F | Clostridium butyricum | Calf Fecal |
| Farm AD | C161-27F | Clostridium butyricum | Calf Fecal |
| Farm GR | PA52-17-27F | Clostridium butyricum | Calf Fecal |
| Farm CR | C106-27F | Clostridium butyricum | Calf Fecal |
| Farm S | C159-27F | Clostridium butyricum | Cow Fecal |
| | Clostridium butyricum DSM 10702(T) | Clostridium butyricum | |
| Farm CR | G6-5-27F | Clostridium butyricum | Calf Fecal |
| Farm GR | C156-27F | Clostridium butyricum | Calf Fecal |
| Farm BE | C120-27F | Clostridium butyricum | Calf Fecal |
| Farm MI | PA26-10-27F | Clostridium butyricum | Calf Fecal |
| Farm BA | C150-27F | Clostridium butyricum | Calf Fecal |
| Farm WB | BT25-9-27F | Clostridium beijerinckii group | Cow Fecal |
| Farm WB | BT33-3-27F | Clostridium beijerinckii group | Cow Fecal |
| Farm BA | C151-27F | Clostridium beijerinckii group | Cow Fecal |
| Farm CW | PA86-4-27F | Clostridium beijerinckii group | Cow Fecal |
| Farm BA | PA44-1-27F | Clostridium beijerinckii group | Calf Fecal |
| Farm HN | PA70-12-27F | Clostridium beijerinckii group | Calf Fecal |
| Farm HN | PA69-15-27F | Clostridium beijerinckii group | Calf Fecal |
| Farm WB | BT30-2-27F | Clostridium beijerinckii group | Cow Fecal |
| Farm WB | BT39-3-27F | Clostridium beijerinckii group | Cow Fecal |
| Farm AD | C163-27F | Clostridium beijerinckii group | Cow Fecal |
| Farm WB | BT30-3-27F | Clostridium beijerinckii group | Cow Fecal |
| | Clostridium beijerinckii NCIMB 8052(T) | Clostridium beijerinckii group | |
| Farm WB | BT26-1-27F | Clostridium beijerinckii group | Cow Fecal |
| Farm WB | BT2-9-27F | Clostridium beijerinckii group | Cow Fecal |
| Farm BA | C153-27F | Clostridium beijerinckii group | Cow Fecal |
| Farm WB | BT30-9-27F | Clostridium beijerinckii group | Cow Fecal |
| Farm HN | C167-27F | Clostridium beijerinckii group | Calf Fecal |
| Farm LP | C143-27F | Clostridium beijerinckii group | Cow Fecal |
| Farm HN | C169-27F | Clostridium beijerinckii group | Cow Fecal |
| Farm CW | C-85 | Clostridium beijerinckii group | Corn Silage |
| Farm WB | BT9-9-27F | Clostridium beijerinckii group | Cow Fecal |
| Farm HN | PA70-20-27F | Clostridium beijerinckii group | Calf Fecal |
| Farm WB | BT31-3-27F | Clostridium beijerinckii group | Cow Fecal |
| Farm LP | C146-27F | Clostridium beijerinckii group | Cow Fecal |
| Farm G | I3-18-27F | Clostridium beijerinckii group | Cow Fecal |
| Farm LP | PA40-1-27F | Clostridium beijerinckii group | Cow Fecal |
| Farm WB | BT38-9-27F | Clostridium beijerinckii group | Cow Fecal |
| Farm WB | BT44-3-27F | Clostridium beijerinckii group | Cow Fecal |
| Farm WB | BT37-1-27F | Clostridium beijerinckii group | Cow Fecal |
| Farm BA | PA46-1-27F | Clostridium beijerinckii group | Cow Fecal |
| | Clostridium diolis DSM 5431(T) | Clostridium beijerinckii group | |
| Farm WB | BT49-5-27F | Clostridium beijerinckii group | Cow Fecal |
| Farm WB | BT29-1-27F | Clostridium beijerinckii group | Cow Fecal |
| Farm BA | C152-27F | Clostridium beijerinckii group | Cow Fecal |
| Farm WB | BT47-7-27F | Clostridium beijerinckii group | Cow Fecal |
| Farm BA | PA48-2-27F | Clostridium beijerinckii group | Cow Fecal |

FIG. 39 (Cont.)

| | | | |
|---|---|---|---|
| Farm BA | C152-27F | Clostridium beijerinckii group | Cow Fecal |
| Farm WB | BT47-7-27F | Clostridium beijerinckii group | Cow Fecal |
| Farm BA | PA48-2-27F | Clostridium beijerinckii group | Cow Fecal |
| | Clostridium neonatale LCDC no.99-A-005 | ############################. | ########. |
| Farm BE | C125-27F | Clostridium uliginosum group | Cow Fecal |
| Farm BE | PA16-2-27F | Clostridium uliginosum group | Cow Fecal |
| Farm GR | PA52-10-27F | Clostridium uliginosum group | Calf Fecal |
| | Clostridium uliginosum CK55(T) | Clostridium uliginosum group | |
| Farm G | I7-14-27F | Clostridium colicanis | Calf Fecal |
| Farm G | I7-6-27F | Clostridium colicanis | Calf Fecal |
| | Clostridium colicanis DSM 13634(T) | Clostridium colicanis | |
| Farm CW | C177-27F | Clostridium perfringens | Cow Fecal |
| Farm CW | C180-27F | Clostridium perfringens | Cow Fecal |
| Farm CW | C181-27F | Clostridium perfringens | Cow Fecal |
| Farm CW | C182-27F | Clostridium perfringens | Cow Fecal |
| Farm CW | C183-27F | Clostridium perfringens | Cow Fecal |
| Farm S | PA62-9-27F | Clostridium perfringens | Cow Fecal |
| Farm BE | C122-27F | Clostridium perfringens | Cow Fecal |
| Farm MC | F9-19-27F | Clostridium perfringens | Cow Fecal |
| Farm ME | D9-3-27F | Clostridium perfringens | Cow Fecal |
| Farm MV | C-68 | Clostridium perfringens | Oatlage |
| Farm CW | C179-27F | Clostridium perfringens | Cow Fecal |
| Farm HA | C140-27F | Clostridium perfringens | Cow Fecal |
| Farm MV | C-69 | Clostridium perfringens | Oatlage |
| Farm CR | G10-18-27F | Clostridium perfringens | Cow Fecal |
| Farm MV | C176-27F | Clostridium perfringens | Cow Fecal |
| Farm AD | PA66-20-27F | Clostridium perfringens | Calf Fecal |
| | Clostridium perfringens ATCC 13124(T) | Clostridium perfringens | |
| Farm LP | PA38-3-27F | Clostridium perfringens | Cow Fecal |
| Farm CW | PA85-11-27F | Clostridium perfringens | Cow Fecal |
| Farm CR | G4-4-27F | Clostridium perfringens | Cow Fecal |
| Farm G | I8-19-27F | Clostridium perfringens | Cow Fecal |
| Farm G | I8-16-27F | Clostridium perfringens | Cow Fecal |
| Farm LP | C142-27F | Terrisporobacter | Calf Fecal |
| Farm MC | F1_3_18-27F | Terrisporobacter | Calf Fecal |
| Farm MC | F1_1_2-27F | Terrisporobacter | Calf Fecal |
| Farm MC | F2_3_7-27F | Terrisporobacter | Calf Fecal |
| Farm OO | Oost_CS-2-27F | Terrisporobacter | Corn Silage |
| Farm MC | F1_3_14-27F | Terrisporobacter | Calf Fecal |
| Farm MC | F1_2_14-27F | <Undetermined> | Calf Fecal |
| | Terrisporobacter glycolicus DSM 1288(T) | Terrisporobacter | |
| | Terrisporobacter mayombei DSM 6539(T) | Terrisporobacter | |
| | Peptoclostridium difficile JCM 1296 | Clostridium difficile | |
| | Clostridium ghonii NCIMB 10636(T) | Clostridium sordellii group | |
| | Eubacterium tenue DSM 20695(T) | Clostridium sordellii group | |
| Farm HN | C-75 | Clostridium sordellii group | Corn Silage |
| Farm HN | PA74-16-27F | Clostridium sordellii group | Cow Fecal |
| Farm HN | C170-27F | Clostridium sordellii group | Cow Fecal |
| Farm WB | PA24-8-27F | Clostridium sordellii group | Cow Fecal |
| Farm HN | PA74-3-27F | Clostridium sordellii group | Cow Fecal |
| Farm MC | F8-13-27F | Clostridium sordellii group | Calf Fecal |
| | Clostridium sordellii ATCC 9714(T) | Clostridium sordellii group | |

BACILLUS COMPOSITIONS AND METHODS OF USE WITH RUMINANTS

CROSS-REFERENCE TO RELATED APPLICATIONS

This application claims priority to U.S. Provisional Patent Application No. 62/341,332 filed May 25, 2016, the entirety of which is incorporated by reference herein.

FIELD OF THE DISCLOSURE

The disclosure relates to compositions and methods of *Bacillus* strains. In one embodiment, the disclosure relates to *Bacillus* strains, compositions and methods for controlling the growth of microorganisms, for example in a feed or fodder. In one embodiment, the disclosure relates to *Bacillus* strains, compositions and methods for improving performance of an animal; and more particularly relates to a *Bacillus* strain based direct fed microbial for improving performance of a ruminant

BACKGROUND

Organisms of the genus *Clostridium* are gram-positive, anaerobic, endospore-forming bacteria. *Clostridium* are normal inhabitants of the soil and intestinal tract of animals including dairy cows and calves. Many species are ubiquitous on dairy farms commonly found in haylage, corn silage, straw, manure, colostrum and cattle bedding material. *Clostridium* growth is limited in fermented forages by reducing the pH to less than 5.0 but the organisms may survive for an extended period even in well fermented forages.

There are over 100 species of *Clostridium* recognized, some of which are known to cause enteric disease while others are nonpathogenic with a broad range of enzymatic function and industrial uses. The species recognized to cause enteric disease in animals include *C. perfringens, C. septicum, C. sordellii* and *C. botulinum*. Examples of diseases caused by these organisms include necrotic enteritis, hemorrhagic bowel syndrome (HBS), malignant edema, abomasal disease and botulism.

*C. perfringens*-mediated diseases are a significant cause of economic loss to livestock industries. In dairy production, HBS is among the leading causes of digestive deaths and was reported to be responsible for at least 2% of the deaths of dairy animals in a survey conducted in 2000 in the US (Baker 2002). In more recent times, the incidence of HBS is thought to be increasing but additional estimates of incidence are unavailable because there is a marked seasonality to the disease, symptoms mimic common ruminant digestive diseases and a large proportion of afflicted cattle are not submitted for necropsy.

HBS was first reported in 1991, observed in five high-producing Holstein cows from one dairy in Idaho (Sockett, 2004). Symptoms included point-source sub-mucosal hematomas, each affecting 10-20 cm of the jejunum. One of the five cows exhibited a ruptured hematoma with exsanguination into the lumen of the jejunum. Common symptoms of HBS include a sudden drop in milk production, abdominal pain due to obstructed bowel and anemia (Anderson, 2002). Clinical signs of the disease are decreased feed intake, depression, decreased milk production, dehydration, abdominal distension and dark clotted blood in the feces (Dennison et al., 2002). Death comes within 48 hours from the onset of the obstructing blood clot plug.

Although *Aspergillus fumigatus* and *Clostridium perfringens* are known to be involved in the etiology of HBS (Ceci et al., 2006; Dennison et al., 2005), the syndrome is better described as being poly-microbial and multi-factorial in nature. Increased consumption of a high-energy diet seems to be the most plausible common pathway for all the risk factors that have been described (Berghaus et al., 2005).

In addition to *Clostridium* species causing enteric disease, other *Clostridium* species isolated from rumen fluid and fecal samples of dairy cows are species known to produce high levels of acetone, butanol, 1,3 propanediol and butyric acid as end products of their metabolism. These metabolic end products are known to inhibit rumen and gastrointestinal bacteria and can affect rumen and digestive function and decrease efficiency. If present in the silage these organisms can reduce nutritional value of the crop.

Due to the sporadic, acute etiology of enteric clostridial infections therapeutic treatments are not known to be highly efficacious. Therefore, prophylactic strategies such as the use of probiotics to control clostridial proliferation in the GI tract are the preferred direction for disease control. Non-toxigenic clostridial challenges can also be controlled using probiotics. In accordance with one aspect of the present invention, inventors have conducted a search for an effective probiotic capable of inhibiting a broad range of pathogenic and non-pathogenic clostridia species. Over eons, *Bacillus* have competed with clostridia in the soil ecosystem. Through this process, certain strains of the genus *Bacillus* have developed effective mechanisms for inhibiting clostridia species. In accordance with one aspect of the present invention, the inventors have isolated and identified several strains of *Bacillus* capable of inhibiting a broad spectrum of clostridia that impact ruminant productivity. The predominant bacteriocins produced by bacilli are a variety of functionally and structurally diverse peptides. They are often hydrophobic and cyclic with unusual amino acids and resistant to peptidases and proteases. They may be synthesized ribosomally or nonribosomally by multi-enzyme complexes, often followed by post-translational modifications. *Bacillus* strains often produce nonribosomally synthesized lipopeptides, fatty acids attached to small cyclic peptides. These nonribosomally synthesized peptides are structurally diverse (Luo et al., 2015a), as they are assembled from a heterogeneous group of precursors, but their synthesis by a multicarrier thiotemplate mechanism is conserved (Luo et al., 2015b).

Silage is a significant source of clostridial organisms in ruminant production systems. Silage and forages can support the growth of a variety of spoilage microorganisms, such as clostridia, bacilli, yeasts and molds that contribute to the degradation of nutrient value. Because of the many variables that prevent ideal conditions for preserving silage, lactic acid bacteria are often utilized as silage inoculates to promote proper fermentation and optimal preservation of silage. Lactic acid bacteria grow quickly in anaerobic conditions and become the dominant microorganisms present in the crop, and lower the pH through the production of lactic acid. Although coliforms and molds are inhibited by lowering the pH to less than pH 5, clostridia are more difficult to control with low pH as they can survive even at pHs less than 5.0. Therefore, traditional lactic acid bacteria silage inoculates are not completely effective at controlling clostridia in silage.

Controlling clostridia organisms in silage is important to prevent the detrimental effects these bacteria have on silage quality and ruminant performance. Clostridia activity in silage is undesirable due to the reduced intake observed in cattle when the clostridia activity is present and because of the reduced nutritional quality of the silage that results from clostridia fermentation. The fermentation of lactic acid to butyric acid by the butyrate producing clostridia results in approximately 50% loss in dry matter and 18% loss in gross energy from the silage feedstuff (McDonald et al., 1991). Furthermore, clostridia spoilage organisms have a detrimental effect on the health of the cattle as evidenced by greater incidence of acidosis when cattle are fed clostridial silage (Seglar, 2003).

Although bacilli are considered silage spoilage organisms, some members of the *Bacillus* genera are known to produce antimicrobial compounds capable controlling the growth and survival of clostridia (Hong et al., 2005). Bacilli can result in accelerating the spoilage of silage following exposure to oxygen, but rarely impact fermentation of the crop under the anaerobic conditions of the silo (Muck, 2010). Therefore, *Bacillus* organisms could be used at the time of ensiling to control the growth of clostridia spoilage organisms. *Bacillus* strains identified in one embodiment of the present invention, produce multiple compounds with inhibitory activity against a wide variety of clostridia.

*Bacillus* strains impact the overall ecology of the rumen and intestinal tract by inhibiting the clostridia that produce non-nutritional end-products such as acetone and butanol, which can negatively impact rumen function. The activity of *Bacillus* strains reduces not only the levels, but also the overall diversity of *C. perfringens* and non-toxigenic clostridia.

The immunomodulatory activities attributed to *Bacillus* strains used as probiotics is one of many ways in which they contribute to overall health and well-being (reviewed by Hong et al., 2005). *Bacillus* spores have been reported to pass into the intestinal Peyer's patches and mesenteric lymph nodes following oral administration, and to be phagocytosed by macrophages in vitro studies (Duc et al., 2003, 2004). The oral administration of *B. subtilis* induced production of the cytokine, interferon-X, by mononuclear cells in the blood (Kosaka et al., 1998), indicating *Bacillus* elicit a systemic effect as well as a local effect at the intestinal level. Furthermore, an increase in the messenger RNA expression of toll-like receptor (TLR)-2 and TLR-4 in the intestinal jejunum and ileum was observed following administration to broiler chickens as well as members of the downstream TLR signaling pathway. MyD88, TRAF6 and NF-κB (Rajput et al., 2017).

*Bacillus* strains have a number of activities that make them efficacious as direct-fed microbials including the production of extracellular enzymes, antimicrobials and immune modulating molecules. In addition, *Bacillus* form endospores that make them stable in feed and other feed components. These spores are heat resistant and thus will survive normal feed pelleting processes. The spores are recalcitrant to drying and mineral salts making them stable in vitamin and trace mineral premixes.

Both in vitro data and in vivo trials indicate the effectiveness of these *Bacillus* strains in inhibiting clostridia, such as *C. perfringens*, thereby decreasing the disease-burden in commercial dairy operations. These same trials have demonstrated the effectiveness of the *Bacillus* strains to inhibit non-toxigenic clostridia capable of producing inhibitory metabolites. These strains are now available as probiotics for improving dairy productivity and reducing digestive disease in cattle.

BRIEF SUMMARY

The inventors have developed a direct fed microbial composition comprising an isolated *Bacillus* strain for use in reducing a *Clostridium* in a digestive system of a ruminant having ingested an effective amount of said direct fed microbial composition, wherein the isolated *Bacillus* strain selected from the group consisting of: *Bacillus subtilis* 1104, *Bacillus subtilis* 1781, *Bacillus subtilis* 747, *Bacillus subtilis* 1541, *Bacillus subtilis* 1999, and *Bacillus subtilis* 2018.

In one aspect of the invention, a direct fed microbial composition may inhibit a clostridia selected from a group consisting of: *Clostridium perfringens, Clostridium bifermentans, Clostridium beijerinckii, Clostridium butyricum, Clostridium tertium*, and *Clostridium sordellii.*

In one aspect of the invention, wherein the *Clostridium* is *Clostridium bifermentans*, the isolated *Bacillus* strain may inhibit the production of 1, 3-propanediol in the digestive system of the ruminant having ingested an effective amount of said direct fed microbial composition.

In one aspect of the invention, wherein the *Clostridium* is *Clostridium beijerinckii*, the isolated *Bacillus* strain may inhibit the production of butanol in the digestive system of the ruminant having ingested an effective amount of said direct fed microbial composition.

In one aspect of the invention, wherein the *Clostridium* is *Clostridium beijerinckii*, the isolated *Bacillus* strain may inhibit the production of acetone in the digestive system of the ruminant having ingested an effective amount of said direct fed microbial composition.

In one aspect of the invention, wherein the *Clostridium* is *Clostridium butyricum*, the isolated *Bacillus* strain may inhibit the production of butyrate in the digestive system of the ruminant having ingested an effective amount of said direct fed microbial composition.

In one aspect of the invention, wherein the *Clostridium* is *Clostridium perfringens*, the isolated *Bacillus* strain may reduce the occurrence of a digestive disorder such as hemorrhagic bowel syndrome in the ruminant having ingested an effective amount of said direct fed microbial composition.

In one aspect of the invention, the direct fed microbial composition may further comprise a cryoprotectant disposed about the isolated *Bacillus* strain, and wherein said isolated *Bacillus* strain is a biologically pure, powdered lyophilized strain.

In one aspect of the invention, the direct fed microbial composition may be a biologically pure, powdered lyophilized *Bacillus* strain that comprises *Bacillus* spores.

In one aspect of the invention, the direct fed microbial composition may further comprising a carrier.

In one aspect of the invention, the effective amount of the direct fed microbial composition ingested by the ruminant per day may comprise a concentration of the isolated *Bacillus* strain of between about $2\times10^8$ CFU/ruminant and about $2.0\times10^{10}$ CFU/ruminant.

In one aspect of the invention, the effective amount of the direct fed microbial composition ingested by the ruminant per day may comprise a concentration of the isolated *Bacillus* strain of about $2\times10^9$ CFU/ruminant.

In another aspect of the invention, a method of improving ruminant performance is provided, comprising the steps of introducing into the digestive system of one or more ruminants an effective amount of the direct fed microbial composition according to claim 1, and providing at least one benefit chosen from: (1) inhibiting a pathogen chosen from at least one of *Clostridium perfringens, Clostridium bifermentans, Clostridium beijerinckii, Clostridium butyricum, Clostridium tertium*, and *Clostridium sordellii*. in the one or more ruminants; (2) decreasing a mortality rate of the one or more ruminants; (3) improving the feed efficiency of the one or more ruminants; (4) reducing the occurrence of hemorrhagic bowel syndrome in the one or more ruminants; (5) improve rumen fermentation in the one or more ruminants; (6) improve milk production in the one or more ruminants; and, (7) modulating immune responses of inflammatory cytokines in systemic and intestinal immune cells in the one or more ruminants.

In another aspect of the invention, the method of administering the direct fed microbial composition may provide the benefit of decreasing diversity of *Clostridium perfringens* strains in the one or more ruminants.

In another aspect of the invention, the method of administering the direct fed microbial composition may provide the benefit of decreasing diversity of non-toxigenic clostridial strains in the one or more ruminants.

In another aspect of the invention, the method of administering the direct fed microbial composition may provide the benefit of increasing average energy corrected milk production in the one or more ruminants when the one or more ruminants are dairy cows.

In another aspect of the invention, the method of administering the direct fed microbial composition may provide the benefit of decreasing a digestive system related mortality rate of the one or more ruminants during a period of direct fed microbial administration.

In another aspect of the invention, the method of administering the direct fed microbial composition may include adding the direct fed microbial composition to a ruminant feed.

In another aspect of the invention, the inventors have developed a cryoprotectant disposed about a powdered lyophilized isolated *Bacillus* strain of spores chosen from at least one of: *Bacillus subtilis* 1104, *Bacillus subtilis* 1781, *Bacillus subtilis* 747, *Bacillus subtilis* 1541, *Bacillus subtilis* 1999, and *Bacillus subtilis* 2018; and a carrier, wherein the composition may inhibit at least one pathogen selected from: *Clostridium perfringens*, *Clostridium bifermentans*, *Clostridium beijerinckii*, and *Clostridium butyricum* in a digestion system of a ruminant having ingested an effective amount of said direct fed microbial composition, and wherein the effective amount of said direct fed microbial composition may comprise a concentration of the isolated *Bacillus* strain of between about $2 \times 10^8$ CFU/ruminant/day and about $2.0 \times 10^{10}$ CFU/ruminant/day.

In another aspect of the invention, the inventors have developed a composition for reducing a *Clostridium* comprising an effective amount of a biologically pure culture of a *Bacillus* strain selected from the group consisting of *Bacillus* 1104, *Bacillus* 1781, *Bacillus* 747, *Bacillus* 1541, *Bacillus* 1999, and *Bacillus* 2018.

In another aspect of the invention, the *Clostridium* inhibited is selected from a group consisting of *Clostridium perfringens*, *Clostridium bifermentans*, *Clostridium beijerinckii*, and *Clostridium butyricum*, *Clostridium tertium*, and *Clostridium sordellii*.

In another aspect of the invention, the composition also comprising a cryoprotectant disposed about the isolated *Bacillus* strain, and said isolated *Bacillus* strain is a powdered lyophilized strain.

In another aspect of the invention, the composition includes biologically pure, powdered lyophilized *Bacillus* strain is in the form of *Bacillus* spores.

In another aspect of the invention, the composition may be used as a direct fed microbial to control the clostridia in a digestive system of a ruminant having ingested an effective amount of said direct fed microbial.

In another aspect of the invention, the effective amount of the direct fed microbial ingested by the ruminant per day comprises a concentration of the isolated *Bacillus* strain of between about $2 \times 10^8$ CFU/ruminant and about $2.0 \times 10^{10}$ CFU/ruminant.

In another aspect of the invention, the effective amount of said direct fed microbial ingested by the ruminant per day comprises a concentration of the isolated *Bacillus* strain of about $2 \times 10^9$ CFU/ruminant.

In another aspect of the invention, the composition may be used as a silage control microbial to inhibit the growth of *Clostridium* in a volume of silage comprising an effective amount of said composition mixed with a volume of a fodder that yields said silage.

In another aspect of the invention, the biologically pure culture of the *Bacillus* strain inhibits growth of a pathogenic microorganism selected from the group consisting of *E. coli*, *Clostridium perfringens*, *Clostridium bifermentans*, *Clostridium beijerinckii*, *Clostridium butyricum*, *Clostridium tertium*, *Clostridium sordellii*, coliforms, yeasts, and molds.

In another aspect of the invention, the biologically pure culture of the *Bacillus* strain increases concentration of lactic acid and acetic acid in the silage.

In another aspect of the invention, the biologically pure culture of the *Bacillus* strain reduces spoilage of the silage.

In another aspect of the invention, a method for reducing growth of pathogenic microorganisms in silage comprising mixing a volume of a fodder with an effective amount of the composition to reduce growth of the pathogenic microorganism is provided.

In another aspect of the invention, a *Bacillus* strain is selected from the group consisting of *Bacillus* 1104, *Bacillus* 1781, *Bacillus* 747, *Bacillus* 1541, *Bacillus* 1999, and *Bacillus* 2018 for use in a direct fed microbial to control a *Clostridium* in a digestive systems of a ruminant.

In another aspect of the invention, a *Bacillus* strain is selected from the group consisting of *Bacillus* 1104, *Bacillus* 1781, *Bacillus* 747, *Bacillus* 1541, *Bacillus* 1999, and *Bacillus* 2018 for use in manufacture of a direct fed microbial to control a *Clostridium* in a digestive systems of a ruminant.

In another aspect of the invention, a *Bacillus* strain is selected from the group consisting of *Bacillus* 1104, *Bacillus* 1781, *Bacillus* 747, *Bacillus* 1541, *Bacillus* 1999, and *Bacillus* 2018 for use in a silage control microbial to inhibit the growth of a *Clostridium* in silage.

In another aspect of the invention, a *Bacillus* strain is selected from the group consisting of *Bacillus* 1104, *Bacillus* 1781, *Bacillus* 747, *Bacillus* 1541, *Bacillus* 1999, and *Bacillus* 2018 for use in manufacture of a silage control microbial to inhibit the growth of a *Clostridium* in silage.

Other objects, features and advantages of the present invention will become apparent after review of the specification, claims and drawings.

BRIEF DESCRIPTION OF THE DRAWINGS

FIG. 1 is a pie chart showing proportions of *Clostridium perfringens* and non-toxigenic clostridia isolated from feed samples in accordance with one embodiment of the present invention, pursuant to Example 1;

FIG. 2 is a pie chart showing the major non-toxigenic clostridia identified in feed samples (n=345) in accordance with one embodiment of the present invention, pursuant to Example 1;

DETAILED DESCRIPTION

Figure 3:
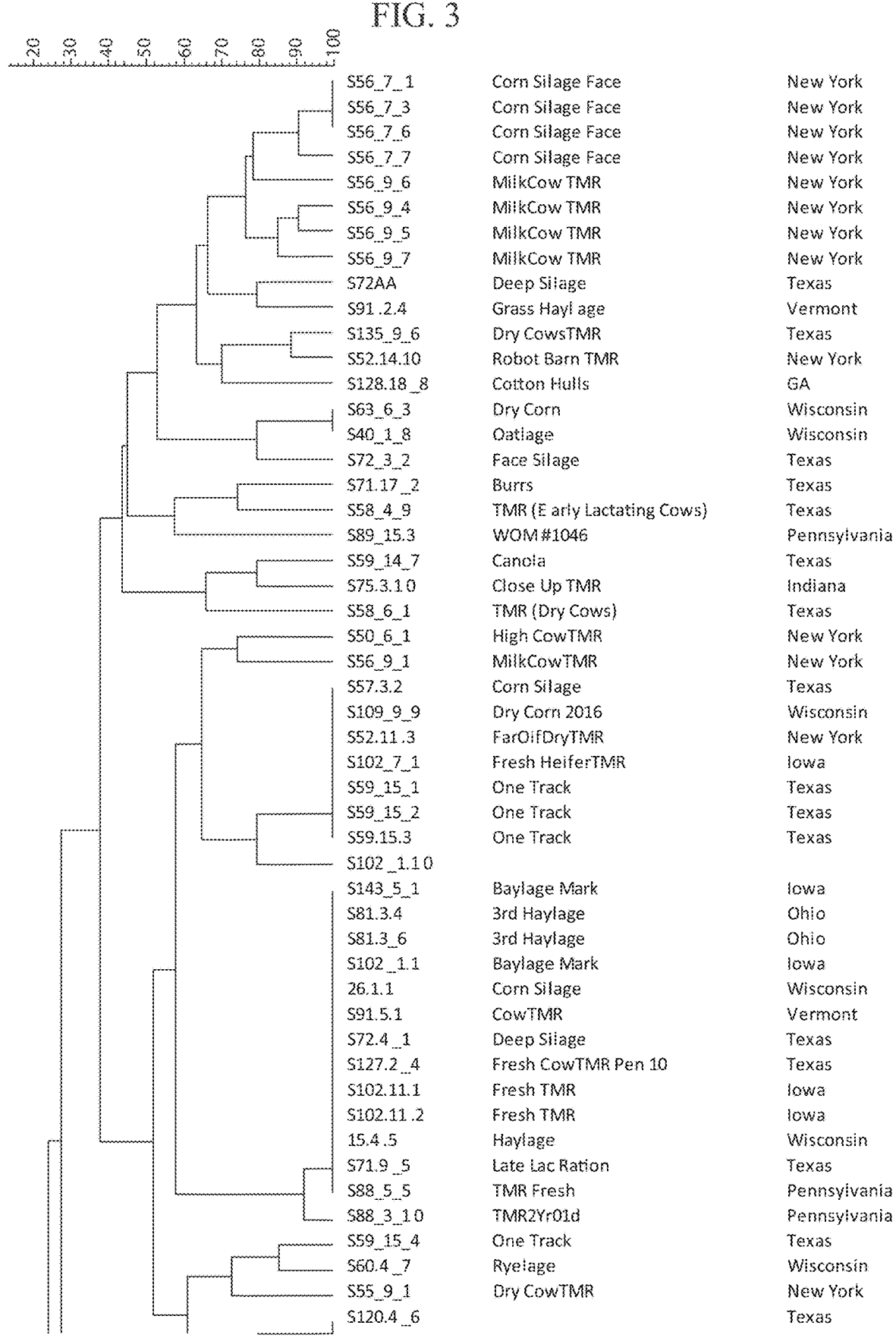
FIG. 3 is a dendrogram displaying the differences between feed clostridia isolates based on genetic fingerprints generated by RAPD PCR in accordance with one embodiment of the present invention, pursuant to Example 1.
Figure 3:
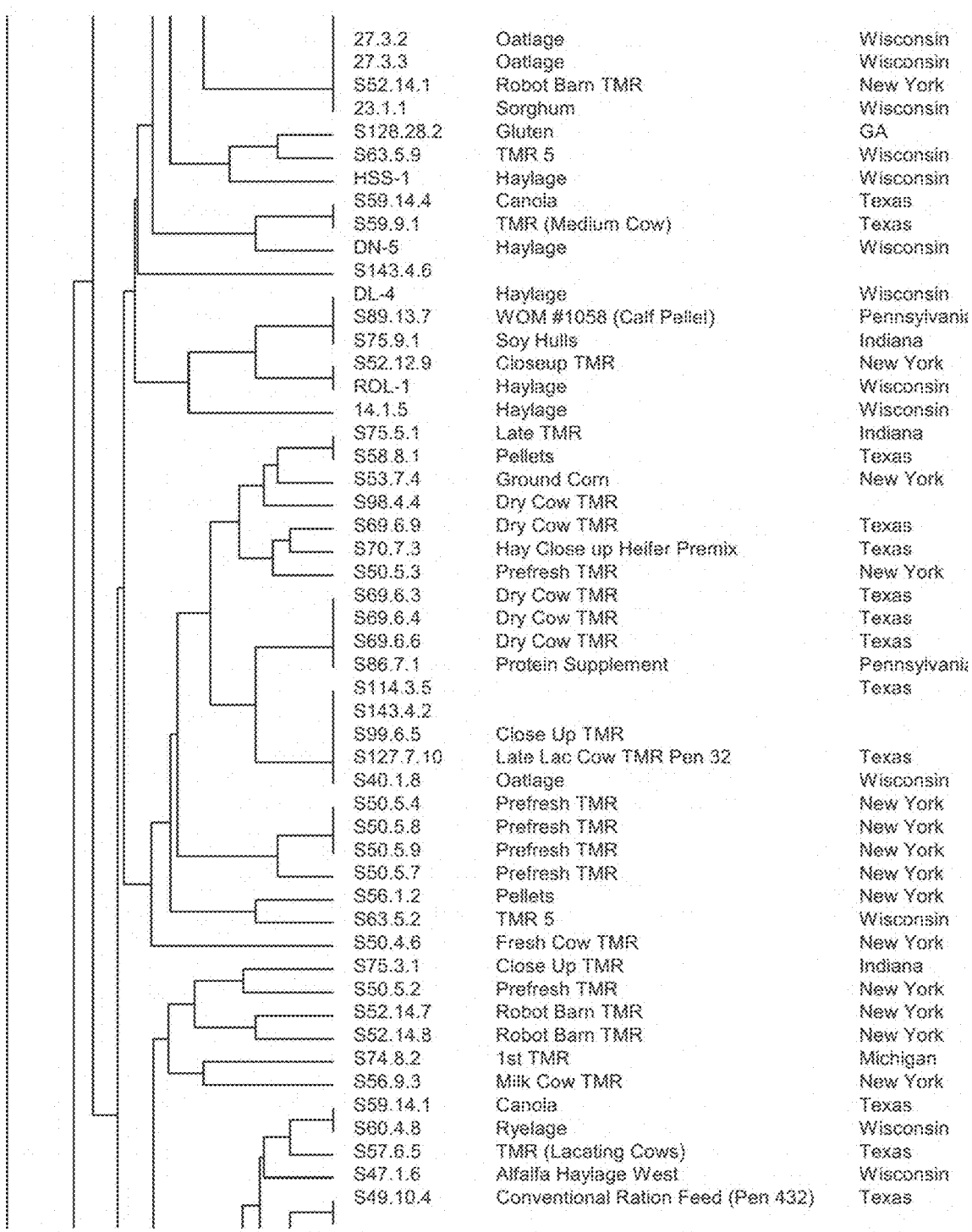
Figure 3:
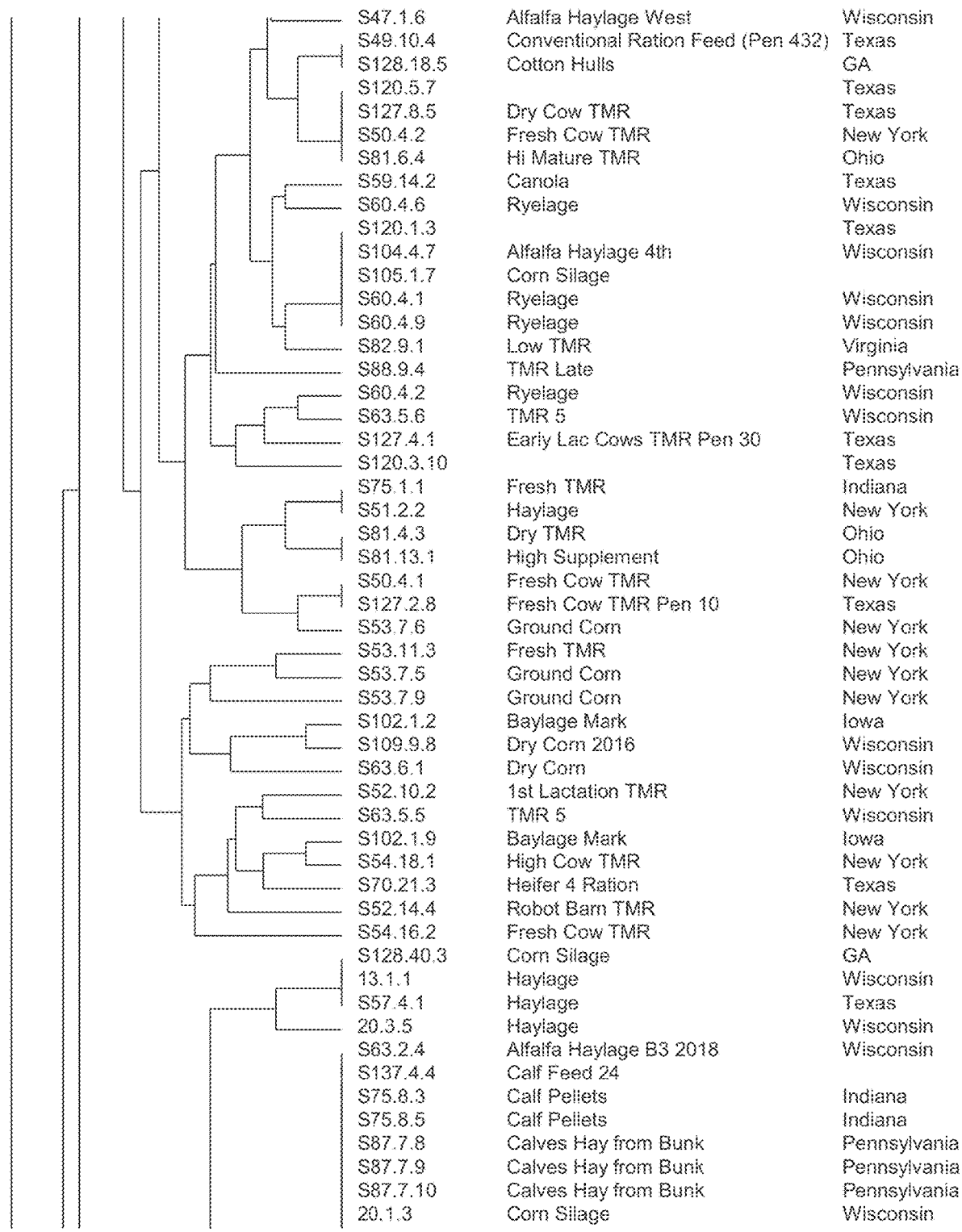
Figure 3:
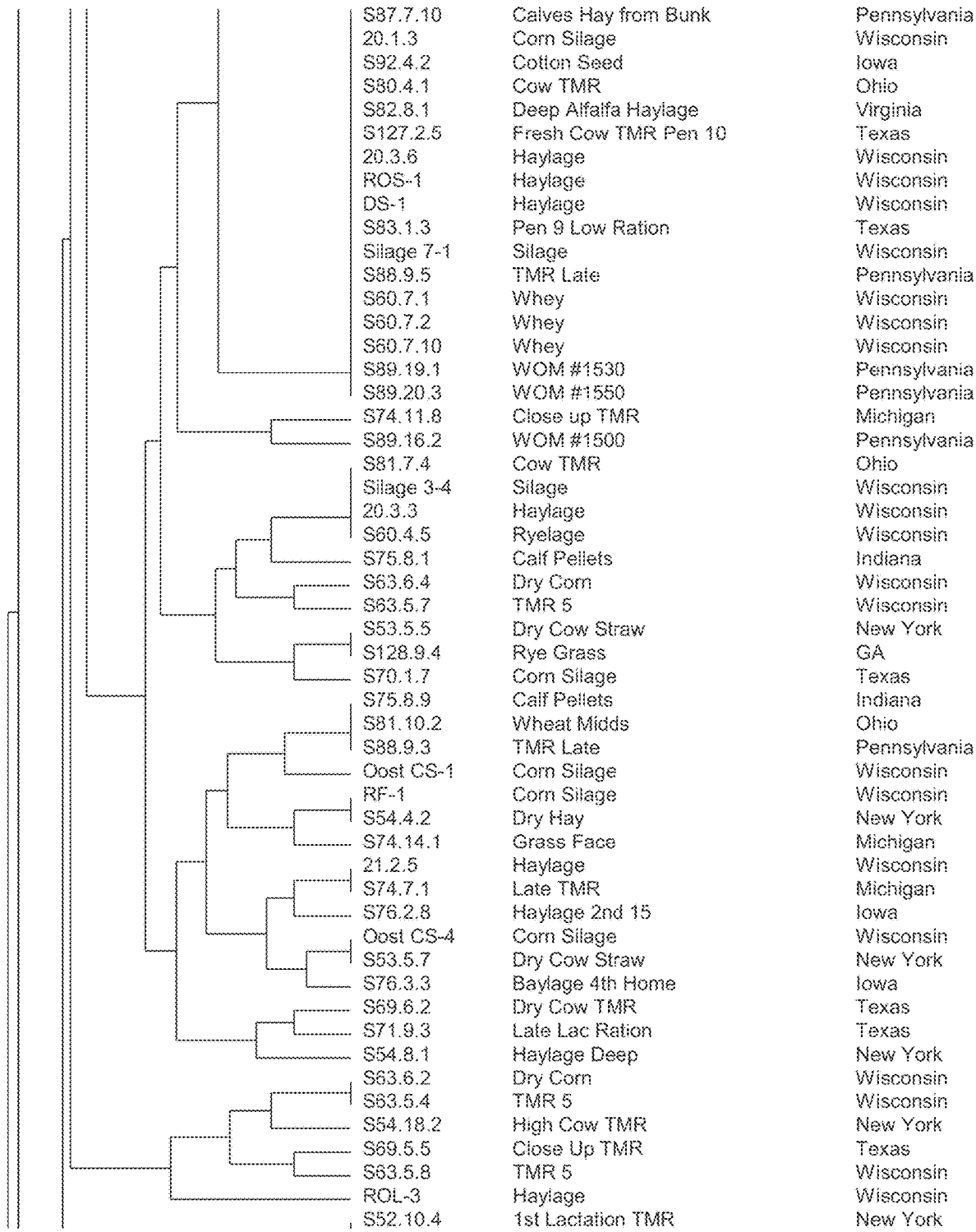
Figure 3:
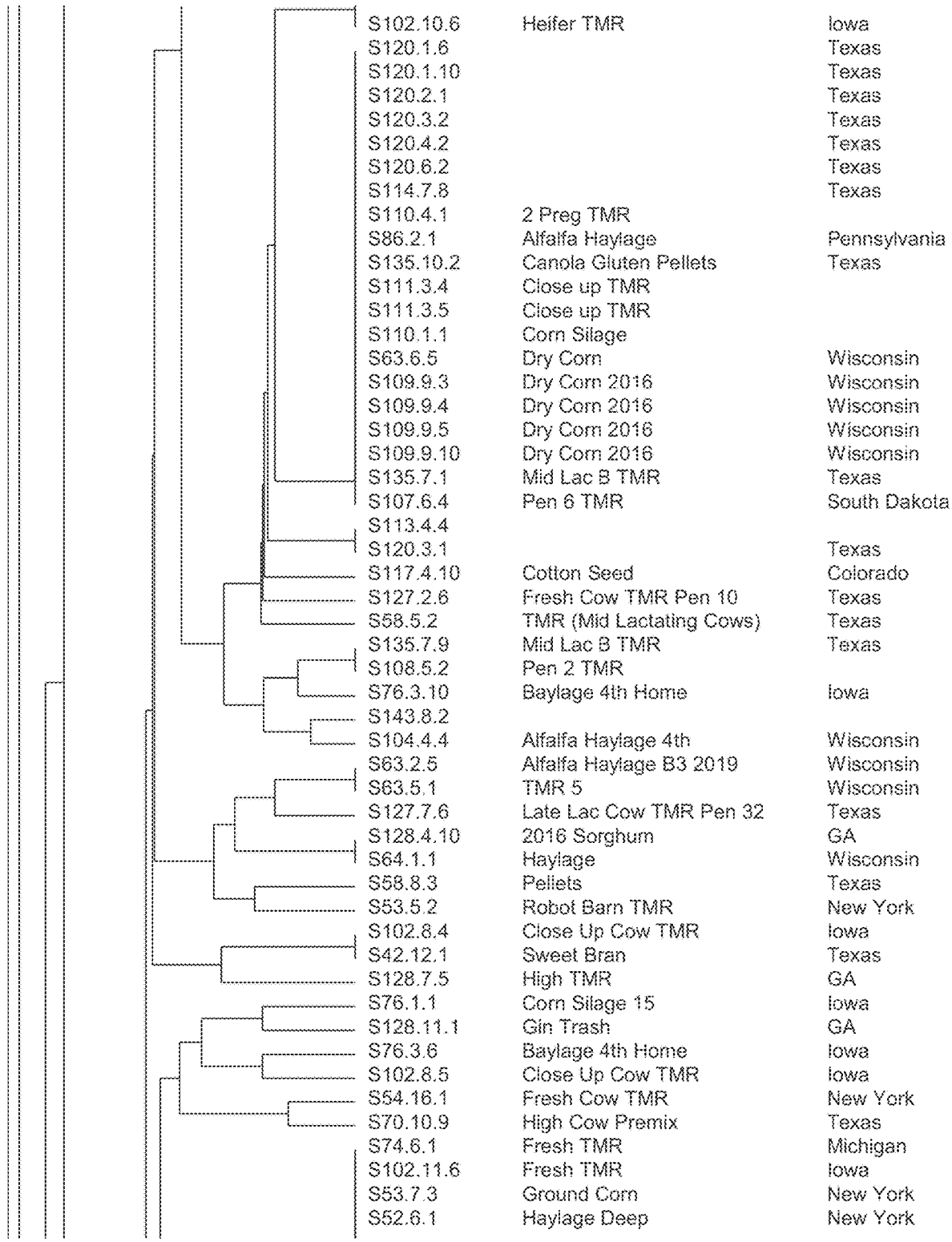

Unless defined otherwise, all technical and scientific terms used herein have the same meaning as commonly understood by one of ordinary skill in the art to which this disclosure belongs.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

It is noted that, as used in the specification and the appended claims, the singular forms "a," "an," and "the" include plural referents unless the context clearly dictates otherwise.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, "administer" is meant the action of introducing the strain or a composition to an environment.

As used herein, the term "animal" includes but is not limited to human, mammal, amphibian, bird, reptile, pigs, cows, cattle, goats, horses, sheep, poultry, and other animals kept or raised on a farm or ranch, sheep, big-horn sheep, buffalo, antelope, oxen, donkey, mule, deer, elk, caribou, water buffalo, camel, llama, alpaca, rabbit, mouse, rat, guinea pig, hamster, ferret, dog, cat, and other pets, primate, monkey, ape, and gorilla. In some embodiments, the animals are ruminants, including but not limited to cattle, sheep, goats, etc.

As used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention and/or by animals ability to avoid the negative effects of necrotic enteritis and/or by the immune response of the subject.

By "at least one strain," is meant a single strain but also mixtures of strains comprising at least two strains of bacteria. By "a mixture of at least two strains," is meant a mixture of two, three, four, five, six or even more strains. In some embodiments of a mixture of strains, the proportions can vary from 1% to 99%. When a mixture comprises more than two strains, the strains can be present in substantially equal proportions in the mixture or in different proportions.

As used herein, a "biologically pure strain" refers to a strain containing no other bacterial strains in quantities sufficient to interfere with replication of the strain or to be detectable by normal bacteriological techniques. "Isolated" when used in connection with the organisms and cultures described herein includes not only a biologically pure strain, but also any culture of organisms that is grown or maintained other than as it is found in nature.

As used herein, *Clostridium perfringens* (formerly known as *C. welchii*, or *Bacillus welchii*) is a Gram-positive, rod-shaped, anaerobic, spore-forming pathogenic bacterium of the genus *Clostridium.*

As used herein the term "contacted" refers to the indirect or direct application of the strains, silage control microbials ("SCMs"), or composition disclosed herein to a product, including but not limited to a feed. Examples of the application methods which may be used, include, but are not limited to, treating the product in a material comprising a bacterial strain, a SCM, or a composition, direct application by mixing a bacterial strain, a SCM, or a composition with the product, spraying a bacterial strain, a SCM, or a composition onto the product surface or dipping the product into a preparation of the a bacterial strain, a SCM, or a composition.

As used herein, the term "compound feed" refers to a commercial feed in the form of a meal, a pellet, nuts, cake or a crumble. Compound feeds may be blended from various raw materials and additives. These blends are formulated according to the specific requirements of the target animal.

In one embodiment, "effective amount" refers to a quantity of SCM to reduce growth of clostridia in a feed, including but not limited to silage and fodder.

In another embodiment, "effective amount" is meant a quantity of DFM to improve performance of an animal. Improvement in performance can be measured as described herein or by other methods known in the art. An effective amount can be administered to the animal by providing ad libitum access to feed containing the DFM and exogenous enzymes. The DFM and exogenous enzymes can also be administered in one or more doses.

As used herein, "energy digestibility" means the gross energy of the feed consumed minus the gross energy of the feces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the feces, urine, and gaseous products of digestion. Energy digestibility and metabolizable energy may be measured as the difference between the intake of gross energy and the gross energy excreted in the feces or the digesta present in specified segment of the gastro-intestinal tract using the same methods to measure the digestibility of nutrients, with appropriate corrections for nitrogen excretion to calculate metabolizable energy of feed.

As used herein, the term "feed" is used synonymously herein with "feedstuff."

As used herein, the "feedstuff" may comprise feed materials comprising maize or corn, wheat, barley, triticale, rye, rice, tapioca, sorghum, and/or any of the by-products, as well as protein rich components like soybean mean, rape seed meal, canola meal, cotton seed meal, sunflower seed mean, animal-by-product meals and mixtures thereof. More preferably, the feedstuff may comprise animal fats and/or vegetable oils. The feedstuff may also contain additional minerals such as, for example, calcium and/or additional vitamins.

As used herein, the term "feed efficiency" refers to the amount of weight gain in an animal that occurs when the animal is fed ad-libitum or a specified amount of food during a period of time.

As used herein, the term "feed conversion ratio" refers to the amount of feed fed to an animal to increase the weight of the animal by a specified amount.

By "lower feed conversion ratio" or "improved feed conversion ratio" it is meant that the use of a DFM or composition in feed results in a lower amount of feed being required to be fed to an animal to increase the weight of the animal by a specified amount compared to the amount of feed required to increase the weight of the animal by the same amount when the feed does not comprise the DFM or composition.

As used herein, the term "fodder" refers to any food that is provided to an animal (rather than the animal having to forage for it themselves). Fodder encompasses plants that have been cut. The term fodder includes hay, straw, silage, compressed and pelleted feeds, oils and mixed rations, and also sprouted grains and legumes.

As used herein, "improved animal performance" means there is increased feed efficiency, and/or increased weight gain and/or reduced feed conversion ratio and/or improved digestibility of nutrients or energy in a feed and/or by improved nitrogen retention and/or by improved ability to avoid the negative effects of necrotic enteritis and/or by an improved immune response in the subject resulting from a bacterial strain, DFM, SCM, or composition disclosed herein in comparison to a subject not fed the bacterial strain, DMF, SCM, or composition.

As used herein, "immune response" means one of the multiple ways in which bacterial strains, SCMs, DFMs or compositions disclosed herein modulate the immune system of animals, including increased antibody production, up-regulation of cell mediated immunity, up-regulation of pro-inflammatory cytokines, and augmented toll-like receptor signalling. It is understood that immuno-stimulation of the gastro intestinal tract by bacterial strains, SCMs, DFMs or compositions disclosed herein may be advantageous to protect the host against disease, and that immuno-suppression of the gastro intestinal tract may be advantageous to the host because less nutrients and energy are used to support the immune function.

As used herein, the term "livestock" refers to any farmed animal. In one embodiment, livestock is one or more of ruminants such as cattle (e.g. cows or bulls (including calves)), mono-gastric animals such as poultry (including broilers, chickens and turkeys), pigs (including piglets), birds, aquatic animals such as fish, agastric fish, gastric fish, freshwater fish such as salmon, cod, trout and carp, e.g. koi carp, marine fish such as sea bass, and crustaceans such as shrimps, mussels and scallops), horses (including race horses), sheep (including lambs).

As used herein, the term "microbial" is used interchangeably with "microorganism."

As used herein, "nitrogen retention" means a subject's ability to retain nitrogen from the diet as body mass. A negative nitrogen balance occurs when the excretion of nitrogen exceeds the daily intake and is often seen when the muscle is being lost. A positive nitrogen balance is often associated with muscle growth, particularly in growing animals. Nitrogen retention may be measured as the difference between the intake of nitrogen and the excreted nitrogen by means of the total collection of excreta and urine during a period of time. It is understood that excreted nitrogen includes undigested protein from the feed, endogenous proteinaceous secretions, microbial protein, and urinary nitrogen.

As used herein, "nutrient digestibility" means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum. Nutrient digestibility may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

As used herein, "reducing the growth of microorganism" includes but is not limited to reducing the growth of microorganisms by a percentage or range of percentages at least greater than 1%.

As used herein, "silage" refers to a fermented, high-moisture stored fodder that can be fed to cattle, sheep and other such ruminants (cud-chewing animals) or used as a biofuel feedstock for anaerobic digesters. It is fermented and stored in a process called ensilage, ensiling or silaging, and is usually made from grass crops, including maize, sorghum or other cereals, using the entire green plant (not just the grain). Silage can be made from many field crops, and special terms may be used depending on type (oatlage for oats, haylage for alfalfa—but see below for the different British use of the term haylage).

As used herein, a "variant" has at least 80% identity of genetic sequences with the disclosed strains using random amplified polymorphic DNA polymerase chain reaction (RAPD-PCR) analysis. The degree of identity of genetic sequences can vary. In some embodiments, the variant has at least 85%, 90%, 95%, 96%, 97%, 98%, or 99% identity of genetic sequences with the disclosed strains using RAPD-PCR analysis. Six primers that can be used for RAPD-PCR analysis include the following: Primer 1 (5'-GGT-GCGGGAA-3') (SEQ ID No. 1), PRIMER 2 (5'-GTTTCGCTCC-3') (SEQ ID No. 2), PRIMER 3 (5'-GTA-GACCCGT-3') (SEQ ID No. 3), PRIMER 4 (5'-AAGAGCCCGT-3') (SEQ ID No. 4), PRIMER 5 (5'-AACGCGCAAC-3') (SEQ ID No. 5), PRIMER 6 (5'-CCCGTCAGCA-3') (SEQ ID No. 6). RAPD analysis can be performed using Ready-to-Go™ RAPD Analysis Beads (Amersham Biosciences, Sweden), which are designed as pre-mixed, pre-dispensed reactions for performing RAPD analysis.

As used herein, the term "viable microorganism" refers to a microorganism which is metabolically active or able to differentiate.

In one embodiment, the disclosure is directed to bacterial strains, SCMs, compositions and methods for controlling clostridia growth in feedstuffs. In another embodiment, the disclosure is directed to bacterial strains, SCMs, compositions and methods for controlling clostridia growth in silage.

In one embodiment, the disclosure is directed to bacterial strains, DFMs, compositions and methods for improving performance of an animal. Certain *Bacillus* strains and combinations and compositions thereof can be used to increase performance measures of an animal.

I. Microbials

In one embodiment, the disclosure relates to one or more bacterial strains. In yet another embodiment, the disclosure relates to compositions comprising or consisting of or consisting essentially of one or more bacterial strains. In one embodiment, a composition may be a heterogeneous mixture, a homogeneous mixture, a powder, lyophilized, freeze-dried, or any combination thereof.

A. Silage Control Microbials

Silage control microbials (SCMs) are microorganisms that reduce spoilage of a substrate, including but not limited to feed, silage and fodder. In one embodiment, the SCM comprises a viable microorganism. In another embodiment, the SCM comprises a viable bacterium.

In one embodiment the SCM may be a spore forming bacterium and hence the term SCM may be comprised of or contain spores, e.g. bacterial spores. Therefore, in one embodiment the term "viable microorganism" as used herein may include microbial spores, such as endospores.

In another embodiment, the disclosure relates to compositions that are not comprised of or do not contain microbial spores, e.g. endospores.

In one embodiment, the SCM is a combination comprising two or more bacterial strains.

In one embodiment, the bacterium or bacteria is or are isolated. In another embodiment, the SCM is a biologically pure culture of a bacterium. In still another embodiment, the SCM is a composition that comprises at least two bacterial strains that contain no other microorganisms. In still another embodiment, the SCM is a composition that comprises at least two bacterial strains that contain no other microorganisms that are found in a native environment.

In one embodiment the SCM may be a viable or inviable microorganism that is used in isolated or semi-isolated form. The SCM may be used in combination with or without the growth medium in which it was cultured.

In one embodiment, the SCM is capable of producing colony forming units when grown on an appropriate media. The appropriate media may comprise (or consist of) a feed or a feed constituent.

In one embodiment, the SCM is incapable of producing colony forming units when grown on an appropriate media. Irrespective of whether the SCM is capable or incapable of producing colony forming units when grown on an appropriate media—the cells may be still metabolically active (e.g. even if they are unable to divide).

In one embodiment the SCM may be administered as inviable cells. In one embodiment the SCM may be administered as a viable microorganism.

In one embodiment the SCM may be selected from the following *Bacillus* spp: *Bacillus subtilis*, *Bacillus cereus*, *Bacillus licheniformis*, *Bacillus amyloliquefaciens*, *Bacillus pumilus*. In one embodiment the SCM may be a *Bacillus* strain.

In one embodiment the SCM may be a *Bacillus subtilis*. In one embodiment the SCM may be selected from the group consisting of: *Bacillus subtilis* 1104.

In another embodiment, the SCM may be a *Bacillus subtilis*. In still another embodiment, the SCM may be *Bacillus subtilis* 1781. In still another embodiment, the SCM may be *Bacillus subtilis* 747.

In another embodiment, the SCM is a multi-strain SCM comprising *Bacillus subtilis* 747, 1104, 1541, 1781, 1999 and 2018.

a. Formulation of a SCM

In one embodiment, the SCM formulations contained the *Bacillus* inoculant 50% of each strain 1104 and 1781.

In another embodiment, the SCM is a multi-strain SCM comprising *Bacillus subtilis* 1104 and 1781 and LAB strains. The LAB composition comprised 30% Lp115 (*Lactobacillus plantarum*), 30% Pj300 (*Pediococcus acidilactici*), 30% P751 (*P. pentosaceus*), and 10% *Enterococcus faecium*.

In another embodiment, the inoculant target application rates per gram of silage ranged for *Bacillus* from about 5,000 CFU/g to about 5,000,000 CFU/g. The LAB incolulant may be applied at about 150,000 CFU/g.

b. Dosing

In one embodiment, the SCM and compositions disclosed herein may be designed for one-time application. In one embodiment, the SCM and compositions disclosed herein may be mixed with a substrate, such as silage or fodder, to prevent clostridial spoilage.

The optimum amount of the composition (and each component therein) to be used in the combination may depend on the product to be treated and/or the method of contacting the product with the composition and/or the intended use for the same. The amount of SCM should be a sufficient amount to be effective and to remain sufficiently effective in reducing spoilage of a substrate.

B. Direct Fed Microbials

Direct fed microbials (DFMs) are microorganisms that improve performance of an animal. In one embodiment, the DFM comprises a viable microorganism. In another embodiment, the DFM comprises a viable bacterium.

In one embodiment the DFM may be a spore forming bacterium and hence the term DFM may be comprised of or contain spores, e.g. bacterial spores. Therefore, in one embodiment the term "viable microorganism" as used herein may include microbial spores, such as endospores or conidia.

In another embodiment, the disclosure relates to compositions that are not comprised of or do not contain microbial spores, e.g. endospores.

In one embodiment, the DFM is a combination comprising two or more bacterial strains.

In one embodiment, the bacterium or bacteria is or are isolated. In another embodiment, the DFM is a biologically pure culture of a bacterium. In still another embodiment, the DFM is a composition that comprises at least two bacterial strains that contain no other microorganisms. In still another embodiment, the DFM is a composition that comprises at least two bacterial strains that contain no other microorganisms found in a native environment.

In one embodiment, the DFM may be a viable or inviable microorganism which is used in isolated or semi-isolated form. The DFM may be used in combination with or without the growth medium in which it was cultured.

In one embodiment, the DFM is capable of producing colony forming units when grown on an appropriate media. The appropriate media may comprise (or consist of) a feed or a feed constituent.

In one embodiment, the DFM is incapable of producing colony forming units when grown on an appropriate media. Irrespective of whether the DFM is capable or incapable of producing colony forming units when grown on an appropriate media—the cells may be still metabolically active (e.g. even if they are unable to divide).

In one embodiment the DFM may be administered as inviable cells.

In one embodiment the DFM may be a *Bacillus subtilis*. In one embodiment the DFM may be selected from the group consisting of: *Bacillus subtilis* 747, 1104, 1541, 1781, 1999, 2018.

In one embodiment, the DFM is a multi-strain DFM comprising *Bacillus subtilis* 747, 1104, 1541, 1781, 1999, 2018.

a. Formulation of a DFM

In one embodiment, one or more carrier(s) or other ingredients can be added to the DFM. The DFM may be presented in various physical forms, for example, as a top dress, as a water soluble concentrate for use as a liquid drench or to be added to a milk replacer, gelatin capsule, or gels.

In one embodiment of the top dress form, freeze-dried fermentation product is added to a carrier, such as whey, maltodextrin, sucrose, dextrose, limestone (calcium carbonate), rice hulls, yeast culture, dried starch, and/or sodium silico aluminate.

In one embodiment of the water soluble concentrate for a liquid drench or milk replacer supplement, freeze-dried fermentation product is added to a water soluble carrier, such as whey, maltodextrin, sucrose, dextrose, dried starch, sodium silico aluminate, and a liquid is added to form the drench or the supplement is added to milk or a milk replacer.

In one embodiment of the gelatin capsule form, freeze-dried fermentation product is added to a carrier, such as whey, maltodextrin, sugar, limestone (calcium carbonate), rice hulls, yeast culture dried starch, and/or sodium silico aluminate.

In one embodiment, the bacteria and carrier are enclosed in a degradable gelatin capsule. In one embodiment of the gels form, freeze-dried fermentation product is added to a carrier, such as vegetable oil, sucrose, silicon dioxide, polysorbate 80, propylene glycol, butylated hydroxyanisole, citric acid, ethoxyquin, and/or artificial coloring to form the gel.

The DFM(s) may optionally be admixed with a dry formulation of additives including but not limited to growth substrates, enzymes, sugars, carbohydrates, extracts and growth promoting micro-ingredients. The sugars could include the following: lactose; maltose; dextrose; maltodextrin; glucose; fructose; mannose; tagatose; sorbose; raffinose; and galactose. The sugars range from 50-95%, either individually or in combination. The extracts could include yeast or dried yeast fermentation solubles ranging from 5-50%. The growth substrates could include: trypticase, ranging from 5-25%; sodium lactate, ranging from 5-30%; and, Tween 80, ranging from 1-5%. The carbohydrates could include mannitol, sorbitol, adonitol and arabitol. The carbohydrates range from 5-50% individually or in combination. The micro-ingredients could include the following: calcium carbonate, ranging from 0.5-5.0%; calcium chloride, ranging from 0.5-5.0%; dipotassium phosphate, ranging from 0.5-5.0%; calcium phosphate, ranging from 0.5-5.0%; manganese proteinate, ranging from 0.25-1.00%; and, manganese, ranging from 0.25-1.0%.

To prepare DFMs described herein, the culture(s) and carrier(s) (where used) can be added to a ribbon or paddle mixer and mixed for about 15 minutes, although the timing can be increased or decreased. The components are blended such that a uniform mixture of the cultures and carriers result. The final product is preferably a dry, flowable powder. The DFM(s) or composition comprising same can then be added to animal feed or a feed premix, added to an animal's water, or administered in other ways known in the art (preferably simultaneously with the enzymes of the present invention). A feed for an animal can be supplemented with one or more DFM(s) described herein or with a composition described herein.

In one embodiment, the DFMs and compositions disclosed herein may be in the form of a concentrate. Typically these concentrates comprise a substantially high concentration of a DFM.

Powders, granules and liquid compositions in the form of concentrates may be diluted with water or resuspended in water or other suitable diluents, for example, an appropriate growth medium such as milk or mineral or vegetable oils, to give compositions ready for use.

The DFM and compositions disclosed herein in the form of concentrates may be prepared according to methods known in the art.

b. Dosing

In one embodiment, DFMs and compositions disclosed herein provide a content of viable cells (colony forming units, CFUs) in the range selected of about $10^8$ CFU/head/day to about $5 \times 10^9$ CFU/head/day.

In one embodiment, a DFM in the form of a concentrate may have a content of viable cells in the range of at least $10^9$ CFU/g to about $10^{12}$ CFU/g, or at least $10^{11}$ CFU/g to about $10^{12}$ CFU/g.

In one embodiment, the DFM and/or feed additive composition disclosed herein may be designed for one-time dosing or may be designed for feeding on a daily basis. The optimum amount of the composition (and each component therein) to be used in the combination will depend on the product to be treated and/or the method of contacting the product with the composition and/or the intended use for the same. The amount of DFM used in the compositions should be a sufficient amount to be effective and to remain sufficiently effective in improving the performance of the animal fed feed products containing said composition. This length of time for effectiveness should extend up to at least the time of utilization of the product (e.g. feed additive composition or feed containing same).

C. Deposits Under the Budapest Treaty

*Bacillus* strains 747, 1104, 1541, 1781 and 2018 were deposited on May 24, 2016 at the Agricultural Research Service Culture Collection (NRRL), 1815 North University Street, Peoria, Ill., 61604 and given accession numbers NRRL B-67257 for strain *B. subtilis* 747, NRRL B-67258 for strain *B. subtilis* 1104, NRRL B-67260 for strain *B. subtilis* 1541, NRRL B-67259 for strain *B. subtilis* 1781 and NRRL B-67261 for strain *B. subtilis* 2018. Strain *B. subtilis* 1999 was deposited on Sep. 15, 2016 and given the accession number NRRL B-67318. All deposits were made under the provisions of the Budapest Treaty on the International Recognition of the Deposit of Microorganisms for the Purposes of Patent Procedure.

D. Methods of Culturing Strains

The *Bacillus* strains can be produced by fermentation of the bacterial strains. Fermentation can be started by scaling-up a seed culture. This involves repeatedly and aseptically transferring the culture to a larger and larger volume to serve as the inoculum for the fermentation, which is carried out in large stainless steel fermentors in medium containing proteins, carbohydrates, and minerals necessary for optimal growth. A non-limiting exemplary medium is Tyticase Soy Broth (TSB). After the inoculum is added to the fermentation vessel, the temperature and agitation are controlled to allow maximum growth. Once the culture reaches a maximum population density, the culture is harvested by separating the cells from the fermentation medium. This is commonly done by centrifugation.

The count of the culture can then be determined. A colony forming unit (CFU) is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

In one embodiment, the *Bacillus* strains disclosed herein can be fermented between $5 \times 10^8$ CFU/ml to about $5 \times 10^{11}$ CFU/ml.

In at least one embodiment, a level of $2 \times 10^9$ CFU/ml is used. The bacteria are harvested by centrifugation, and the supernatant is removed. The supernatant can be used in the methods described herein. In at least some embodiments, the bacteria are pelleted. In at least some embodiments, the bacteria are freeze-dried. In at least some embodiments, the bacteria are mixed with a carrier. However, it is not necessary to freeze-dry the *Bacillus* before using them. The strains can also be used with or without preservatives, and in concentrated, unconcentrated, or diluted form.

In one embodiment, the disclosure relates to a biologically pure culture comprising, consisting of, or consisting essentially of one or more *Bacillus* strains disclosed herein at a concentration of about $5 \times 10^2$ CFU/ml to about $5 \times 10^9$ CFU/ml.

In one embodiment, the disclosure relates to a culture comprising, consisting of, or consisting essentially of one or more *Bacillus* strains disclosed herein at a concentration selected from the group consisting of $5 \times 10^{11}$ CFU/ml, $5 \times 10^{12}$ CFU/ml, and $5 \times 10^{13}$ CFU/ml.

In one embodiment, the disclosure relates to a culture comprising, consisting of, or consisting essentially of one or more *Bacillus* strains disclosed herein at a concentration of $5 \times 10^{10}$ CFU/ml to $10^{12}$ CFU/ml or $5 \times 10^{11}$ CFU/ml to $10^{12}$ CFU/ml.

II. Compositions

In one embodiment, the disclosure relates to a composition comprising one or more *Bacillus* strains disclosed herein. In yet another embodiment, the disclosure relates to a composition comprising one or more SCMs. In yet another embodiment, the disclosure relates to a composition comprising one or more DFMs.

In one embodiment, the disclosure relates to a composition comprising one or more *Bacillus* strain selected from the group consisting of *Bacillus subtilis* 781 and *Bacillus subtilis* 747, wherein the composition is free of other microbial organisms.

In one embodiment, the disclosure relates to a composition comprising one or more *Bacillus* strain selected from the group consisting of *Bacillus subtilis* 747, 1781, 1104, 1541, 1999 and 2018, wherein the *Bacillus* strains are biologically pure prior to formation of the composition.

In one embodiment, the disclosure relates to a composition comprising one or more *Bacillus* strain selected from the group consisting of *Bacillus subtilis* 1781, and *Bacillus subtilis* 747; (b) a carrier and (c) a preservative. In another embodiment, one or more of the *Bacillus* strains are at a concentration of at least $10^9$ CFU/ml.

In another embodiment, the disclosure relates to a composition comprising (a) one or more *Bacillus* strain selected from the group consisting of *Bacillus subtilis* 1781, *Bacillus subtilis* 747, and (b) a feed. In yet another embodiment, the disclosure relates to a feed comprising (a) one or more *Bacillus* strain selected from the group consisting of *Bacillus subtilis* 1104, 1781 and 2018 (b) silage or fodder, wherein the feed has a lower concentration of Clostridia as compared to a feed lacking the *Bacillus* strains.

III. Feed/Feedstuff

In one embodiment, the strains, SCMs, DFMs, and compositions disclosed herein may be used as—or in the preparation of—a feed. In one embodiment, the feed is fodder. In another embodiment, the feed is silage.

Forage that has been grown while still green and nutritious can be conserved through a natural 'pickling' process. Lactic acid is produced when the sugars in the forage plants are fermented by bacteria in a sealed container ('silo') with no air. Forage conserved this way is known as 'ensiled forage' or 'silage' and will keep for up to three years without deteriorating. Silage is very palatable to livestock and can be fed at any time.

The feed may be in the form of a solution or as a solid—depending on the use and/or the mode of application and/or the mode of administration. When used as—or in the preparation of—a feed—such as functional feed—the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

In one embodiment, the strains, SCMs, DFMs, and compositions disclosed herein are admixed with a feed component to form a feedstuff. In one embodiment, the feed may be a fodder, or a premix thereof, a compound feed, or a premix thereof. In one embodiment, the strains, SCMs, DFMs, and compositions disclosed herein may be admixed with a compound feed, a compound feed component or to a premix of a compound feed or to a fodder, a fodder component, or a premix of a fodder.

In still another embodiment, the strains, SCMs, DFMs, and compositions disclosed herein can me mixed with silage, compressed and pelleted feeds, oils and mixed rations, and also sprouted grains and legumes. Fodder may be obtained from one or more of the plants selected from: barley rapeseed (canola), corn (maize), millet, oats, sorghum, soybeans, wheat, and legumes.

Any feedstuff disclosed herein may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, wet-cake (particularly corn based wet-cake), Distillers Dried Grain (DDG) (particularly corn based Distillers Dried Grain (cDDG)), Distillers Dried Grain Solubles (DDGS) (particularly corn based Distillers Dried Grain Solubles (cDDGS)), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

A feedstuff may contain at least 10%, at least 20%, at least 30% or at least 50% by weight corn and soybean meal or corn and full fat soy, or wheat meal or sunflower meal.

A feedstuff may contain between about 0 to about 40% corn DDGS. If the feedstuff contain any corn DDGS it may contain between about 5 to about 40% corn DDGS. For poultry—where corn DDGS is present the feedstuff on average may contain between about 7 to 15% corn DDGS. For swine (pigs)—where corn DDGS is present the feedstuff may contain on average 5 to 40% corn DDGS.

A feedstuff may contain corn as a single grain, in which case the feedstuff may comprise between about 35% to about 80% corn.

In one embodiment, the feed may be one or more of the following: a compound feed and premix, including pellets, nuts or (cattle) cake; a crop or crop residue: corn, soybeans, sorghum, oats, barley, copra, chaff, sugar beet waste; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

In one embodiment, a bacterial strain, SCM, DFM, or composition disclosed herein is admixed with the product (e.g. feedstuff). In another embodiment, a bacterial strain, a SCM, DFM, or a composition may be included in the emulsion or raw ingredients of a feedstuff. For some applications, it is important that the composition is made available on or to the surface of a product to be affected/treated. This allows the composition to impart one or more of the following favourable characteristics: performance benefits.

In one embodiment, a bacterial strain, a SCM, DFM, or a composition disclosed herein may be applied to intersperse, coat and/or impregnate a product (e.g. feedstuff or raw ingredients of a feedstuff).

In one embodiment, a bacterial strain, a SCM, a DFM, or a composition disclosed herein can be added in suitable concentrations—such as for example in concentrations in the final feed product which offer a daily dose of from about $2\times10^5$ CFU to about $2\times10^{11}$ CFU, suitably from about $2\times10^6$ to about $1\times10^{10}$, or between about $3.75\times10^7$ CFU to about $1\times10^{10}$ CFU.

In yet another embodiment, a bacterial strain, a SCM, a DFM, or a composition will be thermally stable to heat treatment up to about 70° C.; up to about 85° C.; or up to about 95° C. The heat treatment may be performed for up to about 1 minute; up to about 5 minutes; up to about 10 minutes; up to about 30 minutes; up to about 60 minutes. The term thermally stable means that at least about 75% of the bacterial strain or SCM that were present/active in the additive before heating to the specified temperature are still present/active after it cools to room temperature. In one embodiment, at least about 80% of the bacterial strain or SCM that were present and active in the additive before heating to the specified temperature are still present and active after it cools to room temperature.

In one embodiment, a bacterial strain, a SCM, a DFM, or a composition disclosed herein are homogenized to produce a powder.

IV. Forms

In one embodiment, a bacterial strain, a SCM, a DFM, or a composition and other components and/or the feedstuff comprising same may be used in any suitable form. A bacterial strain, a SCM, a DFM, or a composition disclosed herein may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, a bacterial strain, a SCM, a DFM, or a composition disclosed herein may be mixed with feed or administered in the drinking water. In one embodiment the dosage range for inclusion into water is about $1\times10^8$ CFU/animal/day to about $1\times10^{10}$ CFU/animal/day, and more preferably about $1\times10^9$ CFU/animal/day.

Suitable examples of forms include one or more of: powders, pastes, boluses, pellets, tablets, pills, capsules, ovules, solutions or suspensions, which may contain flavouring or colouring agents, for immediate-, delayed-, modified-, sustained-, pulsed- or controlled-release applications.

By way of example, if a bacterial strain, a SCM, a DFM, or a composition disclosed herein is used in a solid, e.g. pelleted form, it may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethyl cellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

In one embodiment, excipients for the forms include lactose, starch, a cellulose, milk sugar or high molecular weight polyethylene glycols.

For aqueous suspensions and/or elixirs, a bacterial strain, a SCM, a DFM, or a composition disclosed herein may be combined with various sweetening or flavoring agents, coloring matter or dyes, with emulsifying and/or suspending agents and with diluents such as water, propylene glycol and glycerin, and combinations thereof.

In one embodiment, non-hydroscopic whey can be used as a carrier for a bacterial strain, a SCM, a DFM, or a composition disclosed herein (particularly bacterial DFMs) and is a good medium to initiate growth. A bacterial strain, a SCM, a DFM, or a composition disclosed herein containing pastes may be formulated with vegetable oil and inert gelling ingredients.

In one embodiment, fungal products may be formulated with grain by-products as carriers.

The dry powder or granules may be prepared by means known to those skilled in the art, such as, in top-spray fluid bed coater, in a bottom spray Wurster or by drum granulation (e.g. High sheer granulation), extrusion, pan coating or in a microingredients mixer.

In another embodiment, the bacterial strains, SCMs, DFMs or compositions disclosed herein may be coated, for example encapsulated. In some embodiments, such as where the bacterial strain is capable of producing endospores, the bacterial strains, SCMs, DFMs or compositions disclosed herein may be provided without any coating.

V. Methods of Treating Feed with an DFM

In one embodiment, the disclosure relates to methods of reducing spoilage of feed comprising mixing a SCM or composition disclosed herein with feed in an effective amount to reduce spoilage of silage in comparison to feed not mixed with the SCM or composition. In one embodiment, the feed is silage or fodder.

In one embodiment, spoilage of feed is reduced by a percentage selected from the group consisting of: at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least, at least 95%, and at least 99% as compared to feed not treated with an SCM or composition.

In one embodiment, spoilage of the feed is reduced from 2 to 5%, or from 5 to 10%, or from 10 to 15%, or from 15 to 20%, or from 20 to 25%, or from 25 to 30%, or from 30 to 35%, or from 35 to 40%, or from 40 to 45%, or from 45 to 50%, or from 50 to 55%, or from 55 to 60%, or from 60 to 65%, or from 65 to 70%, or from 70 to 75%, or from 75 to 80%, or from 80 to 85%, or from 85 to 90%, or from 90 to 95%, or from 95 to 99% as compared to feed not treated with an SCM or composition.

In another embodiment, the disclosure relates to methods of controlling growth of microorganisms in feed comprising mixing an SCM or composition disclosed herein with feed in an effective amount to control growth of microorganisms in feed.

In another embodiment, the disclosure relates to methods of reducing growth of clostridia in feed comprising mixing an SCM or composition disclosed herein with feed in an effective amount to control growth of clostridia in feed.

In another embodiment, the disclosure relates to methods of reducing growth of clostridia in fodder comprising: (a) mixing an SCM or composition disclosed herein in a liquid; (b) mixing the liquid with fodder; and (c) placing the fodder in a sealed container.

In another embodiment, the disclosure relates to methods of reducing growth of clostridia in fodder comprising: (a) mixing an SCM or composition disclosed herein in a dry form with fodder; and (b) placing the fodder in a sealed container.

In another embodiment, the disclosure relates to methods of reducing growth of clostridia in fodder comprising: (a) spraying an SCM or composition disclosed herein onto fodder; and (b) placing the fodder in a sealed container.

In one embodiment, the disclosure relates to methods of producing silage comprising: (a) mixing an SCM or composition disclosed herein in a liquid; (b) mixing the liquid with fodder; (c) placing the fodder in a sealed container for a suitable period of time; and (d) obtaining silage from the container.

In another embodiment, the disclosure relates to methods of producing silage comprising: (a) mixing an SCM or composition disclosed herein in a dry form with fodder; (b) placing the fodder in a sealed container; and (c) obtaining or harvesting silage from the container.

In another embodiment, the disclosure relates to methods of producing silage comprising: (a) spraying an SCM or composition disclosed herein onto fodder; (b) placing the fodder in a sealed container; and (c) obtaining or harvesting silage from the container.

In one embodiment, the SCM or composition is mixed or sprayed with a percentage of the fodder selected from the group consisting of: 5-10%, 10-220%, 20-30%, 30-40%, 40-50%, 50-60%, 60-70%, 70-80%, 80-90%, 90-95%, and 95-99% and 100% of the fodder.

In one embodiment, the SCM or composition is mixed or sprayed with at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 99% and 100%.

In one embodiment, the sealed container is a silo. In another embodiment, the sealed container is a plastic bag.

In one embodiment, the silage has a lower concentration of pathogenic microorganisms, such as clostridia, as compared to silage obtained from fodder not treated with *Bacillus* strains.

In one embodiment, growth of clostridia is reduced by a percentage selected from the group consisting of: at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least, at least 95%, and at least 99% as compared to feed not treated with an SCM or composition.

In one embodiment, growth of clostridia is reduced from 2 to 5%, or from 5 to 10%, or from 10 to 15%, or from 15 to 20%, or from 20 to 25%, or from 25 to 30%, or from 30 to 35%, or from 35 to 40%, or from 40 to 45%, or from 45 to 50%, or from 50 to 55%, or from 55 to 60%, or from 60 to 65%, or from 65 to 70%, or from 70 to 75%, or from 75 to 80%, or from 80 to 85%, or from 85 to 90%, or from 90 to 95%, or from 95 to 99% as compared to feed not treated with an SCM or composition.

In one embodiment, the clostridia is *Clostridium tetani, Clostridium botulinum, Clostridium perfringens, Clostridium acetobutylicum, Clostridium difficile, Clostridium novyi*

In one embodiment, the clostridia is *Clostridium perfringens*.

In another embodiment, the disclosure relates to methods of increasing the shelf life or storage of feed comprising mixing an SCM or composition with feed in an effective amount to increase the shelf life or storage duration of feed in comparison to feed not mixed with an SCM or composition.

In one embodiment, the SCM comprises one or more *Bacillus* strains. In one embodiment, the *Bacillus* strains are at a concentration selected from the group consisting of: 5,000 CFU/g, 10,000 CFU/g, 15,000 CFU/g, 20,000 CFU/g, 25,000 CFU/g, 30,000 CFU/g, 35,000 CFU/g, 40,000 CFU/g, 45,000 CFU/g, 50,000 CFU/g, 55,000 CFU/g, 60,000 CFU/g, 65,000 CFU/g, 70,000 CFU/g, 75,000 CFU/g, 80,000 CFU/g, 85,000 CFU/g, 90,000 CFU/g, 95,000 CFU/g, and 100,000 CFU/g. In one embodiment, the SCM is a composition of *Bacillus amyloliquefaciens* 1104 and *Bacillus subtilis* 1781.

In yet another embodiment, the *Bacillus* strains are at a concentration selected from the group consisting of: from 5,000 CFU/g to 10,000 CFU/g.

In yet another embodiment, the *Bacillus* strains are at a concentration selected from the group consisting of: from 10,000 CFU/g to 75,000 CFU/g.

In yet another embodiment, the *Bacillus* strains are at a concentration selected from the group consisting of: $10^3$ CFU/g, $10^4$ CFU/g, $10^5$ CFU/g, $10^6$ CFU/g, $10^7$ CFU/g, $10^8$ CFU/g, $10^9$ CFU/g, and $10^{10}$ CFU/g.

In another embodiment, the composition further comprises a preservative.

In one embodiment, the SCM is a composition of lactic acid bacteria and *Bacillus*. In one embodiment, the CFU of the lactic acid bacteria is 2× the CFUs of the *Bacillus* strains in the composition. In yet another embodiment, the CFU of the lactic acid bacteria is 3× the CFUs of the *Bacillus* strains in the composition.

In one embodiment, the concentration of the lactic acid bacteria is selected from the group consisting of 50,000 CFU/g, 75,000 CFU/g, 100,000 CFU/g, 125,000 CFU/g, 150,000 CFU/g, 200,000 CFU/g, 250,000 CFU/g, 275,000 CFU/g, 300,000 CFU/g, 325,000 CFU/g, 350,000 CFU/g, 375,000 CFU/g, and 400,000 CFU/g.

In still another embodiment, the concentration of the *Bacillus* strain is selected from the group consisting of: 25,000 CFU/g, 50,000 CFU/g, 75,000 CFU/g, 100,000 CFU/g, 125,000 CFU/g, 150,000 CFU/g, and 200,000 CFU/g.

In yet another embodiment, the SCM is a composition comprising *Bacillus amyloliquefaciens* 1104 and *Bacillus subtilis* 1781 and one or more of the following strains: *Enterococcus faecium, Lactobacillus plantarum* LP 115,

*Pediococcus acidilactici* PJ300 and *Pediococcus pentosaceus* P751. In one embodiment, the concentration of the *Bacillus* strains in the composition is from about 25,000 CFU/g to about 75,000 CFU/g. In another embodiment, the concentration of the lactic acid bacteria is from about 75,000 CFU/g to about 225,000 CFU/g.

VI. Methods of Administering DFMs to an Animal

In one embodiment, the disclosure relates to methods of increasing performance metrics of an animal. In another embodiment, the disclosure relates to methods of increasing performance metrics of a ruminant.

In yet another embodiment, the disclosure relates to a method comprising administering to an animal a composition comprising a DFM. In still another embodiment, the disclosure relates to a method comprising administering to an animal an effective amount of a composition comprising DFMs to increase performance of the animal. This effective amount can be administered to the animal in one or more doses.

In another embodiment, the disclosure relates to a method comprising administering to an animal an effective amount of a composition comprising DFMs to increase average daily feed intake.

In another embodiment, the disclosure relates to a method comprising administering to an animal an effective amount of a composition comprising DFMs to increase average daily weight gain.

In another embodiment, the disclosure relates to a method comprising administering to an animal an effective amount of a composition comprising DFMs to increase total weight gain.

In another embodiment, the disclosure relates to a method comprising administering to an animal an effective amount of a composition comprising DFMs to increase feed conversion, which can be measured by either feed:gain or gain:feed.

In another embodiment, the disclosure relates to a method comprising administering to an animal an effective amount of a composition comprising DFMs to increase feed efficiency.

In another embodiment, the disclosure relates to a method comprising administering to an animal an effective amount of a composition comprising DFMs and exogenous feed enzymes to decrease mortality.

In another embodiment, the disclosure relates to a method comprising administering to an animal an effective amount of a composition comprising DFMs to decrease actual production costs.

In still another embodiment, the DFM is *Bacillus subtilis* 1104 or a strain having all of the identifying characteristics of *Bacillus subtilis* 1104. In still another embodiment, the DFM is *Bacillus subtilis* 1781 or a strain having all of the identifying characteristics of *Bacillus subtilis* 1781. In still another embodiment, the DFM is *Bacillus subtilis* 747 or a strain having all of the identifying characteristics of *Bacillus subtilis* 747. In still another embodiment, the DFM is *Bacillus subtilis* 1541 or a strain having all of the identifying characteristics of *Bacillus subtilis* 1541. In still another embodiment, the DFM is *Bacillus subtilis* 1999 or a strain having all of the identifying characteristics of *Bacillus subtilis* 1999. In still another embodiment, the DFM is *Bacillus subtilis* 2018 or a strain having all of the identifying characteristics of *Bacillus subtilis* 2018.

In still another embodiment, the DFM is a multi-strain comprising *Bacillus subtilis* 747 and *Bacillus subtilis* 1781.

In some embodiments, the one or more *Bacillus* strain(s) is (are) added to an animal's feed at a rate of at least $1 \times 10^9$ CFU/animal/day. In some embodiments, the one or more *Bacillus* strain(s) is(are) fed at about $1 \times 10^9$ CFU/g feed to about $1 \times 10^{10}$ CFU/g feed.

The DFM provided herein can be administered, for example, as the strain-containing culture solution, the strain-containing supernatant, or the bacterial product of a culture solution.

Administration of a DFM or a composition disclosed herein to an animal can increase the performance of the animal. In one embodiment, administration of a DFM provided herein to an animal can increase the average daily feed intake (ADFI), average daily gain (ADG), or feed efficiency (gain:feed; G:F) (collectively, "performance metrics"). One or more than one of these performance metrics may be improved.

The composition comprising DFMs may be administered to the animal in one of many ways. For example, the composition can be administered in a solid form as a veterinary pharmaceutical, may be distributed in an excipient, preferably water, and directly fed to the animal, may be physically mixed with feed material in a dry form, or the composition may be formed into a solution and thereafter sprayed onto feed material. The method of administration of the compositions disclosed herein to the animal is considered to be within the skill of the artisan.

When used in combination with a feed material, the feed material for ruminants can be grain or hay or silage or grass, or combinations thereof. Included amongst such feed materials are corn, dried grain, alfalfa, any feed ingredients and food or feed industry by-products as well as bio fuel industry by-products and corn meal and mixtures thereof. For monogastric diets, the feed material can include corn, soybean meal, byproducts like distillers dried grains with solubles (DDGS), and vitamin/mineral supplement. Other feed materials can also be used. Administration is possible at any time with or without feed. However, the bacterium is preferably administered with or immediately before feed.

Thus, in at least some embodiments, the effective amount of the composition comprising DFMs is administered to an animal by supplementing a feed intended for the animal. As used herein, "supplementing," refers to the action of incorporating the effective amount of bacteria provided herein directly into the feed intended for the animal. Thus, the animal, when feeding, ingests the bacteria provided herein. In one embodiment, the disclosure relates to *Bacillus* strains. In one embodiment the *Bacillus* strain is *Bacillus subtilis* 1104. In still another embodiment, the *Bacillus* strain is *Bacillus subtilis* 1781. In still another embodiment, the *Bacillus* strain is *Bacillus subtilis* 747. In still another embodiment, the *Bacillus* strain is *Bacillus subtilis* 1541. In still another embodiment, the *Bacillus* strain is *Bacillus subtilis* 2018.

In one embodiment, the disclosure relates to a composition comprising two or more of the following *Bacillus* strains: *Bacillus subtilis* 1104, *Bacillus subtilis* 1781, *Bacillus subtilis* 747, *Bacillus subtilis* 1541, *Bacillus subtilis* 1999, and *Bacillus subtilis* 2018.

In still another embodiment, the disclosure relates to a composition comprising *Bacillus subtilis* 747 and one or more of the following *Bacillus* strains: *Bacillus subtilis* 1104, *Bacillus subtilis* 1781, *Bacillus subtilis* 1541, *Bacillus subtilis* 1999, and *Bacillus subtilis* 2018.

In still another embodiment, the disclosure relates to a composition comprising *Bacillus subtilis* 1781 and one or more of the following *Bacillus* strains: *Bacillus subtilis* 1104, *Bacillus subtilis* 747, *Bacillus subtilis* 1541, *Bacillus subtilis* 1999, and *Bacillus subtilis* 2018.

In yet another embodiment, the disclosure relates to a composition comprising *Bacillus subtilis* 747 and *Bacillus subtilis* 1781.

In yet another embodiment, the disclosure relates to a composition comprising one or more *Bacillus* strains selected from the group consisting of: *Bacillus subtilis* 1104, *Bacillus subtilis* 1781, and *Bacillus subtilis* 747, *Bacillus subtilis* 1541, *Bacillus subtilis* 1999, *Bacillus subtilis* 2018 and a preservative.

In yet another embodiment, the disclosure relates to a composition comprising one or more *Bacillus* strains selected from the group consisting of: *Bacillus subtilis* 1104, *Bacillus subtilis* 1781, and *Bacillus subtilis* 747, *Bacillus subtilis* 1541, *Bacillus subtilis* 1999, *Bacillus subtilis* 2018 and *Lactobacillus plantarum*.

In another embodiment, the disclosure relates to *Bacillus* strains, compositions, and methods for controlling or reducing spoilage of a feed, including but not limited to fodder and silage.

In another embodiment, the disclosure relates to *Bacillus* strains, compositions and methods for controlling or reducing growth of microorganisms. In another embodiment, compositions and methods are disclosed for controlling or reducing growth of microorganisms in a feed, including but not limited to silage and/or fodder.

In still another embodiment, *Bacillus* strains, compositions and methods are disclosed for controlling or reducing growth of Clostridia. In still another embodiment, *Bacillus* strains, compositions and methods are disclosed for controlling or reducing growth of Clostridia in feed including but not limited to silage and/or fodder.

In one embodiment, the disclosure relates to a composition comprising one or more spoilage control microbials. In another embodiment, the disclosure relates to a composition comprising one or more spoilage control microbials and one or more additional component(s).

In another embodiment, the disclosure relates to *Bacillus* strains, compositions and methods for improving the performance of an animal. In another embodiment, the disclosure relates to one or more direct fed microbials for improving the performance of an animal.

In another embodiment, the disclosure relates to a method for increasing the shelf life of silage or fodder comprising: mixing an effective amount of at least one *Bacillus* strain with silage to increase the shelf life of the silage or fodder. In still another embodiment, the disclosure relates to a method for increasing the shelf life of silage or fodder comprising: mixing a composition comprising at least one spoilage control microbial with silage to increase the shelf life of the silage or fodder. In still another embodiment, the disclosure relates to a method for increasing the shelf life of silage or fodder comprising: mixing a composition comprising at least two spoilage control microbials with silage to increase the shelf life of the silage or fodder.

In yet another embodiment, the disclosure relates to a method of controlling growth of a microorganism in silage or fodder comprising mixing an effective amount of at least one *Bacillus* strain with the silage or fodder. In one embodiment, the *Bacillus* strain is mixed with the silage at the time of ensiling.

In still another embodiment, the disclosure relates to a method of controlling growth of a microorganism in silage or fodder comprising: mixing a composition comprising at least one spoilage control microbial with silage or fodder to control growth of a microorganism in the silage or fodder. In still another embodiment, the disclosure relates to a method of controlling growth of a microorganism in silage or fodder comprising: mixing a composition comprising at least two spoilage control microbials with silage or fodder.

In yet another embodiment, the disclosure relates to a method for improving performance of an animal comprising administering one or more *Bacillus* strains, one or more direct fed microbials or a composition to an animal to improve performance of said animal in comparison to an animal not fed the *Bacillus* strain, the direct fed microbial or the composition.

In one embodiment, the disclosure relates to a method of controlling, or treating or preventing growth of a pathogen in an animal comprising administering one or more *Bacillus* strains, one or more direct fed microbials or a composition to an animal to control, treat, or prevent growth of a pathogen as compared to an animal not fed the *Bacillus* strain, the direct fed microbial or the composition. In one embodiment, the pathogen is *Clostridium perfringens*.

In still another embodiment, the disclosure relates to a feed for an animal comprising one or more *Bacillus* strain, one or more DFM or one or more composition.

DESCRIPTION OF A PREFERRED EMBODIMENT

Examples

Example 1: Selection of *Bacillus* Strains to Inhibit *Clostridium perfringens* and Non-Toxigenic Clostridia Isolated from Feed Samples Introduction:

The ensiling process is a means of preserving the nutritional value of a moist crop by promoting anaerobic fermentation of the sugars present in the crop and converting them to lactic acid and other beneficial acidic compounds that preserve the material (Muck, 2010). The moist crop can support the growth of a variety of spoilage microorganisms, such as clostridia, bacilli, yeasts and molds that contribute to the degradation of nutrient value particularly when anaerobic conditions are not maintained or when the lactic acid end-product of anaerobic fermentation is inadequate to sufficiently decrease pH (Driehuis and Oude Elferink, 2000). Therefore, the ensiling process allows for long-term storage of feeding material for ruminant livestock when fresh forage is unavailable.

Because of the many variables that prevent ideal conditions for preserving silage, lactic acid bacteria are often utilized as silage inoculants to promote proper fermentation and optimal preservation of silage. Lactic acid bacteria grow quickly in anaerobic conditions and become the dominant microorganisms present in the crop, and lower the pH through the production of lactic acid, their fermentation end product. Enterobacteria and bacilli are controlled by lowering the pH to less than 5, whereas clostridia are more difficult to inhibit as some can grow at a lower pH (Driehuis, 2013). Therefore a lower pH may be needed to preserve the crop and prevent the growth of clostridial spoilage organisms when conditions are less optimal for lactic acid bacteria fermentation, such as in conditions of high moisture (Driehuis and Oude Elferink, 2000). These spoilage clostridia tend to have their negative effects on silage quality after the lactic acid bacteria have ceased growing.

Controlling clostridia organisms in silage is important to prevent the detrimental effects these bacteria have on silage quality. Generally, clostridia spoilage organisms are categorized into three groups including proteolytic clostridia that ferment amino acids and produce ammonia, amines, and carbon dioxide, the *Clostridium butyricum* group that ferments carbohydrates, and the *C. tyrobutyricum* group that ferments sugars and lactic acid, the latter two groups producing butyric acid, acetic acid, hydrogen, and carbon dioxide as end products (Muck, 2010). Clostridia activity in silage is undesirable due to the reduced intake observed in cattle when clostridial activity is present and because of the reduced nutritional quality of the silage that results from clostridial fermentation. The fermentation of lactic acid to butyric acid by the butyrate producing clostridia results in approximately 50% loss in dry matter and 18% loss in gross energy from the silage feedstuff (McDonald et al., 1991). Furthermore, clostridia spoilage organisms have a detrimental effect on the health of the cattle as evidenced by greater incidence of acidosis when cattle are fed clostridial silage (Seglar, 2003).

Clostridia fermentation in silage is controlled using lactic acid bacteria as silage inoculants to support the preservation of the crop and by ensuring the crop is harvested and ensiled under low-moisture conditions. However, managing the on-farm conditions such as weather that would impact the moisture content of the crop at harvest is not always practical or possible, and often ensiling occurs under suboptimal conditions. Although bacilli are considered silage spoilage organisms, members of the *Bacillus* genera are known to produce antimicrobial compounds capable of inhibiting competing bacteria in the surrounding environment, and have demonstrated efficacy in controlling the growth of clostridia Bacilli usually result in accelerating the spoilage of silage following exposure to oxygen, but rarely impact fermentation of the crop under the anaerobic conditions of the silo (Muck, 2010). Therefore, *Bacillus* strains are needed that can be added at the time of ensiling to control the growth of clostridia spoilage organisms in silage harvested under high-moisture conditions.

Materials and Methods:

Forage samples were gathered from 111 different dairies. Samples were diluted 1:10 with sterile peptone, heat shocked for 10 minutes at 50° C., enumerated in sterile peptone and pour plated on Tryptose Sulphite Cycloserine (TSC) agar with D-cycloserine (400 mg/L) to select for clostridia. Agar plates were incubated at 37° C. anaerobically for 24 hours for clostridia growth. If present, isolated sulphite-reducing colonies were picked to Reinforced Clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions of the cultures were performed in 96-well blocks containing 500 µl presumptive clostridia culture per well. Cells were harvested by centrifugation at 4,700 rpm for 10 minute and the supernatant was discarded. Cells were re-suspended in 500 µl of 50 mM of EDTA-2Na (pH=8.0). Aliquots of 300 µl of the suspended cells were transferred to a new 96-well block and combined with 20 µl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 µl of lysis buffer (6 M Guanidine, 20% Triton-X 100, 10 mM Tris-HCL, pH 7.5) was added, mixed then incubated at room temperature for 15 minutes. Following the incubation 20 µl of Proteinase K (NEB, 800 U/mL) was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed by centrifuging 750 µl of Column Wash Solution (Promega, A1318) at 4700 rpms for 1 minute and 30 seconds and discarding the flow through at the end of each spin. The binding plate was centrifuged for an additional 10 minutes at 4,700 rpm to remove any residual ethanol. A clean elution plate was then placed under the binding plate and DNA was eluted with 200 µl of Nuclease Free Water (Promega, P1195) pre-warmed to 55° C.

DNA was screened for toxin genes (α, β, ε, and ι) specific to *C. perfringens* using polymerase chain reaction (PCR). Amplification of toxin genes was executed using a multiplex PCR containing four primer sets (Yoo et al., 1997) (Table 1). The PCR mixture contained 2.5 µl 10×PCR Buffer, 2 µl of 50 mM $MgCl_2$, 0.5 µM of each primer, 0.1 µl of Invitrogen™ Platinum™ Taq DNA Polymerase, 2.5 µl of DNA, and sterile water to achieve 25 µl for a total reaction volume. The mixture underwent 5 minutes at 94° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved.

TABLE 1

Primers used to amplify *C. perfringens* toxin genes from the clostridia isolates collected, generate RAPD profiles from the *C. perfringens* positive isolates, and amplify the 16S rRNA gene from representatives of the non-toxigenic clostridia for DNA sequencing.

| Primer | Nucleotide sequence |
|---|---|
| Alpha Toxin Forward | 5'-GTTGATAGCGCAGGACATGTTAAG-3' (SEQ ID No. 7) |
| Alpha Toxin Reverse | 5'-CATGTAGTCATCTGTTCCAGCATC-3' (SEQ ID No. 8) |
| Beta Toxin Forward | 5'-ACTATACAGACAGATCATTCAACC-3' (SEQ ID No. 9) |
| Beta Toxin Reverse | 5'-TTAGGAGCAGTTAGAACTACAGAC-3' (SEQ ID No. 10) |
| Epsilon Toxin Forward | 5'-ACTGCAACTACTACTCATACTGTG-3' (SEQ ID No. 11) |
| Epsilon Toxin Reverse | 5'-CTGGTGCCTTAATAGAAAGACTCC-3' (SEQ ID No. 12) |
| Iota Toxin Forward | 5'-GCGATGAAAAGCCTACACCACTAC-3' (SEQ ID No. 13) |
| Iota Toxin Reverse | 5'-GGTATATCCTCCACGCATATAGTC-3' (SEQ ID No. 14) |
| RAPD primer 2 | GTTTCGCTCC (SEQ ID No. 15) |
| 16S_27F-YM | AGAGTTTGATYMTGGCTCAG (SEQ ID No. 16) |
| 16S_1492R-Y | TACCTTGTTAYGACTT (SEQ ID No. 17) |

Unique strain-specific genetic fingerprints were generated using Random Amplification of Polymorphic DNA (RAPD) analysis to determine diversity among silage clostridia isolates. The PCR contained 5 µl of DNA, 2.5 µl RAPD primer 2 (10 M; Table 4), and 17.5 µl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes, and finishing with a final elongation of 5 minutes at 72° C. The PCR products were observed on a Fragment Analyzer (Advanced Analytics) to determine amplification patterns and were imported into BioNumerics, bioinformatics software for analysis. RAPD patterns were compared with a band based Dice correlation analysis method to determine the similarity between RAPD patterns.

To identify non-toxigenic *Clostridium* isolates, a PCR reaction was performed on forage samples to amplify the 16S region of rDNA using primers 27F-YM and 1492R-Y (Table 1). The PCR mixture contained 5 µl of 10×PCR Buffer, 2 µl of 50 mM $MgCl_2$, of 50 mM dNTPs, 0.4 µM of each primer (Table 3.), 0.2 µl of Invitrogen™ Platinum™ Taq DNA Polymerase, 5 µl of DNA, and sterile water was added to achieve 50 µl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to MWG operon to obtain the sequences for the 16S genes. Sequences were compared to known typed bacterial strains obtained from EZbiocloud online electronic database. Based on comparisons of these sequences a bacterial identification was assigned to the isolates.

Antimicrobial screening was done on *C. perfringens* isolates and non-toxigenic clostridia isolates obtained from feed samples to gauge the effectiveness of the antimicrobial bacteriocin produced by the inventors' identified *Bacillus* strains 747, 1104, 1541, 1781, and 2018. Strain 1999 was tested against non-toxigenic clostridia isolates. Bacteriocin was harvested by growing each strain at 32° C. in a shaking incubator at 150 rpms for 24 hours in Brain Heart Infusion (BHI) broth. A 1% transfer of the 24 hour culture to fresh BHI broth was executed after incubation. The *Bacillus* were then incubated for 36-48 hours in a 32° C. shaking incubator at 150 rpms. The culture was then centrifuged at 14,000×g for 20 minutes, supernatant was then filtered with a 0.2 m filter to remove any residual cells.

A bacteriocin turbidity assay was executed by growing clostridia strains isolated from silage samples in Reinforced Clostridial Medium (RCM) for 24 hours, anaerobically, at 37° C. Overnight culture was transferred (1%) to sterile RCM and immediately used in the assay. Four replicates of each clostridia isolate were plated in a sterile 48 well reaction plate. Each clostridia isolate was tested as follows: 600 µl inoculated clostridia culture (positive control), 600 µl RCM+70 µl bacteriocin from *Bacillus* 2018, 600 µl RCM+70 µl bacteriocin from *Bacillus* 1104, 600 µl RCM+70 µl bacteriocin from *Bacillus* 1541, 600 µl RCM+70 µl bacteriocin from *Bacillus* 1781, 600 µl RCM+70 µl bacteriocin from *Bacillus* 747, and 670 RCM (negative control). Plates were incubated anaerobically at 37° C. for 24 hours then read using a BioTek Epoch Microplate Spectrophotometer with readings obtained at a wavelength of 600 nm. Before readings, 70 µl of sterile water was added to the positive control to ensure equal volumes in each well. Optical density readings from the negative controls were subtracted from all OD readings and percent inhibition was calculated using the each bacteriocin treatment relative to the positive control.

Results: Clostridia enumeration results, from 1,169 tested feed samples from 111 different locations, indicated the average level of clostridia CFU/g across all samples was 4.2 E+03 CFU/g. Individual samples ranged from <10 to 4.1 E+06 CFU/g (Table 2).

Figures 1, 2:
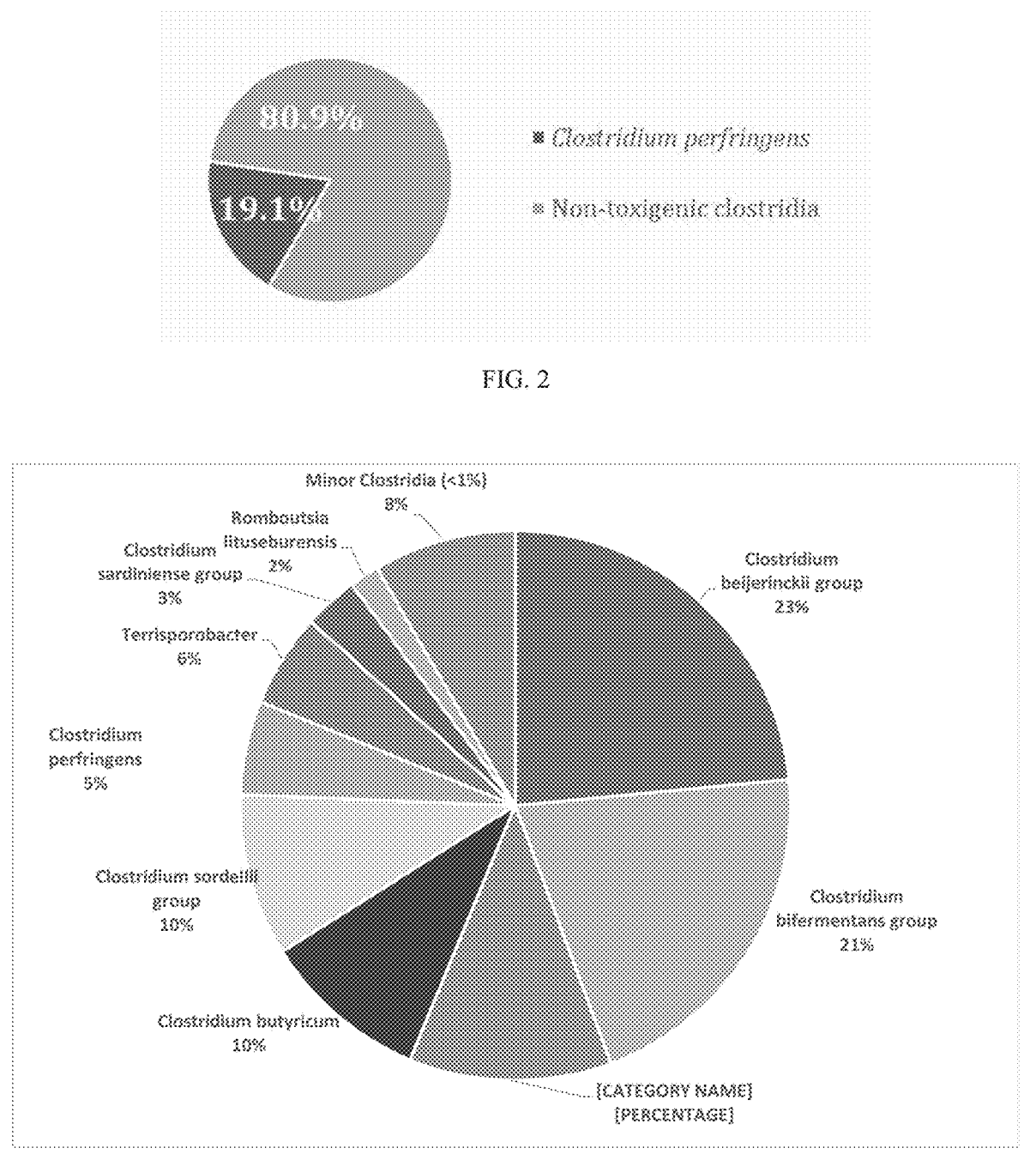

A total of 3,958 presumptive clostridia isolates have been tested for the indicated *C. perfringens* toxin genes. Isolates tested were harvested from silage samples collected from >100 different agricultural locations. Of the 3,958 isolates screened, 756 isolates (19.1%) tested positive for at least 1 of the toxin genes (FIG. 1). From the 756 toxin gene positive isolates 635 (84%) were identified as Type A (α toxin only), however β, ε and ι, toxins were also detected in the clostridia silage isolates.

Genetic RAPD fingerprint patterns displayed diversity among the 590 feed isolates that successfully amplified. These isolates were obtained from 70 different farm's samples and formed 133 clusters based on 75% similarity according to the Dice correlation method. The largest cluster was 40 isolates (9.7%) (FIG. 3).

Out of the 3,958 isolates collected 3,202 isolates (80.9%) were found to be non-toxigenic clostridia. Sequencing representatives (n=345) from the non-toxigenic Clostridia displayed two dominate clostridia groups: *C. bifermentans* (*Paraclostridium bifermentans* and *P. benzoelyticum*) and *C. beijerinckii* group (*C. diolis, C. beijerinckii, C. chromiireducens, C. saccharoperbutylacetonicum, C. puniceum,* and *C. saccharobutylicum*). *C. beijerinckii* species are known producers of acetone and butanol. *C. bifermentans* species are rare opportunistic pathogens that can produce 1, 3-propanediol. These two main identification types of the non-toxigenic clostridia group made up 44% of the non-toxigenic isolates (FIG. 2.).

Representatives (n=196) from each individual farm's RAPD dendrogram were selected to capture the diversity of the *C. perfringens* population and subjected to inhibition assays. The combined data of the individual locations is made up of 41 different sites (Table 3). Antimicrobial testing using the bacteriocin turbidity assay displayed good inhibition of most feed *C. perfringens* isolates using bacteriocin harvested from 747, 1104, 1541, 1781, and 2018. The bacteriocin from at least one of the strains 747, 1104, 1541, 1781, and 2018 were able to inhibit the growth >60% of 126 (64.3%) of the 196 isolates tested. At least one bacteriocin strain was able to inhibit the growth of 97 (49.5%) of the 196 isolates tested by greater than 79%. Strain 747 had the highest overall inhibition across all *C. perfringens* silage isolates tested at 54.9%.

Non-toxigenic clostridia isolates (n=14) collected from two different dairies in Texas were also subjected to inhibition assays. The isolates tested consisted of *C. bifermentans* group, *C. butyricum, C. beijerinckii* group, *C. ghonii, Clostridium tertium* group, and *C. sordellii* (Table 4). The bacteriocin from at least one of the strains 747, 1104, 1541, 1781, 1999 and 2018 were able to inhibit the growth >60% of 11 (78.6%) of the 14 isolates tested. At least one bacteriocin strain was able to inhibit the growth of 9(64.3%) of the 14 isolates tested by greater than 79%. Strain 747 had the highest overall inhibition across all non-toxigenic clostridia silage isolates tested at 77.2%.

TABLE 2

Number of samples and average clostridia count results by location

| Location | Sample # | Average Clostridia (CFU/g) |
|---|---|---|
| 1 | 4 | 1.0E+01 |
| 2 | 1 | 4.0E+01 |
| 3 | 2 | 2.3E+01 |
| 4 | 6 | 1.2E+03 |
| 5 | 18 | 8.7E+01 |
| 6 | 34 | 1.6E+02 |
| 7 | 2 | 3.5E+01 |
| 8 | 9 | 5.6E+02 |
| 9 | 26 | 6.8E+01 |
| 10 | 26 | 5.0E+01 |
| 11 | 24 | 7.9E+01 |
| 12 | 15 | 3.3E+03 |
| 13 | 4 | 4.9E+02 |
| 14 | 2 | 3.0E+01 |
| 15 | 14 | 5.7E+01 |
| 16 | 6 | 4.7E+01 |
| 17 | 1 | 9.5E+01 |
| 18 | 1 | 2.5E+01 |
| 19 | 1 | 1.0E+01 |
| 20 | 1 | 5.0E+01 |
| 21 | 12 | 3.1E+01 |
| 22 | 6 | 2.9E+01 |
| 23 | 2 | 1.0E+01 |
| 24 | 19 | 3.1E+01 |
| 25 | 2 | 5.1E+02 |
| 26 | 31 | 5.5E+03 |
| 27 | 3 | 6.7E+00 |
| 28 | 1 | 3.0E+01 |
| 29 | 5 | 1.1E+02 |
| 30 | 9 | 7.2E+02 |
| 31 | 4 | 2.3E+02 |
| 32 | 33 | 3.6E+01 |
| 33 | 18 | 1.9E+02 |
| 34 | 1 | 1.5E+01 |
| 35 | 5 | 1.9E+03 |
| 36 | 2 | 1.0E+01 |
| 37 | 13 | 7.7E+01 |
| 38 | 6 | 9.2E+00 |
| 39 | 17 | 3.4E+02 |
| 40 | 10 | 9.0E+01 |
| 41 | 47 | 4.0E+02 |
| 42 | 11 | 1.2E+02 |
| 43 | 9 | 5.3E+01 |
| 44 | 13 | 6.1E+03 |
| 45 | 3 | 3.7E+01 |
| 46 | 4 | 2.0E+02 |
| 47 | 4 | 1.4E+01 |
| 48 | 12 | 3.4E+05 |
| 49 | 5 | 9.0E+00 |
| 50 | 12 | 2.9E+01 |
| 51 | 20 | 2.0E+01 |
| 52 | 34 | 1.1E+02 |
| 53 | 14 | 6.4E+02 |
| 54 | 2 | 1.0E+01 |
| 55 | 1 | 0.0E+00 |
| 56 | 9 | 3.4E+03 |
| 57 | 5 | 9.2E+02 |
| 58 | 10 | 2.7E+01 |

TABLE 2-continued

Number of samples and average clostridia count results by location

| Location | Sample # | Average Clostridia (CFU/g) |
|---|---|---|
| 59 | 2 | 1.0E+01 |
| 60 | 13 | 7.5E+01 |
| 61 | 6 | 2.7E+03 |
| 62 | 2 | 1.9E+02 |
| 63 | 8 | 2.0E+02 |
| 64 | 2 | 7.5E+00 |
| 65 | 7 | 1.0E+02 |
| 66 | 13 | 6.0E+01 |
| 67 | 21 | 2.3E+02 |
| 68 | 21 | 7.6E+03 |
| 69 | 2 | 1.5E+01 |
| 70 | 37 | 9.7E+02 |
| 71 | 17 | 3.0E+02 |
| 72 | 4 | 9.5E+01 |
| 73 | 7 | 1.6E+02 |
| 74 | 3 | 1.1E+02 |
| 75 | 10 | 5.5E+01 |
| 76 | 11 | 7.1E+01 |
| 77 | 4 | 4.0E+02 |
| 78 | 5 | 9.6E+01 |
| 79 | 9 | 3.3E+01 |
| 80 | 9 | 1.2E+02 |
| 81 | 47 | 8.9E+01 |
| 82 | 14 | 5.1E+01 |
| 83 | 8 | 1.7E+04 |
| 84 | 2 | 7.5E+00 |
| 85 | 1 | 5.0E+01 |
| 86 | 9 | 4.2E+01 |
| 87 | 7 | 3.3E+01 |
| 88 | 13 | 3.3E+01 |
| 89 | 4 | 1.5E+01 |
| 90 | 13 | 1.2E+02 |
| 91 | 14 | 1.3E+02 |
| 92 | 7 | 2.6E+01 |
| 93 | 7 | 2.4E+04 |
| 94 | 12 | 1.1E+04 |
| 95 | 3 | 1.2E+01 |
| 96 | 2 | 1.0E+01 |
| 97 | 2 | 4.8E+01 |
| 98 | 3 | 2.2E+01 |
| 99 | 1 | 1.0E+03 |
| 100 | 3 | 8.3E+00 |
| 101 | 7 | 8.6E+00 |
| 102 | 10 | 2.5E+04 |
| 103 | 2 | 8.5E+01 |
| 104 | 44 | 7.5E+02 |
| 105 | 17 | 9.5E+01 |
| 106 | 1 | 3.0E+01 |
| 107 | 12 | 7.0E+01 |
| 108 | 17 | 1.3E+02 |
| 109 | 46 | 3.2E+01 |
| 110 | 14 | 3.0E+01 |
| 111 | 3 | 8.3E+00 |
| Total Samples | 1,169 | |
| Average Clostridial level | | 4.2E+03 |

TABLE 3

Percent inhibition of each silage *C. perfringens* isolate tested against bacteriocin harvested from *Bacillus* isolates.

| | | | *Bacillus* Strains | | | | |
|---|---|---|---|---|---|---|---|
| Isolate ID | Location | Sample Type | 747 | 1104 | 1541 | 1781 | 2018 |
| S72.11.1 | Location 4 | Dry Alfalfa | 8.0% | 2.6% | 0.0% | 5.3% | 20.3% |
| S72.11.4 | Location 4 | Dry Alfalfa | 0.0% | 0.0% | 99.3% | 0.0% | 3.6% |
| S72.18.7 | Location 4 | Pellets | 88.2% | 99.8% | 99.7% | 98.3% | 61.2% |
| S72.4.6 | Location 4 | Deep Silage | 58.6% | 79.8% | 79.2% | 58.0% | 69.5% |

TABLE 3-continued

Percent inhibition of each silage *C. perfringens* isolate tested against bacteriocin harvested from *Bacillus* isolates.

| | | | *Bacillus* Strains | | | | |
|---|---|---|---|---|---|---|---|
| Isolate ID | Location | Sample Type | 747 | 1104 | 1541 | 1781 | 2018 |
| S114.3.5 | Location 5 | TMR Pen 3 | 99.2% | 73.6% | 79.1% | 87.6% | 87.2% |
| S114.7.3 | Location 5 | Dry Cow TMR | 99.6% | 99.8% | 99.8% | 99.5% | 99.5% |
| S120.1.8 | Location 9 | Dry Cow TMR | 100.2% | 5.6% | 99.9% | 12.6% | 43.6% |
| S120.3.1 | Location 9 | 1st Calf Heifer TMR | 99.0% | 25.6% | 100.0% | 23.0% | 25.9% |
| S120.3.10 | Location 9 | 1st Calf Heifer TMR | 0.0% | 0.0% | 0.0% | 0.0% | 0.0% |
| S120.3.3 | Location 9 | 1st Calf Heifer TMR | 18.8% | 0.0% | 0.0% | 0.0% | 0.0% |
| S120.4.2 | Location 9 | Fresh Cow TMR | 100.0% | 97.5% | 100.0% | 10.6% | 81.0% |
| S120.4.6 | Location 9 | Fresh Cow TMR | 76.5% | 75.1% | 77.0% | 75.3% | 69.7% |
| S120.5.6 | Location 9 | Lac. Cow TMR P5 | 26.9% | 0.0% | 0.0% | 0.0% | 0.0% |
| S120.5.7 | Location 9 | Lac. Cow TMR P10 | 0.0% | 0.0% | 0.0% | 0.0% | 0.0% |
| S120.7.1 | Location 9 | Ground Corn | 0.0% | 0.0% | 0.0% | 0.0% | 0.0% |
| S97.16.2 | Location 10 | Grass Hay | 74.6% | 74.1% | 73.7% | 74.6% | 74.6% |
| S50.4.1 | Location 14 | Fresh Cow TMR | 0.0% | 0.0% | 0.0% | 0.0% | 0.0% |
| S50.4.6 | Location 14 | Fresh Cow TMR | 0.0% | 0.0% | 0.0% | 0.0% | 0.0% |
| S50.5.3 | Location 14 | Prefresh TMR | 0.0% | 0.0% | 0.0% | 0.0% | 0.0% |
| S50.5.5 | Location 14 | Prefresh TMR | 0.0% | 0.0% | 0.0% | 0.0% | 0.0% |
| S50.5.8 | Location 14 | Prefresh TMR | 0.0% | 0.0% | 0.0% | 10.4% | 13.9% |
| S50.6.1 | Location 14 | High Cow TMR | 0.0% | 0.0% | 0.0% | 0.0% | 0.0% |
| S50.6.3 | Location 14 | High Cow TMR | 0.0% | 0.0% | 0.0% | 0.0% | 0.0% |
| S53.11.1 | Location 17 | Fresh | 0.0% | 0.0% | 0.0% | 0.0% | 0.0% |
| S53.5.5 | Location 17 | Dry Cows | 0.0% | 0.0% | 0.0% | 0.0% | 2.1% |
| S53.5.6 | Location 17 | Dry Cows | 32.6% | 35.9% | 9.1% | 41.1% | 40.7% |
| S53.5.7 | Location 17 | Dry Cows | 0.0% | 0.0% | 0.0% | 0.0% | 0.0% |
| S53.7.3 | Location 17 | Ground Corn | 0.0% | 6.4% | 0.0% | 7.3% | 0.0% |
| S53.7.6 | Location 17 | Ground Corn | 0.0% | 0.0% | 0.0% | 0.0% | 0.0% |
| S53.7.7 | Location 17 | Ground Corn | 10.9% | 0.0% | 0.0% | 0.0% | 8.4% |
| 30.4.2 | Location 19 | Corn Silage B7 | 43.0% | 43.0% | 46.0% | 45.0% | 43.0% |
| S54.1.1 | Location 20 | Wet Brewers Grain | 89.8% | 91.3% | 93.1% | 0.0% | 2.6% |
| S54.16.2 | Location 20 | Fresh Cow TMR | 0.0% | 0.0% | 0.0% | 0.0% | 0.0% |
| S54.18.3 | Location 20 | High Cow TMR | 0.0% | 0.0% | 0.0% | 0.0% | 0.0% |
| S54.19.4 | Location 20 | Far Off Dry TMR | 0.0% | 0.0% | 0.0% | 0.0% | 0.0% |
| S70.1.6 | Location 22 | Corn Silage | 99.6% | 99.7% | 81.4% | 99.7% | 99.6% |
| S70.1.7 | Location 22 | Corn Silage | 99.7% | 99.7% | 100.0% | 99.7% | 99.7% |
| S70.10.9 | Location 22 | High Cow Premix | 99.8% | 100.0% | 100.0% | 100.0% | 100.0% |
| S117.2.6 | Location 25 | Canola | 97.0% | 38.5% | 21.6% | 0.0% | 27.6% |
| S117.4.10 | Location 25 | Cotton Seed | 67.4% | 27.1% | 5.1% | 17.9% | 22.6% |
| S41.10.1 | Location 27 | Protein Mix | 98.9% | 98.8% | 97.1% | 98.7% | 98.7% |
| S41.12.2 | Location 27 | Molasses | 84.2% | 78.8% | 83.4% | 84.9% | 82.8% |
| S63.1.1 | Location 27 | Corn Silage B1 2015 | 98.6% | 96.1% | 98.9% | 99.2% | 99.2% |
| S63.2.2 | Location 27 | Alfalfa Haylage B3 2015 | 7.7% | 67.1% | 23.4% | 41.9% | 50.0% |
| S63.2.4 | Location 27 | Alfalfa Haylage B3 2015 | 89.0% | 74.3% | 89.6% | 88.7% | 87.8% |
| S63.3.1 | Location 27 | Alfalfa Haylage B4 2nd 2016 | 98.1% | 54.4% | 98.1% | 37.5% | 98.1% |
| S63.5.10 | Location 27 | TMR 5 | 71.9% | 9.1% | 59.8% | 56.5% | 63.6% |
| S63.5.2 | Location 27 | TMR 5 | 92.2% | 56.7% | 68.8% | 82.0% | 67.1% |
| S63.5.3 | Location 27 | TMR 5 | 46.8% | 65.5% | 53.4% | 66.5% | 61.8% |
| S63.5.4 | Location 27 | TMR 5 | 75.8% | 10.5% | 53.8% | 50.3% | 35.7% |
| S63.5.5 | Location 27 | TMR 5 | 82.9% | 15.9% | 89.9% | 87.7% | 86.4% |
| S63.5.6 | Location 27 | TMR 5 | 99.5% | 99.8% | 94.7% | 99.3% | 99.1% |
| S63.5.7 | Location 27 | TMR 5 | 96.4% | 94.6% | 79.8% | 97.3% | 82.0% |
| S63.5.9 | Location 27 | TMR 5 | 98.0% | 26.5% | 93.4% | 93.9% | 79.8% |
| S63.6.1 | Location 27 | Dry Corn | 98.8% | 20.6% | 95.6% | 98.1% | 95.6% |
| S63.6.3 | Location 27 | Dry Corn | 32.0% | 43.1% | 45.5% | 0.0% | 52.2% |
| S63.6.5 | Location 27 | Dry Corn | 99.5% | 20.1% | 96.4% | 62.3% | 99.3% |
| S63.9.1 | Location 27 | Protein Blend with Bacillus | 3.6% | 36.1% | 86.8% | 53.6% | 80.0% |
| S73.8.1 | Location 28 | Haylage Deep | 24.9% | 0.0% | 0.0% | 25.5% | 0.0% |
| S73.8.2 | Location 28 | Haylage Deep | 18.3% | 0.0% | 0.0% | 23.7% | 0.0% |
| S59.10.2 | Location 33 | High Cow Ration Pen 13 | 33.9% | 33.9% | 28.8% | 45.7% | 24.2% |
| S59.10.3 | Location 33 | High Cow Ration Pen 13 | 44.0% | 44.9% | 44.7% | 45.0% | 45.7% |
| S59.11.1 | Location 33 | Dry Cow Ration | 87.0% | 71.3% | 62.5% | 76.0% | 68.5% |
| S59.14.1 | Location 33 | Canola | 0.0% | 0.0% | 0.0% | 0.0% | 0.0% |
| S59.14.4 | Location 33 | Canola | 65.5% | 37.8% | 33.9% | 75.6% | 33.1% |
| S59.14.7 | Location 33 | Canola | 35.1% | 0.0% | 0.0% | 7.9% | 0.0% |
| S59.15.2 | Location 33 | One Track | 3.4% | 2.6% | 0.0% | 5.5% | 5.0% |
| S59.8.1 | Location 33 | Close Up Cow Pen 8 | 12.7% | 5.3% | 4.8% | 6.7% | 0.0% |
| S59.8.2 | Location 33 | Close Up Cow Pen 8 | 17.4% | 22.2% | 18.7% | 14.0% | 22.1% |
| S59.8.3 | Location 33 | Close Up Cow Pen 8 | 10.1% | 17.2% | 13.9% | 46.5% | 12.6% |

TABLE 3-continued

Percent inhibition of each silage *C. perfringens* isolate tested against bacteriocin harvested from *Bacillus* isolates.

| Isolate ID | Location | Sample Type | *Bacillus* Strains | | | | |
|---|---|---|---|---|---|---|---|
| | | | 747 | 1104 | 1541 | 1781 | 2018 |
| S59.9.1 | Location 33 | Medium Cow Ration Pen 4 | 95.5% | 61.9% | 58.7% | 100.0% | 43.9% |
| S59.9.2 | Location 33 | Medium Cow Ration Pen 4 | 83.9% | 62.1% | 44.0% | 72.5% | 64.1% |
| S69.5.5 | Location 34 | Close Up TMR | 100.0% | 100.0% | 100.0% | 100.0% | 100.0% |
| S69.6.2 | Location 34 | Dry Cow TMR | 6.2% | 0.0% | 4.7% | 4.8% | 9.3% |
| S69.6.6 | Location 34 | Dry Cow TMR | 28.0% | 0.0% | 2.7% | 19.6% | 30.9% |
| S57.6.5 | Location 36 | Cow Ration Lac | 0.0% | 0.0% | 0.0% | 0.0% | 0.0% |
| S58.4.1 | Location 36 | Early Lac Ration | 34.9% | 57.8% | 34.1% | 96.2% | 37.9% |
| S58.4.10 | Location 36 | Early Lac Ration | 100.0% | 100.0% | 100.0% | 100.0% | 100.0% |
| S58.4.2 | Location 36 | Early Lac Ration | 50.1% | 15.2% | 24.7% | 86.1% | 15.3% |
| S58.4.9 | Location 36 | Early Lac Ration | 15.9% | 0.0% | 0.0% | 0.0% | 100.0% |
| S58.5.1 | Location 36 | Mid Lac Ration | 8.5% | 14.3% | 9.0% | 9.8% | 5.6% |
| S58.5.2 | Location 36 | Mid Lac Ration | 68.9% | 47.2% | 44.9% | 73.7% | 37.3% |
| S58.6.1 | Location 36 | Dry Cow Ration | 6.1% | 0.0% | 0.0% | 3.4% | 100.0% |
| S58.8.1 | Location 36 | Dry Cow Ration | 95.6% | 55.1% | 100.0% | 100.0% | 0.0% |
| S58.8.3 | Location 36 | Pellets | 88.1% | 59.2% | 55.7% | 94.9% | 80.8% |
| S58.9.4 | Location 36 | Cotton | 49.3% | 38.6% | 14.5% | 100.0% | 22.8% |
| S58.9.5 | Location 36 | Cotton | 78.2% | 40.6% | 45.5% | 77.9% | 49.0% |
| 21.2.3 | Location 39 | Haylage B3 | 100.0% | 98.0% | 74.0% | 99.0% | 97.0% |
| 21.2.4 | Location 39 | Haylage | 33.9% | 5.2% | 4.7% | 2.2% | 5.3% |
| 21.2.5 | Location 39 | Haylage B3 | 98.0% | 49.0% | 42.0% | 94.0% | 48.0% |
| 21.2.7 | Location 39 | Haylage B3 | 98.0% | 96.0% | 96.0% | 98.0% | 96.0% |
| S51.2.2 | Location 43 | Haylage | 1.9% | 0.0% | 0.0% | 0.0% | 0.0% |
| S104.4.4 | Location 44 | Alfalfa Haylage 4th | 0.0% | 0.0% | 0.0% | 0.0% | 95.2% |
| S104.4.7 | Location 44 | Alfalfa Haylage 4th | 0.0% | 0.0% | 0.0% | 0.0% | 0.0% |
| CSS-4 | Location 44 | Corn Silage | 29.5% | 31.7% | 96.2% | 38.3% | 28.6% |
| HSS-1 | Location 44 | Haylage | 99.9% | 100.0% | 99.9% | 100.0% | 99.9% |
| 28.1.2 | Location 44 | Ryelage | 64.0% | 63.0% | 91.0% | 63.0% | 69.0% |
| S74.7.1 | Location 45 | Ground Corn | 73.9% | 65.9% | 46.1% | 35.3% | 65.9% |
| S76.3.5 | Location 46 | Baylage 4th Home | 77.5% | 36.4% | 100.0% | 37.2% | 73.6% |
| S76.3.8 | Location 46 | Baylage 4th Home | 50.7% | 14.2% | 97.8% | 51.6% | 42.7% |
| S75.3.1 | Location 47 | Close-up TMR | 100.0% | 99.2% | 100.0% | 100.0% | 100.0% |
| S75.3.10 | Location 47 | Close-up TMR | 100.0% | 100.0% | 100.0% | 100.0% | 100.0% |
| S75.5.1 | Location 47 | Late TMR | 34.4% | 24.2% | 40.7% | 60.0% | 43.1% |
| S75.8.1 | Location 47 | Calf Pellets | 100.0% | 100.0% | 100.0% | 100.0% | 100.0% |
| S75.8.3 | Location 47 | Calf Pellets | 100.0% | 99.8% | 99.7% | 100.0% | 100.0% |
| S75.8.5 | Location 47 | Calf Pellets | 100.0% | 100.0% | 100.0% | 100.0% | 99.2% |
| S75.8.9 | Location 47 | Calf Pellets | 100.0% | 100.0% | 100.0% | 100.0% | 100.0% |
| S75.9.1 | Location 47 | Soy Hulls | 100.0% | 100.0% | 99.7% | 100.0% | 99.7% |
| S75.9.2 | Location 47 | Soy Hulls | 99.7% | 100.0% | 99.5% | 99.8% | 99.8% |
| S61.10.6 | Location 52 | TMR 1 | 44.5% | 20.2% | 6.8% | 54.3% | 16.4% |
| S61.12.1 | Location 52 | TMR 3 | 57.1% | 0.0% | 40.8% | 12.8% | 9.3% |
| S61.12.10 | Location 52 | TMR 3 | 0.0% | 0.0% | 0.0% | 0.0% | 0.0% |
| S61.12.5 | Location 52 | TMR 3 | 0.0% | 0.0% | 0.0% | 0.0% | 0.0% |
| S61.12.7 | Location 52 | TMR 3 | 0.0% | 0.0% | 0.0% | 0.0% | 0.0% |
| S61.3.2 | Location 52 | Corn Silage Face | 95.0% | 92.8% | 92.3% | 90.3% | 89.9% |
| S61.3.4 | Location 52 | Corn Silage Face | 0.0% | 94.4% | 94.4% | 0.0% | 92.1% |
| S61.5.3 | Location 52 | Dry Hay Ontario | 95.3% | 7.7% | 98.3% | 89.8% | 95.1% |
| S99.6.5 | Location 53 | Close Up TMR | 0.0% | 1.3% | 16.7% | 0.0% | 0.0% |
| Silage 3-3 | Location 54 | Silage | 98.9% | 99.6% | 100.0% | 99.3% | 99.8% |
| Silage 3-4 | Location 54 | Silage | 98.4% | 100.0% | 100.0% | 98.8% | 100.0% |
| Silage 3-5 | Location 54 | Silage | 34.1% | 0.0% | 29.8% | 3.8% | 30.8% |
| Silage 8-1 | Location 54 | Silage | 86.7% | 100.0% | 86.7% | 86.7% | 100.0% |
| S36.1.6 | Location 55 | Face Wheatlage | 100.0% | 100.0% | 100.0% | 100.0% | 100.0% |
| S36.1.7 | Location 55 | Face Wheatlage | 100.0% | 0.0% | 100.0% | 0.0% | 100.0% |
| S81.10.6 | Location 59 | Wheat Midds | 100.0% | 100.0% | 100.0% | 100.0% | 100.0% |
| S81.11.1 | Location 59 | Bird Seed Screening | 91.5% | 82.3% | 91.1% | 83.0% | 80.1% |
| S81.11.7 | Location 59 | Bird Seed Screening | 30.5% | 32.9% | 22.6% | 37.2% | 27.1% |
| S81.3.6 | Location 59 | 3rd Haylage | 25.4% | 0.0% | 0.0% | 0.0% | 0.0% |
| S81.7.4 | Location 59 | Cow TMR | 94.5% | 90.9% | 89.5% | 92.4% | 92.0% |
| S89.15.3 | Location 60 | WOM #1046 | 2.8% | 0.0% | 0.0% | 8.3% | 30.0% |
| S89.20.7 | Location 60 | WOM #1550 | 11.3% | 0.0% | 0.0% | 21.0% | 24.7% |
| S89.20.9 | Location 60 | WOM #1550 | 0.0% | 0.0% | 0.0% | 0.0% | 28.8% |
| S89.3.1 | Location 60 | Ryegrass Haylage | 26.9% | 4.3% | 0.0% | 13.1% | 5.0% |
| S49.10.4 | Location 60 | Pen 432 Conventional 30 Ration | 0.0% | 0.0% | 0.0% | 0.0% | 0.0% |
| S49.5.3 | Location 60 | Pen 146 Natural Starter | 22.4% | 12.7% | 19.5% | 2.6% | 18.1% |
| S71.10.10 | Location 63 | Dry Cow Ration | 59.7% | 66.2% | 44.7% | 10.4% | 36.8% |
| S71.17.1 | Location 63 | Burrs | 0.7% | 0.0% | 10.5% | 14.7% | 34.2% |
| S71.17.2 | Location 63 | Burrs | 0.0% | 0.0% | 8.7% | 1.9% | 19.6% |
| S71.9.3 | Location 63 | Late Lac Ration | 79.5% | 34.5% | 20.3% | 49.5% | 39.8% |

TABLE 3-continued

Percent inhibition of each silage *C. perfringens* isolate tested against bacteriocin harvested from *Bacillus* isolates.

| | | | Bacillus Strains | | | | |
|---|---|---|---|---|---|---|---|
| Isolate ID | Location | Sample Type | 747 | 1104 | 1541 | 1781 | 2018 |
| S71.9.5 | Location 63 | Late Lac Ration | 65.7% | 63.5% | 64.9% | 69.5% | 54.8% |
| 3.1.3 | Location 65 | Corn Silage | 100.0% | 100.0% | 100.0% | 100.0% | 100.0% |
| 3.1.4 | Location 65 | Corn Silage | 72.0% | 68.0% | 91.0% | 70.0% | 80.0% |
| 31.2.1 | Location 65 | Haylage | 43.0% | 37.0% | 36.0% | 41.0% | 41.0% |
| 27.2.11 | Location 67 | Haylage | 98.0% | 91.0% | 81.0% | 95.0% | 91.0% |
| 27.3.2 | Location 67 | Oatlage | 93.0% | 66.0% | 66.0% | 80.0% | 75.0% |
| 27.3.3 | Location 67 | Oatlage | 100.0% | 100.0% | 100.0% | 100.0% | 100.0% |
| S91.2.4 | Location 68 | Grass Haylage | 82.4% | 77.4% | 80.5% | 86.6% | 82.2% |
| S91.2.5 | Location 68 | Grass Haylage | 77.9% | 50.5% | 57.2% | 74.1% | 40.4% |
| S91.3.5 | Location 68 | Pre Fresh | 65.5% | 73.5% | 76.1% | 64.5% | 66.7% |
| S91.5.4 | Location 68 | Low TMR | 73.8% | 76.3% | 74.9% | 62.4% | 66.0% |
| S56.1.2 | Location 72 | Pellets | 98.1% | 96.7% | 97.5% | 96.6% | 96.2% |
| S56.1.3 | Location 72 | Pellets | 11.8% | 1.9% | 5.5% | 0.0% | 4.5% |
| S56.7.6 | Location 72 | Corn Silage Face | 38.8% | 4.5% | 0.0% | 13.2% | 32.4% |
| S56.9.1 | Location 72 | Milk Cow TMR | 40.6% | 39.7% | 56.7% | 39.8% | 54.8% |
| S56.9.3 | Location 72 | Milk Cow TMR | 4.6% | 0.0% | 6.1% | 0.0% | 11.5% |
| S56.9.6 | Location 72 | Milk Cow TMR | 0.0% | 0.0% | 0.0% | 0.0% | 0.0% |
| S56.9.7 | Location 72 | Milk Cow TMR | 0.0% | 0.0% | 0.0% | 0.0% | 0.0% |
| S52.14.1 | Location 76 | Robot Barn | 0.0% | 0.0% | 11.8% | 20.6% | 69.0% |
| S52.14.7 | Location 76 | Robot Barn | 0.0% | 0.0% | 0.0% | 0.0% | 0.0% |
| S57.4.1 | Location 80 | New Alfalfa Haylage Compost | 0.0% | 0.0% | 0.0% | 0.0% | 0.0% |
| RF-1 | Location 85 | Corn Silage | 100.0% | 100.0% | 100.0% | 100.0% | 100.0% |
| ROL-1 | Location 85 | Haylage-Old | 92.6% | 94.7% | 94.5% | 94.4% | 89.5% |
| ROL-3 | Location 85 | Haylage-Old | 99.9% | 100.0% | 99.8% | 99.9% | 99.7% |
| ROS-1 | Location 85 | Haylage-Old | 35.9% | 16.1% | 17.4% | 17.0% | 18.5% |
| ROS-3 | Location 85 | Haylage-Old | 100.0% | 20.3% | 28.9% | 25.1% | 50.5% |
| S102.1.10 | Location 85 | Baylage Mark | 58.5% | 62.1% | 66.4% | 57.4% | 57.3% |
| S102.1.3 | Location 85 | Baylage Mark | 35.8% | 44.2% | 45.8% | 29.2% | 41.2% |
| S102.1.9 | Location 85 | Baylage Mark | 49.2% | 51.3% | 43.4% | 50.9% | 53.4% |
| S102.11.1 | Location 85 | Fresh TMR | 0.0% | 11.7% | 0.0% | 0.0% | 0.0% |
| S102.7.3 | Location 85 | Fresh Heifer TMR | 80.3% | 1.3% | 63.3% | 74.4% | 76.7% |
| S102.8.4 | Location 85 | Close Up Cow TMR | 67.8% | 49.4% | 85.5% | 71.1% | 65.3% |
| S102.8.5 | Location 85 | Close Up Cow TMR | 59.2% | 40.0% | 71.6% | 62.4% | 55.8% |
| S102.8.8 | Location 85 | Close Up Cow TMR | 80.5% | 59.8% | 80.0% | 85.2% | 85.4% |
| S111.4.9 | Location 86 | Lactation 1 TMR | 75.7% | 73.4% | 99.5% | 80.1% | 92.3% |
| 20.1.3 | Location 87 | Corn Silage B1 | 12.0% | 12.0% | 11.0% | 17.0% | 12.0% |
| 20.1.5 | Location 87 | Corn Silage B1 | 21.0% | 18.0% | 37.0% | 25.0% | 19.0% |
| 20.3.1 | Location 87 | Haylage B6 | 85.0% | 89.0% | 84.0% | 90.0% | 80.0% |
| 20.3.3 | Location 87 | Haylage | 90.0% | 92.7% | 94.1% | 93.1% | 93.0% |
| 20.3.5 | Location 87 | Haylage | 99.7% | 100.0% | 99.9% | 99.9% | 100.0% |
| 20.4.6 | Location 87 | Corn Silage B7 | 100.0% | 100.0% | 100.0% | 100.0% | 100.0% |
| S80.4.1 | Location 91 | Cow TMR | 0.0% | 0.0% | 0.0% | 33.7% | 13.4% |
| S55.9.1 | Location 92 | Dry Cow TMR | 30.4% | 5.7% | 0.0% | 19.2% | 0.0% |
| S40.1.8 | Location 99 | Oatlage | 98.4% | 86.8% | 97.0% | 95.8% | 93.5% |
| S47.1.6 | Location 99 | Alfalfa Haylage West | 19.3% | 0.0% | 5.9% | 0.0% | 28.6% |
| S60.4.1 | Location 99 | Ryelage | 96.9% | 50.5% | 96.9% | 97.5% | 96.9% |
| S60.4.10 | Location 99 | Ryelage | 95.4% | 94.8% | 95.4% | 96.1% | 94.8% |
| S60.4.4 | Location 99 | Ryelage | 99.0% | 99.1% | 99.0% | 98.8% | 99.0% |
| S60.4.6 | Location 99 | Ryelage | 99.4% | 94.6% | 99.5% | 99.4% | 99.5% |
| S60.4.8 | Location 99 | Ryelage | 97.9% | 19.5% | 97.9% | 98.0% | 98.5% |
| S60.5.1 | Location 99 | Milk Cow TMR | 97.6% | 27.6% | 93.3% | 89.8% | 83.5% |
| S60.7.1 | Location 99 | Whey | 98.8% | 99.3% | 99.0% | 98.8% | 99.0% |
| S60.7.10 | Location 99 | Whey | 98.4% | 10.1% | 98.7% | 97.6% | 94.3% |
| S60.7.3 | Location 99 | Whey | 99.1% | 97.9% | 99.0% | 98.5% | 98.6% |
| S60.7.8 | Location 99 | Whey | 82.6% | 85.5% | 98.6% | 98.6% | 99.0% |
| S60.7.9 | Location 99 | Whey | 98.8% | 96.2% | 98.6% | 98.2% | 98.8% |
| S77.6.3 | Location 100 | Heifer Haylage Deep | 96.3% | 96.3% | 96.3% | 97.9% | 95.5% |
| | | Average Percent Inhibition | 54.9% | 43.4% | 51.4% | 50.14% | 51.55% |

TABLE 4

Percent inhibition of non-toxigenic clostridia isolates collected from Texas feed samples against bacteriocin harvested from *Bacillus* isolates.

| | | *Bacillus* Strains | | | | | |
|---|---|---|---|---|---|---|---|
| Isolate ID | 16S ID | 747 | 1104 | 1541 | 1781 | 1999 | 2018 |
| S35.1.1 | *C. butyricum* | 76.8% | 51.8% | 41.4% | 43.8% | 41.2% | 76.3% |
| S37.1.1 | *Clostridium tertium* group | 94.8% | 0.0% | 34.2% | 29.3% | Not Tested | 84.0% |
| S37.11.1 | *Clostridium sordellii* group | 24.5% | 23.1% | 23.0% | 23.6% | Not Tested | 24.2% |
| S37.11.2 | *Clostridium beijerinckii* group | 24.3% | 22.8% | 21.8% | 20.0% | Not Tested | 20.3% |
| S37.11.3 | *Clostridium beijerinckii* group | 24.1% | 21.9% | 25.5% | 21.1% | Not Tested | 28.9% |
| S37.11.4 | *Clostridium sordellii* group | 97.3% | 97.2% | 96.5% | 96.4% | Not Tested | 97.0% |
| S37.11.5 | *Clostridium tertium* group | 96.0% | 36.6% | 77.4% | 80.0% | Not Tested | 80.7% |
| S37.11.6 | *Clostridium sordellii* group | 75.5% | 0.0% | 7.8% | 74.8% | Not Tested | 76.2% |
| S37.11.7 | *Clostridium sartagoforme* | 89.8% | 30.8% | 47.9% | 70.0% | Not Tested | 79.0% |
| S37.11.8 | *Clostridium sartagoforme* | 94.1% | 0.0% | 33.9% | 0.0% | Not Tested | 57.4% |
| S37.11.9 | *C. beijerinckii* | 96.9% | 45.7% | 62.0% | 39.3% | 36.9% | 66.2% |
| S37.12.3 | *Clostridium sordellii* group | 97.2% | 49.4% | 96.0% | 96.3% | Not Tested | 86.9% |
| S37.12.4 | *Clostridium sordellii* group | 93.5% | 0.0% | 0.0% | 15.3% | Not Tested | 27.6% |
| S37.12.5 | *C. bifermentans* group | 96.0% | 70.0% | 68.5% | 69.3% | 74.8% | 69.5% |
| Average Percent Inhibition | | 77.2% | 32.1% | 45.4% | 48.5% | 51.0% | 62.4% |

Conclusion:

Feed samples (1,169) were collected from 111 different locations and tested for levels of clostridia. These levels ranged from <10 to 4.1 E+06 CFU/g, with an average enumeration count of 4.2 E+03 CFU/g across all samples. All locations, except for one site, where only one sample was collected, had detectable levels of clostridia.

Of the 3,958 presumptive clostridia isolates collected from 100 different locations, 756 tested positive for at least one *C. perfringens* toxin gene. The majority (84%) of these positive isolates were identified as Type A. Genetic analysis by RAPD PCR of 590 of these toxigenic clostridia isolates showed a diverse population consisting of 133 clusters. For the most part, isolates did not seem to group based on location, except for a few smaller clusters. There were 38 isolates that did not cluster with any other isolates.

Representative isolates (345) from the non-toxigenic isolates (3202) were identified by sequencing of the 16S rRNA gene. *C. beijerinckii* group (23%) and *C. bifermentans* group (21%) were predominant. Other non-toxigenic species identified included *C. tertium* group, *C. butyricum, C. sordellii* group, *C. perfringens, Terrisporobacter* species, *C. sardiniense* group and *Romboutsia lituserburensis.*

Antimicrobial screening against both toxigenic and non-toxigenic clostridia showed inhibition by the inventors' identified *Bacillus* strains. One or more of the *Bacillus* strains 747, 1104, 1541, 1781, and 2018 inhibited 126 of the 196 *C. perfringens* isolates. For the non-toxigenic isolates, 11 of the 14, were inhibited by one or more of the *Bacillus* strains 747, 1104, 1541, 1781, 1999, and 2018.

Example 2: The Effect of a Combination of *Bacillus* Strains on the Ensiling of Alfalfa in Mini-Silos Introduction:

Clostridia fermentation in silage is controlled using lactic acid bacteria as silage inoculants to support the preservation of the crop and by ensuring the crop is harvested and ensiled under low-moisture conditions. However, managing the on-farm conditions such as weather that would impact the moisture content of the crop at harvest is not always practical or possible, and often ensiling occurs under sub-optimal conditions. Although bacilli are considered silage spoilage organisms, members of the *Bacillus* genera are known to produce antimicrobial compounds capable of inhibiting competing bacteria in the surrounding environment, and have demonstrated efficacy in controlling the growth of clostridia. The purpose of this study was to determine the efficacy of *Bacillus* strains, in accordance with this embodiment of the present invention, at controlling the growth of clostridia spoilage organisms in alfalfa ensiled in mini-silos.

Materials and Methods:

Two of the *Bacillus* strains, in accordance with this embodiment of the present invention, *Bacillus* 1104 and 1781, were combined in equal proportions as a silage inoculant and applied to forage to test the effect of a *Bacillus*-based silage inoculant on the physical and chemical properties of the forage material, as well as its ability to suppress secondary fermentation associated with clostridia growth.

Freshly cut alfalfa haylage was treated with the following silage inoculant treatments:

1) Control without silage inoculant;
2) Low Dose *Bacillus* inoculant;
3) High Dose *Bacillus* inoculant
4) Lactic acid bacteria (LAB) inoculant
5) High Dose *Bacillus* inoculant+LAB inoculant
6) Mega Dose *Bacillus* inoculant+LAB inoculant The *Bacillus* inoculant contained 50% strains 1104 1781. The LAB inoculant contained 30% Lp115 (*Lactobacillus plantarum*), 30% Pj300 (*Pediococcus acidilactici*), 30% P751 (*P. pentosaceus*), and 10% *Enterococcus faecium*. Inoculant target application rates per gram of silage were: Low Dose *Bacillus* at 5,000 CFU/g, High Dose *Bacillus* at 50,000 CFU/g, LAB at 150,000 CFU/g, High Dose *Bacillus*+LAB at a combination of respective *Bacillus* and LAB treatment rates, Mega Dose *Bacillus*+LAB at 5,000,000 CFU/g *Bacillus* and the respective LAB rate (Table 5).

TABLE 5

Inoculant Doses of Six Treatments Applied to Alfalfa Forage Material

| Treatment | *Bacillus* Dose, CFU/g | LAB Dose, CFU/g |
|---|---|---|
| Control | 0 | 0 |
| Low Dose *Bacillus* | 5,000 | 0 |
| High Dose *Bacillus* | 50,000 | 0 |
| LAB | 0 | 150,000 |
| High Dose *Bacillus* + LAB | 50,000 | 150,000 |
| Mega Dose *Bacillus* + LAB | 5,000,000 | 150,000 |

Each treatment was applied to 1,000 g of forage material and packed in 8 oz glass ball jars with sealed lids at a density of 39 lb/ft$^3$. Jars were stored at room temperature and enumerations were performed on days 7, 30, 78, 90, and 182 for bacteria and microbes of interest (*Bacillus*, LAB, *Escherichia coli* and coliforms, clostridia, yeast and mold). The untreated sample (control) was tested on Day 0 for pH and initial background bacteria present. At each time point, pH readings were also recorded for each treated sample and analyzed for presence and concentration of volatile fatty acids (VFAs) on an as-sampled basis. The following VFAs were evaluated: lactic acid, acetic acid, butyric acid, isobutyric acid, propionic acid, valeric acid, and isovaleric acid. Final VFA results were reported as the average of duplicate values.

Figure 4:
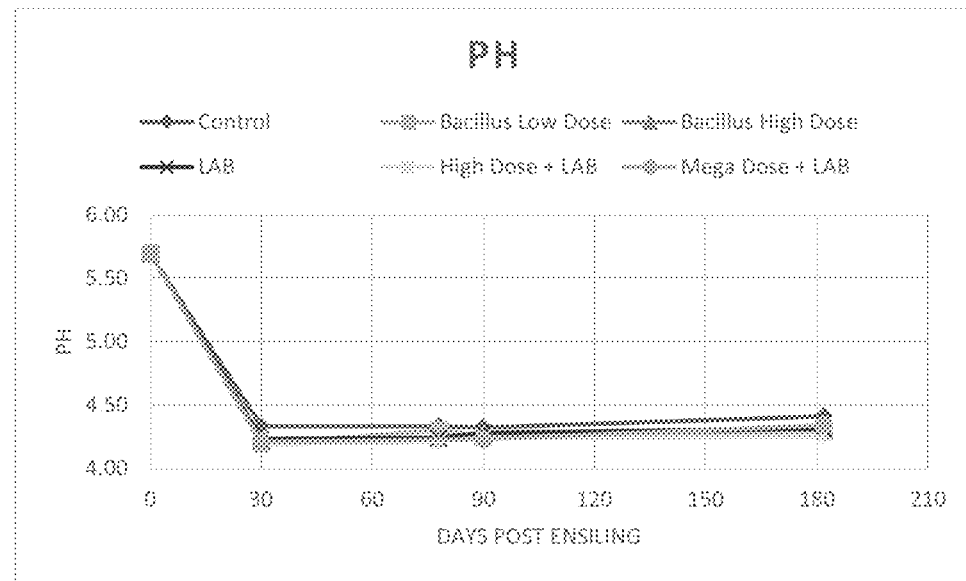
FIG. 4 is a line graph showing measurements of pH versus time for six mini-silo inoculant treatments in accordance with one embodiment of the present invention, pursuant to Example 2.

Results and Discussion:

The pH levels for all six treatments dropped from 5.70 on Day 0 to 4.19-4.33 by Day 30 (FIG. 4). From Day 30 to Day 182, the pH values for all treatments remained mostly stable with the Control maintaining the highest pH level over this time compared to samples treated with inoculant. This data suggests that the addition of *Bacillus* in applied silage inoculants can help lower the pH rapidly, starting the fermentation process sooner, and can help maintain a more stable pH during the stable phase (or storage phase) of the ensiling process. A lower pH can help inhibit spoilage bacteria, improve the digestibility of the feed, reduces proteolytic enzymes, inhibits anaerobic bacteria, shifts fermentation end products, and increases hydrolysis of hemicellulose

*E. coli* population in the control and the other five treatments dropped from 43 CFU/g on Day 0 to 10 CFU/g on Day 78 (Table 6). From Day 78 to Day 182, *E. coli* levels for the control and all treatments stayed consistently at 10 CFU/g. Coliform counts were maintained at 10 CFU/g for both the control sample and other four treatment samples from Day 78 to Day 182. The addition of *Bacillus* in the applied silage inoculant treatments did not result in the *E. coli* or coliform population levels increasing over time during the ensiling process.

TABLE 6

*E. coli* and coliform population changes over time per treatment

| Day | Treatment | *E. coli* (CFU/g) | Coliforms (CFU/g) |
|---|---|---|---|
| 0 | Control | 43 | N/A |
| 78 | Control | 10 | 10 |
| 78 | *Bacillus* Low Dose | 10 | 10 |
| 78 | *Bacillus* High Dose | 10 | 10 |
| 78 | LAB | 10 | 10 |
| 78 | High Dose + LAB | 10 | 10 |
| 90 | Control | 10 | 10 |
| 90 | *Bacillus* Low Dose | 10 | 10 |
| 90 | *Bacillus* High Dose | 10 | 10 |
| 90 | LAB | 10 | 10 |
| 90 | High Dose + LAB | 10 | 10 |
| 90 | Mega Dose + LAB | 10 | 10 |
| 182 | Control | 10 | 10 |
| 182 | *Bacillus* Low Dose | 10 | 10 |
| 182 | *Bacillus* High Dose | 10 | 10 |
| 182 | LAB | 10 | 10 |
| 182 | High Dose + LAB | 10 | 10 |
| 182 | Mega Dose + LAB | 10 | 10 |

Figure 5:
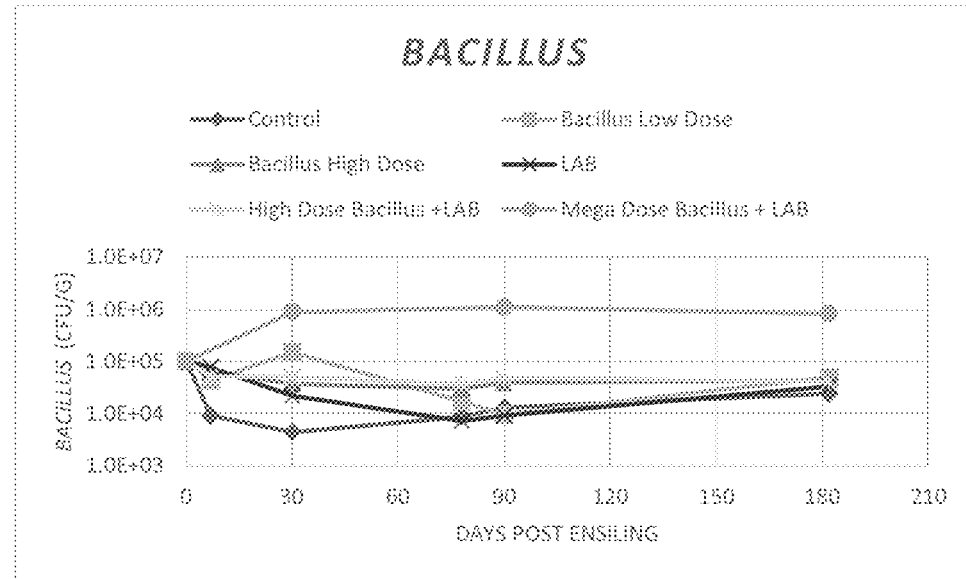
FIG. 5 is a line graph showing change in counts of *Bacillus* over time for six mini-silo inoculant treatments in accordance with one embodiment of the present invention, pursuant to Example 2.
Figure 6:
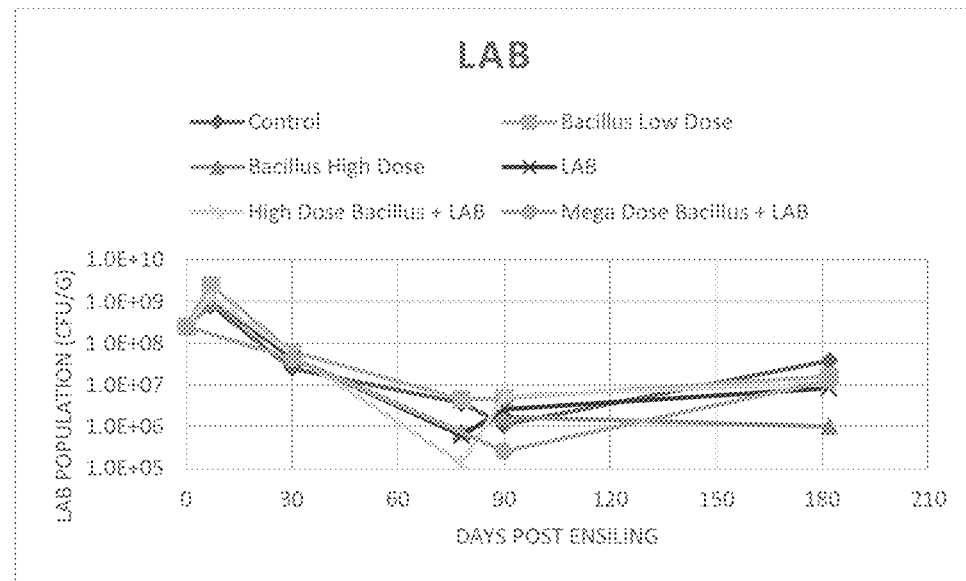
FIG. 6 is a line graph showing lactic acid bacteria (LAB) population change over time for six mini-silo inoculant treatments in accordance with one embodiment of the present invention, pursuant to Example 2.

As expected, treatments without *Bacillus* added (Control and LAB) had the lowest *Bacillus* counts over the time course of measurements compared to treatments with added *Bacillus* (FIG. 5). Generally, *Bacillus* levels in the Control and LAB treatment were lower than the other five treatments at all time points. The Mega Dose *Bacillus*+LAB Treatment had the highest level of *Bacillus* growth throughout the trial compared to all other treatments. By trial end, all samples treated with inoculant had higher levels of *Bacillus* detected in them than in the Control, indicating that the *Bacillus* strains present in the silage inoculant remained stable and experienced little to no die off throughout the ensiling process. LAB populations were reduced by 2-3 logs after 60 d post ensiling for all treatments, indicating a normal lactic acid bacterial fermentation to preserve the forage (FIG. 6).

Figure 7:
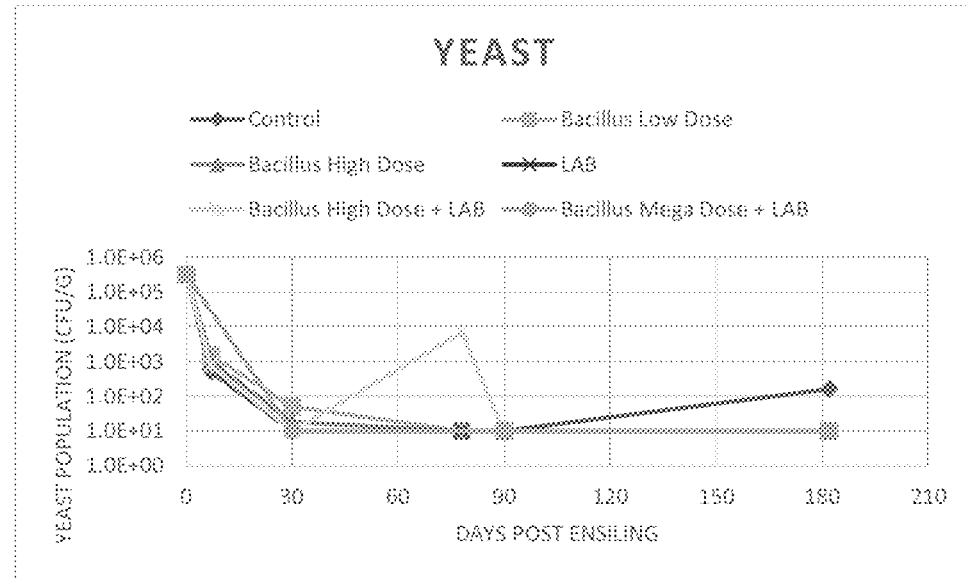
FIG. 7 is a line graph showing change in yeast population over time for six mini-silo inoculant treatments in accordance with one embodiment of the present invention, pursuant to Example 2.

Yeast counts decreased from Day 0 to Day 30 for all treatments and the control (FIG. 7). After Day 30 all treatments, with the exception of the *Bacillus* High Dose+LAB treatment on Day 78, had consistent yeast counts of 10 CFU/g and stayed at this concentration throughout the remainder of the experiment, except for the Control. The Control had the highest levels of yeast growth among the treatments tested by the end of the trial on Day 180. This data indicates that the addition of *Bacillus* did not negatively affect the ability of the lactic acid bacteria inoculant to inhibit yeast spoilage organism growth during silage preservation.

Figure 8:
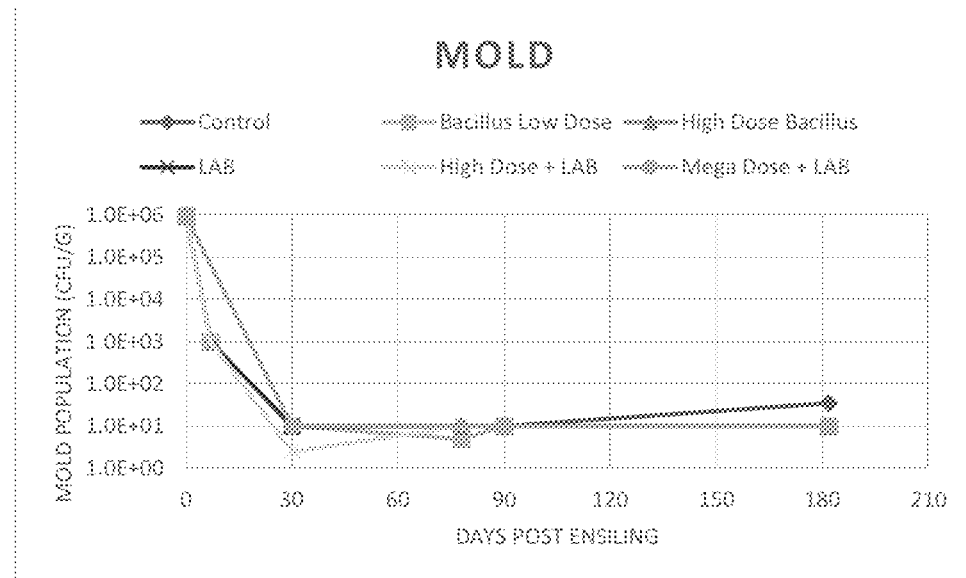
FIG. 8 is a line graph showing change in mold population over time for the six silage inoculant treatments in accordance with one embodiment of the present invention, pursuant to Example 2.

Mold counts decreased from Day 0 to Day 30 for all treatments and the Control (FIG. 8). After Day 30 all treatments had consistent mold counts of 10 CFU/g for the remainder of the time points tested, whereas the Control treatment had a mold count of 10 CFU/g from Day 30 to Day 90 and then increased to 3.5 CFU/g for the last plating on Day 182. These data indicate that the addition of *Bacillus* did not negatively affect the ability of the lactic acid bacteria inoculant to reduce and control mold spoilage organism growth.

Figure 9:
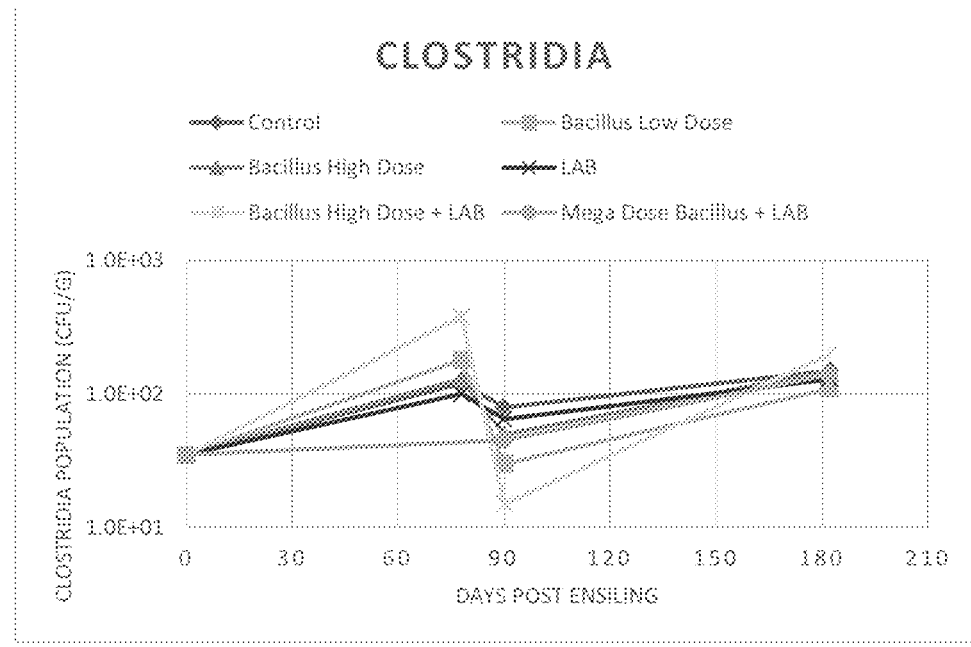
FIG. 9 is a line graph showing change in Clostridia population over time for the six silage inoculant treatments in accordance with one embodiment of the present invention, pursuant to Example 2.

All the inoculant treatments with the exception of the *Bacillus* High Dose+LAB, had similar or lower clostridia levels by the end of the experiment compared to the Control (FIG. 9). The *Bacillus* Low Dose had the lowest levels of clostridia for the last two time points tested out of all of the treatments. This data indicates that *Bacillus* by itself and/or in combination with LAB is controlling clostridia growth and secondary fermentation more effectively than when no treatment is administered.

Lactic acid concentration increased in all treatments from Day 0 to Day 78 and then decreased from Day 78 to Day 90

Figure 10:
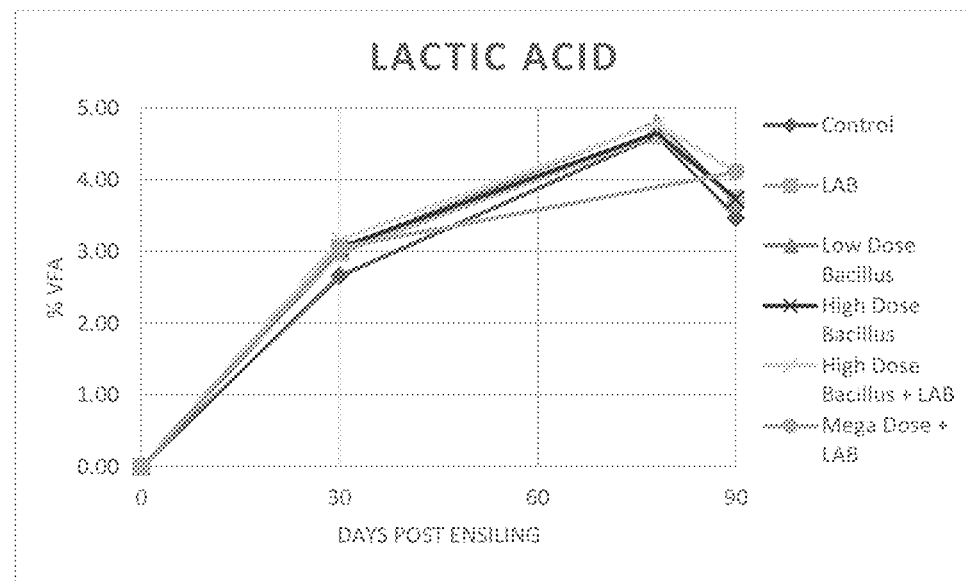
FIG. 10 is a line graph showing change in lactic acid concentration over time for the six silage inoculant treatments on an as-sampled basis in accordance with one embodiment of the present invention, pursuant to Example 2.
Figure 11:
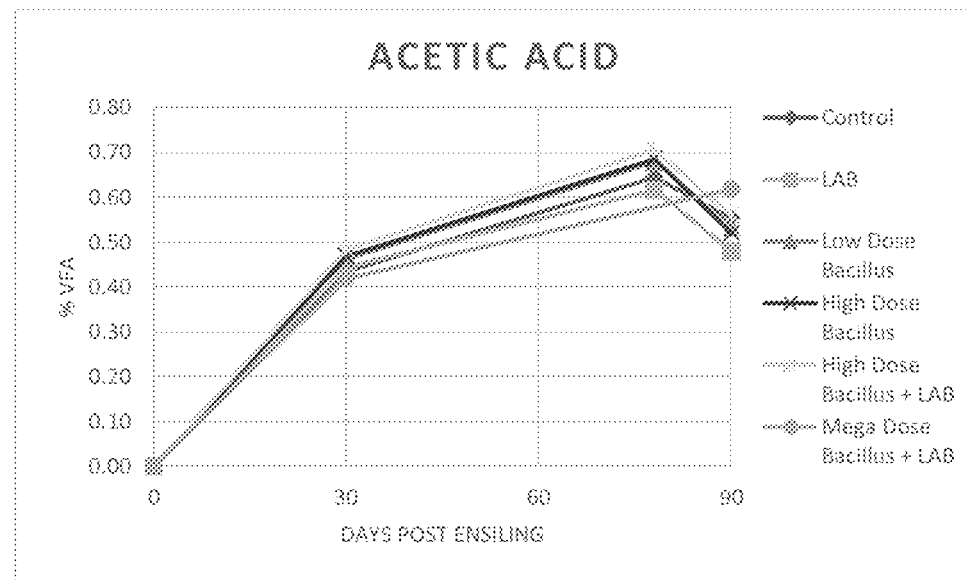
FIG. 11 is a line graph showing change in acetic acid concentration over time for the six silage inoculant treatments on an as-sampled basis in accordance with one embodiment of the present invention, pursuant to Example 2.

(FIG. 10). The control showed consistently lower levels of lactic acid at each time point compared to samples treated with the microbial inoculants. The highest levels of lactic acid were observed in the High Dose *Bacillus*+LAB treatment compared to all other treatments for each time point tested. Acetic acid concentrations increased in all treatment samples from Day 0 to Day 78 and then decreased from Day 78 to Day 90 (FIG. 11). For each time point tested, the High Dose *Bacillus*+LAB treatment had the highest concentration of acetic acid compared to all of the other treatments. The LAB treatment had the lowest concentration of acetic acid for all time points, except for Day 30 where the Mega Dose treatment was slightly lower. Concentrations of butyric acid, isobutyric acid, propionic acid, valeric acid, and isovaleric acid were not detected in any of the treatment samples at any of the time points measured.

Conclusions:

The pH dropped drastically within the first 30 days from a starting point of 5.7. From this point on, the pH readings were stable at this range until the end of the trial. All samples treated with *Bacillus* silage inoculant had lower pH compared to the controls. Lactic acid bacteria increased within the first few days of ensiling and then generally decreased over the course of the experiments, while *Bacillus* levels for all treated samples were higher than that of the controls. Both yeast and mold counts dropped drastically within the first 30 day of ensiling and then evened out until trial end. Treated samples had counts that were ten times lower than that of the control. Treated samples, except for the *Bacillus* High Dose+LAB treatment, had slightly lower levels of clostridia by trial end.

This data indicates that silage preservation is not negatively affected by the addition of these *Bacillus* strains as a silage inoculant. In fact, the *Bacillus* by itself and/or in combination with LAB is controlling clostridia growth and secondary fermentation, as well as yeast and mold growth, more effectively than when no treatment is administered.

Example 3: The Effect of a Combination of *Bacillus* Strains as Silage Inoculants on Alfalfa Silage on Farm and in Mini-Silos Introduction:

Clostridia fermentation in silage is controlled using lactic acid bacteria as silage inoculants to support the preservation of the crop and by ensuring the crop is harvested and ensiled under low-moisture conditions. However, managing the on-farm conditions such as weather that would impact the moisture content of the crop at harvest is not always practical or possible, and often ensiling occurs under suboptimal conditions. Although bacilli are considered silage spoilage organisms, members of the *Bacillus* genera are known to produce antimicrobial compounds capable of inhibiting competing bacteria in the surrounding environment, and have demonstrated efficacy in controlling the growth of clostridia. The purpose of this study was to determine the efficacy of *Bacillus* strains, in accordance with this embodiment of the present invention, at controlling the growth of clostridia spoilage organisms in alfalfa ensiled on farm and in mini-silos.

Materials and Methods:

Two of the *Bacillus* strains, in accordance with this embodiment of the present invention, *Bacillus* 1104 and 1781, were combined in equal proportions as a silage inoculant and applied to forage to test the effect of a *Bacillus*-based silage inoculant on the physical and chemical properties of the forage material, as well as its ability to suppress secondary fermentation associated with clostridia growth.

The study utilized alfalfa silage from second cutting and treatments consisted of a Control, silage inoculant treatment applied on the farm, silage inoculant treatment applied at a 1× dose in the laboratory, and silage inoculant treatment applied at a 10× dose in the laboratory. Both the farm and lab silage inoculant treatments contained 12.5% strains 1104 and 1781), 7% En. *faecium*, 22.5% each of LP 115 (*L. plantarum*), Pj300 (*P. acidilactici*), and P751 (*P. pentosaceus*).

Inoculant target application rate for the both the farm and laboratory applied silage inoculant treatments was 200,000 CFU/gram of crop, consisting of 150,000 CFU Lactic Acid bacteria (LAB) and 50,000 CFU *Bacillus*. The 10× dose included 2,000,000 CFU/gram of crop, consisting of 1,500,000 CFU LAB and 500,000 CFU *Bacillus*. Laboratory inoculant treatments were applied to 1,000 g of forage material and all treatments were packed in 8 oz glass ball jars with sealed lids at a density of 39 lb/ft$^3$. Jars were stored at room temperature and enumerations were performed on days 8, 14, 28, 60, 90, and 176 days for bacteria of interest (*Bacillus*, LAB, *E. coli* and coliforms, clostridia, yeast and mold).

Initial background bacteria and pH was recorded for all treatments on Day 0. At each time point, pH readings were obtained for each treated sample and analyzed for presence and concentration of VFAs on an as-sampled basis. Volatile fatty acids, including lactic acid, acetic acid, butyric acid, isobutyric acid, propionic acid, valeric acid, and isovaleric acid, were processed in duplicate and measured. Final VFA results were reported as the average of the duplicate values.

Figure 12:
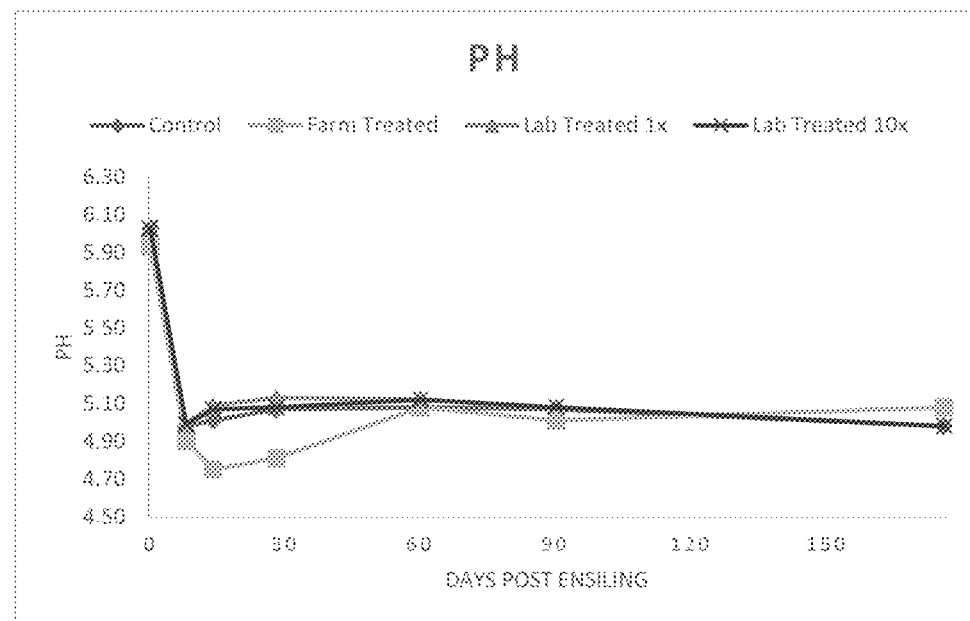
FIG. 12 is a line graph showing pH measurements over time for the four silage inoculant treatments on an as-sampled basis in accordance with one embodiment of the present invention, pursuant to Example 3.

Results and Discussion:

The pH decreased for all treatments in the initial measurement following treatment administration and was maintained over the course of the study (FIG. 12). The observed decrease in pH indicates active fermentation of the forage material and that long term silage preservation is not being negatively affected by the addition of *Bacillus* strains in a silage inoculant.

Figure 13:
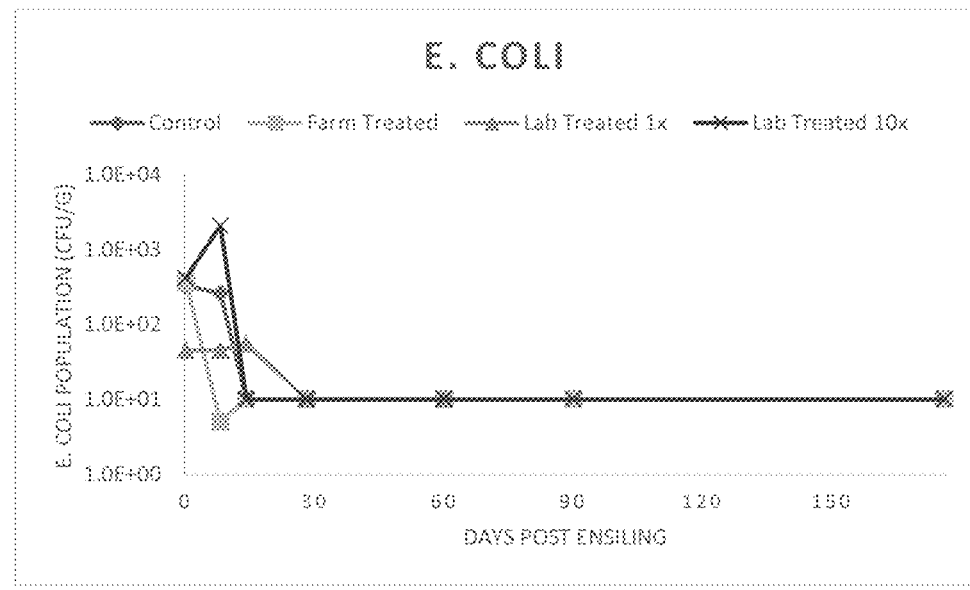
FIG. 13 is a line graph showing *E. coli* population change over time for the four silage inoculant treatments on an as-sampled basis in accordance with one embodiment of the present invention, pursuant to Example 3.
Figure 14:
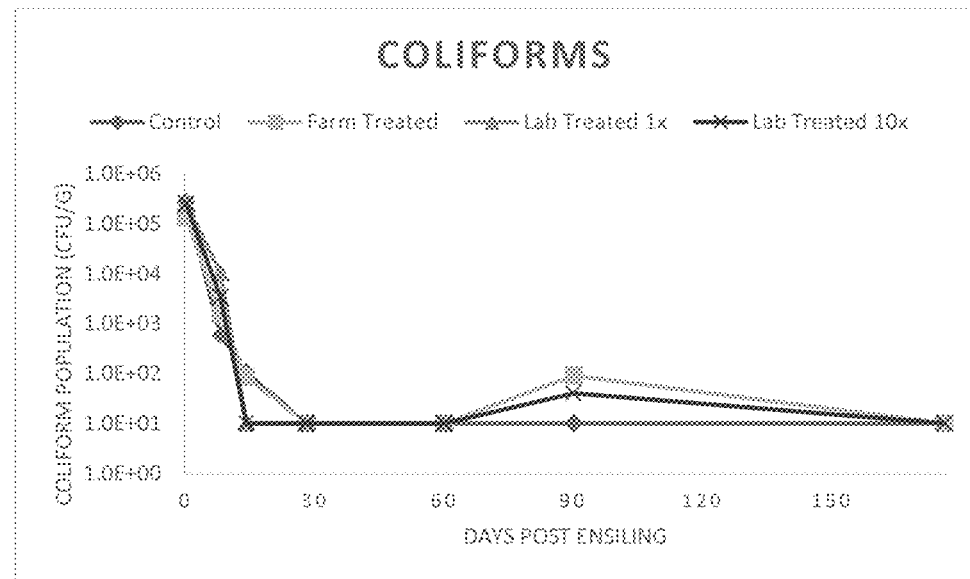
FIG. 14 is a line graph showing Coliform population change over time for the four silage inoculant treatments on an as-sampled basis in accordance with one embodiment of the present invention, pursuant to Example 3.

Except for the 10× silage inoculant dose, *E. coli* counts were reduced in inoculant treatment samples at a faster rate initially compared to the Control (FIG. 13). After Day 30, all treatments maintained a low level of *E. coli* (10 CFU/g) for the remainder of the experimental period. A similar reduction in coliform levels was observed for the inoculant treatment samples during the first 30 days of testing (FIG. 14). These data indicate that the treatments are controlling spoilage organism growth over the course of the fermentation process.

Figure 15:
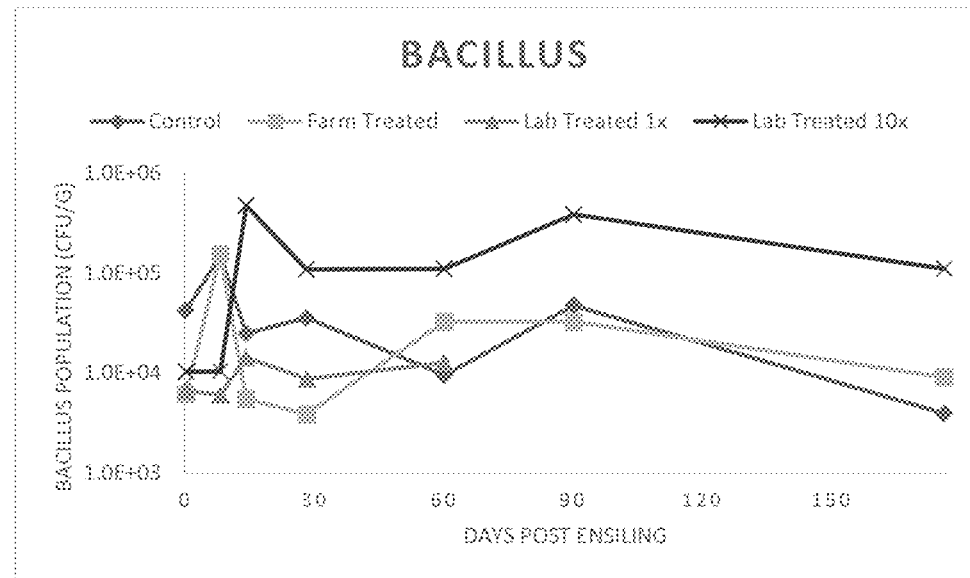
FIG. 15 is a line graph showing *Bacillus* population change over time for the four silage inoculant treatments on an as-sampled basis in accordance with one embodiment of the present invention, pursuant to Example 3.
Figure 16:
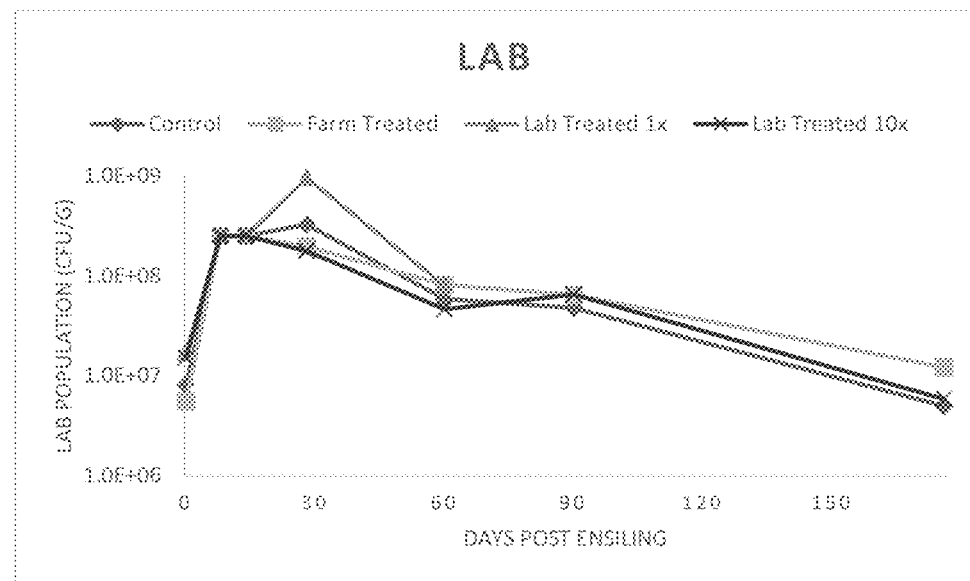
FIG. 16 is a line graph showing Lactic acid bacteria (LAB) population change over time for the four silage inoculant treatments on an as-sampled basis in accordance with one embodiment of the present invention, pursuant to Example 3.

During the study, total *Bacillus* counts ranged between $6.7 \times 10^3$ and $4.7 \times 10^5$ CFU/g, with the highest *Bacillus* counts observed in the 10× silage inoculant dose treatment. After the *Bacillus* community was established in the treated samples after Day 60, *Bacillus* levels did not fluctuate much for the remainder of the trial. This shows that *Bacillus* is stable in feed samples and maintains activity under a wide range of conditions (FIG. 15). LAB counts increased initially to Day 30, and then decreased gradually over the remainder of the test period (FIG. 16).

Figure 17:
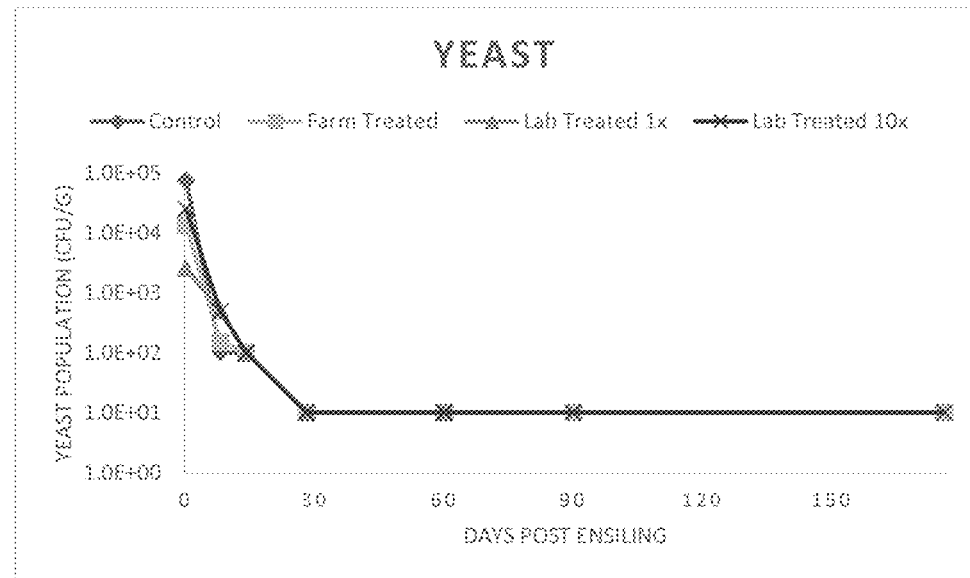
FIG. 17 is a line graph showing yeast population change over time for the four silage inoculant treatments on an as-sampled basis in accordance with one embodiment of the present invention, pursuant to Example 3.
Figure 18:
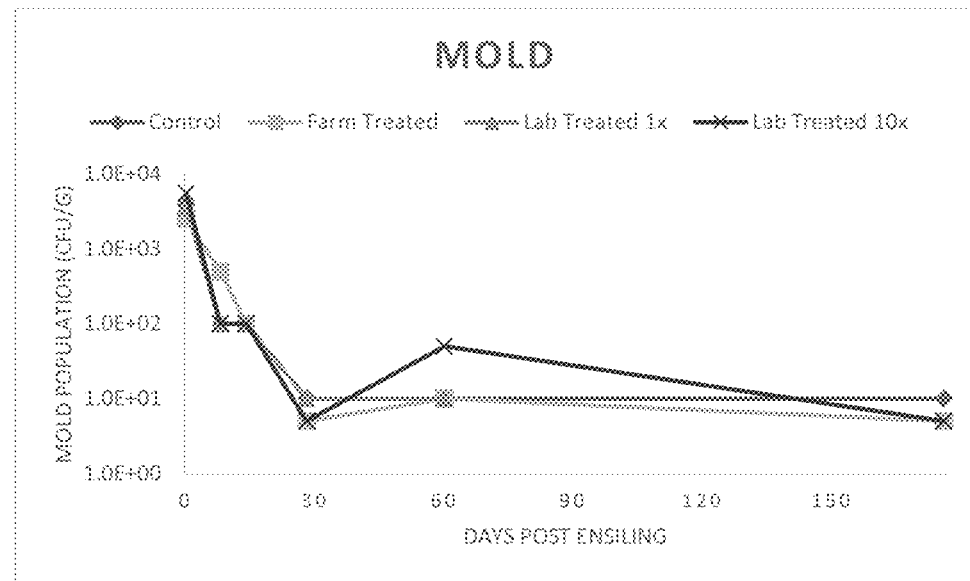
FIG. 18 is a line graph showing mold population change over time for the four silage inoculant treatments on an as-sampled basis in accordance with one embodiment of the present invention, pursuant to Example 3.

During the first 30 days of the trial, the yeast population for all treatments and the Control were reduced and were maintained at low levels (10 CFU/g) over the course of the experimental period (FIG. 17). Mold counts responded similarly for all treatments through the trial period (FIG. 18). This data indicate that the fermentation process controlled yeast and mold spoilage in the silage and that practical application of the silage inoculant on the farm resulted in similar benefits as when the inoculant was applied under experimental conditions in the laboratory.

Figure 19:
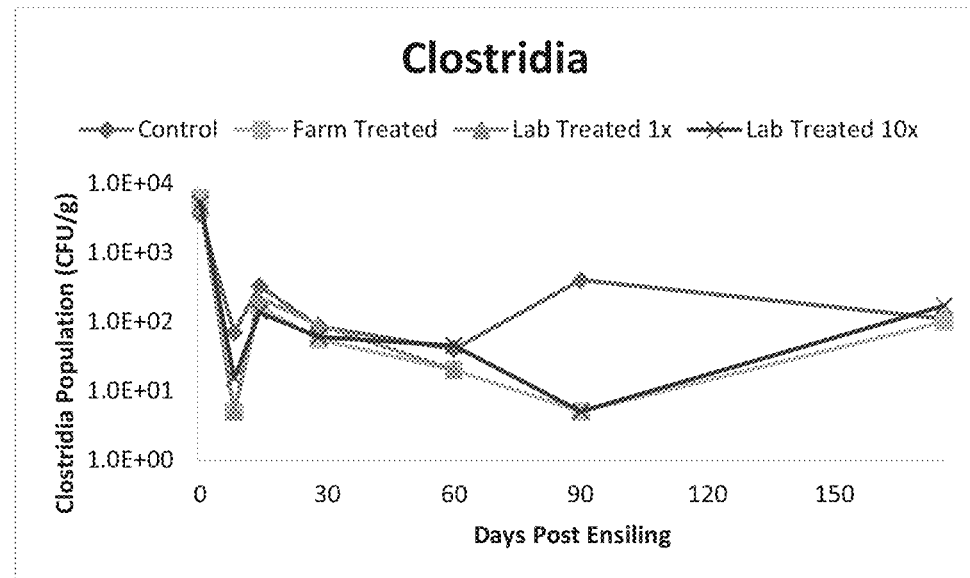
FIG. 19 is a line graph showing clostridia population change over time for the four silage inoculant treatments on an as-sampled basis in accordance with one embodiment of the present invention, pursuant to Example 3.

Clostridia counts were reduced in the first seven days of the trial for all treatments. (FIG. 19). All silage inoculant treatments had similar or lower counts of clostridia compared to the control treatment that was not administered a bacterial inoculant. This data indicates that the addition of silage inoculants to forage is controlling clostridia growth and secondary fermentation more effectively than when no treatment is administered.

Figure 20:
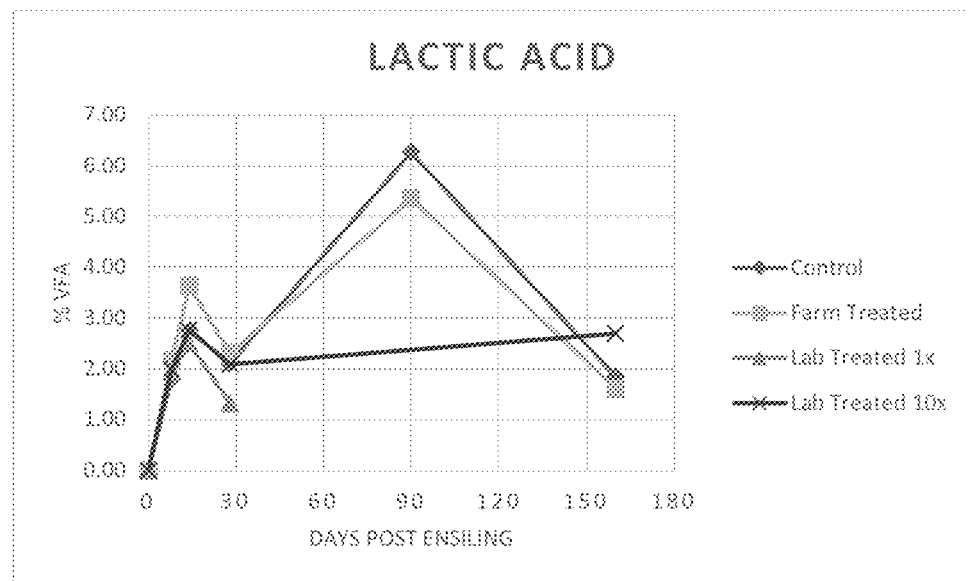
FIG. 20 is a line graph showing lactic acid level over time for the four silage inoculant treatments on an as-sampled basis in accordance with one embodiment of the present invention, pursuant to Example 3.
Figure 21:
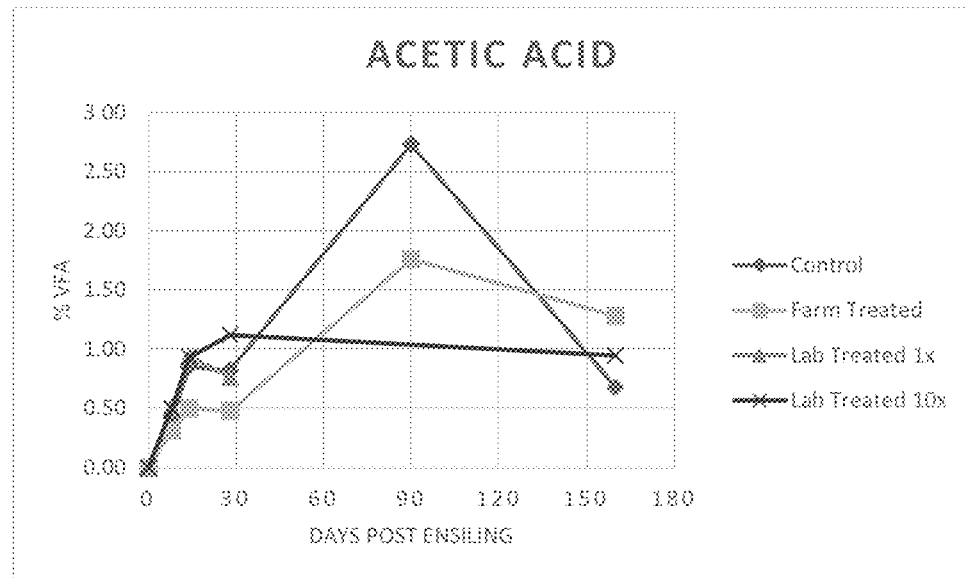
FIG. 21 is a line graph showing acetic acid level change over time for the four silage inoculant treatments on an as-sampled basis in accordance with one embodiment of the present invention, pursuant to Example 3.

Higher concentrations of lactic acid were observed in samples from all treatments at Day 14 and Day 90 compared to other sampling days (FIG. 20). The 10× silage inoculant dose had the highest levels of lactic acid the end of the trial period compared to the other treatments, indicating this treatment resulted in well preserved forage. A similar trend was observed for acetic acid concentrations, in which acetic acid levels increased by 1-3 fold from Day 0 to Day 90 (FIG. 21). Both the 10× silage inoculant dose administered in the laboratory and the silage inoculant administered on-farm had greater concentrations of acetic acid present at the end of the trial period compared to the untreated control, indicating that these treatments provided a more stable fermentation process for silage preservation.

Conclusions:

The pH decreased for all treatments in the initial measurement following treatment administration and was maintained over the course of the study. *E. coli* and coliform counts were reduced in inoculant treatment samples at a faster rate compared to the Control, except for the 10× silage inoculant dose. Treated samples had slightly lower levels of mold present compared to their untreated controls.

This data indicates that silage preservation is not negatively affected by the addition of these *Bacillus* strains to a silage inoculant. In fact, the *Bacillus* in combination with LAB improved the reduction of coliforms and prevented mold growth, more effectively than when no treatment was administered. The pH decreased for all treatments in the initial measurement following treatment administration and was maintained over the course of the study (FIG. 12). The observed decrease in pH indicates active fermentation of the forage material and that long term silage preservation is not being negatively affected by the addition of *Bacillus* strains in a silage inoculant.

Example 4: On-Farm Application of a Silage Inoculant Containing *Bacillus* Strains as a Biological Control Agent for Clostridia in Silage Introduction:

Clostridia fermentation in silage is controlled using lactic acid bacteria as silage inoculants to support the preservation of the crop and by ensuring the crop is harvested and ensiled under low-moisture conditions. However, managing the on-farm conditions such as weather that would impact the moisture content of the crop at harvest is not always practical or possible, and often ensiling occurs under sub-optimal conditions. Although bacilli are considered silage spoilage organisms, members of the *Bacillus* genera are known to produce antimicrobial compounds capable of inhibiting competing bacteria in the surrounding environment, and have demonstrated efficacy in controlling the growth of clostridia. The purpose of this study was to determine the efficacy of *Bacillus* strains, in accordance with this embodiment of the present invention, at controlling the growth of clostridia spoilage organisms in alfalfa ensiled on farm and in mini-silos.

Materials and Methods:

The use of a silage inoculant containing *Bacillus* strains to control clostridia spoilage organisms in preserved forage was investigated to document the efficacy of the inoculant when applied on-farm. Second cut alfalfa haylage was used in the study, and treatments consisted of an untreated control and the silage inoculant applied to the forage on the farm at cutting. The silage inoculant contained 12.5% *Bacillus* 1104 and 12.5% *Bacillus* 1781, 7% *Enterococcus faecium*, 22.5% each of LP 115 (*Lactobacillus plantarum*), PJ 300 (*Pediococcus acidilactici*), and P 751 (*P. pentosaceus*). The target application rate of the silage inoculant was 200,000 CFU/gram consisting of 150,000 CFU lactic acid bacteria (LAB) and 50,000 CFU *Bacillus*. Each treatment was applied to 1,000 g of forage material and packed in 8 oz glass ball jars with sealed lids at a density of 39 lb/ft$^3$. Jars were stored at room temperature and enumerations were performed on days 0, 7, 14, 28, 58, 91, and 175 days for bacteria of interest (*Bacillus*, LAB, *E. coli* and coliforms, clostridia, yeast and mold). Both treated and untreated samples were tested on Day 0 for pH and initial background bacteria present in the samples. At each time point, pH readings were also recorded for each sample and analyzed for presence and concentration of VFAs, including lactic acid, acetic acid, butyric acid, isobutyric acid, propionic acid, valeric acid, and isovaleric acid on an as-sampled basis. VFA results were reported as the average of duplicate values.

Figure 22:
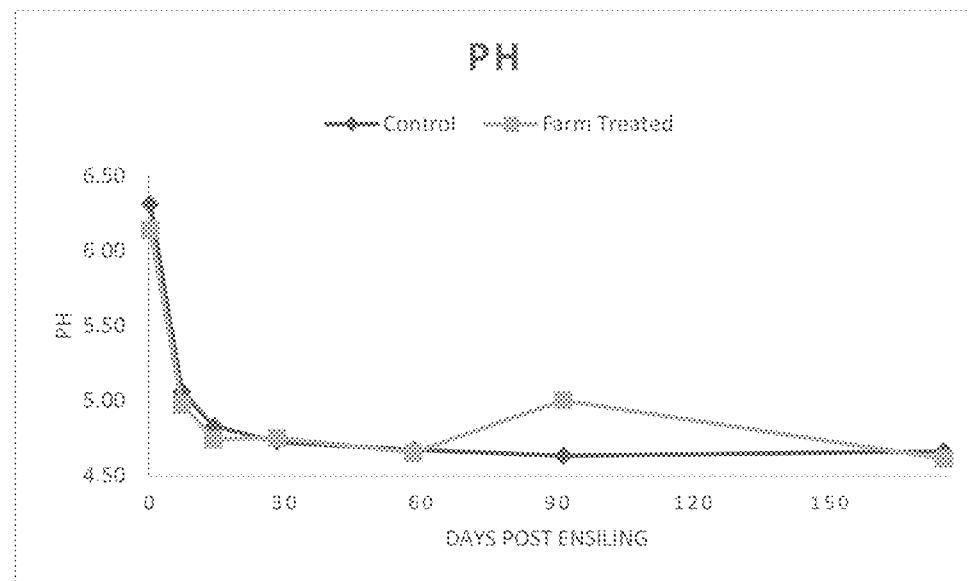
FIG. 22 is a line graph showing pH measurements over time comparing on-farm application of a silage inoculant containing *Bacillus* and an untreated control in accordance with one embodiment of the present invention, pursuant to Example 4.

Results and Discussion:

During the ensiling process, the pH of the forage samples from both treatments decreased from Day 0 to Day 14 (FIG. 22). This lowered pH level was maintained over the course of the experimental period. This data suggests that the addition of *Bacillus* in applied silage inoculants can help lower the pH rapidly, starting the fermentation process sooner, and can help maintain a more stable pH during the stable phase (or storage phase) of the ensiling process. A lower pH can help inhibition of spoilage bacteria, improve the digestibility of the feed, reduces proteolytic enzymes, inhibits anaerobic bacteria, shifts fermentation end products, and increases hydrolysis of hemicellulose.

Figure 23:
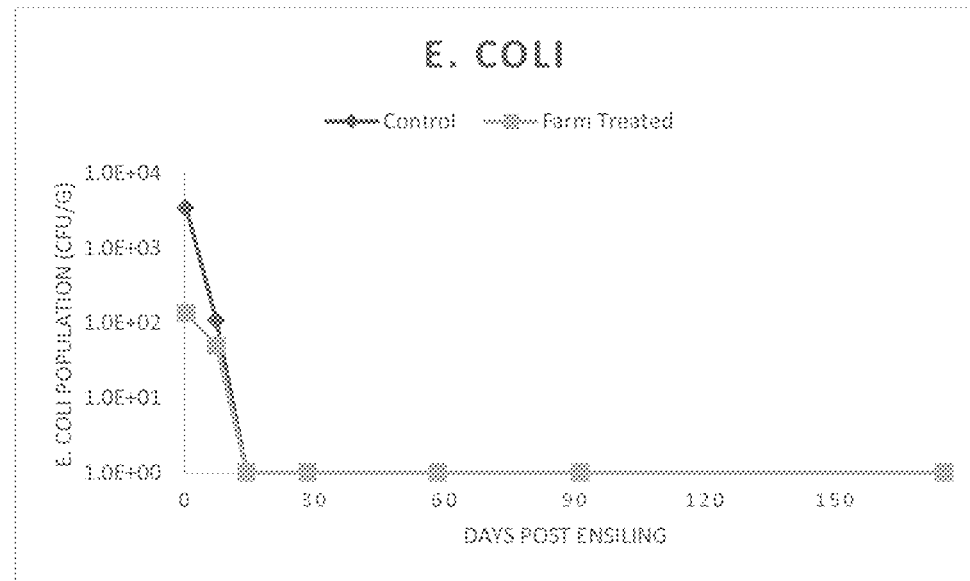
FIG. 23 is a line graph showing *E. coli* counts (CFU/g) over time comparing on-farm application of a silage inoculant containing *Bacillus* and an untreated control in accordance with one embodiment of the present invention, pursuant to Example 4.
Figure 24:
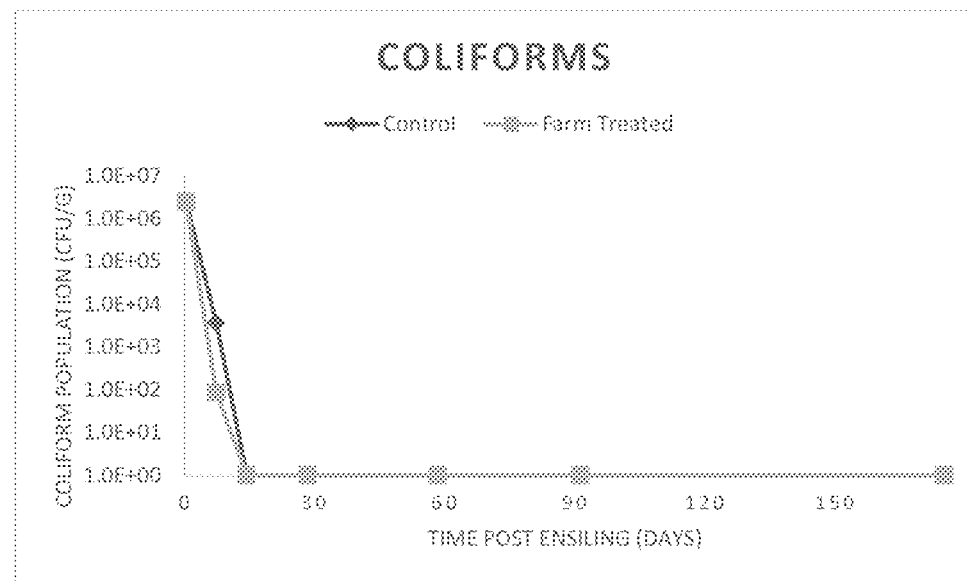
FIG. 24 is a line graph showing coliform counts (CFU/g) over time comparing on-farm application of a silage inoculant containing *Bacillus* and an untreated control in accordance with one embodiment of the present invention, pursuant to Example 4.

*E. coli* and coliform populations were reduced from Day 0 to Day 14 in samples from both treatments (FIG. 23; FIG. 24). Following Day 14, *E. coli* and coliform counts remained at non-detectable limits for the remaining measurements. Both *E. coli* and coliform levels were lower in the sample administered the bacterial treatment on Day 7 compared to the untreated control sample, indicating that bacterial treatment more effectively controlled these spoilage organisms than the untreated sample.

Figure 25:
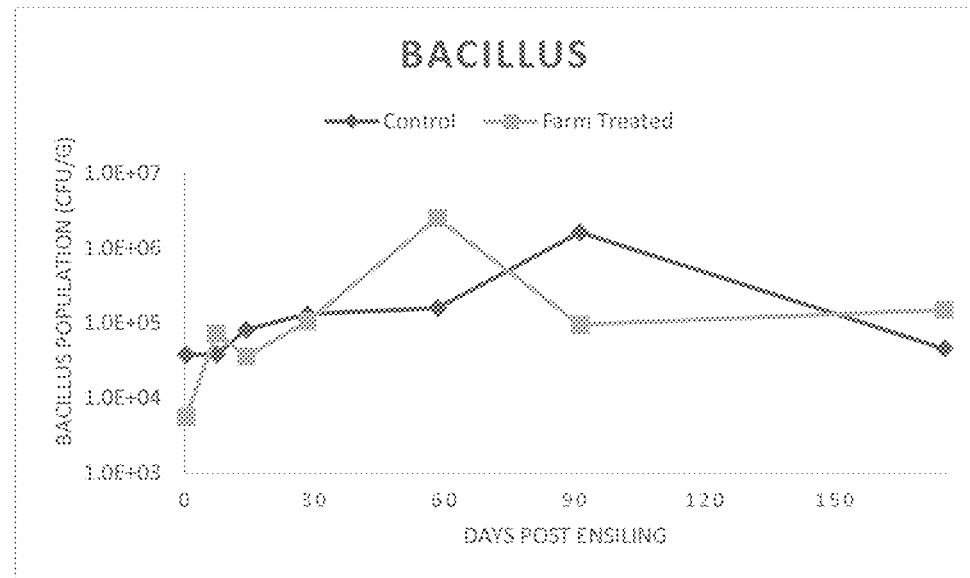
FIG. 25 is a line graph showing *Bacillus* counts (CFU/g) over time comparing on-farm application of a silage inoculant containing *Bacillus* and an untreated control in accordance with one embodiment of the present invention, pursuant to Example 4.
Figure 26:
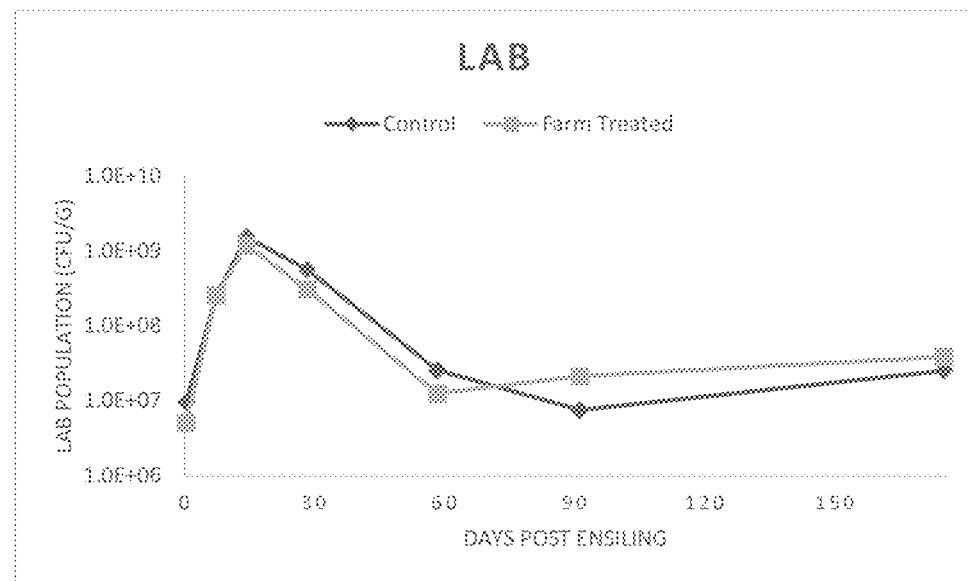
FIG. 26 is a line graph showing lactic acid bacteria (LAB) counts (CFU/g) over time comparing on-farm application of a silage inoculant containing *Bacillus* and an untreated control in accordance with one embodiment of the present invention, pursuant to Example 4.

*Bacillus* organisms were present as background counts for both treatments at the initial measurement at Day 0 (FIG. 25). By the end of the trial, *Bacillus* counts were higher when the forage was treated with the bacterial silage inoculant compared to Day 0. Furthermore, the administration of *Bacillus* represented in the bacterial inoculant did not result in substantially different *Bacillus* counts over the course of the experimental period compared to the untreated control, indicating the *Bacillus* administered in the inoculant did not overgrow and act as a spoilage organism. LAB counts were similar between the untreated control and when a bacterial silage inoculant was administered (FIG. 26).

Figure 27:
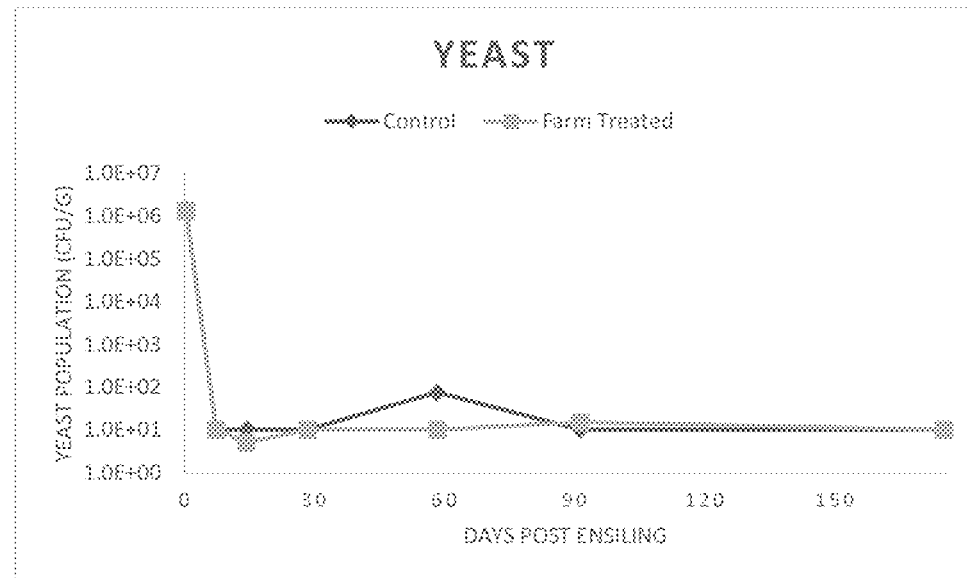
FIG. 27 is a line graph showing yeast counts (CFU/g) over time comparing on-farm application of a silage inoculant containing *Bacillus* and an untreated control in accordance with one embodiment of the present invention, pursuant to Example 4.
Figure 28:
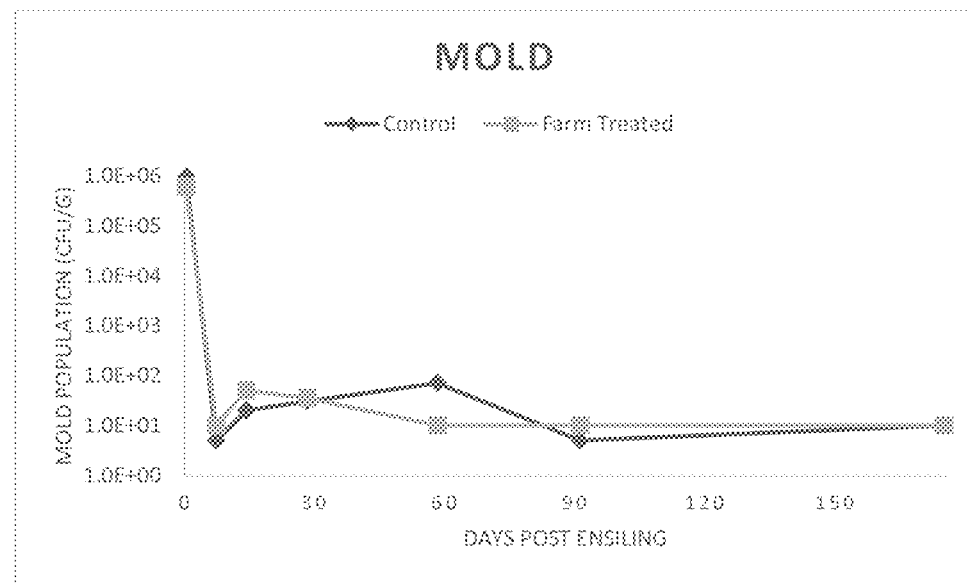
FIG. 28 is a line graph showing mold counts (CFU/g) over time comparing on-farm application of a silage inoculant containing *Bacillus* and an untreated control in accordance with one embodiment of the present invention, pursuant to Example 4.

Yeast and mold counts decreased by approximately 5 logs within the first 7 days post ensiling, and remained low (<1.0 E+02 CFU/g) for both treatments throughout the remainder of the experimental period (FIGS. 27 and 28), indicating an effective fermentation process to preserve the forage.

Figure 29:
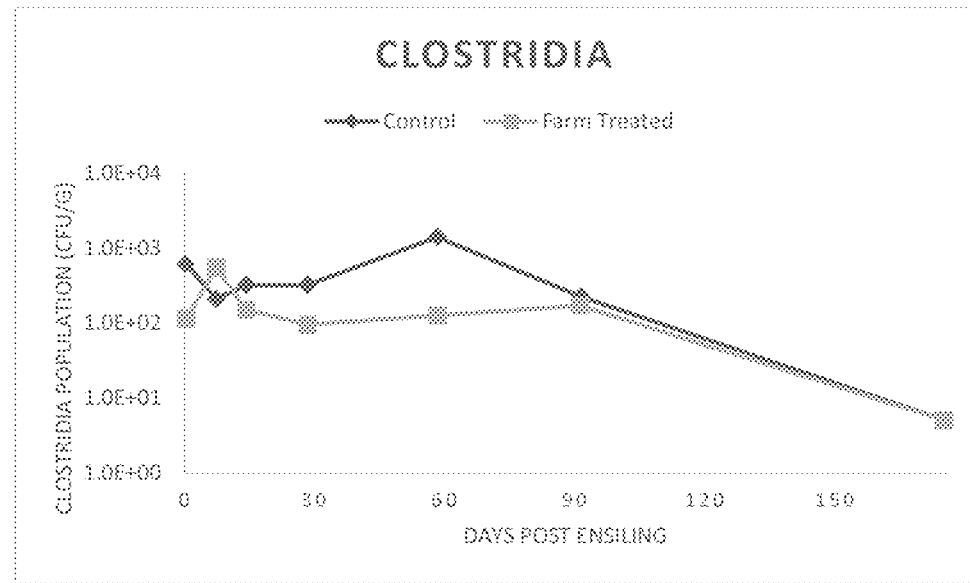
FIG. 29 is a line graph showing clostridia counts (CFU/g) over time comparing on-farm application of a silage inoculant containing *Bacillus* and an untreated control in accordance with one embodiment of the present invention, pursuant to Example 4.

Clostridia counts for the samples treated with inoculant were similar or lower than those of the Control for the entire trial (FIG. 29). This data indicates that the addition of silage inoculants to forage is controlling clostridia growth and secondary fermentation more effectively than when no treatment is administered.

Figure 30:
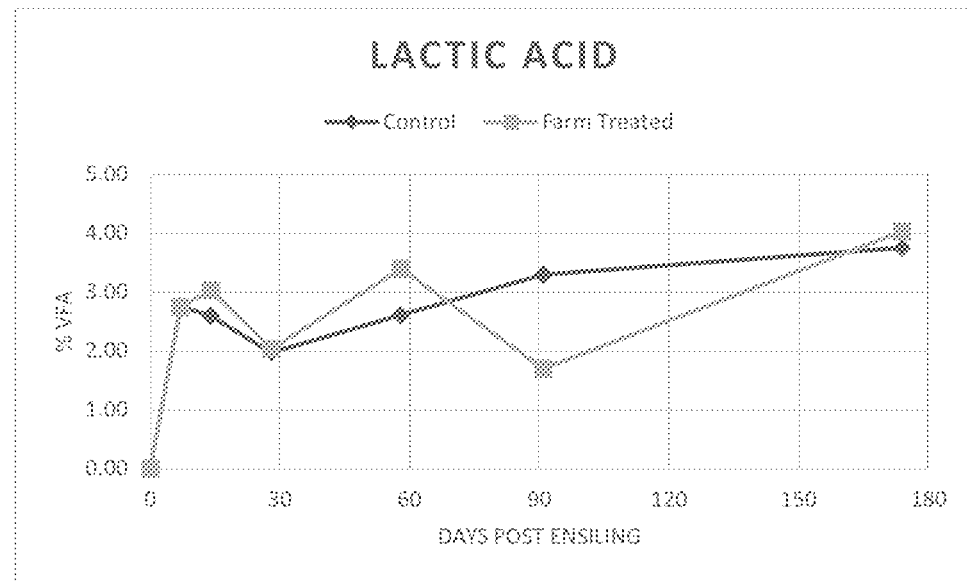
FIG. 30 is a line graph showing lactic acid concentration over time comparing on-farm application of a silage inoculant containing *Bacillus* and an untreated control in accordance with one embodiment of the present invention, pursuant to Example 4.
Figure 31:
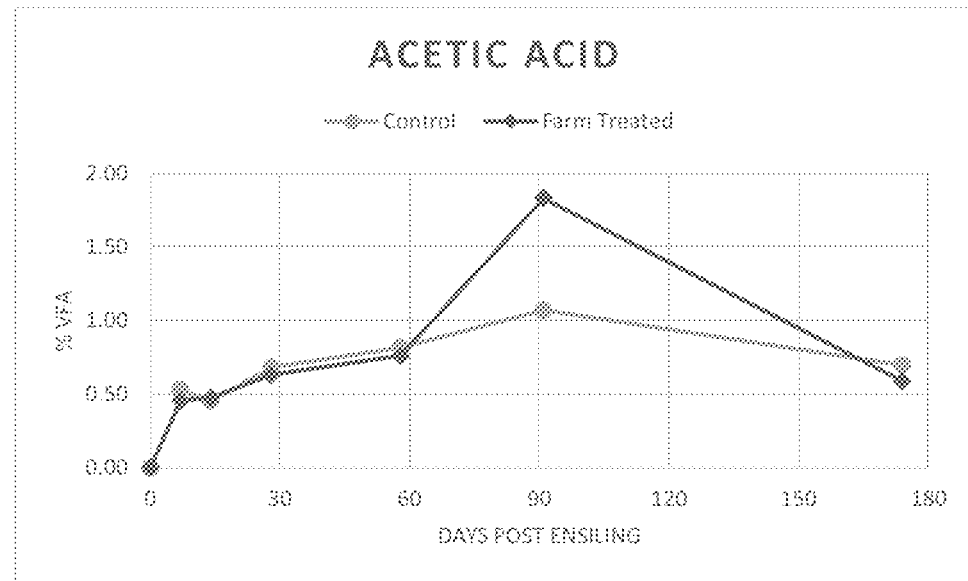
FIG. 31 is a line graph showing acetic acid concentration over time comparing on-farm application of a silage inoculant containing *Bacillus* and an untreated control in accordance with one embodiment of the present invention, pursuant to Example 4.
Figure 32:
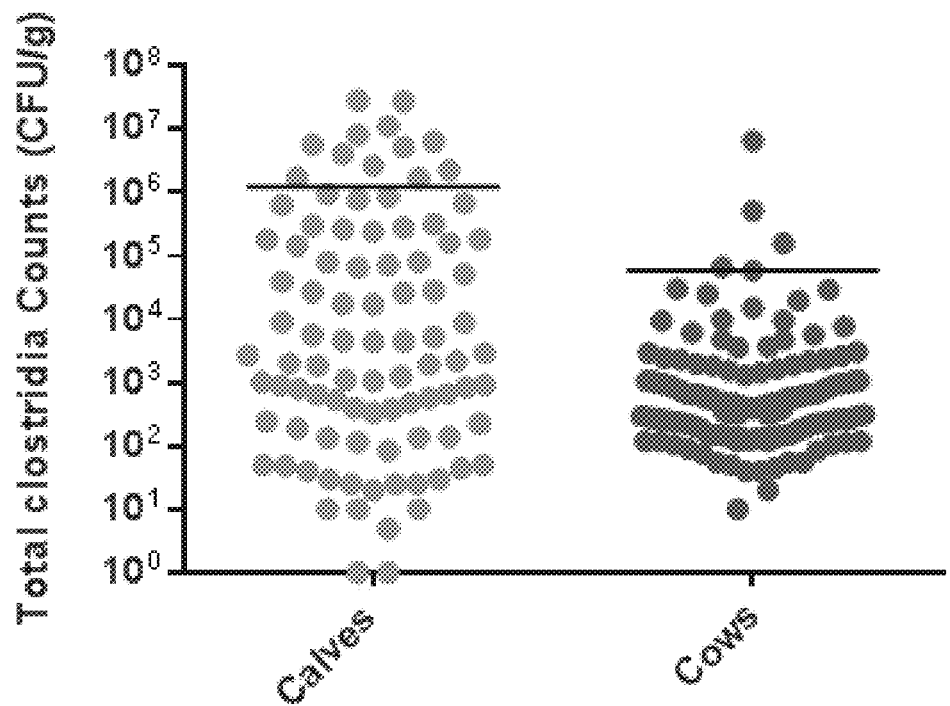
FIG. 32 is a chart showing enumeration results of all clostridia (no differentiation of *Clostridium* sp.) by individual fecal sample for cows and calves in Wisconsin in accordance with one embodiment of the present invention, pursuant to Example 5.
Figure 33:
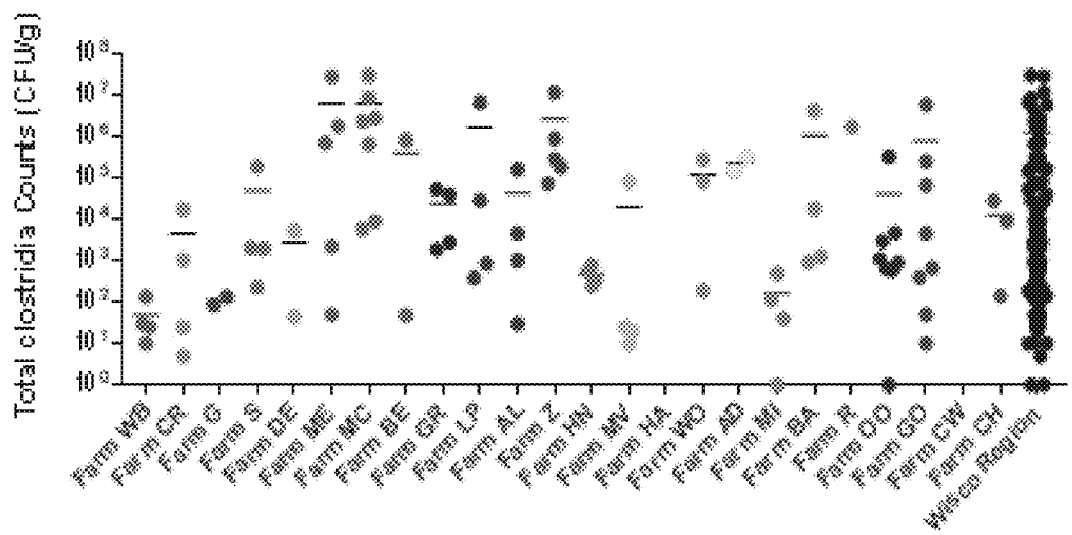
FIG. 33 is a chart showing enumeration results of total clostridia (no differentiation of *Clostridium* sp.) by individual farm calf fecal samples for each farm sampled in Wisconsin in accordance with one embodiment of the present invention, pursuant to Example 5.
Figure 34:
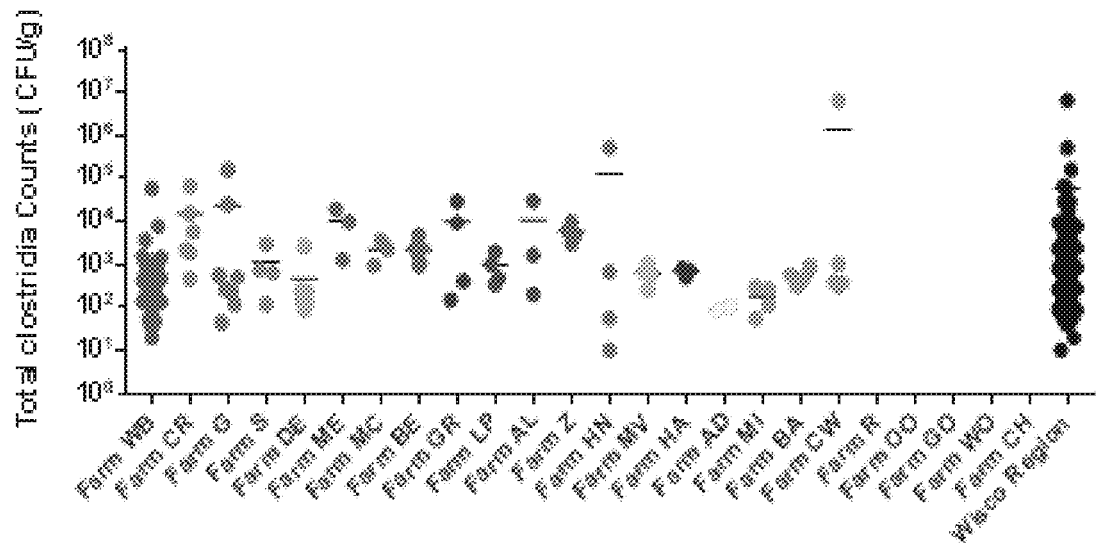
FIG. 34 is a chart showing enumeration results of total clostridia (no differentiation of *Clostridium* sp.) by individual farm cow fecal samples for each farm sampled from Wisconsin in accordance with one embodiment of the present invention, pursuant to Example 5.
Figure 35:
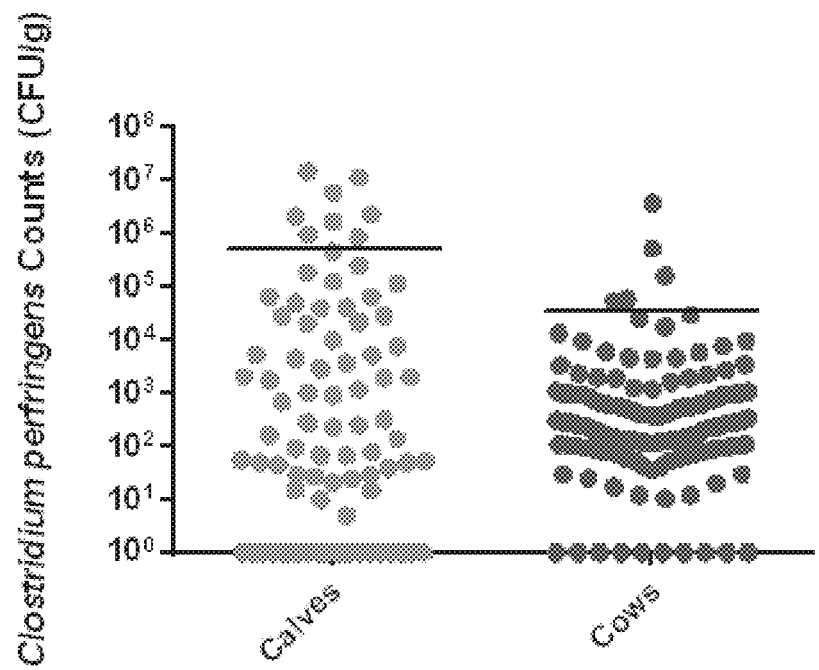
FIG. 35 is a chart showing calculated counts of *C. perfringens* by fecal sample, from fecal samples collected in Wisconsin. *C. perfringens* counts were estimated by multiplying each sample's total clostridia count by the percent that were confirmed to be *C. perfringens* in accordance with one embodiment of the present invention, pursuant to Example 5.
Figure 36:
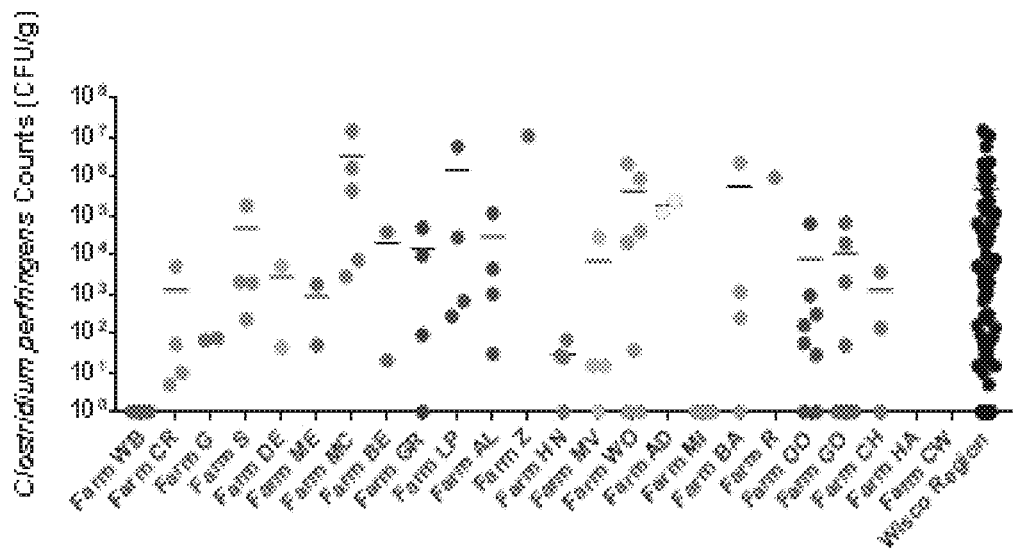
FIG. 36 is a chart showing calculated counts of *C. perfringens* by individual calf fecal sample from Wisconsin. *C. perfringens* counts were estimated by multiplying each sample's clostridia count by the percent that were confirmed to be *C. perfringens*. Results are reported for each farm in accordance with one embodiment of the present invention, pursuant to Example 5.
Figure 37:
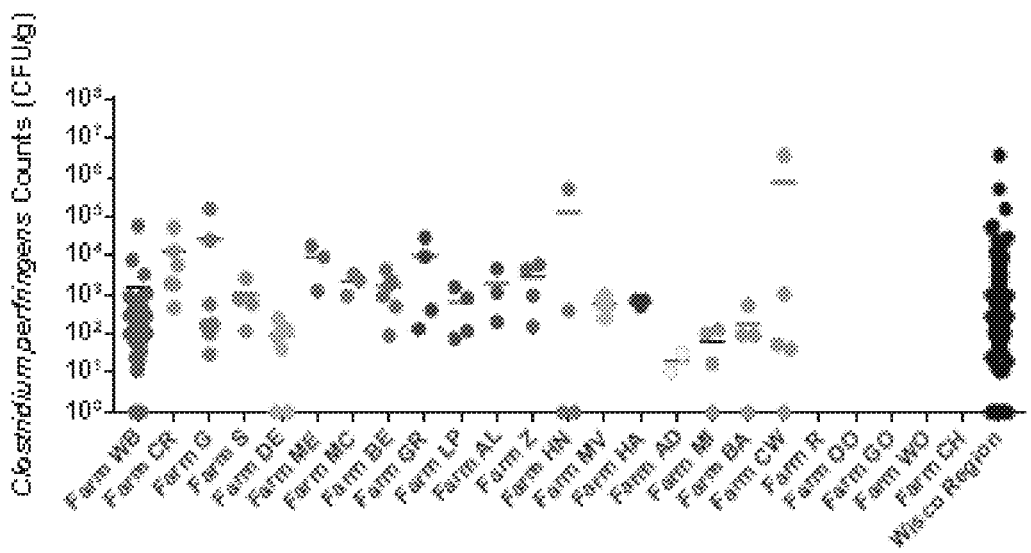
FIG. 37 is a chart showing calculated counts of *C. perfringens* by individual cow fecal sample collected from Wisconsin. *C. perfringens* counts were estimated by multiplying each sample's clostridia count by the percent that were confirmed to be *C. perfringens*. Results are reported for each farm in accordance with one embodiment of the present invention, pursuant to Example 5.
Figure 38:
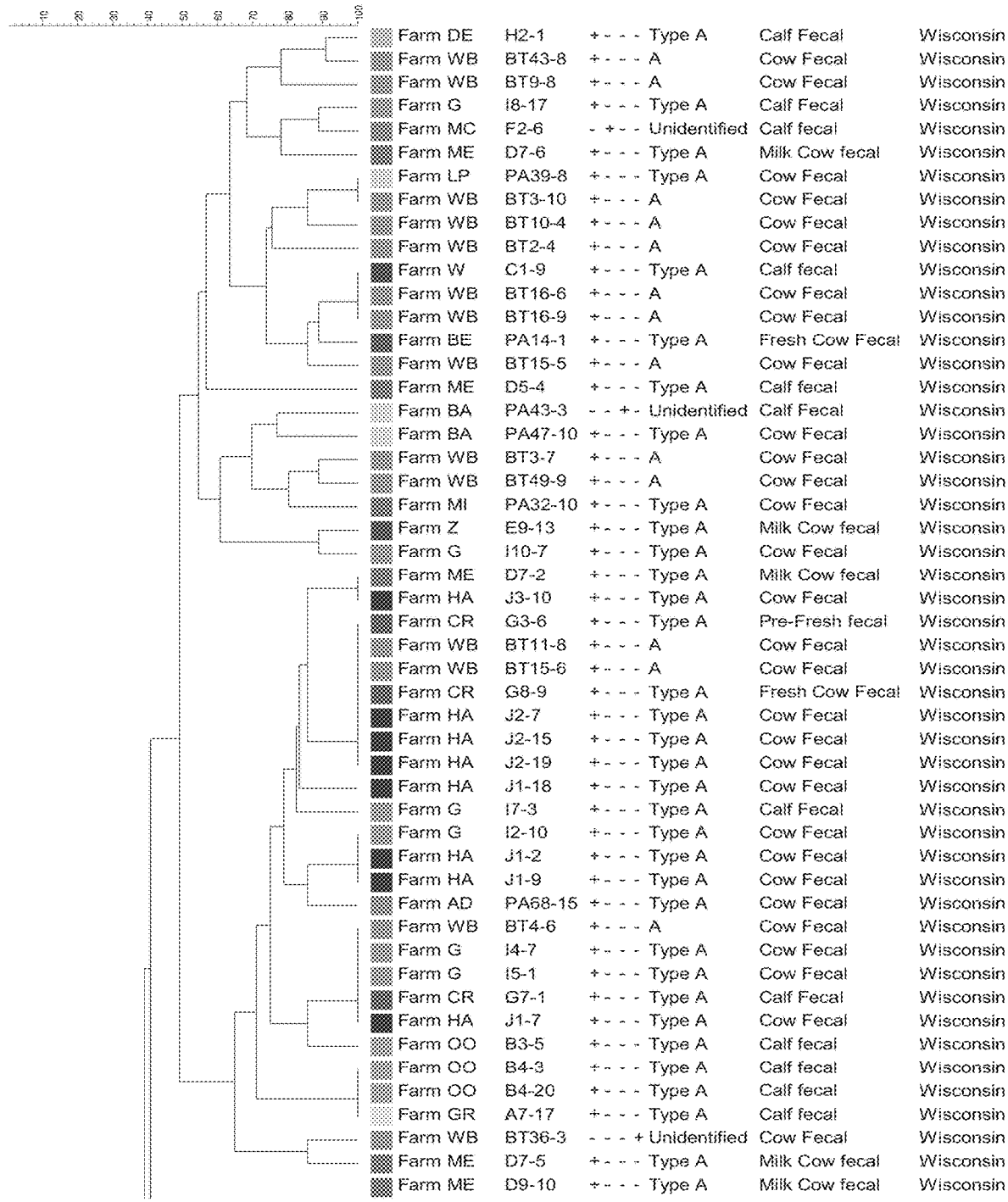
FIG. 38 is a dendrogram showing *Clostridium perfringens* (n=1,522) isolated from Wisconsin, with a cluster cutoff at 75% similarity wherein information about each isolate (n=1,522) is listed on the right: farm, ID number, Alpha, Beta, Epsilon and Iota toxin results, Toxin type, Source and State; and representatives were selected based on dendrogram clusters for screening in bacteriocin inhibition assays in accordance with one embodiment of the present invention, pursuant to Example 5.
Figure 38:
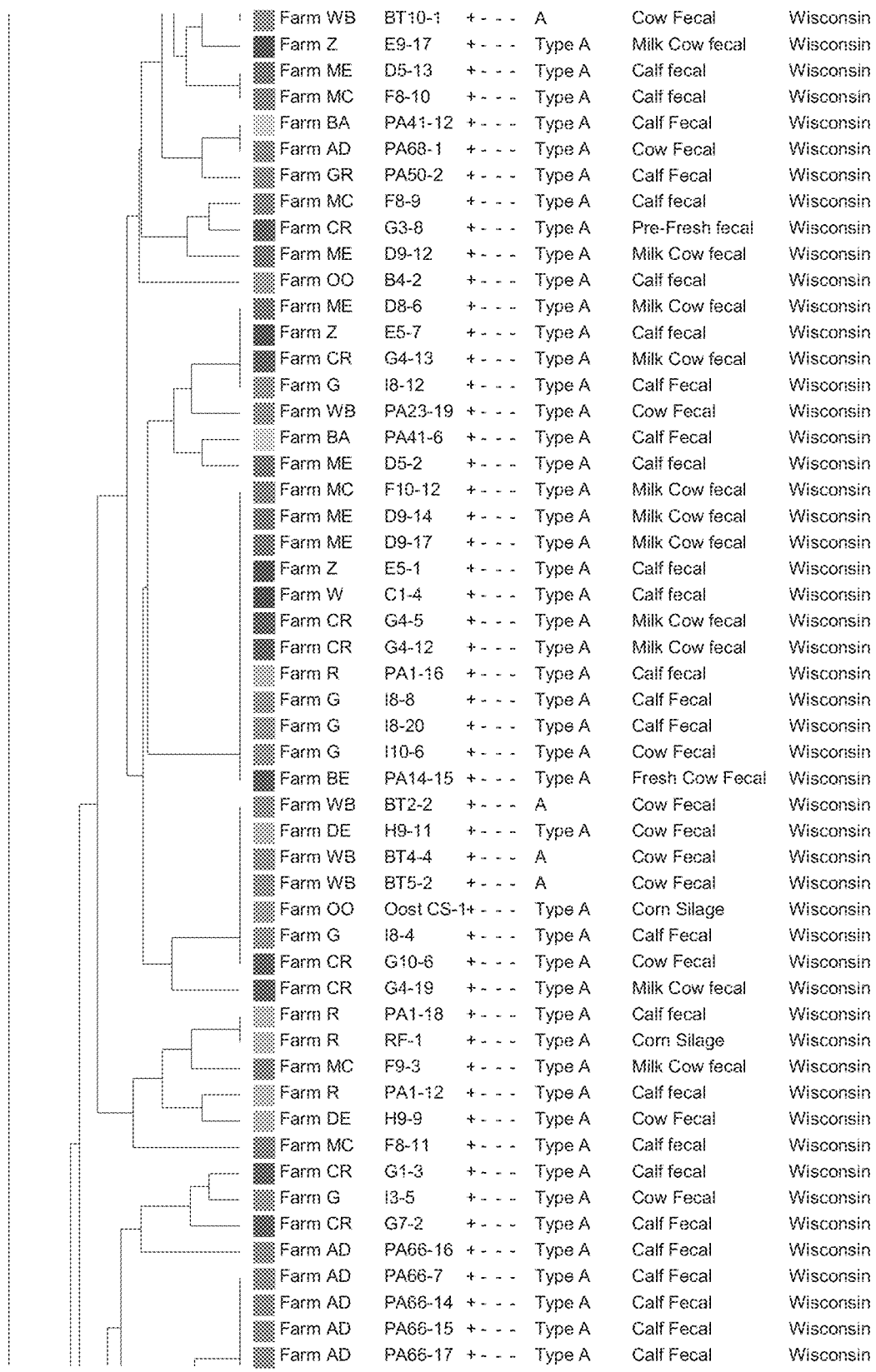
Figure 38:
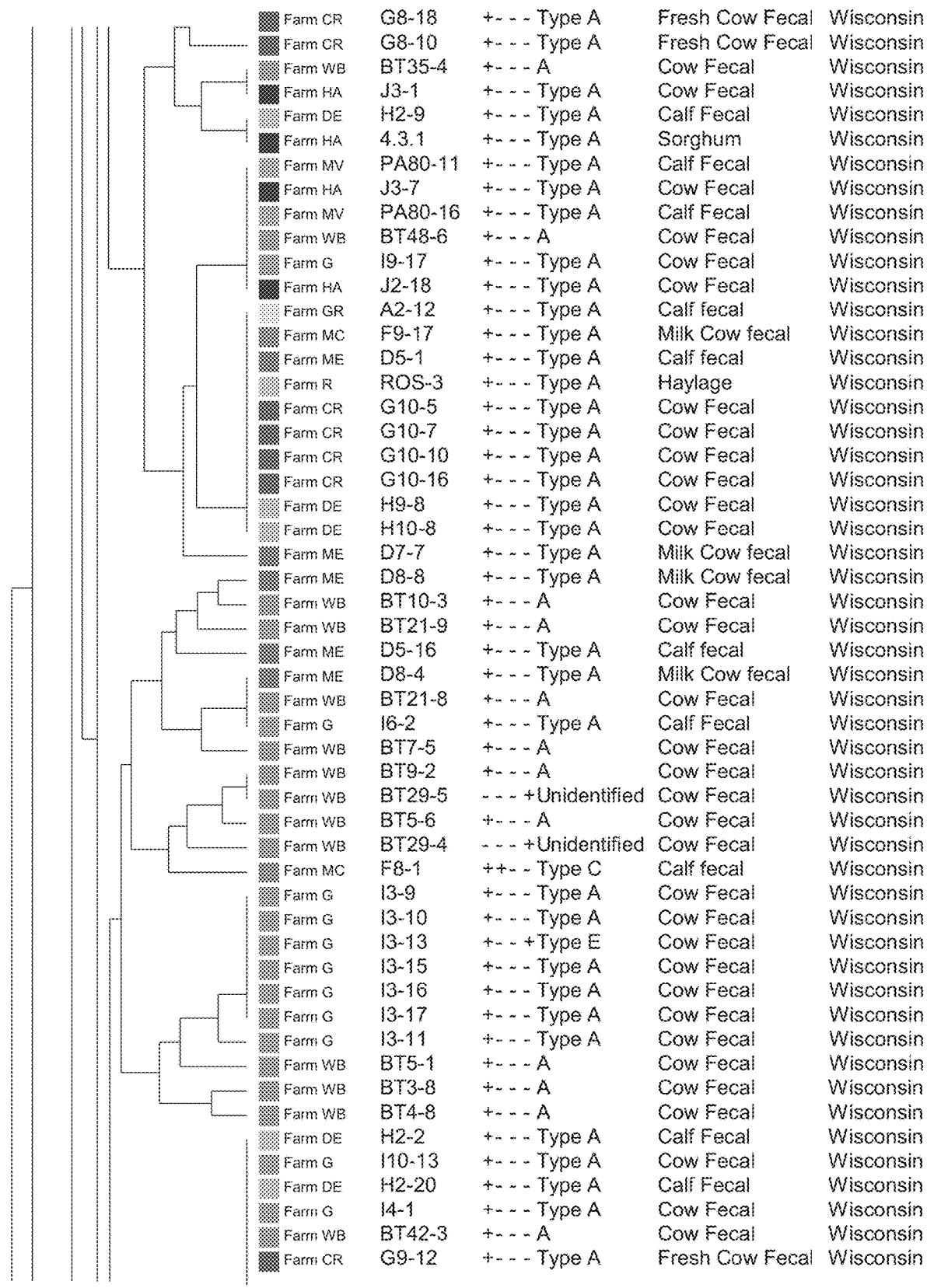
Figure 38:
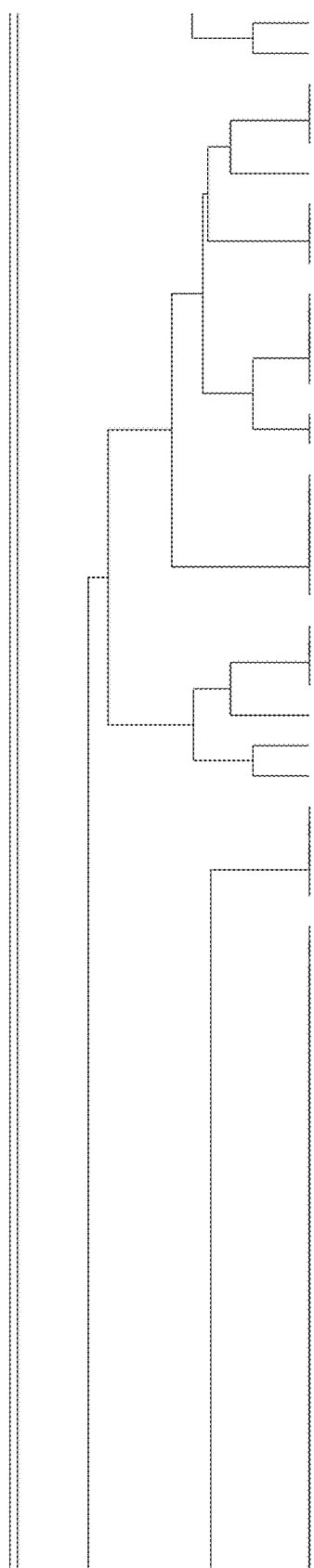
Figure 38:
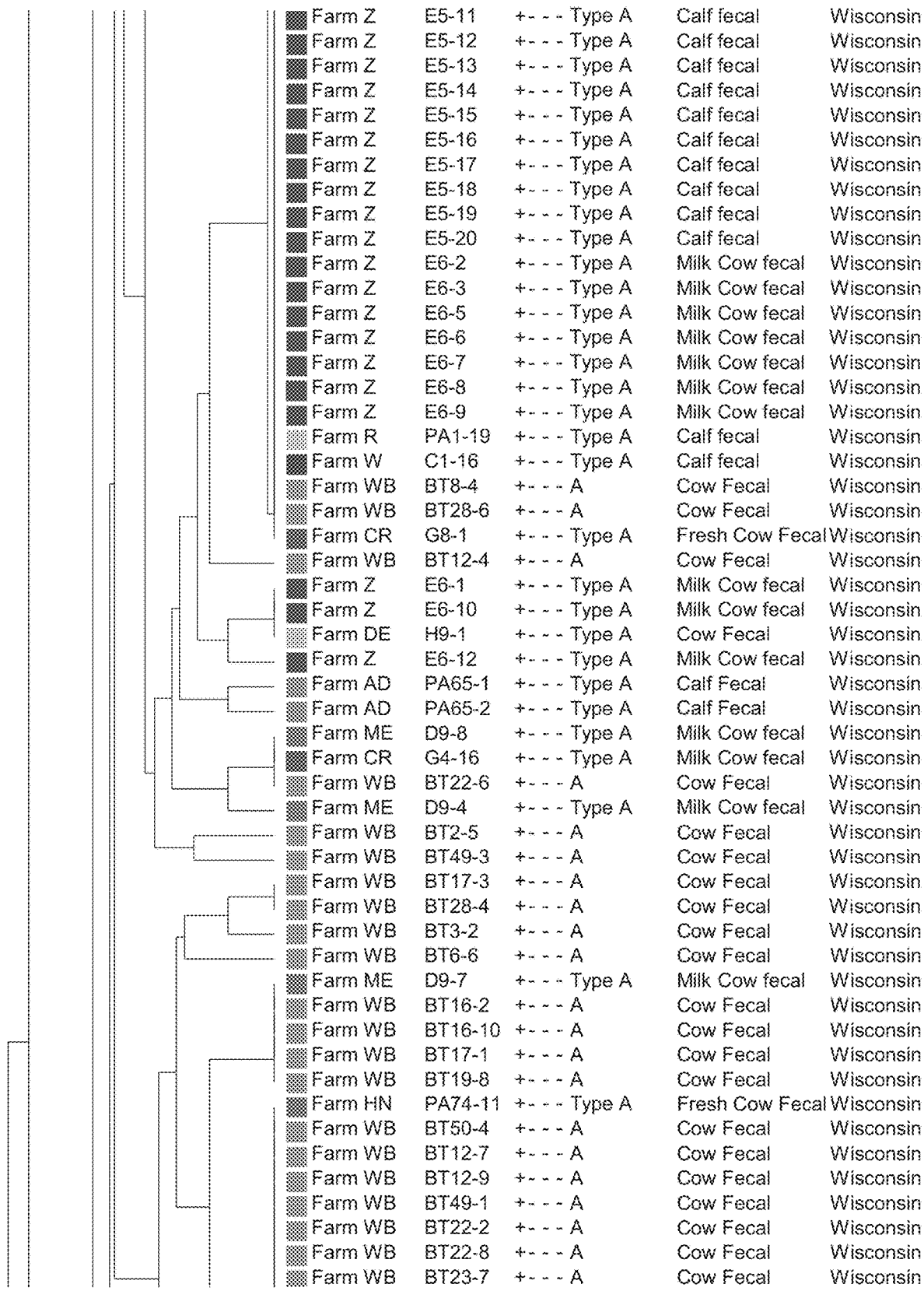
Figure 38:
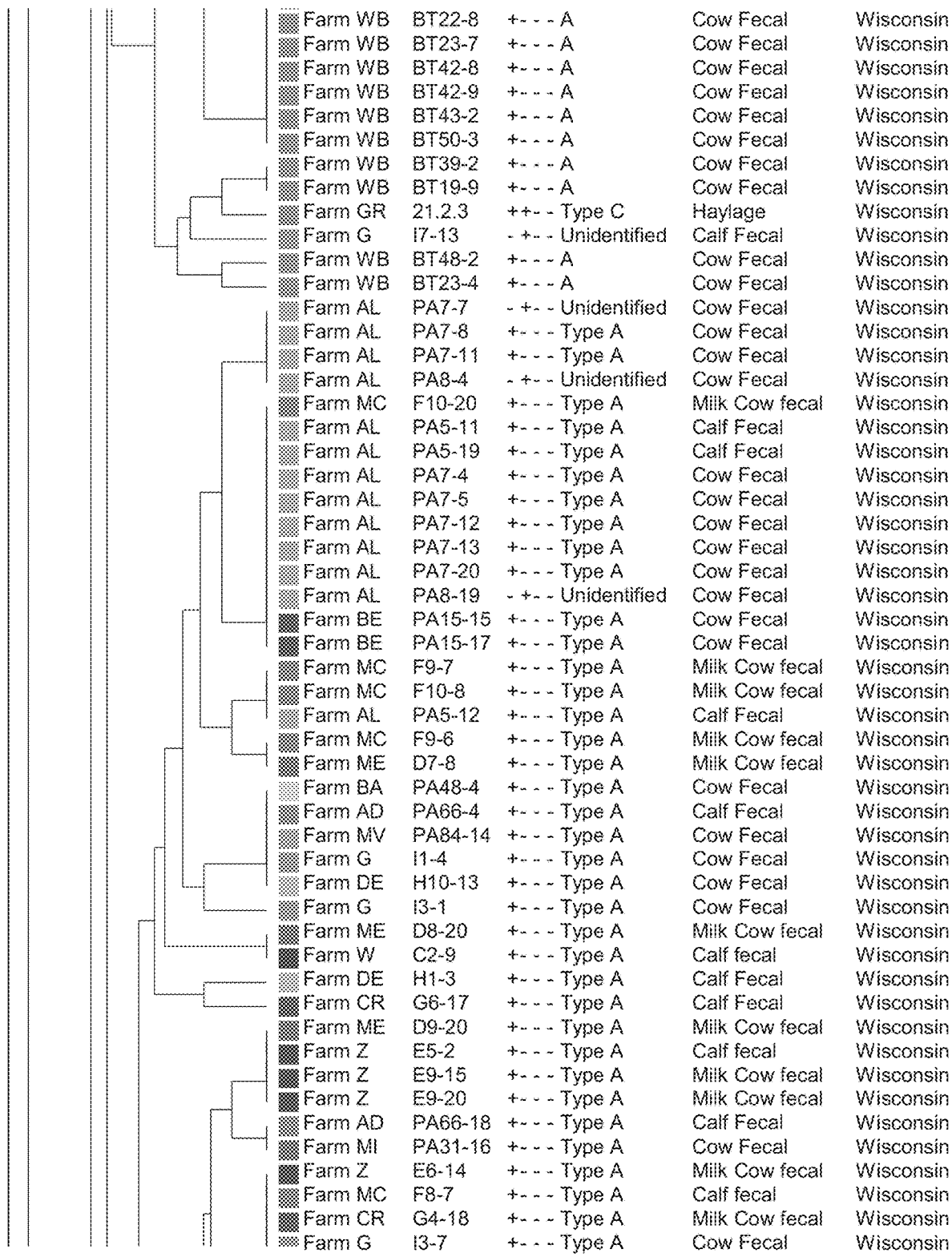
Figure 38:
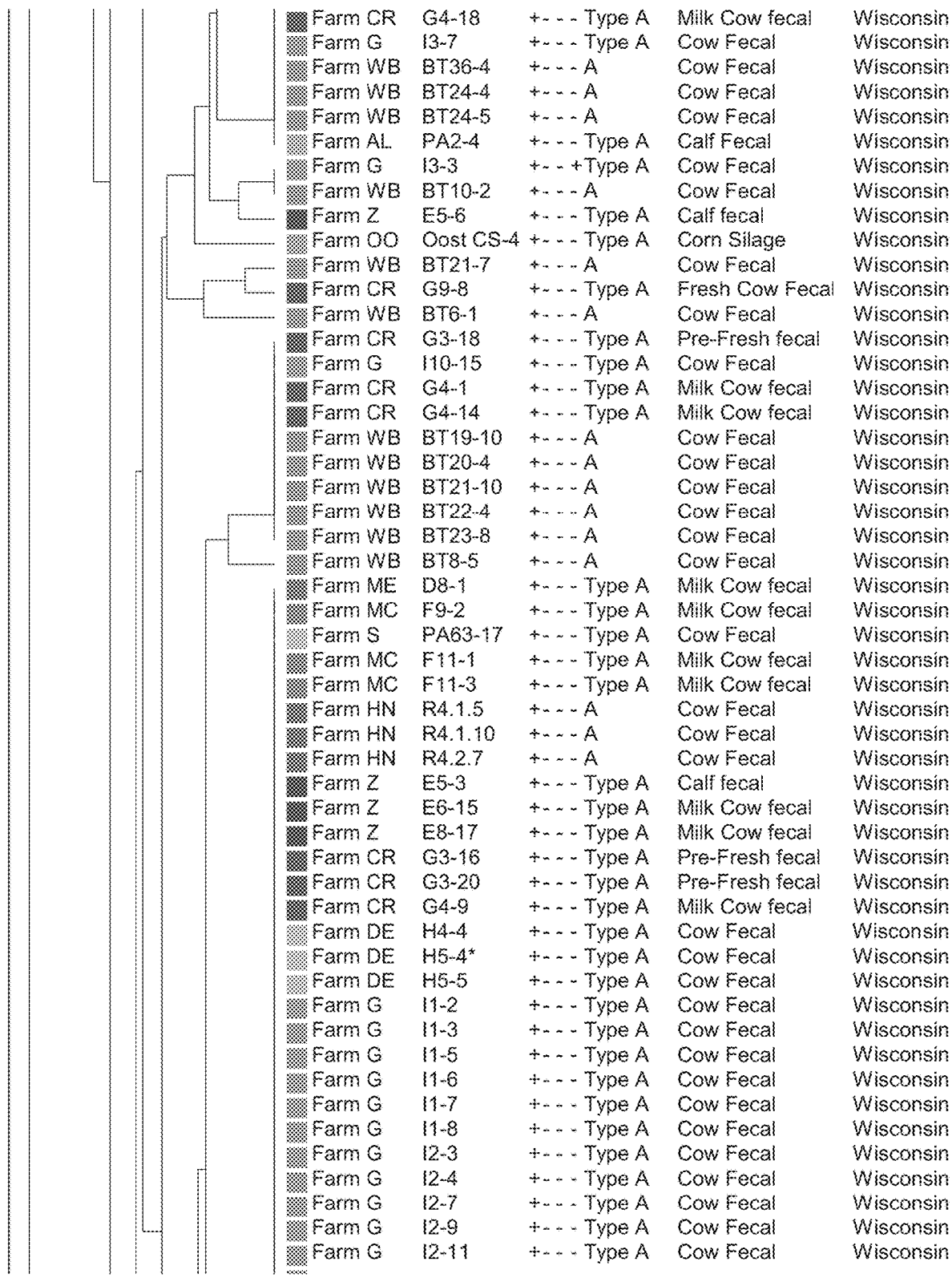
Figure 38:
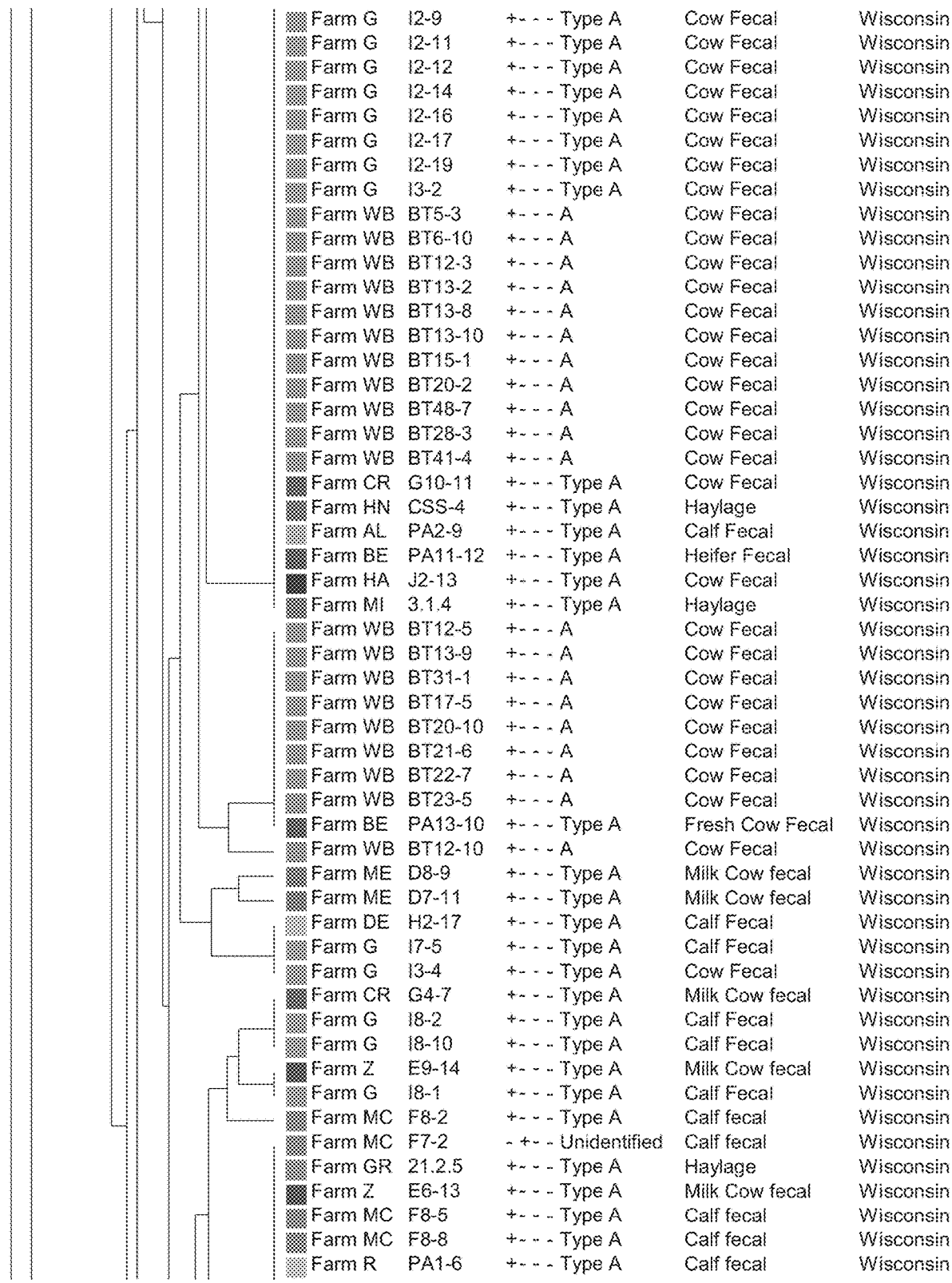
Figure 38:
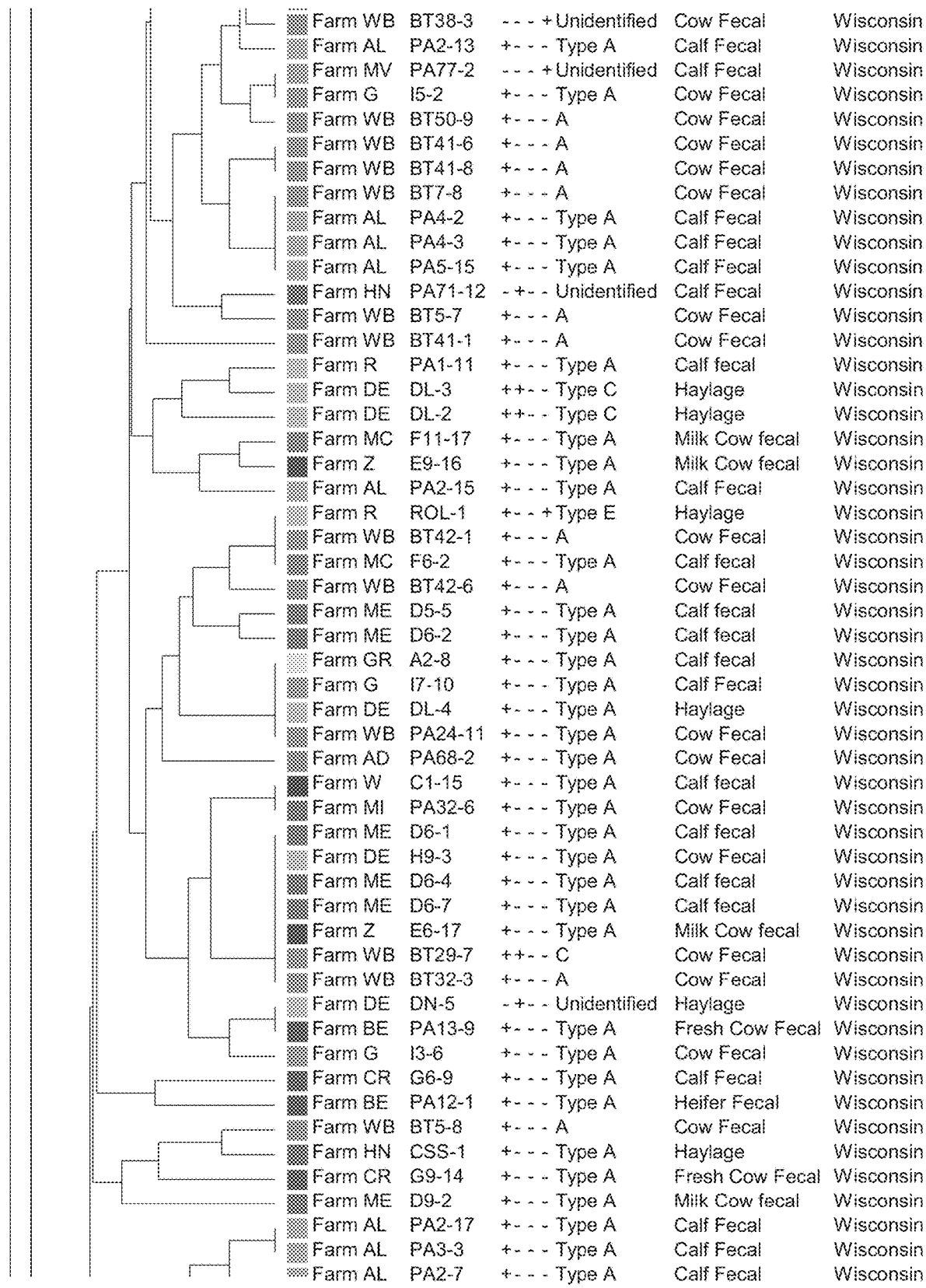
Figure 38:
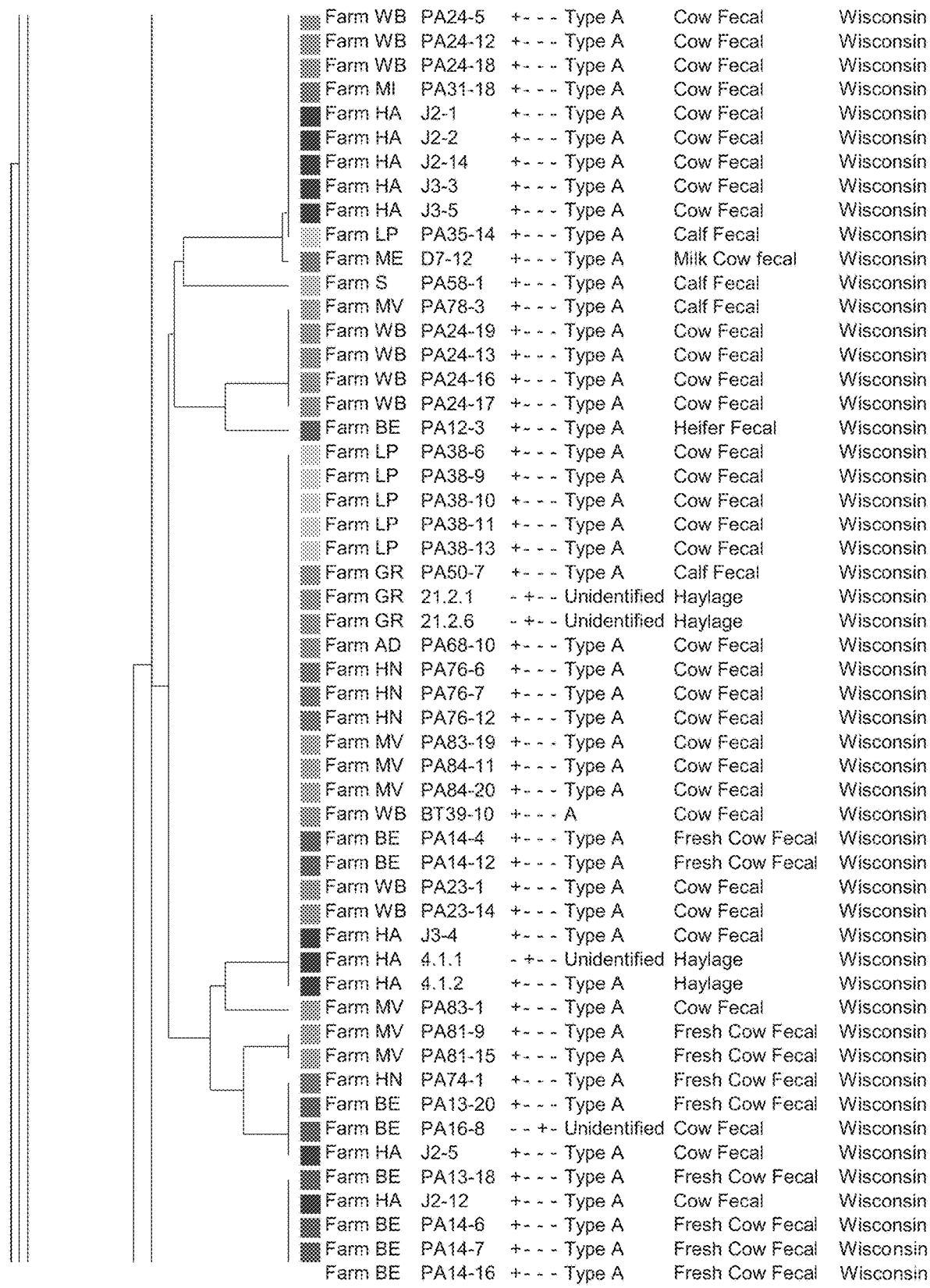
Figure 38:
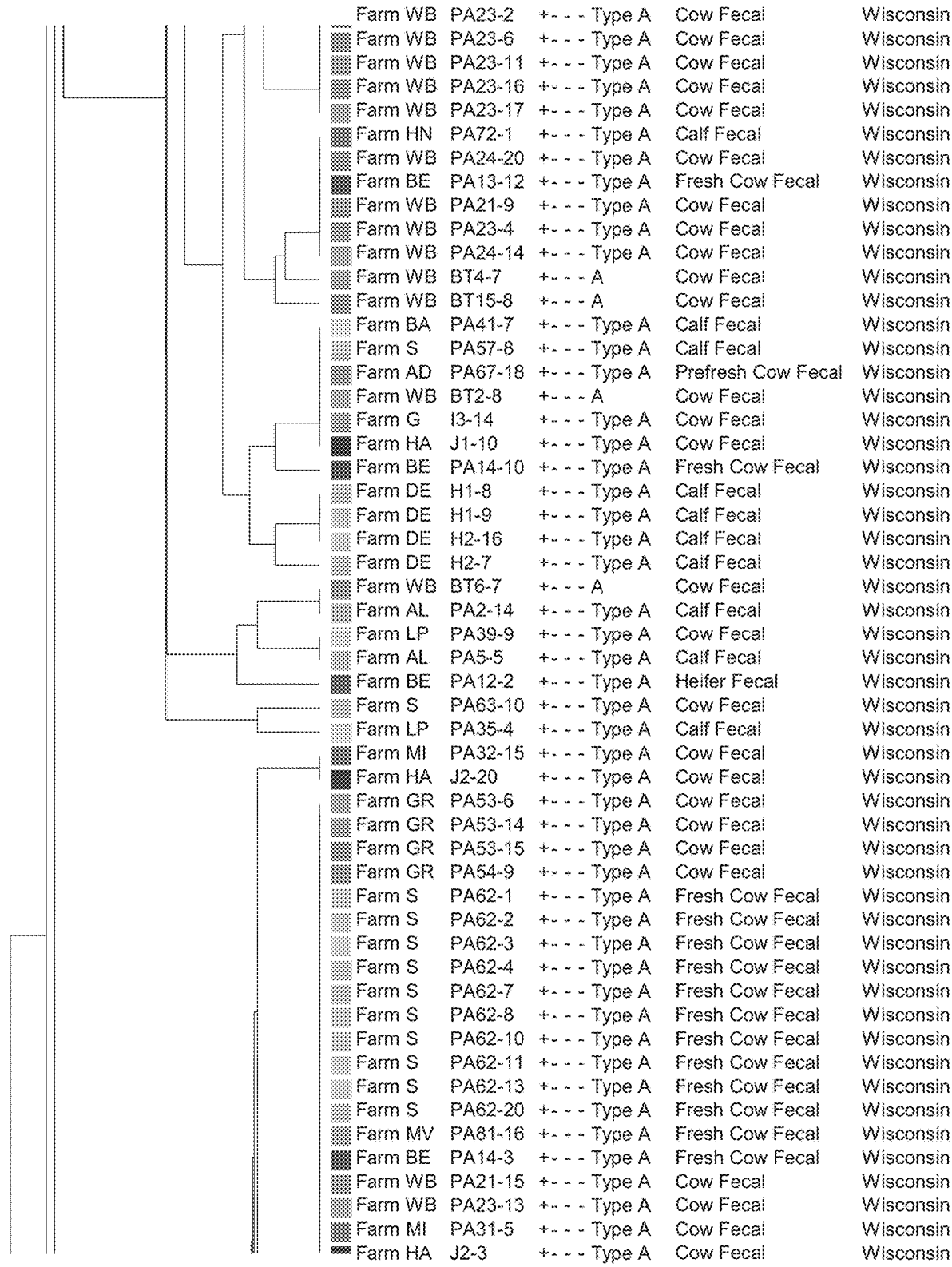
Figure 38:
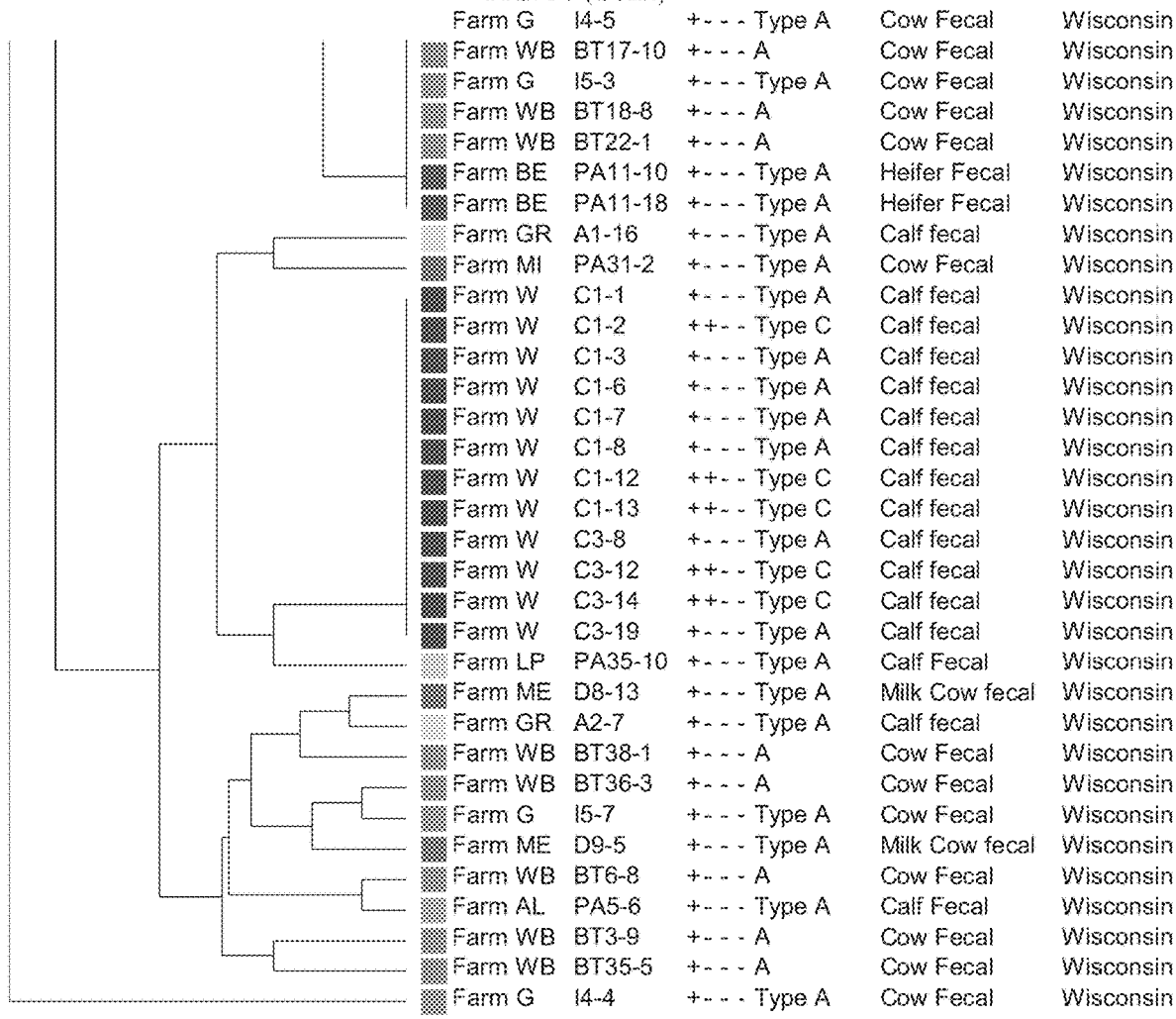
Figure 39:
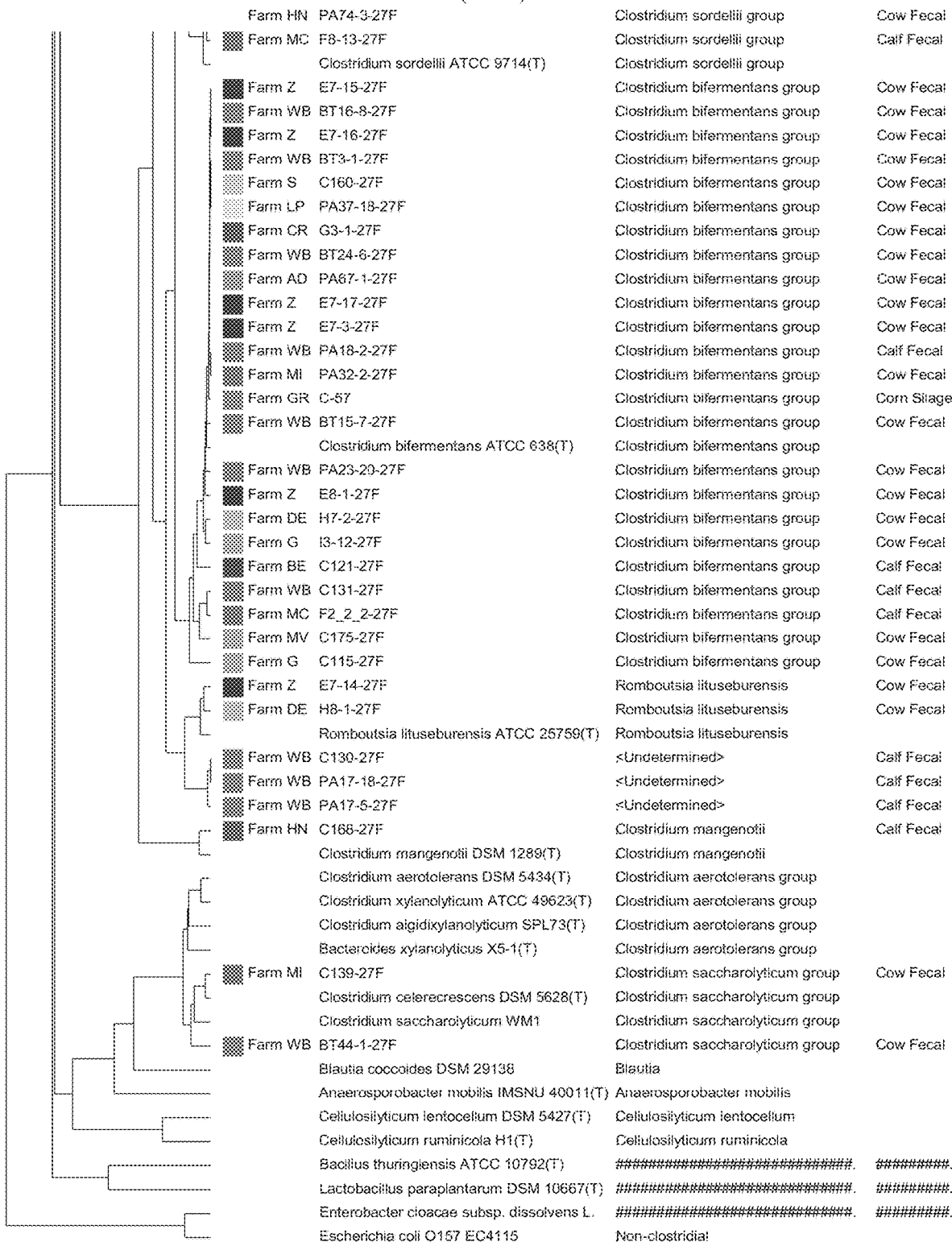
FIG. 39 is a dendrogram of non-toxigenic clostridia (n=183) displaying similarities between 16S DNA sequences from each isolate from Wisconsin; wherein information about each isolate is listed from left to right, including: farm, ID number or Type strain identification, identification, source of isolate in accordance with one embodiment of the present invention, pursuant to Example 5.

Lactic acid and acetic acid levels were similar between the two treatments throughout the course of the study (FIG. 30; FIG. 31). Some fluctuation was observed in levels of these VFAs on Day 90, but similar values were again observed between the two treatments on the last sampling time point.

Conclusion:

The pH decreased for all treatments in the initial measurement following treatment administration and was maintained over the course of the study. E. coli and coliform counts were reduced in inoculant treatment samples at a faster rate compared to the Control. Treated samples had slightly lower levels of mold present compared to their untreated controls. Clostridia counts for the samples treated with inoculant were similar or lower than those of the Control for the entire trial. This data indicates that the addition of silage inoculants to forage is controlling clostridia growth and secondary fermentation more effectively than when no treatment is administered.

This data indicates that silage preservation is not negatively affected by the addition of these *Bacillus* strains to a silage inoculant. In fact, the *Bacillus* in combination with LAB improved the reduction of coliforms and prevented mold growth, more effectively than when no treatment was administered. Clostridial growth and secondary fermentation was controlled more effectively than when no treatment is administered.

Example 5: Selection of *Bacillus* Strains to Inhibit *Clostridium Perfringens* and Non-Toxigenic Clostridia Isolated from Ruminant Fecal Samples. (Wisconsin)

Introduction:

*Clostridium* is a genus of Gram-positive, spore-forming bacteria that are common residents of the gastrointestinal tract. A number of *Clostridium* species have been linked to enteric disease in ruminants including hemorrhagic bowel syndrome (HBS), a disease often correlated to elevated levels of *C. perfringens* Type A (Dennison et al., 2005). While most of the enteric diseases caused by clostridia are acute and occur sporadically in herds, in general, the prognosis is poor and the first sign of illness may be death. Based on recent results sub-acute enteric clostridia disease challenges may be a more wide spread issue than acute challenges. Due to a low success rate from treatment in acute disease challenges a more common, emphasis needs to be placed on prophylactic measures.

The purpose of this research was to characterize the distribution and diversity of clostridia in ruminants and ensure inhibition of these isolates using novel *Bacillus* strains as a method to control the clostridia populations.

Materials and Methods:

Fecal samples (228) from cows, heifers and calves gathered from 24 farms in Wisconsin were diluted 1:10 with sterile peptone, heat shocked for 30 minutes at 60° C., enumerated in sterile peptone and pour plated on Tryptose Sulphite Cycloserine (TSC) agar with D-cycloserine (400 mg/L) to select for clostridia species. Agar plates were incubated at 37° C. anaerobically for 24 hours. If present, isolated sulphite-reducing colonies were counted for a total clostridia count (CFU/g) and representative isolates were picked into Reinforced clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions were performed in 96-well blocks containing 500 µl presumptive clostridia culture per well. Cells were harvested by centrifugation at 4,700 rpm for 10 minutes, the supernatant was removed. Cells were re-suspended in 500 µl of 50 mM of EDTA-2Na (pH=8.0). Aliquots of 300 µl of the suspended cells were transferred to a new 96-well block and combined with 20 µl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 µl of lysis buffer (6 M Guanidine, 20% Triton-X 100, 10 mM Tris-HCL, pH 7.5) was added, mixed then incubated at room temperature for 15 minutes. Following the incubation 20 µl of Proteinase K (NEB, 800 U/mL) was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed centrifuging 750 µl of Column Wash Solution (Promega, A1318) at 4700 rpms for 1 minute and 30 seconds discarding flow through at the end of each spin. The binding plate was centrifuged for an additional 10 minutes at 4,700 rpm to remove any residual ethanol. A clean elution plate was then placed under the binding plate and DNA was eluted with 200 µl, pre-warmed (55° C.), Nuclease Free Water (Promega, P1195).

DNA was screened for toxin genes (a, 0, c, and t) specific to *C. perfringens* using polymerase chain reaction (PCR). Amplification of toxin genes was executed using a multiplex PCR containing four primer sets (Yoo et al., 1997) (Table 1.) The PCR mixture contained 2.5 µl 10×PCR Buffer, 2 µl of 50 mM MgCl$_2$, 0.5 µM of each primer (Table 1.), 0.1 µl of Invitrogen™ Platinum™ Taq DNA Polymerase, 2.5 µl of DNA, sterile water was added to achieve 25 µl for a total reaction volume. The mixture underwent 5 minutes at 94° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved. If one or multiple toxin genes were observed a toxin type identification was assigned to each isolate based on their toxin gene profile (Songer, 1996). *C. perfringens* positive to total clostridia isolate ratio was used to calculate an estimated *C. perfringens* count based on the total clostridia count.

Unique strain-specific genetic fingerprints were generated using Random Amplification of Polymorphic DNA (RAPD) analysis on select isolates to determine diversity among fecal *C. perfringens* isolates. The PCR contained 5 µl of DNA, 2.5 µl RAPD primer 2 (10 µM) (Table 1.), and 17.5 µl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes finishing with a final elongation of 5 minutes at 72° C. PCR products observed on a Fragment Analyzer (Advanced Analytics) to determine amplification patterns and were imported into BioNumerics, bioinformatics software, for analysis. RAPD patterns were compared with a band based Dice correlation analysis method to determine the similarity between RAPD patterns as a way to monitor diversity between isolates.

Antimicrobial screening was done on *C. perfringens* isolates obtained from ruminant samples to gauge the effectiveness of the antimicrobial bacteriocin produced by the inventors' identified *Bacillus* strains 747, 1104, 1541, 1781, and 2018. Bacteriocin was harvested by growing each strain at 32° C. in a shaking incubator at 150 rpms for 24 hours in Brain Heart Infusion (BHI) broth. A 1% transfer of the 24-hour culture to fresh BHI broth was executed after incubation. The *Bacillus* were then incubated for 36-48 hours in a 32° C. shaking incubator at 150 rpms. The culture was then centrifuged at 14,000×g for 20 minutes, supernatant was then filtered with a 0.2 m filter to remove any residual cells.

A bacteriocin turbidity assay was executed by growing *C. perfringens* strains isolated from ruminant fecal samples in RCM for 24 hours, anaerobically, at 37° C. Overnight culture was transferred (1%) to sterile RCM and immediately used in the assay. For each *C. perfringens* isolate at least six wells were run in a sterile 48 well reaction plate, 600 μl inoculated culture (positive control), 600 μl inoculated RCM+70 μl bacteriocin (747, 1104, 1541, 1781, and 2018) and 670 RCM (un-inoculated, negative control). Plates were incubated anaerobically at 37° C. for 24 hours then read using a BioTek Epoch Microplate Spectrophotometer, readings were taken at a wavelength of 600 nm. Optical density readings from the negative controls were subtracted from all OD readings and percent inhibition was calculated using the positive control and each bacteriocin treatment.

To identify clostridia that did not have at least one toxin gene specific to *C. perfringens*, a PCR reaction was performed on the isolate DNA to amplify the 16S region of rDNA using primers 27F-YM and 1492R-Y (Table 1). This was done on 20% of the isolates that did not contain a toxin gene specific to *C. perfringens*. The PCR mixture contained 5 μl of 10×PCR Buffer, 2 μl of 50 mM $MgCl_2$, 1 μl of 50 mM dNTPs, 0.4 μM of each primer (Table 1.), 0.2 μl of Invitrogen™ Platinum™ Taq DNA Polymerase, 5 μl of DNA, and sterile water was added to achieve 50 μl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to gene wiz to obtain the sequences for the 16S genes. Sequences were compared to known typed bacterial strains obtained from EZbiocloud online electronic database. Based on comparisons of these sequences a bacterial identification was assigned to the isolates.

A bacteriocin turbidity assay was executed by growing non-toxigenic, non-*C. perfringens*, clostridia strains isolated from ruminant fecal and feed samples in RCM for 24 hours, anaerobically, at 37° C. Overnight culture was transferred (1%) to sterile RCM and immediately used in the assay. For each *C. perfringens* isolate at least six wells were run in a sterile 48 well reaction plate, 600 μl inoculated culture (positive control), 600 μl inoculated RCM+70 μl bacteriocin (747, 1104, 1541, 1781, 1999 and 2018) and 670 RCM (un-inoculated, negative control). Plates were incubated anaerobically at 37° C. for 24 hours then read using a BioTek Epoch Microplate Spectrophotometer, readings were taken at a wavelength of 600 nm. Optical density readings from the negative controls were subtracted from all OD readings and percent inhibition was calculated using the positive control and each bacteriocin treatment.

Results:

Fecal samples, 228, were collect from 24 Wisconsin dairy farms from which 2914 presumptive clostridia strains were isolated as representatives of the clostridial diversity in Wisconsin dairies (Table 7.).

Clostridia enumeration results indicated the average level of clostridia CFU/g across all calf fecal samples was 1,240,000 CFU/g with individual fecal samples ranging from <10 to 28,900,000 CFU/g. While the average level of clostridia CFU/g across all cow fecal samples was 59,200 CFU/g with individual fecal samples ranging from 10 to 6,700,000 CFU/g (FIG. 32.). Samples appeared to range in clostridia levels for both calves (FIG. 33.) and cows (FIG. 34.).

*C. perfringens* enumeration results displayed the average level of *C. perfringens* CFU/g across all calf fecal samples was 495,000 CFU/g with individual samples ranging from <10 to 14,500,000 CFU/g. While the average level of *C. perfringens* CFU/g across all cow fecal samples was 36,200 CFU/g with individual samples ranging from <10 to 3,690,000 CFU/g (FIG. 35.). Samples appeared to range in clostridia levels for both calves (FIG. 36.) and cows (FIG. 37.).

Analysis of the toxin multiplex PCR results displayed which isolates contained toxin genes specific to *C. perfringens*. A total of 1,737 presumptive clostridia isolates from cow fecal samples have been tested for the indicated *C. perfringens* toxin genes. Of the 1,737 cow clostridia isolates screened, 1,219 isolates (70.2%) tested positive for at least 1 of the toxin genes. From the 1,219 toxin-gene positive isolates 1,203 (98.5%) were identified as Type A (a toxin only), however β, ε and ι, toxins were also detected in the clostridia cow fecal isolates. A total of 1,177 presumptive clostridia isolates from calf fecal samples have been tested for the indicated *C. perfringens* toxin genes. Of the 1,177 calf clostridia isolates screened 482 (41.0%) tested positive for at least 1 of the toxin genes. From the 482 toxin gene positive isolates 438 (90.9%) were identified as Type A (αtoxin only), however β, ε and ι, toxins were also detected in the clostridia calf fecal isolates.

Gentic RAPD fingerprint patterns displayed diversity among the 1,522 isolates that successful amplified. The isolates tested were harvested from calf fecal, cow fecal and feed and did not cluster strictly based on the sample type or farm. Isolates formed 170 clusters based on 75% similarity according to the Dice correlation method. The largest cluster was 148 isolates (9.7%) and comprised of isolates from 11 different farms, all but two isolates were *C. perfringens* Type A (FIG. 38.).

Representatives from the RAPD dendrogram were selected to capture the diversity of the *C. perfringens* population from this region and subjected to inhibition assays. Antimicrobial testing using the bacteriocin turbidity assay displayed good inhibition of most ruminant fecal *C. perfringens* isolates using bacteriocin harvested from 747, 1104, 1541, 1781, and 2018. The bacteriocin from at least one of the strains 747, 1104, 1541, 1781, and 2018 were able to inhibit the growth >60% of 244 of the 271 isolates tested representing a total of 93.4% inhibition of the *C. perfringens* population based on the dendrogram (Table 8).

Out of the 2,914 isolates collected 1,207 isolates (41%) were found to be non-toxigenic clostridia. Sequencing representatives (n=183) from the non-toxigenic clostridia displayed three dominate clostridia groups (FIG. 39.). *Clostridium bifermentans* group (*Paraclostridium bifermentans* and *P. benzoelyticum*), *Clostridium butyricum* and

Figure 40:
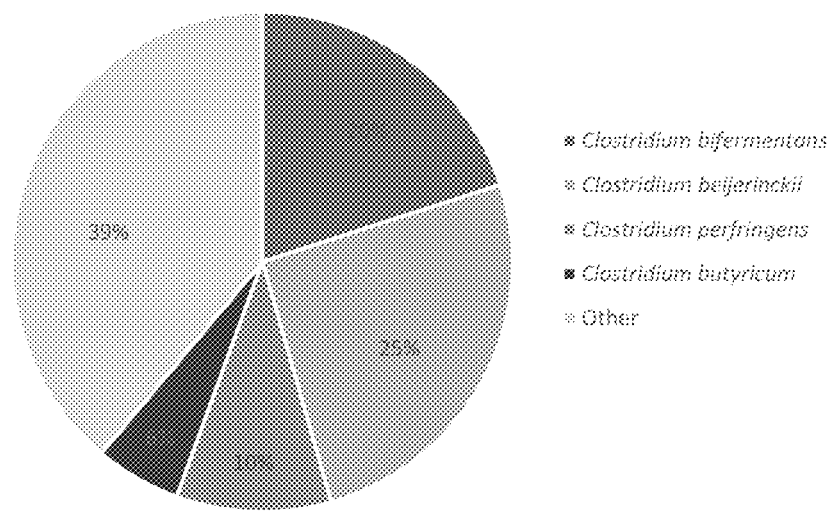
FIG. 40 is a pie graph showing major non-toxigenic clostridia (n=183) species compared to all other non-toxigenic types in accordance with one embodiment of the present invention, pursuant to Example 5.
Figure 41:
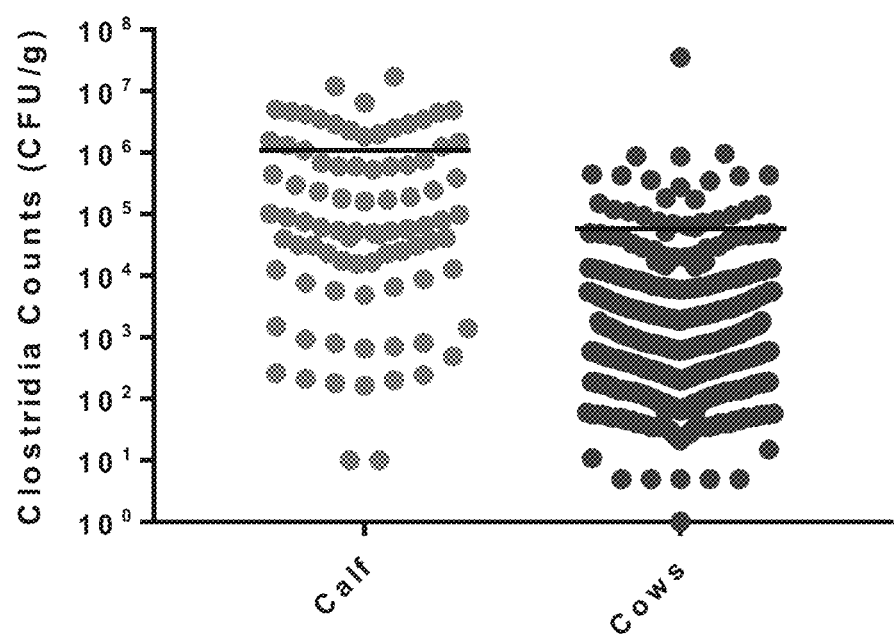
FIG. 41 is a chart showing enumeration results of all clostridia (no differentiation of *Clostridium* sp.) by individual fecal sample for cows and calves in Texas in accordance with one embodiment of the present invention, pursuant to Example 6.
Figure 42:
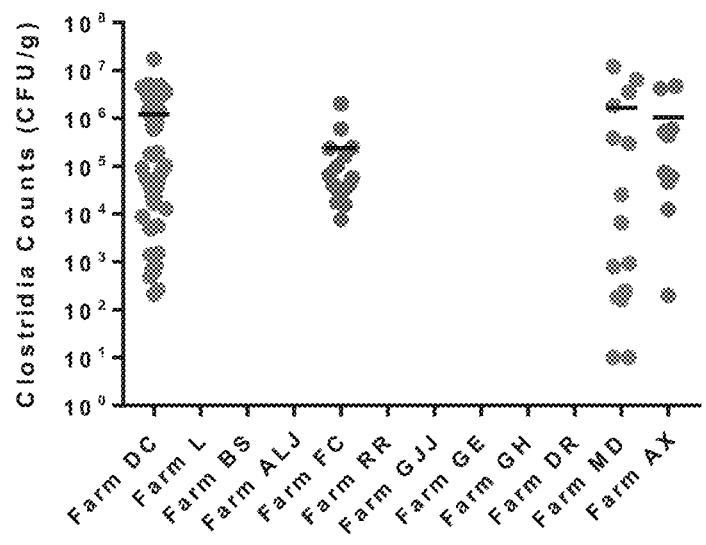
FIG. 42 is a chart showing enumeration results of total clostridia (no differentiation of *Clostridium* sp.) by individual farm calf fecal samples for each farm sampled in Texas in accordance with one embodiment of the present invention, pursuant to Example 6.
Figure 43:
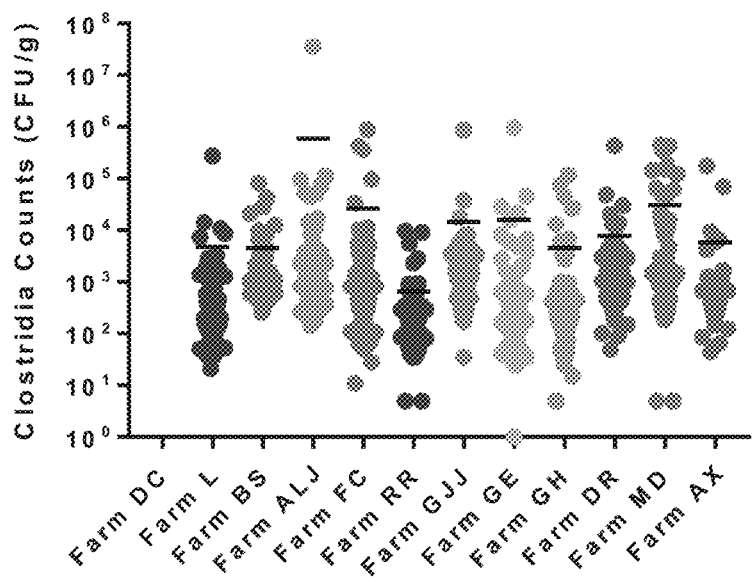
FIG. 43 is a chart showing enumeration results of total clostridia (no differentiation of *Clostridium* sp.) by individual farm cow fecal samples for each farm sampled from Texas in accordance with one embodiment of the present invention, pursuant to Example 6.
Figure 44:
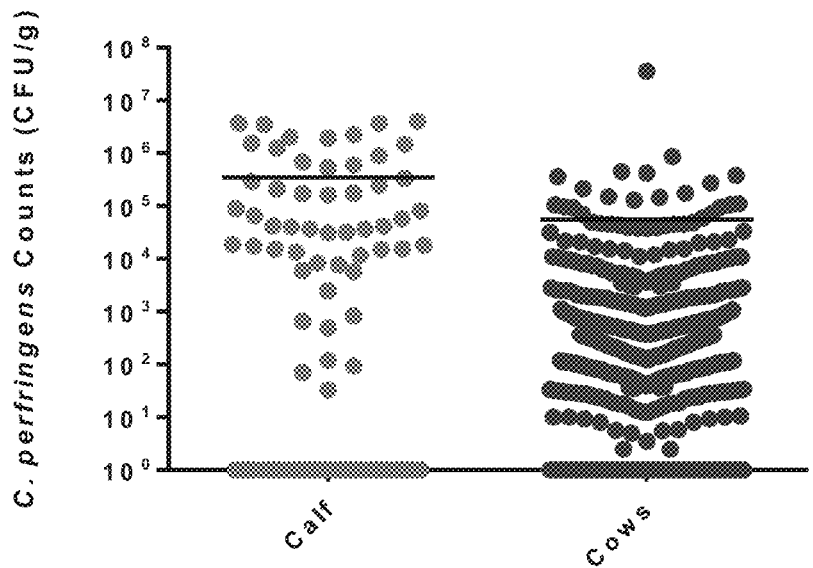
FIG. 44 is a chart showing calculated counts of *C. perfringens* by fecal sample, from fecal samples collected in Texas, where *C. perfringens* counts were estimated by multiplying each sample's total clostridia count by the percent that were confirmed to be *C. perfringens* in accordance with one embodiment of the present invention, pursuant to Example 6.
Figure 45:
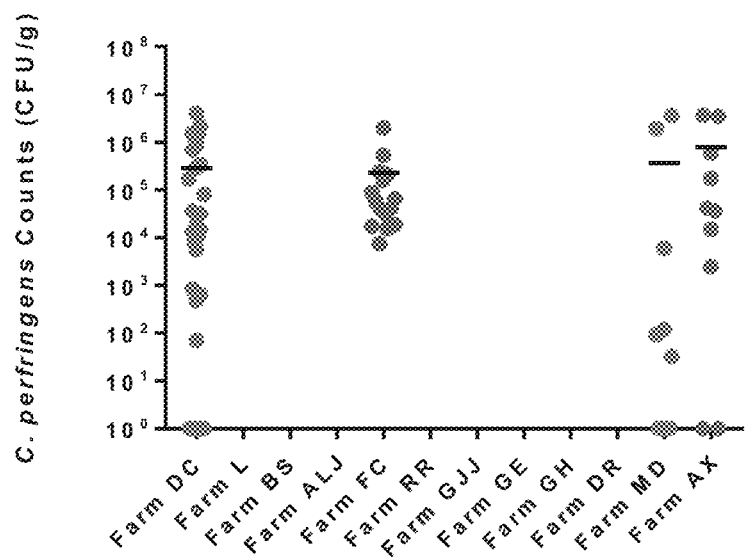
FIG. 45 is a chart showing calculated counts per farm of *C. perfringens* by individual calf fecal samples from Texas, where *C. perfringens* counts were estimated by multiplying each sample's clostridia count by the percent that were confirmed to be *C. perfringens* in accordance with one embodiment of the present invention, pursuant to Example 6.
Figure 46:
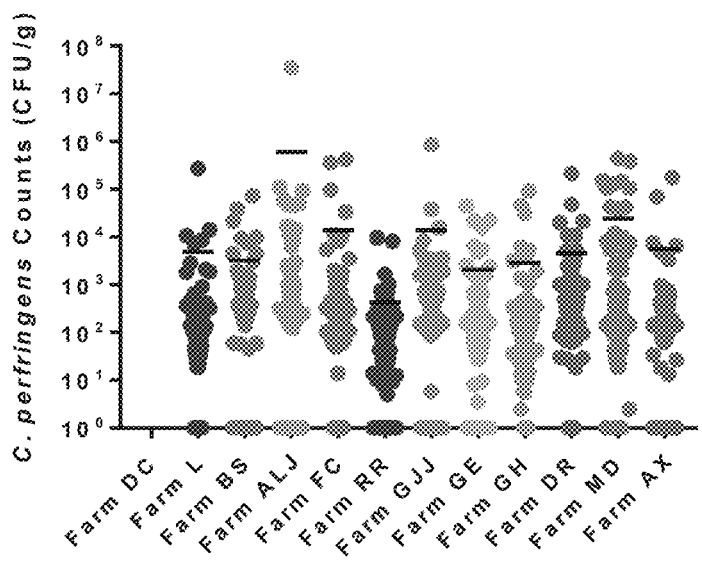
FIG. 46 is a chart showing calculated counts per farm of *C. perfringens* by individual cow fecal sample collected from Texas, where *C. perfringens* counts were estimated by multiplying each sample's clostridia count by the percent that were confirmed to be *C. perfringens* in accordance with one embodiment of the present invention, pursuant to Example 6.
Figure 47:
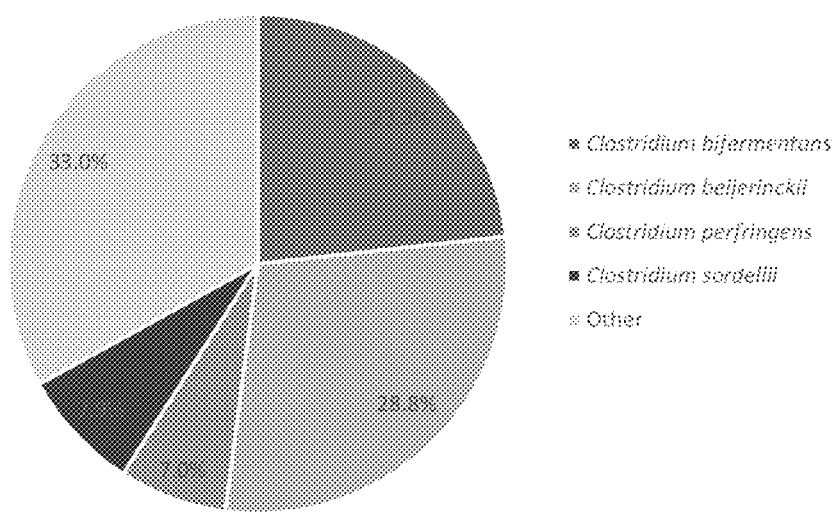
FIG. 47 is a pie graph showing the major species of non-toxigenic clostridia (n=215) isolated from Texas samples compared to all other non-toxigenic types in accordance with one embodiment of the present invention, pursuant to Example 6.
Figure 48:
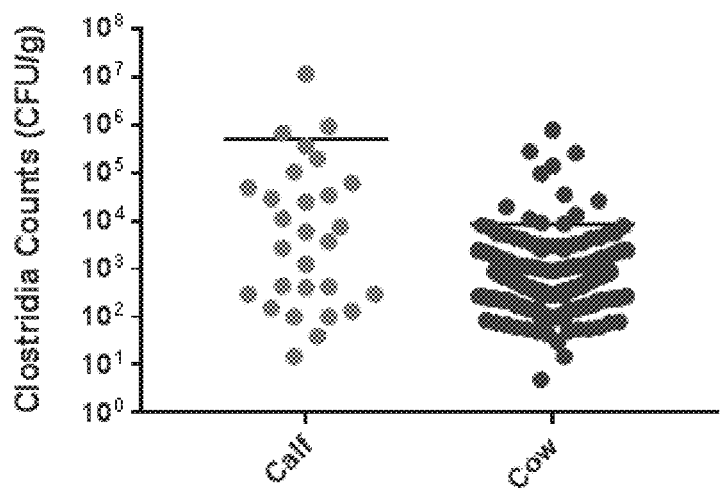
FIG. 48 is a chart showing enumeration results of all clostridia (no differentiation of *Clostridium* sp.) by individual fecal sample for cows and calves from the Upper Midwest region in accordance with one embodiment of the present invention, pursuant to Example 7.
Figure 49:
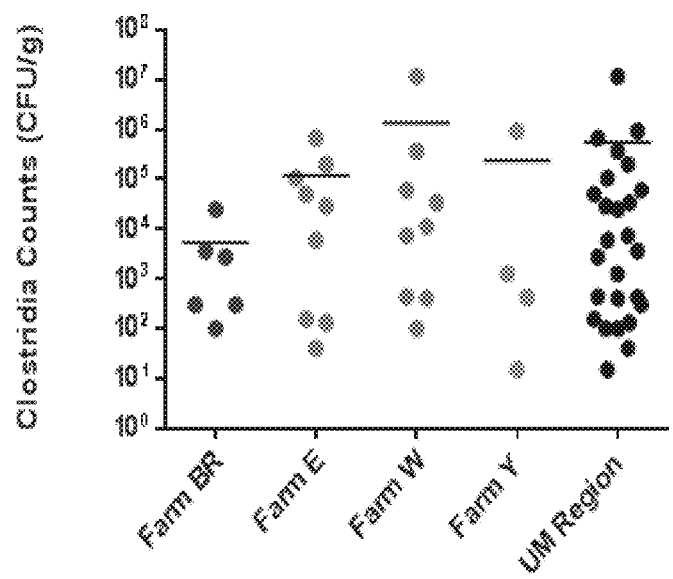
FIG. 49 is a chart showing enumeration results of total clostridia (no differentiation of *Clostridium* sp.) by individual farm calf fecal samples for each farm sampled from the Upper Midwest region in accordance with one embodiment of the present invention, pursuant to Example 7.
Figure 50:
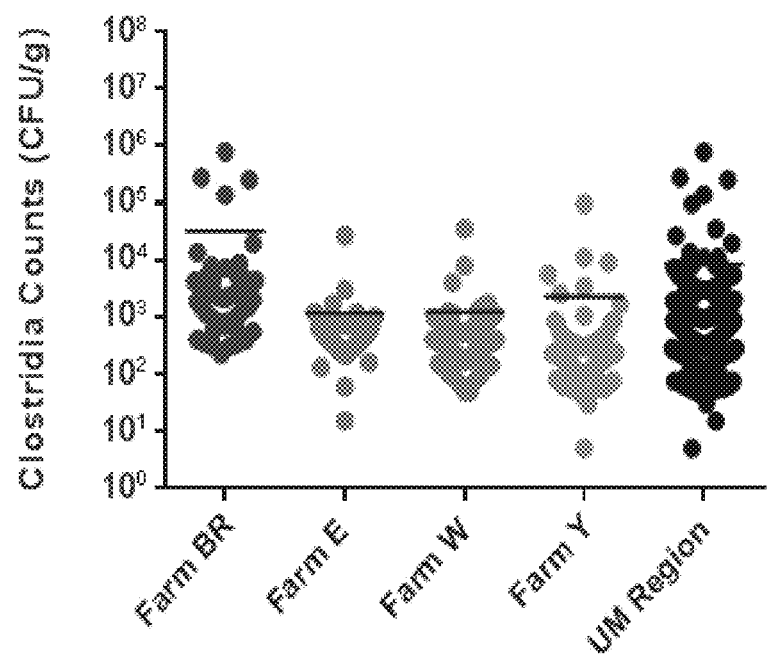
FIG. 50 is a chart showing enumeration results of total clostridia (no differentiation of *Clostridium* sp.) by individual farm cow fecal samples for each farm sampled from the Upper Midwest region in accordance with one embodiment of the present invention, pursuant to Example 7.
Figure 51:
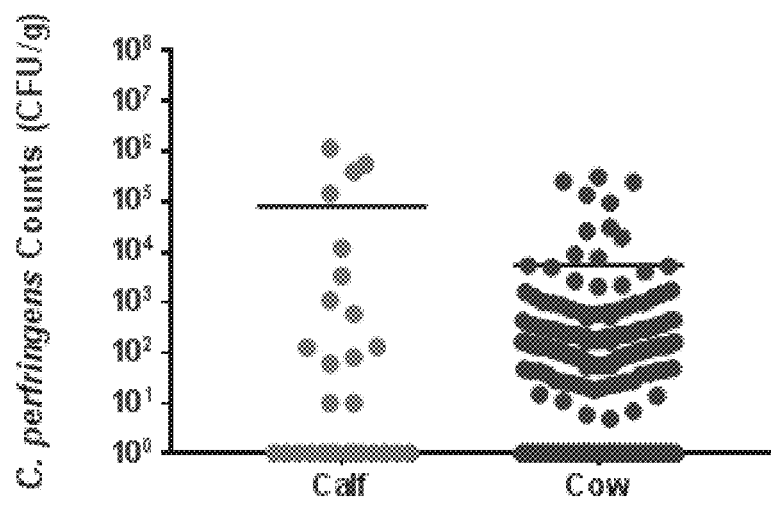
FIG. 51 is a chart showing calculated counts of *C. perfringens* by fecal sample, from fecal samples collected from the Upper Midwest region, where *C. perfringens* counts were estimated by multiplying each sample's total clostridia count by the percent that were confirmed to be *C. perfringens* in accordance with one embodiment of the present invention, pursuant to Example 7.
Figure 52:
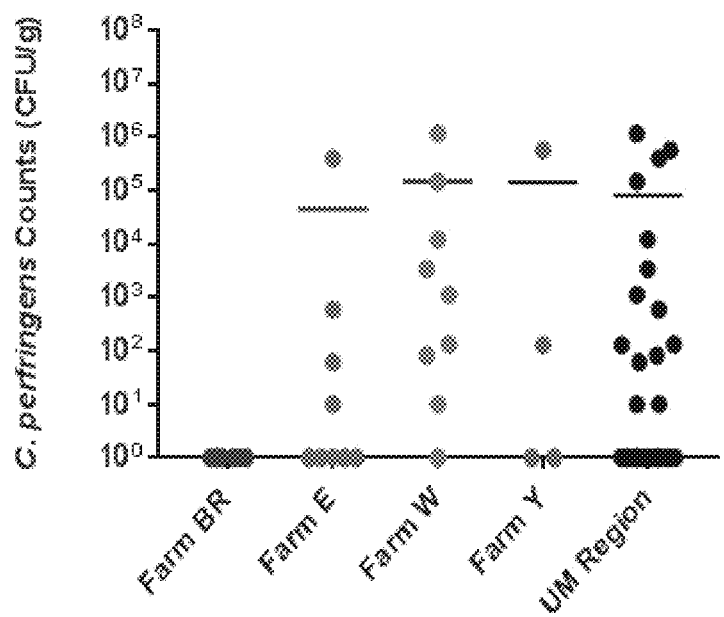
FIG. 52 is a chart showing calculated counts of *C. perfringens* for each farm by individual calf fecal sample from the Upper Midwest region, where *C. perfringens* counts were estimated by multiplying each sample's clostridia count by the percent that were confirmed to be *C. perfringens* in accordance with one embodiment of the present invention, pursuant to Example 7.
Figure 53:
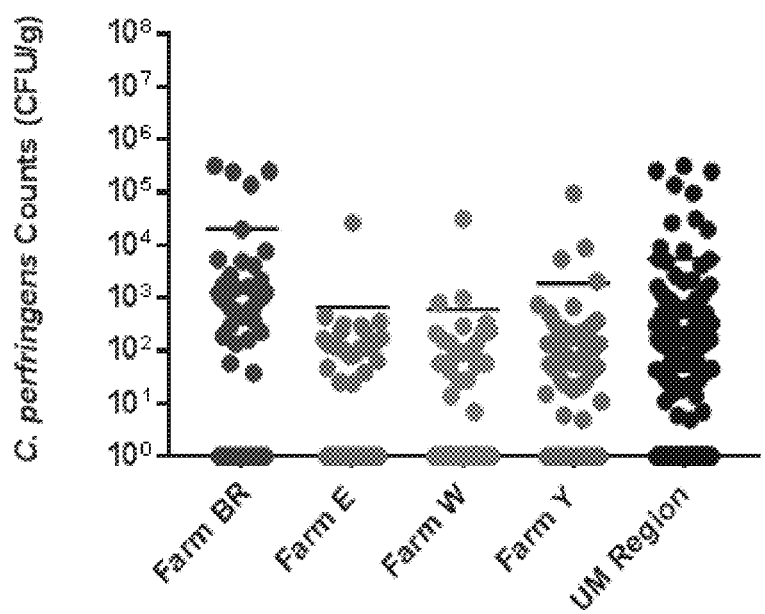
FIG. 53 is a chart showing calculated counts of *C. perfringens* for each farm by individual cow fecal sample collected from the Upper Midwest region, where *C. perfringens* counts were estimated by multiplying each sample's clostridia count by the percent that were confirmed to be *C. perfringens* in accordance with one embodiment of the present invention, pursuant to Example 7.
Figure 54:
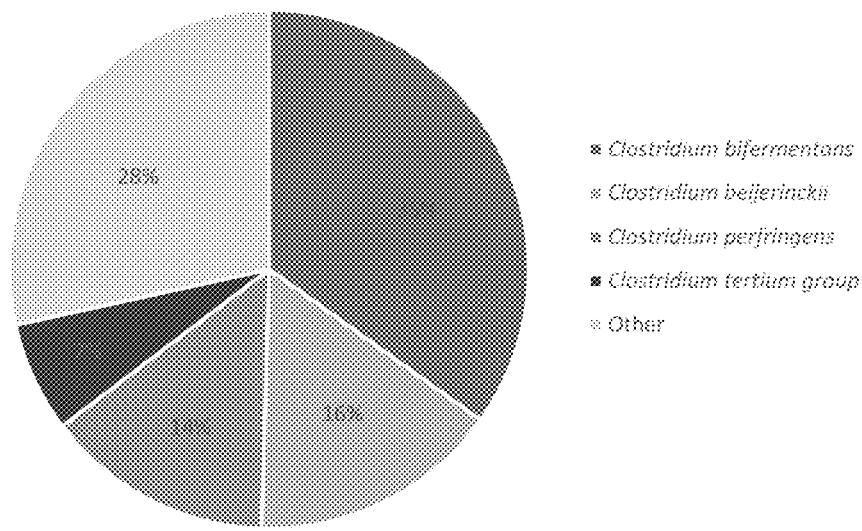
FIG. 54 is a pie graph showing Pie graph of non-toxigenic clostridia (n=218), showing the two major identification types (the *C. bifermentans* group and the *C. beijerinckii* group) compared to all other non-toxigenic types isolated from the Upper Midwest region in accordance with one embodiment of the present invention, pursuant to Example 7.
Figure 55:
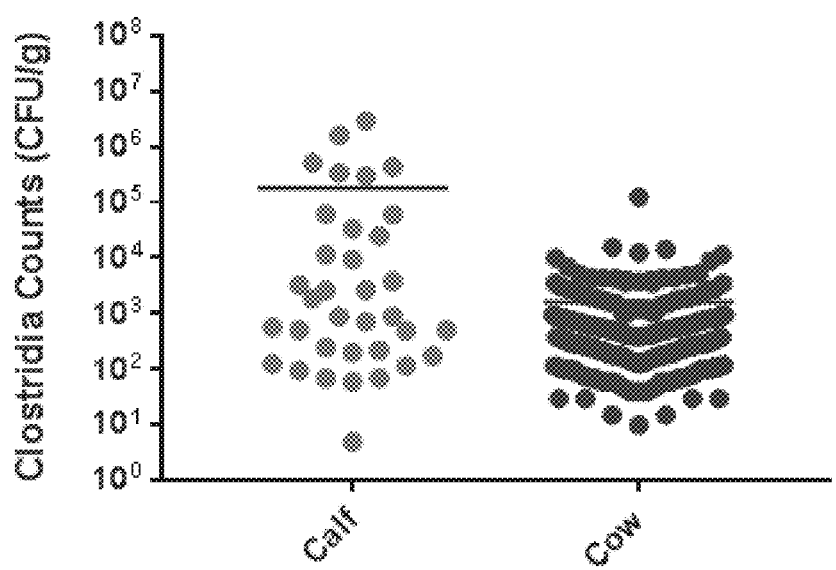
FIG. 55 is a chart showing enumeration results of all clostridia (no differentiation of *Clostridium* sp.) by individual fecal sample for cows and calves from the Great Lakes region in accordance with one embodiment of the present invention, pursuant to Example 7.
Figure 56:
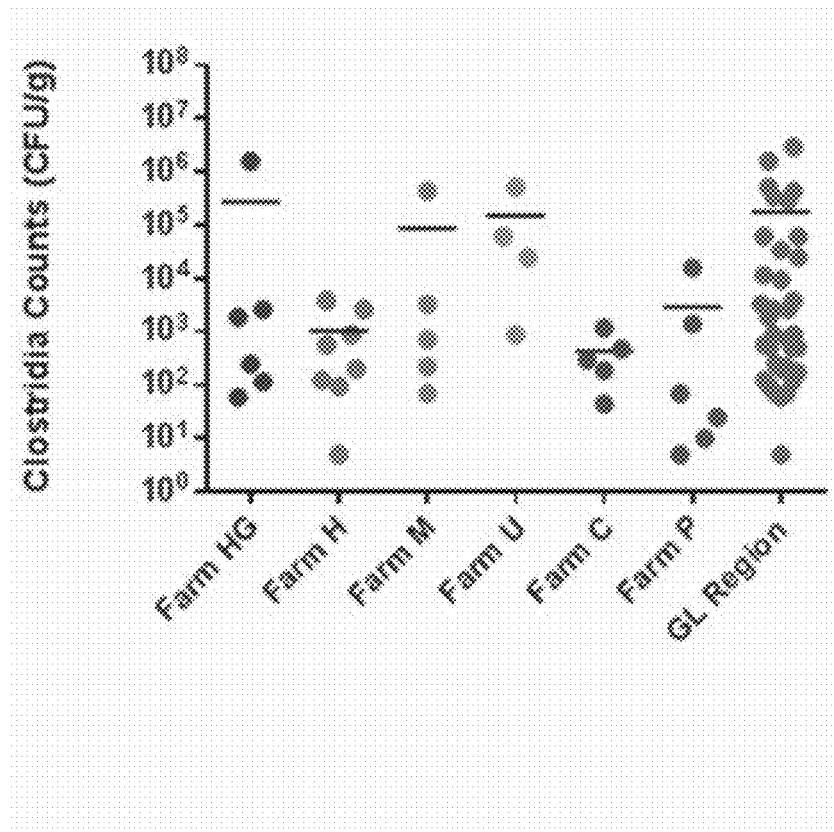
FIG. 56 is a chart showing enumeration results of total clostridia (no differentiation of *Clostridium* sp.) by individual farm calf fecal samples for each farm sampled from the Great Lakes region in accordance with one embodiment of the present invention, pursuant to Example 8.
Figure 57:
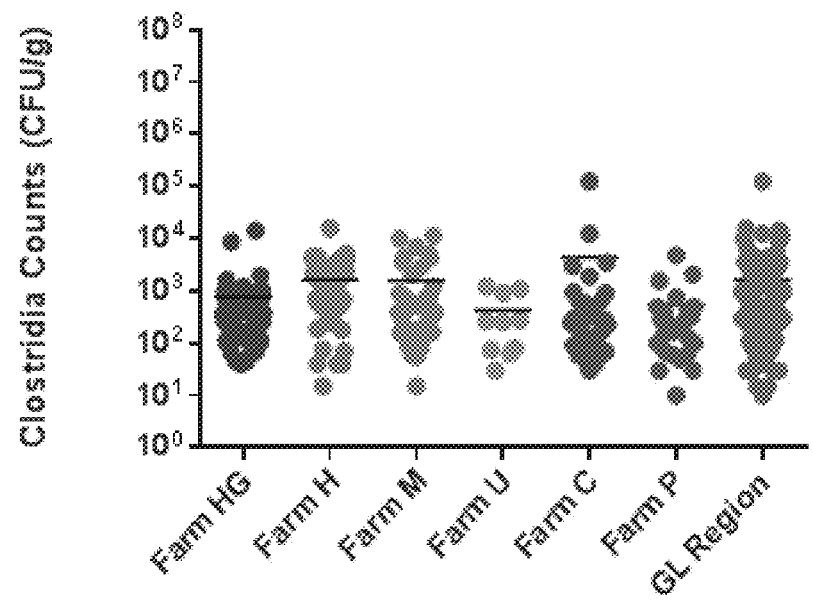
FIG. 57 is a chart showing enumeration results of total clostridia (no differentiation of *Clostridium* sp.) by individual farm cow fecal samples for each farm sampled from the Great Lakes region in accordance with one embodiment of the present invention, pursuant to Example 8.
Figure 58:
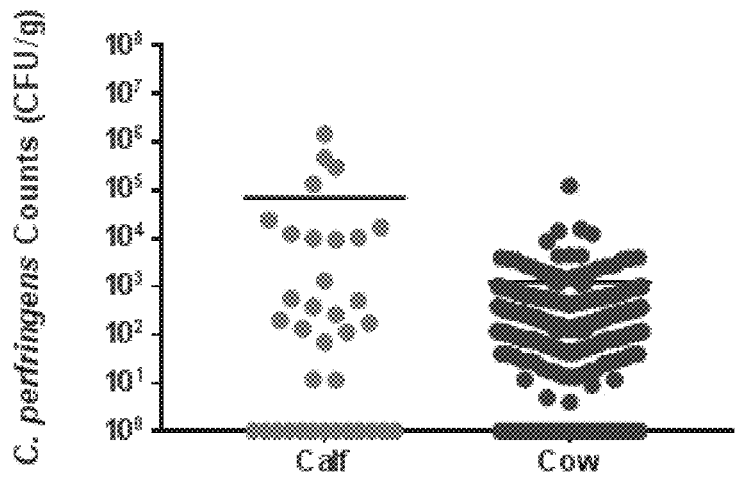
FIG. 58 is a chart showing calculated counts of *C. perfringens* by fecal sample, from fecal samples collected from the Great Lakes region, where *C. perfringens* counts were estimated by multiplying each sample's total clostridia count by the percent that were confirmed to the 1-29 Corridor region in accordance with one embodiment of the present invention, pursuant to Example 11.
Figure 59:
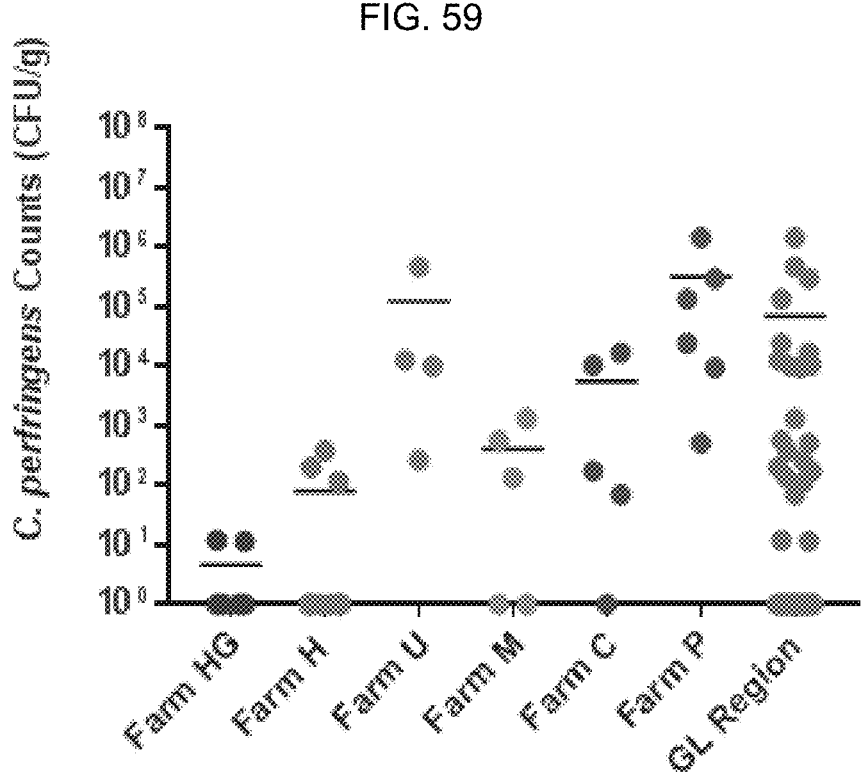
Figure 60:
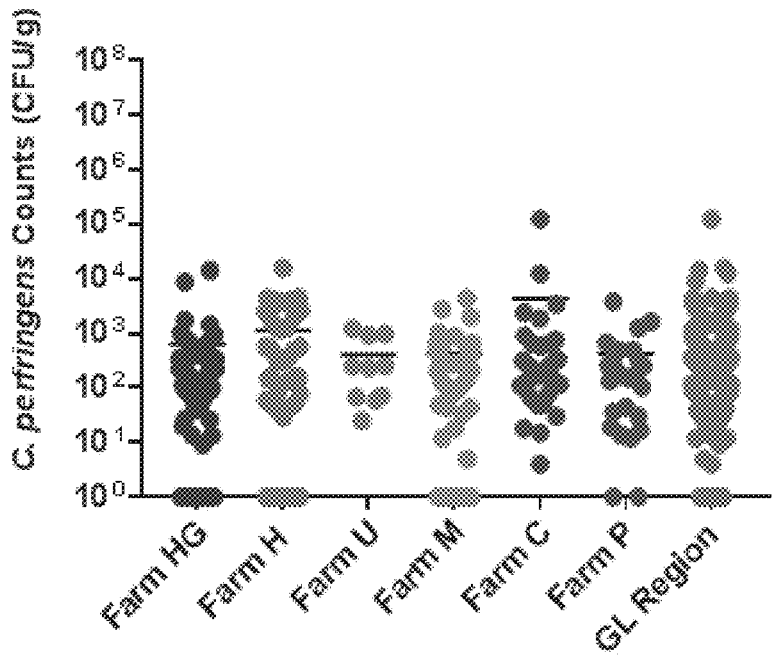
Figure 61:
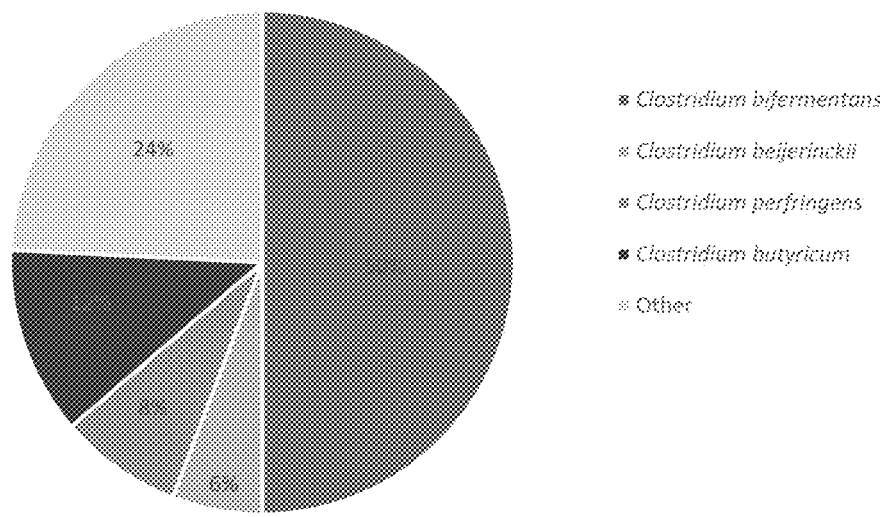

*Clostridium beijerinckii* group (*C. diolis, C. beijerinckii, C. chromiireducens, C. saccharoperbutylacetonicum, C. puniceum,* and *C. saccharobutylicum*), the three main groups of the non-toxigenic clostridia group made up 47.5% of the non-toxigenic isolates (FIG. 40.).

Six isolates with known 16S identifications from Wisconsin were selected for antimicrobial testing using the bacteriocin turbidity assay. Results displayed good inhibition of most ruminant non-toxigenic isolates tested using bacteriocin harvested from 747, 1104, 1541, 1781, 1999 and 2018. The bacteriocin from at least one of the strains 747, 1104, 1541, 1781, 1999 and 2018 were able to inhibit the growth >60% of 6 of the 6 isolates tested (Table 9).

Discussion:

Fecal samples were used as the most readily available sample type to estimate the level and obtain isolates of clostridia and *C. perfringens* within the digestive system of ruminants. From the 228 fecal samples collected throughout Wisconsin all but two contained detectable levels of clostridia. The survey results indicated clostridia is present in almost all fecal samples at various levels. The majority of the isolates harvested (59%) from the ruminant samples contained a toxin gene specific to *C. perfringens. C. perfringens* was detected in 92% of the cow fecal samples and in 77% of the calf fecal samples. The high presence of clostridia and *C. perfringens* indicates the risk for sub-acute enteric clostridia disease challenges in most ruminants throughout Wisconsin. *C. perfringens* isolates were diverse according to the RAPD genetic fingerprints but were not specific to sample type or farm. Diverse representatives of *C. perfringens* were mostly inhibited (>60%) by at least one bacteriocin from the following strains 747, 1104, 1541, 1781 or 2018. From the 271 isolates tested 244 isolates were inhibited by greater than 60% by at least one of the strains, representing inhibition of 93.4% of the total *C. perfringens* population based on representation from clusters on the RAPD dendrogram. This indicates the *Bacillus* strains 747, 1104, 1541, 1781 and 2018 can inhibit a wide range of diversity of *C. perfringens* isolates. The *Bacillus* strains are not limited to specific clostridia strain(s) like a vaccine which may be missing large groups of the clostridia populations based on the genetic diversity observed in the RAPD dendrogram. DNA sequencing of the non-toxigenic clostridia revealed three major identifications of *Clostridium* species. *C. bifermentans* group, which is known to produce 1,3-propanediol (Leja et al., 2014; Myszka et al., 2012) *C. beijerinckii* group known to produce butanol and acetone (Hou et al., 2017), and *C. butyricum* (Weng et al., 2015) producer of butyrate. The production of the metabolic end products of these species could be having an impact in the rumen, reducing performance parameters such as milk production within a dairy cow. Non-toxigenic clostridia tested were all inhibited (>60%) by the bacteriocin from at least one of the following strains 747, 1104, 1541, 1781, 1999 or 2018. The inhibition of the non-toxigenic clostridia could also be a potential mode of action that *Bacillus* strains are using to increase performance parameters. The high inhibition level against the clostridia isolates in vitro indicates a potential mode of action of the *Bacillus* strains 747, 1104, 1541, 1781, 1999 and 2018.

The *Bacillus* strains offer a prophylactic effect on the clostridia populations which may not only increase rumen efficiency leading to increased milk production, but prevent acute levels of *C. perfringens* reducing the occurrence of digestive deaths. The high prevalence of clostridia and *C. perfringens* in fecal samples collected suggests efficiency improvement opportunities in many ruminants throughout Wisconsin. This example displays the diversity of clostridia isolates from the ruminant fecal and feed samples collected from Wisconsin. The *Bacillus* strains tested 747, 1104, 1541, 1781, 1999 and 2018, could inhibit most of the clostridia diversity observed in Wisconsin. The product, in accordance with this embodiment of the present invention could inhibit both toxigenic and non-toxigenic clostridia isolated from ruminants in Wisconsin indicating a benefit in rumen efficiency if fed to dairy cows as a direct fed microbial (DFM).

TABLE 7

Fecal samples, 228, were collected from Wisconsin dairies separated by farm (24) and age (cow or calf) which were enumerated for clostridia, tested for *C. perfringens*, isolates were genotyped and tested for inhibition.

| Farm Name | Cow Fecal | Calf Fecal |
|---|---|---|
| Farm WB | 54 | 4 |
| Farm CR | 6 | 4 |
| Farm G | 8 | 2 |
| Farm S | 4 | 4 |
| Farm DE | 8 | 2 |
| Farm ME | 3 | 6 |
| Farm MC | 3 | 8 |
| Farm BE | 6 | 2 |
| Farm GR | 4 | 4 |
| Farm LP | 4 | 4 |
| Farm AL | 3 | 4 |
| Farm Z | 4 | 5 |
| Farm HN | 4 | 4 |
| Farm MV | 4 | 4 |
| Farm HA | 3 | 0 |
| Farm WO | 0 | 7 |
| Farm AD | 2 | 2 |
| Farm MI | 4 | 4 |
| Farm BA | 4 | 4 |
| Farm R | 0 | 1 |
| Farm OO | 0 | 9 |
| Farm GO | 0 | 8 |
| Farm CW | 5 | 0 |
| Farm CH | 0 | 3 |
| Total | 133 | 95 |

TABLE 8

Bacteriocin assay results displaying each isolate tested and the source of that isolate, isolated from Wisconsin fecal samples. Inhibition was calculated based on the percent of growth for each treatment well compared to the positive control.

| Isolate ID | Farm | Sample Type | Group | *Bacillus* Strains 747 | 1104 | 1541 | 1781 | 2018 |
|---|---|---|---|---|---|---|---|---|
| PA65-2 | Farm AD | Calf Fecal | Calf | 98% | 98% | 98% | 98% | 99% |
| PA65-3 | Farm AD | Calf Fecal | Calf | 100% | 71% | 98% | 98% | 100% |

TABLE 8-continued Bacteriocin assay results displaying each isolate tested and the source of that isolate, isolated from Wisconsin fecal samples. Inhibition was calculated based on the percent of growth for each treatment well compared to the positive control.

| Isolate ID | Farm | Sample Type | Group | \multicolumn{5}{c}{*Bacillus* Strains} |
| | | | | 747 | 1104 | 1541 | 1781 | 2018 |
|---|---|---|---|---|---|---|---|---|
| PA66-1 | Farm AD | Calf Fecal | Calf | 86% | 100% | 100% | 100% | 100% |
| PA66-16 | Farm AD | Calf Fecal | Calf | 0% | 0% | 0% | 0% | 0% |
| PA66-8 | Farm AD | Calf Fecal | Calf | 100% | 100% | 100% | 100% | 100% |
| PA68-1 | Farm AD | Cow Fecal | Mature Cow | 100% | 100% | 100% | 100% | 100% |
| PA66-11 | Farm AD | Calf Fecal | Calf | 99.7% | 99.9% | 99.8% | 99.8% | 99.8% |
| PA67-12 | Farm AD | Cow Fecal | Prefresh | 83.9% | 80.3% | 88.8% | 89.5% | 88.0% |
| PA68-16 | Farm AD | Cow Fecal | Mature | 49.5% | 48.2% | 51.5% | 51.9% | 51.2% |
| PA68-2 | Farm AD | Cow Fecal | Mature | 99.9% | 99.2% | 99.8% | 99.1% | 99.8% |
| PA3-6 | Farm AL | Calf Fecal | Calf | 100% | 100% | 100% | 100% | 100% |
| PA3-7 | Farm AL | Calf Fecal | Calf | 100% | 99% | 100% | 100% | 100% |
| PA4-5 | Farm AL | Calf Fecal | Calf | 2% | 9% | 4% | 9% | 8% |
| PA5-8 | Farm AL | Calf Fecal | Calf | 100% | 94% | 99% | 99% | 100% |
| PA7-11 | Farm AL | Cow Fecal | Cow Fecal | 100% | 92% | 94% | 98% | 95% |
| PA7-15 | Farm AL | Cow Fecal | Cow Fecal | 61% | 43% | 41% | 69% | 59% |
| PA7-2 | Farm AL | Cow Fecal | Cow Fecal | 32% | 0% | 0% | 32% | 6% |
| PA7-5 | Farm AL | Cow Fecal | Cow Fecal | 100% | 97% | 98% | 100% | 98% |
| PA8-1 | Farm AL | Cow Fecal | Cow Fecal | 98% | 90% | 93% | 97% | 97% |
| PA3-2 | Farm AL | Calf Fecal | Calf | 98.6% | 72.4% | 85.1% | 75.8% | 95.1% |
| PA3-5 | Farm AL | Calf Fecal | Calf | 99.8% | 99.8% | 99.8% | 99.9% | 99.8% |
| PA4-1 | Farm AL | Calf Fecal | Calf | 81.3% | 82.0% | 82.0% | 81.7% | 82.0% |
| PA4-3 | Farm AL | Calf Fecal | Calf | 97.7% | 97.3% | 97.5% | 97.5% | 97.9% |
| PA5-12 | Farm AL | Calf Fecal | Calf | 99.4% | 95.7% | 99.7% | 99.6% | 99.1% |
| PA5-3 | Farm AL | Calf Fecal | Calf | 99.8% | 99.9% | 99.9% | 99.6% | 99.9% |
| PA5-4 | Farm AL | Calf Fecal | Calf | 0.0% | 25.9% | 0.0% | 53.1% | 45.9% |
| PA5-5 | Farm AL | Calf Fecal | Calf | 99.2% | 99.6% | 99.5% | 99.6% | 99.4% |
| PA5-6 | Farm AL | Calf Fecal | Calf | 89.4% | 49.8% | 48.8% | 70.0% | 71.7% |
| PA5-7 | Farm AL | Calf Fecal | Calf | 85.6% | 50.5% | 36.8% | 65.9% | 45.1% |
| PA5-9 | Farm AL | Calf Fecal | Calf | 99.8% | 85.4% | 92.9% | 97.3% | 99.6% |
| PA6-2 | Farm AL | Cow Fecal | Cow Fecal | 98.9% | 85.2% | 88.0% | 94.2% | 88.6% |
| PA42-19 | Farm BA | Calf Fecal | Calf | 94% | 54% | 92% | 88% | 97% |
| PA46-8 | Farm BA | Cow Fecal | 1st Lactation | 22% | 25% | 25% | 24% | 25% |
| PA47-10 | Farm BA | Cow Fecal | 3rd Lactation | 24% | 25% | 26% | 25% | 26% |
| PA48-4 | Farm BA | Cow Fecal | Mature | 100% | 100% | 100% | 100% | 100% |
| PA41-11 | Farm BA | Calf Fecal | Calf | 100.0% | 9.1% | 100.0% | 79.8% | 99.9% |
| PA42-11 | Farm BA | Calf Fecal | Calf | 100.0% | 52.7% | 70.6% | 87.2% | 82.0% |

TABLE 8-continued

Bacteriocin assay results displaying each isolate tested and the source of that isolate, isolated from Wisconsin fecal samples. Inhibition was calculated based on the percent of growth for each treatment well compared to the positive control.

| Isolate ID | Farm | Sample Type | Group | \multicolumn{5}{c}{Bacillus Strains} |
| --- | --- | --- | --- | --- | --- | --- | --- | --- |
| | | | | 747 | 1104 | 1541 | 1781 | 2018 |
| PA9-9 | Farm BE | Calf Fecal | Calf | 19.8% | 23.4% | 16.6% | 20.5% | 19.7% |
| PA11-1 | Farm BE | Cow Fecal | Heifer | 100% | 96% | 100% | 100% | 100% |
| PA11-12 | Farm BE | Cow Fecal | Heifer | 75% | 58% | 55% | 85% | 73% |
| PA11-2 | Farm BE | Cow Fecal | Heifer | 100% | 100% | 100% | 100% | 100% |
| PA14-14 | Farm BE | Cow Fecal | Fresh | 86% | 84% | 85% | 97% | 82% |
| PA14-15 | Farm BE | Cow Fecal | Fresh | 98% | 96% | 97% | 97% | 97% |
| PA10-5 | Farm BE | Calf Fecal | Calf | 7.7% | 6.2% | 2.6% | 12.4% | 8.7% |
| PA11-13 | Farm BE | Cow Fecal | Heifer | 99.9% | 99.8% | 99.1% | 99.9% | 100.0% |
| PA11-19 | Farm BE | Cow Fecal | Heifer | 99.5% | 99.8% | 99.7% | 99.8% | 99.7% |
| PA11-5 | Farm BE | Cow Fecal | Heifer | 99.2% | 93.4% | 95.1% | 96.9% | 92.0% |
| PA11-6 | Farm BE | Cow Fecal | Heifer | 99.7% | 100.0% | 99.7% | 99.7% | 99.7% |
| PA11-7 | Farm BE | Cow Fecal | Heifer | 100.0% | 100.0% | 100.0% | 100.0% | 100.0% |
| PA12-1 | Farm BE | Cow Fecal | Heifer | 100.0% | 33.4% | 62.2% | 70.3% | 94.9% |
| PA13-10 | Farm BE | Cow Fecal | Fresh | 38.4% | 36.8% | 40.9% | 40.6% | 39.3% |
| PA13-12 | Farm BE | Cow Fecal | Fresh | 99.6% | 48.9% | 66.6% | 45.7% | 77.9% |
| PA13-15 | Farm BE | Cow Fecal | Fresh | 99.7% | 100.0% | 99.9% | 99.8% | 99.8% |
| PA13-19 | Farm BE | Cow Fecal | Fresh | 99.7% | 95.5% | 98.2% | 99.3% | 99.9% |
| PA13-9 | Farm BE | Cow Fecal | Fresh | 99.9% | 99.9% | 99.9% | 99.9% | 99.8% |
| PA14-1 | Farm BE | Cow Fecal | Fresh | 48.1% | 0.0% | 1.6% | 4.7% | 4.7% |
| PA14-18 | Farm BE | Cow Fecal | Fresh | 99.9% | 99.8% | 99.8% | 99.9% | 99.9% |
| PA14-2 | Farm BE | Cow Fecal | Fresh | 99.7% | 99.6% | 99.7% | 99.6% | 99.8% |
| PA14-3 | Farm BE | Cow Fecal | Fresh | 99.7% | 99.8% | 99.8% | 99.8% | 99.8% |
| PA14-4 | Farm BE | Cow Fecal | Fresh | 100.0% | 100.0% | 100.0% | 100.0% | 100.0% |
| PA15-17 | Farm BE | Cow Fecal | 2nd year Cow | 99.6% | 84.3% | 79.1% | 87.2% | 86.3% |
| PA16-8 | Farm BE | Cow Fecal | Mature | 0.0% | 0.0% | 0.0% | 0.0% | 0.0% |
| 30.4.2 | Farm CW | Feed | Corn Silage B7 | 43% | 43% | 46% | 45% | 43% |
| PA85-3 | Farm CW | Cow Fecal | Fresh | 100% | 100% | 100% | 100% | 100% |
| PA87-1 | Farm CW | Cow Fecal | Fresh | 0% | 0% | 0% | 0% | 0% |
| PA50-2 | Farm GR | Calf Fecal | Calf | 100% | 100% | 100% | 100% | 100% |
| 21.2.3 | Farm GR | Feed | Haylage B3 | 100% | 98% | 74% | 99% | 97% |
| 21.2.5 | Farm GR | Feed | Haylage B3 | 98% | 49% | 42% | 94% | 48% |
| 21.2.7 | Farm GR | Feed | Haylage B3 | 98% | 96% | 96% | 98% | 96% |
| 21.2.4 | Farm GR | Feed | Haylage | 33.9% | 5.2% | 4.7% | 2.2% | 5.3% |
| PA55-14 | Farm GR | Cow Fecal | Fresh | 99.7% | 100.0% | 99.8% | 99.7% | 99.8% |
| PA55-19 | Farm GR | Cow Fecal | Fresh | 99.8% | 99.9% | 99.7% | 99.8% | 99.8% |

TABLE 8-continued

Bacteriocin assay results displaying each isolate tested and the source of that isolate, isolated from Wisconsin fecal samples. Inhibition was calculated based on the percent of growth for each treatment well compared to the positive control.

| Isolate ID | Farm | Sample Type | Group | \multicolumn{5}{c}{*Bacillus* Strains} |
| | | | | 747 | 1104 | 1541 | 1781 | 2018 |
|---|---|---|---|---|---|---|---|---|
| PA55-6 | Farm GR | Cow Fecal | Fresh | 99.8% | 99.9% | 99.9% | 99.9% | 99.9% |
| PA56-20 | Farm GR | Cow Fecal | Fresh | 99.3% | 99.7% | 99.7% | 99.7% | 99.5% |
| J2-12 | Farm HA | Cow Fecal | Lactating | 99.9% | 100.0% | 100.0% | 99.9% | 100.0% |
| CSS-4 | Farm HN | Feed | Corn Silage | 29.5% | 31.7% | 96.2% | 38.3% | 28.6% |
| HSS-1 | Farm HN | Feed | Haylage | 99.9% | 100.0% | 99.9% | 100.0% | 99.9% |
| 28.1.2 | Farm HN | Feed | Ryelage | 64% | 63% | 91% | 63% | 69% |
| PA69-1 | Farm HN | Calf Fecal | Calf | 95% | 91% | 53% | 100% | 99% |
| PA69-2 | Farm HN | Calf Fecal | Calf | 99% | 16% | 64% | 92% | 98% |
| PA69-12 | Farm HN | Calf Fecal | Calf | 99.9% | 99.8% | 99.9% | 99.9% | 100.0% |
| PA71-12 | Farm HN | Calf Fecal | Calf | 97.1% | 97.8% | 96.5% | 97.2% | 97.5% |
| PA74-1 | Farm HN | Cow Fecal | Fresh | 100.0% | 100.0% | 100.0% | 100.0% | 100.0% |
| PA74-11 | Farm HN | Cow Fecal | Fresh | 100.0% | 0.0% | 0.0% | 99.7% | 45.4% |
| PA74-12 | Farm HN | Cow Fecal | Fresh | 100.0% | 100.0% | 100.0% | 100.0% | 100.0% |
| PA74-15 | Farm HN | Cow Fecal | Fresh | 100.0% | 26.3% | 40.0% | 29.0% | 72.4% |
| PA74-4 | Farm HN | Cow Fecal | Fresh | 100.0% | 49.4% | 18.7% | 73.1% | 98.6% |
| PA76-4 | Farm HN | Cow Fecal | Lactating | 98.3% | 99.1% | 98.8% | 99.1% | 99.0% |
| PA76-11 | Farm HN | Cow Fecal | Lactating | 100% | 100% | 100% | 100% | 100% |
| PA76-17 | Farm HN | Cow Fecal | Lactating | 100% | 100% | 100% | 100% | 100% |
| PA76-19 | Farm HN | Cow Fecal | Lactating | 100% | 100% | 100% | 100% | 100% |
| A1-17 | Farm GO | Calf Fecal | Calf | 98.2% | 74.1% | 47.4% | 95.7% | 62.3% |
| A1-11 | Farm GO | Calf Fecal | Calf | 99.6% | 100.0% | 99.7% | 99.7% | 100.0% |
| A1-16 | Farm GO | Calf Fecal | Calf | 97.2% | 62.1% | 51.2% | 94.5% | 49.9% |
| A2-12 | Farm GO | Calf Fecal | Calf | 96.3% | 26.2% | 59.9% | 98.2% | 23.3% |
| A2-4 | Farm GO | Calf Fecal | Calf | 86.7% | 47.4% | 68.3% | 63.3% | 72.3% |
| A2-5 | Farm GO | Calf Fecal | Calf | 97.6% | 66.3% | 65.7% | 96.2% | 70.0% |
| A2-7 | Farm GO | Calf Fecal | Calf | 79.0% | 13.4% | 24.2% | 39.2% | 43.0% |
| A2-8 | Farm GO | Calf Fecal | Calf | 99.4% | 95.4% | 94.9% | 98.2% | 93.6% |
| A7-1 | Farm GO | Calf Fecal | Calf | 99.8% | 99.9% | 100.0% | 99.6% | 100.0% |
| A7-11 | Farm GO | Calf Fecal | Calf | 90.9% | 32.7% | 16.8% | 59.6% | 28.6% |
| A7-17 | Farm GO | Calf Fecal | Calf | 99.9% | 99.9% | 100.0% | 99.9% | 99.9% |
| PA35-4 | Farm LP | Calf Fecal | Calf | 100% | 100% | 100% | 100% | 100% |
| PA37-8 | Farm LP | Cow Fecal | Lactating | 100% | 100% | 100% | 100% | 100% |
| PA39-8 | Farm LP | Cow Fecal | Lactating | 17% | 29% | 13% | 56% | 25% |
| PA33-9 | Farm LP | Calf Fecal | Calf | 96.6% | 59.3% | 74.4% | 78.0% | 81.2% |
| PA35-1 | Farm LP | Calf Fecal | Calf | 99.7% | 99.9% | 99.8% | 99.8% | 99.7% |

TABLE 8-continued

Bacteriocin assay results displaying each isolate tested and the source of that isolate, isolated from Wisconsin fecal samples. Inhibition was calculated based on the percent of growth for each treatment well compared to the positive control.

| Isolate ID | Farm | Sample Type | Group | \multicolumn{5}{c}{*Bacillus* Strains} |
| | | | | 747 | 1104 | 1541 | 1781 | 2018 |
|---|---|---|---|---|---|---|---|---|
| PA35-10 | Farm LP | Calf Fecal | Calf | 99.5% | 99.9% | 99.8% | 99.7% | 99.8% |
| PA35-12 | Farm LP | Calf Fecal | Calf | 99.9% | 99.9% | 99.8% | 100.0% | 99.9% |
| PA36-13 | Farm LP | Calf Fecal | Calf | 99.7% | 100.0% | 99.7% | 99.9% | 99.8% |
| PA38-17 | Farm LP | Cow Fecal | Lactating | 99.8% | 100.0% | 99.9% | 100.0% | 99.9% |
| PA40-2 | Farm LP | Cow Fecal | Lactating | 99.6% | 99.7% | 99.8% | 99.6% | 99.9% |
| 3.1.3 | Farm MI | Feed | Corn Silage | 100% | 100% | 100% | 100% | 100% |
| 3.1.4 | Farm MI | Feed | Corn Silage | 72% | 68% | 91% | 70% | 80% |
| 31.2.1 | Farm MI | Feed | Haylage | 43% | 37% | 36% | 41% | 41% |
| PA31-16 | Farm MI | Cow Fecal | Cow Fecal | 100% | 100% | 100% | 100% | 100% |
| PA32-10 | Farm MI | Cow Fecal | Cow Fecal | 22% | 21% | 24% | 25% | 18% |
| PA32-11 | Farm MI | Cow Fecal | Cow Fecal | 100% | 8% | 100% | 89% | 91% |
| PA31-2 | Farm MI | Cow Fecal | Cow Fecal | 99.8% | 88.5% | 89.6% | 89.4% | 94.7% |
| PA31-5 | Farm MI | Cow Fecal | Cow Fecal | 100.0% | 100.0% | 99.9% | 100.0% | 100.0% |
| PA31-6 | Farm MI | Cow Fecal | Cow Fecal | 100.0% | 100.0% | 99.9% | 100.0% | 100.0% |
| PA32-15 | Farm MI | Cow Fecal | Cow Fecal | 100.0% | 100.0% | 100.0% | 100.0% | 100.0% |
| PA32-6 | Farm MI | Cow Fecal | Cow Fecal | 99.9% | 100.0% | 99.9% | 99.8% | 99.9% |
| 27.2.11 | Farm MV | Feed | Haylage | 98% | 91% | 81% | 95% | 91% |
| 27.3.2 | Farm MV | Feed | Oatlage | 93% | 66% | 66% | 80% | 75% |
| 27.3.3 | Farm MV | Feed | Oatlage | 100% | 100% | 100% | 100% | 100% |
| PA80-5 | Farm MV | Calf Fecal | Calf | 100% | 100% | 100% | 100% | 100% |
| PA82-2 | Farm MV | Cow Fecal | Fresh | 97% | 98% | 97% | 97% | 98% |
| PA83-7 | Farm MV | Cow Fecal | Lactating | 89% | 18% | 0% | 70% | 17% |
| PA84-14 | Farm MV | Cow Fecal | Lactating | 100% | 98% | 100% | 100% | 100% |
| PA84-18 | Farm MV | Cow Fecal | Lactating | 100% | 100% | 97% | 100% | 100% |
| PA84-7 | Farm MV | Cow Fecal | Lactating | 100% | 99% | 100% | 100% | 100% |
| PA77-4 | Farm MV | Calf Fecal | Calf | 81.7% | 77.6% | 71.3% | 76.9% | 82.7% |
| PA80-2 | Farm MV | Calf Fecal | Calf | 100.0% | 100.0% | 100.0% | 100.0% | 99.7% |
| PA81-3 | Farm MV | Cow Fecal | Fresh | 98.4% | 98.5% | 82.0% | 97.8% | 98.7% |
| PA81-8 | Farm MV | Cow Fecal | Fresh | 100.0% | 99.9% | 99.9% | 99.9% | 99.9% |
| PA82-11 | Farm MV | Cow Fecal | Fresh | 99.8% | 99.8% | 99.7% | 99.8% | 99.9% |
| PA82-4 | Farm MV | Cow Fecal | Fresh | 100.0% | 99.9% | 99.7% | 99.9% | 99.9% |
| PA83-16 | Farm MV | Cow Fecal | Lactating | 99.7% | 99.9% | 99.6% | 99.8% | 99.7% |
| PA83-19 | Farm MV | Cow Fecal | Lactating | 99.9% | 99.8% | 99.7% | 99.9% | 99.7% |
| PA83-2 | Farm MV | Cow Fecal | Lactating | 99.6% | 99.8% | 99.8% | 99.8% | 99.8% |
| PA84-5 | Farm MV | Cow Fecal | Lactating | 99.1% | 98.6% | 98.8% | 98.8% | 98.7% |

TABLE 8-continued

Bacteriocin assay results displaying each isolate tested and the source of that isolate, isolated from Wisconsin fecal samples. Inhibition was calculated based on the percent of growth for each treatment well compared to the positive control.

| Isolate ID | Farm | Sample Type | Group | Bacillus Strains 747 | 1104 | 1541 | 1781 | 2018 |
|---|---|---|---|---|---|---|---|---|
| PA84-6 | Farm MV | Cow Fecal | Lactating | 99.7% | 99.8% | 99.8% | 99.8% | 99.9% |
| B1-1 | Farm OO | Calf Fecal | Calf | 45.2% | 46.0% | 48.7% | 48.1% | 51.7% |
| B1-15 | Farm OO | Calf Fecal | Calf | 32.7% | 0.0% | 26.2% | 0.0% | 27.0% |
| B3-6 | Farm OO | Calf Fecal | Calf | 79.3% | 48.7% | 54.1% | 59.5% | 59.9% |
| B4-2 | Farm OO | Calf Fecal | Calf | 100.0% | 100.0% | 100.0% | 100.0% | 100.0% |
| B4-6 | Farm OO | Calf Fecal | Calf | 99.9% | 99.9% | 100.0% | 99.9% | 99.8% |
| PA1-2 | Farm R | Calf Fecal | Calf | 99.7% | 84.2% | 99.8% | 99.6% | 100.0% |
| PA1-3 | Farm R | Calf Fecal | Calf | 99.8% | 100.0% | 99.8% | 100.0% | 100.0% |
| PA1-6 | Farm R | Calf Fecal | Calf | 100.0% | 41.0% | 86.0% | 86.2% | 100.0% |
| PA1-10 | Farm R | Calf Fecal | Calf | 100.0% | 26.1% | 80.4% | 76.1% | 100.0% |
| PA1-11 | Farm R | Calf Fecal | Calf | 100.0% | 8.7% | 81.1% | 78.4% | 100.0% |
| PA1-16 | Farm R | Calf Fecal | Calf | 100.0% | 38.5% | 82.4% | 77.7% | 100.0% |
| PA1-19 | Farm R | Calf Fecal | Calf | 100.0% | 0.6% | 80.3% | 65.5% | 100.0% |
| PA1-20 | Farm R | Calf Fecal | Calf | 99.9% | 16.9% | 83.2% | 76.1% | 100.0% |
| RF-1 | Farm R | Feed | Corn Silage | 100.0% | 100.0% | 100.0% | 100.0% | 100.0% |
| ROL-1 | Farm R | Feed | Haylage-Old | 92.6% | 94.7% | 94.5% | 94.4% | 89.5% |
| ROL-3 | Farm R | Feed | Haylage-Old | 99.9% | 100.0% | 99.8% | 99.9% | 99.7% |
| ROS-1 | Farm R | Feed | Haylage-Old | 35.9% | 16.1% | 17.4% | 17.0% | 18.5% |
| ROS-3 | Farm R | Feed | Haylage-Old | 100.0% | 20.3% | 28.9% | 25.1% | 50.5% |
| 20.1.3 | Farm S | Feed | Corn Silage B1 | 12% | 12% | 11% | 17% | 12% |
| 20.1.5 | Farm S | Feed | Corn Silage B1 | 21% | 18% | 37% | 25% | 19% |
| 20.3.1 | Farm S | Feed | Haylage B6 | 85% | 89% | 84% | 90% | 80% |
| 20.4.6 | Farm S | Feed | Corn Silage B7 | 100% | 100% | 100% | 100% | 100% |
| PA57-14 | Farm S | Calf Fecal | Calf | 100% | 100% | 100% | 100% | 100% |
| PA57-7 | Farm S | Calf Fecal | Calf | 100% | 100% | 100% | 100% | 100% |
| PA58-11 | Farm S | Calf Fecal | Calf | 100% | 100% | 100% | 100% | 100% |
| PA59-11 | Farm S | Calf Fecal | Calf | 100% | 100% | 100% | 100% | 100% |
| PA63-17 | Farm S | Cow Fecal | Lactating | 100% | 100% | 100% | 100% | 100% |
| 20.3.3 | Farm S | Feed | Haylage | 90.0% | 92.7% | 94.1% | 93.1% | 93.0% |
| 20.3.5 | Farm S | Feed | Haylage | 99.7% | 100.0% | 99.9% | 99.9% | 100.0% |
| PA57-9 | Farm S | Calf Fecal | Calf | 99.7% | 100.0% | 99.9% | 99.9% | 100.0% |
| PA58-1 | Farm S | Calf Fecal | Calf | 99.5% | 100.0% | 99.8% | 99.8% | 99.8% |
| PA58-19 | Farm S | Calf Fecal | Calf | 99.9% | 100.0% | 100.0% | 100.0% | 100.0% |
| PA61-3 | Farm S | Cow Fecal | Fresh | 99.8% | 99.9% | 99.8% | 99.9% | 99.8% |
| PA62-16 | Farm S | Cow Fecal | Fresh | 99.7% | 99.9% | 99.8% | 99.9% | 99.9% |
| PA62-5 | Farm S | Cow Fecal | Fresh | 99.2% | 99.5% | 99.4% | 99.6% | 99.4% |
| PA63-10 | Farm S | Cow Fecal | Lactating | 100.0% | 100.0% | 100.0% | 99.9% | 99.9% |
| PA63-19 | Farm S | Cow Fecal | Lactating | 100.0% | 99.9% | 100.0% | 99.8% | 100.0% |
| PA23-3 | Farm WB | Cow Fecal | Cow Fecal | 100% | 100% | 100% | 100% | 100% |

TABLE 8-continued

Bacteriocin assay results displaying each isolate tested and the source of that isolate, isolated from Wisconsin fecal samples. Inhibition was calculated based on the percent of growth for each treatment well compared to the positive control.

| Isolate ID | Farm | Sample Type | Group | \multicolumn{5}{c}{*Bacillus* Strains} |
| --- | --- | --- | --- | --- | --- | --- | --- | --- |
| | | | | 747 | 1104 | 1541 | 1781 | 2018 |
| PA23-5 | Farm WB | Cow Fecal | Cow Fecal | 100% | 100% | 100% | 100% | 100% |
| PA24-7 | Farm WB | Cow Fecal | Cow Fecal | 100% | 68% | 0% | 100% | 100% |
| PA21-1 | Farm WB | Cow Fecal | Cow Fecal | 99.9% | 100.0% | 99.9% | 99.9% | 99.9% |
| PA21-20 | Farm WB | Cow Fecal | Cow Fecal | 99.5% | 99.6% | 99.6% | 99.5% | 99.6% |
| PA22-1 | Farm WB | Cow Fecal | Cow Fecal | 99.6% | 99.7% | 99.7% | 99.6% | 99.6% |
| PA22-3 | Farm WB | Cow Fecal | Cow Fecal | 99.4% | 99.6% | 99.4% | 99.6% | 99.5% |
| PA23-13 | Farm WB | Cow Fecal | Cow Fecal | 99.7% | 99.9% | 99.6% | 99.9% | 99.9% |
| PA23-14 | Farm WB | Cow Fecal | Cow Fecal | 99.8% | 100.0% | 100.0% | 99.9% | 100.0% |
| PA23-15 | Farm WB | Cow Fecal | Cow Fecal | 99.8% | 99.9% | 99.8% | 99.8% | 99.8% |
| PA24-19 | Farm WB | Cow Fecal | Cow Fecal | 100.0% | 100.0% | 100.0% | 100.0% | 100.0% |
| C1-12 | Farm WO | Calf Fecal | Calf | 97.5% | 92.7% | 90.8% | 96.7% | 91.2% |
| C1-15 | Farm WO | Calf Fecal | Calf | 99.8% | 99.9% | 100.0% | 99.7% | 100.0% |
| C1-16 | Farm WO | Calf Fecal | Calf | 98.8% | 100.0% | 100.0% | 100.0% | 100.0% |
| C1-2 | Farm WO | Calf Fecal | Calf | 95.0% | 79.0% | 79.5% | 91.3% | 79.6% |
| C1-4 | Farm WO | Calf Fecal | Calf | 100.0% | 100.0% | 100.0% | 100.0% | 100.0% |
| C1-7 | Farm WO | Calf Fecal | Calf | 98.2% | 93.3% | 92.8% | 96.8% | 92.3% |
| C1-9 | Farm WO | Calf Fecal | Calf | 100.0% | 99.9% | 100.0% | 99.9% | 100.0% |
| C2-7 | Farm WO | Calf Fecal | Calf | 99.9% | 100.0% | 99.9% | 99.8% | 100.0% |
| C2-9 | Farm WO | Calf Fecal | Calf | 98.0% | 94.2% | 93.7% | 93.2% | 93.4% |
| C3-16 | Farm WO | Calf Fecal | Calf | 99.9% | 100.0% | 100.0% | 99.8% | 100.0% |
| C3-17 | Farm WO | Calf Fecal | Calf | 99.9% | 100.0% | 100.0% | 100.0% | 100.0% |
| C3-18 | Farm WO | Calf Fecal | Calf | 98.3% | 43.0% | 95.0% | 97.7% | 93.5% |
| C3-8 | Farm WO | Calf Fecal | Calf | 100.0% | 100.0% | 100.0% | 100.0% | 100.0% |
| C4-19 | Farm WO | Calf Fecal | Calf | 99.3% | 94.7% | 94.0% | 98.3% | 92.8% |
| C5-18 | Farm WO | Calf Fecal | Calf | 99.7% | 93.1% | 87.8% | 98.6% | 93.0% |
| BT10-9 | Farm WB | Cow Fecal | Dry | 98.52% | 98.11% | 96.23% | 95.55% | 96.23% |
| BT1-2 | Farm WB | Cow Fecal | Pre-Fresh | 75.64% | 65.36% | 69.74% | 69.89% | 71.41% |
| BT13-6 | Farm WB | Cow Fecal | Post Fresh | 98.44% | 95.10% | 95.32% | 92.20% | 93.10% |
| BT16-10 | Farm WB | Cow Fecal | Late Lactation | 98.73% | 99.37% | 98.99% | 98.99% | 99.11% |
| BT18-2 | Farm WB | Cow Fecal | Late Lactation | 86.00% | 66.00% | 50.00% | 26.00% | 38.00% |
| BT18-3 | Farm WB | Cow Fecal | Late Lactation | 98.25% | 94.99% | 93.73% | 91.73% | 92.48% |
| BT19-10 | Farm WB | Cow Fecal | Late Lactation | 98.82% | 36.74% | 95.48% | 93.52% | 94.30% |
| BT20-7 | Farm WB | Cow Fecal | Late Lactation | 99.47% | 99.47% | 99.21% | 98.95% | 99.08% |
| BT21-8 | Farm WB | Cow Fecal | Post Fresh | 99.14% | 99.28% | 98.99% | 98.99% | 99.14% |
| BT2-2 | Farm WB | Cow Fecal | Pre-Fresh | 89.90% | 99.05% | 85.13% | 97.41% | 98.50% |

TABLE 8-continued

Bacteriocin assay results displaying each isolate tested and the source of that isolate, isolated from Wisconsin fecal samples. Inhibition was calculated based on the percent of growth for each treatment well compared to the positive control.

| Isolate ID | Farm | Sample Type | Group | *Bacillus* Strains | | | | |
|---|---|---|---|---|---|---|---|---|
| | | | | 747 | 1104 | 1541 | 1781 | 2018 |
| BT22-5 | Farm WB | Cow Fecal | Post Fresh | 98.77% | 98.77% | 98.42% | 98.25% | 98.42% |
| BT22-8 | Farm WB | Cow Fecal | Post Fresh | 94.64% | 96.43% | 93.75% | 94.64% | 93.75% |
| BT23-5 | Farm WB | Cow Fecal | Post Fresh | 99.38% | 99.00% | 99.00% | 99.13% | 99.13% |
| BT23-8 | Farm WB | Cow Fecal | Post Fresh | 98.77% | 98.77% | 98.43% | 98.65% | 98.20% |
| BT24-2 | Farm WB | Cow Fecal | Post Fresh | 90.59% | 92.94% | 89.41% | 90.59% | 90.59% |
| BT24-3 | Farm WB | Cow Fecal | Post Fresh | 96.27% | 95.52% | 94.78% | 94.03% | 96.27% |
| BT27-9 | Farm WB | Cow Fecal | Breeding | 99.17% | 99.31% | 99.03% | 98.89% | 99.03% |
| BT28-4 | Farm WB | Cow Fecal | Breeding | 98.79% | 99.46% | 99.06% | 99.06% | 99.33% |
| BT28-6 | Farm WB | Cow Fecal | Breeding | 98.44% | 98.83% | 98.64% | 98.64% | 98.83% |
| BT29-5 | Farm WB | Cow Fecal | Breeding | 83.90% | 0.00% | 21.95% | 0.00% | 33.17% |
| BT29-7 | Farm WB | Cow Fecal | Breeding | 86.35% | 78.59% | 68.47% | 79.76% | 58.35% |
| BT31-1 | Farm WB | Cow Fecal | Breeding | 99.09% | 99.39% | 99.24% | 99.09% | 98.93% |
| BT31-2 | Farm WB | Cow Fecal | Breeding | 97.63% | 97.89% | 97.89% | 97.63% | 97.89% |
| BT32-8 | Farm WB | Cow Fecal | Breeding | 98.33% | 18.87% | 98.63% | 96.50% | 96.35% |
| BT35-4 | Farm WB | Cow Fecal | Breeding | 87.73% | 51.72% | 40.10% | 57.45% | 60.23% |
| BT36-1 | Farm WB | Cow Fecal | Breeding | 90.79% | 52.63% | 6.58% | 36.84% | 51.32% |
| BT36-3 | Farm WB | Cow Fecal | Breeding | 85.67% | 62.39% | 66.42% | 65.67% | 73.13% |
| BT36-6 | Farm WB | Cow Fecal | Breeding | 98.13% | 98.75% | 96.88% | 96.57% | 98.44% |
| BT37-4 | Farm WB | Cow Fecal | Breeding | 79.45% | 16.60% | 0.00% | 34.78% | 66.80% |
| BT37-5 | Farm WB | Cow Fecal | Breeding | 98.67% | 28.79% | 78.60% | 72.54% | 98.30% |
| BT3-8 | Farm WB | Cow Fecal | Pre-Fresh | 94.70% | 94.70% | 50.00% | 19.70% | 86.36% |
| BT3-9 | Farm WB | Cow Fecal | Pre-Fresh | 98.46% | 83.82% | 97.30% | 94.99% | 94.99% |
| BT39-10 | Farm WB | Cow Fecal | Breeding | 98.00% | 98.75% | 98.50% | 98.50% | 98.50% |
| BT39-7 | Farm WB | Cow Fecal | Breeding | 98.17% | 97.87% | 95.73% | 96.34% | 97.56% |
| BT40-4 | Farm WB | Cow Fecal | Breeding | 93.63% | 71.04% | 97.75% | 96.50% | 96.13% |
| BT41-1 | Farm WB | Cow Fecal | Breeding/Preg | 98.66% | 97.05% | 98.93% | 97.05% | 99.20% |
| BT41-2 | Farm WB | Cow Fecal | Breeding/Preg | 87.56% | 52.86% | 60.07% | 72.50% | 61.05% |
| BT42-7 | Farm WB | Cow Fecal | Breeding/Preg | 49.16% | 31.14% | 52.02% | 55.89% | 66.16% |
| BT43-10 | Farm WB | Cow Fecal | Breeding/Preg | 98.99% | 76.71% | 98.99% | 98.99% | 50.73% |
| BT43-8 | Farm WB | Cow Fecal | Breeding/Preg | 98.05% | 98.05% | 97.40% | 98.05% | 98.05% |
| BT45-4 | Farm WB | Cow Fecal | Breeding/Preg | 99.25% | 98.95% | 99.10% | 99.10% | 98.95% |
| BT47-3 | Farm WB | Cow Fecal | Bred | 0.00% | 0.00% | 0.00% | 0.00% | 0.00% |
| BT48-6 | Farm WB | Cow Fecal | Bred | 98.89% | 99.45% | 99.17% | 99.03% | 99.31% |
| BT48-8 | Farm WB | Cow Fecal | Bred | 99.19% | 99.19% | 99.19% | 99.06% | 99.19% |

TABLE 8-continued

Bacteriocin assay results displaying each isolate tested and the source of that isolate, isolated from Wisconsin fecal samples. Inhibition was calculated based on the percent of growth for each treatment well compared to the positive control.

| Isolate ID | Farm | Sample Type | Group | Bacillus Strains 747 | 1104 | 1541 | 1781 | 2018 |
|---|---|---|---|---|---|---|---|---|
| BT49-9 | Farm WB | Cow Fecal | Bred | 94.41% | 41.04% | 63.53% | 93.39% | 93.39% |
| BT50-2 | Farm WB | Cow Fecal | Bred | 35.46% | 32.57% | 24.20% | 40.94% | 32.27% |
| BT50-3 | Farm WB | Cow Fecal | Bred | 99.64% | 99.45% | 99.55% | 99.27% | 99.45% |
| BT50-5 | Farm WB | Cow Fecal | Bred | 98.59% | 99.12% | 98.59% | 98.59% | 99.12% |
| BT6-6 | Farm WB | Cow Fecal | Dry | 95.59% | 97.94% | 95.74% | 96.04% | 96.92% |
| BT6-7 | Farm WB | Cow Fecal | Dry | 98.86% | 98.37% | 98.53% | 97.88% | 98.53% |
| BT8-6 | Farm WB | Cow Fecal | Dry | 3.66% | 45.12% | 45.93% | 0.00% | 96.75% |
| BT9-4 | Farm WB | Cow Fecal | Dry | 98.82% | 98.97% | 98.82% | 98.82% | 98.97% |
| BT8-3 | Farm WB | Cow Fecal | Dry | 35.80% | 32.67% | 18.75% | 48.86% | 29.55% |
| BT10-5 | Farm WB | Cow Fecal | Dry | 99.89% | 99.89% | 99.79% | 98.72% | 99.79% |
| BT21-2 | Farm WB | Cow Fecal | Post Fresh | 99.05% | 99.29% | 98.35% | 99.29% | 99.05% |
| BT24-9 | Farm WB | Cow Fecal | Post Fresh | 98.96% | 99.22% | 98.69% | 98.96% | 98.69% |
| BT31-1 | Farm WB | Cow Fecal | Breeding | 99.20% | 99.52% | 99.20% | 99.20% | 97.92% |
| BT41-7 | Farm WB | Cow Fecal | Breeding/Preg | 99.61% | 99.61% | 99.61% | 99.42% | 99.42% |
| BT42-4 | Farm WB | Cow Fecal | Breeding/Preg | 99.71% | 89.80% | 99.57% | 99.71% | 99.43% |
| BT43-5 | Farm WB | Cow Fecal | Breeding/Preg | 99.58% | 99.79% | 99.58% | 99.15% | 99.36% |
| BT43-9 | Farm WB | Cow Fecal | Breeding/Preg | 0.00% | 0.00% | 0.00% | 0.00% | 0.00% |
| BT45-7 | Farm WB | Cow Fecal | Breeding/Preg | 98.86% | 99.71% | 98.57% | 99.14% | 98.86% |
| BT48-2 | Farm WB | Cow Fecal | Bred | 99.29% | 99.82% | 99.47% | 99.47% | 99.47% |
| BT8-2 | Farm WB | Cow Fecal | Dry | 99.45% | 98.53% | 99.26% | 96.51% | 99.45% |
| BT9-5 | Farm WB | Cow Fecal | Dry | 99.70% | 99.55% | 99.55% | 99.39% | 95.61% |

TABLE 9

Bacteriocin assay results displaying each isolate tested from Wisconsin. Inhibition was calculated based on the percent of growth for each treatment well compared to the positive control.

| Clostridium sp. | Bacillus Strains 747 | 1104 | 1541 | 1781 | 1999 | 2018 |
|---|---|---|---|---|---|---|
| C. bifermentans | 95.4% | 70.5% | 69.6% | 69.3% | 75.1% | 69.6% |
| C. bifermentans | 85.1% | 46.1% | 58.4% | 89.6% | 43.3% | 61.4% |
| C. bifermentans | 97.2% | 97.4% | 97.4% | 97.3% | 96.0% | 98.1% |
| C. bifermentans | 72.5% | 65.6% | 47.0% | 68.3% | 65.7% | 29.1% |
| C. bifermentans | 85.9% | 48.2% | 53.4% | 72.4% | 46.8% | 65.7% |
| C. beijerinckii | 27.9% | 0.3% | 14.0% | 24.4% | 78.2% | 24.4% |

Example 6: Selection of *Bacillus* Strains to Inhibit *Clostridium Perfringens* and Non-Toxigenic Clostridia Isolated from Ruminant Fecal Samples. (Texas)

Introduction:

*Clostridium* is a genus of Gram-positive, spore-forming bacteria that are common residents of the gastrointestinal tract. A number of *Clostridium* species have been linked to enteric disease in ruminants including hemorrhagic bowel syndrome (HBS), a disease often correlated to elevated levels of *Clostridium perfringens* Type A. While most of the enteric diseases caused by clostridia are acute and occur sporadically in herds, in general, the prognosis is poor and the first sign of illness may be death. Based on recent results sub-acute enteric clostridia disease challenges may be a more wide spread issue than acute challenges. Due to a low success rate from treatment in acute disease challenges a more common, emphasis needs to be placed on prophylactic measures.

The purpose of this research was to characterize the distribution and diversity of clostridia in ruminants and ensure inhibition of these isolates using novel *Bacillus* strains as a method to control the clostridia populations The objectives were to determine level of clostridia and *C. perfringens* in cow fecal and feed samples. Determine genotype of non-toxigenic clostridia population. Determine genotype of *C. perfringens* and test representative isolates sensitivity to the inventors' identified *Bacillus* strains 747, 1104, 1541, 1781, and 2018. The purpose of this research was to characterize the distribution and diversity of clostridia in ruminants and ensure inhibition of these isolates using novel *Bacillus* strains as a method to control the clostridia populations.

Materials and Methods:

Fecal samples (827) from cows, heifers and calves gathered from 12 farms in Texas were diluted 1:10 with sterile peptone, heat shocked for 30 minutes at 60° C., enumerated in sterile peptone and pour plated on Tryptose Sulphite Cycloserine (TSC) agar with D-cycloserine (400 mg/L) to select for clostridia species. Agar plates were incubated at 37° C. anaerobically for 24 hours. If present, isolated sulphite-reducing colonies were counted for a total clostridia count (CFU/g) and representative isolates were picked into Reinforced clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions were performed in 96-well blocks containing 500 µl presumptive clostridia culture per well. Cells were harvested by centrifugation at 4,700 rpm for 10 minutes, the supernatant was removed. Cells were re-suspended in 500 µl of 50 mM of EDTA-2Na (pH=8.0). Aliquots of 300 µl of the suspended cells were transferred to a new 96-well block and combined with 20 µl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 µl of lysis buffer (6 M Guanidine, 20% Triton-X 100, 10 mM Tris-HCL, pH 7.5) was added, mixed then incubated at room temperature for 15 minutes. Following the incubation 20 µl of Proteinase K (NEB, 800 U/mL) was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed centrifuging 750 µl of Column Wash Solution (Promega, A1318) at 4700 rpms for 1 minute and 30 seconds discarding flow through at the end of each spin. The binding plate was centrifuged for an additional 10 minutes at 4,700 rpm to remove any residual ethanol. A clean elution plate was then placed under the binding plate and DNA was eluted with 200 µl, pre-warmed (55° C.), Nuclease Free Water (Promega, P1195).

DNA was screened for toxin genes ($\alpha$, $\beta$, $\epsilon$, and $\iota$) specific to *C. perfringens* using polymerase chain reaction (PCR). Amplification of toxin genes was executed using a multiplex PCR containing four primer sets (Yoo et al., 1997) (Table 1.) The PCR mixture contained 2.5 µl 10×PCR Buffer, 2 µl of 50 mM MgCl$_2$, 0.5 µM of each primer (Table 1.), 0.1 µl of Invitrogen™ Platinum™ Taq DNA Polymerase, 2.5 µl of DNA, sterile water was added to achieve 25 µl for a total reaction volume. The mixture underwent 5 minutes at 940° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved. If one or multiple toxin genes were observed a toxin type identification was assigned to each isolate based on their toxin gene profile (Songer, 1996). *C. perfringens* positive to total clostridia isolate ratio was used to calculate an estimated *C. perfringens* count based on the total clostridia count.

Unique strain-specific genetic fingerprints were generated using Random Amplification of Polymorphic DNA (RAPD) analysis on select isolates to determine diversity among fecal *C. perfringens* isolates. The PCR contained 5 µl of DNA, 2.5 µl RAPD primer 2 (10 µM) (Table 1.), and 17.5 µl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes finishing with a final elongation of 5 minutes at 72° C. PCR products observed on a Fragment Analyzer (Advanced Analytics) to determine amplification patterns and were imported into BioNumerics, bioinformatics software, for analysis. RAPD patterns were compared with a band based Dice correlation analysis method to determine the similarity between RAPD patterns as a way to monitor diversity between isolates.

Antimicrobial screening was done on *C. perfringens* isolates obtained from ruminant samples to gauge the effectiveness of the antimicrobial bacteriocin produced by the inventors' identified *Bacillus* strains 747, 1104, 1541, 1781, and 2018. Bacteriocin was harvested by growing each strain at 32° C. in a shaking incubator at 150 rpms for 24 hours in Brain Heart Infusion (BHI) broth. A 1% transfer of the 24-hour culture to fresh BHI broth was executed after incubation. The *Bacillus* were then incubated for 36-48 hours in a 32° C. shaking incubator at 150 rpms. The culture was then centrifuged at 14,000×g for 20 minutes, supernatant was then filtered with a 0.2 m filter to remove any residual cells.

A bacteriocin turbidity assay was executed by growing *C. perfringens* strains isolated from ruminant fecal samples in RCM for 24 hours, anaerobically, at 37° C. Overnight culture was transferred (1%) to sterile RCM and immediately used in the assay. For each *C. perfringens* isolate at least six wells were run in a sterile 48 well reaction plate, 600 µl inoculated culture (positive control), 600 µl inoculated RCM+70 µl bacteriocin (747, 1104, 1541, 1781, and 2018) and 670 RCM (un-inoculated, negative control). Plates were incubated anaerobically at 37° C. for 24 hours then read using a BioTek Epoch Microplate Spectrophotometer, readings were taken at a wavelength of 600 nm. Optical density readings from the negative controls were subtracted from all OD readings and percent inhibition was calculated using the positive control and each bacteriocin treatment.

To identify clostridia sp. that did not have at least one toxin gene specific to *C. perfringens*, a PCR reaction was performed on the isolate DNA to amplify the 16S region of rDNA using primers 27F-YM and 1492R-Y (Table 1). This was done on 20% of the isolates that did not contain a toxin gene specific to *C. perfringens*. The PCR mixture contained 5 µl of 10×PCR Buffer, 2 µl of 50 mM MgCl$_2$, 1 µl of 50 mM dNTPs, 0.4 µM of each primer (Table 1.), 0.2 µl of Invitrogen™ Platinum™ Taq DNA Polymerase, 5 µl of DNA, and sterile water was added to achieve 50 µl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to gene wiz to obtain the sequences for the 16S genes. Sequences were compared to known typed bacterial strains obtained from EZbiocloud online electronic database. Based on comparisons of these sequences a bacterial identification was assigned to the isolates.

A bacteriocin turbidity assay was executed by growing non-toxigenic, clostridia strains isolated from ruminant fecal and feed samples in RCM for 24 hours, anaerobically, at 37° C. Overnight culture was transferred (1%) to sterile RCM and immediately used in the assay. For each C. perfringens isolate at least six wells were run in a sterile 48 well reaction plate, 600 μl inoculated culture (positive control), 600 μl inoculated RCM+70 μl bacteriocin (747, 1104, 1541, 1781, 1999 and 2018) and 670 RCM (un-inoculated, negative control). Plates were incubated anaerobically at 37° C. for 24 hours then read using a BioTek Epoch Microplate Spectrophotometer, readings were taken at a wavelength of 600 nm. Optical density readings from the negative controls were subtracted from all OD readings and percent inhibition was calculated using the positive control and each bacteriocin treatment.

Results:

Fecal samples, 827, were collect from 12 Texas farms from which 7,046 presumptive clostridia strains were isolated as representatives of the clostridial diversity in Texas (Table 10.).

Clostridia enumeration results indicated the average level of clostridia CFU/g across all calf fecal samples was 1,110,000 CFU/g with individual fecal samples ranging from 10 to 17,300,000 CFU/g. While the average level of clostridia CFU/g across all cow fecal samples was 59,700 CFU/g with individual fecal samples ranging from <10 to 35,500,000 CFU/g (FIG. 41.). Samples appeared to range in clostridia levels for both calves (FIG. 42.) and cows (FIG. 43.).

*C. perfringens* enumeration results displayed the average level of *C. perfringens* CFU/g across all calf fecal samples was 353,000 CFU/g with individual samples ranging from <10 to 4,020,000 CFU/g. While the average level of *C. perfringens* CFU/g across all cow fecal samples was 56,100 CFU/g with individual samples ranging from <10 to 35,500,000 CFU/g (FIG. 44.). Samples appeared to range in clostridia levels for both calves (FIG. 45.) and cows (FIG. 46.).

Analysis of the toxin multiplex PCR results displayed which isolates contained toxin genes specific to *C. perfringens*. A total of 7,046 presumptive clostridia isolates from fecal samples have been tested for the indicated *C. perfringens* toxin genes. Of the 7,046 clostridia isolates screened, 3,697 isolates (52.5%) tested positive for at least 1 of the toxin genes. From the 3,697 toxin-gene positive isolates 3,588 (97%) were identified as Type A (αtoxin only), however β, ε and ι, toxins were also detected in the clostridia fecal isolates.

Gentic RAPD fingerprint patterns displayed diversity among the 3,460 isolates that successful amplified. The isolates tested were harvested from calf fecal, cow fecal and feed and did not cluster strictly based on the sample type or farm. Isolates formed 513 clusters based on 75% similarity according to the Dice correlation method.

Representatives from the RAPD dendrogram were selected to capture the diversity of the *C. perfringens* population from this region and subjected to inhibition assays. Antimicrobial testing using the bacteriocin turbidity assay displayed good inhibition of most ruminant fecal *C. perfringens* isolates using bacteriocin harvested from 747, 1104, 1541, 1781, and 2018. The bacteriocin from at least one of the strains 747, 1104, 1541, 1781, and 2018 were able to inhibit the growth greater than 60% of 877 of the 983 isolates tested representing a total of 92.7% inhibition of the *C. perfringens* population based on the dendrogram (Table 11.).

Out of the 7,046 isolates collected 3,349 isolates (47.5%) were found to be non-toxigenic clostridia. Sequencing representatives (n=215) from the non-toxigenic clostridia displayed two dominate clostridia groups. *Clostridium bifermentans* group (*Paraclostridium bifermentans* and *P. benzoelyticum*) and *Clostridium beijerinckii* group (*C. diolis, C. beijerinckii, C. chromiireducens, C. saccharoperbutylacetonicum, C. puniceum*, and *C. saccharobutylicum*), the two main groups of the non-toxigenic clostridia group made up 52.1% of the non-toxigenic isolates (FIG. 47.).

Non-toxigenic isolates (n=105) with known 16S identifications from Texas were selected for antimicrobial testing using the bacteriocin turbidity assay. Isolates were selected to cover a diverse representation of non-toxigenic isolates. Results displayed good inhibition of most ruminant non-toxigenic isolates tested using bacteriocin harvested from 747, 1104, 1541, 1781, 1999 and 2018. The bacteriocin from at least one of the strains 747, 1104, 1541, 1781, 1999 and 2018 were able to inhibit the growth >60% for 71 of the 105 isolates tested (Table 12.).

Discussion:

Fecal samples were used as the most readily available sample type to estimate the level and obtain isolates of clostridia and *C. perfringens* within the digestive system of ruminants. From the 827 fecal samples collected throughout Texas all but one contained a detectable level of clostridia. The survey results indicated clostridia is present in almost all fecal samples at various levels. The majority of the isolates harvested (52.5%) from the ruminant samples contained a toxin gene specific to *C. perfringens*. *C. perfringens* was detected in 86% of the cow fecal samples and in 60% of the calf fecal samples. The high presence of clostridia and *C. perfringens* indicates the risk for sub-acute enteric clostridia disease challenges in most ruminants throughout Texas. *C. perfringens* isolates were diverse according to the RAPD genetic fingerprints but were not specific to sample type or farm. Diverse representatives of *C. perfringens* were mostly inhibited (>60%) by at least one bacteriocin from the following strains 747, 1104, 1541, 1781 or 2018. From the 983 isolates tested 877 isolates were inhibited by greater than 60% by at least one of the strains, representing inhibition of 92.7% of the *C. perfringens* population based on representation from clusters on the RAPD dendrogram. This indicates the *Bacillus* strains 747, 1104, 1541, 1781 and 2018 can inhibit a wide range of diversity of *C. perfringens* isolates. The *Bacillus* strains are not limited to specific clostridia strain(s) like a vaccine which may be missing large groups of the clostridia populations based on the genetic diversity observed in the RAPD dendrogram. DNA sequencing of the non-toxigenic clostridia revealed two major identifications of *Clostridium* species. *C. bifermentans* group which is known to produce 1,3-propanediol (Leja et al., 2014; Myszka et al., 2012) and *C. beijerinckii* group known to produce butanol and acetone (Hou et al., 2017). The production of the metabolic end products of these species could be having an impact in the rumen, reducing performance parameters such as milk production within a dairy cow. Non-toxigenic clostridia isolates tested were mostly inhibited (71/105) greater than 60% by the bacteriocin from at least one of the following strains 747, 1104, 1541, 1781, 1999 or 2018. The inhibition of the non-toxigenic clostridia could also be a potential mode of action that *Bacillus* strains are using to increase performance parameters. The high inhibition level against the clostridia isolates in vitro indicates a potential mode of action of the *Bacillus* strains 747, 1104, 1541, 1781, 1999 and 2018.

The *Bacillus* strains offer a prophylactic effect on the clostridia populations which may not only increase rumen efficiency leading to increased milk production, but prevent acute levels of *C. perfringens* reducing the occurrence of digestive deaths. The high prevalence of clostridia and *C. perfringens* in fecal samples collected suggests efficiency improvement opportunities in many ruminants throughout Texas. This example displays the diversity of clostridia isolates from the ruminant fecal and feed samples collected from Texas. The *Bacillus* strains tested 747, 1104, 1541, 1781, 1999 and 2018, could inhibit most of the clostridia diversity observed in Texas. The product, in accordance with this embodiment of the present invention could inhibit both toxigenic and non-toxigenic clostridia isolated from ruminants in Texas indicating a benefit in rumen efficiency if fed to dairy cows as a direct fed microbial (DFM).

TABLE 10

Fecal samples, 827, were collected from Texas farms separated by farm (12) and age (cow or calf) which were enumerated for clostridia, tested for *C. perfringens*, isolates were genotyped and tested for inhibition.

| Farm Name | Cow Fecal | Calf Fecal |
|---|---|---|
| Farm DC | 0 | 46 |
| Farm L | 70 | 0 |
| Farm BS | 60 | 0 |
| Farm ALJ | 60 | 0 |
| Farm FC | 70 | 15 |
| Farm RR | 70 | 0 |
| Farm GJJ | 70 | 0 |
| Farm GE | 70 | 0 |
| Farm GH | 69 | 0 |
| Farm DR | 82 | 0 |
| Farm MD | 71 | 15 |
| Farm AX | 50 | 10 |

TABLE 11

Bacteriocin assay results displaying each isolate tested and the source of that isolate, isolated from Texas fecal samples. Inhibition was calculated based on the percent of growth for each treatment well compared to the positive control.

| | | *Bacillus* strains | | | | |
|---|---|---|---|---|---|---|
| Isolate ID | Sample | 747 | 1104 | 1541 | 1781 | 2018 |
| R2.35.10 | Cow Fecal | 2.0% | 1.5% | 0.0% | 2.0% | 6.1% |
| R2.35.5 | Cow Fecal | 100.0% | 100.0% | 100.0% | 100.0% | 100.0% |
| R2.36.2 | Cow Fecal | 0.0% | 0.0% | 1.7% | 0.0% | 0.0% |
| R2.36.3 | Cow Fecal | 100.0% | 100.0% | 100.0% | 100.0% | 100.0% |
| R2.36.5 | Cow Fecal | 100.0% | 100.0% | 100.0% | 100.0% | 100.0% |
| R2.36.8 | Cow Fecal | 100.0% | 100.0% | 100.0% | 100.0% | 100.0% |
| R2.39.3 | Cow Fecal | 98.8% | 98.6% | 98.8% | 99.0% | 91.3% |
| R2.39.8 | Cow Fecal | 99.4% | 100.0% | 100.0% | 100.0% | 100.0% |
| R2.40.1 | Cow Fecal | 89.2% | 85.7% | 87.4% | 91.1% | 92.0% |
| R2.40.10 | Cow Fecal | 100.0% | 100.0% | 100.0% | 100.0% | 100.0% |
| R2.40.6 | Cow Fecal | 100.0% | 100.0% | 100.0% | 100.0% | 100.0% |
| R2.40.8 | Cow Fecal | 100.0% | 100.0% | 100.0% | 100.0% | 100.0% |
| R2.42.2 | Cow Fecal | 98.0% | 0.0% | 30.1% | 0.0% | 28.9% |
| R2.42.3 | Cow Fecal | 0.0% | 0.0% | 0.0% | 0.0% | 0.0% |
| R2.42.6 | Cow Fecal | 11.3% | 12.6% | 14.0% | 15.7% | 14.2% |
| R2.44.5 | Cow Fecal | 14.8% | 4.1% | 12.9% | 13.6% | 9.0% |
| R2.45.5 | Cow Fecal | 100.0% | 100.0% | 100.0% | 100.0% | 100.0% |
| R2.45.7 | Cow Fecal | 27.5% | 26.6% | 28.9% | 26.6% | 27.5% |
| R2.45.8 | Cow Fecal | 100.0% | 100.0% | 100.0% | 100.0% | 100.0% |
| R2.46.3 | Cow Fecal | 100.0% | 100.0% | 100.0% | 100.0% | 100.0% |
| R2.46.5 | Cow Fecal | 100.0% | 100.0% | 100.0% | 99.8% | 100.0% |
| R2.46.6 | Cow Fecal | 96.8% | 68.7% | 99.7% | 99.7% | 99.4% |
| R2.49.5 | Cow Fecal | 100.0% | 100.0% | 100.0% | 100.0% | 100.0% |
| R2.50.2 | Cow Fecal | 1.3% | 4.1% | 0.0% | 0.4% | 0.0% |
| R2.50.4 | Cow Fecal | 100.0% | 100.0% | 100.0% | 100.0% | 100.0% |
| R2.51.6 | Cow Fecal | 100.0% | 100.0% | 100.0% | 100.0% | 100.0% |
| R2.51.7 | Cow Fecal | 99.9% | 100.0% | 100.0% | 100.0% | 100.0% |
| R2.52.2 | Cow Fecal | 100.0% | 100.0% | 100.0% | 100.0% | 100.0% |
| R2.52.3 | Cow Fecal | 100.0% | 100.0% | 100.0% | 100.0% | 99.9% |
| R2.52.8 | Cow Fecal | 99.8% | 99.8% | 99.9% | 99.4% | 99.7% |
| R2.54.3 | Cow Fecal | 36.0% | 29.6% | 34.2% | 35.3% | 37.3% |
| R2.56.1 | Cow Fecal | 100.0% | 100.0% | 100.0% | 100.0% | 100.0% |
| R2.56.2 | Cow Fecal | 100.0% | 0.0% | 0.0% | 0.0% | 0.0% |
| R2.57.3 | Cow Fecal | 3.3% | 1.5% | 3.7% | 4.3% | 2.7% |
| R2.59.6 | Cow Fecal | 1.9% | 0.0% | 0.0% | 3.7% | 5.4% |
| R2.61.3 | Cow Fecal | 99.9% | 99.2% | 100.0% | 99.5% | 99.9% |
| R2.61.4 | Cow Fecal | 73.6% | 59.0% | 51.3% | 62.8% | 15.9% |
| R2.61.7 | Cow Fecal | 100.0% | 99.6% | 100.0% | 100.0% | 100.0% |
| R2.62.1 | Cow Fecal | 100.0% | 60.8% | 77.1% | 75.5% | 86.7% |
| R2.64.10 | Cow Fecal | 100.0% | 100.0% | 100.0% | 100.0% | 100.0% |
| R2.64.2 | Cow Fecal | 100.0% | 97.9% | 100.0% | 100.0% | 100.0% |
| R2.64.4 | Cow Fecal | 100.0% | 100.0% | 100.0% | 100.0% | 100.0% |
| R2.65.4 | Cow Fecal | 100.0% | 100.0% | 99.7% | 100.0% | 100.0% |
| R2.66.10 | Cow Fecal | 100.0% | 60.8% | 77.1% | 75.5% | 86.7% |
| R2.66.4 | Cow Fecal | 1.9% | 0.0% | 0.0% | 3.7% | 5.4% |
| R2.67.3 | Cow Fecal | 100.0% | 100.0% | 100.0% | 100.0% | 100.0% |
| R2.67.5 | Cow Fecal | 100.0% | 100.0% | 100.0% | 99.7% | 99.7% |
| R2.68.2 | Cow Fecal | 100.0% | 0.0% | 0.0% | 0.0% | 0.0% |
| R2.68.3 | Cow Fecal | 89.1% | 68.3% | 79.4% | 84.9% | 78.4% |
| R2.68.5 | Cow Fecal | 100.0% | 97.9% | 100.0% | 100.0% | 100.0% |
| R2.68.7 | Cow Fecal | 81.8% | 78.8% | 80.6% | 81.3% | 82.4% |
| R2.69.10 | Cow Fecal | 100.0% | 99.2% | 100.0% | 99.7% | 100.0% |
| R2.69.2 | Cow Fecal | 100.0% | 99.3% | 100.0% | 99.6% | 100.0% |
| R2.70.3 | Cow Fecal | 3.3% | 1.5% | 3.7% | 4.3% | 2.7% |
| R2.70.7 | Cow Fecal | 73.6% | 59.0% | 51.3% | 62.8% | 15.9% |
| R2.70.9 | Cow Fecal | 100.0% | 99.6% | 100.0% | 100.0% | 100.0% |
| R3.1.8 | Cow Fecal | 100.0% | 100.0% | 100.0% | 100.0% | 100.0% |
| R3.11.1 | Cow Fecal | 100.0% | 100.0% | 74.2% | 100.0% | 100.0% |
| R3.11.4 | Cow Fecal | 91.3% | 84.5% | 86.3% | 86.6% | 92.5% |
| R3.11.8 | Cow Fecal | 84.7% | 72.0% | 81.1% | 82.5% | 83.0% |
| R3.11.9 | Cow Fecal | 100.0% | 100.0% | 100.0% | 100.0% | 100.0% |
| R3.12.1 | Cow Fecal | 100.0% | 100.0% | 100.0% | 100.0% | 100.0% |
| R3.13.2 | Cow Fecal | 18.4% | 18.5% | 18.7% | 15.5% | 17.7% |
| R3.15.2 | Cow Fecal | 21.2% | 17.1% | 18.9% | 22.8% | 21.9% |
| R3.16.4 | Cow Fecal | 100.0% | 100.0% | 100.0% | 100.0% | 100.0% |
| R3.19.1 | Cow Fecal | 30.1% | 27.6% | 28.2% | 34.6% | 28.5% |
| R3.19.5 | Cow Fecal | 51.7% | 49.4% | 46.5% | 52.4% | 47.6% |
| R3.2.2 | Cow Fecal | 56.3% | 48.5% | 51.3% | 52.8% | 52.5% |
| R3.21.5 | Cow Fecal | 62.4% | 33.4% | 52.1% | 24.6% | 53.8% |
| R3.22.1 | Cow Fecal | 99.8% | 100.0% | 100.0% | 100.0% | 100.0% |
| R3.23.1 | Cow Fecal | 100.0% | 100.0% | 100.0% | 100.0% | 100.0% |
| R3.23.5 | Cow Fecal | 100.0% | 100.0% | 100.0% | 100.0% | 100.0% |
| R3.23.8 | Cow Fecal | 100.0% | 95.1% | 98.8% | 96.9% | 98.8% |
| R3.23.9 | Cow Fecal | 32.8% | 24.8% | 100.0% | 24.8% | 22.1% |
| R3.25.7 | Cow Fecal | 100.0% | 84.6% | 100.0% | 89.6% | 100.0% |
| R3.28.6 | Cow Fecal | 23.1% | 19.2% | 21.2% | 24.6% | 23.6% |
| R3.28.8 | Cow Fecal | 100.0% | 100.0% | 100.0% | 100.0% | 100.0% |
| R3.29.1 | Cow Fecal | 100.0% | 100.0% | 100.0% | 100.0% | 100.0% |
| R3.30.2 | Cow Fecal | 100.0% | 95.1% | 99.0% | 96.8% | 99.7% |
| R3.32.2 | Cow Fecal | 100.0% | 100.0% | 100.0% | 100.0% | 100.0% |
| R3.32.5 | Cow Fecal | 100.0% | 100.0% | 100.0% | 100.0% | 100.0% |
| R3.32.8 | Cow Fecal | 100.0% | 100.0% | 100.0% | 100.0% | 100.0% |
| R3.41.2 | Cow Fecal | 69.5% | 41.0% | 41.6% | 93.7% | 61.8% |
| R3.41.4 | Cow Fecal | 100.0% | 100.0% | 100.0% | 100.0% | 100.0% |
| R3.42.2 | Cow Fecal | 100.0% | 100.0% | 100.0% | 100.0% | 100.0% |
| R3.42.3 | Cow Fecal | 100.0% | 100.0% | 100.0% | 100.0% | 100.0% |
| R3.43.2 | Cow Fecal | 100.0% | 43.9% | 71.3% | 67.8% | 70.7% |
| R3.44.1 | Cow Fecal | 100.0% | 100.0% | 100.0% | 100.0% | 100.0% |
| R3.44.5 | Cow Fecal | 76.9% | 58.7% | 62.7% | 60.8% | 72.4% |
| R3.45.5 | Cow Fecal | 92.4% | 87.1% | 91.0% | 91.4% | 95.8% |
| R3.47.1 | Cow Fecal | 0.0% | 0.0% | 0.0% | 0.0% | 0.0% |
| R3.48.2 | Cow Fecal | 100.0% | 100.0% | 100.0% | 100.0% | 100.0% |
| R3.48.9 | Cow Fecal | 69.3% | 61.9% | 67.3% | 70.8% | 68.1% |
| R3.49.4 | Cow Fecal | 38.8% | 7.6% | 26.5% | 0.0% | 26.7% |

TABLE 11-continued

Bacteriocin assay results displaying each isolate tested and the source of that isolate, isolated from Texas fecal samples. Inhibition was calculated based on the percent of growth for each treatment well compared to the positive control.

| Isolate ID | Sample | Bacillus strains | | | | |
|---|---|---|---|---|---|---|
| | | 747 | 1104 | 1541 | 1781 | 2018 |
| R3.51.1 | Cow Fecal | 99.6% | 4.1% | 99.9% | 0.0% | 99.3% |
| R3.51.4 | Cow Fecal | 98.8% | 98.8% | 98.8% | 99.5% | 99.0% |
| R3.52.5 | Cow Fecal | 100.0% | 100.0% | 100.0% | 100.0% | 98.8% |
| R3.52.7 | Cow Fecal | 97.5% | 94.0% | 95.1% | 95.2% | 96.8% |
| R3.54.4 | Cow Fecal | 100.0% | 100.0% | 100.0% | 100.0% | 100.0% |
| R3.57.5 | Cow Fecal | 100.0% | 98.4% | 100.0% | 99.5% | 100.0% |
| R3.58.3 | Cow Fecal | 100.0% | 100.0% | 100.0% | 100.0% | 100.0% |
| R3.58.4 | Cow Fecal | 68.4% | 59.6% | 61.1% | 61.3% | 64.9% |
| R3.6.5 | Cow Fecal | 47.2% | 25.9% | 54.1% | 19.4% | 44.4% |
| R3.60.3 | Cow Fecal | 99.9% | 100.0% | 100.0% | 100.0% | 99.9% |
| R3.7.1 | Cow Fecal | 100.0% | 100.0% | 100.0% | 99.7% | 100.0% |
| R3.7.10 | Cow Fecal | 100.0% | 100.0% | 100.0% | 100.0% | 100.0% |
| R3.7.4 | Cow Fecal | 100.0% | 100.0% | 100.0% | 99.5% | 100.0% |
| R3.7.9 | Cow Fecal | 100.0% | 96.7% | 98.4% | 97.6% | 98.6% |
| R3.8.1 | Cow Fecal | 100.0% | 35.5% | 40.3% | 11.5% | 17.8% |
| R3.8.3 | Cow Fecal | 100.0% | 100.0% | 100.0% | 100.0% | 100.0% |
| R5.12.10 | Cow Fecal | 95.8% | 7.3% | 100.0% | 2.0% | 94.4% |
| R5.12.3 | Cow Fecal | 100.0% | 100.0% | 100.0% | 98.4% | 100.0% |
| R5.12.6 | Cow Fecal | 100.0% | 100.0% | 100.0% | 100.0% | 100.0% |
| R5.13.4 | Cow Fecal | 100.0% | 100.0% | 100.0% | 100.0% | 100.0% |
| R5.13.5 | Cow Fecal | 100.0% | 100.0% | 100.0% | 100.0% | 100.0% |
| R5.13.9 | Cow Fecal | 100.0% | 100.0% | 100.0% | 100.0% | 100.0% |
| R5.14.2 | Cow Fecal | 84.4% | 44.0% | 91.8% | 10.1% | 100.0% |
| R5.18.4 | Cow Fecal | 100.0% | 100.0% | 100.0% | 100.0% | 100.0% |
| R5.21.5 | Cow Fecal | 18.2% | 20.5% | 23.8% | 20.7% | 17.7% |
| R5.22.9 | Cow Fecal | 100.0% | 100.0% | 100.0% | 100.0% | 100.0% |
| R5.24.2 | Cow Fecal | 100.0% | 100.0% | 100.0% | 100.0% | 100.0% |
| R5.3.3 | Cow Fecal | 100.0% | 100.0% | 100.0% | 100.0% | 100.0% |
| R5.3.5 | Cow Fecal | 100.0% | 100.0% | 100.0% | 100.0% | 100.0% |
| R5.3.6 | Cow Fecal | 100.0% | 100.0% | 100.0% | 100.0% | 100.0% |
| R5.3.8 | Cow Fecal | 100.0% | 100.0% | 100.0% | 100.0% | 100.0% |
| R5.35.3 | Cow Fecal | 4.7% | 17.6% | 4.6% | 24.5% | 18.0% |
| R5.35.4 | Cow Fecal | 100.0% | 100.0% | 100.0% | 100.0% | 100.0% |
| R5.36.7 | Cow Fecal | 100.0% | 100.0% | 100.0% | 100.0% | 100.0% |
| R5.4.1 | Cow Fecal | 100.0% | 100.0% | 100.0% | 97.9% | 100.0% |
| R5.4.5 | Cow Fecal | 100.0% | 100.0% | 100.0% | 100.0% | 100.0% |
| R5.40.5 | Cow Fecal | 100.0% | 100.0% | 100.0% | 100.0% | 100.0% |
| R5.49.2 | Cow Fecal | 100.0% | 100.0% | 100.0% | 100.0% | 100.0% |
| R5.49.8 | Cow Fecal | 100.0% | 100.0% | 100.0% | 100.0% | 100.0% |
| R5.5.2 | Cow Fecal | 100.0% | 96.6% | 100.0% | 100.0% | 100.0% |
| R5.55.1 | Cow Fecal | 100.0% | 100.0% | 100.0% | 97.9% | 100.0% |
| R5.55.2 | Cow Fecal | 100.0% | 100.0% | 100.0% | 100.0% | 100.0% |
| R5.58.10 | Cow Fecal | 100.0% | 100.0% | 100.0% | 100.0% | 100.0% |
| R5.58.5 | Cow Fecal | 100.0% | 100.0% | 100.0% | 92.5% | 100.0% |
| R5.58.7 | Cow Fecal | 100.0% | 100.0% | 100.0% | 100.0% | 100.0% |
| R5.58.8 | Cow Fecal | 100.0% | 100.0% | 100.0% | 100.0% | 100.0% |
| R5.6.10 | Cow Fecal | 100.0% | 100.0% | 100.0% | 100.0% | 98.6% |
| R5.6.5 | Cow Fecal | 99.7% | 99.3% | 100.0% | 100.0% | 100.0% |
| R5.60.4 | Cow Fecal | 100.0% | 100.0% | 100.0% | 100.0% | 100.0% |
| R5.7.3 | Cow Fecal | 100.0% | 68.5% | 100.0% | 90.4% | 99.6% |
| R5.8.10 | Cow Fecal | 100.0% | 100.0% | 100.0% | 100.0% | 100.0% |
| R5.8.4 | Cow Fecal | 100.0% | 100.0% | 100.0% | 85.8% | 100.0% |
| R5.8.6 | Cow Fecal | 100.0% | 100.0% | 100.0% | 100.0% | 100.0% |
| R7.1.10 | Calf Fecal | 100.0% | 100.0% | 100.0% | 100.0% | 100.0% |
| R7.1.2 | Calf Fecal | 100.0% | 100.0% | 100.0% | 100.0% | 100.0% |
| R7.10.7 | Calf Fecal | 99.3% | 92.7% | 91.6% | 100.0% | 96.0% |
| R7.11.8 | Calf Fecal | 100.0% | 51.7% | 88.4% | 56.8% | 98.4% |
| R7.12.7 | Calf Fecal | 100.0% | 100.0% | 100.0% | 100.0% | 100.0% |
| R7.12.8 | Calf Fecal | 98.3% | 99.3% | 100.0% | 99.4% | 99.9% |
| R7.13.3 | Calf Fecal | 100.0% | 100.0% | 96.9% | 100.0% | 100.0% |
| R7.13.9 | Calf Fecal | 100.0% | 100.0% | 100.0% | 100.0% | 100.0% |
| R7.14.5 | Calf Fecal | 100.0% | 15.9% | 99.8% | 7.6% | 100.0% |
| R7.14.6 | Calf Fecal | 62.7% | 16.7% | 9.0% | 33.6% | 29.4% |
| R7.15.1 | Calf Fecal | 100.0% | 100.0% | 100.0% | 100.0% | 100.0% |
| R7.15.2 | Calf Fecal | 100.0% | 100.0% | 100.0% | 100.0% | 100.0% |
| R7.15.5 | Calf Fecal | 100.0% | 99.7% | 100.0% | 99.3% | 100.0% |
| R7.17.9 | Cow Fecal | 100.0% | 100.0% | 100.0% | 69.8% | 99.6% |
| R7.19.2 | Cow Fecal | 98.1% | 98.5% | 97.2% | 99.3% | 78.4% |
| R7.2.1 | Calf Fecal | 58.2% | 36.2% | 9.8% | 70.5% | 0.0% |
| R7.2.5 | Calf Fecal | 79.8% | 55.5% | 19.1% | 93.3% | 0.0% |
| R7.2.6 | Calf Fecal | 100.0% | 91.9% | 90.6% | 84.2% | 100.0% |
| R7.2.7 | Calf Fecal | 100.0% | 78.5% | 89.6% | 74.7% | 100.0% |
| R7.21.5 | Cow Fecal | 100.0% | 100.0% | 100.0% | 100.0% | 87.7% |
| R7.23.4 | Cow Fecal | 98.8% | 100.0% | 70.9% | 100.0% | 77.6% |
| R7.26.10 | Cow Fecal | 100.0% | 100.0% | 83.2% | 100.0% | 98.9% |
| R7.27.10 | Cow Fecal | 100.0% | 100.0% | 100.0% | 100.0% | 100.0% |
| R7.3.2 | Calf Fecal | 100.0% | 100.0% | 100.0% | 70.5% | 100.0% |
| R7.30.1 | Cow Fecal | 98.4% | 97.8% | 93.2% | 98.5% | 79.0% |
| R7.34.9 | Cow Fecal | 98.5% | 98.6% | 96.9% | 98.4% | 72.8% |
| R7.39.3 | Cow Fecal | 100.0% | 100.0% | 100.0% | 100.0% | 100.0% |
| R7.4.2 | Calf Fecal | 100.0% | 54.0% | 97.9% | 51.8% | 100.0% |
| R7.47.2 | Cow Fecal | 100.0% | 100.0% | 100.0% | 100.0% | 66.2% |
| R7.48.1 | Cow Fecal | 100.0% | 0.0% | 0.0% | 0.0% | 100.0% |
| R7.49.2 | Cow Fecal | 100.0% | 100.0% | 100.0% | 100.0% | 100.0% |
| R7.5.6 | Calf Fecal | 28.9% | 18.4% | 19.5% | 7.4% | 21.6% |
| R7.50.4 | Cow Fecal | 99.9% | 78.2% | 100.0% | 99.5% | 99.3% |
| R7.50.5 | Cow Fecal | 9.4% | 10.0% | 13.7% | 16.1% | 9.8% |
| R7.51.1 | Cow Fecal | 100.0% | 100.0% | 100.0% | 100.0% | 100.0% |
| R7.51.5 | Cow Fecal | 100.0% | 100.0% | 100.0% | 100.9% | 100.0% |
| R7.54.4 | Cow Fecal | 99.7% | 100.0% | 100.0% | 100.0% | 74.7% |
| R7.55.2 | Cow Fecal | 84.9% | 78.6% | 31.0% | 100.0% | 0.0% |
| R7.55.3 | Cow Fecal | 100.0% | 100.0% | 99.9% | 99.7% | 99.3% |
| R7.55.9 | Cow Fecal | 100.0% | 99.5% | 99.5% | 99.8% | 100.0% |
| R7.59.9 | Cow Fecal | 100.0% | 100.0% | 100.0% | 100.0% | 100.0% |
| R7.64.2 | Cow Fecal | 100.0% | 100.0% | 99.9% | 100.0% | 100.0% |
| R7.65.1 | Cow Fecal | 100.0% | 100.0% | 100.0% | 100.0% | 100.0% |
| R7.67.8 | Cow Fecal | 100.0% | 100.0% | 100.0% | 100.0% | 100.0% |
| R7.68.1 | Cow Fecal | 53.6% | 83.3% | 2.1% | 100.0% | 0.0% |
| R7.68.3 | Cow Fecal | 100.0% | 100.0% | 100.0% | 100.0% | 100.0% |
| R7.69.1 | Cow Fecal | 100.0% | 99.7% | 99.3% | 100.0% | 38.9% |
| R7.72.3 | Cow Fecal | 100.0% | 100.0% | 100.0% | 99.9% | 81.5% |
| R7.73.2 | Cow Fecal | 88.0% | 100.0% | 48.4% | 100.0% | 81.6% |
| R7.83.1 | Cow Fecal | 100.0% | 100.0% | 93.9% | 100.0% | 31.6% |
| R17.1.2 | Cow Fecal | 97.8% | 99.6% | 90.2% | 100.0% | 100.0% |
| R17.10.3 | Cow Fecal | 40.5% | 37.3% | 52.7% | 53.0% | 48.0% |
| R17.10.4 | Cow Fecal | 100.0% | 100.0% | 24.1% | 100.0% | 98.9% |
| R17.10.5 | Cow Fecal | 43.5% | 57.9% | 21.0% | 20.5% | 21.2% |
| R17.11.10 | Cow Fecal | 100.0% | 100.0% | 100.0% | 100.0% | 100.0% |
| R17.11.2 | Cow Fecal | 100.0% | 100.0% | 100.0% | 100.0% | 100.0% |
| R17.13.8 | Cow Fecal | 67.9% | 73.2% | 72.2% | 100.0% | 31.9% |
| R17.14.10 | Cow Fecal | 99.2% | 100.0% | 82.1% | 78.6% | 94.9% |
| R17.14.2 | Cow Fecal | 34.9% | 96.2% | 37.9% | 34.1% | 57.8% |
| R17.15.1 | Cow Fecal | 99.8% | 99.3% | 100.0% | 100.0% | 100.0% |
| R17.17.1 | Cow Fecal | 100.0% | 100.0% | 100.0% | 99.9% | 100.0% |
| R17.2.2 | Cow Fecal | 46.8% | 74.0% | 77.8% | 85.7% | 58.2% |
| R17.2.4 | Cow Fecal | 99.9% | 100.0% | 78.1% | 65.3% | 77.3% |
| R17.2.7 | Cow Fecal | 100.0% | 100.0% | 36.6% | 100.0% | 100.0% |
| R17.2.9 | Cow Fecal | 59.9% | 76.3% | 2.6% | 24.7% | 35.9% |
| R17.20.2 | Cow Fecal | 100.0% | 100.0% | 98.8% | 96.0% | 100.0% |
| R17.21.1 | Cow Fecal | 100.0% | 100.0% | 99.9% | 99.7% | 100.0% |
| R17.22.4 | Cow Fecal | 100.0% | 100.0% | 100.0% | 100.0% | 57.0% |
| R17.22.5 | Cow Fecal | 100.0% | 67.7% | 88.9% | 69.1% | 59.2% |
| R17.23.1 | Cow Fecal | 97.6% | 100.0% | 37.1% | 81.3% | 94.7% |
| R17.23.3 | Cow Fecal | 68.8% | 65.1% | 71.6% | 60.1% | 60.4% |
| R17.23.5 | Cow Fecal | 100.0% | 96.2% | 90.1% | 92.6% | 100.0% |
| R17.23.6 | Cow Fecal | 100.0% | 100.0% | 100.0% | 100.0% | 100.0% |
| R17.25.6 | Cow Fecal | 99.3% | 100.0% | 79.9% | 95.5% | 98.3% |
| R17.25.9 | Cow Fecal | 71.6% | 79.7% | 89.3% | 78.6% | 85.9% |
| R17.26.5 | Cow Fecal | 100.0% | 87.3% | 100.0% | 0.0% | 0.0% |
| R17.26.6 | Cow Fecal | 35.2% | 100.0% | 100.0% | 99.4% | 99.7% |
| R17.26.8 | Cow Fecal | 100.0% | 100.0% | 100.0% | 100.0% | 100.0% |
| R17.28.2 | Cow Fecal | 57.5% | 48.4% | 41.7% | 58.8% | 59.2% |
| R17.28.3 | Cow Fecal | 91.9% | 78.8% | 91.6% | 77.5% | 83.0% |
| R17.28.6 | Cow Fecal | 95.2% | 79.6% | 96.0% | 64.1% | 95.9% |
| R17.29.1 | Cow Fecal | 100.0% | 100.0% | 100.0% | 100.0% | 100.0% |
| R17.29.2 | Cow Fecal | 24.0% | 24.5% | 28.7% | 17.7% | 26.2% |
| R17.29.4 | Cow Fecal | 95.2% | 99.0% | 83.8% | 43.9% | 91.7% |
| R17.29.5 | Cow Fecal | 96.9% | 100.0% | 44.2% | 52.3% | 42.2% |
| R17.29.6 | Cow Fecal | 96.3% | 99.8% | 98.3% | 100.0% | 100.0% |
| R17.29.8 | Cow Fecal | 77.9% | 82.8% | 75.2% | 77.0% | 78.5% |
| R17.29.9 | Cow Fecal | 0.0% | 0.0% | 0.0% | 0.0% | 0.0% |
| R17.30.1 | Cow Fecal | 93.0% | 92.9% | 23.1% | 40.2% | 88.7% |

TABLE 11-continued

Bacteriocin assay results displaying each isolate tested and the source of that isolate, isolated from Texas fecal samples. Inhibition was calculated based on the percent of growth for each treatment well compared to the positive control.

| | | Bacillus strains | | | | |
|---|---|---|---|---|---|---|
| Isolate ID | Sample | 747 | 1104 | 1541 | 1781 | 2018 |
| R17.30.7 | Cow Fecal | 77.4% | 85.6% | 78.3% | 51.8% | 78.3% |
| R17.31.4 | Cow Fecal | 19.4% | 13.9% | 20.7% | 11.9% | 15.0% |
| R17.31.5 | Cow Fecal | 100.0% | 99.9% | 100.0% | 99.4% | 100.0% |
| R17.31.7 | Cow Fecal | 80.8% | 97.9% | 66.9% | 84.0% | 87.6% |
| R17.32.3 | Cow Fecal | 41.0% | 68.8% | 77.9% | 81.1% | 75.3% |
| R17.32.5 | Cow Fecal | 100.0% | 100.0% | 73.4% | 93.4% | 100.0% |
| R17.32.6 | Cow Fecal | 100.0% | 100.0% | 100.0% | 100.0% | 100.0% |
| R17.33.2 | Cow Fecal | 100.0% | 77.8% | 19.2% | 100.0% | 100.0% |
| R17.33.6 | Cow Fecal | 100.0% | 100.0% | 100.0% | 100.0% | 100.0% |
| R17.34.3 | Cow Fecal | 42.4% | 99.5% | 99.6% | 98.8% | 99.8% |
| R17.35.10 | Cow Fecal | 39.0% | 37.0% | 38.6% | 39.1% | 39.6% |
| R17.35.2 | Cow Fecal | 100.0% | 100.0% | 100.0% | 100.0% | 100.0% |
| R17.35.4 | Cow Fecal | 47.9% | 48.4% | 50.7% | 47.7% | 49.5% |
| R17.35.9 | Cow Fecal | 100.0% | 100.0% | 72.6% | 95.1% | 100.0% |
| R17.36.10 | Cow Fecal | 59.2% | 87.7% | 31.7% | 79.2% | 62.7% |
| R17.36.3 | Cow Fecal | 49.3% | 38.3% | 37.5% | 34.1% | 35.4% |
| R17.36.7 | Cow Fecal | 89.8% | 98.7% | 69.0% | 78.8% | 86.7% |
| R17.38.5 | Cow Fecal | 74.2% | 66.8% | 84.6% | 58.6% | 88.5% |
| R17.38.6 | Cow Fecal | 100.0% | 100.0% | 100.0% | 29.2% | 100.0% |
| R17.38.9 | Cow Fecal | 100.0% | 100.0% | 100.0% | 100.0% | 100.0% |
| R17.39.2 | Cow Fecal | 41.6% | 39.9% | 42.7% | 40.7% | 44.1% |
| R17.39.8 | Cow Fecal | 57.1% | 100.0% | 0.0% | 14.4% | 88.6% |
| R17.40.9 | Cow Fecal | 0.0% | 0.0% | 0.0% | 0.0% | 1.7% |
| R17.41.2 | Cow Fecal | 0.0% | 0.0% | 0.0% | 0.0% | 0.0% |
| R17.43.2 | Cow Fecal | 50.1% | 86.1% | 15.3% | 24.7% | 15.2% |
| R17.43.3 | Cow Fecal | 100.0% | 100.0% | 100.0% | 100.0% | 100.0% |
| R17.44.8 | Cow Fecal | 50.7% | 22.0% | 100.0% | 99.7% | 21.7% |
| R17.47.1 | Cow Fecal | 98.2% | 91.0% | 99.4% | 93.4% | 100.0% |
| R17.48.2 | Cow Fecal | 99.5% | 99.8% | 99.6% | 99.9% | 100.0% |
| R17.49.8 | Cow Fecal | 86.5% | 99.8% | 99.8% | 100.0% | 99.9% |
| R17.51.6 | Cow Fecal | 99.7% | 81.7% | 100.0% | 100.0% | 100.0% |
| R17.54.6 | Cow Fecal | 0.0% | 0.0% | 0.0% | 0.0% | 0.0% |
| R17.58.4 | Cow Fecal | 100.0% | 100.0% | 97.1% | 99.5% | 100.0% |
| R17.58.7 | Cow Fecal | 61.6% | 98.9% | 54.7% | 54.8% | 85.9% |
| R17.60.2 | Cow Fecal | 93.4% | 100.0% | 100.0% | 81.9% | 78.5% |
| R17.60.3 | Cow Fecal | 53.0% | 37.8% | 23.7% | 44.4% | 45.6% |
| R17.60.5 | Cow Fecal | 53.6% | 74.6% | 73.4% | 61.2% | 56.9% |
| R17.64.10 | Cow Fecal | 90.3% | 88.3% | 0.0% | 46.9% | 54.7% |
| R17.64.9 | Cow Fecal | 81.0% | 85.7% | 57.3% | 62.0% | 51.4% |
| R17.67.9 | Cow Fecal | 13.0% | 51.7% | 0.0% | 11.8% | 10.9% |
| R17.68.2 | Cow Fecal | 100.0% | 100.0% | 100.0% | 100.0% | 100.0% |
| R17.68.9 | Cow Fecal | 100.0% | 100.0% | 100.0% | 100.0% | 100.0% |
| R17.7.2 | Cow Fecal | 90.0% | 94.7% | 93.9% | 85.2% | 89.8% |
| R17.7.7 | Cow Fecal | 100.0% | 100.0% | 80.8% | 66.2% | 82.9% |
| R17.7.9 | Cow Fecal | 100.0% | 100.0% | 100.0% | 100.0% | 100.0% |
| R17.8.2 | Cow Fecal | 66.3% | 74.3% | 71.3% | 71.3% | 71.3% |
| R17.8.9 | Cow Fecal | 0.0% | 84.6% | 72.2% | 0.0% | 0.0% |
| R18.1.2 | Cow Fecal | 38.5% | 90.6% | 33.8% | 38.3% | 39.3% |
| R18.1.3 | Cow Fecal | 0.0% | 57.0% | 0.0% | 0.0% | 0.0% |
| R18.1.8 | Cow Fecal | 100.0% | 100.0% | 100.0% | 100.0% | 100.0% |
| R18.1.10 | Cow Fecal | 97.6% | 87.3% | 52.1% | 82.7% | 84.2% |
| R18.2.4 | Cow Fecal | 100.0% | 100.0% | 100.0% | 100.0% | 100.0% |
| R18.2.6 | Cow Fecal | 88.1% | 69.2% | 55.1% | 84.4% | 74.8% |
| R18.2.8 | Cow Fecal | 100.0% | 100.0% | 100.0% | 100.0% | 100.0% |
| R18.3.3 | Cow Fecal | 99.8% | 100.0% | 100.0% | 100.0% | 100.0% |
| R18.5.2 | Cow Fecal | 100.0% | 100.0% | 100.0% | 100.0% | 100.0% |
| R18.7.7 | Cow Fecal | 99.0% | 100.0% | 96.6% | 100.0% | 100.0% |
| R18.8.3 | Cow Fecal | 81.1% | 56.9% | 35.6% | 60.8% | 70.8% |
| R18.8.4 | Cow Fecal | 100.0% | 100.0% | 100.0% | 100.0% | 100.0% |
| R18.8.5 | Cow Fecal | 24.0% | 49.3% | 74.4% | 43.0% | 73.1% |
| R18.8.8 | Cow Fecal | 100.0% | 100.0% | 100.0% | 100.0% | 100.0% |
| R18.10.3 | Cow Fecal | 83.2% | 60.8% | 100.0% | 100.0% | 63.3% |
| R18.10.10 | Cow Fecal | 99.8% | 100.0% | 100.0% | 61.2% | 100.0% |
| R18.11.4 | Cow Fecal | 99.7% | 99.8% | 100.0% | 100.0% | 100.0% |
| R18.13.6 | Cow Fecal | 100.0% | 100.0% | 100.0% | 100.0% | 100.0% |
| R18.13.8 | Cow Fecal | 100.0% | 100.0% | 100.0% | 100.0% | 100.0% |
| R18.16.4 | Cow Fecal | 100.0% | 100.0% | 100.0% | 100.0% | 100.0% |
| R18.16.5 | Cow Fecal | 4.4% | 11.7% | 9.1% | 10.8% | 8.4% |
| R18.17.3 | Cow Fecal | 100.0% | 100.0% | 100.0% | 100.0% | 100.0% |
| R18.18.5 | Cow Fecal | 100.0% | 100.0% | 100.0% | 100.0% | 100.0% |
| R18.18.7 | Cow Fecal | 70.6% | 79.4% | 6.4% | 8.8% | 26.1% |
| R18.18.9 | Cow Fecal | 100.0% | 99.7% | 100.0% | 100.0% | 100.0% |
| R18.18.10 | Cow Fecal | 100.0% | 56.9% | 100.0% | 91.1% | 74.0% |
| R18.20.3 | Cow Fecal | 96.9% | 100.0% | 44.2% | 52.3% | 42.2% |
| R18.20.4 | Cow Fecal | 100.0% | 100.0% | 100.0% | 82.5% | 80.8% |
| R18.21.3 | Cow Fecal | 69.6% | 65.4% | 32.1% | 34.4% | 3.8% |
| R18.21.6 | Cow Fecal | 31.9% | 17.1% | 12.5% | 0.0% | 3.6% |
| R18.21.9 | Cow Fecal | 57.1% | 100.0% | 0.0% | 14.4% | 88.7% |
| R18.21.10 | Cow Fecal | 48.1% | 51.0% | 34.1% | 0.0% | 44.6% |
| R18.22.8 | Cow Fecal | 36.5% | 64.4% | 41.5% | 59.0% | 96.4% |
| R18.23.1 | Cow Fecal | 99.7% | 97.7% | 80.1% | 58.3% | 57.3% |
| R18.23.2 | Cow Fecal | 19.4% | 66.5% | 0.0% | 0.4% | 6.7% |
| R18.25.1 | Cow Fecal | 70.8% | 67.8% | 70.7% | 49.8% | 51.6% |
| R18.25.2 | Cow Fecal | 93.2% | 99.7% | 100.0% | 85.7% | 79.2% |
| R18.25.3 | Cow Fecal | 100.0% | 100.0% | 100.0% | 100.0% | 100.0% |
| R18.25.5 | Cow Fecal | 46.5% | 48.1% | 100.0% | 45.4% | 35.2% |
| R18.25.6 | Cow Fecal | 96.0% | 83.1% | 65.6% | 88.6% | 77.2% |
| R18.26.2 | Cow Fecal | 100.0% | 81.7% | 75.4% | 32.0% | 79.6% |
| R18.26.4 | Cow Fecal | 96.3% | 72.6% | 58.9% | 31.0% | 76.0% |
| R18.26.7 | Cow Fecal | 99.7% | 100.0% | 100.0% | 100.0% | 100.0% |
| R18.26.8 | Cow Fecal | 100.0% | 100.0% | 100.0% | 100.0% | 100.0% |
| R18.27.2 | Cow Fecal | 63.3% | 84.6% | 40.8% | 60.2% | 48.3% |
| R18.27.5 | Cow Fecal | 100.0% | 30.1% | 42.1% | 14.8% | 16.1% |
| R18.27.7 | Cow Fecal | 100.0% | 100.0% | 100.0% | 61.5% | 100.0% |
| R18.28.1 | Cow Fecal | 42.3% | 47.9% | 34.3% | 13.2% | 11.9% |
| R18.28.8 | Cow Fecal | 87.3% | 100.0% | 100.0% | 52.4% | 76.0% |
| R18.28.9 | Cow Fecal | 100.0% | 99.9% | 100.0% | 100.0% | 100.0% |
| R18.29.1 | Cow Fecal | 100.0% | 100.0% | 100.0% | 100.0% | 100.0% |
| R18.29.2 | Cow Fecal | 93.8% | 76.0% | 100.0% | 98.8% | 96.5% |
| R18.29.3 | Cow Fecal | 30.3% | 21.9% | 23.7% | 9.3% | 22.9% |
| R18.30.2 | Cow Fecal | 100.0% | 98.0% | 100.0% | 88.7% | 100.0% |
| R18.30.8 | Cow Fecal | 0.0% | 100.0% | 100.0% | 79.1% | 93.9% |
| R18.31.2 | Cow Fecal | 100.0% | 100.0% | 100.0% | 100.0% | 100.0% |
| R18.31.3 | Cow Fecal | 100.0% | 100.0% | 100.0% | 60.5% | 100.0% |
| R18.31.6 | Cow Fecal | 100.0% | 100.0% | 100.0% | 100.0% | 100.0% |
| R18.31.7 | Cow Fecal | 100.0% | 100.0% | 100.0% | 100.0% | 100.0% |
| R18.31.9 | Cow Fecal | 82.8% | 75.2% | 48.5% | 59.7% | 49.8% |
| R18.31.10 | Cow Fecal | 100.0% | 100.0% | 100.0% | 100.0% | 100.0% |
| R18.32.2 | Cow Fecal | 16.4% | 11.2% | 9.8% | 2.4% | 15.3% |
| R18.32.3 | Cow Fecal | 100.0% | 100.0% | 96.9% | 100.0% | 96.7% |
| R18.34.3 | Cow Fecal | 19.3% | 18.8% | 23.8% | 27.6% | 51.8% |
| R18.36.3 | Cow Fecal | 56.5% | 20.3% | 41.5% | 42.8% | 49.0% |
| R18.36.5 | Cow Fecal | 100.0% | 100.0% | 98.2% | 52.6% | 98.7% |
| R18.36.8 | Cow Fecal | 99.5% | 100.0% | 93.3% | 98.9% | 100.0% |
| R18.37.2 | Cow Fecal | 100.0% | 99.8% | 100.0% | 100.0% | 99.5% |
| R18.37.8 | Cow Fecal | 69.6% | 47.7% | 90.4% | 63.2% | 74.8% |
| R18.37.10 | Cow Fecal | 100.0% | 100.0% | 100.0% | 100.0% | 100.0% |
| R18.39.1 | Cow Fecal | 28.4% | 29.1% | 25.1% | 27.1% | 26.8% |
| R18.39.8 | Cow Fecal | 100.0% | 57.7% | 75.5% | 45.7% | 67.6% |
| R18.39.10 | Cow Fecal | 16.2% | 19.2% | 17.5% | 17.3% | 16.7% |
| R18.41.5 | Cow Fecal | 100.0% | 100.0% | 100.0% | 100.0% | 100.0% |
| R18.41.8 | Cow Fecal | 23.7% | 57.8% | 64.7% | 31.8% | 39.2% |
| R18.42.6 | Cow Fecal | 100.0% | 100.0% | 100.0% | 100.0% | 100.0% |
| R18.42.7 | Cow Fecal | 100.0% | 100.0% | 100.0% | 100.0% | 100.0% |
| R18.43.3 | Cow Fecal | 100.0% | 100.0% | 100.0% | 74.3% | 88.7% |
| R18.44.6 | Cow Fecal | 100.0% | 100.0% | 100.0% | 100.0% | 100.0% |
| R18.45.6 | Cow Fecal | 100.0% | 100.0% | 100.0% | 100.0% | 100.0% |
| R18.46.8 | Cow Fecal | 73.3% | 99.1% | 37.3% | 42.4% | 21.1% |
| R18.46.10 | Cow Fecal | 70.5% | 100.0% | 45.5% | 46.2% | 60.3% |
| R18.48.1 | Cow Fecal | 68.0% | 100.0% | 38.6% | 35.8% | 31.2% |
| R18.48.2 | Cow Fecal | 100.0% | 100.0% | 100.0% | 100.0% | 100.0% |
| R18.48.7 | Cow Fecal | 100.0% | 99.9% | 99.9% | 100.0% | 100.0% |
| R18.48.9 | Cow Fecal | 74.4% | 79.0% | 62.4% | 41.8% | 42.2% |
| R18.49.7 | Cow Fecal | 100.0% | 96.1% | 100.0% | 0.0% | 0.0% |
| R18.50.3 | Cow Fecal | 79.4% | 100.0% | 100.0% | 100.0% | 100.0% |
| R18.50.5 | Cow Fecal | 31.1% | 30.8% | 27.1% | 28.0% | 28.0% |
| R18.51.6 | Cow Fecal | 45.1% | 51.6% | 45.1% | 40.5% | 44.6% |
| R18.52.1 | Cow Fecal | 100.0% | 100.0% | 100.0% | 100.0% | 100.0% |
| R18.53.3 | Cow Fecal | 75.9% | 51.5% | 100.0% | 50.6% | 41.9% |
| R18.53.5 | Cow Fecal | 51.4% | 41.4% | 20.1% | 26.0% | 3.6% |
| R18.55.6 | Cow Fecal | 73.1% | 46.0% | 28.9% | 28.1% | 29.7% |
| R18.55.8 | Cow Fecal | 63.8% | 54.2% | 1.4% | 0.0% | 0.0% |

TABLE 11-continued

Bacteriocin assay results displaying each isolate tested and the source of that isolate, isolated from Texas fecal samples. Inhibition was calculated based on the percent of growth for each treatment well compared to the positive control.

| | | Bacillus strains | | | | |
|---|---|---|---|---|---|---|
| Isolate ID | Sample | 747 | 1104 | 1541 | 1781 | 2018 |
| R18.56.1 | Cow Fecal | 96.6% | 92.6% | 61.8% | 61.0% | 85.1% |
| R18.56.4 | Cow Fecal | 98.2% | 91.0% | 99.4% | 93.4% | 100.0% |
| R18.56.9 | Cow Fecal | 64.4% | 96.7% | 48.5% | 43.1% | 60.9% |
| R18.58.1 | Cow Fecal | 98.8% | 99.8% | 99.2% | 99.7% | 100.0% |
| R18.58.2 | Cow Fecal | 100.0% | 100.0% | 36.6% | 100.0% | 100.0% |
| R18.58.9 | Cow Fecal | 80.1% | 64.2% | 36.0% | 65.6% | 70.0% |
| R18.58.10 | Cow Fecal | 100.0% | 95.4% | 94.5% | 0.0% | 0.0% |
| R18.60.1 | Cow Fecal | 99.1% | 99.8% | 99.0% | 99.6% | 98.8% |
| R18.60.3 | Cow Fecal | 80.7% | 100.0% | 100.0% | 66.3% | 53.8% |
| R18.60.4 | Cow Fecal | 19.0% | 15.1% | 20.8% | 14.4% | 19.6% |
| R18.60.5 | Cow Fecal | 100.0% | 100.0% | 100.0% | 100.0% | 100.0% |
| R18.60.10 | Cow Fecal | 100.0% | 100.0% | 100.0% | 100.0% | 100.0% |
| R18.61.7 | Cow Fecal | 3.8% | 1.3% | 10.1% | 0.8% | 0.7% |
| R19.1.5 | Cow Fecal | 86.5% | 100.0% | 54.8% | 23.6% | 69.1% |
| R19.10.7 | Cow Fecal | 100.0% | 100.0% | 100.0% | 100.0% | 100.0% |
| R19.12.5 | Cow Fecal | 15.0% | 14.8% | 32.5% | 15.0% | 5.1% |
| R19.13.1 | Cow Fecal | 100.0% | 100.0% | 100.0% | 100.0% | 100.0% |
| R19.13.10 | Cow Fecal | 100.0% | 100.0% | 100.0% | 100.0% | 100.0% |
| R19.15.3 | Cow Fecal | 100.0% | 100.0% | 40.8% | 68.0% | 98.5% |
| R19.15.4 | Cow Fecal | 43.4% | 66.4% | 17.7% | 71.2% | 5.1% |
| R19.15.6 | Cow Fecal | 100.0% | 100.0% | 100.0% | 100.0% | 100.0% |
| R19.15.7 | Cow Fecal | 30.4% | 11.6% | 19.8% | 24.7% | 28.2% |
| R19.15.8 | Cow Fecal | 100.0% | 100.0% | 100.0% | 100.0% | 100.0% |
| R19.15.9 | Cow Fecal | 100.0% | 100.0% | 64.9% | 37.6% | 94.2% |
| R19.16.9 | Cow Fecal | 100.0% | 100.0% | 66.8% | 35.9% | 84.6% |
| R19.17.2 | Cow Fecal | 15.4% | 16.9% | 28.9% | 17.9% | 20.4% |
| R19.17.8 | Cow Fecal | 56.5% | 22.4% | 48.5% | 23.7% | 29.3% |
| R19.18.1 | Cow Fecal | 100.0% | 100.0% | 100.0% | 100.0% | 100.0% |
| R19.23.3 | Cow Fecal | 100.0% | 100.0% | 100.0% | 100.0% | 100.0% |
| R19.23.4 | Cow Fecal | 100.0% | 100.0% | 41.8% | 100.0% | 100.0% |
| R19.23.8 | Cow Fecal | 62.1% | 87.2% | 68.5% | 38.9% | 52.1% |
| R19.24.1 | Cow Fecal | 97.5% | 100.0% | 83.0% | 100.0% | 100.0% |
| R19.24.2 | Cow Fecal | 84.7% | 15.9% | 64.0% | 83.2% | 74.1% |
| R19.26.2 | Cow Fecal | 40.1% | 85.7% | 39.6% | 102.5% | 38.8% |
| R19.27.10 | Cow Fecal | 36.7% | 100.0% | 39.8% | 41.8% | 41.6% |
| R19.27.5 | Cow Fecal | 68.6% | 100.0% | 63.2% | 45.0% | 56.8% |
| R19.27.7 | Cow Fecal | 100.0% | 70.6% | 94.0% | 100.0% | 34.7% |
| R19.28.10 | Cow Fecal | 100.0% | 100.0% | 100.0% | 100.0% | 82.1% |
| R19.28.5 | Cow Fecal | 95.7% | 47.1% | 100.0% | 80.5% | 45.7% |
| R19.28.6 | Cow Fecal | 100.0% | 100.0% | 83.8% | 85.9% | 88.5% |
| R19.29.3 | Cow Fecal | 100.0% | 100.0% | 100.0% | 100.0% | 100.0% |
| R19.29.4 | Cow Fecal | 100.0% | 100.0% | 75.2% | 81.4% | 20.3% |
| R19.29.5 | Cow Fecal | 100.0% | 100.0% | 67.5% | 51.3% | 82.7% |
| R19.29.7 | Cow Fecal | 100.0% | 100.0% | 100.0% | 100.0% | 100.0% |
| R19.29.9 | Cow Fecal | 97.9% | 54.5% | 66.5% | 36.6% | 87.9% |
| R19.3.3 | Cow Fecal | 100.0% | 100.0% | 74.0% | 99.2% | 88.6% |
| R19.30.1 | Cow Fecal | 100.0% | 100.0% | 100.0% | 100.0% | 100.0% |
| R19.30.11 | Cow Fecal | 100.0% | 100.0% | 95.0% | 89.2% | 99.0% |
| R19.30.2 | Cow Fecal | 92.5% | 94.5% | 72.2% | 84.6% | 57.6% |
| R19.30.5 | Cow Fecal | 58.7% | 16.8% | 73.6% | 64.9% | 37.5% |
| R19.30.6 | Cow Fecal | 100.0% | 100.0% | 33.7% | 83.0% | 40.0% |
| R19.31.10 | Cow Fecal | 99.9% | 72.2% | 97.9% | 61.8% | 94.1% |
| R19.31.8 | Cow Fecal | 17.4% | 49.0% | 66.3% | 50.2% | 67.6% |
| R19.34.1 | Cow Fecal | 85.0% | 100.0% | 75.4% | 93.3% | 99.1% |
| R19.35.10 | Cow Fecal | 83.9% | 76.8% | 81.1% | 52.4% | 83.3% |
| R19.35.5 | Cow Fecal | 100.0% | 100.0% | 100.0% | 100.0% | 100.0% |
| R19.35.8 | Cow Fecal | 100.0% | 100.0% | 100.0% | 100.0% | 100.0% |
| R19.35.9 | Cow Fecal | 100.0% | 55.1% | 100.0% | 91.5% | 96.5% |
| R19.36.4 | Cow Fecal | 100.0% | 100.0% | 100.0% | 100.0% | 100.0% |
| R19.36.5 | Cow Fecal | 99.4% | 90.1% | 100.0% | 100.0% | 100.0% |
| R19.37.1 | Cow Fecal | 100.0% | 100.0% | 100.0% | 100.0% | 100.0% |
| R19.37.10 | Cow Fecal | 100.0% | 100.0% | 100.0% | 100.0% | 100.0% |
| R19.37.2 | Cow Fecal | 98.0% | 100.0% | 100.0% | 23.6% | 97.9% |
| R19.37.6 | Cow Fecal | 100.0% | 100.0% | 100.0% | 100.0% | 100.0% |
| R19.38.10 | Cow Fecal | 100.0% | 100.0% | 100.0% | 100.0% | 100.0% |
| R19.38.2 | Cow Fecal | 100.0% | 100.0% | 95.2% | 16.6% | 83.6% |
| R19.38.3 | Cow Fecal | 13.4% | 0.0% | 0.0% | 0.0% | 0.0% |
| R19.38.6 | Cow Fecal | 74.8% | 65.6% | 0.0% | 97.9% | 98.5% |
| R19.38.7 | Cow Fecal | 25.2% | 1.7% | 0.0% | 0.0% | 0.0% |
| R19.39.1 | Cow Fecal | 98.9% | 100.0% | 100.0% | 100.0% | 101.3% |
| R19.39.10 | Cow Fecal | 100.0% | 100.0% | 100.0% | 100.0% | 100.0% |
| R19.39.7 | Cow Fecal | 99.1% | 24.3% | 87.5% | 76.3% | 26.4% |
| R19.39.9 | Cow Fecal | 100.0% | 100.0% | 100.0% | 100.0% | 100.0% |
| R19.40. | Cow Fecal | 100.0% | 100.0% | 100.0% | 100.0% | 100.0% |
| R19.40.1 | Cow Fecal | 100.0% | 100.0% | 100.0% | 100.0% | 100.0% |
| R19.40.10 | Cow Fecal | 27.8% | 49.9% | 33.9% | 29.1% | 8.6% |
| R19.40.4 | Cow Fecal | 100.0% | 100.0% | 100.0% | 100.0% | 100.0% |
| R19.40.7 | Cow Fecal | 100.0% | 100.0% | 100.0% | 100.0% | 100.0% |
| R19.41.10 | Cow Fecal | 74.9% | 47.9% | 51.2% | 45.9% | 51.3% |
| R19.41.7 | Cow Fecal | 96.7% | 97.0% | 86.6% | 88.1% | 100.0% |
| R19.41.8 | Cow Fecal | 100.0% | 100.0% | 100.0% | 100.0% | 100.0% |
| R19.42.3 | Cow Fecal | 100.0% | 100.0% | 100.0% | 100.0% | 100.0% |
| R19.42.6 | Cow Fecal | 100.0% | 100.0% | 100.0% | 100.0% | 100.0% |
| R19.43.2 | Cow Fecal | 62.2% | 58.2% | 58.8% | 51.3% | 58.7% |
| R19.44.6 | Cow Fecal | 0.0% | 0.0% | 0.0% | 0.0% | 0.0% |
| R19.46.10 | Cow Fecal | 72.6% | 81.3% | 26.0% | 43.6% | 54.8% |
| R19.46.2 | Cow Fecal | 100.0% | 100.0% | 100.0% | 100.0% | 100.0% |
| R19.46.4 | Cow Fecal | 100.0% | 100.0% | 100.0% | 100.0% | 100.0% |
| R19.47.10 | Cow Fecal | 100.0% | 100.0% | 100.0% | 100.0% | 100.0% |
| R19.47.2 | Cow Fecal | 100.0% | 100.0% | 85.5% | 100.0% | 100.0% |
| R19.47.3 | Cow Fecal | 34.3% | 25.2% | 15.0% | 16.1% | 17.5% |
| R19.47.5 | Cow Fecal | 100.0% | 100.0% | 100.0% | 100.0% | 100.0% |
| R19.48.3 | Cow Fecal | 0.0% | 100.0% | 100.0% | 100.0% | 97.4% |
| R19.48.5 | Cow Fecal | 100.0% | 100.0% | 100.0% | 100.0% | 100.0% |
| R19.48.8 | Cow Fecal | 100.0% | 73.9% | 55.9% | 31.1% | 57.3% |
| R19.49.10 | Cow Fecal | 100.0% | 100.0% | 100.0% | 100.0% | 100.0% |
| R19.49.3 | Cow Fecal | 100.0% | 100.0% | 100.0% | 100.0% | 100.0% |
| R19.49.4 | Cow Fecal | 48.6% | 71.9% | 3.8% | 18.3% | 81.0% |
| R19.49.5 | Cow Fecal | 0.0% | 0.0% | 0.0% | 0.0% | 0.0% |
| R19.49.6 | Cow Fecal | 100.0% | 19.4% | 47.3% | 43.3% | 45.4% |
| R19.49.9 | Cow Fecal | 36.3% | 26.8% | 26.9% | 20.4% | 22.5% |
| R19.5.6 | Cow Fecal | 99.5% | 46.7% | 0.0% | 19.5% | 41.9% |
| R19.50.2 | Cow Fecal | 100.0% | 100.0% | 100.0% | 100.0% | 100.0% |
| R19.50.4 | Cow Fecal | 100.0% | 100.0% | 100.0% | 100.0% | 100.0% |
| R19.51.1 | Cow Fecal | 100.0% | 100.0% | 100.0% | 100.0% | 100.0% |
| R19.51.3 | Cow Fecal | 100.0% | 100.0% | 100.0% | 100.0% | 100.0% |
| R19.52.2 | Cow Fecal | 85.1% | 99.2% | 48.4% | 22.7% | 76.8% |
| R19.52.3 | Cow Fecal | 100.0% | 100.0% | 100.0% | 97.7% | 100.0% |
| R19.52.5 | Cow Fecal | 100.0% | 100.0% | 100.0% | 100.0% | 100.0% |
| R19.52.9 | Cow Fecal | 76.3% | 48.6% | 49.3% | 40.5% | 26.7% |
| R19.53.1 | Cow Fecal | 100.0% | 100.0% | 100.0% | 100.0% | 97.4% |
| R19.53.10 | Cow Fecal | 99.9% | 99.1% | 70.9% | 41.9% | 93.8% |
| R19.53.8 | Cow Fecal | 65.0% | 80.7% | 58.9% | 32.0% | 43.2% |
| R19.54.1 | Cow Fecal | 46.6% | 27.2% | 20.8% | 33.4% | 3.5% |
| R19.54.7 | Cow Fecal | 55.0% | 0.0% | 0.0% | 10.8% | 0.0% |
| R19.55.2 | Cow Fecal | 79.5% | 36.8% | 38.1% | 39.4% | 34.8% |
| R19.55.8 | Cow Fecal | 47.7% | 51.4% | 51.1% | 46.5% | 27.7% |
| R19.56.10 | Cow Fecal | 100.0% | 100.0% | 100.0% | 100.0% | 100.0% |
| R19.56.4 | Cow Fecal | 100.0% | 100.0% | 100.0% | 100.0% | 100.0% |
| R19.56.7 | Cow Fecal | 70.7% | 92.4% | 61.7% | 70.6% | 60.3% |
| R19.57.10 | Cow Fecal | 27.0% | 29.6% | 24.2% | 24.2% | 22.7% |
| R19.57.2 | Cow Fecal | 62.9% | 89.2% | 79.5% | 76.9% | 77.6% |
| R19.57.5 | Cow Fecal | 76.2% | 75.0% | 0.0% | 64.8% | 29.8% |
| R19.58.10 | Cow Fecal | 53.7% | 49.4% | 35.5% | 26.8% | 46.1% |
| R19.58.7 | Cow Fecal | 100.0% | 100.0% | 100.0% | 100.0% | 100.0% |
| R19.58.8 | Cow Fecal | 100.0% | 100.0% | 100.0% | 100.0% | 100.0% |
| R19.59.7 | Cow Fecal | 76.5% | 50.1% | 45.9% | 28.1% | 22.8% |
| R19.59.9 | Cow Fecal | 73.2% | 58.9% | 50.9% | 29.4% | 55.6% |
| R19.60.10 | Cow Fecal | 100.0% | 100.0% | 100.0% | 100.0% | 100.0% |
| R19.60.12 | Cow Fecal | 100.0% | 100.0% | 100.0% | 100.0% | 100.0% |
| R19.60.14 | Cow Fecal | 100.0% | 100.0% | 78.8% | 56.2% | 67.2% |
| R19.62.4 | Cow Fecal | 31.9% | 27.3% | 30.6% | 32.3% | 27.2% |
| R19.62.7 | Cow Fecal | 37.0% | 37.2% | 25.8% | 50.1% | 10.8% |
| R19.62.9 | Cow Fecal | 100.0% | 83.1% | 38.2% | 27.1% | 58.4% |
| R19.63.3 | Cow Fecal | 67.2% | 75.3% | 54.6% | 39.5% | 45.6% |
| R19.63.4 | Cow Fecal | 100.0% | 100.0% | 100.0% | 100.0% | 100.0% |
| R19.63.7 | Cow Fecal | 100.0% | 100.0% | 100.0% | 100.0% | 100.0% |
| R19.64.3 | Cow Fecal | 98.0% | 94.0% | 10.5% | 10.2% | 31.8% |
| R19.65.1 | Cow Fecal | 14.0% | 2.2% | 20.6% | 0.0% | 30.3% |
| R19.65.10 | Cow Fecal | 100.0% | 100.0% | 100.0% | 100.0% | 100.0% |
| R19.65.2 | Cow Fecal | 47.9% | 45.7% | 48.6% | 45.0% | 46.0% |
| R19.65.5 | Cow Fecal | 31.4% | 31.0% | 32.9% | 32.0% | 31.7% |

TABLE 11-continued

Bacteriocin assay results displaying each isolate tested and the source of that isolate, isolated from Texas fecal samples. Inhibition was calculated based on the percent of growth for each treatment well compared to the positive control.

| | | Bacillus strains | | | | |
|---|---|---|---|---|---|---|
| Isolate ID | Sample | 747 | 1104 | 1541 | 1781 | 2018 |
| R19.65.6 | Cow Fecal | 100.0% | 100.0% | 100.0% | 100.0% | 100.0% |
| R19.66.10 | Cow Fecal | 100.0% | 100.0% | 100.0% | 100.0% | 100.0% |
| R19.66.8 | Cow Fecal | 88.9% | 71.0% | 69.4% | 92.5% | 85.4% |
| R19.7.9 | Cow Fecal | 100.0% | 76.1% | 93.9% | 100.0% | 59.8% |
| R19.70.6 | Cow Fecal | 54.5% | 48.2% | 58.9% | 53.6% | 53.6% |
| R19.70.8 | Cow Fecal | 91.2% | 93.6% | 55.3% | 2.8% | 33.3% |
| R19.9.3 | Cow Fecal | 100.0% | 100.0% | 100.0% | 100.0% | 100.0% |
| R19.9.9 | Cow Fecal | 100.0% | 67.2% | 49.8% | 24.2% | 75.9% |
| R23.10.4 | Cow Fecal | 100.0% | 3.1% | 99.8% | 97.2% | 99.6% |
| R23.10.8 | Cow Fecal | 99.7% | 99.6% | 99.5% | 99.7% | 99.6% |
| R23.11.2 | Cow Fecal | 59.6% | 0.0% | 1.3% | 17.6% | 40.7% |
| R23.11.9 | Cow Fecal | 77.5% | 10.2% | 2.3% | 61.1% | 65.0% |
| R23.12.2 | Cow Fecal | 0.8% | 0.0% | 0.0% | 14.1% | 10.5% |
| R23.13.1 | Cow Fecal | 99.9% | 99.7% | 99.4% | 99.7% | 99.7% |
| R23.14.5 | Cow Fecal | 74.5% | 75.2% | 71.4% | 75.2% | 75.2% |
| R23.15.1 | Cow Fecal | 16.8% | 79.5% | 94.5% | 94.9% | 57.3% |
| R23.15.10 | Cow Fecal | 99.8% | 100.0% | 100.0% | 99.5% | 99.6% |
| R23.17.5 | Cow Fecal | 96.7% | 97.8% | 99.2% | 97.3% | 98.0% |
| R23.18.2 | Cow Fecal | 88.9% | 100.5% | 100.5% | 99.8% | 100.5% |
| R23.18.5 | Cow Fecal | 99.8% | 99.8% | 99.7% | 99.7% | 99.7% |
| R23.18.9 | Cow Fecal | 99.6% | 51.7% | 99.2% | 82.1% | 99.4% |
| R23.22.9 | Cow Fecal | 99.1% | 99.4% | 99.1% | 98.9% | 99.1% |
| R23.23.8 | Cow Fecal | 99.3% | 99.1% | 98.9% | 99.1% | 99.1% |
| R23.24.1 | Cow Fecal | 99.1% | 99.1% | 98.9% | 99.3% | 99.3% |
| R23.24.3 | Cow Fecal | 99.0% | 99.3% | 98.8% | 99.3% | 99.3% |
| R23.25.3 | Cow Fecal | 95.0% | 94.7% | 81.1% | 95.7% | 94.4% |
| R23.28.6 | Cow Fecal | 99.7% | 100.0% | 51.8% | 97.4% | 99.8% |
| R23.28.8 | Cow Fecal | 98.0% | 97.9% | 94.6% | 97.7% | 97.6% |
| R23.3.5 | Cow Fecal | 89.1% | 0.0% | 0.0% | 80.1% | 11.9% |
| R23.31.6 | Cow Fecal | 99.4% | 99.6% | 99.6% | 99.0% | 99.6% |
| R23.32.1 | Cow Fecal | 99.6% | 73.2% | 98.4% | 99.3% | 99.3% |
| R23.32.5 | Cow Fecal | 24.3% | 5.7% | 47.1% | 11.7% | 2.7% |
| R23.32.6 | Cow Fecal | 95.8% | 92.1% | 92.7% | 92.9% | 97.3% |
| R23.33.5 | Cow Fecal | 99.7% | 100.0% | 99.3% | 99.9% | 99.1% |
| R23.34.4 | Cow Fecal | 99.6% | 90.2% | 99.6% | 22.8% | 99.7% |
| R23.35.1 | Cow Fecal | 99.0% | 99.4% | 99.1% | 99.4% | 99.4% |
| R23.35.10 | Cow Fecal | 99.4% | 99.2% | 82.9% | 99.7% | 99.1% |
| R23.35.4 | Cow Fecal | 99.4% | 99.7% | 99.1% | 99.7% | 99.3% |
| R23.35.8 | Cow Fecal | 99.5% | 99.9% | 98.5% | 98.6% | 99.2% |
| R23.36.1 | Cow Fecal | 22.1% | 25.3% | 63.2% | 0.0% | 69.5% |
| R23.36.3 | Cow Fecal | 99.2% | 100.1% | 97.5% | 99.7% | 99.4% |
| R23.36.4 | Cow Fecal | 99.5% | 100.0% | 98.1% | 0.0% | 99.3% |
| R23.36.6 | Cow Fecal | 97.7% | 99.6% | 98.3% | 97.5% | 99.0% |
| R23.39.7 | Cow Fecal | 99.5% | 99.6% | 99.5% | 99.8% | 99.8% |
| R23.4.7 | Cow Fecal | 99.7% | 99.8% | 99.6% | 99.5% | 99.6% |
| R23.40.6 | Cow Fecal | 99.6% | 99.9% | 12.5% | 99.6% | 99.4% |
| R23.41.10 | Cow Fecal | 91.8% | 30.9% | 14.5% | 92.9% | 86.6% |
| R23.42.8 | Cow Fecal | 68.1% | 0.0% | 0.0% | 44.1% | 13.6% |
| R23.44.10 | Cow Fecal | 99.5% | 100.0% | 99.7% | 98.1% | 99.7% |
| R23.44.4 | Cow Fecal | 94.8% | 19.5% | 95.1% | 91.2% | 0.0% |
| R23.44.6 | Cow Fecal | 99.9% | 97.2% | 98.2% | 96.9% | 98.1% |
| R23.44.8 | Cow Fecal | 95.0% | 84.5% | 84.5% | 95.9% | 96.3% |
| R23.45.2 | Cow Fecal | 76.8% | 76.8% | 87.1% | 76.8% | 84.9% |
| R23.45.9 | Cow Fecal | 99.3% | 100.0% | 99.6% | 98.1% | 98.8% |
| R23.48.3 | Cow Fecal | 97.5% | 91.6% | 86.4% | 94.4% | 92.4% |
| R23.48.6 | Cow Fecal | 7.6% | 10.9% | 0.0% | 0.0% | 20.6% |
| R23.49.1 | Cow Fecal | 95.1% | 97.9% | 95.3% | 96.9% | 98.3% |
| R23.49.4 | Cow Fecal | 98.5% | 94.7% | 93.0% | 96.0% | 97.0% |
| R23.49.5 | Cow Fecal | 82.0% | 99.8% | 84.4% | 99.9% | 51.2% |
| R23.5.5 | Cow Fecal | 86.0% | 76.4% | 95.1% | 85.5% | 93.1% |
| R23.50.3 | Cow Fecal | 96.5% | 97.6% | 98.5% | 97.2% | 97.8% |
| R23.51.1 | Cow Fecal | 99.5% | 99.1% | 95.1% | 97.9% | 99.0% |
| R23.51.10 | Cow Fecal | 27.5% | 0.0% | 100.0% | 14.7% | 24.6% |
| R23.51.8 | Cow Fecal | 99.8% | 95.4% | 87.4% | 96.6% | 98.9% |
| R23.52.3 | Cow Fecal | 87.7% | 74.5% | 77.2% | 80.0% | 87.1% |
| R23.53.8 | Cow Fecal | 6.3% | 0.0% | 0.0% | 0.0% | 23.8% |
| R23.56.5 | Cow Fecal | 64.8% | 99.8% | 81.8% | 0.0% | 10.9% |
| R23.56.9 | Cow Fecal | 99.5% | 76.2% | 45.0% | 21.2% | 93.3% |
| R23.57.1 | Cow Fecal | 0.0% | 0.0% | 0.0% | 0.0% | 12.9% |
| R23.58.2 | Cow Fecal | 100.0% | 0.0% | 99.9% | 99.8% | 99.8% |
| R23.60.3 | Cow Fecal | 55.3% | 86.6% | 99.2% | 81.0% | 90.5% |
| R23.61.1 | Cow Fecal | 1.9% | 0.0% | 99.6% | 99.6% | 0.0% |
| R23.61.3 | Cow Fecal | 99.8% | 99.8% | 100.0% | 99.7% | 99.3% |
| R23.64.7 | Cow Fecal | 0.0% | 0.0% | 4.1% | 0.0% | 23.7% |
| R23.66.2 | Cow Fecal | 100.0% | 100.0% | 100.0% | 100.0% | 100.0% |
| R23.66.7 | Cow Fecal | 15.6% | 0.0% | 69.1% | 21.0% | 36.3% |
| R23.66.8 | Cow Fecal | 100.0% | 100.0% | 100.0% | 100.0% | 100.0% |
| R23.67.9 | Cow Fecal | 28.1% | 0.0% | 38.9% | 24.1% | 33.8% |
| R23.68.10 | Cow Fecal | 96.8% | 96.8% | 96.8% | 96.8% | 96.8% |
| R23.8.8 | Cow Fecal | 99.4% | 99.4% | 99.1% | 99.3% | 99.5% |
| R23.9.7 | Cow Fecal | 99.3% | 99.5% | 99.3% | 99.4% | 99.1% |
| R24.1.1 | Cow Fecal | 100.0% | 100.0% | 100.0% | 100.0% | 100.0% |
| R24.1.6 | Cow Fecal | 99.8% | 100.0% | 100.0% | 100.0% | 99.9% |
| R24.10.1 | Cow Fecal | 69.8% | 71.1% | 64.4% | 62.2% | 69.6% |
| R24.10.10 | Cow Fecal | 66.9% | 68.0% | 67.6% | 67.8% | 71.3% |
| R24.10.2 | Cow Fecal | 94.8% | 61.1% | 75.0% | 99.9% | 81.3% |
| R24.10.7 | Cow Fecal | 99.5% | 99.2% | 98.8% | 99.5% | 97.7% |
| R24.11.5 | Cow Fecal | 100.0% | 100.0% | 100.0% | 99.9% | 99.9% |
| R24.11.6 | Cow Fecal | 99.7% | 99.9% | 99.7% | 99.5% | 99.3% |
| R24.12.9 | Cow Fecal | 100.0% | 100.0% | 100.0% | 100.0% | 100.0% |
| R24.13.1 | Cow Fecal | 86.1% | 93.7% | 100.0% | 91.9% | 94.0% |
| R24.13.4 | Cow Fecal | 75.8% | 77.8% | 76.2% | 82.7% | 85.9% |
| R24.13.6 | Cow Fecal | 99.7% | 100.0% | 99.7% | 99.9% | 99.2% |
| R24.13.7 | Cow Fecal | 99.8% | 99.9% | 99.9% | 99.9% | 99.7% |
| R24.13.8 | Cow Fecal | 90.6% | 96.9% | 94.4% | 91.5% | 94.2% |
| R24.13.9 | Cow Fecal | 98.0% | 97.9% | 97.9% | 99.4% | 98.9% |
| R24.14.3 | Cow Fecal | 95.6% | 93.3% | 90.3% | 90.6% | 94.8% |
| R24.14.7 | Cow Fecal | 95.8% | 96.0% | 95.5% | 96.0% | 95.8% |
| R24.14.8 | Cow Fecal | 99.0% | 99.6% | 99.2% | 99.7% | 95.4% |
| R24.14.9 | Cow Fecal | 100.0% | 100.0% | 100.0% | 99.8% | 99.8% |
| R24.15.1 | Cow Fecal | 25.9% | 0.0% | 51.3% | 89.5% | 45.2% |
| R24.15.10 | Cow Fecal | 93.4% | 97.0% | 99.5% | 97.8% | 96.0% |
| R24.15.2 | Cow Fecal | 100.0% | 99.6% | 99.9% | 99.9% | 99.4% |
| R24.15.4 | Cow Fecal | 89.7% | 72.1% | 91.0% | 76.4% | 99.4% |
| R24.15.6 | Cow Fecal | 99.7% | 99.9% | 99.6% | 99.6% | 98.2% |
| R24.15.7 | Cow Fecal | 0.0% | 0.0% | 0.0% | 0.0% | 0.0% |
| R24.15.8 | Cow Fecal | 100.0% | 100.0% | 100.0% | 100.0% | 100.0% |
| R24.16.3 | Cow Fecal | 82.1% | 13.6% | 18.2% | 43.3% | 41.9% |
| R24.16.6 | Cow Fecal | 99.3% | 99.5% | 6.7% | 99.5% | 71.1% |
| R24.16.7 | Cow Fecal | 100.0% | 100.0% | 93.6% | 100.0% | 92.2% |
| R24.17.1 | Cow Fecal | 99.9% | 99.9% | 100.0% | 99.9% | 99.9% |
| R24.17.2 | Cow Fecal | 87.4% | 97.2% | 89.4% | 0.0% | 91.7% |
| R24.17.4 | Cow Fecal | 100.0% | 100.0% | 93.1% | 100.0% | 99.9% |
| R24.17.6 | Cow Fecal | 99.8% | 99.9% | 99.6% | 99.8% | 99.2% |
| R24.17.7 | Cow Fecal | 86.5% | 88.7% | 77.0% | 93.1% | 84.9% |
| R24.18.5 | Cow Fecal | 100.0% | 100.0% | 100.0% | 100.0% | 99.9% |
| R24.18.9 | Cow Fecal | 100.0% | 100.0% | 100.0% | 100.0% | 100.0% |
| R24.19.1 | Cow Fecal | 99.3% | 99.0% | 0.0% | 99.0% | 17.1% |
| R24.19.2 | Cow Fecal | 99.2% | 99.0% | 98.8% | 99.0% | 99.0% |
| R24.19.3 | Cow Fecal | 99.8% | 99.7% | 99.7% | 99.8% | 99.5% |
| R24.19.7 | Cow Fecal | 100.0% | 99.8% | 86.4% | 99.8% | 83.8% |
| R24.2.2 | Cow Fecal | 99.4% | 99.9% | 99.7% | 99.7% | 99.7% |
| R24.2.3 | Cow Fecal | 99.9% | 100.0% | 100.0% | 100.0% | 100.0% |
| R24.2.7 | Cow Fecal | 99.6% | 99.6% | 99.6% | 99.6% | 99.0% |
| R24.21.2 | Cow Fecal | 83.4% | 36.2% | 60.2% | 91.5% | 59.2% |
| R24.21.6 | Cow Fecal | 100.0% | 93.9% | 80.3% | 100.0% | 97.7% |
| R24.22.2 | Cow Fecal | 100.0% | 100.0% | 100.0% | 99.8% | 100.0% |
| R24.22.4 | Cow Fecal | 100.0% | 100.0% | 100.0% | 100.0% | 99.7% |
| R24.22.5 | Cow Fecal | 98.8% | 99.0% | 69.2% | 98.8% | 72.8% |
| R24.23.2 | Cow Fecal | 99.0% | 100.0% | 97.8% | 100.0% | 99.6% |
| R24.23.8 | Cow Fecal | 99.5% | 99.9% | 99.7% | 98.7% | 99.7% |
| R24.23.9 | Cow Fecal | 99.9% | 99.5% | 99.6% | 99.8% | 99.3% |
| R24.25.1 | Cow Fecal | 99.8% | 99.5% | 99.2% | 99.6% | 96.7% |
| R24.27.10 | Cow Fecal | 99.9% | 100.0% | 99.8% | 99.9% | 99.6% |
| R24.27.5 | Cow Fecal | 99.9% | 99.6% | 99.8% | 99.9% | 99.6% |
| R24.27.7 | Cow Fecal | 99.7% | 99.8% | 100.0% | 99.6% | 99.8% |
| R24.27.9 | Cow Fecal | 100.0% | 99.8% | 99.9% | 99.8% | 99.8% |
| R24.28.10 | Cow Fecal | 90.2% | 100.0% | 100.0% | 98.0% | 99.0% |
| R24.28.6 | Cow Fecal | 100.0% | 100.0% | 100.0% | 100.0% | 99.1% |
| R24.28.8 | Cow Fecal | 100.0% | 100.0% | 99.9% | 99.8% | 99.0% |
| R24.3.1 | Cow Fecal | 98.6% | 99.3% | 98.9% | 99.2% | 99.0% |
| R24.3.5 | Cow Fecal | 99.7% | 100.0% | 99.9% | 99.8% | 99.7% |

TABLE 11-continued

Bacteriocin assay results displaying each isolate tested and the source of that isolate, isolated from Texas fecal samples. Inhibition was calculated based on the percent of growth for each treatment well compared to the positive control.

| | | Bacillus strains | | | | |
|---|---|---|---|---|---|---|
| Isolate ID | Sample | 747 | 1104 | 1541 | 1781 | 2018 |
| R24.3.6 | Cow Fecal | 99.4% | 100.0% | 93.3% | 99.4% | 88.4% |
| R24.31.1 | Cow Fecal | 100.0% | 100.0% | 100.0% | 100.0% | 99.6% |
| R24.31.9 | Cow Fecal | 88.7% | 88.7% | 71.1% | 75.8% | 71.7% |
| R24.32.8 | Cow Fecal | 98.7% | 98.2% | 96.8% | 97.3% | 93.0% |
| R24.33.1 | Cow Fecal | 99.7% | 99.9% | 99.9% | 99.8% | 99.8% |
| R24.34.5 | Cow Fecal | 97.6% | 94.1% | 0.0% | 95.9% | 77.2% |
| R24.35.2 | Cow Fecal | 99.9% | 100.0% | 100.0% | 100.0% | 99.9% |
| R24.36.8 | Cow Fecal | 100.0% | 100.0% | 100.0% | 100.0% | 100.0% |
| R24.37.8 | Cow Fecal | 100.0% | 100.0% | 100.0% | 100.0% | 100.0% |
| R24.38.3 | Cow Fecal | 90.3% | 92.8% | 0.0% | 92.8% | 29.2% |
| R24.39.1 | Cow Fecal | 72.3% | 0.0% | 0.0% | 0.0% | 0.0% |
| R24.39.10 | Cow Fecal | 100.2% | 100.2% | 99.0% | 100.2% | 99.9% |
| R24.39.3 | Cow Fecal | 99.6% | 100.0% | 100.0% | 99.8% | 99.6% |
| R24.39.5 | Cow Fecal | 83.1% | 0.0% | 100.0% | 17.4% | 99.9% |
| R24.39.7 | Cow Fecal | 52.1% | 52.4% | 57.5% | 59.9% | 53.4% |
| R24.4.10 | Cow Fecal | 100.0% | 98.8% | 96.9% | 98.9% | 99.5% |
| R24.40.10 | Cow Fecal | 99.4% | 56.7% | 55.1% | 100.0% | 93.7% |
| R24.40.5 | Cow Fecal | 100.0% | 99.8% | 100.0% | 100.0% | 99.8% |
| R24.41.4 | Cow Fecal | 99.9% | 100.0% | 99.9% | 100.0% | 99.8% |
| R24.42.1 | Cow Fecal | 100.0% | 99.9% | 99.5% | 99.9% | 98.9% |
| R24.42.5 | Cow Fecal | 100.0% | 99.9% | 24.3% | 100.0% | 98.8% |
| R24.44.1 | Cow Fecal | 99.9% | 99.9% | 99.5% | 99.9% | 100.0% |
| R24.44.8 | Cow Fecal | 100.0% | 100.0% | 100.0% | 100.0% | 100.0% |
| R24.47.5 | Cow Fecal | 99.9% | 99.9% | 92.8% | 99.9% | 99.7% |
| R24.47.8 | Cow Fecal | 99.6% | 99.2% | 99.5% | 99.5% | 97.7% |
| R24.48.1 | Cow Fecal | 99.0% | 98.6% | 99.0% | 98.6% | 98.8% |
| R24.5.1 | Cow Fecal | 99.8% | 100.0% | 100.0% | 99.6% | 99.6% |
| R24.5.8 | Cow Fecal | 99.5% | 99.5% | 100.0% | 99.5% | 98.0% |
| R24.50.6 | Cow Fecal | 98.7% | 91.4% | 75.3% | 99.0% | 88.5% |
| R24.51.5 | Cow Fecal | 99.6% | 99.4% | 99.3% | 99.4% | 98.8% |
| R24.52.10 | Cow Fecal | 98.4% | 100.0% | 97.1% | 100.0% | 100.0% |
| R24.52.4 | Cow Fecal | 99.4% | 99.1% | 42.8% | 99.4% | 94.7% |
| R24.52.6 | Cow Fecal | 60.5% | 47.9% | 48.9% | 58.5% | 55.7% |
| R24.52.7 | Cow Fecal | 83.8% | 84.3% | 81.3% | 77.9% | 81.0% |
| R24.52.9 | Cow Fecal | 97.1% | 99.9% | 100.0% | 99.9% | 99.9% |
| R24.53.1 | Cow Fecal | 99.7% | 99.6% | 99.3% | 99.8% | 84.6% |
| R24.54.10 | Cow Fecal | 100.0% | 100.0% | 100.0% | 100.0% | 100.0% |
| R24.55.1 | Cow Fecal | 100.0% | 100.0% | 100.0% | 100.0% | 100.0% |
| R24.55.2 | Cow Fecal | 100.0% | 100.0% | 100.0% | 100.0% | 100.0% |
| R24.59.2 | Cow Fecal | 100.0% | 96.7% | 45.3% | 100.0% | 83.8% |
| R24.59.6 | Cow Fecal | 99.5% | 47.3% | 5.5% | 100.0% | 60.8% |
| R24.6.3 | Cow Fecal | 99.6% | 99.6% | 99.4% | 99.8% | 96.7% |
| R24.6.5 | Cow Fecal | 100.0% | 15.9% | 0.0% | 100.0% | 15.5% |
| R24.6.9 | Cow Fecal | 100.0% | 100.0% | 100.0% | 100.0% | 99.8% |
| R24.64.2 | Cow Fecal | 99.8% | 99.7% | 99.6% | 99.7% | 97.8% |
| R24.65.7 | Cow Fecal | 100.0% | 86.2% | 96.4% | 100.0% | 100.0% |
| R24.65.9 | Cow Fecal | 100.0% | 100.0% | 100.0% | 100.0% | 100.0% |
| R24.66.3 | Cow Fecal | 100.0% | 99.6% | 100.0% | 85.9% | 100.0% |
| R24.66.4 | Cow Fecal | 52.4% | 54.2% | 49.8% | 53.9% | 54.9% |
| R24.66.5 | Cow Fecal | 99.6% | 99.4% | 81.1% | 99.6% | 99.5% |
| R24.66.9 | Cow Fecal | 100.0% | 100.0% | 100.0% | 100.0% | 100.0% |
| R24.67.1 | Cow Fecal | 0.0% | 0.0% | 0.0% | 0.0% | 0.0% |
| R24.67.10 | Cow Fecal | 80.2% | 27.6% | 0.0% | 15.6% | 64.5% |
| R24.7.10 | Cow Fecal | 75.8% | 72.0% | 77.2% | 73.2% | 85.5% |
| R24.7.9 | Cow Fecal | 0.0% | 8.4% | 0.0% | 0.0% | 0.0% |
| R24.70.3 | Cow Fecal | 97.6% | 98.5% | 85.7% | 92.0% | 96.7% |
| R24.71.5 | Cow Fecal | 99.8% | 100.0% | 100.0% | 99.4% | 99.4% |
| R24.71.6 | Cow Fecal | 99.8% | 99.6% | 99.5% | 99.9% | 99.0% |
| R24.72.3 | Cow Fecal | 100.0% | 100.0% | 100.0% | 100.0% | 100.0% |
| R24.72.4 | Cow Fecal | 99.9% | 100.0% | 100.0% | 99.9% | 100.0% |
| R24.72.8 | Cow Fecal | 100.0% | 100.0% | 100.0% | 100.0% | 99.9% |
| R24.73.1 | Cow Fecal | 100.0% | 82.8% | 99.9% | 99.9% | 99.9% |
| R24.73.2 | Cow Fecal | 99.7% | 99.7% | 100.0% | 99.1% | 99.9% |
| R24.73.3 | Cow Fecal | 100.0% | 100.0% | 100.0% | 100.0% | 100.0% |
| R24.73.6 | Cow Fecal | 99.7% | 99.9% | 99.7% | 99.6% | 99.7% |
| R24.73.7 | Cow Fecal | 25.0% | 10.1% | 16.2% | 22.1% | 24.3% |
| R24.73.8 | Cow Fecal | 99.4% | 99.8% | 99.6% | 99.6% | 99.6% |
| R24.73.9 | Cow Fecal | 100.0% | 100.0% | 100.0% | 99.4% | 100.0% |
| R24.74.10 | Cow Fecal | 98.8% | 99.1% | 83.5% | 99.0% | 97.7% |
| R24.74.5 | Cow Fecal | 92.8% | 65.4% | 72.1% | 75.8% | 82.9% |
| R24.75.8 | Cow Fecal | 78.7% | 88.0% | 70.8% | 73.9% | 66.1% |
| R24.76.3 | Cow Fecal | 99.7% | 99.9% | 100.0% | 99.7% | 99.9% |
| R24.78.8 | Cow Fecal | 99.3% | 99.3% | 84.6% | 99.3% | 99.3% |
| R24.80.10 | Cow Fecal | 100.0% | 100.0% | 99.9% | 98.9% | 99.9% |
| R24.81.3 | Cow Fecal | 99.6% | 99.8% | 98.0% | 99.7% | 99.3% |
| R24.81.4 | Cow Fecal | 100.0% | 100.0% | 100.0% | 100.0% | 100.0% |
| R24.81.6 | Cow Fecal | 100.0% | 100.0% | 100.0% | 100.0% | 99.9% |
| R24.81.9 | Cow Fecal | 99.7% | 99.1% | 93.1% | 99.5% | 99.3% |
| R24.82.10 | Cow Fecal | 99.5% | 99.3% | 84.7% | 99.7% | 98.8% |
| R24.82.5 | Cow Fecal | 99.9% | 99.7% | 36.8% | 99.8% | 99.0% |
| R24.82.7 | Cow Fecal | 98.2% | 98.7% | 59.4% | 98.6% | 96.7% |
| R24.82.8 | Cow Fecal | 100.0% | 100.0% | 100.0% | 100.0% | 100.0% |
| R24.9.10 | Cow Fecal | 99.4% | 99.9% | 99.1% | 99.3% | 98.2% |
| R25.10.3 | Calf Fecal | 99.9% | 100.0% | 99.2% | 99.9% | 99.9% |
| R25.10.5 | Calf Fecal | 99.8% | 100.0% | 99.6% | 99.9% | 99.8% |
| R25.10.6 | Calf Fecal | 99.9% | 100.0% | 100.0% | 100.0% | 100.0% |
| R25.10.7 | Calf Fecal | 100.0% | 100.0% | 99.5% | 100.0% | 99.9% |
| R25.14.4 | Calf Fecal | 96.9% | 76.8% | 35.5% | 89.5% | 80.6% |
| R25.16.1 | Cow Fecal | 84.6% | 79.0% | 70.8% | 83.9% | 69.0% |
| R25.16.8 | Cow Fecal | 99.5% | 100.0% | 99.8% | 100.0% | 100.0% |
| R25.17.2 | Cow Fecal | 99.8% | 99.8% | 99.6% | 99.8% | 99.6% |
| R25.18.10 | Cow Fecal | 99.8% | 100.0% | 99.3% | 98.9% | 99.2% |
| R25.18.3 | Cow Fecal | 99.9% | 100.0% | 99.3% | 98.7% | 98.7% |
| R25.18.6 | Cow Fecal | 99.9% | 100.0% | 100.0% | 100.0% | 100.0% |
| R25.20.1 | Cow Fecal | 99.6% | 100.0% | 98.9% | 98.5% | 99.4% |
| R25.20.3 | Cow Fecal | 99.2% | 100.0% | 99.2% | 100.0% | 99.7% |
| R25.20.5 | Cow Fecal | 98.3% | 99.8% | 99.1% | 99.7% | 99.0% |
| R25.21.4 | Cow Fecal | 99.9% | 100.0% | 99.6% | 100.0% | 99.6% |
| R25.21.7 | Cow Fecal | 0.0% | 0.0% | 0.0% | 0.0% | 0.0% |
| R25.22.2 | Cow Fecal | 100.0% | 94.4% | 71.1% | 99.1% | 85.3% |
| R25.22.8 | Cow Fecal | 99.9% | 99.9% | 99.9% | 100.0% | 99.9% |
| R25.23.9 | Cow Fecal | 99.9% | 100.0% | 99.6% | 100.0% | 98.6% |
| R25.24.8 | Cow Fecal | 85.4% | 45.5% | 15.9% | 35.8% | 52.4% |
| R25.25.2 | Cow Fecal | 100.0% | 99.9% | 99.2% | 98.8% | 100.0% |
| R25.26.1 | Cow Fecal | 99.5% | 99.1% | 98.7% | 97.3% | 97.9% |
| R25.26.10 | Cow Fecal | 100.0% | 98.3% | 98.8% | 97.4% | 98.0% |
| R25.26.7 | Cow Fecal | 99.7% | 99.7% | 99.3% | 98.5% | 99.7% |
| R25.26.9 | Cow Fecal | 100.0% | 99.9% | 99.8% | 98.6% | 99.8% |
| R25.27.7 | Cow Fecal | 99.9% | 99.4% | 89.5% | 97.8% | 94.2% |
| R25.28.1 | Cow Fecal | 99.8% | 100.0% | 100.0% | 98.8% | 99.6% |
| R25.28.5 | Cow Fecal | 80.0% | 75.3% | 80.4% | 51.4% | 39.7% |
| R25.29.1 | Cow Fecal | 99.8% | 99.5% | 98.4% | 97.8% | 98.4% |
| R25.29.2 | Cow Fecal | 100.0% | 99.8% | 98.5% | 95.5% | 98.2% |
| R25.31.10 | Cow Fecal | 99.9% | 99.9% | 99.0% | 98.2% | 99.6% |
| R25.31.2 | Cow Fecal | 98.8% | 88.9% | 87.2% | 79.8% | 79.0% |
| R25.31.4 | Cow Fecal | 99.9% | 99.7% | 99.0% | 99.1% | 99.6% |
| R25.31.5 | Cow Fecal | 100.0% | 100.0% | 99.7% | 98.6% | 99.8% |
| R25.31.8 | Cow Fecal | 99.9% | 99.4% | 99.4% | 97.7% | 98.2% |
| R25.32.10 | Cow Fecal | 100.0% | 100.0% | 100.0% | 100.0% | 100.0% |
| R25.32.6 | Cow Fecal | 99.8% | 99.8% | 90.1% | 99.4% | 99.7% |
| R25.32.8 | Cow Fecal | 100.0% | 99.9% | 99.9% | 100.0% | 99.9% |
| R25.32.9 | Cow Fecal | 99.8% | 99.8% | 99.8% | 98.4% | 99.5% |
| R25.33.4 | Cow Fecal | 91.9% | 98.9% | 4.2% | 89.1% | 95.4% |
| R25.33.9 | Cow Fecal | 99.9% | 100.0% | 100.0% | 99.8% | 99.8% |
| R25.34.7 | Cow Fecal | 100.0% | 99.8% | 98.7% | 98.4% | 99.8% |
| R25.34.9 | Cow Fecal | 99.8% | 98.8% | 96.5% | 98.1% | 99.8% |
| R25.35.2 | Cow Fecal | 99.8% | 99.9% | 100.0% | 99.3% | 99.8% |
| R25.37.10 | Cow Fecal | 100.0% | 100.0% | 100.0% | 99.7% | 100.0% |
| R25.37.2 | Cow Fecal | 99.8% | 99.8% | 98.5% | 99.7% | 99.9% |
| R25.37.3 | Cow Fecal | 100.0% | 100.0% | 99.7% | 99.7% | 99.9% |
| R25.37.8 | Cow Fecal | 100.0% | 100.0% | 99.9% | 99.7% | 99.9% |
| R25.38.3 | Cow Fecal | 99.3% | 99.8% | 100.0% | 99.1% | 99.6% |
| R25.39.3 | Cow Fecal | 100.0% | 99.9% | 100.0% | 100.0% | 99.9% |
| R25.39.7 | Cow Fecal | 99.9% | 99.5% | 99.9% | 100.0% | 99.8% |
| R25.39.9 | Cow Fecal | 99.9% | 99.5% | 96.9% | 99.9% | 99.9% |
| R25.40.5 | Cow Fecal | 100.0% | 99.8% | 98.8% | 98.9% | 99.8% |
| R25.40.6 | Cow Fecal | 99.9% | 96.0% | 84.9% | 94.8% | 99.2% |
| R25.40.7 | Cow Fecal | 99.9% | 100.0% | 100.0% | 99.6% | 100.0% |
| R25.41.2 | Cow Fecal | 99.0% | 98.6% | 89.6% | 97.5% | 95.1% |
| R25.41.3 | Cow Fecal | 99.5% | 92.7% | 88.3% | 98.8% | 98.5% |
| R25.41.5 | Cow Fecal | 97.2% | 98.8% | 99.2% | 98.1% | 99.8% |
| R25.41.6 | Cow Fecal | 99.2% | 99.2% | 97.8% | 99.2% | 98.9% |

TABLE 11-continued

Bacteriocin assay results displaying each isolate tested and the source of that isolate, isolated from Texas fecal samples. Inhibition was calculated based on the percent of growth for each treatment well compared to the positive control.

| Isolate ID | Sample | Bacillus strains | | | | |
|---|---|---|---|---|---|---|
| | | 747 | 1104 | 1541 | 1781 | 2018 |
| R25.42.6 | Cow Fecal | 99.3% | 99.2% | 99.2% | 98.0% | 98.6% |
| R25.43.2 | Cow Fecal | 98.2% | 98.6% | 15.1% | 98.7% | 78.0% |
| R25.43.4 | Cow Fecal | 98.2% | 99.1% | 81.1% | 97.9% | 97.6% |
| R25.43.6 | Cow Fecal | 99.7% | 99.3% | 99.4% | 97.7% | 98.8% |
| R25.43.7 | Cow Fecal | 100.0% | 99.7% | 99.0% | 97.8% | 99.9% |
| R25.43.9 | Cow Fecal | 99.9% | 99.8% | 98.5% | 98.0% | 99.5% |
| R25.44.5 | Cow Fecal | 96.7% | 93.4% | 96.7% | 89.4% | 96.0% |
| R25.44.6 | Cow Fecal | 91.5% | 76.1% | 0.0% | 86.4% | 87.4% |
| R25.45.2 | Cow Fecal | 100.0% | 100.0% | 99.9% | 100.0% | 99.9% |
| R25.45.6 | Cow Fecal | 99.8% | 99.4% | 95.7% | 94.1% | 98.2% |
| R25.46.3 | Cow Fecal | 87.3% | 40.8% | 0.0% | 82.7% | 61.4% |
| R25.47.9 | Cow Fecal | 92.2% | 83.3% | 0.0% | 87.5% | 91.8% |
| R25.48.8 | Cow Fecal | 0.0% | 0.0% | 0.0% | 0.0% | 0.0% |
| R25.49.4 | Cow Fecal | 99.4% | 98.8% | 98.1% | 97.0% | 98.1% |
| R25.49.5 | Cow Fecal | 99.5% | 99.4% | 98.8% | 95.4% | 98.2% |
| R25.51.8 | Cow Fecal | 94.2% | 85.5% | 0.0% | 84.5% | 89.4% |
| R25.52.2 | Cow Fecal | 98.7% | 89.3% | 72.7% | 92.3% | 83.4% |
| R25.52.9 | Cow Fecal | 99.1% | 0.0% | 4.4% | 81.1% | 66.8% |
| R25.53.3 | Cow Fecal | 95.1% | 79.8% | 14.8% | 89.2% | 86.9% |
| R25.56.3 | Cow Fecal | 17.6% | 0.0% | 0.0% | 0.0% | 0.0% |
| R25.57.5 | Cow Fecal | 73.1% | 87.3% | 63.8% | 94.3% | 66.0% |
| R25.58.1 | Cow Fecal | 0.0% | 0.0% | 0.0% | 0.0% | 0.0% |
| R25.63.1 | Cow Fecal | 4.7% | 14.0% | 0.0% | 10.0% | 0.0% |
| R25.63.3 | Cow Fecal | 99.0% | 40.0% | 0.0% | 93.1% | 99.0% |
| R25.67.5 | Cow Fecal | 63.9% | 75.8% | 91.3% | 63.9% | 76.7% |
| R25.70.10 | Cow Fecal | 92.4% | 79.1% | 51.2% | 94.6% | 89.2% |
| R25.70.4 | Cow Fecal | 57.3% | 15.8% | 39.6% | 87.0% | 50.6% |
| R25.70.8 | Cow Fecal | 65.8% | 61.7% | 87.2% | 72.5% | 63.1% |
| R25.72.2 | Cow Fecal | 99.0% | 99.9% | 100.0% | 99.0% | 100.0% |
| R25.73.2 | Cow Fecal | 26.1% | 0.0% | 52.2% | 0.0% | 69.6% |
| R25.73.3 | Cow Fecal | 98.7% | 98.9% | 99.9% | 99.7% | 98.9% |
| R25.76.2 | Cow Fecal | 98.2% | 99.9% | 99.8% | 99.0% | 99.3% |
| R25.76.5 | Cow Fecal | 99.9% | 100.0% | 100.0% | 98.0% | 100.0% |
| R25.79.10 | Cow Fecal | 97.2% | 96.6% | 67.2% | 94.6% | 93.7% |
| R25.79.9 | Cow Fecal | 95.7% | 84.4% | 35.9% | 94.0% | 86.6% |
| R25.80.5 | Cow Fecal | 50.7% | 42.2% | 28.8% | 46.6% | 39.9% |
| R25.82.3 | Cow Fecal | 76.8% | 69.0% | 71.4% | 84.1% | 74.5% |
| R25.83.5 | Cow Fecal | 38.0% | 97.0% | 47.3% | 65.3% | 87.0% |
| R25.85.1 | Cow Fecal | 78.2% | 58.4% | 48.8% | 69.9% | 71.6% |
| R25.86.3 | Cow Fecal | 99.9% | 61.5% | 48.1% | 75.2% | 97.8% |
| R25.86.6 | Cow Fecal | 56.9% | 40.3% | 25.3% | 65.9% | 66.9% |
| R25.86.8 | Cow Fecal | 78.8% | 62.0% | 59.8% | 78.9% | 63.5% |
| R26.1.4 | Calf Fecal | 51.3% | 54.4% | 90.2% | 42.1% | 67.4% |
| R26.1.5 | Calf Fecal | 78.4% | 56.5% | 73.9% | 77.3% | 80.9% |
| R26.10.3 | Calf Fecal | 99.0% | 59.8% | 17.1% | 78.7% | 49.8% |
| R26.11.10 | Cow Fecal | 55.0% | 39.3% | 11.2% | 45.2% | 37.4% |
| R26.11.9 | Cow Fecal | 38.9% | 54.0% | 0.0% | 66.1% | 49.5% |
| R26.13.3 | Cow Fecal | 99.7% | 47.2% | 17.7% | 99.0% | 59.6% |
| R26.13.6 | Cow Fecal | 100.0% | 100.0% | 99.8% | 99.5% | 99.8% |
| R26.14.2 | Cow Fecal | 100.0% | 100.0% | 100.0% | 100.0% | 100.0% |
| R26.15.2 | Cow Fecal | 98.0% | 100.0% | 95.9% | 99.0% | 100.0% |
| R26.15.3 | Cow Fecal | 41.6% | 55.0% | 45.0% | 57.2% | 52.3% |
| R26.15.7 | Cow Fecal | 93.8% | 97.9% | 95.6% | 95.6% | 48.0% |
| R26.16.8 | Cow Fecal | 95.8% | 69.1% | 60.2% | 70.9% | 86.1% |
| R26.18.5 | Cow Fecal | 95.5% | 76.7% | 63.0% | 77.7% | 88.9% |
| R26.19.4 | Cow Fecal | 77.9% | 90.6% | 72.3% | 57.2% | 80.5% |
| R26.19.6 | Cow Fecal | 100.0% | 100.0% | 94.2% | 89.7% | 96.8% |
| R26.2.4 | Calf Fecal | 100.0% | 100.0% | 100.0% | 0.0% | 100.0% |
| R26.20.3 | Cow Fecal | 100.0% | 100.0% | 100.0% | 100.0% | 100.0% |
| R26.20.4 | Cow Fecal | 100.0% | 33.3% | 49.2% | 36.4% | 100.0% |
| R26.20.6 | Cow Fecal | 11.4% | 24.3% | 9.5% | 0.0% | 0.0% |
| R26.20.7 | Cow Fecal | 100.0% | 100.0% | 100.0% | 97.2% | 96.4% |
| R26.21.10 | Cow Fecal | 100.0% | 100.0% | 99.1% | 99.6% | 100.0% |
| R26.21.4 | Cow Fecal | 90.3% | 80.8% | 75.9% | 84.6% | 88.0% |
| R26.21.7 | Cow Fecal | 100.0% | 94.6% | 95.7% | 96.6% | 99.3% |
| R26.21.8 | Cow Fecal | 100.0% | 100.0% | 100.0% | 100.0% | 100.0% |
| R26.23.10 | Cow Fecal | 92.9% | 97.3% | 96.7% | 98.8% | 98.0% |
| R26.23.2 | Cow Fecal | 99.7% | 99.7% | 98.8% | 100.0% | 98.9% |
| R26.23.3 | Cow Fecal | 100.0% | 99.9% | 96.2% | 97.5% | 89.3% |
| R26.23.6 | Cow Fecal | 100.0% | 100.0% | 98.5% | 97.7% | 98.5% |
| R26.23.7 | Cow Fecal | 68.3% | 78.7% | 71.7% | 85.0% | 85.7% |
| R26.23.8 | Cow Fecal | 100.0% | 100.0% | 100.0% | 100.0% | 100.0% |
| R26.23.9 | Cow Fecal | 100.0% | 100.0% | 100.0% | 100.0% | 100.0% |
| R26.24.9 | Cow Fecal | 100.0% | 99.8% | 98.4% | 97.4% | 98.9% |
| R26.26.2 | Cow Fecal | 100.0% | 99.8% | 97.6% | 97.9% | 99.4% |
| R26.26.4 | Cow Fecal | 0.0% | 13.2% | 0.0% | 0.0% | 0.0% |
| R26.27.8 | Cow Fecal | 99.8% | 98.1% | 97.2% | 95.7% | 97.6% |
| R26.28.6 | Cow Fecal | 99.9% | 99.6% | 99.6% | 97.9% | 98.7% |
| R26.28.8 | Cow Fecal | 96.5% | 98.1% | 97.9% | 95.7% | 97.3% |
| R26.3.5 | Calf Fecal | 27.3% | 0.0% | 38.9% | 63.2% | 99.4% |
| R26.30.10 | Cow Fecal | 0.0% | 33.8% | 89.2% | 0.0% | 0.0% |
| R26.30.2 | Cow Fecal | 99.7% | 97.4% | 98.0% | 94.0% | 96.0% |
| R26.31.3 | Cow Fecal | 92.6% | 90.7% | 99.3% | 92.5% | 98.6% |
| R26.31.8 | Cow Fecal | 100.0% | 99.5% | 99.3% | 97.9% | 98.9% |
| R26.32.1 | Cow Fecal | 99.5% | 98.6% | 95.5% | 94.8% | 97.1% |
| R26.33.4 | Cow Fecal | 99.9% | 99.3% | 97.2% | 97.0% | 98.7% |
| R26.34.5 | Cow Fecal | 100.0% | 98.3% | 97.1% | 96.3% | 98.0% |
| R26.35.5 | Cow Fecal | 99.6% | 99.5% | 96.8% | 96.7% | 98.5% |
| R26.38.1 | Cow Fecal | 99.3% | 98.6% | 96.1% | 96.1% | 97.2% |
| R26.38.10 | Cow Fecal | 99.9% | 97.7% | 97.4% | 96.5% | 97.5% |
| R26.39.6 | Cow Fecal | 99.9% | 98.4% | 96.3% | 96.6% | 97.5% |
| R26.41.10 | Cow Fecal | 100.0% | 93.1% | 2.0% | 87.9% | 92.7% |
| R26.41.2 | Cow Fecal | 98.9% | 97.8% | 87.1% | 89.2% | 93.5% |
| R26.43.6 | Cow Fecal | 0.0% | 0.0% | 0.0% | 0.0% | 0.0% |
| R26.44.7 | Cow Fecal | 100.1% | 100.0% | 98.9% | 99.5% | 100.1% |
| R26.47.4 | Cow Fecal | 100.0% | 99.1% | 94.6% | 95.5% | 100.0% |
| R26.5.1 | Calf Fecal | 100.0% | 100.0% | 100.0% | 99.2% | 100.0% |
| R26.5.2 | Calf Fecal | 72.8% | 86.6% | 66.1% | 98.4% | 79.2% |
| R26.5.5 | Calf Fecal | 91.1% | 100.0% | 98.5% | 98.4% | 99.2% |
| R26.5.9 | Calf Fecal | 65.7% | 74.1% | 50.3% | 93.0% | 94.1% |
| R26.51.1 | Cow Fecal | 100.0% | 100.0% | 99.2% | 99.3% | 100.0% |
| R26.52.3 | Cow Fecal | 91.1% | 89.0% | 7.9% | 84.7% | 87.6% |
| R26.52.5 | Cow Fecal | 76.9% | 75.1% | 77.2% | 78.3% | 81.0% |
| R26.52.6 | Cow Fecal | 85.6% | 84.6% | 83.6% | 81.3% | 78.7% |
| R26.53.10 | Cow Fecal | 100.0% | 100.0% | 99.3% | 98.5% | 100.0% |
| R26.54.4 | Cow Fecal | 100.0% | 100.0% | 99.3% | 99.4% | 100.0% |
| R26.54.8 | Cow Fecal | 100.0% | 100.0% | 100.0% | 99.0% | 99.7% |
| R26.55.4 | Cow Fecal | 93.7% | 76.3% | 9.0% | 95.2% | 39.0% |
| R26.55.5 | Cow Fecal | 100.0% | 99.3% | 100.0% | 98.6% | 100.0% |
| R26.56.1 | Cow Fecal | 100.0% | 99.8% | 99.8% | 98.0% | 100.0% |
| R26.56.6 | Cow Fecal | 100.0% | 99.9% | 99.1% | 98.9% | 100.0% |
| R26.57.6 | Cow Fecal | 99.6% | 98.7% | 97.9% | 98.6% | 98.9% |
| R26.57.9 | Cow Fecal | 100.0% | 100.0% | 100.0% | 100.0% | 100.0% |
| R26.59.1 | Cow Fecal | 100.0% | 100.0% | 100.0% | 100.0% | 100.0% |
| R26.59.10 | Cow Fecal | 100.0% | 99.9% | 99.9% | 99.5% | 100.0% |
| R26.59.6 | Cow Fecal | 99.9% | 100.0% | 100.0% | 100.0% | 100.0% |
| R26.59.7 | Cow Fecal | 100.0% | 100.0% | 99.3% | 98.7% | 100.0% |
| R26.59.8 | Cow Fecal | 99.7% | 99.6% | 99.6% | 99.6% | 99.6% |
| R26.60.7 | Cow Fecal | 99.9% | 99.3% | 99.4% | 99.2% | 99.5% |
| R26.8.4 | Calf Fecal | 100.0% | 94.4% | 98.7% | 87.3% | 98.8% |
| R26.8.9 | Calf Fecal | 99.9% | 94.5% | 63.4% | 29.2% | 96.8% |
| R26.9.10 | Calf Fecal | 97.4% | 50.7% | 0.0% | 88.4% | 46.4% |
| R26.9.3 | Calf Fecal | 63.4% | 44.5% | 99.9% | 57.3% | 68.6% |
| R26.9.6 | Calf Fecal | 89.8% | 48.9% | 99.6% | 99.6% | 100.0% |
| R26.9.7 | Calf Fecal | 0.0% | 47.4% | 52.1% | 0.0% | 41.6% |
| R26.9.8 | Calf Fecal | 92.2% | 99.7% | 98.1% | 97.7% | 93.6% |
| R1.10.4 | Calf Fecal | 100.0% | 100.0% | 100.0% | 100.0% | 100.0% |
| R1.10.5 | Calf Fecal | 100.0% | 100.0% | 100.0% | 100.0% | 99.9% |
| R1.11.3 | Calf Fecal | 100.0% | 100.0% | 100.0% | 100.0% | 100.0% |
| R1.11.4 | Calf Fecal | 100.0% | 100.0% | 99.9% | 100.0% | 100.0% |
| R1.12.10 | Calf Fecal | 100.0% | 100.0% | 100.0% | 100.0% | 100.0% |
| R1.12.5 | Calf Fecal | 100.0% | 100.0% | 100.0% | 100.0% | 100.0% |
| R1.12.8 | Calf Fecal | 100.0% | 100.0% | 100.0% | 100.0% | 100.0% |
| R1.13.1 | Calf Fecal | 100.0% | 0.6% | 98.5% | 27.9% | 100.0% |
| R1.14.3 | Calf Fecal | 100.0% | 100.0% | 100.0% | 100.0% | 100.0% |
| R1.15.1 | Calf Fecal | 100.0% | 100.0% | 100.0% | 100.0% | 100.0% |
| R1.15.10 | Calf Fecal | 100.0% | 100.0% | 100.0% | 100.0% | 100.0% |
| R1.15.2 | Calf Fecal | 100.0% | 100.0% | 100.0% | 100.0% | 100.0% |
| R1.15.4 | Calf Fecal | 100.0% | 100.0% | 100.0% | 100.0% | 100.0% |
| R1.15.7 | Calf Fecal | 100.0% | 100.0% | 100.0% | 100.0% | 100.0% |
| R1.15.9 | Calf Fecal | 100.0% | 100.0% | 100.0% | 100.0% | 100.0% |
| R1.16.1 | Calf Fecal | 100.0% | 99.8% | 100.0% | 100.0% | 100.0% |

TABLE 11-continued

Bacteriocin assay results displaying each isolate tested and the source of that isolate, isolated from Texas fecal samples. Inhibition was calculated based on the percent of growth for each treatment well compared to the positive control.

| | | *Bacillus* strains | | | | |
|---|---|---|---|---|---|---|
| Isolate ID | Sample | 747 | 1104 | 1541 | 1781 | 2018 |
| R1.16.6 | Calf Fecal | 100.0% | 100.0% | 100.0% | 100.0% | 100.0% |
| R1.17.2 | Calf Fecal | 100.0% | 100.0% | 100.0% | 100.0% | 100.0% |
| R1.18.1 | Calf Fecal | 100.0% | 100.0% | 100.0% | 100.0% | 100.0% |
| R1.18.10 | Calf Fecal | 100.0% | 100.0% | 100.0% | 100.0% | 100.0% |
| R1.18.2 | Calf Fecal | 100.0% | 100.0% | 100.0% | 100.0% | 100.0% |
| R1.18.4 | Calf Fecal | 100.0% | 100.0% | 100.0% | 100.0% | 100.0% |
| R1.18.6 | Calf Fecal | 0.0% | 0.0% | 0.0% | 0.0% | 0.0% |
| R1.18.7 | Calf Fecal | 100.0% | 100.0% | 100.0% | 100.0% | 100.0% |
| R1.18.9 | Calf Fecal | 100.0% | 100.0% | 100.0% | 100.0% | 100.0% |
| R1.19.3 | Calf Fecal | 100.0% | 100.0% | 100.0% | 100.0% | 100.0% |
| R1.21.2 | Calf Fecal | 100.0% | 99.8% | 100.0% | 100.0% | 100.0% |
| R1.21.4 | Calf Fecal | 100.0% | 100.0% | 100.0% | 100.0% | 100.0% |
| R1.22.2 | Calf Fecal | 100.0% | 100.0% | 100.0% | 100.0% | 100.0% |
| R1.22.4 | Calf Fecal | 100.0% | 100.0% | 100.0% | 100.0% | 100.0% |
| R1.22.6 | Calf Fecal | 100.0% | 100.0% | 100.0% | 100.0% | 100.0% |
| R1.22.9 | Calf Fecal | 99.3% | 99.7% | 99.6% | 99.5% | 99.6% |
| R1.23.5 | Calf Fecal | 100.0% | 100.0% | 100.0% | 100.0% | 100.0% |
| R1.23.8 | Calf Fecal | 100.0% | 100.0% | 100.0% | 100.0% | 100.0% |
| R1.23.9 | Calf Fecal | 99.9% | 100.0% | 100.0% | 100.0% | 100.0% |
| R1.24.1 | Calf Fecal | 100.0% | 100.0% | 100.0% | 100.0% | 100.0% |
| R1.24.8 | Calf Fecal | 100.0% | 100.0% | 100.0% | 99.9% | 100.0% |
| R1.25.1 | Calf Fecal | 100.0% | 100.0% | 100.0% | 100.0% | 100.0% |
| R1.25.2 | Calf Fecal | 100.0% | 100.0% | 100.0% | 100.0% | 100.0% |
| R1.25.4 | Calf Fecal | 100.0% | 100.0% | 100.0% | 99.8% | 100.0% |
| R1.25.5 | Calf Fecal | 100.0% | 100.0% | 100.0% | 100.0% | 100.0% |
| R1.25.7 | Calf Fecal | 100.0% | 100.0% | 100.0% | 100.0% | 100.0% |
| R1.26.4 | Calf Fecal | 100.0% | 12.0% | 98.0% | 0.2% | 100.0% |
| R1.27.6 | Calf Fecal | 100.0% | 100.0% | 100.0% | 100.0% | 100.0% |
| R1.27.9 | Calf Fecal | 100.0% | 100.0% | 100.0% | 100.0% | 100.0% |
| R1.28.4 | Calf Fecal | 100.0% | 100.0% | 100.0% | 100.0% | 100.0% |
| R1.34.3 | Calf Fecal | 100.0% | 100.0% | 100.0% | 100.0% | 100.0% |
| R1.34.8 | Calf Fecal | 100.0% | 100.0% | 100.0% | 100.0% | 100.0% |
| R1.35.7 | Calf Fecal | 100.0% | 100.0% | 100.0% | 100.0% | 100.0% |
| R1.46.2 | Calf Fecal | 100.0% | 100.0% | 100.0% | 99.8% | 100.0% |
| R1.46.4 | Calf Fecal | 100.0% | 100.0% | 100.0% | 100.0% | 100.0% |
| R1.9.4 | Calf Fecal | 100.0% | 100.0% | 100.0% | 100.0% | 100.0% |
| R1.9.9 | Calf Fecal | 100.0% | 100.0% | 100.0% | 100.0% | 100.0% |

TABLE 12

Bacteriocin assay results displaying each isolate tested from Texas. Inhibition was calculated based on the percent of growth for each treatment well compared to the positive control.

| 16S ID | Isolate ID | Sample Type | Farm | *Bacillus* Strains | | | | | |
|---|---|---|---|---|---|---|---|---|---|
| | | | | 747 | 1104 | 1541 | 1781 | 1999 | 2018 |
| *C. beijerinckii* group | R3.9.4 | Cow Fecal | Farm BS | 98.7% | 98.8% | 98.1% | 71.2% | 76.8% | 99.7% |
| *C. beijerinckii* group | S37.11.9 | Ground Corn | Farm BS | 96.9% | 45.7% | 62.0% | 39.3% | 36.9% | 66.2% |
| *C. beijerinckii* group | R3.60.2 | Cow Fecal | Farm BS | 99.0% | 99.0% | 98.5% | 99.1% | 79.9% | 98.7% |
| *C. beijerinckii* group | R5.15.1 | Cow Fecal | Farm ALJ | 98.6% | 79.9% | 97.8% | 49.3% | 52.4% | 80.0% |
| *C. beijerinckii* group | R5.42.1 | Cow Fecal | Farm ALJ | 75.6% | 53.9% | 96.5% | 51.2% | 70.6% | 79.9% |
| *C. beijerinckii* group | R5.41.1 | Cow Fecal | Farm ALJ | 97.2% | 64.2% | 94.5% | 26.0% | 24.6% | 42.5% |
| *C. bifermentans* group | S37.12.5 | Gluten Feed | Farm BS | 96.0% | 70.0% | 68.5% | 69.3% | 74.8% | 69.5% |
| *C. butyricum* | R1.26.7 | Calf Fecal | Farm DC | 90.7% | 26.9% | 35.3% | 52.9% | 40.9% | 72.8% |
| *C. butyricum* | R3.5.7 | Cow Fecal | Farm BS | 99.1% | 99.3% | 98.7% | 79.8% | 79.3% | 99.2% |
| *C. butyricum* | R3.4.5 | Cow Fecal | Farm BS | 98.5% | 98.2% | 97.5% | 97.7% | 97.5% | 97.5% |
| *C. butyricum* | S35.1.1 | Texture Feed #1 | Farm DC | 76.8% | 51.8% | 41.4% | 43.8% | 41.2% | 76.3% |
| *C. paraputrificum* | R1.10.7 | Calf Fecal | Farm DC | 97.1% | 97.6% | 96.7% | 90.4% | 95.3% | 97.1% |
| *C. paraputrificum* | R1.19.10 | Calf Fecal | Farm DC | 94.0% | 85.4% | 61.2% | 50.4% | 81.0% | 48.6% |
| *Clostrdium perfringens* | R1.12.7 | Calf Fecal | Farm DC | 96.9% | 33.3% | 96.8% | 97.0% | Not Tested | 97.0% |
| *Clostrdium perfringens* | R1.12.4 | Calf Fecal | Farm DC | 96.3% | 22.2% | 96.2% | 96.1% | Not Tested | 96.7% |
| *Clostrdium tertium* | R1.3.10 | Calf Fecal | Farm DC | 82.5% | 5.6% | 22.3% | 33.5% | Not Tested | 89.8% |
| *Clostrdium tertium* | R1.3.9 | Calf Fecal | Farm DC | 87.4% | 35.6% | 47.0% | 52.8% | Not Tested | 93.8% |
| *Clostrdium tertium* | R1.17.3 | Calf Fecal | Farm DC | 85.2% | 2.9% | 19.2% | 32.0% | Not Tested | 92.5% |
| *Clostrdium tertium* | R1.20.10 | Calf Fecal | Farm DC | 85.3% | 0.0% | 33.3% | 35.7% | Not Tested | 92.0% |
| *Clostrdium tertium* | R1.20.9 | Calf Fecal | Farm DC | 82.9% | 1.0% | 21.8% | 31.7% | Not Tested | 92.0% |
| *Clostrdium tertium* | R1.19.9 | Calf Fecal | Farm DC | 84.1% | 27.7% | 39.7% | 58.6% | Not Tested | 89.3% |
| *Clostrdium tertium* | R1.36.7 | Calf Fecal | Farm DC | 85.2% | 9.8% | 25.9% | 32.7% | Not Tested | 96.2% |
| *Clostrdium tertium* | R1.32.5 | Calf Fecal | Farm DC | 96.9% | 14.2% | 77.4% | 60.3% | Not Tested | 96.6% |
| *Clostrdium tertium* | R1.39.4 | Calf Fecal | Farm DC | 97.2% | 6.1% | 60.5% | 69.4% | Not Tested | 96.8% |
| *Clostrdium tertium* | R1.33.8 | Calf Fecal | Farm DC | 71.4% | 31.8% | 24.2% | 47.6% | Not Tested | 83.0% |
| *Clostrdium tertium* | R1.32.6 | Calf Fecal | Farm DC | 89.2% | 0.0% | 10.0% | 25.7% | Not Tested | 95.9% |
| *Clostrdium tertium* | R1.33.9 | Calf Fecal | Farm DC | 70.7% | 27.8% | 17.4% | 45.3% | Not Tested | 60.0% |
| *Clostrdium tertium* | R1.41.8 | Calf Fecal | Farm DC | 80.7% | 0.0% | 25.8% | 29.2% | Not Tested | 91.0% |
| *Clostrdium tertium* | R1.46.7 | Calf Fecal | Farm DC | 96.2% | 45.5% | 64.7% | 71.9% | Not Tested | 96.5% |
| *Clostridium algidixylanolyticum* | R5.35.6 | Cow Fecal | Farm ALJ | 37.3% | 30.7% | 39.1% | 38.6% | Not Tested | 37.5% |
| *Clostridium algidixyllanolyticum* | R3.13.1 | Cow Fecal | Farm BS | 13.6% | 21.4% | 9.6% | 15.2% | Not Tested | 12.4% |
| *Clostridium algidixyllanolyticum* | R3.2.3 | Cow Fecal | Farm BS | 42.8% | 34.3% | 28.9% | 37.7% | Not Tested | 27.8% |
| *Clostridium algidixyllanolyticum* | R3.36.2 | Cow Fecal | Farm BS | 25.6% | 21.8% | 25.6% | 24.8% | Not Tested | 25.7% |

TABLE 12-continued

Bacteriocin assay results displaying each isolate tested from Texas. Inhibition was calculated based on the percent of growth for each treatment well compared to the positive control.

| | Isolate | Sample | | Bacillus Strains | | | | | |
|---|---|---|---|---|---|---|---|---|---|
| 16S ID | ID | Type | Farm | 747 | 1104 | 1541 | 1781 | 1999 | 2018 |
| Clostridium algidixyllanolyticum | R3.37.2 | Cow Fecal | Farm BS | 23.0% | 11.8% | 22.1% | 20.4% | Not Tested | 19.2% |
| Clostridium algidixyllanolyticum | R3.47.7 | Cow Fecal | Farm BS | 15.8% | 0.0% | 10.2% | 11.6% | Not Tested | 11.8% |
| Clostridium algidixyllanolyticum | R3.50.1 | Cow Fecal | Farm BS | 5.5% | 0.0% | 4.4% | 4.5% | Not Tested | 5.6% |
| Clostridium algidixyllanolyticum | R3.53.4 | Cow Fecal | Farm BS | 0.0% | 0.0% | 0.0% | 0.0% | Not Tested | 0.0% |
| Clostridium algidixyllanolyticum | R3.55.7 | Cow Fecal | Farm BS | 6.6% | 4.1% | 5.2% | 7.3% | Not Tested | 7.7% |
| Clostridium argentinense | R5.59.10 | Cow Fecal | Farm ALJ | 95.6% | 71.1% | 90.4% | 90.9% | Not Tested | 94.3% |
| Clostridium beijerinkckii group | R3.21.4 | Cow Fecal | Farm BS | 26.4% | 26.9% | 26.3% | 27.5% | Not Tested | 26.3% |
| Clostridium beijerinkckii group | R3.17.2 | Cow Fecal | Farm BS | 11.6% | 10.1% | 15.1% | 10.3% | Not Tested | 16.8% |
| Clostridium beijerinkckii group | R3.16.2 | Cow Fecal | Farm BS | 21.2% | 24.8% | 22.3% | 23.2% | Not Tested | 23.1% |
| Clostridium beijerinkckii group | R3.38.3 | Cow Fecal | Farm BS | 27.0% | 26.4% | 26.7% | 25.7% | Not Tested | 30.4% |
| Clostridium beijerinkckii group | R3.33.1 | Cow Fecal | Farm BS | 19.5% | 18.5% | 19.0% | 18.7% | Not Tested | 17.2% |
| Clostridium beijerinkckii group | R3.45.5 | Cow Fecal | Farm BS | 28.5% | 28.0% | 27.3% | 27.5% | Not Tested | 27.6% |
| Clostridium beijerinkckii group | R3.52.2 | Cow Fecal | Farm BS | 23.7% | 21.4% | 19.7% | 19.1% | Not Tested | 18.7% |
| Clostridium beijerinkckii group | R3.43.3 | Cow Fecal | Farm BS | 31.3% | 29.7% | 30.2% | 30.9% | Not Tested | 31.2% |
| Clostridium beijerinkckii group | R3.59.4 | Cow Fecal | Farm BS | 8.3% | 26.7% | 12.3% | 14.0% | Not Tested | 8.3% |
| Clostridium beijerinkckii group | S37.11.3 | Ground Corn | Farm BS | 24.1% | 21.9% | 25.5% | 21.1% | Not Tested | 28.9% |
| Clostridium beijerinkckii group | S37.11.2 | Ground Corn | Farm BS | 24.3% | 22.8% | 21.8% | 20.0% | Not Tested | 20.3% |
| Clostridium beijerinkckii group | R5.1.1 | Cow Fecal | Farm ALJ | 23.9% | 23.6% | 22.5% | 21.0% | Not Tested | 20.5% |
| Clostridium beijerinkckii group | R5.12.4 | Cow Fecal | Farm ALJ | 17.9% | 17.6% | 20.6% | 19.7% | Not Tested | 39.8% |
| Clostridium beijerinkckii group | R5.23.10 | Cow Fecal | Farm ALJ | 59.8% | 71.7% | 64.9% | 68.1% | Not Tested | 65.9% |
| Clostridium beijerinkckii group | R5.24.3 | Cow Fecal | Farm ALJ | 66.1% | 77.3% | 50.6% | 79.3% | Not Tested | 51.8% |
| Clostridium beijerinkckii group | R5.19.1 | Cow Fecal | Farm ALJ | 21.7% | 22.3% | 20.3% | 21.9% | Not Tested | 22.3% |
| Clostridium beijerinkckii group | R5.14.10 | Cow Fecal | Farm ALJ | 20.0% | 22.1% | 17.7% | 17.8% | Not Tested | 18.6% |
| Clostridium beijerinkckii group | R5.21.1 | Cow Fecal | Farm ALJ | 89.1% | 7.0% | 7.3% | 86.7% | Not Tested | 7.5% |
| Clostridium beijerinkckii group | R5.38.3 | Cow Fecal | Farm ALJ | 71.2% | 0.0% | 16.0% | 1.3% | Not Tested | 40.9% |
| Clostridium beijerinkckii group | R5.27.9 | Cow Fecal | Farm ALJ | 27.9% | 26.9% | 34.7% | 27.6% | Not Tested | 26.5% |
| Clostridium beijerinkckii group | R5.28.1 | Cow Fecal | Farm ALJ | 16.6% | 17.3% | 17.9% | 17.0% | Not Tested | 21.1% |
| Clostridium beijerinkckii group | R5.50.1 | Cow Fecal | Farm ALJ | 22.5% | 23.7% | 20.5% | 23.2% | Not Tested | 18.8% |
| Clostridium beijerinkckii group | R5.59.1 | Cow Fecal | Farm ALJ | 20.0% | 23.2% | 27.4% | 21.5% | Not Tested | 21.9% |
| Clostridium beijerinkckii group | R5.41.1 | Cow Fecal | Farm ALJ | 21.6% | 24.1% | 22.3% | 19.8% | Not Tested | 20.6% |
| Clostridium bifermentans group | R3.31.4 | Cow Fecal | Farm BS | 95.2% | 90.4% | 94.6% | 94.6% | Not Tested | 94.9% |
| Clostridium bifermentans group | S37.11.4 | Ground Corn | Farm BS | 97.3% | 97.2% | 96.5% | 96.4% | Not Tested | 97.0% |
| Clostridium bifermentans group | R5.20.1 | Cow Fecal | Farm ALJ | 97.1% | 65.3% | 96.3% | 96.1% | Not Tested | 96.8% |
| Clostridium bifermentans group | R5.53.1 | Cow Fecal | Farm ALJ | 92.2% | 0.0% | 89.9% | 89.0% | Not Tested | 90.1% |
| Clostridium bifermentans group | R5.52.1 | Cow Fecal | Farm ALJ | 96.9% | 28.1% | 95.9% | 78.5% | Not Tested | 95.3% |
| Clostridium butyricum | R1.26.7 | | Farm DC | 96.3% | 0.0% | 40.4% | 0.0% | Not Tested | 91.4% |

TABLE 12-continued

Bacteriocin assay results displaying each isolate tested from Texas. Inhibition was calculated based on the percent of growth for each treatment well compared to the positive control.

| 16S ID | Isolate ID | Sample Type | Farm | Bacillus Strains | | | | | |
|---|---|---|---|---|---|---|---|---|---|
| | | | | 747 | 1104 | 1541 | 1781 | 1999 | 2018 |
| Clostridium butyricum | R1.46.8 | Calf Fecal | Farm DC | 97.6% | 97.7% | 97.1% | 97.1% | Not Tested | 97.2% |
| Clostridium cadaveris | R1.21.3 | Calf Fecal | Farm DC | 97.0% | 0.0% | 82.4% | 0.0% | Not Tested | 97.2% |
| Clostridium cadaveris | R1.30.6 | Calf Fecal | Farm DC | 96.7% | 0.0% | 91.2% | 0.0% | Not Tested | 96.6% |
| Clostridium cadaveris | R1.37.1 | Calf Fecal | Farm DC | 97.7% | 0.4% | 90.2% | 18.0% | Not Tested | 97.7% |
| Clostridium cadaveris | R1.45.1 | Calf Fecal | Farm DC | 97.6% | 0.0% | 89.9% | 38.8% | Not Tested | 97.0% |
| Clostridium cadaveris | R1.45.2 | Calf Fecal | Farm DC | 97.4% | 0.0% | 89.6% | 48.2% | Not Tested | 96.6% |
| Clostridium cadaveris | R3.22.2 | Cow Fecal | Farm BS | 95.5% | 0.0% | 83.3% | 45.7% | Not Tested | 94.2% |
| Clostridium cadaveris | R3.26.9 | Cow Fecal | Farm BS | 97.6% | 0.0% | 94.2% | 55.2% | Not Tested | 95.8% |
| Clostridium cadaveris | R5.11.10 | Cow Fecal | Farm ALJ | 88.5% | 87.6% | 86.8% | 85.6% | Not Tested | 87.0% |
| Clostridium celerecrescens | R5.26.3 | Cow Fecal | Farm ALJ | 14.9% | 10.5% | 15.7% | 14.5% | Not Tested | 13.6% |
| Clostridium ghonii | S37.11.1 | Ground Corn | Farm BS | 24.5% | 23.1% | 23.0% | 23.6% | Not Tested | 24.2% |
| Clostridium ghonii | S37.12.4 | Gluten Feed | Farm BS | 93.5% | 0.0% | 0.0% | 15.3% | Not Tested | 27.6% |
| Clostridium ghonii | S37.11.6 | Ground Corn | Farm BS | 75.5% | 0.0% | 7.8% | 74.8% | Not Tested | 76.2% |
| Clostridium ghonii | R5.17.1 | Cow Fecal | Farm ALJ | 32.5% | 0.0% | 0.0% | 0.0% | Not Tested | 0.0% |
| Clostridium paraputrificum | R1.11.9 | Calf Fecal | Farm DC | 96.0% | 53.3% | 81.2% | 86.3% | Not Tested | 96.1% |
| Clostridium paraputrificum | R1.17.1 | Calf Fecal | Farm DC | 94.3% | 17.9% | 87.7% | 79.8% | Not Tested | 91.8% |
| Clostridium paraputrificum | R1.19.10 | Calf Fecal | Farm DC | 97.1% | 56.9% | 89.2% | 91.8% | Not Tested | 96.1% |
| Clostridium paraputrificum | R1.31.4 | Calf Fecal | Farm DC | 96.0% | 29.9% | 93.5% | 89.8% | Not Tested | 96.0% |
| Clostridium paraputrificum | R1.40.3 | Calf Fecal | Farm DC | 96.4% | 50.9% | 81.1% | 85.5% | Not Tested | 96.0% |
| Clostridium paraputrificum | R1.44.3 | Calf Fecal | Farm DC | 95.8% | 38.1% | 88.1% | 73.6% | Not Tested | 97.0% |
| Clostridium paraputrificum | R1.43.8 | Calf Fecal | Farm DC | 96.8% | 35.3% | 95.0% | 92.4% | Not Tested | 97.0% |
| Clostridium sartagoforme | R3.14.3 | Cow Fecal | Farm BS | 44.1% | 49.8% | 63.5% | 71.0% | Not Tested | 70.0% |
| Clostridium sartagoforme | R3.29.4 | Cow Fecal | Farm BS | 32.2% | 23.0% | 36.5% | 34.2% | Not Tested | 34.1% |
| Clostridium sartagoforme | R3.46.1 | Cow Fecal | Farm BS | 83.6% | 0.0% | 52.0% | 43.3% | Not Tested | 64.5% |
| Clostridium sartagoforme | S37.11.5 | Ground Corn | Farm BS | 96.0% | 36.6% | 77.4% | 80.0% | Not Tested | 80.7% |
| Clostridium sartagoforme | S37.11.7 | Ground Corn | Farm BS | 89.8% | 30.8% | 47.9% | 70.0% | Not Tested | 79.0% |
| Clostridium sartagoforme | S37.1.1 | Face Corn | Farm BS | 94.8% | 0.0% | 34.2% | 29.3% | Not Tested | 84.0% |
| Clostridium sartagoforme | S37.11.8 | Ground Corn | Farm BS | 94.1% | 0.0% | 33.9% | 0.0% | Not Tested | 57.4% |
| Clostridium sartagoforme | R5.48.10 | Cow Fecal | Farm ALJ | 92.4% | 32.3% | 74.8% | 83.1% | Not Tested | 91.6% |
| Clostridium sartagoforme | R5.57.10 | Cow Fecal | Farm ALJ | 87.6% | 1.6% | 42.2% | 42.8% | Not Tested | 64.1% |
| Clostridium sordellii | S37.12.3 | Gluten Feed | Farm BS | 97.2% | 49.4% | 96.0% | 96.3% | Not Tested | 86.9% |
| Clostridium sporogenes | R3.25.10 | Cow Fecal | Farm BS | 74.9% | 0.0% | 8.1% | 0.0% | Not Tested | 8.0% |
| Clostridium subterminale | R5.47.3 | Cow Fecal | Farm ALJ | 77.1% | 57.9% | 72.5% | 49.8% | Not Tested | 75.3% |
| Clostridium subterminale | R5.56.1 | Cow Fecal | Farm ALJ | 77.0% | 0.0% | 55.2% | 48.2% | Not Tested | 59.8% |
| Clostridium sulfidigenes | R5.45.2 | Cow Fecal | Farm ALJ | 55.8% | 46.9% | 50.2% | 46.5% | Not Tested | 52.2% |
| Clostridium uliginosum | R3.34.4 | Cow Fecal | Farm BS | 90.1% | 85.8% | 84.8% | 83.5% | Not Tested | 84.3% |

Example 7: Selection of *Bacillus* Strains to Inhibit *Clostridium Perfringens* and Non-Toxigenic Clostridia Isolated from Ruminant Fecal Samples. (Upper Midwest)

Introduction:

*Clostridium* is a genus of Gram-positive, spore-forming bacteria that are common residents of the gastrointestinal tract. A number of *Clostridium* species have been linked to enteric disease in ruminants including hemorrhagic bowel syndrome (HBS), a disease often correlated to elevated levels of *Clostridium perfringens* Type A. While most of the enteric diseases caused by clostridia are acute and occur sporadically in herds, in general, the prognosis is poor and the first sign of illness may be death. Based on recent results sub-acute enteric clostridia disease challenges may be a more wide spread issue than acute challenges. Due to a low success rate from treatment in acute disease challenges a more common, emphasis needs to be placed on prophylactic measures.

The purpose of this research was to characterize the distribution and diversity of clostridia in ruminants and ensure inhibition of these isolates using novel *Bacillus* strains as a method to control the clostridia populations.

Materials and Methods:

Fecal samples (248) from cows, heifers and calves gathered from 4 farms in the Upper Midwest region were diluted 1:10 with sterile peptone, heat shocked for 30 minutes at 60° C., enumerated in sterile peptone and pour plated on Tryptose Sulphite Cycloserine (TSC) agar with D-cycloserine (400 mg/L) to select for clostridia species. Agar plates were incubated at 37° C. anaerobically for 24 hours. If present, isolated sulphite-reducing colonies were counted for a total clostridia count (CFU/g) and representative isolates were picked into Reinforced clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions were performed in 96-well blocks containing 500 µl presumptive clostridia culture per well. Cells were harvested by centrifugation at 4,700 rpm for 10 minutes, the supernatant was removed. Cells were re-suspended in 500 µl of 50 mM of EDTA-2Na (pH=8.0). Aliquots of 300 µl of the suspended cells were transferred to a new 96-well block and combined with 20 µl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 µl of lysis buffer (6 M Guanidine, 20% Triton-X 100, 10 mM Tris-HCL, pH 7.5) was added, mixed then incubated at room temperature for 15 minutes. Following the incubation 20 µl of Proteinase K (NEB, 800 U/mL) was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed centrifuging 750 µl of Column Wash Solution (Promega, A1318) at 4700 rpms for 1 minute and 30 seconds discarding flow through at the end of each spin. The binding plate was centrifuged for an additional 10 minutes at 4,700 rpm to remove any residual ethanol. A clean elution plate was then placed under the binding plate and DNA was eluted with 200 µl, pre-warmed (55° C.), Nuclease Free Water (Promega, P1195).

DNA was screened for toxin genes ($\alpha$, $\beta$, $\epsilon$, and $\iota$) specific to *C. perfringens* using polymerase chain reaction (PCR). Amplification of toxin genes was executed using a multiplex PCR containing four primer sets (Yoo et al., 1997) (Table 1.) The PCR mixture contained 2.5 µl 10×PCR Buffer, 2 µl of 50 mM $MgCl_2$, 0.5 µM of each primer (Table 1.), 0.1 µl of Invitrogen™ Platinum™ Taq DNA Polymerase, 2.5 µl of DNA, sterile water was added to achieve 25 µl for a total reaction volume. The mixture underwent 5 minutes at 94° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved. If one or multiple toxin genes were observed a toxin type identification was assigned to each isolate based on their toxin gene profile (Songer, 1996). *C. perfringens* positive to total clostridia isolate ratio was used to calculate an estimated *C. perfringens* count based on the total clostridia count.

Unique strain-specific genetic fingerprints were generated using Random Amplification of Polymorphic DNA (RAPD) analysis on select isolates to determine diversity among fecal *C. perfringens* isolates. The PCR contained 5 µl of DNA, 2.5 µl RAPD primer 2 (10 µM) (Table 1.), and 17.5 µl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes finishing with a final elongation of 5 minutes at 72° C. PCR products observed on a Fragment Analyzer (Advanced Analytics) to determine amplification patterns and were imported into BioNumerics, bioinformatics software, for analysis. RAPD patterns were compared with a band based Dice correlation analysis method to determine the similarity between RAPD patterns as a way to monitor diversity between isolates.

Antimicrobial screening was done on *C. perfringens* isolates obtained from ruminant samples to gauge the effectiveness of the antimicrobial bacteriocin produced by the inventors' identified *Bacillus* strains 747, 1104, 1541, 1781, and 2018. Bacteriocin was harvested by growing each strain at 32° C. in a shaking incubator at 150 rpms for 24 hours in Brain Heart Infusion (BHI) broth. A 1% transfer of the 24-hour culture to fresh BHI broth was executed after incubation. The *Bacillus* were then incubated for 36-48 hours in a 32° C. shaking incubator at 150 rpms. The culture was then centrifuged at 14,000×g for 20 minutes, supernatant was then filtered with a 0.2 m filter to remove any residual cells.

A bacteriocin turbidity assay was executed by growing *C. perfringens* strains isolated from ruminant fecal samples in RCM for 24 hours, anaerobically, at 37° C. Overnight culture was transferred (1%) to sterile RCM and immediately used in the assay. For each *C. perfringens* isolate at least six wells were run in a sterile 48 well reaction plate, 600 µl inoculated culture (positive control), 600 µl inoculated RCM+70 µl bacteriocin (747, 1104, 1541, 1781, and 2018) and 670 RCM (un-inoculated, negative control). Plates were incubated anaerobically at 37° C. for 24 hours then read using a BioTek Epoch Microplate Spectrophotometer, readings were taken at a wavelength of 600 nm. Optical density readings from the negative controls were subtracted from all OD readings and percent inhibition was calculated using the positive control and each bacteriocin treatment.

To identify clostridia that did not have at least one toxin gene specific to *C. perfringens*, a PCR reaction was performed on the isolate DNA to amplify the 16S region of rDNA using primers 27F-YM and 1492R-Y (Table 1). This was done on 20% of the isolates that did not contain a toxin gene specific to *C. perfringens*. The PCR mixture contained 5 μl of 10×PCR Buffer, 2 μl of 50 mM $MgCl_2$, 1 μl of 50 mM dNTPs, 0.4 μM of each primer (Table 1.), 0.2 μl of Invitrogen™ Platinum™ Taq DNA Polymerase, 5 μl of DNA, and sterile water was added to achieve 50 μl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to gene wiz to obtain the sequences for the 16S genes. Sequences were compared to known typed bacterial strains obtained from EZbiocloud online electronic database. Based on comparisons of these sequences a bacterial identification was assigned to the isolates.

Results:

Fecal samples, 248, were collect from 4 Upper Midwest Regional farms (Minnesota and South Dakota) from which 2,419 presumptive clostridia strains were isolated as representatives of the clostridial diversity in the Upper Midwest region (Table 13.).

Clostridia enumeration results indicated the average level of clostridia CFU/g across all calf fecal samples was 505,000 CFU/g with individual fecal samples ranging from 15 to 1,160,000 CFU/g. While the average level of clostridia CFU/g across all cow fecal samples was 8,480 CFU/g with individual fecal samples ranging from 5 to 785,000 CFU/g (FIG. 48.). Samples appeared to range in clostridia levels for both calves (FIG. 49.) and cows (FIG. 50.).

*C. perfringens* enumeration results displayed the average level of *C. perfringens* CFU/g across all calf fecal samples was 81,800 CFU/g with individual samples ranging from <10 to 1,160,000 CFU/g. While the average level of *C. perfringens* CFU/g across all cow fecal samples was 5,490 CFU/g with individual samples ranging from <10 to 314,000 CFU/g (FIG. 51.). Samples appeared to range in clostridia levels for both calves (FIG. 52.) and cows (FIG. 53.).

Analysis of the toxin multiplex PCR results displayed which isolates contained toxin genes specific to *C. perfringens*. A total of 2,419 presumptive clostridia isolates from fecal samples have been tested for the indicated *C. perfringens* toxin genes. Of the 2,419 clostridia isolates screened, 629 isolates (26.0%) tested positive for at least 1 of the toxin genes. From the 629 toxin-gene positive isolates 583 (92.7%) were identified as Type A (αtoxin only), however β, ε and ι, toxins were also detected in the clostridia fecal isolates.

Gentic RAPD fingerprint patterns displayed diversity among the 551 isolates that successful amplified. The isolates tested were harvested from calf fecal, cow fecal and feed and did not cluster strictly based on the sample type or farm. Isolates formed 106 clusters based on 75% similarity according to the Dice correlation method. The largest cluster was 37 isolates which was 6.7% of the total dendrogram.

Representatives from the RAPD dendrogram were selected to capture the diversity of the *C. perfringens* population from this region and subjected to inhibition assays. Antimicrobial testing using the bacteriocin turbidity assay displayed good inhibition of most ruminant fecal *C. perfringens* isolates using bacteriocin harvested from 747, 1104, 1541, 1781, and 2018. The bacteriocin from at least one of the strains 747, 1104, 1541, 1781, and 2018 were able to inhibit the growth >60% of 123 of the 135 isolates tested representing a total of 95.2% inhibition of the *C. perfringens* population based on the dendrogram (Table 14.).

Out of the 2,419 isolates collected 1,790 isolates (74.0%) were found to be non-toxigenic clostridia. Sequencing representatives (n=218) from the non-toxigenic clostridia displayed two dominate clostridia groups *Clostridium bifermentans* group (*Paraclostridium bifermentans* and *P. benzoelyticum*) and the *Clostridium beijerinckii* group (*C. diolis, C. beijerinckii, C. chromiireducens, C. saccharoperbutylacetonicum, C. puniceum*, and *C. saccharobutylicum*), the two main groups of the non-toxigenic clostridia group made up 50.5% of the non-toxigenic isolates (FIG. 54.).

Discussion:

Fecal samples were used as the most readily available sample type to estimate the level and obtain isolates of clostridia and *C. perfringens* within the digestive system of ruminants. From the 248 fecal samples collected throughout the Upper Midwest all samples had detectable levels of clostridia. Many isolates harvested (629 isolates) from the ruminant samples contained a toxin gene specific to *C. perfringens. C. perfringens* was detected in 74% of the cow fecal samples and in 50% of the calf fecal samples. The high presence of clostridia and *C. perfringens* indicates the risk for sub-acute enteric clostridia disease challenges in most ruminants throughout the Upper Midwest. *C. perfringens* isolates were diverse according to the RAPD genetic fingerprints but were not specific to sample type or farm. Diverse representatives of *C. perfringens* were mostly inhibited (>60%) by at least one bacteriocin from the following strains 747, 1104, 1541, 1781 or 2018. From the 135 isolates tested 123 isolates were inhibited by greater than 60% by at least one of the strains, representing inhibition of 95.2% of the total *C. perfringens* population based on representation from clusters on the RAPD dendrogram. This indicates the *Bacillus* strains 747, 1104, 1541, 1781 and 2018 can inhibit a wide range of diversity of *C. perfringens* isolates. The *Bacillus* strains are not limited to specific clostridia strain(s) like a vaccine which may be missing large groups of the clostridia populations based on the genetic diversity observed in the RAPD dendrogram. DNA sequencing of the non-toxigenic clostridia revealed two major identifications of *Clostridium* species. *C. bifermentans* group, which is known to produce 1,3-propanediol (Leja et al., 2014; Myszka et al., 2012) and *C. beijerinckii* group known to produce butanol and acetone (Hou et al., 2017). The production of the metabolic end products of these species could be having an impact in the rumen, reducing performance parameters such as milk production within a dairy cow. The high inhibition level against the clostridia isolates in vitro indicates a potential mode of action of the *Bacillus* strains 747, 1104, 1541, 1781 and 2018.

The *Bacillus* strains offer a prophylactic effect on the clostridia populations which may not only increase rumen efficiency leading to increased milk production, but prevent acute levels of *C. perfringens* reducing the occurrence of digestive deaths. The high prevalence of clostridia and *C. perfringens* in fecal samples collected suggests efficiency improvement opportunities in many ruminants throughout the Upper Midwest. This example displays the diversity of clostridia isolates from the ruminant fecal and feed samples collected from the Upper Midwest. The *Bacillus* strains tested 747, 1104, 1541, 1781 and 2018, could inhibit most of the clostridia diversity observed in the Upper Midwest. The product, in accordance with this embodiment of the present invention could inhibit toxigenic clostridia isolated from ruminants in the Upper Midwest indicating a benefit in rumen efficiency if fed to dairy cows as a direct fed microbial (DFM).

TABLE 13

Fecal samples, 248, were collected from Upper Midwest regional dairies separated by farm (4) and age (cow or calf) which were enumerated for clostridia, tested for *C. perfringens*, isolates were genotyped and tested for inhibition.

| Farm Name | Cow Fecal Samples | Calf Fecal Samples |
|---|---|---|
| Farm BR | 50 | 6 |
| Farm E | 45 | 9 |
| Farm W | 61 | 9 |
| Farm Y | 64 | 4 |
| Total | 220 | 28 |

TABLE 14

Bacteriocin assay results displaying each isolate tested and the source of that isolate, isolated from Upper Midwest regional fecal or feed samples. Inhibition was calculated based on the percent of growth for each treatment well compared to the positive control.

| | | | | *Bacillus* Strains | | | | |
|---|---|---|---|---|---|---|---|---|
| Isolate ID | Farm | Type | Group | 747 | 1104 | 1541 | 1781 | 2018 |
| R27.1.6 | Farm E | Calf | Calf | 99.9% | 99.6% | 99.6% | 98.7% | 99.6% |
| R27.1.7 | Farm E | Calf | Calf | 74.3% | 55.4% | 58.9% | 71.5% | 51.2% |
| R27.13.10 | Farm E | Cow | Close-up | 99.6% | 98.5% | 99.6% | 99.6% | 99.4% |
| R27.13.5 | Farm E | Cow | Close-up | 99.5% | 99.4% | 99.4% | 99.5% | 99.5% |
| R27.13.9 | Farm E | Cow | Close-up | 99.6% | 99.6% | 99.6% | 99.8% | 99.8% |
| R27.18.8 | Farm E | Cow | Close-up | 99.9% | 99.9% | 99.9% | 99.7% | 99.9% |
| R27.2.8 | Farm E | Calf | Calf | 99.8% | 99.5% | 97.0% | 99.8% | 99.5% |
| R27.21.5 | Farm E | Cow | Fresh | 99.6% | 99.3% | 99.8% | 99.6% | 99.3% |
| R27.23.3 | Farm E | Cow | Fresh | 98.5% | 95.7% | 97.5% | 95.7% | 97.5% |
| R27.25.3 | Farm E | Cow | Fresh | 43.8% | 0.0% | 0.0% | 6.4% | 0.0% |
| R27.26.6 | Farm E | Cow | Fresh | 99.9% | 98.9% | 99.9% | 99.3% | 99.7% |
| R27.27.9 | Farm E | Cow | Fresh | 87.0% | 0.0% | 18.9% | 38.5% | 47.8% |
| R27.39.9 | Farm E | Cow | High | 98.4% | 95.6% | 96.6% | 96.6% | 97.5% |
| R27.44.5 | Farm E | Cow | High | 77.3% | 0.0% | 0.4% | 2.4% | 0.0% |
| R27.44.6 | Farm E | Cow | High | 45.7% | 25.8% | 0.0% | 51.6% | 0.0% |
| R27.45.1 | Farm E | Cow | Far off | 99.2% | 99.5% | 99.6% | 98.8% | 99.5% |
| R27.45.9 | Farm E | Cow | Far off | 99.0% | 98.3% | 99.3% | 99.0% | 98.8% |
| R27.47.1 | Farm E | Cow | Far off | 83.9% | 87.5% | 90.8% | 88.2% | 92.0% |
| R27.48.1 | Farm E | Cow | Far off | 99.5% | 99.4% | 99.6% | 99.5% | 99.4% |
| R27.49.4 | Farm E | Cow | Far off | 99.3% | 97.4% | 99.5% | 99.0% | 98.3% |
| R27.50.10 | Farm E | Cow | Far off | 98.1% | 98.3% | 98.5% | 98.0% | 98.0% |
| R27.50.6 | Farm E | Cow | Far off | 99.5% | 98.0% | 97.0% | 99.5% | 99.1% |
| R27.50.9 | Farm E | Cow | Far off | 99.6% | 99.5% | 99.5% | 99.7% | 99.7% |
| R27.51.7 | Farm E | Cow | Far off | 0.0% | 0.0% | 0.0% | 0.0% | 0.0% |
| R27.53.3 | Farm E | Cow | Far off | 99.3% | 90.8% | 99.5% | 87.6% | 99.3% |
| R27.53.5 | Farm E | Cow | Far off | 79.2% | 0.0% | 7.7% | 16.1% | 30.1% |
| R27.54.10 | Farm E | Cow | Far off | 5.7% | 0.0% | 0.0% | 9.4% | 0.0% |
| R27.9.1 | Farm E | Calf | Calf | 99.6% | 99.4% | 99.6% | 99.8% | 99.4% |
| R27.9.10 | Farm E | Calf | Calf | 99.8% | 99.9% | 100.0% | 99.9% | 99.9% |
| R27.9.2 | Farm E | Calf | Calf | 99.4% | 99.8% | 99.8% | 99.6% | 99.5% |
| R27.9.5 | Farm E | Calf | Calf | 99.6% | 99.6% | 99.8% | 99.6% | 99.3% |
| R31.1.7 | Farm Y | Calf | Calf | 99.8% | 99.5% | 99.7% | 99.8% | 85.6% |
| R31.11.1 | Farm Y | Cow | Heifer | 99.6% | 99.5% | 99.8% | 99.5% | 99.5% |
| R31.16.9 | Farm Y | Cow | Fresh Heifer | 100.0% | 57.8% | 38.5% | 100.0% | 99.9% |
| R31.18.3 | Farm Y | Cow | Fresh Heifer | 98.4% | 99.9% | 99.5% | 93.6% | 99.9% |
| R31.2.1 | Farm Y | Calf | Calf | 98.0% | 99.2% | 30.1% | 99.6% | 32.5% |
| R31.22.10 | Farm Y | Cow | Fresh Cow | 62.9% | 99.1% | 98.8% | 83.0% | 99.9% |
| R31.22.5 | Farm Y | Cow | Fresh Cow | 94.8% | 97.1% | 96.2% | 0.0% | 97.5% |
| R31.22.8 | Farm Y | Cow | Fresh Cow | 89.6% | 0.0% | 99.7% | 100.1% | 0.0% |
| R31.24.4 | Farm Y | Cow | Fresh Cow | 94.2% | 5.4% | 99.9% | 68.3% | 99.9% |
| R31.25.3 | Farm Y | Cow | Far off | 0.0% | 0.0% | 0.0% | 4.6% | 0.0% |
| R31.31.10 | Farm Y | Cow | Far off | 2.9% | 0.0% | 0.0% | 0.0% | 14.9% |
| R31.34.8 | Farm Y | Cow | Far off | 42.1% | 0.0% | 0.0% | 0.0% | 29.0% |
| R31.35.1 | Farm Y | Cow | Close-up | 9.6% | 0.0% | 0.0% | 0.0% | 10.3% |
| R31.40.9 | Farm Y | Cow | Close-up | 99.8% | 98.7% | 99.8% | 99.4% | 98.3% |
| R31.45.5 | Farm Y | Cow | 2nd | 99.9% | 99.6% | 99.1% | 99.7% | 41.4% |
| R31.46.1 | Farm Y | Cow | 2nd | 84.4% | 99.4% | 99.8% | 40.0% | 94.1% |
| R31.46.10 | Farm Y | Cow | 2nd | 99.6% | 99.4% | 100.1% | 99.8% | 99.6% |
| R31.46.2 | Farm Y | Cow | 2nd | 99.5% | 0.0% | 99.2% | 99.5% | 98.6% |
| R31.47.2 | Farm Y | Cow | 2nd | 99.7% | 99.4% | 99.8% | 99.8% | 99.5% |
| R31.48.1 | Farm Y | Cow | 2nd | 99.5% | 3.7% | 99.5% | 99.5% | 99.4% |
| R31.48.8 | Farm Y | Cow | 2nd | 98.0% | 0.0% | 99.0% | 98.3% | 99.2% |
| R31.49.3 | Farm Y | Cow | 2nd | 99.2% | 99.5% | 99.5% | 99.3% | 99.2% |
| R31.5.3 | Farm Y | Cow | Heifer | 87.0% | 0.0% | 0.0% | 86.2% | 0.0% |
| R31.51.8 | Farm Y | Cow | 2nd | 47.6% | 99.6% | 99.6% | 20.9% | 99.3% |
| R31.52.2 | Farm Y | Cow | 2nd | 98.7% | 0.0% | 99.1% | 16.9% | 24.0% |

TABLE 14-continued

Bacteriocin assay results displaying each isolate tested and the source of that isolate, isolated from Upper Midwest regional fecal or feed samples. Inhibition was calculated based on the percent of growth for each treatment well compared to the positive control.

| Isolate ID | Farm | Type | Group | *Bacillus* Strains | | | | |
|---|---|---|---|---|---|---|---|---|
| | | | | 747 | 1104 | 1541 | 1781 | 2018 |
| R31.53.1 | Farm Y | Cow | 2nd | 0.0% | 0.0% | 0.0% | 0.0% | 0.0% |
| R31.53.7 | Farm Y | Cow | 2nd | 37.1% | 0.0% | 83.2% | 62.0% | 24.6% |
| R31.54.2 | Farm Y | Cow | 2nd | 98.9% | 0.3% | 28.3% | 98.6% | 53.4% |
| R31.54.3 | Farm Y | Cow | 2nd | 99.4% | 0.3% | 27.4% | 98.8% | 56.9% |
| R31.55.5 | Farm Y | Cow | Low | 67.9% | 0.0% | 95.3% | 0.0% | 32.0% |
| R31.55.7 | Farm Y | Cow | Low | 99.1% | 99.5% | 99.5% | 99.1% | 99.5% |
| R31.55.9 | Farm Y | Cow | Low | 36.7% | 0.0% | 99.5% | 1.1% | 5.6% |
| R31.56.2 | Farm Y | Cow | Low | 99.2% | 25.7% | 99.6% | 45.0% | 68.5% |
| R31.57.4 | Farm Y | Cow | Low | 99.2% | 36.9% | 99.5% | 99.0% | 99.2% |
| R31.58.9 | Farm Y | Cow | Low | 96.6% | 12.2% | 92.6% | 97.1% | 97.4% |
| R31.6.2 | Farm Y | Cow | Heifer | 100.0% | 99.7% | 99.9% | 99.9% | 31.4% |
| R31.6.7 | Farm Y | Cow | Heifer | 99.0% | 99.6% | 99.6% | 99.4% | 99.6% |
| R31.60.7 | Farm Y | Cow | High Mature | 99.0% | 99.0% | 99.3% | 99.2% | 97.5% |
| R31.62.1 | Farm Y | Cow | High Mature | 99.1% | 95.6% | 99.1% | 96.2% | 98.1% |
| R31.62.10 | Farm Y | Cow | High Mature | 99.7% | 99.3% | 99.6% | 99.8% | 99.4% |
| R31.62.7 | Farm Y | Cow | High Mature | 99.5% | 98.7% | 99.5% | 99.5% | 99.5% |
| R31.63.3 | Farm Y | Cow | High Mature | 99.2% | 99.3% | 99.5% | 99.3% | 99.3% |
| R31.63.8 | Farm Y | Cow | High Mature | 9.6% | 94.0% | 99.7% | 99.0% | 98.0% |
| R31.65.10 | Farm Y | Cow | High Mature | 99.5% | 99.5% | 99.6% | 99.5% | 99.4% |
| R31.65.8 | Farm Y | Cow | High Mature | 99.5% | 99.5% | 99.5% | 99.5% | 99.5% |
| R31.68.2 | Farm Y | Cow | High Mature | 99.4% | 0.0% | 78.8% | 71.0% | 78.0% |
| R31.7.10 | Farm Y | Cow | Heifer | 99.7% | 99.5% | 99.7% | 99.7% | 99.7% |
| R31.7.3 | Farm Y | Cow | Heifer | 99.4% | 99.4% | 99.6% | 99.6% | 99.3% |
| R31.8.1 | Farm Y | Cow | Heifer | 99.5% | 99.3% | 99.5% | 99.5% | 99.3% |
| R31.8.7 | Farm Y | Cow | Heifer | 99.3% | 99.3% | 99.4% | 99.4% | 99.4% |
| R32.10.6 | Farm W | Cow | Preg Mature | 99.2% | 99.4% | 99.4% | 99.6% | 99.5% |
| R32.22.7 | Farm W | Cow | Preg Heifer | 99.3% | 99.3% | 99.5% | 99.3% | 99.1% |
| R32.32.8 | Farm W | Cow | Close-up | 99.6% | 99.3% | 99.6% | 99.3% | 99.4% |
| R32.34.3 | Farm W | Cow | Fresh | 99.4% | 98.8% | 99.2% | 99.4% | 99.0% |
| R32.34.9 | Farm W | Cow | Fresh | 99.0% | 99.2% | 99.3% | 99.2% | 99.2% |
| R32.36.3 | Farm W | Cow | Fresh | 98.7% | 99.1% | 99.1% | 97.2% | 13.9% |
| R32.39.3 | Farm W | Cow | Fresh | 99.6% | 99.5% | 99.6% | 99.6% | 99.5% |
| R32.4.3 | Farm W | Calf | Calf | 98.9% | 98.6% | 99.2% | 98.9% | 98.6% |
| R32.40.7 | Farm W | Cow | Fresh | 99.2% | 98.9% | 59.5% | 99.2% | 99.2% |
| R32.44.1 | Farm W | Cow | 1st High | 99.4% | 99.4% | 99.4% | 99.4% | 99.2% |
| R32.45.2 | Farm W | Cow | 1st High | 99.6% | 13.1% | 25.5% | 99.5% | 40.6% |
| R32.45.5 | Farm W | Cow | 1st High | 0.0% | 0.0% | 0.0% | 0.0% | 0.0% |
| R32.48.6 | Farm W | Cow | 1st High | 99.3% | 98.3% | 99.5% | 99.3% | 99.3% |
| R32.48.9 | Farm W | Cow | 1st High | 99.3% | 98.8% | 99.1% | 99.1% | 99.1% |
| R32.49.6 | Farm W | Cow | 1st High | 81.5% | 54.9% | 53.1% | 88.7% | 58.1% |
| R32.51.2 | Farm W | Cow | High Mature | 99.4% | 99.0% | 99.4% | 99.4% | 99.5% |
| R32.7.8 | Farm W | Calf | Calf | 99.6% | 99.3% | 99.4% | 99.3% | 99.3% |
| R33.12.5 | Farm BR | Cow | 1st High | 99.0% | 99.0% | 96.5% | 99.2% | 99.0% |
| R33.14.8 | Farm BR | Cow | 1st High | 99.4% | 99.4% | 99.7% | 99.6% | 99.7% |
| R33.15.6 | Farm BR | Cow | 1st High | 99.5% | 99.2% | 99.8% | 99.5% | 99.3% |
| R33.16.10 | Farm BR | Cow | Fresh | 99.2% | 99.2% | 99.2% | 99.2% | 99.0% |
| R33.16.2 | Farm BR | Cow | Fresh | 99.5% | 99.4% | 99.5% | 99.5% | 99.4% |
| R33.23.1 | Farm BR | Cow | Fresh | 99.3% | 99.2% | 99.3% | 99.3% | 99.2% |
| R33.23.2 | Farm BR | Cow | Fresh | 99.4% | 99.1% | 99.3% | 99.4% | 99.3% |
| R33.23.7 | Farm BR | Cow | Fresh | 99.2% | 99.6% | 99.6% | 99.4% | 99.6% |
| R33.23.9 | Farm BR | Cow | Fresh | 99.0% | 99.2% | 99.4% | 99.2% | 99.0% |
| R33.25.3 | Farm BR | Cow | Fresh | 99.5% | 99.5% | 99.6% | 99.6% | 99.3% |
| R33.26.1 | Farm BR | Cow | High Jerseys | 99.6% | 99.4% | 99.3% | 99.6% | 99.6% |
| R33.26.3 | Farm BR | Cow | High Jerseys | 99.3% | 94.9% | 96.5% | 99.3% | 41.2% |
| R33.27.3 | Farm BR | Cow | High Jerseys | 99.3% | 99.3% | 99.6% | 99.6% | 99.3% |
| R33.27.4 | Farm BR | Cow | High Jerseys | 99.7% | 99.5% | 99.9% | 99.9% | 99.9% |
| R33.27.5 | Farm BR | Cow | High Jerseys | 99.9% | 99.8% | 99.9% | 99.9% | 99.6% |
| R33.28.2 | Farm BR | Cow | High Jerseys | 99.9% | 99.9% | 99.8% | 99.6% | 99.8% |
| R33.29.3 | Farm BR | Cow | High Jerseys | 99.6% | 99.6% | 99.8% | 99.6% | 99.6% |
| R33.30.1 | Farm BR | Cow | High Jerseys | 99.6% | 99.0% | 99.0% | 99.6% | 99.2% |
| R33.32.8 | Farm BR | Cow | High Jerseys | 99.4% | 99.5% | 98.9% | 99.5% | 99.5% |
| R33.33.10 | Farm BR | Cow | High Jerseys | 99.1% | 29.2% | 33.4% | 66.3% | 41.3% |
| R33.33.2 | Farm BR | Cow | High Jerseys | 99.4% | 99.4% | 99.4% | 99.4% | 99.2% |
| R33.33.4 | Farm BR | Cow | High Jerseys | 99.1% | 60.9% | 99.4% | 99.3% | 99.3% |
| R33.33.9 | Farm BR | Cow | High Jerseys | 97.4% | 37.9% | 50.4% | 99.2% | 60.2% |
| R33.34.1 | Farm BR | Cow | High Jerseys | 99.1% | 75.6% | 96.1% | 99.1% | 98.9% |
| R33.34.9 | Farm BR | Cow | High Jerseys | 99.9% | 100.0% | 100.2% | 100.4% | 100.3% |
| R33.36.5 | Farm BR | Cow | High X's | 99.5% | 99.2% | 99.4% | 99.4% | 99.2% |
| R33.37.2 | Farm BR | Cow | High X's | 99.5% | 98.1% | 100.2% | 100.2% | 99.5% |
| R33.38.10 | Farm BR | Cow | High X's | 99.3% | 98.7% | 99.7% | 99.5% | 99.5% |
| R33.38.6 | Farm BR | Cow | High X's | 84.5% | 48.6% | 42.9% | 99.2% | 50.6% |
| R33.42.1 | Farm BR | Cow | Late | 99.6% | 99.5% | 99.8% | 99.6% | 99.5% |

TABLE 14-continued

Bacteriocin assay results displaying each isolate tested and the source of that isolate, isolated from Upper Midwest regional fecal or feed samples. Inhibition was calculated based on the percent of growth for each treatment well compared to the positive control.

| | | | | Bacillus Strains | | | | |
|---|---|---|---|---|---|---|---|---|
| Isolate ID | Farm | Type | Group | 747 | 1104 | 1541 | 1781 | 2018 |
| R33.42.10 | Farm BR | Cow | Late | 99.5% | 99.1% | 99.5% | 99.5% | 99.1% |
| R33.42.2 | Farm BR | Cow | Late | 99.5% | 99.5% | 99.8% | 99.6% | 99.6% |
| R33.42.4 | Farm BR | Cow | Late | 99.6% | 99.5% | 99.6% | 99.5% | 99.5% |
| R33.9.1 | Farm BR | Cow | High 1st | 99.5% | 99.4% | 93.4% | 99.7% | 44.1% |
| S73.8.1 | Farm E | Silage | Haylage Deep | 24.9% | 0.0% | 0.0% | 25.5% | 0.0% |
| S73.8.2 | Farm E | Silage | Haylage Deep | 18.3% | 0.0% | 0.0% | 23.7% | 0.0% |
| S77.6.3 | Farm Y | Silage | Heifer Haylage Deep | 96.3% | 96.3% | 96.3% | 97.9% | 95.5% |

Example 8: Selection of *Bacillus* Strains to Inhibit *Clostridium Perfringens* and Non-Toxigenic Clostridia Isolated from Ruminant Fecal Samples. (Great Lakes)

Introduction:

*Clostridium* is a genus of Gram-positive, spore-forming bacteria that are common residents of the gastrointestinal tract. A number of *Clostridium* species have been linked to enteric disease in ruminants including hemorrhagic bowel syndrome (HBS), a disease often correlated to elevated levels of *Clostridium perfringens* Type A. While most of the enteric diseases caused by clostridia are acute and occur sporadically in herds, in general, the prognosis is poor and the first sign of illness may be death. Based on recent results sub-acute enteric clostridia disease challenges may be a more wide spread issue than acute challenges. Due to a low success rate from treatment in acute disease challenges a more common, emphasis needs to be placed on prophylactic measures.

The purpose of this research was to characterize the distribution and diversity of clostridia in ruminants and ensure inhibition of these isolates using novel *Bacillus* strains as a method to control the clostridia populations.

Materials and Methods:

Fecal samples (265) from cows, heifers and calves gathered from 6 farms in the Great Lakes region were diluted 1:10 with sterile peptone, heat shocked for 30 minutes at 60° C., enumerated in sterile peptone and pour plated on Tryptose Sulphite Cycloserine (TSC) agar with D-cycloserine (400 mg/L) to select for clostridia species. Agar plates were incubated at 37° C. anaerobically for 24 hours. If present, isolated sulphite-reducing colonies were counted for a total clostridia count (CFU/g) and representative isolates were picked into Reinforced clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions were performed in 96-well blocks containing 500 μl presumptive clostridia culture per well. Cells were harvested by centrifugation at 4,700 rpm for 10 minutes, the supernatant was removed. Cells were re-suspended in 500 μl of 50 mM of EDTA-2Na (pH=8.0). Aliquots of 300 μl of the suspended cells were transferred to a new 96-well block and combined with 20 μl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 μl of lysis buffer (6 M Guanidine, 20% Triton-X 100, 10 mM Tris-HCL, pH 7.5) was added, mixed then incubated at room temperature for 15 minutes. Following the incubation 20 μl of Proteinase K (NEB, 800 U/mL) was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed centrifuging 750 μl of Column Wash Solution (Promega, A1318) at 4700 rpms for 1 minute and 30 seconds discarding flow through at the end of each spin. The binding plate was centrifuged for an additional 10 minutes at 4,700 rpm to remove any residual ethanol. A clean elution plate was then placed under the binding plate and DNA was eluted with 200 μl, pre-warmed (55° C.), Nuclease Free Water (Promega, P1195).

DNA was screened for toxin genes (α, β, ε, and ι) specific to *C. perfringens* using polymerase chain reaction (PCR). Amplification of toxin genes was executed using a multiplex PCR containing four primer sets (Yoo et al., 1997) (Table 1.) The PCR mixture contained 2.5 μl 10×PCR Buffer, 2 μl of 50 mM $MgCl_2$, 0.5 μM of each primer (Table 1.), 0.1 μl of Invitrogen™ Platinum™ Taq DNA Polymerase, 2.5 μl of DNA, sterile water was added to achieve 25 μl for a total reaction volume. The mixture underwent 5 minutes at 94° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved. If one or multiple toxin genes were observed a toxin type identification was assigned to each isolate based on their toxin gene profile (Songer, 1996). *C. perfringens* positive to total clostridia isolate ratio was used to calculate an estimated *C. perfringens* count based on the total clostridia count.

Unique strain-specific genetic fingerprints were generated using Random Amplification of Polymorphic DNA (RAPD) analysis on select isolates to determine diversity among fecal *C. perfringens* isolates. The PCR contained 5 μl of DNA, 2.5 μl RAPD primer 2 (10 μM) (Table 1.), and 17.5 μl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes finishing with a final elongation of 5 minutes at 72° C. PCR products observed on a Fragment Analyzer (Advanced Analytics) to determine amplification patterns and were imported into BioNumerics, bioinformatics software, for analysis. RAPD patterns were compared with a band based Dice correlation analysis method to determine the similarity between RAPD patterns as a way to monitor diversity between isolates.

Antimicrobial screening was done on *C. perfringens* isolates obtained from ruminant samples to gauge the effectiveness of the antimicrobial bacteriocin produced by the inventors' identified *Bacillus* strains 747, 1104, 1541, 1781, and 2018. Bacteriocin was harvested by growing each strain at 32° C. in a shaking incubator at 150 rpms for 24 hours in Brain Heart Infusion (BHI) broth. A 1% transfer of the 24-hour culture to fresh BHI broth was executed after incubation. The *Bacillus* were then incubated for 36-48 hours in a 32° C. shaking incubator at 150 rpms. The culture was then centrifuged at 14,000×g for 20 minutes, supernatant was then filtered with a 0.2 m filter to remove any residual cells.

A bacteriocin turbidity assay was executed by growing *C. perfringens* strains isolated from ruminant fecal samples in RCM for 24 hours, anaerobically, at 37° C. Overnight culture was transferred (1%) to sterile RCM and immediately used in the assay. For each *C. perfringens* isolate at least six wells were run in a sterile 48 well reaction plate, 600 μl inoculated culture (positive control), 600 μl inoculated RCM+70 μl bacteriocin (747, 1104, 1541, 1781, and 2018) and 670 RCM (un-inoculated, negative control). Plates were incubated anaerobically at 37° C. for 24 hours then read using a BioTek Epoch Microplate Spectrophotometer, readings were taken at a wavelength of 600 nm. Optical density readings from the negative controls were subtracted from all OD readings and percent inhibition was calculated using the positive control and each bacteriocin treatment.

To identify clostridia that did not have at least one toxin gene specific to *C. perfringens*, a PCR reaction was performed on the isolate DNA to amplify the 16S region of rDNA using primers 27F-YM and 1492R-Y (Table 1). This was done on 20% of the isolates that did not contain a toxin gene specific to *C. perfringens*. The PCR mixture contained 5 μl of 10×PCR Buffer, 2 μl of 50 mM $MgCl_2$, 1 μl of 50 mM dNTPs, 0.4 μM of each primer (Table 1.), 0.2 μl of Invitrogen™ Platinum™ Taq DNA Polymerase, 5 μl of DNA, and sterile water was added to achieve 50 μl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to gene wiz to obtain the sequences for the 16S genes. Sequences were compared to known typed bacterial strains obtained from EZbiocloud online electronic database. Based on comparisons of these sequences a bacterial identification was assigned to the isolates.

Results:

Fecal samples, 265, were collect from 6 Great Lakes Regional farms (Michigan, Indiana, Ohio, New York) from which 2,715 presumptive clostridia isolates were isolated as representatives of the clostridial diversity in the Great Lakes region (Table 15.).

Clostridia enumeration results indicated the average level of clostridia CFU/g across all calf fecal samples was 180, 000 CFU/g with individual fecal samples ranging from 50 to 2,910,000 CFU/g. While the average level of clostridia CFU/g across all cow fecal samples was 69,800 CFU/g with individual fecal samples ranging from 10 to 125,000 CFU/g (FIG. 55.). Samples appeared to range in clostridia levels for both calves (FIG. 56.) and cows (FIG. 57.).

*C. perfringens* enumeration results displayed the average level of *C. perfringens* CFU/g across all calf fecal samples was 1,620 CFU/g with individual samples ranging from <10 to 1,450,000 CFU/g. While the average level of *C. perfringens* CFU/g across all cow fecal samples was 1,250 CFU/g with individual samples ranging from <10 to 125,000 CFU/g (FIG. 58.). Samples appeared to range in clostridia levels for both calves (FIG. 59.) and cows (FIG. 60.).

Analysis of the toxin multiplex PCR results displayed which isolates contained toxin genes specific to *C. perfringens*. A total of 2,715 presumptive clostridia isolates from fecal samples have been tested for the indicated *C. perfringens* toxin genes. Of the 2,715 clostridia isolates screened, 1,456 isolates (53.6%) tested positive for at least 1 of the toxin genes. From the 1,456 toxin-gene positive isolates 1,427 (98%) were identified as Type A (αtoxin only), however β, ε and ι, toxins were also detected in the clostridia fecal isolates.

Gentic RAPD fingerprint patterns displayed diversity among the 1,276 isolates that successful amplified. The isolates tested were harvested from calf fecal, cow fecal and feed and did not cluster strictly based on the sample type or farm. Isolates formed 162 clusters based on 75% similarity according to the Dice correlation method. The largest cluster was 102 isolates (8.0%) and comprised of isolates from all six farms.

Representatives from the RAPD dendrogram were selected to capture the diversity of the *C. perfringens* population from this region and subjected to inhibition assays. Antimicrobial testing using the bacteriocin turbidity assay displayed good inhibition of most ruminant fecal *C. perfringens* isolates using bacteriocin harvested from 747, 1104, 1541, 1781, and 2018. The bacteriocin from at least one of the strains 747, 1104, 1541, 1781, and 2018 were able to inhibit the growth >60% of 221 of the 254 isolates tested representing a total of 89.0% inhibition of the *C. perfringens* population based on the dendrogramb (Table 16).

Out of the 2,715 isolates collected 1,259 isolates (46%) were found to be non-toxigenic clostridia. Sequencing representatives (n=190) from the non-toxigenic clostridia displayed one dominate clostridia group, *Clostridium bifermentans* group (*Paraclostridium bifermentans* and *P. benzoelyticum*). *Clostridium bifermentans* made up 50.0% of the non-toxigenic isolates (FIG. 61.).

Discussion:

Fecal samples were used as the most readily available sample type to estimate the level and obtain isolates of clostridia and *C. perfringens* within the digestive system of ruminants. From the 265 fecal samples collected throughout the Great Lakes region all samples had detectable levels of clostridia. The majority of isolates harvested (53.6%) from the ruminant samples contained a toxin gene specific to *C. perfringens*. *C. perfringens* was detected in 86% of the cow fecal samples and in 63% of the calf fecal samples. The high presence of clostridia and *C. perfringens* indicates the risk for sub-acute enteric clostridia disease challenges in most ruminants throughout the Great Lakes region. *C. perfringens* isolates were diverse according to the RAPD genetic fingerprints but were not specific to sample type or farm. Diverse representatives of *C. perfringens* were mostly inhibited (>60%) by at least one bacteriocin from the following strains 747, 1104, 1541, 1781 or 2018. From the 254 isolates tested 221 isolates were inhibited by greater than 60% by at least one of the strains, representing inhibition of 89.0% of the total *C. perfringens* population based on representation from clusters on the RAPD dendrogram. This indicates the *Bacillus* strains 747, 1104, 1541, 1781 and 2018 could inhibit a wide range of diversity of *C. perfringens* isolates. The *Bacillus* strains are not limited to specific clostridia strain(s) like a vaccine which may be missing large groups of the clostridia populations based on the genetic diversity observed in the RAPD dendrogram. DNA sequencing of the non-toxigenic clostridia revealed one major identification of *Clostridium* species, *Clostridium bifermentans*. The high inhibition level against the clostridia isolates in vitro indicates a potential mode of action of the *Bacillus* strains 747, 1104, 1541, 1781 and 2018.

The *Bacillus* strains offer a prophylactic effect on the clostridia populations which may not only increase rumen efficiency leading to increased milk production, but prevent acute levels of *C. perfringens* reducing the occurrence of digestive deaths. The high prevalence of clostridia and *C. perfringens* in fecal samples collected suggests efficiency improvement opportunities in many ruminants throughout the Great Lakes region. This example displays the diversity of clostridia isolates from the ruminant fecal and feed samples collected from the Great Lakes region. The *Bacillus* strains tested 747, 1104, 1541, 1781 and 2018, were able to inhibit most of the clostridia diversity observed in the Great Lakes region. The product, in accordance with this embodiment of the present invention was able to inhibit toxigenic clostridia isolated from ruminants in the Great Lakes region indicating a benefit in rumen efficiency if fed to dairy cows as a direct fed microbial (DFM).

TABLE 15

Fecal samples, 265, were collected from Great Lakes regional dairies separated by farm (6) and age (cow or calf) which were enumerated for clostridia, tested for *C. perfringens*, isolates were genotyped and tested for inhibition.

| Farm Name | State | Cow Fecal | Calf Fecal |
|---|---|---|---|
| Farm HG | Michigan | 65 | 6 |
| Farm H | Indiana | 55 | 9 |
| Farm M | Ohio | 40 | 5 |
| Farm U | Ohio | 10 | 4 |
| Farm C | New York | 35 | 5 |
| Farm P | New York | 25 | 6 |
| Total | | 230 | 35 |

TABLE 16

Bacteriocin assay results displaying each isolate tested and the source of that isolate, isolated from Great Lakes regional fecal samples. Inhibition was calculated based on the percent of growth for each treatment well compared to the positive control.

| | | | | *Bacillus* Strains | | | | |
|---|---|---|---|---|---|---|---|---|
| Isolate ID | Farm | Type | Group | 747 | 1104 | 1541 | 1781 | 2018 |
| R12.1.2 | Farm C | Calf Fecal | Calf | 96.9% | 95.8% | 96.0% | 95.0% | 94.6% |
| R12.1.6 | Farm C | Calf Fecal | Calf | 97.3% | 95.5% | 96.4% | 95.0% | 94.8% |
| R12.11.1 | Farm C | Cow Fecal | Medium | 85.8% | 79.9% | 0.0% | 66.7% | 67.6% |
| R12.11.4 | Farm C | Cow Fecal | Medium | 97.1% | 94.7% | 94.8% | 92.9% | 92.8% |
| R12.11.9 | Farm C | Cow Fecal | Medium | 92.8% | 84.9% | 88.9% | 84.4% | 82.5% |
| R12.12.1 | Farm C | Cow Fecal | Medium | 95.4% | 93.7% | 95.4% | 93.3% | 94.2% |
| R12.12.3 | Farm C | Cow Fecal | Medium | 97.2% | 95.8% | 97.2% | 96.6% | 96.4% |
| R12.12.4 | Farm C | Cow Fecal | Medium | 95.3% | 94.0% | 95.1% | 94.6% | 95.4% |
| R12.13.3 | Farm C | Cow Fecal | Medium | 97.1% | 96.4% | 96.3% | 95.2% | 96.0% |
| R12.13.6 | Farm C | Cow Fecal | Medium | 94.2% | 95.3% | 92.7% | 91.2% | 93.1% |
| R12.14.4 | Farm C | Cow Fecal | Medium | 96.3% | 95.4% | 95.5% | 94.9% | 95.5% |
| R12.14.7 | Farm C | Cow Fecal | Medium | 96.3% | 95.4% | 95.7% | 94.0% | 96.2% |
| R12.14.9 | Farm C | Cow Fecal | Medium | 96.1% | 87.7% | 93.3% | 92.6% | 78.7% |
| R12.15.7 | Farm C | Cow Fecal | Medium | 95.9% | 95.3% | 95.3% | 94.4% | 95.5% |
| R12.16.1 | Farm C | Cow Fecal | High | 95.0% | 98.6% | 100.0% | 100.0% | 100.0% |
| R12.16.5 | Farm C | Cow Fecal | High | 49.5% | 66.3% | 74.7% | 70.9% | 70.4% |
| R12.17.10 | Farm C | Cow Fecal | High | 96.4% | 95.9% | 96.5% | 95.4% | 96.5% |
| R12.18.1 | Farm C | Cow Fecal | High | 60.5% | 71.8% | 66.6% | 66.2% | 85.0% |
| R12.18.8 | Farm C | Cow Fecal | High | 97.2% | 96.4% | 96.8% | 96.4% | 97.2% |
| R12.18.9 | Farm C | Cow Fecal | High | 50.8% | 12.1% | 45.5% | 55.6% | 67.0% |
| R12.19.3 | Farm C | Cow Fecal | High | 0.0% | 0.0% | 4.6% | 2.3% | 0.0% |
| R12.19.4 | Farm C | Cow Fecal | High | 90.0% | 85.6% | 89.5% | 83.7% | 84.5% |
| R12.20.3 | Farm C | Cow Fecal | High | 95.8% | 94.1% | 94.9% | 94.4% | 95.7% |
| R12.20.5 | Farm C | Cow Fecal | High | 98.5% | 98.5% | 96.8% | 95.2% | 98.3% |
| R12.21.1 | Farm C | Cow Fecal | High | 97.0% | 96.2% | 96.8% | 96.5% | 97.0% |
| R12.21.2 | Farm C | Cow Fecal | High | 93.8% | 94.8% | 92.6% | 91.5% | 92.8% |
| R12.21.3 | Farm C | Cow Fecal | High | 91.3% | 0.0% | 0.0% | 18.9% | 0.0% |
| R12.21.4 | Farm C | Cow Fecal | High | 96.6% | 94.8% | 96.1% | 93.8% | 94.6% |
| R12.21.5 | Farm C | Cow Fecal | High | 97.2% | 95.2% | 96.2% | 94.7% | 95.5% |
| R12.22.4 | Farm C | Cow Fecal | High | 98.7% | 99.0% | 98.9% | 98.4% | 98.4% |
| R12.22.6 | Farm C | Cow Fecal | High | 98.7% | 97.9% | 17.5% | 98.4% | 97.9% |
| R12.24.1 | Farm C | Cow Fecal | High | 0.0% | 0.0% | 0.0% | 0.0% | 0.0% |
| R12.24.10 | Farm C | Cow Fecal | High | 99.1% | 98.7% | 99.3% | 98.8% | 98.8% |
| R12.24.7 | Farm C | Cow Fecal | High | 98.3% | 98.1% | 98.8% | 97.9% | 98.1% |
| R12.24.9 | Farm C | Cow Fecal | High | 98.6% | 97.7% | 98.6% | 98.2% | 98.2% |
| R12.25.2 | Farm C | Cow Fecal | High | 92.8% | 99.7% | 96.4% | 92.9% | 100.0% |
| R12.25.3 | Farm C | Cow Fecal | High | 95.4% | 97.8% | 100.0% | 96.6% | 100.0% |
| R12.25.5 | Farm C | Cow Fecal | High | 100.0% | 100.0% | 100.0% | 100.0% | 100.0% |
| R12.25.8 | Farm C | Cow Fecal | High | 95.4% | 93.1% | 96.0% | 96.0% | 94.0% |
| R12.25.9 | Farm C | Cow Fecal | High | 98.5% | 22.5% | 97.8% | 98.7% | 19.9% |
| R12.26.2 | Farm C | Cow Fecal | Far off dry | 95.0% | 94.2% | 95.1% | 95.3% | 91.2% |
| R12.26.3 | Farm C | Cow Fecal | Far off dry | 85.3% | 95.6% | 46.5% | 85.5% | 95.9% |
| R12.26.8 | Farm C | Cow Fecal | Far off dry | 97.3% | 96.7% | 96.7% | 96.2% | 95.7% |
| R12.26.9 | Farm C | Cow Fecal | Far off dry | 97.6% | 96.8% | 97.9% | 98.0% | 97.0% |
| R12.27.7 | Farm C | Cow Fecal | Far off dry | 98.2% | 98.5% | 99.1% | 98.1% | 98.1% |

TABLE 16-continued Bacteriocin assay results displaying each isolate tested and the source of that isolate, isolated from Great Lakes regional fecal samples. Inhibition was calculated based on the percent of growth for each treatment well compared to the positive control.

| | | | | Bacillus Strains | | | | |
|---|---|---|---|---|---|---|---|---|
| Isolate ID | Farm | Type | Group | 747 | 1104 | 1541 | 1781 | 2018 |
| R12.28.2 | Farm C | Cow Fecal | Far off dry | 91.0% | 89.1% | 92.9% | 89.6% | 90.0% |
| R12.29.5 | Farm C | Cow Fecal | Far off dry | 100.0% | 97.4% | 100.0% | 100.0% | 100.0% |
| R12.29.7 | Farm C | Cow Fecal | Far off dry | 100.0% | 98.6% | 100.0% | 100.0% | 98.7% |
| R12.3.1 | Farm C | Calf Fecal | Calf | 96.8% | 93.4% | 94.0% | 92.3% | 92.0% |
| R12.3.6 | Farm C | Calf Fecal | Calf | 97.1% | 95.0% | 94.4% | 93.6% | 92.5% |
| R12.3.7 | Farm C | Calf Fecal | Calf | 0.0% | 0.0% | 0.0% | 0.0% | 0.0% |
| R12.3.9 | Farm C | Calf Fecal | Calf | 8.1% | 0.0% | 0.0% | 0.0% | 0.0% |
| R12.30.5 | Farm C | Cow Fecal | Far off dry | 98.7% | 98.1% | 98.7% | 98.1% | 98.1% |
| R12.30.6 | Farm C | Cow Fecal | Far off dry | 98.5% | 97.4% | 98.3% | 98.7% | 98.1% |
| R12.32.4 | Farm C | Cow Fecal | Fresh | 95.3% | 89.3% | 94.7% | 94.0% | 100.7% |
| R12.32.8 | Farm C | Cow Fecal | Fresh | 99.1% | 98.8% | 99.7% | 98.3% | 98.8% |
| R12.33.10 | Farm C | Cow Fecal | Fresh | 98.9% | 98.5% | 99.4% | 98.5% | 98.7% |
| R12.34.3 | Farm C | Cow Fecal | Fresh | 99.2% | 98.3% | 99.1% | 98.5% | 98.4% |
| R12.37.3 | Farm C | Cow Fecal | Close Up | 98.7% | 98.6% | 99.1% | 98.5% | 98.2% |
| R12.38.10 | Farm C | Cow Fecal | Close Up | 96.5% | 95.1% | 96.9% | 95.3% | 95.1% |
| R12.4.2 | Farm C | Calf Fecal | Calf | 57.7% | 39.7% | 0.0% | 17.9% | 2.6% |
| R12.4.4 | Farm C | Calf Fecal | Calf | 0.0% | 0.0% | 0.0% | 0.0% | 0.0% |
| R12.4.9 | Farm C | Calf Fecal | Calf | 95.4% | 93.5% | 92.5% | 91.0% | 90.1% |
| R12.40.2 | Farm C | Cow Fecal | Close Up | 74.1% | 71.6% | 80.2% | 76.5% | 72.8% |
| R12.5.1 | Farm C | Calf Fecal | Calf | 97.0% | 94.9% | 18.1% | 93.7% | 59.8% |
| R12.5.2 | Farm C | Calf Fecal | Calf | 77.8% | 51.5% | 58.6% | 34.3% | 32.3% |
| R12.5.5 | Farm C | Calf Fecal | Calf | 84.9% | 75.3% | 71.0% | 65.6% | 64.5% |
| R12.5.8 | Farm C | Calf Fecal | Calf | 55.3% | 0.0% | 6.4% | 0.0% | 0.0% |
| R12.6.10 | Farm C | Cow Fecal | Medium | 96.7% | 95.8% | 95.8% | 94.9% | 95.5% |
| R12.7.2 | Farm C | Cow Fecal | Medium | 97.7% | 96.8% | 96.6% | 95.9% | 96.5% |
| R12.7.7 | Farm C | Cow Fecal | Medium | 95.4% | 92.2% | 91.9% | 89.8% | 87.6% |
| R12.9.2 | Farm C | Cow Fecal | Medium | 97.3% | 96.4% | 95.9% | 95.4% | 95.9% |
| R12.9.3 | Farm C | Cow Fecal | Medium | 95.6% | 92.7% | 92.4% | 89.5% | 89.2% |
| R13.1.5 | Farm P | Calf Fecal | Calf | 95.5% | 92.7% | 31.7% | 94.7% | 28.6% |
| R13.1.8 | Farm P | Calf Fecal | Calf | 93.2% | 59.4% | 0.0% | 93.7% | 1.0% |
| R13.10.10 | Farm P | Cow Fecal | Robot North | 96.3% | 95.5% | 81.0% | 95.1% | 91.4% |
| R13.10.3 | Farm P | Cow Fecal | Robot North | 96.1% | 94.3% | 91.3% | 88.4% | 18.6% |
| R13.10.6 | Farm P | Cow Fecal | Robot North | 98.9% | 98.6% | 99.2% | 98.4% | 98.5% |
| R13.10.9 | Farm P | Cow Fecal | Robot North | 99.1% | 61.1% | 39.8% | 97.4% | 63.1% |
| R13.11.2 | Farm P | Cow Fecal | Robot North | 94.7% | 88.6% | 90.9% | 92.1% | 89.7% |
| R13.11.6 | Farm P | Cow Fecal | Robot North | 9.7% | 15.9% | 20.9% | 6.1% | 29.7% |
| R13.11.8 | Farm P | Cow Fecal | Robot North | 27.3% | 93.9% | 0.0% | 95.0% | 4.3% |
| R13.11.9 | Farm P | Cow Fecal | Robot North | 96.2% | 95.6% | 95.7% | 95.2% | 96.0% |
| R13.12.10 | Farm P | Cow Fecal | Robot South | 59.1% | 5.1% | 0.0% | 80.0% | 43.7% |
| R13.12.3 | Farm P | Cow Fecal | Robot South | 95.1% | 94.1% | 70.9% | 93.7% | 92.9% |
| R13.13.4 | Farm P | Cow Fecal | Robot South | 96.2% | 0.6% | 0.0% | 97.7% | 29.9% |
| R13.13.8 | Farm P | Cow Fecal | Robot South | 77.5% | 42.9% | 0.6% | 69.9% | 15.8% |
| R13.14.3 | Farm P | Cow Fecal | Robot South | 60.0% | 51.7% | 12.3% | 68.7% | 35.8% |
| R13.15.4 | Farm P | Cow Fecal | Robot South | 89.3% | 69.4% | 35.5% | 89.2% | 76.0% |
| R13.16.5 | Farm P | Cow Fecal | Far Dry | 96.3% | 28.3% | 7.5% | 95.9% | 11.7% |
| R13.16.7 | Farm P | Cow Fecal | Far Dry | 49.2% | 16.1% | 1.8% | 54.5% | 4.3% |
| R13.16.9 | Farm P | Cow Fecal | Far Dry | 95.0% | 14.5% | 5.1% | 97.8% | 35.0% |
| R13.17.1 | Farm P | Cow Fecal | Far Dry | 88.1% | 15.2% | 0.0% | 85.7% | 64.8% |
| R13.17.5 | Farm P | Cow Fecal | Far Dry | 0.0% | 0.0% | 0.0% | 0.0% | 0.0% |
| R13.18.3 | Farm P | Cow Fecal | Far Dry | 0.0% | 0.0% | 0.0% | 0.0% | 0.0% |
| R13.19.4 | Farm P | Cow Fecal | Far Dry | 73.2% | 72.5% | 8.4% | 73.7% | 61.1% |
| R13.2.2 | Farm P | Calf Fecal | Calf | 92.0% | 3.4% | 0.0% | 91.3% | 1.5% |
| R13.2.3 | Farm P | Calf Fecal | Calf | 99.2% | 99.0% | 99.4% | 99.6% | 98.3% |
| R13.21.1 | Farm P | Cow Fecal | Far Dry | 95.4% | 14.0% | 0.0% | 95.0% | 0.0% |
| R13.21.5 | Farm P | Cow Fecal | Far Dry | 5.7% | 12.7% | 16.0% | 0.0% | 12.0% |
| R13.22.7 | Farm P | Cow Fecal | 1st Lact | 0.0% | 5.2% | 5.6% | 0.0% | 10.8% |
| R13.23.2 | Farm P | Cow Fecal | 1st Lact | 0.0% | 0.0% | 0.8% | 0.0% | 15.9% |
| R13.23.5 | Farm P | Cow Fecal | 1st Lact | 55.5% | 45.5% | 17.6% | 66.3% | 46.5% |
| R13.23.7 | Farm P | Cow Fecal | 1st Lact | 96.8% | 31.5% | 48.1% | 47.5% | 39.5% |
| R13.25.5 | Farm P | Cow Fecal | 1st Lact | 78.5% | 45.9% | 10.3% | 76.3% | 60.3% |
| R13.25.6 | Farm P | Cow Fecal | 1st Lact | 86.0% | 23.1% | 0.0% | 6.5% | 48.3% |
| R13.25.9 | Farm P | Cow Fecal | 1st Lact | 93.5% | 85.0% | 38.8% | 94.5% | 29.8% |
| R13.26.4 | Farm P | Cow Fecal | 1st Lact | 83.4% | 57.0% | 20.2% | 89.0% | 61.4% |
| R13.26.5 | Farm P | Cow Fecal | 1st Lact | 72.9% | 62.8% | 0.0% | 80.5% | 51.9% |
| R13.27.7 | Farm P | Cow Fecal | Close-up Dry | 42.0% | 0.0% | 7.2% | 28.8% | 36.8% |
| R13.28.1 | Farm P | Cow Fecal | Close-up Dry | 75.7% | 63.3% | 0.0% | 85.8% | 52.9% |
| R13.28.2 | Farm P | Cow Fecal | Close-up Dry | 88.8% | 32.6% | 16.2% | 27.5% | 57.7% |
| R13.31.4 | Farm P | Cow Fecal | Close-up Dry | 92.9% | 28.6% | 25.5% | 99.7% | 51.0% |
| R13.4.1 | Farm P | Calf Fecal | Calf | 93.8% | 61.8% | 90.8% | 88.9% | 17.3% |
| R13.5.10 | Farm P | Calf Fecal | Calf | 94.1% | 91.6% | 7.2% | 93.9% | 17.8% |
| R13.5.3 | Farm P | Calf Fecal | Calf | 96.7% | 95.9% | 96.1% | 96.0% | 96.5% |
| R13.5.5 | Farm P | Calf Fecal | Calf | 89.0% | 85.3% | 54.0% | 83.4% | 55.7% |

TABLE 16-continued

Bacteriocin assay results displaying each isolate tested and the source of that isolate, isolated from Great Lakes regional fecal samples. Inhibition was calculated based on the percent of growth for each treatment well compared to the positive control.

| | | | | Bacillus Strains | | | | |
|---|---|---|---|---|---|---|---|---|
| Isolate ID | Farm | Type | Group | 747 | 1104 | 1541 | 1781 | 2018 |
| R13.5.7 | Farm P | Calf Fecal | Calf | 96.4% | 95.3% | 94.0% | 93.0% | 93.7% |
| R13.5.8 | Farm P | Calf Fecal | Calf | 95.1% | 50.9% | 51.4% | 91.7% | 20.5% |
| R13.6.10 | Farm P | Calf Fecal | Calf | 93.7% | 93.5% | 91.2% | 76.5% | 85.4% |
| R13.7.5 | Farm P | Cow Fecal | Robot North | 22.5% | 3.0% | 0.0% | 85.4% | 6.4% |
| R13.7.7 | Farm P | Cow Fecal | Robot North | 95.9% | 95.2% | 96.3% | 95.4% | 96.1% |
| R13.8.3 | Farm P | Cow Fecal | Robot North | 100.0% | 99.7% | 99.9% | 100.0% | 100.0% |
| R13.9.5 | Farm P | Cow Fecal | Robot North | 95.6% | 94.7% | 93.7% | 95.5% | 95.0% |
| R13.9.6 | Farm P | Cow Fecal | Robot North | 96.7% | 95.1% | 0.0% | 96.3% | 0.0% |
| R13.9.8 | Farm P | Cow Fecal | Robot North | 15.9% | 5.4% | 10.8% | 14.9% | 13.9% |
| R28.16.5 | Farm HG | Cow Fecal | Fresh | 99.7% | 99.8% | 99.8% | 88.1% | 100.0% |
| R28.21.3 | Farm HG | Cow Fecal | Close-up | 97.4% | 95.8% | 99.5% | 94.9% | 97.2% |
| R28.26.2 | Farm HG | Cow Fecal | Close-up | 27.0% | 0.0% | 0.0% | 6.7% | 40.4% |
| R28.26.3 | Farm HG | Cow Fecal | Close-up | 21.0% | 19.0% | 0.0% | 0.0% | 7.6% |
| R28.26.4 | Farm HG | Cow Fecal | Close-up | 96.3% | 97.3% | 90.7% | 96.0% | 95.6% |
| R28.29.5 | Farm HG | Cow Fecal | First | 96.5% | 95.5% | 92.2% | 94.8% | 96.5% |
| R28.39.3 | Farm HG | Cow Fecal | High | 98.0% | 98.2% | 99.9% | 97.6% | 98.4% |
| R28.39.8 | Farm HG | Cow Fecal | High | 18.2% | 0.0% | 0.0% | 0.0% | 2.8% |
| R28.42.5 | Farm HG | Cow Fecal | High | 92.2% | 91.9% | 88.2% | 92.6% | 95.7% |
| R28.47.1 | Farm HG | Cow Fecal | Late | 100.2% | 99.8% | 99.8% | 99.8% | 100.2% |
| R28.51.1 | Farm HG | Cow Fecal | Far Off | 99.1% | 67.0% | 100.0% | 100.0% | 78.9% |
| R28.52.4 | Farm HG | Cow Fecal | Far Off | 74.5% | 22.0% | 76.7% | 70.0% | 71.4% |
| R28.58.4 | Farm HG | Cow Fecal | Far Off | 100.0% | 98.2% | 100.0% | 100.0% | 99.8% |
| R28.62.10 | Farm HG | Cow Fecal | Negative | 98.5% | 40.8% | 98.8% | 99.2% | 99.9% |
| R28.65.4 | Farm HG | Cow Fecal | Negative | 86.1% | 82.6% | 80.6% | 88.6% | 92.1% |
| R28.65.5 | Farm HG | Cow Fecal | Negative | 98.5% | 98.8% | 98.7% | 98.2% | 99.1% |
| R28.65.8 | Farm HG | Cow Fecal | Negative | 100.0% | 100.0% | 100.0% | 100.0% | 99.3% |
| R28.65.9 | Farm HG | Cow Fecal | Negative | 100.5% | 99.9% | 98.8% | 95.9% | 100.5% |
| R28.67.5 | Farm HG | Cow Fecal | Negative | 58.8% | 44.8% | 67.0% | 60.5% | 68.6% |
| R28.68.6 | Farm HG | Cow Fecal | Negative | 46.1% | 100.0% | 100.0% | 94.2% | 95.5% |
| R28.7.5 | Farm HG | Cow Fecal | Fresh | 52.5% | 52.5% | 0.0% | 39.7% | 44.0% |
| R28.7.8 | Farm HG | Cow Fecal | Fresh | 71.7% | 76.3% | 0.0% | 79.9% | 75.9% |
| R28.70.1 | Farm HG | Cow Fecal | Negative | 100.0% | 99.4% | 99.9% | 100.0% | 100.0% |
| R28.70.2 | Farm HG | Cow Fecal | Negative | 100.0% | 99.7% | 100.0% | 100.0% | 100.0% |
| R28.70.3 | Farm HG | Cow Fecal | Negative | 98.0% | 98.4% | 97.8% | 97.0% | 98.4% |
| R28.71.8 | Farm HG | Cow Fecal | Negative | 51.2% | 0.0% | 34.4% | 36.3% | 66.4% |
| R28.8.1 | Farm HG | Cow Fecal | Fresh | 78.9% | 83.5% | 83.5% | 78.6% | 79.9% |
| R29.1.1 | Farm H | Calf Fecal | Calf | 77.2% | 78.5% | 70.6% | 74.7% | 81.2% |
| R29.10.6 | Farm H | Cow Fecal | Fresh | 100.0% | 91.9% | 99.5% | 99.8% | 99.8% |
| R29.12.2 | Farm H | Cow Fecal | Fresh | 100.0% | 42.8% | 100.0% | 98.7% | 99.8% |
| R29.16.10 | Farm H | Cow Fecal | Fresh | 99.6% | 99.8% | 99.8% | 99.8% | 99.9% |
| R29.17.1 | Farm H | Cow Fecal | Fresh | 97.4% | 85.2% | 84.6% | 97.7% | 96.7% |
| R29.19.5 | Farm H | Cow Fecal | Fresh | 34.7% | 28.3% | 26.0% | 32.3% | 33.4% |
| R29.20.2 | Farm H | Cow Fecal | Fresh | 100.0% | 99.7% | 97.0% | 98.9% | 100.0% |
| R29.21.10 | Farm H | Cow Fecal | Fresh | 100.0% | 100.0% | 99.4% | 98.6% | 100.0% |
| R29.21.9 | Farm H | Cow Fecal | Fresh | 100.0% | 100.0% | 99.4% | 98.8% | 91.7% |
| R29.22.1 | Farm H | Cow Fecal | Fresh | 100.0% | 100.0% | 99.8% | 98.6% | 100.0% |
| R29.22.5 | Farm H | Cow Fecal | Fresh | 100.0% | 100.0% | 100.0% | 99.1% | 100.0% |
| R29.22.7 | Farm H | Cow Fecal | Fresh | 100.0% | 100.0% | 100.0% | 99.1% | 99.8% |
| R29.23.10 | Farm H | Cow Fecal | Fresh | 100.0% | 100.0% | 98.5% | 98.5% | 99.4% |
| R29.23.8 | Farm H | Cow Fecal | Fresh | 100.0% | 100.0% | 98.5% | 98.6% | 99.6% |
| R29.24.1 | Farm H | Cow Fecal | Fresh | 90.3% | 88.0% | 85.8% | 89.4% | 90.8% |
| R29.24.3 | Farm H | Cow Fecal | Fresh | 100.0% | 97.8% | 96.3% | 97.4% | 98.7% |
| R29.24.9 | Farm H | Cow Fecal | Fresh | 100.0% | 99.8% | 99.1% | 97.2% | 98.4% |
| R29.25.7 | Farm H | Cow Fecal | Close-up | 100.0% | 14.0% | 99.6% | 97.6% | 98.7% |
| R29.26.4 | Farm H | Cow Fecal | Close-up | 100.0% | 96.9% | 99.9% | 96.0% | 98.4% |
| R29.26.7 | Farm H | Cow Fecal | Close-up | 100.0% | 39.3% | 100.0% | 84.6% | 96.8% |
| R29.28.1 | Farm H | Cow Fecal | Close-up | 100.0% | 100.0% | 100.0% | 100.0% | 100.0% |
| R29.28.7 | Farm H | Cow Fecal | Close-up | 99.6% | 56.5% | 37.5% | 99.3% | 97.7% |
| R29.31.1 | Farm H | Cow Fecal | Close-up | 100.0% | 0.0% | 100.0% | 0.0% | 100.0% |
| R29.31.3 | Farm H | Cow Fecal | Close-up | 99.7% | 0.0% | 100.0% | 6.5% | 100.0% |
| R29.35.7 | Farm H | Cow Fecal | Pregnant | 100.0% | 67.0% | 70.9% | 100.0% | 99.9% |
| R29.35.8 | Farm H | Cow Fecal | Pregnant | 100.0% | 99.1% | 100.0% | 100.0% | 99.9% |
| R29.36.2 | Farm H | Cow Fecal | Pregnant | 100.0% | 0.0% | 60.5% | 0.0% | 0.0% |
| R29.36.8 | Farm H | Cow Fecal | Pregnant | 99.7% | 0.0% | 13.3% | 99.3% | 98.7% |
| R29.40.9 | Farm H | Cow Fecal | Pregnant | 74.8% | 71.0% | 73.1% | 71.2% | 70.6% |
| R29.49.2 | Farm H | Cow Fecal | High | 100.0% | 99.0% | 100.0% | 100.0% | 100.0% |
| R29.49.9 | Farm H | Cow Fecal | High | 61.9% | 58.5% | 64.7% | 61.0% | 62.0% |
| R29.60.3 | Farm H | Cow Fecal | Late | 100.0% | 100.0% | 100.0% | 100.0% | 99.6% |
| R29.63.3 | Farm H | Cow Fecal | Late | 100.0% | 100.0% | 100.0% | 100.0% | 100.0% |
| R29.63.5 | Farm H | Cow Fecal | Late | 100.0% | 99.3% | 43.9% | 100.0% | 93.6% |
| R29.63.6 | Farm H | Cow Fecal | Late | 100.0% | 99.4% | 100.0% | 100.0% | 100.0% |
| R29.63.7 | Farm H | Cow Fecal | Late | 100.0% | 99.1% | 100.0% | 100.0% | 100.0% |

TABLE 16-continued

Bacteriocin assay results displaying each isolate tested and the source of that isolate, isolated from Great Lakes regional fecal samples. Inhibition was calculated based on the percent of growth for each treatment well compared to the positive control.

| | | | | Bacillus Strains | | | | |
|---|---|---|---|---|---|---|---|---|
| Isolate ID | Farm | Type | Group | 747 | 1104 | 1541 | 1781 | 2018 |
| R29.63.8 | Farm H | Cow Fecal | Late | 54.9% | 46.2% | 45.7% | 53.4% | 67.5% |
| R34.11.8 | Farm U | Cow Fecal | Lact. Cows | 100.0% | 65.0% | 48.3% | 100.0% | 82.8% |
| R34.13.10 | Farm U | Cow Fecal | Lact. Cows | 86.1% | 47.4% | 38.0% | 80.9% | 87.9% |
| R34.14.3 | Farm U | Cow Fecal | Lact. Cows | 97.0% | 17.2% | 21.9% | 24.3% | 61.8% |
| R34.4.4 | Farm U | Calf Fecal | Calf | 99.9% | 97.9% | 99.7% | 100.1% | 99.2% |
| R34.6.1 | Farm U | Cow Fecal | Lact. Cows | 84.1% | 54.0% | 4.3% | 80.0% | 81.8% |
| R34.9.2 | Farm U | Cow Fecal | Lact. Cows | 90.2% | 0.0% | 0.0% | 100.0% | 100.0% |
| R34.9.4 | Farm U | Cow Fecal | Lact. Cows | 71.2% | 46.8% | 49.5% | 83.2% | 31.7% |
| R34.9.8 | Farm U | Cow Fecal | Lact. Cows | 100.0% | 35.7% | 100.0% | 100.0% | 100.0% |
| R35.10.1 | Farm M | Cow Fecal | Hi 2 yr olds | 80.0% | 1.5% | 2.8% | 91.9% | 37.5% |
| R35.10.5 | Farm M | Cow Fecal | Hi 2 yr olds | 34.5% | 99.0% | 99.6% | 100.0% | 99.7% |
| R35.10.6 | Farm M | Cow Fecal | Hi 2 yr olds | 100.0% | 100.0% | 0.0% | 100.0% | 98.0% |
| R35.10.7 | Farm M | Cow Fecal | Hi 2 yr olds | 99.8% | 55.8% | 59.3% | 92.4% | 99.1% |
| R35.11.4 | Farm M | Cow Fecal | Hi 2 yr olds | 99.1% | 97.9% | 0.0% | 95.9% | 15.3% |
| R35.11.6 | Farm M | Cow Fecal | Hi 2 yr olds | 99.8% | 98.1% | 23.3% | 100.0% | 0.0% |
| R35.11.7 | Farm M | Cow Fecal | Hi 2 yr olds | 98.2% | 0.0% | 0.0% | 37.1% | 87.4% |
| R35.11.9 | Farm M | Cow Fecal | Hi 2 yr olds | 98.6% | 0.0% | 90.9% | 87.4% | 62.0% |
| R35.12.9 | Farm M | Cow Fecal | Hi 2 yr olds | 67.2% | 28.0% | 0.0% | 63.0% | 36.2% |
| R35.21.9 | Farm M | Cow Fecal | High Mature cows | 92.9% | 59.8% | 0.0% | 90.7% | 10.5% |
| R35.22.1 | Farm M | Cow Fecal | High Mature cows | 0.0% | 0.0% | 0.0% | 0.0% | 0.0% |
| R35.25.6 | Farm M | Cow Fecal | High Mature cows | 99.8% | 99.8% | 99.8% | 99.8% | 97.1% |
| R35.26.3 | Farm M | Cow Fecal | Low Cows | 100.0% | 98.9% | 100.0% | 100.0% | 100.0% |
| R35.26.5 | Farm M | Cow Fecal | Low Cows | 68.4% | 40.6% | 58.9% | 62.5% | 67.7% |
| R35.28.3 | Farm M | Cow Fecal | Low Cows | 99.8% | 98.8% | 22.4% | 97.6% | 97.2% |
| R35.29.10 | Farm M | Cow Fecal | Low Cows | 100.0% | 99.0% | 100.0% | 100.0% | 100.0% |
| R35.29.8 | Farm M | Cow Fecal | Low Cows | 100.0% | 100.0% | 98.8% | 100.0% | 100.0% |
| R35.3.2 | Farm M | Calf Fecal | Calf | 100.0% | 99.9% | 100.0% | 100.0% | 100.0% |
| R35.30.8 | Farm M | Cow Fecal | Low Cows | 100.0% | 99.1% | 100.0% | 100.0% | 100.0% |
| R35.31.2 | Farm M | Cow Fecal | Low Cows | 99.8% | 98.3% | 98.3% | 99.7% | 99.5% |
| R35.32.10 | Farm M | Cow Fecal | Low Cows | 87.2% | 84.2% | 82.4% | 96.0% | 88.9% |
| R35.33.5 | Farm M | Cow Fecal | Low Cows | 22.8% | 0.0% | 18.4% | 0.0% | 0.0% |
| R35.35.2 | Farm M | Cow Fecal | Dry Cows | 100.0% | 84.1% | 100.0% | 100.0% | 100.0% |
| R35.35.5 | Farm M | Cow Fecal | Dry Cows | 96.4% | 88.3% | 91.5% | 91.6% | 93.1% |
| R35.35.8 | Farm M | Cow Fecal | Dry Cows | 100.0% | 99.6% | 100.0% | 97.7% | 100.0% |
| R35.38.9 | Farm M | Cow Fecal | Dry Cows | 96.3% | 98.3% | 98.1% | 95.5% | 98.7% |
| R35.6.6 | Farm M | Cow Fecal | Hi 2 yr olds | 100.0% | 99.6% | 99.9% | 100.0% | 100.0% |
| R35.6.9 | Farm M | Cow Fecal | Hi 2 yr olds | 91.2% | 0.0% | 0.0% | 96.0% | 43.9% |
| R35.8.2 | Farm M | Cow Fecal | Hi 2 yr olds | 100.0% | 100.0% | 100.0% | 100.0% | 100.0% |
| R35.8.3 | Farm M | Cow Fecal | Hi 2 yr olds | 100.0% | 6.1% | 0.0% | 100.0% | 100.0% |
| R35.9.5 | Farm M | Cow Fecal | Hi 2 yr olds | 100.0% | 100.0% | 11.7% | 100.0% | 100.0% |
| S52.14.1 | Farm P | TMR | Robot Barn | 0.0% | 0.0% | 11.8% | 20.6% | 69.0% |
| S52.14.7 | Farm P | TMR | Robot Barn | 0.0% | 0.0% | 0.0% | 0.0% | 0.0% |
| S53.11.1 | Farm C | TMR | Fresh | 0.0% | 0.0% | 0.0% | 0.0% | 0.0% |
| S53.5.5 | Farm C | Straw | Dry Cows | 0.0% | 0.0% | 0.0% | 0.0% | 2.1% |
| S53.5.6 | Farm C | Straw | Dry Cows | 32.6% | 35.9% | 9.1% | 41.1% | 40.7% |
| S53.5.7 | Farm C | Straw | Dry Cows | 0.0% | 0.0% | 0.0% | 0.0% | 0.0% |
| S53.7.3 | Farm C | Ground Corn | | 0.0% | 6.4% | 0.0% | 7.3% | 0.0% |
| S53.7.6 | Farm C | Ground Corn | | 0.0% | 0.0% | 0.0% | 0.0% | 0.0% |
| S53.7.7 | Farm C | Ground Corn | | 10.9% | 0.0% | 0.0% | 0.0% | 8.4% |
| S74.7.1 | Farm HG | Ground Corn | | 73.9% | 65.9% | 46.1% | 35.3% | 65.9% |
| S75.3.1 | Farm H | TMR | Close-up | 100.0% | 99.2% | 100.0% | 100.0% | 100.0% |
| S75.3.10 | Farm H | TMR | Close-up | 100.0% | 100.0% | 100.0% | 100.0% | 100.0% |
| S75.5.1 | Farm H | TMR | Late | 34.4% | 24.2% | 40.7% | 60.0% | 43.1% |
| S75.8.1 | Farm H | Pellets | Calf | 100.0% | 100.0% | 100.0% | 100.0% | 100.0% |
| S75.8.3 | Farm H | Pellets | Calf | 100.0% | 99.8% | 99.7% | 100.0% | 100.0% |
| S75.8.5 | Farm H | Pellets | Calf | 100.0% | 100.0% | 100.0% | 100.0% | 99.2% |
| S75.8.9 | Farm H | Pellets | Calf | 100.0% | 100.0% | 100.0% | 100.0% | 100.0% |
| S75.9.1 | Farm H | Soy Hulls | | 100.0% | 100.0% | 99.7% | 100.0% | 99.7% |
| S75.9.2 | Farm H | Soy Hulls | | 99.7% | 100.0% | 99.5% | 99.8% | 99.8% |
| S80.4.1 | Farm U | TMR | Cow | 0.0% | 0.0% | 0.0% | 33.7% | 13.4% |
| S81.10.6 | Farm M | Wheat Midds | | 100.0% | 100.0% | 100.0% | 100.0% | 100.0% |
| S81.11.1 | Farm M | Bird Seed Screening | | 91.5% | 82.3% | 91.1% | 83.0% | 80.1% |
| S81.11.7 | Farm M | Bird Seed Screening | | 30.5% | 32.9% | 22.6% | 37.2% | 27.1% |
| S81.3.6 | Farm M | Haylage | 3rd | 25.4% | 0.0% | 0.0% | 0.0% | 0.0% |
| S81.7.4 | Farm M | TMR | Cow | 94.5% | 90.9% | 89.5% | 92.4% | 92.0% |

Example 9: Selection of *Bacillus* Strains to Inhibit *Clostridium Perfringens* and Non-Toxigenic Clostridia Isolated from Ruminant Fecal Samples. (North East)

Introduction:

*Clostridium* is a genus of Gram-positive, spore-forming bacteria that are common residents of the gastrointestinal tract. A number of *Clostridium* species have been linked to enteric disease in ruminants including hemorrhagic bowel syndrome (HBS), a disease often correlated to elevated levels of *Clostridium perfringens* Type A. While most of the enteric diseases caused by clostridia are acute and occur sporadically in herds, in general, the prognosis is poor and the first sign of illness may be death. Based on recent results sub-acute enteric clostridia disease challenges may be a more wide spread issue than acute challenges. Due to a low success rate from treatment in acute disease challenges a more common, emphasis needs to be placed on prophylactic measures.

The purpose of this research was to characterize the distribution and diversity of clostridia in ruminants and ensure inhibition of these isolates using novel *Bacillus* strains as a method to control the clostridia populations.

Materials and Methods:

Fecal samples (339) from cows, heifers and calves gathered from 9 farms in the Northeast region were diluted 1:10 with sterile peptone, heat shocked for 30 minutes at 60° C., enumerated in sterile peptone and pour plated on Tryptose Sulphite Cycloserine (TSC) agar with D-cycloserine (400 mg/L) to select for clostridia species. Agar plates were incubated at 37° C. anaerobically for 24 hours. If present, isolated sulphite-reducing colonies were counted for a total clostridia count (CFU/g) and representative isolates were picked into Reinforced clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions were performed in 96-well blocks containing 500 µl presumptive clostridia culture per well. Cells were harvested by centrifugation at 4,700 rpm for 10 minutes, the supernatant was removed. Cells were re-suspended in 500 µl of 50 mM of EDTA-2Na (pH=8.0). Aliquots of 300 µl of the suspended cells were transferred to a new 96-well block and combined with 20 µl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 µl of lysis buffer (6 M Guanidine, 20% Triton-X 100, 10 mM Tris-HCL, pH 7.5) was added, mixed then incubated at room temperature for 15 minutes. Following the incubation 20 µl of Proteinase K (NEB, 800 U/mL) was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed centrifuging 750 µl of Column Wash Solution (Promega, A1318) at 4700 rpms for 1 minute and 30 seconds discarding flow through at the end of each spin. The binding plate was centrifuged for an additional 10 minutes at 4,700 rpm to remove any residual ethanol. A clean elution plate was then placed under the binding plate and DNA was eluted with 200 µl, pre-warmed (55° C.), Nuclease Free Water (Promega, P1195).

DNA was screened for toxin genes ($\alpha$, $\beta$, $\epsilon$, and $\iota$) specific to *C. perfringens* using polymerase chain reaction (PCR). Amplification of toxin genes was executed using a multiplex PCR containing four primer sets (Yoo et al., 1997) (Table 1.) The PCR mixture contained 2.5 µl 10×PCR Buffer, 2 µl of 50 mM $MgCl_2$, 0.5 µM of each primer (Table 1.), 0.1 µl of Invitrogen™ Platinum™ Taq DNA Polymerase, 2.5 µl of DNA, sterile water was added to achieve 25 µl for a total reaction volume. The mixture underwent 5 minutes at 94° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved. If one or multiple toxin genes were observed a toxin type identification was assigned to each isolate based on their toxin gene profile (Songer, 1996). *C. perfringens* positive to total clostridia isolate ratio was used to calculate an estimated *C. perfringens* count based on the total clostridia count.

Unique strain-specific genetic fingerprints were generated using Random Amplification of Polymorphic DNA (RAPD) analysis on select isolates to determine diversity among fecal *C. perfringens* isolates. The PCR contained 5 µl of DNA, 2.5 µl RAPD primer 2 (10 µM) (Table 1.), and 17.5 µl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes finishing with a final elongation of 5 minutes at 72° C. PCR products observed on a Fragment Analyzer (Advanced Analytics) to determine amplification patterns and were imported into BioNumerics, bioinformatics software, for analysis. RAPD patterns were compared with a band based Dice correlation analysis method to determine the similarity between RAPD patterns as a way to monitor diversity between isolates.

Antimicrobial screening was done on *C. perfringens* isolates obtained from ruminant samples to gauge the effectiveness of the antimicrobial bacteriocin produced by the inventors' identified *Bacillus* strains 747, 1104, 1541, 1781, and 2018. Bacteriocin was harvested by growing each strain at 32° C. in a shaking incubator at 150 rpms for 24 hours in Brain Heart Infusion (BHI) broth. A 1% transfer of the 24-hour culture to fresh BHI broth was executed after incubation. The *Bacillus* were then incubated for 36-48 hours in a 32° C. shaking incubator at 150 rpms. The culture was then centrifuged at 14,000×g for 20 minutes, supernatant was then filtered with a 0.2 m filter to remove any residual cells.

A bacteriocin turbidity assay was executed by growing *C. perfringens* strains isolated from ruminant fecal samples in RCM for 24 hours, anaerobically, at 37° C. Overnight culture was transferred (1%) to sterile RCM and immediately used in the assay. For each *C. perfringens* isolate at least six wells were run in a sterile 48 well reaction plate, 600 µl inoculated culture (positive control), 600 µl inoculated RCM+70 µl bacteriocin (747, 1104, 1541, 1781, and 2018) and 670 RCM (un-inoculated, negative control). Plates were incubated anaerobically at 37° C. for 24 hours then read using a BioTek Epoch Microplate Spectrophotometer, readings were taken at a wavelength of 600 nm. Optical density readings from the negative controls were subtracted from all OD readings and percent inhibition was calculated using the positive control and each bacteriocin treatment.

To identify clostridia that did not have at least one toxin gene specific to *C. perfringens*, a PCR reaction was performed on the isolate DNA to amplify the 16S region of rDNA using primers 27F-YM and 1492R-Y (Table 1). This was done on 20% of the isolates that did not contain a toxin gene specific to *C. perfringens*. The PCR mixture contained 5 µl of 10×PCR Buffer, 2 µl of 50 mM MgCl$_2$, 1 µl of 50 mM dNTPs, 0.4 µM of each primer (Table 1.), 0.2 µl of Invitrogen™ Platinum™ Taq DNA Polymerase, 5 µl of DNA, and sterile water was added to achieve 50 µl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to gene wiz to obtain the sequences for the 16S genes. Sequences were compared to known typed bacterial strains obtained from EZbiocloud online electronic database. Based on comparisons of these sequences a bacterial identification was assigned to the isolates.

Results:

Fecal samples, 339, were collect from 9 Northeast regional farms (Maine, Vermont, and New York) from which 3,252 presumptive clostridia isolates were isolated as representatives of the clostridial diversity in the Northeast region (Table 17.).

Figure 62:
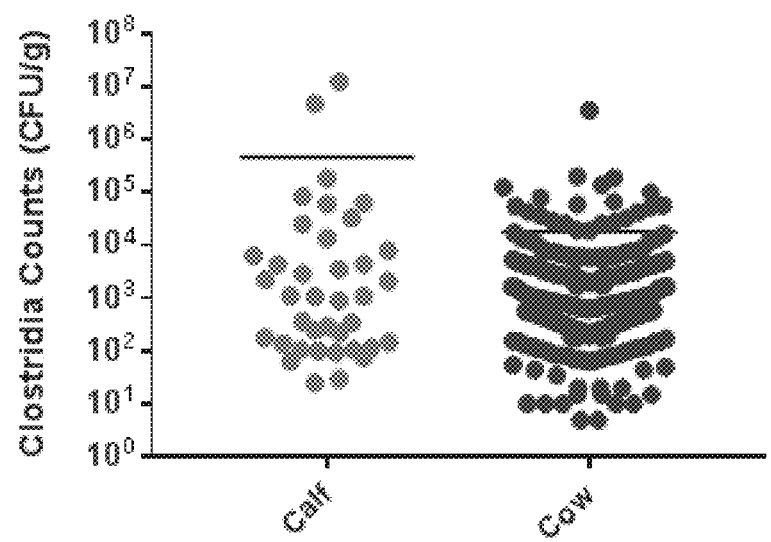
Figure 63:
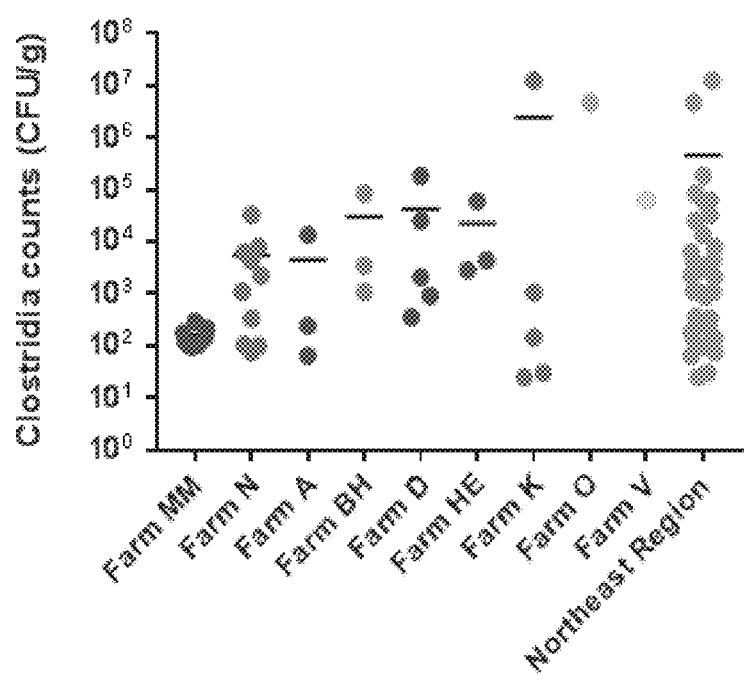
Figure 64:
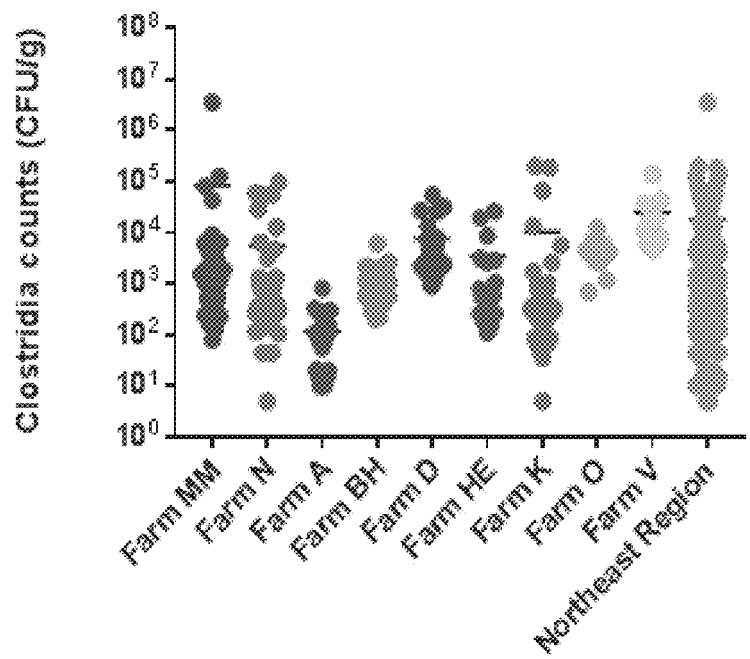

Clostridia enumeration results indicated the average level of clostridia CFU/g across all calf fecal samples was 466,000 CFU/g with individual fecal samples ranging from 25 to 1,250,000 CFU/g. While the average level of clostridia CFU/g across all cow fecal samples was 18,200 CFU/g with individual fecal samples ranging from 5 to 3,540,000 CFU/g (FIG. 62.). Samples appeared to range in clostridia levels for both calves (FIG. 63.) and cows (FIG. 64.).

Figure 65:
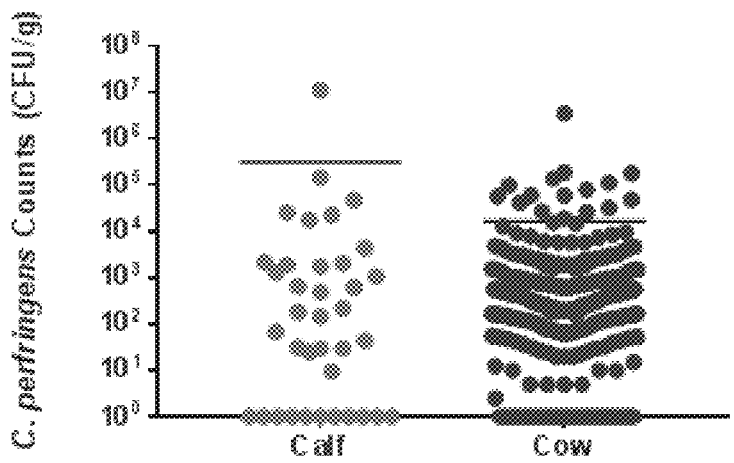
Figure 66:
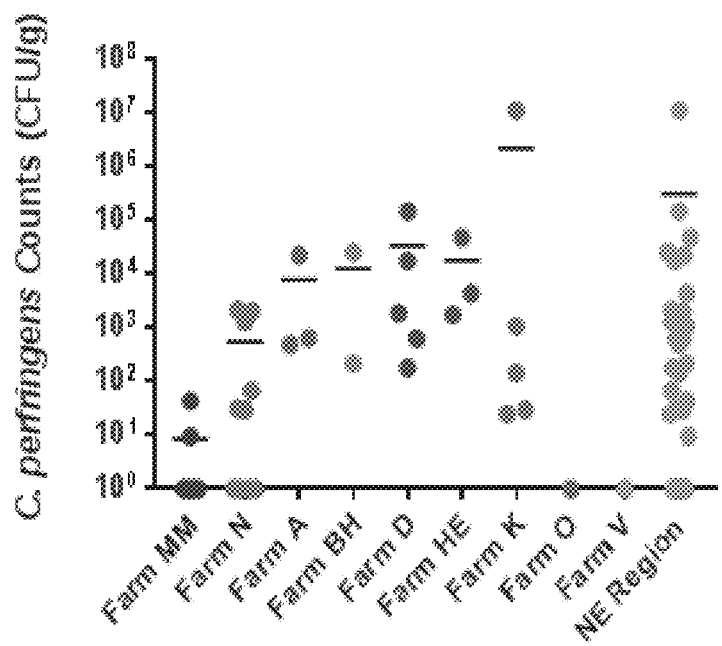
Figure 67:
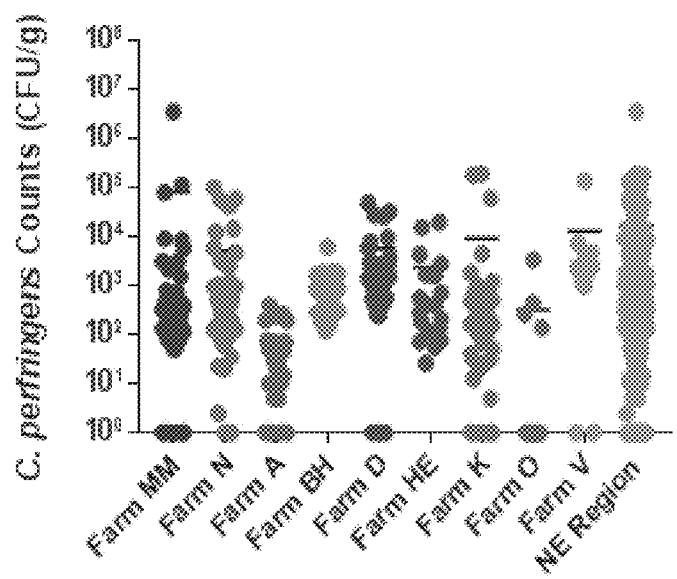

*C. perfringens* enumeration results displayed the average level of *C. perfringens* CFU/g across all calf fecal samples was 311,000 CFU/g with individual samples ranging from <10 to 3,540,000 CFU/g. While the average level of *C. perfringens* CFU/g across all cow fecal samples was 16,700 CFU/g with individual samples ranging from <10 to 3,540,000 CFU/g (FIG. 65.). Samples appeared to range in clostridia levels for both calves (FIG. 66.) and cows (FIG. 67.).

Analysis of the toxin multiplex PCR results displayed which isolates contained toxin genes specific to *C. perfringens*. A total of 3,252 presumptive clostridia isolates from fecal samples have been tested for the indicated *C. perfringens* toxin genes. Of the 3,252 clostridia isolates screened, 1,795 isolates (55.2%) tested positive for at least 1 of the toxin genes. From the 1,795 toxin-gene positive isolates 1,687 (94%) were identified as Type A (αtoxin only), however β, ε and ι, toxins were also detected in the clostridia fecal isolates.

Gentic RAPD fingerprint patterns displayed diversity among the 1,619 isolates that successful amplified. The isolates tested were harvested from calf fecal, cow fecal and feed and did not cluster strictly based on the sample type or farm. Isolates formed 361 clusters based on 75% similarity according to the Dice correlation method. The largest cluster was 82 isolates (5.1%) and comprised of isolates from several farms.

Representatives from the RAPD dendrogram were selected to capture the diversity of the *C. perfringens* population from this region and subjected to inhibition assays. Antimicrobial testing using the bacteriocin turbidity assay displayed good inhibition of most ruminant fecal *C. perfringens* isolates using bacteriocin harvested from 747, 1104, 1541, 1781, and 2018. The bacteriocin from at least one of the strains 747, 1104, 1541, 1781, and 2018 were able to inhibit the growth >60% of 342 of the 412 isolates tested representing a total of 84.6% inhibition of the *C. perfringens* population based on the dendrogram (Table 18.).

Figure 68:
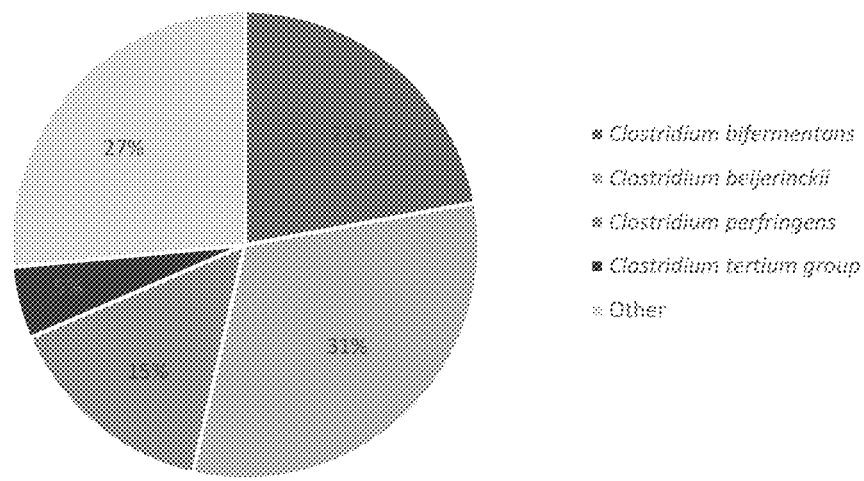
Figure 69:
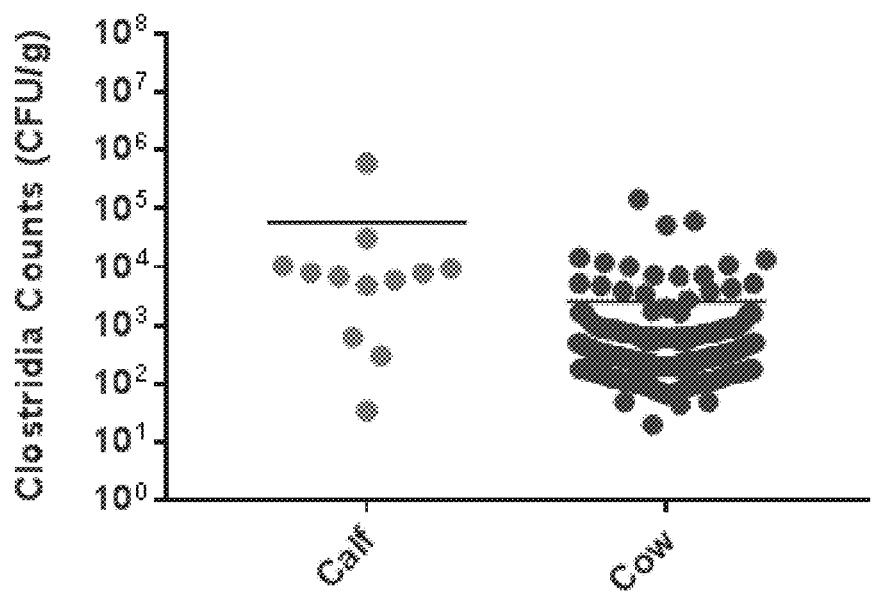
Figure 70:
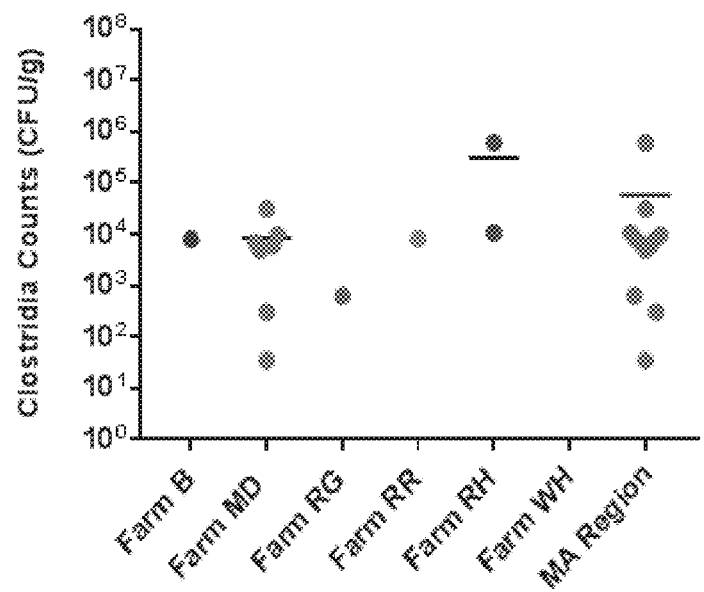
Figure 71:
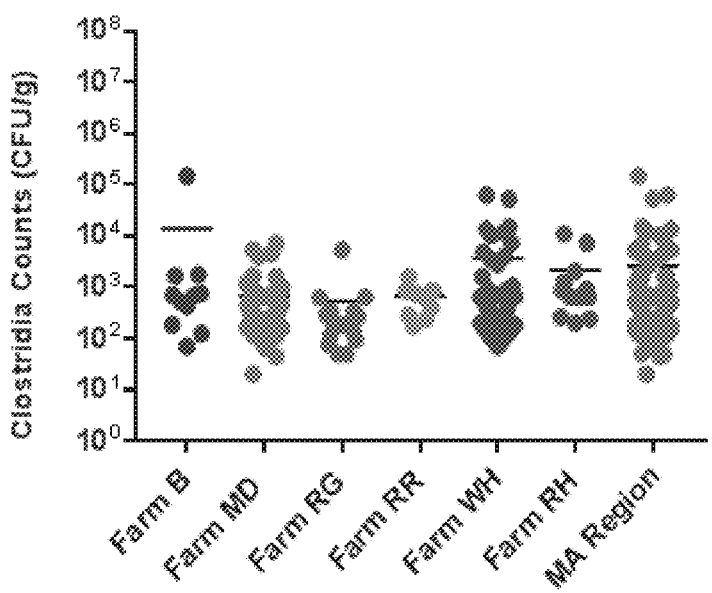
Figure 72:
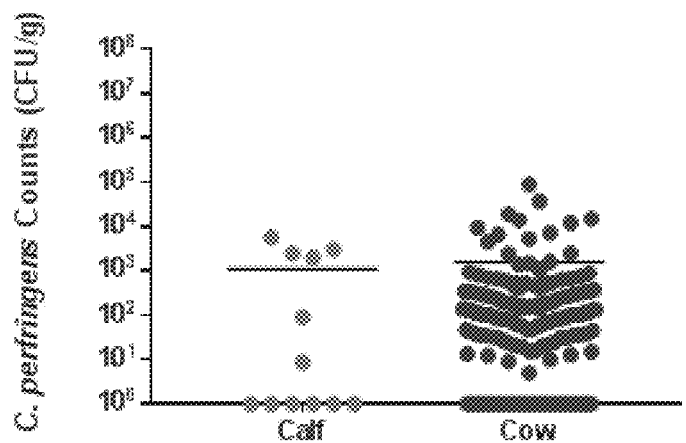
Figure 73:
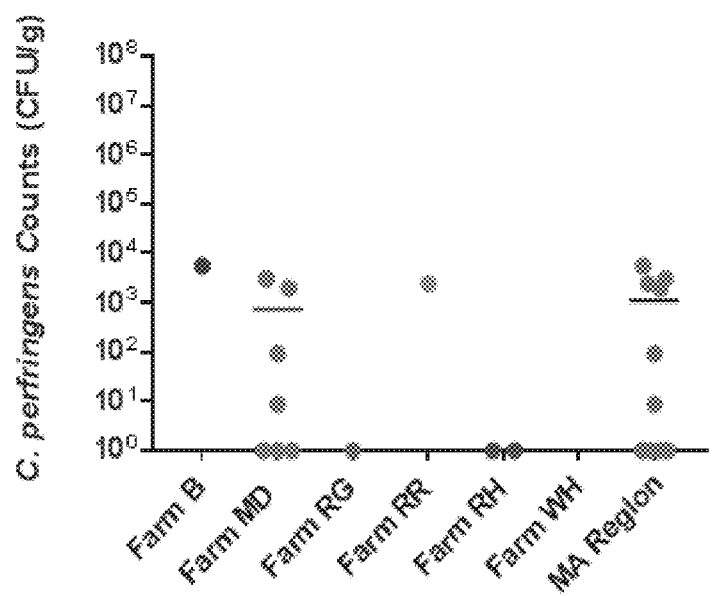
Figure 74:
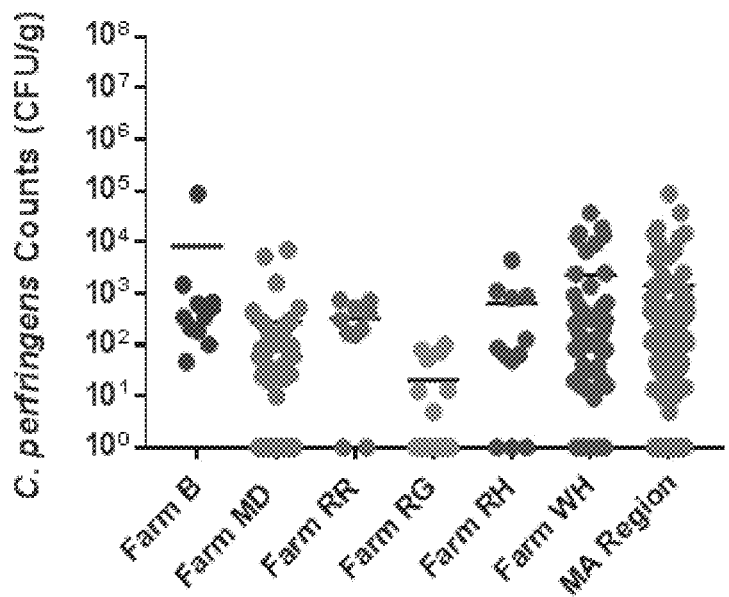
Figure 75:
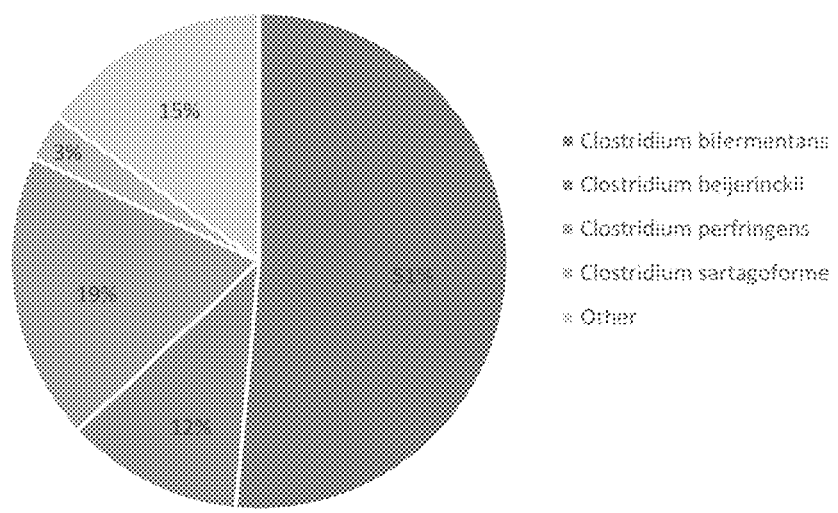

Out of the 3,252 isolates collected 1,457 isolates (44.8%) were found to be non-toxigenic clostridia. Sequencing representatives (n=181) from the non-toxigenic clostridia displayed two dominate clostridia groups *Clostridium bifermentans* group (*Paraclostridium bifermentans* and *P. benzoelyticum*) and *Clostridium beijerinckii* group (*C. diolis, C. beijerinckii, C. chromiireducens, C. saccharoperbutylacetonicum, C. puniceum,* and *C. saccharobutylicum*), the two main groups of the non-toxigenic clostridia group made up 53.6% of the non-toxigenic isolates (FIG. 68.).

Discussion:

Fecal samples were used as the most readily available sample type to estimate the level and obtain isolates of clostridia and *C. perfringens* within the digestive system of ruminants. From the 339 fecal samples collected throughout the Northeast region all samples had detectable levels of clostridia. The majority of the isolates harvested (55.2%) from the ruminant samples contained a toxin gene specific to *C. perfringens*. *C. perfringens* was detected in 90% of the cow fecal samples and in 70% of the calf fecal samples. The high presence of clostridia and *C. perfringens* indicates the risk for sub-acute enteric clostridia disease challenges in most ruminants throughout the Northeast region. *C. perfringens* isolates were diverse according to the RAPD genetic fingerprints but were not specific to sample type or farm. Diverse representatives of *C. perfringens* were mostly inhibited (>60%) by at least one bacteriocin from the following strains 747, 1104, 1541, 1781 or 2018. From the 412 isolates tested 342 isolates were inhibited by greater than 60% by at least one of the strains, representing inhibition of 84.6% of the total *C. perfringens* population based on representation from clusters on the RAPD dendrogram. This indicates the *Bacillus* strains 747, 1104, 1541, 1781 and 2018 can inhibit a wide range of diversity of *C. perfringens* isolates. The *Bacillus* strains are not limited to specific clostridia strain(s) like a vaccine which may be missing large groups of the clostridia populations based on the genetic diversity observed in the RAPD dendrogram. DNA sequencing of the non-toxigenic clostridia revealed two major identifications of *Clostridium* species. *C. bifermentans* group, which is known to produce 1,3-propanediol (Leja et al., 2014; Myszka et al., 2012) and *C. beijerinckii* group known to produce butanol and acetone (Hou et al., 2017). The production of the metabolic end products of these species could be having an impact in the rumen, reducing performance parameters such as milk production within a dairy cow. The high inhibition level against the *C. perfringens* isolates in vitro indicates a potential mode of action of the *Bacillus* strains 747, 1104, 1541, 1781 and 2018.

The *Bacillus* strains offer a prophylactic effect on the clostridia populations which may not only increase rumen efficiency leading to increased milk production, but prevent acute levels of *C. perfringens* reducing the occurrence of digestive deaths. The high prevalence of clostridia and *C. perfringens* in fecal samples collected suggests efficiency improvement opportunities in many ruminants throughout the Northeast region. This example displays the diversity of clostridia isolates from the ruminant fecal and feed samples collected from the Northeast region. The *Bacillus* strains tested 747, 1104, 1541, 1781 and 2018, could inhibit most of the clostridia diversity observed in the Northeast region. The product, in accordance with this embodiment of the present invention could inhibit toxigenic clostridia isolated from ruminants in the Northeast indicating a benefit in rumen efficiency if fed to dairy cows as a direct fed microbial (DFM).

TABLE 17

Fecal samples, 339, were collected from Northeast regional dairies separated by farm (9) and age (cow or calf) which were enumerated for clostridia, tested for *C. perfringens*, isolates were genotyped and tested for inhibition.

| Farm Name | State | Cow Fecal | Calf Fecal |
|---|---|---|---|
| Farm MM | Maine | 46 | 7 |
| Farm N | Vermont | 63 | 10 |
| Farm A | Vermont | 29 | 3 |
| Farm BH | New York | 35 | 3 |
| Farm D | New York | 34 | 5 |
| Farm H | New York | 20 | 3 |
| Farm K | Vermont | 48 | 5 |
| Farm O | New York | 13 | 1 |
| Farm V | New York | 13 | 1 |
| Total | | 301 | 38 |

TABLE 18

Bacteriocin assay results displaying each isolate tested and the source of that isolate, isolated from Northeast regional fecal samples. Inhibition was calculated based on the percent of growth for each treatment well compared to the positive control.

| Isolate ID | Farm | Sample Type | Group | *Bacillus* Strains 747 | 1104 | 1541 | 1781 | 2018 |
|---|---|---|---|---|---|---|---|---|
| R10.1.8 | Farm HE | Cow Fecal | Low Cows | 51.3% | 0.0% | 0.0% | 55.3% | 3.7% |
| R10.12.9 | Farm HE | Cow Fecal | UpClose Cows | 96.2% | 95.2% | 94.7% | 94.3% | 95.4% |
| R10.13.1 | Farm HE | Cow Fecal | UpClose Cows | 96.3% | 95.7% | 96.4% | 96.0% | 96.2% |
| R10.13.3 | Farm HE | Cow Fecal | UpClose Cows | 96.6% | 96.0% | 5.5% | 96.2% | 96.0% |
| R10.13.5 | Farm HE | Cow Fecal | UpClose Cows | 96.6% | 95.4% | 95.4% | 95.0% | 95.8% |
| R10.13.6 | Farm HE | Cow Fecal | UpClose Cows | 96.6% | 96.2% | 97.0% | 96.5% | 96.5% |
| R10.15.7 | Farm HE | Cow Fecal | UpClose Cows | 96.9% | 96.0% | 97.1% | 96.5% | 96.5% |
| R10.16.2 | Farm HE | Cow Fecal | Far Off (Dry) | 96.6% | 95.8% | 96.3% | 96.1% | 96.2% |
| R10.18.6 | Farm HE | Cow Fecal | Far Off (Dry) | 96.1% | 95.6% | 96.4% | 95.7% | 95.9% |
| R10.19.4 | Farm HE | Cow Fecal | Far Off (Dry) | 93.3% | 91.9% | 91.7% | 90.9% | 91.7% |
| R10.2.7 | Farm HE | Cow Fecal | Far Off (Dry) | 96.3% | 96.0% | 96.9% | 96.5% | 96.4% |
| R10.21.5 | Farm HE | Calf Fecal | Calf | 95.2% | 94.2% | 95.1% | 93.5% | 94.8% |
| R10.22.1 | Farm HE | Calf Fecal | Calf | 67.7% | 25.2% | 0.0% | 56.8% | 0.0% |
| R10.22.3 | Farm HE | Calf Fecal | Calf | 68.8% | 39.4% | 0.0% | 67.1% | 0.0% |
| R10.22.4 | Farm HE | Calf Fecal | Calf | 93.1% | 85.1% | 68.1% | 91.3% | 72.4% |
| R10.23.10 | Farm HE | Calf Fecal | Calf | 97.1% | 96.4% | 96.5% | 95.8% | 96.5% |
| R10.23.2 | Farm HE | Calf Fecal | Calf | 8.7% | 0.0% | 9.8% | 22.7% | 21.1% |
| R10.23.3 | Farm HE | Calf Fecal | Calf | 94.8% | 94.2% | 88.6% | 0.0% | 11.2% |
| R10.23.5 | Farm HE | Calf Fecal | Calf | 97.0% | 96.2% | 96.4% | 96.0% | 96.6% |
| R10.23.7 | Farm HE | Calf Fecal | Calf | 95.1% | 94.3% | 95.2% | 93.9% | 93.7% |
| R10.8.4 | Farm HE | Cow Fecal | Low Cows | 97.3% | 96.8% | 97.7% | 96.4% | 96.9% |
| R10.9.6 | Farm HE | Cow Fecal | Low Cows | 92.3% | 91.5% | 93.1% | 92.5% | 0.0% |
| R11.1.5 | Farm BH | Cow Fecal | High Cows | 94.5% | 60.4% | 94.5% | 94.5% | 95.6% |
| R11.11.1 | Farm BH | Cow Fecal | Low Cows | 97.2% | 96.5% | 97.4% | 97.1% | 96.8% |
| R11.11.2 | Farm BH | Cow Fecal | Low Cows | 92.6% | 91.4% | 93.4% | 92.6% | 92.6% |
| R11.12.7 | Farm BH | Cow Fecal | Low Cows | 69.9% | 65.0% | 65.6% | 0.0% | 66.3% |
| R11.14.4 | Farm BH | Cow Fecal | Low Cows | 98.6% | 95.8% | 97.7% | 94.4% | 98.1% |
| R11.15.1. | Farm BH | Cow Fecal | Low Cows | 98.4% | 84.7% | 96.0% | 94.8% | 98.8% |
| R11.15.7 | Farm BH | Cow Fecal | Low Cows | 99.8% | 97.7% | 99.6% | 99.8% | 99.5% |
| R11.15.8 | Farm BH | Cow Fecal | Low Cows | 57.0% | 9.5% | 17.0% | 9.8% | 49.3% |
| R11.16.10 | Farm BH | Cow Fecal | Low Cows | 96.9% | 96.5% | 97.3% | 96.5% | 96.7% |
| R11.16.4 | Farm BH | Cow Fecal | Low Cows | 90.0% | 46.5% | 69.5% | 65.0% | 58.6% |
| R11.16.5 | Farm BH | Cow Fecal | Low Cows | 37.9% | 0.0% | 0.0% | 62.6% | 0.0% |
| R11.16.7 | Farm BH | Cow Fecal | Low Cows | 99.6% | 99.6% | 99.6% | 99.8% | 99.2% |
| R11.16.8 | Farm BH | Cow Fecal | Low Cows | 99.6% | 99.6% | 99.6% | 96.6% | 0.0% |
| R11.17.1 | Farm BH | Cow Fecal | Low Cows | 99.4% | 56.3% | 36.1% | 91.4% | 78.7% |
| R11.17.3 | Farm BH | Cow Fecal | Low Cows | 96.2% | 75.0% | 90.4% | 94.2% | 92.3% |
| R11.17.4 | Farm BH | Cow Fecal | Low Cows | 98.6% | 4.9% | 0.0% | 86.6% | 11.3% |
| R11.17.6 | Farm BH | Cow Fecal | Low Cows | 97.1% | 96.1% | 96.8% | 96.5% | 97.2% |
| R11.17.8 | Farm BH | Cow Fecal | Low Cows | 99.6% | 0.0% | 36.4% | 99.3% | 0.0% |
| R11.18.10 | Farm BH | Cow Fecal | Low Cows | 96.9% | 96.3% | 97.9% | 97.2% | 96.9% |
| R11.18.3 | Farm BH | Cow Fecal | Low Cows | 97.9% | 97.4% | 97.8% | 97.9% | 97.6% |
| R11.18.4 | Farm BH | Cow Fecal | Low Cows | 84.2% | 83.2% | 86.0% | 84.6% | 86.0% |
| R11.18.6 | Farm BH | Cow Fecal | Low Cows | 99.7% | 0.0% | 99.7% | 78.7% | 23.6% |
| R11.19.1 | Farm BH | Cow Fecal | Low Cows | 93.7% | 91.1% | 93.8% | 94.0% | 93.4% |
| R11.2.8 | Farm BH | Cow Fecal | High Cows | 95.8% | 95.1% | 96.0% | 94.7% | 90.9% |
| R11.2.9 | Farm BH | Cow Fecal | High Cows | 96.8% | 96.1% | 96.5% | 95.4% | 96.6% |
| R11.20.3 | Farm BH | Cow Fecal | Low Cows | 96.0% | 95.3% | 97.3% | 96.8% | 96.8% |
| R11.20.4 | Farm BH | Cow Fecal | Low Cows | 0.0% | 0.0% | 0.0% | 0.0% | 0.0% |
| R11.22.1 | Farm BH | Cow Fecal | Pre-Fresh | 0.0% | 0.0% | 0.0% | 0.0% | 0.0% |
| R11.22.2 | Farm BH | Cow Fecal | Pre-Fresh | 99.6% | 99.2% | 98.8% | 99.2% | 98.8% |
| R11.22.3 | Farm BH | Cow Fecal | Pre-Fresh | 24.5% | 0.4% | 12.1% | 0.0% | 10.1% |

TABLE 18-continued

Bacteriocin assay results displaying each isolate tested and the source of that isolate, isolated from Northeast regional fecal samples. Inhibition was calculated based on the percent of growth for each treatment well compared to the positive control.

| | | Sample | | *Bacillus* Strains | | | | |
|---|---|---|---|---|---|---|---|---|
| Isolate ID | Farm | Type | Group | 747 | 1104 | 1541 | 1781 | 2018 |
| R11.22.6 | Farm BH | Cow Fecal | Pre-Fresh | 91.7% | 89.5% | 88.8% | 91.7% | 92.8% |
| R11.22.8 | Farm BH | Cow Fecal | Pre-Fresh | 92.0% | 89.2% | 74.5% | 90.7% | 81.3% |
| R11.23.10 | Farm BH | Cow Fecal | Pre-Fresh | 0.0% | 0.0% | 0.0% | 0.0% | 0.0% |
| R11.23.2 | Farm BH | Cow Fecal | Pre-Fresh | 98.6% | 95.8% | 97.7% | 94.4% | 98.1% |
| R11.23.2 | Farm BH | Cow Fecal | Pre-Fresh | 99.3% | 96.5% | 99.1% | 98.8% | 98.8% |
| R11.23.4 | Farm BH | Cow Fecal | Pre-Fresh | 97.5% | 96.7% | 98.1% | 97.9% | 97.1% |
| R11.23.6 | Farm BH | Cow Fecal | Pre-Fresh | 99.7% | 99.5% | 99.6% | 99.9% | 99.5% |
| R11.24.1 | Farm BH | Cow Fecal | Pre-Fresh | 97.1% | 96.1% | 96.3% | 27.9% | 95.9% |
| R11.24.7 | Farm BH | Cow Fecal | Pre-Fresh | 0.0% | 0.0% | 0.0% | 0.0% | 0.0% |
| R11.25.10 | Farm BH | Cow Fecal | Pre-Fresh | 96.0% | 94.8% | 94.3% | 93.5% | 93.9% |
| R11.25.4 | Farm BH | Cow Fecal | Pre-Fresh | 0.0% | 20.2% | 0.0% | 0.0% | 0.0% |
| R11.25.5 | Farm BH | Cow Fecal | Pre-Fresh | 94.5% | 24.3% | 53.4% | 90.1% | 40.4% |
| R11.25.7 | Farm BH | Cow Fecal | Pre-Fresh | 0.0% | 0.0% | 0.0% | 0.0% | 0.0% |
| R11.26.10 | Farm BH | Cow Fecal | Dry Cows/ Preg Heifers | 98.3% | 97.4% | 98.7% | 98.3% | 98.0% |
| R11.26.4 | Farm BH | Cow Fecal | Dry Cows/ Preg Heifers | 28.8% | 16.4% | 31.9% | 28.8% | 40.3% |
| R11.26.6 | Farm BH | Cow Fecal | Dry Cows/ Preg Heifers | 0.0% | 0.0% | 0.0% | 0.0% | 0.0% |
| R11.27.1 | Farm BH | Cow Fecal | Dry Cows/ Preg Heifers | 100.0% | 96.2% | 100.0% | 100.0% | 100.0% |
| R11.27.10 | Farm BH | Cow Fecal | Dry Cows/ Preg Heifers | 11.5% | 0.0% | 0.0% | 0.0% | 14.9% |
| R11.27.2 | Farm BH | Cow Fecal | Dry Cows/ Preg Heifers | 96.9% | 97.1% | 98.2% | 97.8% | 97.1% |
| R11.27.3 | Farm BH | Cow Fecal | Dry Cows/ Preg Heifers | 78.0% | 70.7% | 86.6% | 81.7% | 84.1% |
| R11.28.3 | Farm BH | Cow Fecal | Dry Cows/ Preg Heifers | 97.2% | 96.8% | 98.1% | 97.4% | 97.2% |
| R11.28.5 | Farm BH | Cow Fecal | Dry Cows/ Preg Heifers | 97.5% | 96.3% | 98.5% | 98.4% | 96.3% |
| R11.3.3 | Farm BH | Cow Fecal | High Cows | 96.2% | 95.2% | 95.8% | 94.6% | 95.4% |
| R11.3.6 | Farm BH | Cow Fecal | High Cows | 99.6% | 99.2% | 99.5% | 99.7% | 99.6% |
| R11.3.9 | Farm BH | Cow Fecal | High Cows | 97.4% | 96.3% | 96.5% | 96.0% | 96.5% |
| R11.33.10 | Farm BH | Cow Fecal | Fresh Cows | 79.6% | 96.3% | 100.0% | 93.5% | 82.4% |
| R11.34.3 | Farm BH | Cow Fecal | Fresh Cows | 95.2% | 69.1% | 66.1% | 65.0% | 78.5% |
| R11.34.8 | Farm BH | Cow Fecal | Fresh Cows | 92.8% | 82.1% | 91.8% | 93.7% | 96.9% |
| R11.35.3 | Farm BH | Cow Fecal | Fresh Cows | 32.8% | 0.0% | 14.3% | 0.0% | 9.7% |
| R11.35.4 | Farm BH | Cow Fecal | Fresh Cows | 96.0% | 96.0% | 96.9% | 95.0% | 95.1% |
| R11.35.6 | Farm BH | Cow Fecal | Fresh Cows | 97.1% | 95.9% | 96.3% | 95.1% | 94.7% |
| R11.35.9 | Farm BH | Cow Fecal | Fresh Cows | 98.9% | 35.5% | 97.8% | 98.9% | 98.2% |
| R11.37.1 | Farm BH | Calf Fecal | Calf | 14.6% | 0.8% | 0.0% | 1.1% | 0.0% |
| R11.37.7 | Farm BH | Calf Fecal | Calf | 72.9% | 63.6% | 21.5% | 55.1% | 57.0% |
| R11.38.5 | Farm BH | Calf Fecal | Calf | 87.5% | 0.0% | 53.0% | 34.5% | 0.0% |
| R11.4.3 | Farm BH | Cow Fecal | High Cows | 98.4% | 84.7% | 96.0% | 94.8% | 98.8% |
| R11.5.2 | Farm BH | Cow Fecal | High Cows | 0.0% | 0.0% | 0.0% | 0.0% | 0.0% |
| R11.5.7 | Farm BH | Cow Fecal | High Cows | 97.5% | 96.5% | 96.8% | 96.2% | 97.1% |
| R11.7.5 | Farm BH | Cow Fecal | High Cows | 0.0% | 0.0% | 0.0% | 0.0% | 0.0% |
| R11.7.8 | Farm BH | Cow Fecal | High Cows | 97.5% | 96.8% | 97.6% | 97.4% | 97.4% |
| R11.8.5 | Farm BH | Cow Fecal | High Cows | 96.7% | 96.0% | 96.9% | 96.9% | 96.4% |
| R11.9.6 | Farm BH | Cow Fecal | High Cows | 97.0% | 96.5% | 97.6% | 97.4% | 97.1% |
| R14.1.10 | Farm D | Calf Fecal | Calf | 40.8% | 14.3% | 14.5% | 49.9% | 43.6% |
| R14.1.9 | Farm D | Calf Fecal | Calf | 88.9% | 2.8% | 0.0% | 95.0% | 4.3% |
| R14.10.10 | Farm D | Cow Fecal | Far Dry | 100.0% | 26.3% | 71.0% | 100.0% | 0.0% |
| R14.10.7 | Farm D | Cow Fecal | Far Dry | 88.3% | 85.9% | 88.3% | 97.0% | 96.6% |
| R14.10.8 | Farm D | Cow Fecal | Far Dry | 100.0% | 100.0% | 100.0% | 100.0% | 100.0% |
| R14.11.2 | Farm D | Cow Fecal | Far Dry | 26.3% | 0.0% | 0.0% | 0.0% | 46.7% |
| R14.11.6 | Farm D | Cow Fecal | Far Dry | 100.0% | 100.0% | 100.0% | 100.0% | 100.0% |
| R14.13.4 | Farm D | Cow Fecal | Close Dry | 96.3% | 45.7% | 89.5% | 89.1% | 0.0% |
| R14.14.9 | Farm D | Cow Fecal | Close Dry | 0.0% | 0.0% | 0.0% | 0.0% | 0.0% |
| R14.15.10 | Farm D | Cow Fecal | Low | 0.0% | 0.0% | 0.0% | 0.0% | 0.0% |
| R14.16.1 | Farm D | Cow Fecal | Low | 83.1% | 32.8% | 44.4% | 50.8% | 49.2% |
| R14.16.2 | Farm D | Cow Fecal | Low | 0.0% | 0.0% | 0.0% | 0.0% | 0.0% |
| R14.16.5 | Farm D | Cow Fecal | Low | 11.8% | 0.0% | 8.5% | 23.1% | 1.1% |
| R14.17.1 | Farm D | Cow Fecal | Low | 97.0% | 96.3% | 96.5% | 97.4% | 95.8% |
| R14.17.9 | Farm D | Cow Fecal | Low | 97.0% | 96.0% | 97.1% | 96.6% | 96.1% |
| R14.18.5 | Farm D | Cow Fecal | Low | 93.6% | 91.4% | 93.6% | 93.8% | 91.9% |
| R14.2.6 | Farm D | Calf Fecal | Calf | 95.2% | 9.7% | 0.0% | 94.1% | 20.4% |
| R14.2.7 | Farm D | Calf Fecal | Calf | 96.2% | 95.1% | 96.2% | 96.6% | 96.6% |
| R14.20.5 | Farm D | Cow Fecal | High | 97.3% | 96.9% | 97.3% | 97.6% | 96.4% |
| R14.20.7 | Farm D | Cow Fecal | High | 95.9% | 95.0% | 95.6% | 95.8% | 95.1% |
| R14.21.10 | Farm D | Cow Fecal | High | 97.1% | 96.1% | 97.2% | 96.6% | 96.3% |

TABLE 18-continued

Bacteriocin assay results displaying each isolate tested and the source of that isolate, isolated from Northeast regional fecal samples. Inhibition was calculated based on the percent of growth for each treatment well compared to the positive control.

| | | Sample | | *Bacillus* Strains | | | | |
|---|---|---|---|---|---|---|---|---|
| Isolate ID | Farm | Type | Group | 747 | 1104 | 1541 | 1781 | 2018 |
| R14.21.5 | Farm D | Cow Fecal | High | 97.2% | 95.8% | 97.3% | 96.6% | 96.2% |
| R14.21.7 | Farm D | Cow Fecal | High | 66.3% | 67.9% | 75.1% | 67.2% | 67.0% |
| R14.25.9 | Farm D | Cow Fecal | High | 94.4% | 93.1% | 96.0% | 94.6% | 94.2% |
| R14.27.9 | Farm D | Cow Fecal | High | 97.2% | 96.4% | 98.0% | 97.0% | 97.0% |
| R14.28.4 | Farm D | Cow Fecal | High | 97.0% | 95.9% | 97.4% | 97.0% | 96.4% |
| R14.29.6 | Farm D | Cow Fecal | High | 81.8% | 22.0% | 36.8% | 35.5% | 45.6% |
| R14.29.9 | Farm D | Cow Fecal | High | 0.0% | 0.0% | 0.0% | 0.0% | 0.0% |
| R14.3.10 | Farm D | Calf Fecal | Calf | 97.7% | 96.9% | 97.8% | 97.8% | 97.1% |
| R14.3.2 | Farm D | Calf Fecal | Calf | 91.7% | 94.9% | 93.3% | 93.3% | 94.2% |
| R14.3.7 | Farm D | Calf Fecal | Calf | 96.3% | 96.6% | 97.6% | 98.4% | 96.0% |
| R14.31.3 | Farm D | Cow Fecal | Fresh | 97.0% | 95.8% | 97.2% | 96.6% | 96.5% |
| R14.31.8 | Farm D | Cow Fecal | Fresh | 71.2% | 4.4% | 2.9% | 15.3% | 10.9% |
| R14.32.3 | Farm D | Cow Fecal | Fresh | 95.9% | 95.3% | 97.0% | 96.1% | 96.2% |
| R14.39.7 | Farm D | Cow Fecal | Fresh | 97.6% | 98.2% | 97.6% | 89.2% | 97.6% |
| R14.4.3 | Farm D | Calf Fecal | Calf | 97.7% | 97.8% | 97.7% | 97.3% | 97.1% |
| R14.4.7 | Farm D | Calf Fecal | Calf | 97.2% | 99.3% | 99.4% | 96.3% | 96.9% |
| R14.5.1 | Farm D | Calf Fecal | Calf | 0.0% | 78.7% | 99.3% | 99.2% | 68.9% |
| R14.5.7 | Farm D | Calf Fecal | Calf | 83.2% | 83.3% | 82.8% | 88.8% | 97.3% |
| R14.7.1 | Farm D | Cow Fecal | Post Fresh | 97.2% | 96.8% | 97.9% | 96.9% | 97.0% |
| R14.8.10 | Farm D | Cow Fecal | Far Dry | 0.0% | 0.0% | 0.0% | 0.0% | 0.0% |
| R14.8.7 | Farm D | Cow Fecal | Far Dry | 4.2% | 17.1% | 0.0% | 20.7% | 0.0% |
| R14.9.9 | Farm D | Cow Fecal | Far Dry | 80.1% | 0.0% | 0.0% | 58.7% | 0.0% |
| R16.10.5 | Farm V | Cow Fecal | Milk | 96.0% | 96.0% | 95.9% | 96.5% | 91.2% |
| R16.10.8 | Farm V | Cow Fecal | Milk | 96.1% | 96.1% | 96.7% | 96.8% | 96.6% |
| R16.10.9 | Farm V | Cow Fecal | Milk | 96.5% | 96.8% | 97.6% | 97.4% | 97.1% |
| R16.11.3 | Farm V | Cow Fecal | Milk | 96.9% | 26.3% | 12.3% | 57.6% | 53.1% |
| R16.11.7 | Farm V | Cow Fecal | Milk | 36.6% | 11.9% | 87.0% | 24.6% | 10.3% |
| R16.12.8 | Farm V | Cow Fecal | Milk | 96.9% | 97.0% | 97.8% | 98.5% | 97.7% |
| R16.13.6 | Farm V | Cow Fecal | Milk | 69.7% | 89.9% | 94.9% | 42.9% | 45.1% |
| R16.13.9 | Farm V | Cow Fecal | Milk | 90.6% | 90.9% | 90.9% | 93.5% | 92.5% |
| R16.3.7 | Farm V | Cow Fecal | Dry | 94.0% | 94.0% | 0.0% | 94.9% | 94.7% |
| R16.5.3 | Farm V | Cow Fecal | Milk | 85.0% | 0.0% | 0.0% | 0.0% | 0.0% |
| R16.9.4 | Farm V | Cow Fecal | Milk | 100.0% | 96.2% | 100.0% | 100.0% | 100.0% |
| R20.1.1 | Farm K | Calf Fecal | Calf | 96.5% | 95.0% | 92.9% | 92.7% | 89.4% |
| R20.1.2 | Farm K | Calf Fecal | Calf | 96.6% | 93.0% | 94.1% | 90.8% | 90.9% |
| R20.11.6 | Farm K | Cow Fecal | Group 1 - High | 99.3% | 98.5% | 99.1% | 99.1% | 99.0% |
| R20.13.7 | Farm K | Cow Fecal | Group 1 - High | 99.2% | 98.9% | 99.3% | 99.2% | 99.0% |
| R20.14.8 | Farm K | Cow Fecal | Group 1 - High | 3.8% | 0.0% | 0.0% | 0.0% | 0.0% |
| R20.15.1 | Farm K | Cow Fecal | Group 1 - High | 94.4% | 90.9% | 92.5% | 90.8% | 89.0% |
| R20.16.6 | Farm K | Cow Fecal | Group 2- Med | 20.2% | 7.8% | 8.4% | 9.6% | 7.9% |
| R20.17.1 | Farm K | Cow Fecal | Group 2- Med | 0.2% | 0.0% | 0.0% | 0.0% | 0.0% |
| R20.17.2 | Farm K | Cow Fecal | Group 2- Med | 69.4% | 53.3% | 57.8% | 43.9% | 46.5% |
| R20.17.6 | Farm K | Cow Fecal | Group 2- Med | 0.8% | 0.0% | 0.0% | 0.0% | 0.0% |
| R20.17.7 | Farm K | Cow Fecal | Group 2- Med | 0.0% | 1.8% | 0.0% | 5.7% | 0.0% |
| R20.17.8 | Farm K | Cow Fecal | Group 2- Med | 4.8% | 19.4% | 0.0% | 48.9% | 0.0% |
| R20.18.1 | Farm K | Cow Fecal | Group 2- Med | 0.0% | 0.0% | 0.0% | 0.0% | 0.0% |
| R20.18.4 | Farm K | Cow Fecal | Group 2- Med | 98.9% | 98.7% | 99.1% | 99.1% | 98.9% |
| R20.19.2 | Farm K | Cow Fecal | Group 2- Med | 0.0% | 88.7% | 0.0% | 0.0% | 90.1% |
| R20.19.5 | Farm K | Cow Fecal | Group 2- Med | 0.0% | 0.0% | 98.0% | 99.0% | 97.4% |
| R20.19.7 | Farm K | Cow Fecal | Group 2 - Med | 99.4% | 99.2% | 99.3% | 99.4% | 99.2% |
| R20.19.9 | Farm K | Cow Fecal | Group 2- Med | 3.1% | 0.0% | 0.0% | 0.0% | 0.0% |
| R20.2.10 | Farm K | Calf Fecal | Calf | 96.5% | 95.3% | 31.4% | 92.5% | 92.0% |
| R20.2.2 | Farm K | Calf Fecal | Calf | 99.3% | 98.9% | 99.0% | 99.3% | 98.9% |
| R20.2.3 | Farm K | Calf Fecal | Calf | 99.5% | 99.5% | 99.7% | 99.7% | 99.5% |
| R20.2.4 | Farm K | Calf Fecal | Calf | 96.7% | 95.7% | 96.3% | 94.7% | 90.4% |
| R20.2.5 | Farm K | Calf Fecal | Calf | 97.0% | 95.2% | 96.2% | 94.9% | 95.0% |
| R20.2.7 | Farm K | Calf Fecal | Calf | 96.9% | 96.0% | 96.7% | 94.6% | 94.5% |
| R20.2.8 | Farm K | Calf Fecal | Calf | 96.0% | 94.4% | 92.0% | 91.4% | 91.5% |
| R20.2.9 | Farm K | Calf Fecal | Calf | 96.5% | 94.3% | 93.4% | 92.2% | 88.9% |
| R20.20.4 | Farm K | Cow Fecal | Group 2- Med | 34.8% | 12.5% | 0.0% | 4.9% | 13.7% |
| R20.20.5 | Farm K | Cow Fecal | Group 2- Med | 88.0% | 37.5% | 7.7% | 92.8% | 0.0% |
| R20.21.3 | Farm K | Cow Fecal | Group 2- Med | 61.5% | 40.8% | 0.0% | 69.5% | 0.0% |
| R20.22.6 | Farm K | Cow Fecal | Group 2- Med | 100.3% | 100.1% | 99.9% | 100.1% | 100.1% |
| R20.23.1 | Farm K | Cow Fecal | Group 2- Med | 100.3% | 3.4% | 98.3% | 100.1% | 99.9% |
| R20.24.4 | Farm K | Cow Fecal | Group 2- Med | 0.0% | 0.0% | 0.0% | 0.0% | 0.0% |
| R20.24.8 | Farm K | Cow Fecal | Group 2- Med | 0.0% | 0.0% | 0.0% | 0.0% | 0.5% |
| R20.27.1 | Farm K | Cow Fecal | Group 3- Low | 27.4% | 13.4% | 0.0% | 0.0% | 0.0% |
| R20.27.5 | Farm K | Cow Fecal | Group 3- Low | 99.0% | 98.9% | 99.0% | 99.2% | 98.9% |
| R20.28.7 | Farm K | Cow Fecal | Group 3- Low | 1.6% | 0.0% | 3.4% | 2.5% | 0.9% |
| R20.29.4 | Farm K | Cow Fecal | Group 3- Low | 0.0% | 0.0% | 0.0% | 88.5% | 0.0% |
| R20.3.10 | Farm K | Calf Fecal | Calf | 0.0% | 0.0% | 0.0% | 0.0% | 0.0% |
| R20.3.2 | Farm K | Calf Fecal | Calf | 95.7% | 94.3% | 91.5% | 91.4% | 91.2% |

TABLE 18-continued

Bacteriocin assay results displaying each isolate tested and the source of that isolate, isolated from Northeast regional fecal samples. Inhibition was calculated based on the percent of growth for each treatment well compared to the positive control.

| | | Sample | | *Bacillus* Strains | | | | |
|---|---|---|---|---|---|---|---|---|
| Isolate ID | Farm | Type | Group | 747 | 1104 | 1541 | 1781 | 2018 |
| R20.3.4 | Farm K | Calf Fecal | Calf | 25.9% | 0.0% | 0.0% | 57.2% | 24.4% |
| R20.3.6 | Farm K | Calf Fecal | Calf | 96.7% | 93.6% | 94.4% | 91.8% | 91.9% |
| R20.3.7 | Farm K | Calf Fecal | Calf | 95.6% | 94.0% | 93.3% | 92.6% | 93.4% |
| R20.3.8 | Farm K | Calf Fecal | Calf | 95.8% | 93.8% | 92.2% | 91.4% | 91.4% |
| R20.3.9 | Farm K | Calf Fecal | Calf | 97.1% | 96.1% | 96.0% | 0.0% | 95.3% |
| R20.30.3 | Farm K | Cow Fecal | Group 3- Low | 82.0% | 0.0% | 0.0% | 90.8% | 3.4% |
| R20.32.1 | Farm K | Cow Fecal | Group 3- Low | 23.4% | 5.8% | 2.3% | 88.0% | 2.0% |
| R20.32.2 | Farm K | Cow Fecal | Group 3- Low | 97.7% | 30.1% | 47.2% | 98.4% | 47.4% |
| R20.32.3 | Farm K | Cow Fecal | Group 3- Low | 30.1% | 0.0% | 12.3% | 0.0% | 0.6% |
| R20.33.10 | Farm K | Cow Fecal | Group 3- Low | 94.0% | 0.0% | 6.7% | 90.2% | 0.0% |
| R20.33.5 | Farm K | Cow Fecal | Group 3- Low | 4.2% | 1.2% | 0.9% | 0.0% | 4.5% |
| R20.33.8 | Farm K | Cow Fecal | Group 3- Low | 0.0% | 0.0% | 0.0% | 0.0% | 0.0% |
| R20.36.8 | Farm K | Cow Fecal | Group 4- 1st Calf | 4.6% | 2.0% | 0.7% | 0.0% | 0.6% |
| R20.39.5 | Farm K | Cow Fecal | Group 4- 1st Calf | 94.8% | 93.1% | 14.7% | 89.8% | 90.3% |
| R20.4.1 | Farm K | Calf Fecal | Calf | 97.6% | 0.0% | 91.3% | 0.0% | 8.1% |
| R20.4.10 | Farm K | Calf Fecal | Calf | 32.5% | 18.9% | 5.8% | 68.3% | 36.2% |
| R20.4.2 | Farm K | Calf Fecal | Calf | 65.4% | 28.4% | 6.0% | 64.2% | 37.2% |
| R20.4.3 | Farm K | Calf Fecal | Calf | 66.7% | 94.6% | 12.7% | 92.0% | 28.3% |
| R20.4.5 | Farm K | Calf Fecal | Calf | 97.0% | 58.5% | 93.5% | 92.5% | 43.4% |
| R20.4.9 | Farm K | Calf Fecal | Calf | 96.6% | 0.0% | 70.8% | 0.0% | 93.3% |
| R20.41.3 | Farm K | Cow Fecal | Group 4- 1st Calf | 99.1% | 23.6% | 98.9% | 99.5% | 99.2% |
| R20.42.1 | Farm K | Cow Fecal | Group 4- 1st Calf | 0.0% | 15.5% | 98.6% | 21.9% | 98.1% |
| R20.42.10 | Farm K | Cow Fecal | Group 4- 1st Calf | 0.0% | 0.0% | 0.0% | 0.0% | 0.0% |
| R20.44.2 | Farm K | Cow Fecal | Group 4- 1st Calf | 95.9% | 91.4% | 88.9% | 0.0% | 13.2% |
| R20.45.6 | Farm K | Cow Fecal | Group 4- 1st Calf | 96.4% | 91.6% | 92.6% | 90.5% | 0.0% |
| R20.46.2 | Farm K | Cow Fecal | Post Fresh | 0.0% | 91.0% | 91.4% | 90.8% | 55.8% |
| R20.46.3 | Farm K | Cow Fecal | Post Fresh | 96.6% | 91.3% | 91.7% | 46.9% | 87.8% |
| R20.47.2 | Farm K | Cow Fecal | Post Fresh | 25.3% | 85.8% | 24.5% | 0.0% | 7.4% |
| R20.47.5 | Farm K | Cow Fecal | Post Fresh | 94.9% | 92.8% | 91.7% | 21.2% | 66.1% |
| R20.5.2 | Farm K | Calf Fecal | Calf | 96.2% | 59.2% | 29.8% | 91.3% | 2.4% |
| R20.5.3 | Farm K | Calf Fecal | Calf | 97.6% | 75.3% | 32.5% | 92.0% | 37.8% |
| R20.5.4 | Farm K | Calf Fecal | Calf | 95.3% | 25.6% | 22.4% | 51.6% | 68.8% |
| R20.53.3 | Farm K | Cow Fecal | Dry | 82.8% | 0.0% | 30.5% | 82.4% | 22.8% |
| R20.53.7 | Farm K | Cow Fecal | Dry | 0.0% | 0.0% | 98.0% | 0.0% | 97.5% |
| R20.6.3 | Farm K | Cow Fecal | Dry | 15.0% | 0.0% | 0.0% | 0.0% | 0.0% |
| R20.6.5 | Farm K | Cow Fecal | Dry | 12.4% | 8.4% | 2.1% | 10.3% | 4.4% |
| R20.6.6 | Farm K | Cow Fecal | Group 1 - High | 96.5% | 93.4% | 93.7% | 91.4% | 6.5% |
| R20.6.7 | Farm K | Cow Fecal | Group 1 - High | 99.9% | 99.4% | 99.8% | 99.9% | 99.5% |
| R20.6.9 | Farm K | Cow Fecal | Group 1 - High | 99.1% | 98.8% | 99.3% | 99.1% | 99.1% |
| R20.8.8 | Farm K | Cow Fecal | Group 1 - High | 96.3% | 94.5% | 94.9% | 37.3% | 0.0% |
| R20.9.3 | Farm K | Cow Fecal | Group 1 - High | 45.6% | 4.4% | 98.2% | 28.7% | 31.8% |
| R20.9.6 | Farm K | Cow Fecal | Group 1 - High | 15.9% | 0.0% | 4.5% | 0.6% | 2.3% |
| R20.9.7 | Farm K | Cow Fecal | Group 1 - High | 98.0% | 98.4% | 98.4% | 98.7% | 97.7% |
| R21.1.1 | Farm A | Calf Fecal | Calf | 29.6% | 46.2% | 19.0% | 52.8% | 72.7% |
| R21.1.2 | Farm A | Calf Fecal | Calf | 96.4% | 93.1% | 14.4% | 91.3% | 73.8% |
| R21.1.3 | Farm A | Calf Fecal | Calf | 8.9% | 0.0% | 0.0% | 18.1% | 55.2% |
| R21.1.4 | Farm A | Calf Fecal | Calf | 94.3% | 94.0% | 2.6% | 6.2% | 2.0% |
| R21.1.8 | Farm A | Calf Fecal | Calf | 61.8% | 12.4% | 12.4% | 85.9% | 80.8% |
| R21.10.2 | Farm A | Cow Fecal | Group 1 | 98.5% | 95.7% | 99.8% | 99.8% | 78.4% |
| R21.12.2 | Farm A | Cow Fecal | Group 1 | 8.3% | 0.0% | 97.4% | 103.6% | 103.2% |
| R21.14.1 | Farm A | Cow Fecal | Group 2 | 92.4% | 93.8% | 99.5% | 95.3% | 93.4% |
| R21.16.4 | Farm A | Cow Fecal | Group 2 | 100.6% | 100.6% | 100.1% | 100.4% | 100.1% |
| R21.18.2 | Farm A | Cow Fecal | Group 2 | 98.7% | 98.7% | 99.8% | 99.0% | 99.0% |
| R21.2.2 | Farm A | Calf Fecal | Calf | 97.0% | 96.1% | 94.4% | 94.0% | 92.2% |
| R21.2.3 | Farm A | Calf Fecal | Calf | 53.7% | 21.1% | 26.7% | 81.9% | 33.3% |
| R21.2.5 | Farm A | Calf Fecal | Calf | 98.1% | 29.2% | 97.5% | 98.6% | 98.1% |
| R21.2.6 | Farm A | Calf Fecal | Calf | 72.8% | 44.9% | 0.0% | 82.4% | 25.3% |
| R21.2.8 | Farm A | Calf Fecal | Calf | 39.1% | 22.8% | 22.2% | 54.5% | 31.7% |
| R21.2.9 | Farm A | Calf Fecal | Calf | 99.6% | 99.5% | 99.6% | 99.6% | 99.5% |
| R21.22.4 | Farm A | Cow Fecal | Group 2 | 0.0% | 0.0% | 0.0% | 0.0% | 0.0% |
| R21.22.6 | Farm A | Cow Fecal | Group 2 | 94.7% | 90.0% | 90.8% | 87.5% | 88.2% |
| R21.23.2 | Farm A | Cow Fecal | Pre-Fresh | 0.0% | 0.0% | 0.0% | 0.0% | 0.0% |
| R21.23.7 | Farm A | Cow Fecal | Pre-Fresh | 2.4% | 0.0% | 0.0% | 0.0% | 0.0% |
| R21.25.8 | Farm A | Cow Fecal | Pre-Fresh | 100.2% | 100.0% | 99.8% | 100.0% | 100.0% |
| R21.26.10 | Farm A | Cow Fecal | Pre-Fresh | 89.4% | 85.0% | 82.8% | 79.7% | 0.0% |

TABLE 18-continued

Bacteriocin assay results displaying each isolate tested and the source of that isolate, isolated from Northeast regional fecal samples. Inhibition was calculated based on the percent of growth for each treatment well compared to the positive control.

| | Sample | | | Bacillus Strains | | | | |
|---|---|---|---|---|---|---|---|---|
| Isolate ID | Farm | Type | Group | 747 | 1104 | 1541 | 1781 | 2018 |
| R21.26.2 | Farm A | Cow Fecal | Pre-Fresh | 0.0% | 0.0% | 0.5% | 3.5% | 0.0% |
| R21.26.3 | Farm A | Cow Fecal | Pre-Fresh | 100.1% | 100.1% | 100.0% | 100.3% | 100.1% |
| R21.26.5 | Farm A | Cow Fecal | Pre-Fresh | 101.3% | 40.0% | 60.0% | 101.3% | 96.3% |
| R21.26.7 | Farm A | Cow Fecal | Pre-Fresh | 95.4% | 86.8% | 92.7% | 95.7% | 94.9% |
| R21.29.1 | Farm A | Cow Fecal | Dry | 92.6% | 35.6% | 88.8% | 80.8% | 0.0% |
| R21.3.1 | Farm A | Calf Fecal | Calf | 95.8% | 93.0% | 0.0% | 91.4% | 91.1% |
| R21.3.2 | Farm A | Calf Fecal | Calf | 95.5% | 90.5% | 91.5% | 90.8% | 77.7% |
| R21.30.8 | Farm A | Cow Fecal | Dry | 94.7% | 91.6% | 90.2% | 88.2% | 87.6% |
| R21.31.2 | Farm A | Cow Fecal | Dry | 95.1% | 93.8% | 92.0% | 91.8% | 89.6% |
| R21.31.3 | Farm A | Cow Fecal | Dry | 91.9% | 89.2% | 0.0% | 84.6% | 84.2% |
| R21.5.8 | Farm A | Cow Fecal | Group 1 | 96.3% | 92.9% | 4.3% | 91.4% | 2.8% |
| R21.6.1 | Farm A | Cow Fecal | Group 1 | 81.4% | 18.2% | 0.0% | 2.8% | 0.0% |
| R21.7.1 | Farm A | Cow Fecal | Group 1 | 6.8% | 0.0% | 0.0% | 0.0% | 0.0% |
| R21.8.3 | Farm A | Cow Fecal | Group 1 | 88.8% | 0.0% | 78.0% | 70.6% | 71.3% |
| R21.8.6 | Farm A | Cow Fecal | Group 1 | 96.5% | 30.2% | 0.3% | 73.3% | 77.6% |
| R46.14.1 | Farm N | Cow Fecal | Pre-Fresh | 0.0% | 0.0% | 0.0% | 0.0% | 0.0% |
| R46.16.5 | Farm N | Cow Fecal | Pre-Fresh | 99.7% | 98.3% | 99.4% | 99.4% | 99.7% |
| R46.16.9 | Farm N | Cow Fecal | Pre-Fresh | 99.8% | 99.8% | 99.7% | 99.7% | 99.7% |
| R46.17.6 | Farm N | Cow Fecal | Pre-Fresh | 99.6% | 99.6% | 99.4% | 99.6% | 99.6% |
| R46.19.3 | Farm N | Cow Fecal | Pre-Fresh | 99.4% | 99.6% | 99.4% | 99.4% | 99.6% |
| R46.20.1 | Farm N | Cow Fecal | Pre-Fresh | 98.4% | 97.7% | 97.9% | 98.4% | 98.2% |
| R46.22.4 | Farm N | Cow Fecal | Lactating Fresh | 99.7% | 93.5% | 99.4% | 99.4% | 99.6% |
| R46.23.3 | Farm N | Cow Fecal | Lactating Fresh | 99.7% | 99.9% | 99.3% | 99.6% | 99.6% |
| R46.23.5 | Farm N | Cow Fecal | Lactating Fresh | 100.0% | 0.0% | 98.8% | 98.8% | 101.3% |
| R46.25.10 | Farm N | Cow Fecal | Lactating Fresh | 96.7% | 95.5% | 95.4% | 98.2% | 95.3% |
| R46.25.6 | Farm N | Cow Fecal | Lactating Fresh | 100.0% | 100.0% | 99.8% | 100.0% | 99.8% |
| R46.26.6 | Farm N | Cow Fecal | Lactating Fresh | 99.5% | 98.9% | 98.9% | 99.5% | 99.3% |
| R46.27.5 | Farm N | Cow Fecal | Lactating Fresh | 99.9% | 100.0% | 100.0% | 100.0% | 99.9% |
| R46.27.6 | Farm N | Cow Fecal | Lactating Fresh | 0.0% | 0.0% | 0.0% | 0.0% | 0.0% |
| R46.27.8 | Farm N | Cow Fecal | Lactating Fresh | 85.0% | 75.0% | 75.0% | 85.0% | 90.0% |
| R46.27.9 | Farm N | Cow Fecal | Lactating Fresh | 99.8% | 99.8% | 99.4% | 99.7% | 99.7% |
| R46.28.4 | Farm N | Cow Fecal | Lactating Fresh | 99.8% | 99.0% | 99.0% | 99.8% | 99.3% |
| R46.29.8 | Farm N | Cow Fecal | Lactating Fresh | 88.3% | 77.0% | 79.4% | 78.3% | 80.6% |
| R46.3.5 | Farm N | Calf Fecal | Calf | 101.1% | 0.0% | 97.8% | 89.1% | 0.0% |
| R46.31.2 | Farm N | Cow Fecal | Lactating Fresh | 99.7% | 99.7% | 99.6% | 99.7% | 99.6% |
| R46.31.4 | Farm N | Cow Fecal | Lactating Fresh | 90.3% | 88.7% | 90.3% | 91.9% | 91.9% |
| R46.31.5 | Farm N | Cow Fecal | Lactating Fresh | 58.1% | 42.7% | 60.4% | 56.7% | 51.7% |
| R46.31.6 | Farm N | Cow Fecal | Lactating Fresh | 99.4% | 99.4% | 99.1% | 99.3% | 99.3% |
| R46.31.7 | Farm N | Cow Fecal | Lactating Fresh | 100.0% | 100.0% | 100.0% | 100.0% | 100.0% |
| R46.31.9 | Farm N | Cow Fecal | Lactating Fresh | 100.0% | 99.8% | 99.5% | 99.8% | 99.8% |
| R46.34.10 | Farm N | Cow Fecal | 1st Calf | 99.6% | 99.3% | 99.5% | 99.3% | 99.3% |
| R46.35.7 | Farm N | Cow Fecal | 1st Calf | 90.1% | 36.3% | 50.5% | 71.2% | 86.8% |
| R46.35.8 | Farm N | Cow Fecal | 1st Calf | 99.8% | 98.9% | 98.9% | 99.7% | 99.7% |
| R46.35.9 | Farm N | Cow Fecal | 1st Calf | 98.5% | 27.7% | 94.8% | 98.4% | 59.5% |
| R46.37.2 | Farm N | Cow Fecal | 1st Calf | 100.0% | 99.7% | 99.9% | 100.0% | 100.0% |
| R46.40.7 | Farm N | Cow Fecal | 1st Calf | 100.0% | 50.0% | 100.0% | 50.0% | 50.0% |
| R46.42.1 | Farm N | Cow Fecal | Low | 118.2% | 100.0% | 81.8% | 109.1% | 100.0% |
| R46.42.4 | Farm N | Cow Fecal | Low | 97.4% | 98.8% | 97.8% | 98.8% | 94.5% |
| R46.42.6 | Farm N | Cow Fecal | Low | 99.9% | 99.5% | 99.9% | 100.0% | 86.6% |
| R46.42.7 | Farm N | Cow Fecal | Low | 100.1% | 100.1% | 100.0% | 100.0% | 100.0% |
| R46.43.1 | Farm N | Cow Fecal | Low | 97.6% | 100.0% | 26.8% | 0.0% | 100.0% |
| R46.43.3 | Farm N | Cow Fecal | Low | 100.0% | 100.0% | 100.0% | 100.0% | 100.0% |
| R46.43.9 | Farm N | Cow Fecal | Low | 99.9% | 100.0% | 99.4% | 100.0% | 99.9% |
| R46.44.6 | Farm N | Cow Fecal | Low | 100.0% | 96.8% | 99.7% | 100.0% | 100.0% |
| R46.45.3 | Farm N | Cow Fecal | Low | 98.5% | 100.0% | 99.9% | 99.9% | 100.0% |
| R46.45.5 | Farm N | Cow Fecal | Low | 88.3% | 86.0% | 85.4% | 84.7% | 91.8% |
| R46.45.8 | Farm N | Cow Fecal | Low | 100.0% | 0.0% | 100.0% | 58.8% | 100.0% |
| R46.46.3 | Farm N | Cow Fecal | Low | 89.1% | 94.2% | 100.0% | 83.9% | 81.8% |
| R46.46.4 | Farm N | Cow Fecal | Low | 99.5% | 99.8% | 99.6% | 99.5% | 99.6% |
| R46.46.7 | Farm N | Cow Fecal | Low | 100.0% | 99.7% | 99.9% | 100.0% | 99.9% |
| R46.47.2 | Farm N | Cow Fecal | Low | 99.4% | 98.9% | 97.7% | 100.0% | 100.0% |
| R46.47.4 | Farm N | Cow Fecal | Low | 100.0% | 95.9% | 100.0% | 100.0% | 100.0% |
| R46.49.5 | Farm N | Cow Fecal | Low | 100.0% | 69.4% | 100.0% | 100.0% | 100.0% |
| R46.50.10 | Farm N | Cow Fecal | Low | 98.8% | 98.6% | 93.8% | 96.5% | 97.6% |
| R46.50.8 | Farm N | Cow Fecal | Low | 100.0% | 100.0% | 100.0% | 100.0% | 98.8% |
| R46.51.5 | Farm N | Cow Fecal | Low | 100.0% | 100.0% | 99.7% | 100.0% | 100.0% |
| R46.52.1 | Farm N | Cow Fecal | High | 99.8% | 96.3% | 99.8% | 100.0% | 99.8% |
| R46.52.4 | Farm N | Cow Fecal | High | 100.0% | 97.9% | 99.5% | 100.0% | 99.9% |
| R46.53.9 | Farm N | Cow Fecal | High | 0.0% | 0.0% | 0.0% | 0.0% | 0.0% |
| R46.54.1 | Farm N | Cow Fecal | High | 99.0% | 99.2% | 99.0% | 74.8% | 98.6% |
| R46.54.10 | Farm N | Cow Fecal | High | 100.0% | 98.7% | 100.0% | 100.0% | 100.0% |
| R46.54.4 | Farm N | Cow Fecal | High | 100.0% | 99.2% | 99.2% | 100.0% | 99.2% |

TABLE 18-continued

Bacteriocin assay results displaying each isolate tested and the source of that isolate, isolated from Northeast regional fecal samples. Inhibition was calculated based on the percent of growth for each treatment well compared to the positive control.

| | Sample | | | Bacillus Strains | | | | |
|---|---|---|---|---|---|---|---|---|
| Isolate ID | Farm | Type | Group | 747 | 1104 | 1541 | 1781 | 2018 |
| R46.54.6 | Farm N | Cow Fecal | High | 100.0% | 73.6% | 100.0% | 100.0% | 100.0% |
| R46.54.7 | Farm N | Cow Fecal | High | 100.0% | 100.0% | 100.0% | 100.0% | 100.0% |
| R46.58.1 | Farm N | Cow Fecal | High | 12.4% | 0.0% | 94.9% | 0.0% | 97.1% |
| R46.58.6 | Farm N | Cow Fecal | High | 100.0% | 100.0% | 100.0% | 87.5% | 100.0% |
| R46.60.2 | Farm N | Cow Fecal | High | 100.0% | 9.9% | 59.4% | 71.3% | 100.0% |
| R46.60.5 | Farm N | Cow Fecal | High | 0.0% | 28.7% | 0.0% | 0.0% | 0.0% |
| R46.60.6 | Farm N | Cow Fecal | High | 97.7% | 97.4% | 96.1% | 98.3% | 96.4% |
| R46.60.9 | Farm N | Cow Fecal | High | 100.0% | 0.0% | 100.0% | 100.0% | 0.0% |
| R46.61.3 | Farm N | Cow Fecal | High | 80.6% | 0.0% | 0.0% | 83.7% | 46.0% |
| R46.62.2 | Farm N | Cow Fecal | High | 1.3% | 24.1% | 31.6% | 2.5% | 0.0% |
| R46.62.9 | Farm N | Cow Fecal | High | 37.1% | 0.0% | 0.0% | 64.1% | 40.3% |
| R46.64.2 | Farm N | Cow Fecal | Dry | 100.0% | 100.0% | 100.0% | 100.0% | 100.0% |
| R46.65.3 | Farm N | Cow Fecal | Dry | 99.8% | 99.8% | 99.6% | 99.8% | 99.6% |
| R46.65.4 | Farm N | Cow Fecal | Dry | 96.8% | 98.9% | 99.3% | 98.4% | 98.8% |
| R46.65.8 | Farm N | Cow Fecal | Dry | 98.5% | 98.5% | 99.0% | 99.0% | 99.5% |
| R46.66.2 | Farm N | Cow Fecal | Dry | 100.0% | 98.5% | 99.8% | 99.7% | 99.5% |
| R46.66.6 | Farm N | Cow Fecal | Dry | 99.9% | 99.9% | 99.7% | 99.9% | 99.9% |
| R46.67.3 | Farm N | Cow Fecal | Dry | 98.6% | 98.1% | 98.0% | 98.6% | 98.4% |
| R46.68.7 | Farm N | Cow Fecal | Dry | 99.9% | 99.9% | 99.6% | 99.9% | 99.9% |
| R46.69.8 | Farm N | Cow Fecal | Dry | 98.0% | 0.0% | 95.7% | 98.6% | 96.1% |
| R46.7.1 | Farm N | Calf Fecal | Calf | 98.2% | 85.4% | 89.0% | 80.8% | 67.8% |
| R46.7.3 | Farm N | Calf Fecal | Calf | 91.4% | 0.0% | 98.9% | 100.0% | 100.0% |
| R46.72.10 | Farm N | Cow Fecal | Dry | 99.4% | 97.5% | 98.1% | 98.7% | 99.3% |
| R46.73.5 | Farm N | Cow Fecal | Dry | 100.0% | 99.6% | 99.6% | 100.1% | 99.9% |
| R46.73.9 | Farm N | Cow Fecal | Dry | 78.2% | 70.5% | 80.8% | 76.9% | 78.2% |
| R48.1.8 | Farm MM | Calf Fecal | Calf | 99.4% | 99.4% | 99.2% | 99.4% | 98.3% |
| R48.16.3 | Farm MM | Cow Fecal | Pre-Fresh | 69.2% | 65.7% | 75.6% | 59.6% | 74.5% |
| R48.18.10 | Farm MM | Cow Fecal | Pre-Fresh | 98.8% | 99.6% | 99.7% | 99.7% | 93.1% |
| R48.18.7 | Farm MM | Cow Fecal | Pre-Fresh | 91.5% | 83.9% | 99.4% | 95.2% | 94.0% |
| R48.19.1 | Farm MM | Cow Fecal | Pre-Fresh | 99.7% | 88.7% | 99.5% | 99.5% | 98.2% |
| R48.19.10 | Farm MM | Cow Fecal | Pre-Fresh | 86.3% | 97.1% | 99.9% | 89.8% | 99.9% |
| R48.19.2 | Farm MM | Cow Fecal | Pre-Fresh | 97.7% | 98.9% | 99.8% | 93.7% | 98.4% |
| R48.19.3 | Farm MM | Cow Fecal | Pre-Fresh | 100.0% | 96.6% | 88.7% | 100.2% | 100.2% |
| R48.19.7 | Farm MM | Cow Fecal | Pre-Fresh | 98.6% | 74.8% | 93.6% | 94.9% | 95.8% |
| R48.21.9 | Farm MM | Cow Fecal | Pre-Fresh | 98.5% | 63.1% | 74.0% | 99.4% | 65.8% |
| R48.22.3 | Farm MM | Cow Fecal | Pre-Fresh | 43.1% | 45.0% | 49.9% | 43.4% | 45.8% |
| R48.24.5 | Farm MM | Cow Fecal | Fresh | 65.0% | 40.7% | 55.3% | 53.9% | 70.6% |
| R48.24.9 | Farm MM | Cow Fecal | Fresh | 93.2% | 99.7% | 99.7% | 94.9% | 99.7% |
| R48.26.8 | Farm MM | Cow Fecal | Fresh | 55.6% | 55.4% | 44.2% | 56.9% | 57.6% |
| R48.28.1 | Farm MM | Cow Fecal | Fresh | 97.4% | 97.1% | 94.8% | 71.5% | 96.7% |
| R48.28.2 | Farm MM | Cow Fecal | Fresh | 93.8% | 94.0% | 93.5% | 94.9% | 94.5% |
| R48.30.1 | Farm MM | Cow Fecal | Low | 5.9% | 5.9% | 9.1% | 5.4% | 0.2% |
| R48.31.9 | Farm MM | Cow Fecal | Low | 98.2% | 99.6% | 98.9% | 98.7% | 98.7% |
| R48.35.3 | Farm MM | Cow Fecal | Mid-Lac | 99.6% | 99.8% | 99.5% | 99.8% | 99.8% |
| R48.35.8 | Farm MM | Cow Fecal | Mid-Lac | 82.3% | 98.9% | 96.5% | 100.0% | 100.0% |
| R48.36.4 | Farm MM | Cow Fecal | Mid-Lac | 95.6% | 42.1% | 99.7% | 93.8% | 99.8% |
| R48.36.5 | Farm MM | Cow Fecal | Mid-Lac | 98.2% | 93.6% | 97.5% | 83.6% | 97.4% |
| R48.38.4 | Farm MM | Cow Fecal | Mid-Lac | 75.4% | 82.0% | 97.9% | 98.9% | 97.0% |
| R48.40.10 | Farm MM | Cow Fecal | Mid-Lac | 99.4% | 28.3% | 98.5% | 98.9% | 19.7% |
| R48.40.2 | Farm MM | Cow Fecal | Mid-Lac | 99.4% | 68.1% | 98.4% | 99.9% | 100.0% |
| R48.41.9 | Farm MM | Cow Fecal | Mid-Lac | 63.8% | 58.1% | 93.3% | 58.4% | 77.3% |
| R48.44.6 | Farm MM | Cow Fecal | Mid-Lac | 100.0% | 99.9% | 99.3% | 99.6% | 100.0% |
| R48.44.8 | Farm MM | Cow Fecal | Mid-Lac | 61.5% | 19.4% | 66.0% | 56.4% | 75.7% |
| R48.46.8 | Farm MM | Cow Fecal | Mid-Lac | 60.1% | 13.6% | 78.6% | 58.4% | 71.4% |
| R48.46.9 | Farm MM | Cow Fecal | Mid-Lac | 73.8% | 28.4% | 77.1% | 75.4% | 65.0% |
| S50.4.1 | Farm BH | Feed | Fresh Cow TMR | 0.0% | 0.0% | 0.0% | 0.0% | 0.0% |
| S50.4.6 | Farm BH | Feed | Fresh Cow TMR | 0.0% | 0.0% | 0.0% | 0.0% | 0.0% |
| S50.5.3 | Farm BH | Feed | Prefresh TMR | 0.0% | 0.0% | 0.0% | 0.0% | 0.0% |
| S50.5.5 | Farm BH | Feed | Prefresh TMR | 0.0% | 0.0% | 0.0% | 0.0% | 0.0% |
| S50.5.8 | Farm BH | Feed | Prefresh TMR | 0.0% | 0.0% | 0.0% | 10.4% | 13.9% |
| S50.6.1 | Farm BH | Feed | High Cow TMR | 0.0% | 0.0% | 0.0% | 0.0% | 0.0% |
| S50.6.3 | Farm BH | Feed | High Cow TMR | 0.0% | 0.0% | 0.0% | 0.0% | 0.0% |
| S51.2.2 | Farm HE | Feed | Haylage | 1.9% | 0.0% | 0.0% | 0.0% | 0.0% |
| S54.1.1 | Farm D | Feed | Wet Brewers Grain | 89.8% | 91.3% | 93.1% | 0.0% | 2.6% |
| S54.16.2 | Farm D | Feed | Fresh Cow TMR | 0.0% | 0.0% | 0.0% | 0.0% | 0.0% |
| S54.18.3 | Farm D | Feed | High Cow TMR | 0.0% | 0.0% | 0.0% | 0.0% | 0.0% |
| S54.19.4 | Farm D | Feed | Far Off Dry TMR | 0.0% | 0.0% | 0.0% | 0.0% | 0.0% |
| S55.9.1 | Farm V | Feed | Dry Cow TMR | 30.4% | 5.7% | 0.0% | 19.2% | 0.0% |
| S56.1.2 | Farm O | Feed | Pellets | 98.1% | 96.7% | 97.5% | 96.6% | 96.2% |
| S56.1.3 | Farm O | Feed | Pellets | 11.8% | 1.9% | 5.5% | 0.0% | 4.5% |
| S56.7.6 | Farm O | Feed | Corn Silage Face | 38.8% | 4.5% | 0.0% | 13.2% | 32.4% |
| S56.9.1 | Farm O | Feed | Milk Cow TMR | 40.6% | 39.7% | 56.7% | 39.8% | 54.8% |

TABLE 18-continued

Bacteriocin assay results displaying each isolate tested and the source of that isolate, isolated from Northeast regional fecal samples. Inhibition was calculated based on the percent of growth for each treatment well compared to the positive control.

| | Sample | | | Bacillus Strains | | | | |
|---|---|---|---|---|---|---|---|---|
| Isolate ID | Farm | Type | Group | 747 | 1104 | 1541 | 1781 | 2018 |
| S56.9.3 | Farm O | Feed | Milk Cow TMR | 4.6% | 0.0% | 6.1% | 0.0% | 11.5% |
| S56.9.6 | Farm O | Feed | Milk Cow TMR | 0.0% | 0.0% | 0.0% | 0.0% | 0.0% |
| S56.9.7 | Farm O | Feed | Milk Cow TMR | 0.0% | 0.0% | 0.0% | 0.0% | 0.0% |
| S61.10.6 | Farm K | Feed | TMR 1 | 44.5% | 20.2% | 6.8% | 54.3% | 16.4% |
| S61.12.1 | Farm K | Feed | TMR 3 | 57.1% | 0.0% | 40.8% | 12.8% | 9.3% |
| S61.12.10 | Farm K | Feed | TMR 3 | 0.0% | 0.0% | 0.0% | 0.0% | 0.0% |
| S61.12.5 | Farm K | Feed | TMR 3 | 0.0% | 0.0% | 0.0% | 0.0% | 0.0% |
| S61.12.7 | Farm K | Feed | TMR 3 | 0.0% | 0.0% | 0.0% | 0.0% | 0.0% |
| S61.3.2 | Farm K | Feed | Corn Silage Face | 95.0% | 92.8% | 92.3% | 90.3% | 89.9% |
| S61.3.4 | Farm K | Feed | Corn Silage Face | 0.0% | 94.4% | 94.4% | 0.0% | 92.1% |
| S61.5.3 | Farm K | Feed | Dry Hay Ontario | 95.3% | 7.7% | 98.3% | 89.8% | 95.1% |
| S91.2.4 | Farm N | Feed | Grass Haylage | 82.4% | 77.4% | 80.5% | 86.6% | 82.2% |
| S91.2.5 | Farm N | Feed | Grass Haylage | 77.9% | 50.5% | 57.2% | 74.1% | 40.4% |
| S91.3.5 | Farm N | Feed | Pre Fresh | 65.5% | 73.5% | 76.1% | 64.5% | 66.7% |
| S91.5.4 | Farm N | Feed | Low TMR | 73.8% | 76.3% | 74.9% | 62.4% | 66.0% |

Example 10: Selection of Bacillus Strains to Inhibit Clostridium Perfringens and Non-Toxigenic Clostridia Isolated from Ruminant Fecal Samples. (Mid-Atlantic)

Introduction:

Clostridium is a genus of Gram-positive, spore-forming bacteria that are common residents of the gastrointestinal tract. A number of *Clostridium* species have been linked to enteric disease in ruminants including hemorrhagic bowel syndrome (HBS), a disease often correlated to elevated levels of *Clostridium perfringens* Type A. While most of the enteric diseases caused by clostridia are acute and occur sporadically in herds, in general, the prognosis is poor and the first sign of illness may be death. Based on recent results sub-acute enteric clostridia disease challenges may be a more wide spread issue than acute challenges. Due to a low success rate from treatment in acute disease challenges a more common, emphasis needs to be placed on prophylactic measures.

The purpose of this research was to characterize the distribution and diversity of clostridia in ruminants and ensure inhibition of these isolates using novel *Bacillus* strains as a method to control the clostridia populations.

Materials and Methods:

Fecal samples (186) from cows, heifers and calves gathered from 6 farms in the Mid-Atlantic Region were diluted 1:10 with sterile peptone, heat shocked for 30 minutes at 60° C., enumerated in sterile peptone and pour plated on Tryptose Sulphite Cycloserine (TSC) agar with D-cycloserine (400 mg/L) to select for clostridia species. Agar plates were incubated at 37° C. anaerobically for 24 hours. If present, isolated sulphite-reducing colonies were counted for a total clostridia count (CFU/g) and representative isolates were picked into Reinforced clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions were performed in 96-well blocks containing 500 μl presumptive clostridia culture per well. Cells were harvested by centrifugation at 4,700 rpm for 10 minutes, the supernatant was removed. Cells were re-suspended in 500 μl of 50 mM of EDTA-2Na (pH=8.0). Aliquots of 300 μl of the suspended cells were transferred to a new 96-well block and combined with 20 μl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 μl of lysis buffer (6 M Guanidine, 20% Triton-X 100, 10 mM Tris-HCL, pH 7.5) was added, mixed then incubated at room temperature for 15 minutes. Following the incubation 20 μl of Proteinase K (NEB, 800 U/mL) was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed centrifuging 750 μl of Column Wash Solution (Promega, A1318) at 4700 rpms for 1 minute and 30 seconds discarding flow through at the end of each spin. The binding plate was centrifuged for an additional 10 minutes at 4,700 rpm to remove any residual ethanol. A clean elution plate was then placed under the binding plate and DNA was eluted with 200 μl, pre-warmed (55° C.), Nuclease Free Water (Promega, P1195).

DNA was screened for toxin genes (α, β, ε, and ι) specific to *C. perfringens* using polymerase chain reaction (PCR). Amplification of toxin genes was executed using a multiplex PCR containing four primer sets (Yoo et al., 1997) (Table 1.) The PCR mixture contained 2.5 μl 10×PCR Buffer, 2 μl of 50 mM $MgCl_2$, 0.5 μM of each primer (Table 1.), 0.1 μl of Invitrogen™ Platinum™ Taq DNA Polymerase, 2.5 μl of DNA, sterile water was added to achieve 25 μl for a total reaction volume. The mixture underwent 5 minutes at 94° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved. If one or multiple toxin genes were observed a toxin type identification was assigned to each isolate based on their toxin gene profile (Songer, 1996). *C. perfringens* positive to total clostridia isolate ratio was used to calculate an estimated *C. perfringens* count based on the total clostridia count.

Unique strain-specific genetic fingerprints were generated using Random Amplification of Polymorphic DNA (RAPD) analysis on select isolates to determine diversity among fecal *C. perfringens* isolates. The PCR contained 5 μl of DNA, 2.5 μl RAPD primer 2 (10 μM) (Table 1.), and 17.5 μl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes finishing with a final elongation of 5 minutes at 72° C. PCR products observed on a Fragment Analyzer (Advanced Analytics) to determine amplification patterns and were imported into BioNumerics, bioinformatics software, for analysis. RAPD patterns were compared with a band based Dice correlation analysis method to determine the similarity between RAPD patterns as a way to monitor diversity between isolates.

Antimicrobial screening was done on *C. perfringens* isolates obtained from ruminant samples to gauge the effectiveness of the antimicrobial bacteriocin produced by the inventors' identified *Bacillus* strains 747, 1104, 1541, 1781, and 2018. Bacteriocin was harvested by growing each strain at 32° C. in a shaking incubator at 150 rpms for 24 hours in Brain Heart Infusion (BHI) broth. A 1% transfer of the 24-hour culture to fresh BHI broth was executed after incubation. The *Bacillus* were then incubated for 36-48 hours in a 32° C. shaking incubator at 150 rpms. The culture was then centrifuged at 14,000×g for 20 minutes, supernatant was then filtered with a 0.2 m filter to remove any residual cells.

A bacteriocin turbidity assay was executed by growing *C. perfringens* strains isolated from ruminant fecal samples in RCM for 24 hours, anaerobically, at 37° C. Overnight culture was transferred (1%) to sterile RCM and immediately used in the assay. For each *C. perfringens* isolate at least six wells were run in a sterile 48 well reaction plate, 600 μl inoculated culture (positive control), 600 μl inoculated RCM+70 μl bacteriocin (747, 1104, 1541, 1781, and 2018) and 670 RCM (un-inoculated, negative control). Plates were incubated anaerobically at 37° C. for 24 hours then read using a BioTek Epoch Microplate Spectrophotometer, readings were taken at a wavelength of 600 nm. Optical density readings from the negative controls were subtracted from all OD readings and percent inhibition was calculated using the positive control and each bacteriocin treatment.

To identify clostridia that did not have at least one toxin gene specific to *C. perfringens*, a PCR reaction was performed on the isolate DNA to amplify the 16S region of rDNA using primers 27F-YM and 1492R-Y (Table 1). This was done on 20% of the isolates that did not contain a toxin gene specific to *C. perfringens*. The PCR mixture contained 5 μl of 10×PCR Buffer, 2 μl of 50 mM $MgCl_2$, 1 μl of 50 mM dNTPs, 0.4 μM of each primer (Table 1.), 0.2 μl of Invitrogen™ Platinum™ Taq DNA Polymerase, 5 μl of DNA, and sterile water was added to achieve 50 μl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to gene wiz to obtain the sequences for the 16S genes. Sequences were compared to known typed bacterial strains obtained from EZbiocloud online electronic database. Based on comparisons of these sequences a bacterial identification was assigned to the isolates.

Results:

Fecal samples, 186, were collect from 6 Mid-Atlantic region (Pennsylvania and Virginia) dairy farms from which 2,026 presumptive clostridia isolates were isolated as representatives of the clostridial diversity in Mid-Atlantic dairies (Table 19.).

Clostridia enumeration results indicated the average level of clostridia CFU/g across all calf fecal samples was 58,500 CFU/g with individual fecal samples ranging from 35 to 615,000 CFU/g. While the average level of clostridia CFU/g across all cow fecal samples was 2,570 CFU/g with individual fecal samples ranging from 20 to 147,000 CFU/g (FIG. 69.). Samples appeared to range in clostridia levels for both calves (FIG. 70.) and cows (FIG. 71.).

*C. perfringens* enumeration results displayed the average level of *C. perfringens* CFU/g across all calf fecal samples was 1,100 CFU/g with individual samples ranging from <10 to 5,640 CFU/g. While the average level of *C. perfringens* CFU/g across all cow fecal samples was 1,430 CFU/g with individual samples ranging from <10 to 87,900 CFU/g (FIG. 72.). Samples appeared to range in clostridia levels for both calves (FIG. 73.) and cows (FIG. 74.).

Analysis of the toxin multiplex PCR results displayed which isolates contained toxin genes specific to *C. perfringens*. A total of 2,026 presumptive clostridia isolates from Mid Atlantic fecal samples have been tested for the indicated *C. perfringens* toxin genes. Of the 2,026 clostridia isolates screened, 649 isolates (32%) tested positive for at least 1 of the toxin genes. From the 649 toxin-gene positive isolates 630 (97.1%) were identified as Type A (αtoxin only), however β, ε and ι, toxins were also detected in the clostridia isolates.

Gentic RAPD fingerprint patterns displayed diversity among the 582 isolates that successful amplified. The isolates tested were harvested from calf fecal, cow fecal and feed and did not cluster strictly based on the sample type or farm. Isolates formed 85 clusters based on 75% similarity according to the Dice correlation method. The largest cluster was 55 isolates (9.5%) and had a shannon idenx of diversity of 4.07.

Representatives from the RAPD dendrogram were selected to capture the diversity of the *C. perfringens* population from this region and subjected to inhibition assays. Antimicrobial testing using the bacteriocin turbidity assay displayed good inhibition of most ruminant fecal *C. perfringens* isolates using bacteriocin harvested from 747, 1104, 1541, 1781, and 2018. The bacteriocin from at least one of the strains 747, 1104, 1541, 1781, and 2018 were able to inhibit the growth >60% of 103 of the 129 isolates tested representing a total of 85.9% inhibition of the *C. perfringens* population based on the dendrogram (Table 20.).

Out of the 2,026 isolates collected 1,377 isolates (68%) were found to be non-toxigenic clostridia. Sequencing representatives (n=151) from the non-toxigenic clostridia displayed one dominate clostridia groups, *Clostridium bifermentans* group (*Paraclostridium bifermentans* and *P. benzoelyticum*). *Clostridium bifermentans* made up 51.5% of the non-toxigenic isolates (FIG. 75.).

Discussion:

Fecal samples were used as the most readily available sample type to estimate the level and obtain isolates of clostridia and *C. perfringens* within the digestive system of ruminants. From the 186 fecal samples collected throughout the Mid-Atlantic region all samples had detectable levels of clostridia. Many isolates harvested (649 isolates) from the ruminant samples contained a toxin gene specific to *C. perfringens*. *C. perfringens* was detected in 72% of the cow fecal samples and in 50% of the calf fecal samples. The high presence of clostridia and *C. perfringens* indicates the risk for sub-acute enteric clostridia disease challenges in most ruminants throughout the Mid-Atlantic region. *C. perfringens* isolates were diverse according to the RAPD genetic fingerprints but were not specific to sample type or farm. Diverse representatives of *C. perfringens* were mostly inhibited (>60%) by at least one bacteriocin from the following strains 747, 1104, 1541, 1781 or 2018. From the 129 isolates tested 103 isolates were inhibited by greater than 60% by at least one of the strains, representing inhibition of 85.9% of the total *C. perfringens* population based on representation from clusters on the RAPD dendrogram. This indicates the *Bacillus* strains 747, 1104, 1541, 1781 and 2018 can inhibit a wide range of diversity of *C. perfringens* isolates. The *Bacillus* strains are not limited to specific clostridia strain(s) like a vaccine which may be missing large groups of the clostridia populations based on the genetic diversity observed in the RAPD dendrogram. DNA sequencing of the non-toxigenic clostridia revealed one major identification of *Clostridium* species. *C. bifermentans* group, which is known to produce 1,3-propanediol (Leja et al., 2014; Myszka et al., 2012). The high inhibition level against the *C. perfringens* isolates in vitro indicates a potential mode of action of the *Bacillus* strains 747, 1104, 1541, 1781 and 2018.

The *Bacillus* strains offer a prophylactic effect on the clostridia populations which may not only increase rumen efficiency leading to increased milk production, but prevent acute levels of *C. perfringens* reducing the occurrence of digestive deaths. The high prevalence of clostridia and *C. perfringens* in fecal samples collected suggests efficiency improvement opportunities in many ruminants throughout the Mid-Atlantic region. This example displays the diversity of clostridia isolates from the ruminant fecal and feed samples collected from the Mid-Atlantic region. The *Bacillus* strains tested 747, 1104, 1541, 1781 and 2018, were able to inhibit most of the clostridia diversity observed in the Mid-Atlantic region. The product, in accordance with this embodiment of the present invention was able to inhibit toxigenic clostridia isolated from ruminants in the Mid-Atlantic region indicating a benefit in rumen efficiency if fed to dairy cows as a direct fed microbial (DFM).

TABLE 19

Fecal samples, 186, were collected from Mid-Atlantic dairies separated by farm (6) and age (cow or calf) which were enumerated for clostridia, tested for *C. perfringens*, isolates were genotyped and tested for inhibition.

| Farm Name | State | Cow Fecal | Calf Fecal |
| --- | --- | --- | --- |
| Farm B | PA | 11 | 1 |
| Farm MD | PA | 68 | 7 |
| Farm RR | PA | 10 | 1 |
| Farm RG | PA | 17 | 1 |
| Farm RH | VA | 12 | 2 |
| Farm WH | PA | 56 | 0 |
| Total | | 174 | 12 |

TABLE 20

Bacteriocin assay results displaying each isolate tested and the source of that isolate, isolated from the Mid-Atlantic region fecal samples. Inhibition was calculated based on the percent of growth for each treatment well compared to the positive control.

| Isolate ID | Farm | Sample Type | Group | *Bacillus* Strains | | | | |
| --- | --- | --- | --- | --- | --- | --- | --- | --- |
| | | | | 747 | 1104 | 1541 | 1781 | 2018 |
| R37.4.3 | Farm RH | Cow Fecal | Heifer | 100.0% | 99.7% | 99.2% | 99.6% | 100.0% |
| R37.4.9 | Farm RH | Cow Fecal | Heifer | 100.0% | 99.8% | 99.4% | 99.4% | 100.0% |
| R37.4.10 | Farm RH | Cow Fecal | Heifer | 100.0% | 99.6% | 99.6% | 99.0% | 99.8% |
| R37.5.1 | Farm RH | Cow Fecal | Lactating Cow | 95.8% | 90.4% | 89.8% | 93.1% | 94.3% |
| R37.7.5 | Farm RH | Cow Fecal | Lactating Cow | 99.8% | 99.6% | 99.8% | 98.3% | 99.9% |
| R37.10.3 | Farm RH | Cow Fecal | Lactating Cow | 99.7% | 99.7% | 99.7% | 98.5% | 99.7% |
| R37.11.1 | Farm RH | Cow Fecal | Dry Cow | 99.7% | 99.8% | 99.8% | 99.1% | 99.7% |
| R37.11.3 | Farm RH | Cow Fecal | Dry Cow | 100.0% | 39.6% | 99.6% | 99.8% | 100.0% |
| R37.11.4 | Farm RH | Cow Fecal | Dry Cow | 99.9% | 99.6% | 99.5% | 99.6% | 5.9% |
| R37.11.9 | Farm RH | Cow Fecal | Dry Cow | 51.2% | 12.3% | 1.1% | 99.4% | 100.0% |
| R37.12.9 | Farm RH | Cow Fecal | Dry Cow | 27.6% | 25.5% | 6.5% | 66.0% | 14.7% |
| S82.9.1 | Farm RH | TMR | Low | 22.3% | 0.0% | 0.0% | 39.0% | 10.2% |
| R40.3.3 | Farm RG | Cow | Bedpack | 95.5% | 7.6% | 91.5% | 94.9% | 28.6% |
| R40.4.4 | Farm RG | Cow | Free Stall | 99.8% | 73.1% | 4.0% | 98.9% | 99.5% |
| R40.5.6 | Farm RG | Cow | Free Stall | 99.1% | 98.2% | 34.8% | 99.1% | 22.0% |
| R40.5.7 | Farm RG | Cow | Free Stall | 78.3% | 0.0% | 0.0% | 75.7% | 73.2% |
| R40.6.1 | Farm RG | Cow | Free Stall | 0.0% | 0.0% | 0.0% | 0.0% | 0.0% |

TABLE 20-continued

Bacteriocin assay results displaying each isolate tested and the source of that isolate, isolated from the Mid-Atlantic region fecal samples. Inhibition was calculated based on the percent of growth for each treatment well compared to the positive control.

| Isolate ID | Sample Farm | Type | Group | Bacillus Strains 747 | 1104 | 1541 | 1781 | 2018 |
|---|---|---|---|---|---|---|---|---|
| R40.6.8 | Farm RG | Cow | Free Stall | 99.6% | 99.3% | 97.4% | 96.8% | 98.4% |
| R40.6.9 | Farm RG | Cow | Free Stall | 25.5% | 0.0% | 0.0% | 3.2% | 23.4% |
| R41.4.3 | Farm RR | Cow | Mature | 99.6% | 98.9% | 98.2% | 96.8% | 95.0% |
| R41.4.6 | Farm RR | Cow | Mature | 27.1% | 13.1% | 27.1% | 21.6% | 18.0% |
| R41.7.8 | Farm RR | Cow | Mature | 0.0% | 0.0% | 48.6% | 77.2% | 41.6% |
| R41.8.1 | Farm RR | Cow | Mature | 0.0% | 3.1% | 0.0% | 2.9% | 0.0% |
| R41.8.5 | Farm RR | Cow | Mature | 70.3% | 55.2% | 45.4% | 38.8% | 61.7% |
| R41.8.6 | Farm RR | Cow | Mature | 59.9% | 35.4% | 28.8% | 84.4% | 51.0% |
| R41.9.5 | Farm RR | Cow | Mature | 22.7% | 0.0% | 0.0% | 0.0% | 1.5% |
| R41.9.9 | Farm RR | Cow | Mature | 78.6% | 29.6% | 1.8% | 85.8% | 66.9% |
| R41.9.10 | Farm RR | Cow | Mature | 32.5% | 43.5% | 19.6% | 0.0% | 70.9% |
| R41.10.2 | Farm RR | Cow | Mature | 88.2% | 6.4% | 0.0% | 71.9% | 28.5% |
| R41.10.4 | Farm RR | Cow | Mature | 0.0% | 0.0% | 0.0% | 0.0% | 0.0% |
| R41.10.10 | Farm RR | Cow | Mature | 29.0% | 18.2% | 8.9% | 40.0% | 43.6% |
| R41.11.1 | Farm RR | Cow | Mature | 99.8% | 16.2% | 2.7% | 14.0% | 36.5% |
| R41.11.5 | Farm RR | Cow | Mature | 99.8% | 9.4% | 0.0% | 100.0% | 99.8% |
| R42.1.4 | Farm B | Calf | Calf | 100.0% | 98.3% | 100.0% | 100.0% | 99.8% |
| R42.1.5 | Farm B | Calf | Calf | 95.2% | 74.5% | 97.2% | 99.3% | 99.3% |
| R42.1.9 | Farm B | Calf | Calf | 100.1% | 21.7% | 0.0% | 96.6% | 10.8% |
| R42.3.8 | Farm B | Cows | Heifer | 97.6% | 6.8% | 97.8% | 0.0% | 97.2% |
| R42.6.2 | Farm B | Cows | Milk Cows | 0.1% | 0.0% | 0.0% | 1.3% | 8.5% |
| R42.7.1 | Farm B | Cows | Milk Cows | 100.0% | 71.7% | 79.7% | 93.7% | 97.6% |
| R42.7.3 | Farm B | Cows | Milk Cows | 99.3% | 98.8% | 99.3% | 99.3% | 99.3% |
| R42.7.8 | Farm B | Cows | Milk Cows | 89.0% | 73.5% | 72.6% | 85.2% | 82.1% |
| R42.8.5 | Farm B | Cows | Milk Cows | 98.1% | 11.6% | 19.6% | 98.5% | 16.0% |
| R42.8.8 | Farm B | Cows | Milk Cows | 100.0% | 100.0% | 100.0% | 100.0% | 99.9% |
| R42.9.3 | Farm B | Cows | Milk Cows | 97.2% | 58.6% | 31.3% | 96.9% | 68.5% |
| R42.11.7 | Farm B | Cows | Dry Cows | 100.0% | 92.7% | 100.0% | 99.9% | 50.0% |
| R42.12.1 | Farm B | Cows | Dry Cows | 49.9% | 0.0% | 3.7% | 41.0% | 38.0% |
| R43.1.5 | Farm WH | Cows | Fresh | 58.7% | 6.8% | 7.3% | 80.7% | 39.6% |
| R43.2.5 | Farm WH | Cows | Fresh | 85.7% | 0.0% | 2.9% | 89.9% | 10.0% |
| R43.3.1 | Farm WH | Cows | Fresh | 100.0% | 4.9% | 8.6% | 100.0% | 99.9% |
| R43.3.2 | Farm WH | Cows | Fresh | 100.0% | 0.0% | 0.0% | 100.0% | 100.0% |
| R43.3.4 | Farm WH | Cows | Fresh | 49.3% | 29.4% | 4.5% | 99.2% | 56.8% |
| R43.6.10 | Farm WH | Cows | Fresh | 0.0% | 0.0% | 0.0% | 0.0% | 33.2% |
| R43.8.3 | Farm WH | Cows | Fresh | 99.1% | 99.7% | 99.8% | 97.2% | 30.6% |
| R43.9.7 | Farm WH | Cows | Fresh | 99.6% | 99.6% | 13.8% | 99.6% | 99.6% |
| R43.10.1 | Farm WH | Cows | Fresh | 98.9% | 36.9% | 99.2% | 99.3% | 49.8% |
| R43.11.4 | Farm WH | Cows | Mid Lactation | 98.8% | 99.5% | 99.3% | 99.0% | 99.3% |
| R43.12.3 | Farm WH | Cows | Mid Lactation | 99.6% | 99.5% | 99.4% | 99.7% | 99.4% |
| R43.13.10 | Farm WH | Cows | Mid Lactation | 53.4% | 0.0% | 99.3% | 97.9% | 100.0% |
| R43.14.1 | Farm WH | Cows | Mid Lactation | 95.9% | 95.4% | 94.6% | 94.4% | 95.6% |

TABLE 20-continued

Bacteriocin assay results displaying each isolate tested and the source of that isolate, isolated from the Mid-Atlantic region fecal samples. Inhibition was calculated based on the percent of growth for each treatment well compared to the positive control.

| Isolate ID | Farm | Sample Type | Group | \multicolumn{5}{c}{Bacillus Strains} |
|---|---|---|---|---|---|---|---|---|
| | | | | 747 | 1104 | 1541 | 1781 | 2018 |
| R43.14.4 | Farm WH | Cows | Mid Lactation | 99.4% | 99.4% | 98.9% | 99.5% | 99.5% |
| R43.14.9 | Farm WH | Cows | Mid Lactation | 99.8% | 99.4% | 99.7% | 99.8% | 99.7% |
| R43.15.4 | Farm WH | Cows | Mid Lactation | 99.5% | 99.5% | 99.6% | 99.6% | 99.4% |
| R43.15.10 | Farm WH | Cows | Mid Lactation | 34.4% | 41.3% | 25.1% | 87.9% | 29.2% |
| R43.16.5 | Farm WH | Cows | Mid Lactation | 99.2% | 96.6% | 0.0% | 99.4% | 99.6% |
| R43.17.5 | Farm WH | Cows | Mid Lactation | 99.7% | 99.1% | 99.5% | 99.7% | 99.3% |
| R43.18.1 | Farm WH | Cows | High Lactation | 99.5% | 99.5% | 99.7% | 99.5% | 99.6% |
| R43.22.2 | Farm WH | Cows | High Lactation | 99.7% | 99.5% | 99.5% | 99.4% | 99.5% |
| R43.22.6 | Farm WH | Cows | High Lactation | 99.4% | 99.6% | 99.4% | 99.4% | 99.6% |
| R43.24.3 | Farm WH | Cows | High Lactation | 99.4% | 99.4% | 99.4% | 97.2% | 99.3% |
| R43.27.1 | Farm WH | Cows | High Lactation | 99.7% | 99.4% | 83.8% | 99.5% | 99.7% |
| R43.27.3 | Farm WH | Cows | High Lactation | 99.5% | 99.5% | 99.5% | 99.7% | 99.4% |
| R43.27.10 | Farm WH | Cows | High Lactation | 99.2% | 99.6% | 99.5% | 99.5% | 99.4% |
| R43.28.7 | Farm WH | Cows | 2 yr. olds | 99.7% | 26.2% | 97.6% | 97.7% | 99.6% |
| R43.29.5 | Farm WH | Cows | 2 yr. olds | 99.6% | 99.3% | 97.3% | 96.5% | 99.5% |
| R43.30.10 | Farm WH | Cows | 2 yr. olds | 99.4% | 99.1% | 97.3% | 96.5% | 98.8% |
| R43.31.9 | Farm WH | Cows | 2 yr. olds | 99.1% | 98.3% | 97.1% | 79.6% | 98.0% |
| R43.31.10 | Farm WH | Cows | 2 yr. olds | 99.4% | 98.8% | 98.0% | 96.6% | 98.4% |
| R43.34.2 | Farm WH | Cows | 2 yr. olds | 99.4% | 97.3% | 98.6% | 96.9% | 97.9% |
| R43.34.4 | Farm WH | Cows | 2 yr. olds | 99.4% | 98.9% | 99.1% | 97.3% | 98.1% |
| R43.34.9 | Farm WH | Cows | 2 yr. olds | 99.4% | 99.2% | 98.3% | 98.5% | 99.3% |
| R43.35.4 | Farm WH | Cows | Late Lactation | 99.5% | 99.3% | 98.6% | 98.5% | 99.7% |
| R43.36.6 | Farm WH | Cows | Late Lactation | 99.0% | 99.1% | 98.0% | 97.9% | 99.3% |
| R43.36.8 | Farm WH | Cows | Late Lactation | 99.0% | 98.9% | 98.3% | 98.1% | 99.5% |
| R43.37.7 | Farm WH | Cows | Late Lactation | 99.2% | 99.0% | 98.7% | 98.4% | 99.5% |
| R43.37.8 | Farm WH | Cows | Late Lactation | 99.2% | 98.9% | 98.9% | 98.5% | 99.5% |
| R43.39.1 | Farm WH | Cows | Late Lactation | 99.6% | 98.8% | 99.5% | 99.2% | 99.6% |
| R43.39.8 | Farm WH | Cows | Late Lactation | 99.3% | 99.2% | 99.5% | 99.2% | 99.6% |
| R43.39.10 | Farm WH | Cows | Late Lactation | 99.8% | 99.3% | 99.2% | 99.5% | 99.3% |
| R43.40.2 | Farm WH | Cows | Late Lactation | 99.6% | 99.3% | 99.3% | 99.0% | 99.8% |
| R43.40.3 | Farm WH | Cows | Late Lactation | 99.6% | 99.3% | 99.0% | 98.9% | 99.4% |
| R43.42.1 | Farm WH | Cows | Late Dry | 99.2% | 99.2% | 98.9% | 98.8% | 99.5% |
| R43.42.9 | Farm WH | Cows | Late Dry | 99.6% | 99.6% | 99.4% | 99.0% | 99.6% |
| R43.42.10 | Farm WH | Cows | Late Dry | 99.8% | 99.7% | 99.8% | 99.4% | 99.9% |
| R43.43.7 | Farm WH | Cows | Late Dry | 99.6% | 99.6% | 99.8% | 99.3% | 99.6% |

TABLE 20-continued

Bacteriocin assay results displaying each isolate tested and the source of that isolate, isolated from the Mid-Atlantic region fecal samples. Inhibition was calculated based on the percent of growth for each treatment well compared to the positive control.

| Isolate ID | Farm | Sample Type | Group | Bacillus Strains | | | | |
| --- | --- | --- | --- | --- | --- | --- | --- | --- |
| | | | | 747 | 1104 | 1541 | 1781 | 2018 |
| R43.51.7 | Farm WH | Cows | Late Dry | 99.3% | 99.6% | 99.6% | 99.2% | 99.5% |
| R43.55.6 | Farm WH | Cows | Late Dry | 99.7% | 99.3% | 99.7% | 99.4% | 99.6% |
| R43.55.7 | Farm WH | Cows | Late Dry | 92.3% | 95.2% | 99.6% | 98.2% | 99.4% |
| S86.2.1 | Farm RR | Alfalfa Haylage | | 90.5% | 86.9% | 87.9% | 95.5% | 83.4% |
| S88.5.5 | Farm WH | TMR | Fresh | 99.8% | 74.6% | 98.3% | 99.4% | 98.9% |
| S88.9.5 | Farm WH | TMR | Late Lactation | 99.8% | 99.8% | 99.9% | 99.9% | 99.9% |
| R44.2.10 | Farm MD | Calf Fecal | Calf | 26.7% | 0.0% | 23.6% | 10.2% | 29.9% |
| R44.3.5 | Farm MD | Calf Fecal | Calf | 82.7% | 0.0% | 29.3% | 5.4% | 0.0% |
| R44.4.3 | Farm MD | Calf Fecal | Calf | 5.5% | 0.0% | 0.0% | 0.0% | 0.0% |
| R44.9.6 | Farm MD | Cow Fecal | Fresh | 31.9% | 21.4% | 17.1% | 12.1% | 24.1% |
| R44.9.9 | Farm MD | Cow Fecal | Fresh | 66.6% | 14.9% | 10.5% | 3.7% | 11.3% |
| R44.11.3 | Farm MD | Cow Fecal | Fresh | 99.5% | 27.3% | 19.2% | 99.5% | 99.5% |
| R44.12.1 | Farm MD | Cow Fecal | Fresh | 96.9% | 98.5% | 0.0% | 35.0% | 0.0% |
| R44.15.3 | Farm MD | Cow Fecal | Fresh | 99.3% | 99.3% | 99.6% | 99.4% | 99.3% |
| R44.16.7 | Farm MD | Cow Fecal | Fresh | 98.5% | 51.9% | 97.1% | 98.8% | 79.1% |
| R44.16.10 | Farm MD | Cow Fecal | Fresh | 99.8% | 98.9% | 100.0% | 98.9% | 99.4% |
| R44.17.6 | Farm MD | Cow Fecal | Fresh | 99.5% | 99.6% | 99.5% | 99.6% | 98.8% |
| R44.17.8 | Farm MD | Cow Fecal | Fresh | 99.5% | 98.7% | 99.5% | 99.5% | 98.7% |
| R44.22.7 | Farm MD | Cow Fecal | Early Lactation | 99.7% | 99.7% | 99.2% | 99.7% | 99.1% |
| R44.23.9 | Farm MD | Cow Fecal | Early Lactation | 97.7% | 31.9% | 66.0% | 85.3% | 66.0% |
| R44.27.5 | Farm MD | Cow Fecal | Early Lactation | 38.9% | 41.8% | 21.2% | 67.5% | 50.6% |
| R44.28.2 | Farm MD | Cow Fecal | Mid Lactation | 0.0% | 4.0% | 0.0% | 0.0% | 0.0% |
| R44.31.4 | Farm MD | Cow Fecal | Mid Lactation | 99.7% | 90.5% | 33.9% | 99.3% | 98.2% |
| R44.31.5 | Farm MD | Cow Fecal | Mid Lactation | 35.6% | 42.0% | 22.6% | 82.7% | 58.0% |
| R44.33.4 | Farm MD | Cow Fecal | Mid Lactation | 39.6% | 0.0% | 0.0% | 0.0% | 18.8% |
| R44.37.9 | Farm MD | Cow Fecal | Mid Lactation | 29.5% | 0.0% | 19.2% | 21.2% | 17.5% |
| R44.37.10 | Farm MD | Cow Fecal | Mid Lactation | 2.3% | 0.0% | 0.0% | 0.0% | 0.0% |
| R44.43.7 | Farm MD | Cow Fecal | Late Lactation | 22.5% | 0.0% | 0.9% | 0.0% | 19.7% |
| R44.45.7 | Farm MD | Cow Fecal | Late Lactation | 27.5% | 4.6% | 10.3% | 8.4% | 15.5% |
| R44.46.7 | Farm MD | Cow Fecal | Late Lactation | 22.1% | 0.0% | 0.0% | 20.8% | 8.1% |
| R44.72.4 | Farm MD | Cow Fecal | Robot | 21.0% | 0.0% | 7.0% | 15.4% | 37.9% |
| S89.3.1 | Farm MD | Ryegrass Haylage | | 26.9% | 4.3% | 0.0% | 13.1% | 5.0% |
| S89.15.3 | Farm MD | WOM #1046 | | 2.8% | 0.0% | 0.0% | 8.3% | 30.0% |
| S89.20.7 | Farm MD | WOM #1550 | | 11.3% | 0.0% | 0.0% | 21.0% | 24.7% |
| S89.20.9 | Farm MD | WOM #1550 | | 0.0% | 0.0% | 0.0% | 0.0% | 28.8% |

Example 11: Selection of *Bacillus* Strains to Inhibit *Clostridium Perfringens* and Non-Toxigenic Clostridia Isolated from Ruminant Fecal Samples. (Interstate-29 Corridor)

Introduction:

*Clostridium* is a genus of Gram-positive, spore-forming bacteria that are common residents of the gastrointestinal tract. A number of *Clostridium* species have been linked to enteric disease in ruminants including hemorrhagic bowel syndrome (HBS), a disease often correlated to elevated levels of *Clostridium perfringens* Type A. While most of the enteric diseases caused by clostridia are acute and occur sporadically in herds, in general, the prognosis is poor and the first sign of illness may be death. Based on recent results sub-acute enteric clostridia disease challenges may be a more wide spread issue than acute challenges. Due to a low success rate from treatment in acute disease challenges a more common, emphasis needs to be placed on prophylactic measures.

The purpose of this research was to characterize the distribution and diversity of clostridia in ruminants and ensure inhibition of these isolates using novel *Bacillus* strains as a method to control the clostridia populations.

Materials and Methods:

Fecal samples (411) from cows, heifers and calves gathered from 8 farms in the 1-29 Corridor region were diluted 1:10 with sterile peptone, heat shocked for 30 minutes at 60° C., enumerated in sterile peptone and pour plated on Tryptose Sulphite Cycloserine (TSC) agar with D-cycloserine (400 mg/L) to select for clostridia species. Agar plates were incubated at 37° C. anaerobically for 24 hours. If present, isolated sulphite-reducing colonies were counted for a total clostridia count (CFU/g) and representative isolates were picked into Reinforced clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions were performed in 96-well blocks containing 500 µl presumptive clostridia culture per well. Cells were harvested by centrifugation at 4,700 rpm for 10 minutes, the supernatant was removed. Cells were re-suspended in 500 µl of 50 mM of EDTA-2Na (pH=8.0). Aliquots of 300 µl of the suspended cells were transferred to a new 96-well block and combined with 20 µl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 µl of lysis buffer (6 M Guanidine, 20% Triton-X 100, 10 mM Tris-HCL, pH 7.5) was added, mixed then incubated at room temperature for 15 minutes. Following the incubation 20 µl of Proteinase K (NEB, 800 U/mL) was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed centrifuging 750 µl of Column Wash Solution (Promega, A1318) at 4700 rpms for 1 minute and 30 seconds discarding flow through at the end of each spin. The binding plate was centrifuged for an additional 10 minutes at 4,700 rpm to remove any residual ethanol. A clean elution plate was then placed under the binding plate and DNA was eluted with 200 µl, pre-warmed (55° C.), Nuclease Free Water (Promega, P1195).

DNA was screened for toxin genes ($\alpha$, $\beta$, $\epsilon$, and $\iota$) specific to *C. perfringens* using polymerase chain reaction (PCR). Amplification of toxin genes was executed using a multiplex PCR containing four primer sets (Yoo et al., 1997) (Table 1.) The PCR mixture contained 2.5 µl 10×PCR Buffer, 2 µl of 50 mM $MgCl_2$, 0.5 µM of each primer (Table 1.), 0.1 µl of Invitrogen™ Platinum™ Taq DNA Polymerase, 2.5 µl of DNA, sterile water was added to achieve 25 µl for a total reaction volume. The mixture underwent 5 minutes at 94° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved. If one or multiple toxin genes were observed a toxin type identification was assigned to each isolate based on their toxin gene profile (Songer, 1996). *C. perfringens* positive to total clostridia isolate ratio was used to calculate an estimated *C. perfringens* count based on the total clostridia count.

Unique strain-specific genetic fingerprints were generated using Random Amplification of Polymorphic DNA (RAPD) analysis on select isolates to determine diversity among fecal *C. perfringens* isolates. The PCR contained 5 µl of DNA, 2.5 µl RAPD primer 2 (10 µM) (Table 1.), and 17.5 µl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes finishing with a final elongation of 5 minutes at 72° C. PCR products observed on a Fragment Analyzer (Advanced Analytics) to determine amplification patterns and were imported into BioNumerics, bioinformatics software, for analysis. RAPD patterns were compared with a band based Dice correlation analysis method to determine the similarity between RAPD patterns as a way to monitor diversity between isolates.

Antimicrobial screening was done on *C. perfringens* isolates obtained from ruminant samples to gauge the effectiveness of the antimicrobial bacteriocin produced by the inventors' identified *Bacillus* strains 747, 1104, 1541, 1781, and 2018. Bacteriocin was harvested by growing each strain at 32° C. in a shaking incubator at 150 rpms for 24 hours in Brain Heart Infusion (BHI) broth. A 1% transfer of the 24-hour culture to fresh BHI broth was executed after incubation. The *Bacillus* were then incubated for 36-48 hours in a 32° C. shaking incubator at 150 rpms. The culture was then centrifuged at 14,000×g for 20 minutes, supernatant was then filtered with a 0.2 m filter to remove any residual cells.

A bacteriocin turbidity assay was executed by growing *C. perfringens* strains isolated from ruminant fecal samples in RCM for 24 hours, anaerobically, at 37° C. Overnight culture was transferred (1%) to sterile RCM and immediately used in the assay. For each *C. perfringens* isolate at least six wells were run in a sterile 48 well reaction plate, 600 µl inoculated culture (positive control), 600 µl inoculated RCM+70 µl bacteriocin (747, 1104, 1541, 1781, and 2018) and 670 RCM (un-inoculated, negative control). Plates were incubated anaerobically at 37° C. for 24 hours then read using a BioTek Epoch Microplate Spectrophotometer, readings were taken at a wavelength of 600 nm. Optical density readings from the negative controls were subtracted from all OD readings and percent inhibition was calculated using the positive control and each bacteriocin treatment.

To identify clostridia that did not have at least one toxin gene specific to *C. perfringens*, a PCR reaction was performed on the isolate DNA to amplify the 16S region of rDNA using primers 27F-YM and 1492R-Y (Table 1). This was done on 20% of the isolates that did not contain a toxin gene specific to *C. perfringens*. The PCR mixture contained 5 μl of 10×PCR Buffer, 2 μl of 50 mM MgCl$_2$, 1 μl of 50 mM dNTPs, 0.4 μM of each primer (Table 1.), 0.2 μl of Invitrogen™ Platinum™ Taq DNA Polymerase, 5 μl of DNA, and sterile water was added to achieve 50 μl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to gene wiz to obtain the sequences for the 16S genes. Sequences were compared to known typed bacterial strains obtained from EZbiocloud online electronic database. Based on comparisons of these sequences a bacterial identification was assigned to the isolates.

Results:

Fecal samples, 411, were collect from eight 1-29 Corridor Regional farms (Minnesota, South Dakota, and Iowa) from which 3,471 presumptive clostridia isolates were isolated as representatives of the clostridial diversity in the 1-29 Corridor region (Table 21.).

Figure 76:
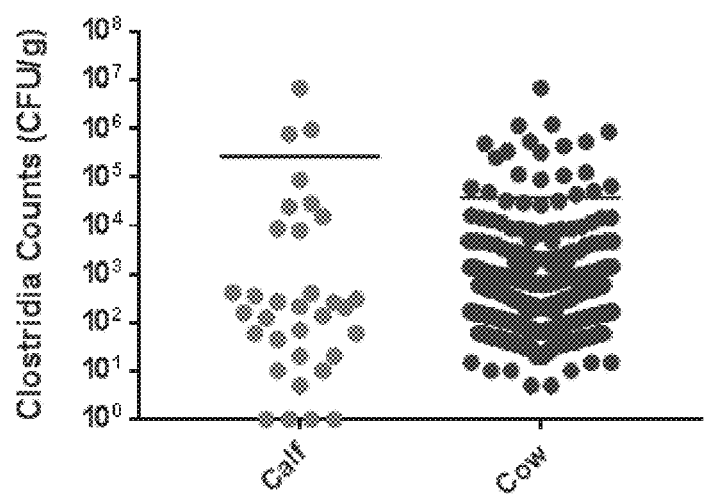
Figure 77:
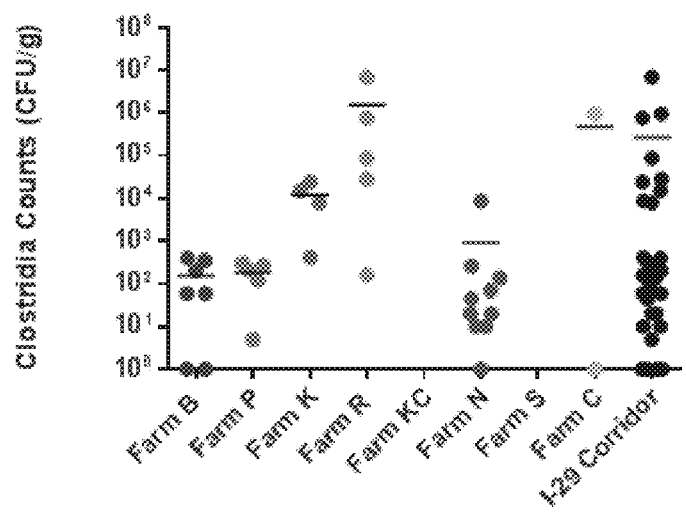
Figure 78:
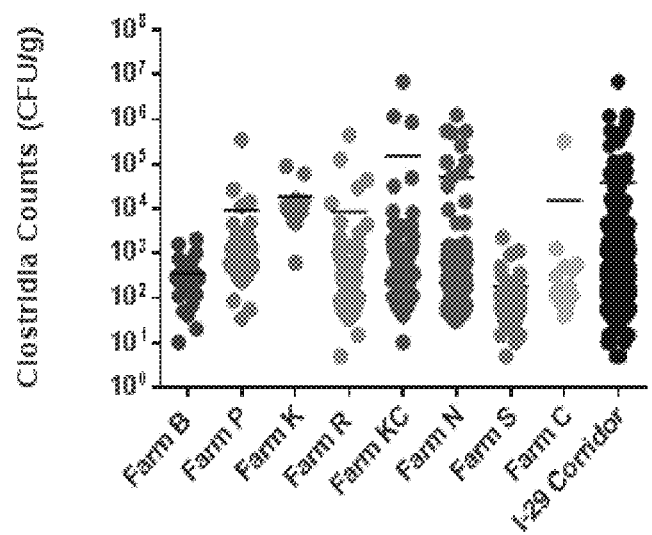
FIG. 78 is a chart showing enumeration results of total clostridia (no differentiation of *Clostridium* sp.) by individual farm cow fecal samples for each farm sampled from the 1-29 Corridor region in accordance with one embodiment of the present invention, pursuant to Example 11.

Clostridia enumeration results indicated the average level of clostridia CFU/g across all calf fecal samples was 270,000 CFU/g with individual fecal samples ranging from <10 to 7,020,000 CFU/g. While the average level of clostridia CFU/g across all cow fecal samples was 38,100 CFU/g with individual fecal samples ranging from 5 to 6,970,000 CFU/g (FIG. 76.). Samples appeared to range in clostridia levels for both calves (FIG. 77.) and cows (FIG. 78.).

Figure 79:
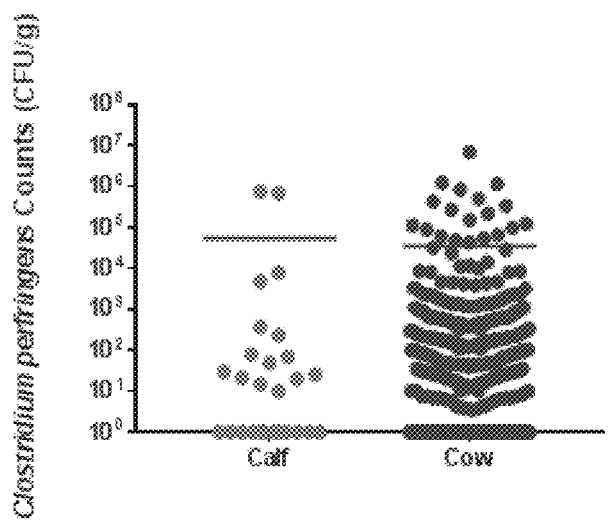
FIG. 79 is a chart showing calculated counts of *C. perfringens* by fecal sample, from fecal samples collected from the 1-29 Corridor region, where *C. perfringens* counts were estimated by multiplying each sample's total clostridia count by the percent that were confirmed to be *C. perfringens* in accordance with one embodiment of the present invention, pursuant to Example 11.
Figure 80:
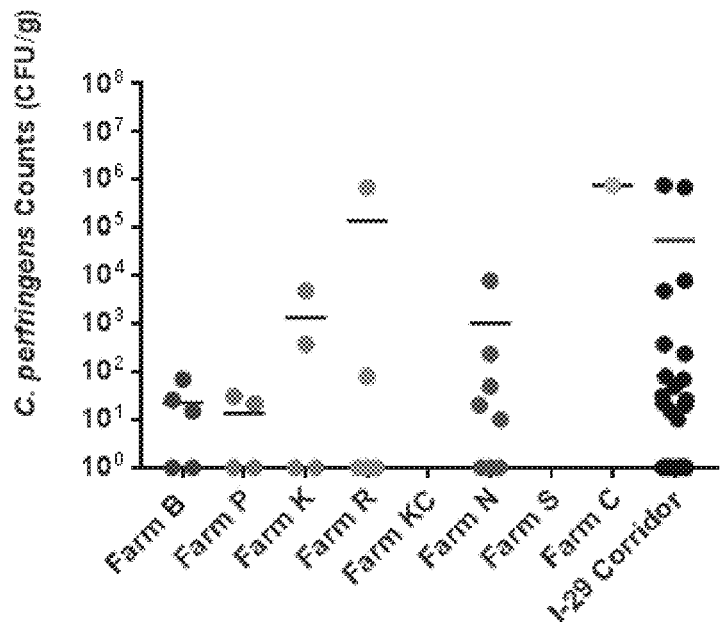
FIG. 80 is a chart showing calculated counts of *C. perfringens* for each farm by individual calf fecal sample from the 1-29 Corridor region, where *C. perfringens* counts were estimated by multiplying each sample's clostridia count by the percent that were confirmed to be *C. perfringens* in accordance with one embodiment of the present invention, pursuant to Example 11.
Figure 81:
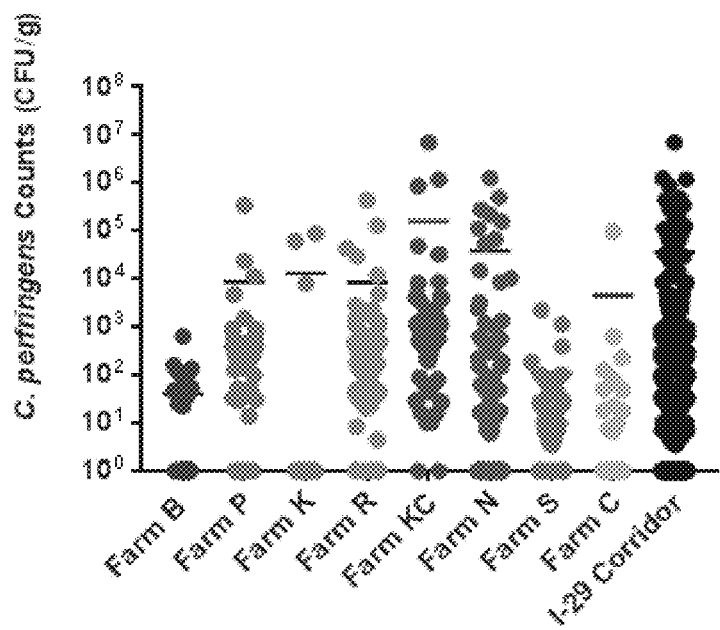
FIG. 81 is a chart showing calculated counts of *C. perfringens* for each farm by individual cow fecal sample collected from the 1-29 Corridor region, where *C. perfringens* counts were estimated by multiplying each sample's clostridia count by the percent that were confirmed to be *C. perfringens* in accordance with one embodiment of the present invention, pursuant to Example 11.

*C. perfringens* enumeration results displayed the average level of *C. perfringens* CFU/g across all calf fecal samples was 54,800 CFU/g with individual samples ranging from <10 to 764,000 CFU/g. While the average level of *C. perfringens* CFU/g across all cow fecal samples was 35,400 CFU/g with individual samples ranging from <10 to 6,970,000 CFU/g (FIG. 79.). Samples appeared to range in clostridia levels for both calves (FIG. 80.) and cows (FIG. 81.).

Analysis of the toxin multiplex PCR results displayed which isolates contained toxin genes specific to *C. perfringens*. A total of 3,471 presumptive clostridia isolates from fecal samples have been tested for the indicated *C. perfringens* toxin genes. Of the 3,471 clostridia isolates screened, 1,549 isolates (44.2%) tested positive for at least 1 of the toxin genes. From the 1,549 toxin-gene positive isolates 1,534 (99%) were identified as Type A (αtoxin only), however β, ε and ι, toxins were also detected in the clostridia isolates.

Gentic RAPD fingerprint patterns displayed diversity among the 1,547 isolates that successful amplified. The isolates tested were harvested from calf fecal, cow fecal and feed and did not cluster strictly based on the sample type or farm. Isolates formed 72 clusters based on 75% similarity according to the Dice correlation method. The largest cluster was 776 isolates which was 50.2% of the total dendrogram.

Representatives from the RAPD dendrogram were selected to capture the diversity of the *C. perfringens* population from this region and subjected to inhibition assays. Antimicrobial testing using the bacteriocin turbidity assay displayed good inhibition of most ruminant fecal *C. perfringens* isolates using bacteriocin harvested from 747, 1104, 1541, 1781, and 2018. The bacteriocin from at least one of the strains 747, 1104, 1541, 1781, and 2018 were able to inhibit the growth >60% of 138 of the 156 isolates tested representing a total of 92.0% inhibition of the *C. perfringens* population based on the dendrogram (Table 22.).

Figure 82:
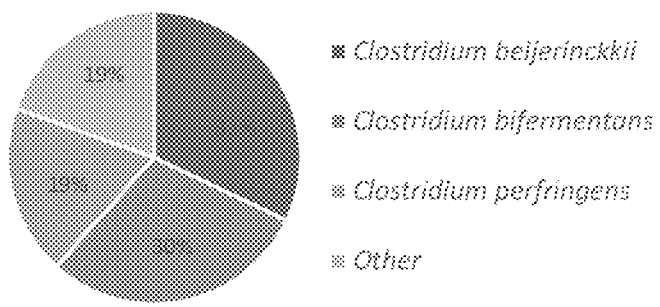
FIG. 82 is a pie graph showing non-toxigenic clostridia (n=399), including the two major identification types (the *C. bifermentans* group and the *C. beijerinckii* group) compared to all other non-toxigenic types isolated from the 1-29 Corridor region in accordance with one embodiment of the present invention, pursuant to Example 11.

Out of the 3,443 isolates collected 1,922 isolates (55.8%) were found to be non-toxigenic clostridia. Sequencing representatives (n=399) from the non-toxigenic clostridia displayed two dominate clostridia groups the *Clostridium bifermentans* group (*Paraclostridium bifermentans* and *P. benzoelyticum*) and the *Clostridium beijerinckii* group (*Clostridium diolis, Clostridium beijerinckii, Clostridium chromiireducens, Clostridium saccharoperbutylacetonicum, Clostridium puniceum,* and *Clostridium saccharobutylicum*), the two main groups of the non-toxigenic clostridia group made up 61.7% of the non-toxigenic isolates (FIG. 82.).

Discussion:

Fecal samples were used as the most readily available sample type to estimate the level and obtain isolates of clostridia and *C. perfringens* within the digestive system of ruminants. From the 411 fecal samples collected throughout the 1-29 Corridor region all samples had detectable levels of clostridia. Many isolates harvested (1,549 isolates) from the ruminant samples contained a toxin gene specific to *C. perfringens*. *C. perfringens* was detected in 76% of the cow fecal samples and in 50% of the calf fecal samples. The high presence of clostridia and *C. perfringens* indicates the risk for sub-acute enteric clostridia disease challenges in most ruminants throughout the 1-29 Corridor. *C. perfringens* isolates were diverse according to the RAPD genetic fingerprints but were not specific to sample type or farm. Diverse representatives of *C. perfringens* were mostly inhibited (>60%) by at least one bacteriocin from the following strains 747, 1104, 1541, 1781 or 2018. From the 156 isolates tested 138 isolates were inhibited by greater than 60% by at least one of the strains, representing inhibition of 92.0% of the *C. perfringens* population based on representation from clusters on the RAPD dendrogram. This indicates the *Bacillus* strains 747, 1104, 1541, 1781 and 2018 can inhibit a wide range of diversity of *C. perfringens* isolates. The *Bacillus* strains are not limited to specific clostridia strain(s) like a vaccine which may be missing large groups of the clostridia populations based on the genetic diversity observed in the RAPD dendrogram. DNA sequencing of the non-toxigenic clostridia revealed two major identification of *Clostridium* species. *C. bifermentans* group, which is known to produce 1,3-propanediol (Leja et al., 2014; Myszka et al., 2012) and *C. beijerinckii* group known to produce butanol and acetone (Hou et al., 2017). The production of the metabolic end products of these species could be having an impact in the rumen, reducing performance parameters such as milk production within a dairy cow.

The *Bacillus* strains offer a prophylactic effect on the clostridia populations which may not only increase rumen efficiency leading to increased milk production, but prevent acute levels of *C. perfringens* reducing the occurrence of digestive deaths. The high prevalence of clostridia and *C. perfringens* in fecal samples collected suggests efficiency improvement opportunities in many ruminants throughout the 1-29 Corridor. This example displays the diversity of clostridia isolates from the ruminant fecal and feed samples collected from the 1-29 Corridor. The *Bacillus* strains tested 747, 1104, 1541, 1781 and 2018, could inhibit most of the clostridia diversity observed in the 1-29 Corridor. The product, in accordance with this embodiment of the present invention could inhibit toxigenic clostridia isolated from ruminants in the 1-29 Corridor indicating a benefit in rumen efficiency if fed to dairy cows as a direct fed microbial (DFM).

TABLE 21

Fecal samples, 411, were collected from I-29 Corridor regional dairies separated by farm (8) and age (cow or calf) which were enumerated for clostridia, tested for *C. perfringens*, isolates were genotyped and tested for inhibition.

| Farm Name | State | Cow Fecal | Calf Fecal |
|---|---|---|---|
| Farm B | Minnesota | 36 | 7 |
| Farm P | Minnesota | 48 | 5 |
| Farm K | Minnesota | 13 | 4 |
| Farm R | Iowa | 82 | 5 |
| Farm KC | South Dakota | 60 | 0 |
| Farm N | Minnesota | 71 | 10 |
| Farm S | Minnesota | 46 | 0 |
| Farm C | Minnesota | 22 | 2 |
| Total | | 378 | 33 |

TABLE 22

Bacteriocin assay results displaying each isolate tested and the source of that isolate, isolated from I-29 Corridor regional fecal or feed samples. Inhibition was calculated based on the percent of growth for each treatment well compared to the positive control.

| Isolate ID | Farm | Sample Type | Group | Bacillus Strains 747 | 1104 | 1541 | 1781 | 2018 |
|---|---|---|---|---|---|---|---|---|
| R50.34.2 | Farm B | Cow Fecal | 2 year Cow | 92.6% | 41.7% | 92.3% | 17.5% | 92.0% |
| R50.30.1 | Farm B | Cow Fecal | 2 year Cow | 86.2% | 61.5% | 68.4% | 74.4% | 69.1% |
| R50.26.4 | Farm B | Cow Fecal | Fresh Cow | 87.2% | 87.6% | 87.2% | 87.2% | 87.0% |
| R50.25.6 | Farm B | Cow Fecal | Fresh Cow | 86.1% | 86.1% | 86.4% | 86.8% | 86.6% |
| R50.24.2 | Farm B | Cow Fecal | Fresh Cow | 91.6% | 24.7% | 91.1% | 15.4% | 90.9% |
| R50.22.3 | Farm B | Cow Fecal | Fresh Cow | 91.8% | 14.8% | 89.6% | 0.0% | 91.2% |
| R50.38.1 | Farm B | Cow Fecal | Mature Cow | 80.2% | 80.5% | 19.8% | 80.7% | 80.5% |
| R50.7.1 | Farm B | Calf Fecal | Calf | 86.6% | 87.5% | 64.6% | 87.0% | 87.3% |
| S97.16.2 | Farm B | Feed | Grass Hay | 74.6% | 74.1% | 73.7% | 74.6% | 74.6% |
| R51.8.6 | Farm P | Cow Fecal | Heifer | 87.6% | 74.3% | 87.4% | 88.0% | 87.6% |
| R51.25.2 | Farm P | Cow Fecal | Fresh | 90.1% | 26.3% | 90.8% | 89.2% | 90.1% |
| R51.20.8 | Farm P | Cow Fecal | Close-up | 90.7% | 0.0% | 90.7% | 0.0% | 90.4% |
| R51.32.9 | Farm P | Cow Fecal | High | 19.9% | 1.4% | 89.0% | 0.0% | 89.7% |
| R51.32.6 | Farm P | Cow Fecal | High | 92.6% | 92.4% | 92.2% | 92.7% | 92.4% |
| R51.31.2 | Farm P | Cow Fecal | High | 80.1% | 80.8% | 80.8% | 80.5% | 80.5% |
| R51.28.2 | Farm P | Cow Fecal | Fresh | 86.2% | 85.3% | 85.6% | 85.8% | 85.3% |
| R51.45.1 | Farm P | Cow Fecal | Late | 90.8% | 17.6% | 91.6% | 91.2% | 91.8% |
| R51.44.2 | Farm P | Cow Fecal | Late | 92.5% | 35.3% | 92.3% | 92.2% | 91.9% |
| R51.42.3 | Farm P | Cow Fecal | Late | 87.1% | 41.0% | 45.3% | 85.2% | 58.8% |
| R51.40.7 | Farm P | Cow Fecal | Late | 23.6% | 13.3% | 88.3% | 0.0% | 88.8% |
| R51.38.7 | Farm P | Cow Fecal | High | 91.6% | 91.7% | 91.3% | 91.6% | 91.4% |
| R51.37.3 | Farm P | Cow Fecal | High | 91.8% | 91.5% | 90.8% | 91.5% | 91.5% |
| R51.51.8 | Farm P | Cow Fecal | Dry | 88.4% | 87.8% | 86.8% | 87.4% | 88.4% |
| R52.4.8 | Farm K | Calf Fecal | Calf | 26.0% | 20.6% | 9.9% | 38.9% | 18.3% |
| R52.4.1 | Farm K | Calf Fecal | Calf | 38.6% | 26.5% | 0.0% | 43.9% | 30.3% |
| R52.17.10 | Farm K | Cow Fecal | Lactating | 88.9% | 91.8% | 91.1% | 91.7% | 91.9% |
| R52.17.7 | Farm K | Cow Fecal | Lactating | 87.5% | 87.7% | 80.1% | 76.2% | 84.0% |
| R52.17.5 | Farm K | Cow Fecal | Lactating | 0.0% | 0.0% | 0.0% | 0.0% | 0.0% |
| R52.17.2 | Farm K | Cow Fecal | Lactating | 91.0% | 90.7% | 90.9% | 91.0% | 91.0% |
| R52.17.1 | Farm K | Cow Fecal | Lactating | 92.4% | 92.3% | 92.2% | 92.3% | 92.4% |
| R52.15.9 | Farm K | Cow Fecal | Lactating | 62.5% | 58.6% | 61.6% | 56.5% | 64.7% |
| R52.15.2 | Farm K | Cow Fecal | Lactating | 88.0% | 88.2% | 80.4% | 83.1% | 83.7% |
| R52.14.5 | Farm K | Cow Fecal | Lactating | 78.1% | 27.9% | 9.3% | 84.0% | 61.8% |
| S99.6.5 | Farm K | Feed | Close Up TMR | 0.0% | 1.3% | 16.7% | 0.0% | 0.0% |
| R53.13.8 | Farm R | Cow Fecal | Close-up Heifer | 89.7% | 35.6% | 15.6% | 80.7% | 71.3% |
| R53.7.10 | Farm R | Cow Fecal | Close-up Heifer | 92.8% | 91.9% | 90.5% | 91.3% | 91.6% |
| R53.5.8 | Farm R | Calf Fecal | Calf | 90.5% | 1.0% | 89.0% | 88.4% | 90.5% |
| R53.22.9 | Farm R | Cow Fecal | Fresh Heifer | 90.0% | 89.2% | 87.8% | 88.3% | 89.7% |
| R53.22.2 | Farm R | Cow Fecal | Fresh Heifer | 87.1% | 88.8% | 86.7% | 86.4% | 88.8% |
| R53.20.10 | Farm R | Cow Fecal | Fresh Heifer | 90.1% | 89.2% | 87.6% | 88.8% | 88.8% |
| R53.19.3 | Farm R | Cow Fecal | Fresh Heifer | 91.4% | 91.0% | 90.4% | 89.5% | 90.7% |
| R53.19.2 | Farm R | Cow Fecal | Fresh Heifer | 91.5% | 90.3% | 90.7% | 89.9% | 91.4% |
| R53.15.7 | Farm R | Cow Fecal | Close-up Heifer | 90.7% | 89.8% | 90.4% | 90.0% | 90.6% |
| R53.34.4 | Farm R | Cow Fecal | High Cows | 92.5% | 91.9% | 92.1% | 92.3% | 92.1% |
| R53.28.8 | Farm R | Cow Fecal | Close-up Cows | 88.6% | 89.7% | 89.4% | 88.3% | 89.3% |
| R53.26.8 | Farm R | Cow Fecal | Close-up Cows | 91.6% | 91.6% | 91.3% | 91.3% | 91.4% |
| R53.25.8 | Farm R | Cow Fecal | Fresh Heifer | 91.2% | 90.8% | 90.7% | 91.0% | 90.8% |

TABLE 22-continued

Bacteriocin assay results displaying each isolate tested and the source of that isolate, isolated from I-29 Corridor regional fecal or feed samples. Inhibition was calculated based on the percent of growth for each treatment well compared to the positive control.

| Isolate ID | Sample Farm | Type | Group | Bacillus Strains 747 | 1104 | 1541 | 1781 | 2018 |
|---|---|---|---|---|---|---|---|---|
| R53.25.3 | Farm R | Cow Fecal | Fresh Heifer | 89.6% | 89.4% | 89.1% | 89.2% | 88.9% |
| R53.44.7 | Farm R | Cow Fecal | Heifer | 90.4% | 89.7% | 89.7% | 90.1% | 89.9% |
| R53.39.2 | Farm R | Cow Fecal | High Cows | 92.5% | 92.8% | 92.8% | 93.0% | 92.6% |
| R53.38.9 | Farm R | Cow Fecal | High Cows | 89.3% | 90.7% | 90.1% | 89.4% | 90.5% |
| R53.35.2 | Farm R | Cow Fecal | High Cows | 91.2% | 91.6% | 91.2% | 90.6% | 92.2% |
| R53.35.1 | Farm R | Cow Fecal | High Cows | 91.7% | 91.7% | 91.7% | 92.0% | 92.0% |
| R53.51.8 | Farm R | Cow Fecal | Heifer | 88.3% | 90.6% | 89.6% | 89.0% | 90.3% |
| R53.48.10 | Farm R | Cow Fecal | Heifer | 91.8% | 91.5% | 91.6% | 91.8% | 91.9% |
| R53.48.1 | Farm R | Cow Fecal | Heifer | 90.7% | 90.7% | 90.4% | 90.8% | 90.7% |
| R53.47.8 | Farm R | Cow Fecal | Heifer | 90.8% | 91.1% | 90.9% | 91.1% | 91.2% |
| R53.63.1 | Farm R | Cow Fecal | High Cows | 3.0% | 1.7% | 38.7% | 30.6% | 45.1% |
| R53.62.8 | Farm R | Cow Fecal | High Cows | 25.6% | 17.6% | 92.4% | 38.1% | 92.6% |
| R53.61.2 | Farm R | Cow Fecal | Fresh Cows | 90.0% | 0.0% | 90.0% | 20.7% | 26.6% |
| R53.56.4 | Farm R | Cow Fecal | Fresh Cows | 0.0% | 0.0% | 90.7% | 8.9% | 91.0% |
| R53.55.7 | Farm R | Cow Fecal | Fresh Cows | 90.7% | 91.2% | 90.7% | 91.2% | 91.3% |
| R53.55.1 | Farm R | Cow Fecal | Fresh Cows | 13.5% | 0.0% | 28.6% | 21.2% | 28.5% |
| R53.71.2 | Farm R | Cow Fecal | Late Cows | 0.0% | 0.0% | 47.3% | 35.5% | 44.4% |
| R53.70.8 | Farm R | Cow Fecal | High Cows | 0.0% | 0.0% | 0.0% | 23.8% | 36.3% |
| R53.69.5 | Farm R | Cow Fecal | High Cows | 9.0% | 0.0% | 8.3% | 41.0% | 48.6% |
| R53.66.3 | Farm R | Cow Fecal | High Cows | 92.1% | 87.6% | 92.2% | 11.8% | 92.4% |
| R53.66.2 | Farm R | Cow Fecal | High Cows | 11.5% | 0.0% | 37.7% | 19.5% | 45.2% |
| R53.75.4 | Farm R | Cow Fecal | Late Cows | 64.5% | 0.0% | 61.6% | 0.0% | 40.1% |
| S102.7.3 | Farm R | Feed | Fresh Heifer TMR | 80.3% | 1.3% | 63.3% | 74.4% | 76.7% |
| S102.1.10 | Farm R | Feed | Baylage Mark | 58.5% | 62.1% | 66.4% | 57.4% | 57.3% |
| S102.1.9 | Farm R | Feed | Baylage Mark | 49.2% | 51.3% | 43.4% | 50.9% | 53.4% |
| S102.1.3 | Farm R | Feed | Baylage Mark | 35.8% | 44.2% | 45.8% | 29.2% | 41.2% |
| R53.88.10 | Farm R | Cow Fecal | Late Cows | 90.5% | 80.5% | 90.7% | 90.7% | 90.8% |
| R53.88.6 | Farm R | Cow Fecal | Late Cows | 31.7% | 22.7% | 28.8% | 17.1% | 13.5% |
| R53.87.3 | Farm R | Cow Fecal | Late Cows | 90.8% | 88.0% | 86.6% | 91.6% | 90.8% |
| R53.85.8 | Farm R | Cow Fecal | Late Cows | 65.5% | 70.4% | 77.4% | 66.3% | 82.7% |
| S102.11.1 | Farm R | Feed | Fresh TMR | 0.0% | 11.7% | 0.0% | 0.0% | 0.0% |
| S102.8.8 | Farm R | Feed | Close Up Cow TMR | 80.5% | 59.8% | 80.0% | 85.2% | 85.4% |
| S102.8.5 | Farm R | Feed | Close Up Cow TMR | 59.2% | 40.0% | 71.6% | 62.4% | 55.8% |
| S102.8.4 | Farm R | Feed | Close Up Cow TMR | 67.8% | 49.2% | 85.5% | 71.1% | 65.3% |
| R59.8.5 | Farm KC | Cow Fecal | 2+ | 95.8% | 97.8% | 94.2% | 97.3% | 97.3% |
| R59.8.4 | Farm KC | Cow Fecal | 2+ | 99.3% | 98.9% | 99.5% | 99.5% | 99.6% |
| R59.7.7 | Farm KC | Cow Fecal | 2+ | 98.9% | 99.6% | 98.9% | 99.2% | 98.9% |
| R59.6.4 | Farm KC | Cow Fecal | 2+ | 99.6% | 99.1% | 99.6% | 99.8% | 99.6% |
| R59.8.10 | Farm KC | Cow Fecal | 2+ | 88.7% | 3.1% | 4.2% | 88.7% | 62.1% |
| R59.22.3 | Farm KC | Cow Fecal | Early Lac. | 99.9% | 99.9% | 99.7% | 99.9% | 99.7% |
| R59.15.9 | Farm KC | Cow Fecal | Mid/Late Lac. | 95.0% | 92.5% | 75.0% | 96.3% | 73.8% |
| R59.39.8 | Farm KC | Cow Fecal | Fresh | 99.1% | 98.4% | 99.4% | 99.1% | 99.1% |
| R59.38.9 | Farm KC | Cow Fecal | Fresh | 99.6% | 99.6% | 99.7% | 99.7% | 99.9% |
| R59.37.5 | Farm KC | Cow Fecal | Fresh | 97.1% | 97.1% | 97.1% | 97.3% | 97.3% |
| R59.35.9 | Farm KC | Cow Fecal | Fresh | 99.3% | 98.6% | 98.9% | 99.3% | 98.9% |
| R59.33.8 | Farm KC | Cow Fecal | Fresh | 97.4% | 97.6% | 97.4% | 96.3% | 97.6% |
| R59.50.7 | Farm KC | Cow Fecal | 1st Lac. | 97.7% | 99.7% | 98.3% | 97.0% | 98.1% |
| R59.48.10 | Farm KC | Cow Fecal | 1st Lac. | 97.7% | 99.7% | 99.6% | 99.6% | 99.4% |
| R59.48.8 | Farm KC | Cow Fecal | 1st Lac. | 99.7% | 99.7% | 99.9% | 98.7% | 99.9% |

TABLE 22-continued

Bacteriocin assay results displaying each isolate tested and the source of that isolate, isolated from I-29 Corridor regional fecal or feed samples. Inhibition was calculated based on the percent of growth for each treatment well compared to the positive control.

| | | Sample | | *Bacillus* Strains | | | | |
|---|---|---|---|---|---|---|---|---|
| Isolate ID | Farm | Type | Group | 747 | 1104 | 1541 | 1781 | 2018 |
| R59.47.6 | Farm KC | Cow Fecal | 1st Lac. | 94.2% | 87.9% | 77.8% | 86.0% | 93.7% |
| R59.47.3 | Farm KC | Cow Fecal | 1st Lac. | 95.4% | 95.2% | 78.3% | 95.8% | 85.2% |
| R59.47.2 | Farm KC | Cow Fecal | 1st Lac. | 99.5% | 99.7% | 99.3% | 99.3% | 99.7% |
| R59.59.3 | Farm KC | Cow Fecal | Close Up | 99.7% | 99.9% | 99.7% | 99.6% | 99.7% |
| R59.59.2 | Farm KC | Cow Fecal | Close Up | 97.8% | 97.8% | 97.9% | 97.8% | 97.9% |
| R59.58.6 | Farm KC | Cow Fecal | Close Up | 96.6% | 96.6% | 96.6% | 96.3% | 96.3% |
| R62.20.6 | Farm S | Cow Fecal | Pregnant | 66.7% | 56.7% | 56.7% | 63.3% | 60.0% |
| R62.24.5 | Farm S | Cow Fecal | Pregnant | 96.0% | 95.5% | 95.5% | 95.7% | 96.0% |
| R62.29.6 | Farm S | Cow Fecal | Pregnant | 97.6% | 97.9% | 97.9% | 97.6% | 97.6% |
| R62.32.2 | Farm S | Cow Fecal | Dry Cow | 96.0% | 95.6% | 95.6% | 96.5% | 96.5% |
| R62.5.1 | Farm S | Cow Fecal | Breeding 2+ | 100.0% | 99.7% | 99.9% | 100.0% | 99.7% |
| R62.9.2 | Farm S | Cow Fecal | Breeding 2+ | 98.9% | 98.2% | 99.0% | 99.0% | 98.2% |
| R63.19.9 | Farm S | Cow Fecal | 1st Lactation Breeding | 98.7% | 98.7% | 96.0% | 98.5% | 98.5% |
| R63.21.3 | Farm S | Cow Fecal | Pregnant | 85.7% | 70.1% | 84.4% | 87.0% | 70.1% |
| R63.22.3 | Farm S | Cow Fecal | Pregnant | 97.8% | 97.0% | 98.2% | 95.7% | 98.2% |
| R63.23.3 | Farm S | Cow Fecal | Pregnant | 98.7% | 98.7% | 98.8% | 98.7% | 98.7% |
| R63.23.9 | Farm S | Cow Fecal | Pregnant | 96.0% | 97.0% | 98.4% | 96.1% | 96.9% |
| R63.27.5 | Farm S | Cow Fecal | Pregnant | 97.9% | 98.3% | 98.1% | 95.0% | 98.5% |
| R63.28.1 | Farm S | Cow Fecal | Pregnant | 96.8% | 97.1% | 96.8% | 97.1% | 97.1% |
| R63.1.7 | Farm C | Cow Fecal | Lactation Pen 2 | 98.7% | 99.2% | 99.1% | 99.1% | 99.4% |
| R63.11.6 | Farm C | Cow Fecal | Lactation Pen 1 | 99.6% | 99.4% | 99.2% | 99.4% | 99.6% |
| R63.18.9 | Farm C | Cow Fecal | Lactation Pen 1 | 99.1% | 97.8% | 96.8% | 97.8% | 98.0% |
| R63.2.6 | Farm C | Cow Fecal | Lactation Pen 2 | 16.8% | 1.5% | 25.7% | 48.9% | 35.0% |
| R63.32.1 | Farm C | Cow Fecal | Close Up | 99.8% | 99.5% | 99.7% | 99.8% | 99.7% |
| R63.34.3 | Farm C | Calf Fecal | Calves | 12.0% | 47.2% | 23.7% | 41.2% | 48.9% |
| R63.34.4 | Farm C | Calf Fecal | Calves | 95.1% | 90.6% | 88.5% | 96.2% | 95.5% |
| R63.34.5 | Farm C | Calf Fecal | Calves | 97.4% | 19.2% | 11.7% | 92.3% | 87.8% |
| R63.4.1 | Farm C | Cow Fecal | Lactation Pen 2 | 98.5% | 68.6% | 98.5% | 99.0% | 98.8% |
| R63.6.4 | Farm C | Cow Fecal | Lactation Pen 2 | 99.4% | 52.3% | 99.2% | 98.9% | 99.4% |
| R63.9.2 | Farm C | Cow Fecal | Lactation Pen 2 | 99.5% | 99.5% | 99.0% | 99.5% | 98.5% |
| S111.4.9 | Farm C | Lactation 1 TMR | Lactation Pen 1 | 75.7% | 73.4% | 99.5% | 80.1% | 92.3% |
| R60.12.10 | Farm N | Cow Fecal | Late | 89.2% | 30.3% | 66.2% | 0.0% | 0.0% |
| R60.14.6 | Farm N | Cow Fecal | Late | 99.9% | 99.8% | 99.6% | 99.6% | 99.8% |
| R60.15.9 | Farm N | Cow Fecal | Late | 99.6% | 98.9% | 99.2% | 98.8% | 99.4% |
| R60.17.6 | Farm N | Cow Fecal | Late | 98.0% | 93.5% | 98.0% | 92.8% | 98.0% |
| R60.2.2 | Farm N | Calf Fecal | Calves | 0.0% | 0.0% | 42.9% | 0.0% | 0.0% |
| R60.21.4 | Farm N | Cow Fecal | High | 96.8% | 33.9% | 89.5% | 55.2% | 67.0% |
| R60.22.8 | Farm N | Cow Fecal | High | 99.5% | 99.1% | 99.4% | 99.1% | 99.4% |
| R60.30.3 | Farm N | Cow Fecal | High | 94.9% | 94.8% | 90.2% | 94.8% | 98.3% |
| R60.31.3 | Farm N | Cow Fecal | High | 61.8% | 69.4% | 70.5% | 66.3% | 60.1% |
| R60.38.2 | Farm N | Cow Fecal | Heifer | 99.9% | 99.5% | 99.7% | 99.7% | 99.5% |
| R60.4.3 | Farm N | Calf Fecal | Calves | 99.6% | 99.0% | 99.2% | 99.4% | 99.2% |
| R60.46.10 | Farm N | Cow Fecal | Close Up | 94.6% | 94.6% | 96.4% | 82.1% | 92.5% |
| R60.52.1 | Farm N | Cow Fecal | Fresh | 98.3% | 79.9% | 72.7% | 97.1% | 95.2% |
| R60.52.7 | Farm N | Cow Fecal | Fresh | 98.3% | 99.3% | 97.9% | 99.4% | 99.5% |
| R60.59.7 | Farm N | Cow Fecal | Fresh | 89.5% | 92.3% | 92.3% | 91.7% | 91.7% |
| R60.59.9 | Farm N | Cow Fecal | Fresh | 99.6% | 99.7% | 99.6% | 99.7% | 99.7% |
| R60.61.2 | Farm N | Cow Fecal | High | 99.8% | 99.8% | 99.8% | 99.6% | 99.6% |
| R60.64.1 | Farm N | Cow Fecal | High | 99.8% | 99.4% | 99.5% | 99.6% | 99.8% |
| R60.64.2 | Farm N | Cow Fecal | High | 97.9% | 97.9% | 97.9% | 96.7% | 98.5% |
| R60.64.3 | Farm N | Cow Fecal | High | 99.8% | 99.6% | 99.6% | 99.8% | 99.7% |
| R60.64.8 | Farm N | Cow Fecal | High | 0.0% | 0.0% | 0.0% | 0.0% | 0.0% |
| R60.66.1 | Farm N | Cow Fecal | High | 99.2% | 99.0% | 98.9% | 98.1% | 99.4% |
| R60.70.4 | Farm N | Cow Fecal | High | 99.1% | 98.7% | 84.2% | 99.1% | 98.1% |
| R60.70.8 | Farm N | Cow Fecal | High | 98.0% | 51.3% | 58.0% | 90.0% | 86.0% |

TABLE 22-continued

Bacteriocin assay results displaying each isolate tested and the source of that isolate, isolated from I-29 Corridor regional fecal or feed samples. Inhibition was calculated based on the percent of growth for each treatment well compared to the positive control.

| Isolate ID | Farm | Sample Type | Group | Bacillus Strains | | | | |
|---|---|---|---|---|---|---|---|---|
| | | | | 747 | 1104 | 1541 | 1781 | 2018 |
| R60.71.10 | Farm N | Cow Fecal | High | 99.4% | 99.4% | 99.6% | 99.7% | 99.6% |
| R60.72.1 | Farm N | Cow Fecal | Close Up | 99.5% | 99.5% | 99.5% | 99.6% | 99.2% |
| R60.72.2 | Farm N | Cow Fecal | Close Up | 98.7% | 98.4% | 98.4% | 98.5% | 98.7% |
| R60.73.1 | Farm N | Cow Fecal | Close Up | 94.7% | 98.6% | 99.0% | 99.0% | 99.0% |
| R60.81.8 | Farm N | Cow Fecal | Close Up | 96.3% | 97.8% | 98.3% | 98.5% | 98.8% |

Example 12: The Effect of a Combination of Bacillus Strains on the Clostridial Populations of Dairy Cows on Farm ALJ in Texas Introduction: Hemorrhagic bowel syndrome (HBS) was first reported in 1991 and observed in five high-producing Holstein cows from one dairy in Idaho (Sockett, 2004). Symptoms included point-source sub-mucosal hematomas, each affecting 10-20 cm of the jejunum. One of the five cows exhibited a ruptured hematoma with exsanguination into the lumen of the jejunum. Although *Aspergillus fumigatus* and *Clostridium perfringens* are known to be involved in the etiology of HBS, the syndrome is better described as being poly-microbial and multi-factorial in nature. Increased consumption of a high-energy diet seems to be the most plausible common pathway for all the risk factors that have been described (Berghaus et al., 2005).

HBS is characterized by sudden drop in milk production, abdominal pain due to obstructed bowel and anemia (Anderson, 2002). Clinical signs of the disease are decreased feed intake, depression, decreased milk production, dehydration, abdominal distension and dark clotted blood in the feces. Death comes within 48 hours from the onset of the obstructing blood clot plug. Due to the sporadic, acute etiology few treatments are known to be effective In addition to *Clostridium* isolates of several species causing enteric disease, other *Clostridium* species produce high levels of acetone, butanol, 1,3 propanediol and butyric acid as end products of their metabolism. If produced in the rumen, these metabolic end products may affect rumen function and decrease efficiency.

The *Bacillus* strains selected by the inventors, to inhibit pathogens, produce multiple compounds with inhibitory activity against other microbes with many strains containing more than ten operons producing antifungal and antibacterial compounds. Multiple bacteriocins are being produced in vitro directly at the site of action by the *Bacillus* strains so a robust blend of bacteriocins are present at doses lower than would be needed if isolated bacteriocins were being added directly to the feed.

The purpose of this study was to measure the levels and diversity of clostridia in dairy cows on Farm ALJ treated with the product, in accordance with this embodiment of the present invention, (referred to herein as "treated"), over 110 days.

Materials and Methods:

A dairy herd in Texas (Farm ALJ) was selected to study the impact of *Bacillus* product, in accordance with this embodiment of the present invention, on clostridial levels and diversity. The herd consists of 2900 milk cows housed in a Saudi style barns and bedded on sand.

The product, in accordance with this embodiment of the present invention was a combination product of two *Bacillus* strains in equal proportions; *Bacillus* 747 and *Bacillus* 1781 incorporated into the total mixed ration (TMR) at a dose of 2 billion CFU per head per day.

Fecal samples were obtained from 90 cows at two time periods before treatment and 63 cows after 110 days on treatment.

Fecal samples from cows were diluted 1:10 with sterile peptone, heat shocked for 30 minutes at 60° C., enumerated in sterile peptone and pour plated on Tryptose Sulphite Cycloserine (TSC) agar with D-cycloserine (400 mg/L) to select for clostridial species. Agar plates were incubated at 37° C. anaerobically for 24 hours. If present, isolated sulphite-reducing colonies were counted for total clostridia counts (CFU/g) and representative isolates were picked into Reinforced Clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions were performed in 96-well blocks containing 500 µl presumptive clostridia culture per well. Cells were harvested by centrifugation at 4,700 rpm for 10 minutes, the supernatant was removed. Cells were re-suspended in 500 µl of 50 mM of EDTA-2Na (pH=8.0). Aliquots of 300 µl of the suspended cells were transferred to a new 96-well block and combined with 20 µl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 µl of lysis buffer (6 M Guanidine, 20% Triton-X 100, 10 mM Tris-HCL, pH 7.5) was added, mixed then incubated at room temperature for 15 minutes. Following the incubation 20 µl of Proteinase K (NEB, 800 U/mL) was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed centrifuging 750 µl of Column Wash Solution (Promega, A1318) at 4700 rpms for 1 minute and 30 seconds discarding flow through at the end of each spin. The binding plate was centrifuged for an additional 10 minutes at 4,700 rpm to remove any residual ethanol. A clean elution plate was then placed under the binding plate and DNA was eluted with 200 µl, pre-warmed (55° C.), Nuclease Free Water (Promega, P1195).

DNA was screened for toxin genes (α, β, ε, and ι) specific to *C. perfringens* using polymerase chain reaction (PCR). Amplification of toxin genes was executed using a multiplex PCR containing four primer sets (Yoo et al., 1997) (Table 1.) The PCR mixture contained 2.5 µl 10×PCR Buffer, 2 µl of 50 mM MgCl$_2$, 0.5 µM of each primer (Table 1.), 0.1 µl of Invitrogen™ Platinum™ Taq DNA Polymerase, 2.5 µl of DNA, sterile water was added to achieve 25 µl for a total reaction volume. The mixture underwent 5 minutes at 94° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved. If one or multiple toxin genes were observed a toxin type identification was assigned to each isolate based on their toxin-gene profile (Songer, 1996). C. perfringens positive to total clostridia isolate ratio was used to calculate an estimated C. perfringens count based on the total clostridia count.

Unique strain-specific genetic fingerprints were generated using Random Amplification of Polymorphic DNA (RAPD) analysis on select isolates to determine diversity among fecal C. perfringens isolates. The PCR contained 5 µl of DNA, 2.5 µl RAPD primer 2 (10 µM) (Table 1.), and 17.5 µl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes finishing with a final elongation of 5 minutes at 72° C. PCR products observed on a Fragment Analyzer (Advanced Analytics) to determine amplification patterns and were imported into BioNumerics, bioinformatics software, for analysis. RAPD patterns were compared with a band based Dice correlation analysis method to determine the similarity between RAPD patterns as a way to monitor diversity between isolates. Cluster cut-off was at 75% similarity.

To identify clostridia that did not have at least one toxin gene specific to C. perfringens, a PCR reaction was performed on the isolate DNA to amplify the 16S region of rDNA using primers 27F-YM and 1492R-Y (Table 1). This was done on 20% of the isolates that did not contain a toxin gene specific to C. perfringens. The PCR mixture contained 5 µl of 10×PCR Buffer, 2 µl of 50 mM MgCl$_2$, 1 µl of 50 mM dNTPs, 0.4 µM of each primer (Table 1.), 0.2 µl of Invitrogen™ Platinum™ Taq DNA Polymerase, 5 µl of DNA, and sterile water was added to achieve 50 µl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to gene wiz to obtain the sequences for the 16S genes. Sequences were compared to known typed bacterial strains obtained from EZbiocloud online electronic database. Based on comparisons of these sequences a bacterial identification was assigned to the isolates.

Figure 83:
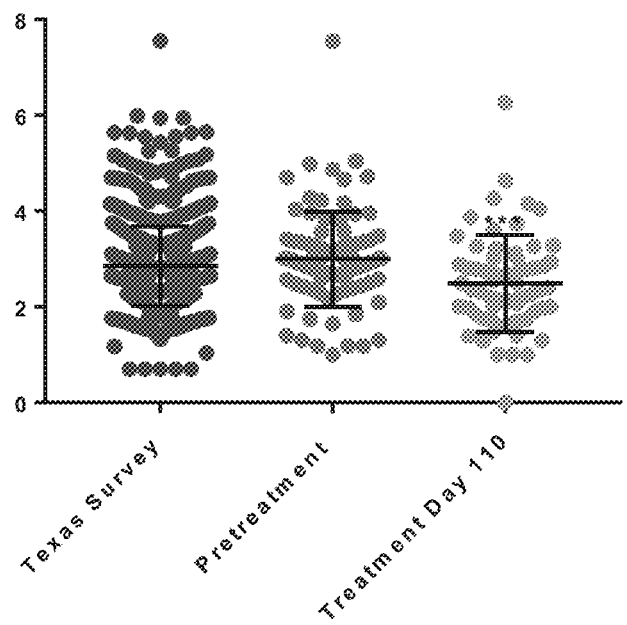
FIG. 83 is a chart showing enumeration results of total clostridia by individual fecal sample for all time points, including those of Example 6, where time points that are significantly different from the pretreatment samples are indicated by asterisks over the mean error bars, in accordance with one embodiment of the present invention, pursuant to Example 12.
Figure 84:
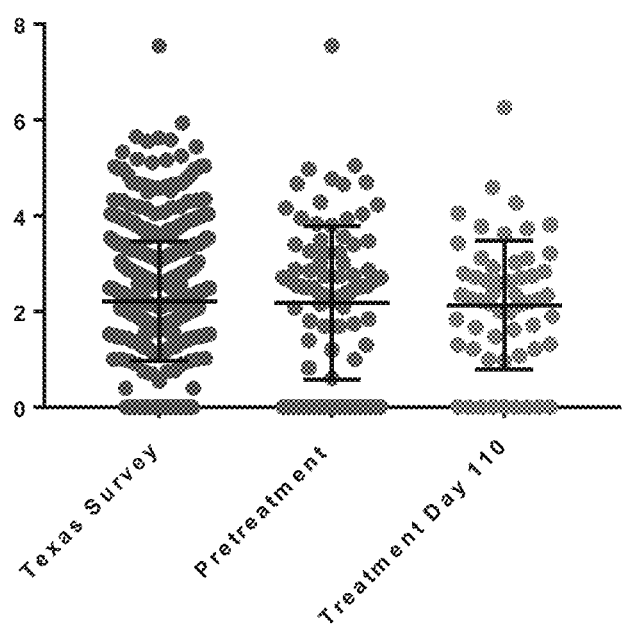
FIG. 84 is a chart showing calculated counts of *Clostridium perfringens* by individual fecal sample for all time points, including those of Example 6 in accordance with one embodiment of the present invention, pursuant to Example 12.
Figure 85:
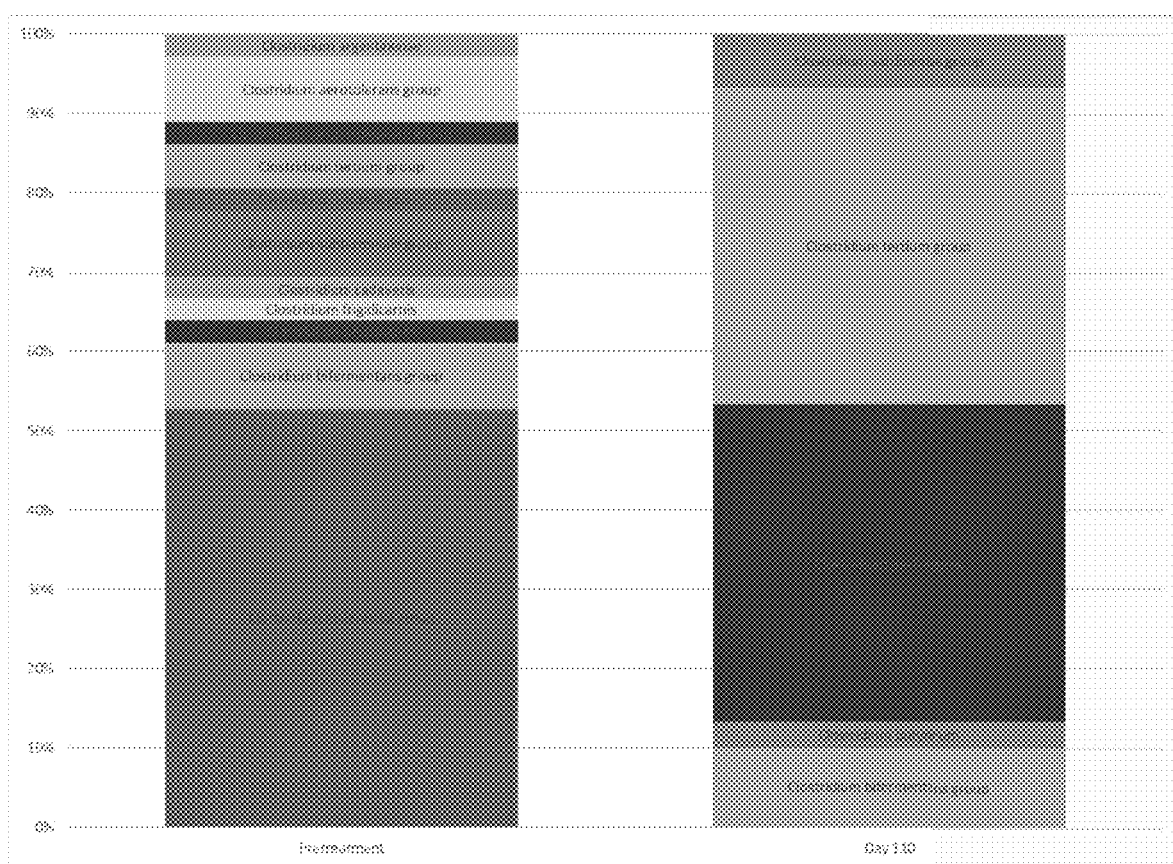
FIG. 85 is a bar graph showing changes in the proportions of non-toxigenic *Clostridium* species over time at Farm ALJ in Texas in accordance with one embodiment of the present invention, pursuant to Example 12.

Results:

Total clostridia counts on Farm ALJ (FIG. 83) were not significantly different than those determined during the Texas survey (Example 6). During the 110 days on the product total clostridia decreased significantly. Although there was no reduction in C. perfringens treatment with the Bacillus blend (FIG. 84), there was less strain diversity in the C. perfringens isolated during treatment as indicated by the Shannon-Wiever index of the C. perfringens RAPD patterns (Table 23). Diversity of the non-toxigenic clostridia was also reduced during treatment and the predominant C. beijerincki group isolates were supplanted by C. tertium group isolates during treatment (FIG. 85 and Table 24).

Discussion:

The blend of Bacillus strains caused a decrease in total clostridial counts and decreased the diversity of C. perfringens strains in the cows. The Bacillus product also reduced the diversity of non-toxigenic clostridial species and caused the displacement of C. beijerinckii group strains by C. tertium group. These data demonstrate that the product causes a reduction in clostridial counts and a reduction in the diversity of C. perfringens isolates and the diversity and types of Clostridium species. The reduction in the proportion of the C. beijerinckii group, which are known to produce high levels of butanol and acetone, will most likely improve rumen fermentation and improve feed efficiency as well as milk production in dairy cows.

TABLE 23

RAPD fingerprint diversity of the Clostridium perfringens isolates over time.

| | Isolates | Clusters | Shannon-Wiener Index of Diversity |
|---|---|---|---|
| Pretreatment | 279 | 44 | 2.88 |
| Treatment Day 110 | 256 | 23 | 2.11 |

TABLE 24

Diversity of non-toxigenic Clostridium species and change in proportions of the two most predominant groups over time.

| Species Diversity | Isolates | Species | Shannon-Wiener Index of Diversity | Clostridium beijerinckii group | Clostridium tertium group |
|---|---|---|---|---|---|
| Pretreatment | 36 | 11 | 2.09 | 53% | 6% |
| Day 110 | 30 | 5 | 1.26 | 0% | 40% |

Example 13: The Effect of a Combination of Bacillus Strains on the Clostridial Populations of Dairy Cows on Farm E in Wisconsin Introduction:

Hemorrhagic bowel syndrome (HBS) was first reported in 1991 and observed in five high-producing Holstein cows from one dairy in Idaho (Sockett, 2004). Symptoms included point-source sub-mucosal hematomas, each affecting 10-20 cm of the jejunum. One of the five cows exhibited a ruptured hematoma with exsanguination into the lumen of the jejunum. Although Aspergillus fumigatus and Clostridium perfringens are known to be involved in the etiology of HBS, the syndrome is better described as being poly-microbial and multi-factorial in nature. Increased consumption of a high-energy diet seems to be the most plausible common pathway for all the risk factors that have been described (Berghaus et al., 2005).

HBS is characterized by sudden drop in milk production, abdominal pain due to obstructed bowel and anemia (Anderson, 2002). Clinical signs of the disease are decreased feed intake, depression, decreased milk production, dehydration, abdominal distension and dark clotted blood in the feces. Death comes within 48 hours from the onset of the obstructing blood clot plug. Due to the sporadic, acute etiology few treatments are known to be effective In addition to Clostridium isolates of several species causing enteric disease, other Clostridium species produce high levels of acetone, butanol, 1,3 propanediol and butyric acid as end products of their metabolism. If produced in the rumen, these metabolic end products may affect rumen function and decrease efficiency.

The *Bacillus* strains selected by the inventors, to inhibit pathogens, produce multiple compounds with inhibitory activity against other microbes with many strains containing more than ten operons producing antifungal and antibacterial compounds. Multiple bacteriocins are being produced in vitro directly at the site of action by the *Bacillus* strains so a robust blend of bacteriocins are present at doses lower than would be needed if isolated bacteriocins were being added directly to the feed.

The purpose of this study was to measure the levels and diversity of clostridia in dairy cows on Wisconsin Farm E treated with the product, in accordance with this embodiment of the present invention, (referred to herein as "treated"), over 220 days.

Materials and Methods:

A dairy herd in Wisconsin (Farm E) was selected to study the impact of a *Bacillus* product, in accordance with this embodiment of the present invention, on clostridial level and diversity. The herd consists of 650 milk cows housed in a free stall barn and the cows are bedded on sand.

The product, in accordance with this embodiment of the present invention was a combination product of three *Bacillus* strains; *Bacillus* 747 (50%), *Bacillus* 1781 (45%) and *Bacillus* 1541 (5%) incorporated into the total mixed ration (TMR) at a dose of about 2 billion CFU per head per day.

Fecal samples were obtained from cows before and during treatment. Sample dates and number of animals sampled are indicated in Table 25.

Fecal samples from cows were diluted 1:10 with sterile peptone, heat shocked for 30 minutes at 60° C., enumerated in sterile peptone and pour plated on Tryptose Sulphite Cycloserine (TSC) agar with D-cycloserine (400 mg/L) to select for clostridial species. Agar plates were incubated at 37° C. anaerobically for 24 hours. If present, isolated sulphite-reducing colonies were counted for total clostridia counts (CFU/g) and representative isolates were picked into Reinforced Clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions were performed in 96-well blocks containing 500 µl presumptive clostridia culture per well. Cells were harvested by centrifugation at 4,700 rpm for 10 minutes, the supernatant was removed. Cells were re-suspended in 500 µl of 50 mM of EDTA-2Na (pH=8.0). Aliquots of 300 µl of the suspended cells were transferred to a new 96-well block and combined with 20 µl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 µl of lysis buffer (6 M Guanidine, 20% Triton-X 100, 10 mM Tris-HCL, pH 7.5) was added, mixed then incubated at room temperature for 15 minutes. Following the incubation 20 µl of Proteinase K (NEB, 800 U/mL) was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed centrifuging 750 µl of Column Wash Solution (Promega, A1318) at 4700 rpms for 1 minute and 30 seconds discarding flow through at the end of each spin. The binding plate was centrifuged for an additional 10 minutes at 4,700 rpm to remove any residual ethanol. A clean elution plate was then placed under the binding plate and DNA was eluted with 200 µl, pre-warmed (55° C.), Nuclease Free Water (Promega, P1195).

DNA was screened for toxin genes ($\alpha$, $\beta$, $\epsilon$, and $\iota$) specific to *C. perfringens* using polymerase chain reaction (PCR). Amplification of toxin genes was executed using a multiplex PCR containing four primer sets (Yoo et al., 1997) (Table 1.) The PCR mixture contained 2.5 µl 10×PCR Buffer, 2 µl of 50 mM MgCl$_2$, 0.5 µM of each primer (Table 1.), 0.1 µl of Invitrogen™ Platinum™ Taq DNA Polymerase, 2.5 µl of DNA, sterile water was added to achieve 25 µl for a total reaction volume. The mixture underwent 5 minutes at 94° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved. If one or multiple toxin genes were observed a toxin type identification was assigned to each isolate based on their toxin-gene profile (Songer, 1996). *C. perfringens* positive to total clostridia isolate ratio was used to calculate an estimated *C. perfringens* count based on the total clostridia count.

Unique strain-specific genetic fingerprints were generated using Random Amplification of Polymorphic DNA (RAPD) analysis on select isolates to determine diversity among fecal *C. perfringens* isolates. The PCR contained 5 µl of DNA, 2.5 µl RAPD primer 2 (10 µM) (Table 1.), and 17.5 µl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes finishing with a final elongation of 5 minutes at 72° C. PCR products observed on a Fragment Analyzer (Advanced Analytics) to determine amplification patterns and were imported into BioNumerics, bioinformatics software, for analysis. RAPD patterns were compared with a band based Dice correlation analysis method to determine the similarity between RAPD patterns as a way to monitor diversity between isolates. Cluster cut-off was at 75% similarity.

To identify clostridia that did not have at least one toxin gene specific to *C. perfringens*, a PCR reaction was performed on the isolate DNA to amplify the 16S region of rDNA using primers 27F-YM and 1492R-Y (Table 1). This was done on 20% of the isolates that did not contain a toxin gene specific to *C. perfringens*. The PCR mixture contained 5 µl of 10×PCR Buffer, 2 µl of 50 mM MgCl$_2$, 1 µl of 50 mM dNTPs, 0.4 µM of each primer (Table 1.), 0.2 µl of Invitrogen™ Platinum™ Taq DNA Polymerase, 5 µl of DNA, and sterile water was added to achieve 50 µl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to gene wiz to obtain the sequences for the 16S genes. Sequences were compared to known typed bacterial strains obtained from EZbiocloud online electronic database. Based on comparisons of these sequences a bacterial identification was assigned to the isolates.

Figure 86:
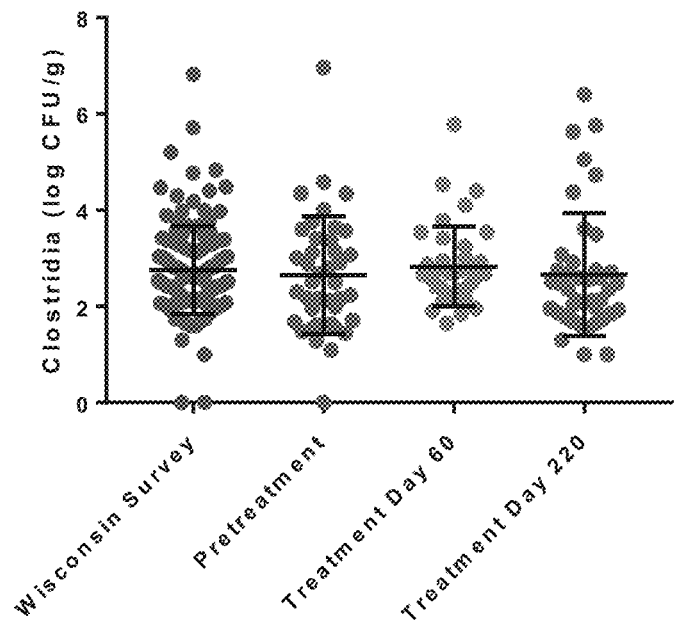
FIG. 86 is a chart showing enumeration results of total clostridia by individual fecal sample for all sampling points for Wisconsin Farm E in accordance with one embodiment of the present invention, pursuant to Example 13.
Figure 87:
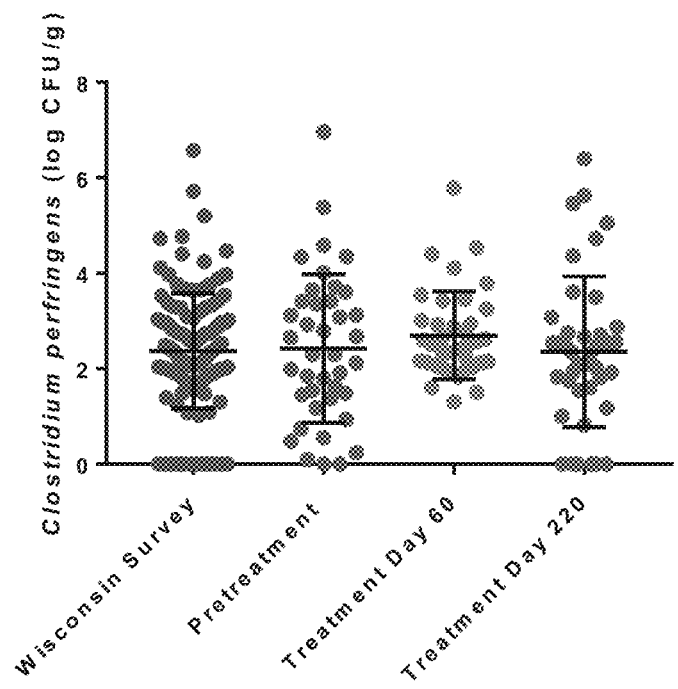
FIG. 87 is a chart showing calculated counts of *Clostridium perfringens* by individual fecal sample over time from Wisconsin Farm E in accordance with one embodiment of the present invention, pursuant to Example 13.
Figure 88:
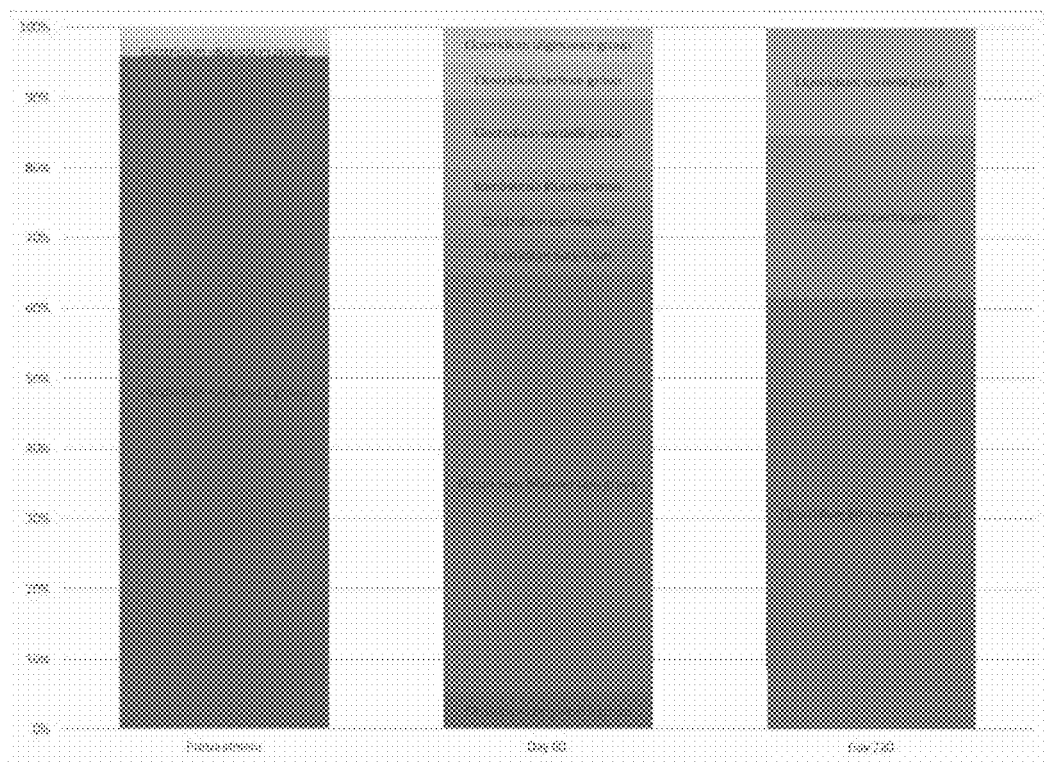
FIG. 88 is a graph showing proportions of non-toxigenic *Clostridium* species over time from Wisconsin Farm E in accordance with one embodiment of the present invention, pursuant to Example 13.

Results:

Total clostridia counts on Farm E (FIG. 86) were not significantly different than those determined during the Wisconsin survey (Example 5). Although there was no reduction in clostridia (FIG. 86) or *C. perfringens* (FIG. 87) during treatment with the *Bacillus* blend, there was less strain diversity in the *C. perfringens* isolated during treatment as indicated by the Shannon-Wiever index of the *C. perfringens* RAPD patterns (Table 26). Diversity of the non-toxigenic clostridia was also reduced during treatment and the predominant *C. beijerincki* group isolates were totally supplanted by *C. bifermentans* group isolates during treatment (FIG. 88 and Table 27).

Discussion:

The blend of *Bacillus* strains selected to inhibit *C. perfringens* decreased the diversity of *C. perfringens* strains in the cows. The *Bacillus* product also reduced the diversity of non-toxigenic clostridial species and caused the displacement of *C. beijerinckii* group strains by *C. bifermentans* and others. These data demonstrate that even when clostridical counts are within the normal range for the region and are not reduced by the product there is still a reduction in the diversity of *C. perfringens* isolates and the diversity and types of *Clostridium* species present. *C. beijerinckii* group was predominant at 96% before treatment, but was not detected after 220 days on treatment. The reduction in the proportion of the *C. beijerinckii* group, which are known to produce high levels of butanol and acetone, will most likely improve rumen fermentation and improve feed efficiency as well as milk production in dairy cows.

TABLE 25

Number of fecal samples collected at each sampling point from Wisconsin Farm E.

| Samples | Date | Cow Fecal |
|---|---|---|
| Pretreatment | May 11, 2016 | 40 |
| Treatment Day 60 | Jul. 13, 2016 | 38 |
| Treatment Day 220 | Dec. 20, 2016 | 41 |

TABLE 26

RAPD fingerprint diversity of the *Clostridium perfringens* isolates over time from Wisconsin Farm E.

| | Isolates | Clusters | Shannon-Wiener Index of Diversity |
|---|---|---|---|
| Pretreatment | 134 | 42 | 3.33 |
| Treatment Day 60 | 282 | 39 | 2.83 |
| Treatment Day 220 | 280 | 16 | 1.78 |

TABLE 27

Diversity of non-toxigenic *Clostridium* species and change in proportions of the two most predominant groups over time.

| Species Diversity | Isolates | Species | Shannon-Wiener Index of Diversity | *Clostridium beijerinckii* group | *Clostridium bifermentans* group |
|---|---|---|---|---|---|
| Pretreatment | 73 | 4 | 0.22 | 96% | 0% |
| Treatment Day 60 | 20 | 8 | 1.40 | 5% | 60% |
| Treatment Day 220 | 13 | 3 | 0.93 | 0% | 62% |

Example 14: The Effect of a Combination of *Bacillus* Strains on the Clostridial Populations of Dairy Cows on Farm BS-TX in Texas Introduction:

Hemorrhagic bowel syndrome (HBS) was first reported in 1991 and observed in five high-producing Holstein cows from one dairy in Idaho (Sockett, 2004). Symptoms included point-source sub-mucosal hematomas, each affecting 10-20 cm of the jejunum. One of the five cows exhibited a ruptured hematoma with exsanguination into the lumen of the jejunum. Although *Aspergillus fumigatus* and *Clostridium perfringens* are known to be involved in the etiology of HBS, the syndrome is better described as being poly-microbial and multi-factorial in nature. Increased consumption of a high-energy diet seems to be the most plausible common pathway for all the risk factors that have been described (Berghaus et al., 2005).

HBS is characterized by sudden drop in milk production, abdominal pain due to obstructed bowel and anemia (Anderson, 2002). Clinical signs of the disease are decreased feed intake, depression, decreased milk production, dehydration, abdominal distension and dark clotted blood in the feces. Death comes within 48 hours from the onset of the obstructing blood clot plug. Due to the sporadic, acute etiology few treatments are known to be effective In addition to *Clostridium* isolates of several species causing enteric disease, other *Clostridium* species produce high levels of acetone, butanol, 1,3 propanediol and butyric acid as end products of their metabolism. If produced in the rumen, these metabolic end products may affect rumen function and decrease efficiency.

The *Bacillus* strains selected by the inventors, to inhibit pathogens, produce multiple compounds with inhibitory activity against other microbes with many strains containing more than ten operons producing antifungal and antibacterial compounds. Multiple bacteriocins are being produced in vitro directly at the site of action by the *Bacillus* strains so a robust blend of bacteriocins are present at doses lower than would be needed if isolated bacteriocins were being added directly to the feed.

The purpose of this study was to measure milk production and the levels and diversity of clostridia in dairy cows on Farm B-TX treated with the product, in accordance with this embodiment of the present invention, (referred to herein as "treated"), over 107 days.

Materials and Methods:

A dairy herd in Texas (Farm BS) was selected to study the impact of *Bacillus* product, in accordance with this embodiment of the present invention, on milk production and clostridia levels and diversity. The herd consists of 5500 milk cows housed in forced air-ventilated barns and the cows are bedded on sand.

The product, in accordance with this embodiment of the present invention was a combination product of two *Bacillus* strains in equal proportions; *Bacillus* 747 and *Bacillus* 1781 incorporated into the total mixed ration (TMR) at a dose of about 2 billion CFU per head per day.

The average Energy Corrected Milk (ECM) production was calculated for the 4 months prior to feeding the *Bacillus* to the dairy cows. The ECM production was calculated for the 4 months after the inclusion of the product into the feed. ECM is a calculation to standardize volume of milk produced on a total energy basis considering fluid milk production (lbs), milk fat (lbs), and milk protein (lbs). The calculation adjusts actual milk fat (lbs) to a standardized 3.5 percent and actual milk protein (lbs) to a standardized 3.2 percent. This calculation allows producers to compare the volume of milk produced on a standardized basis.

The formula for ECM:

$$ECM = (0.327 \times \text{milk pounds}) + (12.95 \times \text{fat pounds}) + (7.65 \times \text{protein pounds})$$

Fecal samples were obtained from 60 cows before treatment and 60 cows after 107 days on treatment.

Fecal samples from cows were diluted 1:10 with sterile peptone, heat shocked for 30 minutes at 60° C., enumerated in sterile peptone and pour plated on Tryptose Sulphite Cycloserine (TSC) agar with D-cycloserine (400 mg/L) to select for clostridial species. Agar plates were incubated at 37° C. anaerobically for 24 hours. If present, isolated sulphite-reducing colonies were counted for total clostridia counts (CFU/g) and representative isolates were picked into Reinforced Clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions were performed in 96-well blocks containing 500 µl presumptive clostridia culture per well. Cells were harvested by centrifugation at 4,700 rpm for 10 minutes, the supernatant was removed. Cells were re-suspended in 500 µl of 50 mM of EDTA-2Na (pH=8.0). Aliquots of 300 µl of the suspended cells were transferred to a new 96-well block and combined with 20 µl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 µl of lysis buffer (6 M Guanidine, 20% Triton-X 100, 10 mM Tris-HCL, pH 7.5) was added, mixed then incubated at room temperature for 15 minutes. Following the incubation 20 µl of Proteinase K (NEB, 800 U/mL) was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed centrifuging 750 µl of Column Wash Solution (Promega, A1318) at 4700 rpms for 1 minute and 30 seconds discarding flow through at the end of each spin. The binding plate was centrifuged for an additional 10 minutes at 4,700 rpm to remove any residual ethanol. A clean elution plate was then placed under the binding plate and DNA was eluted with 200 µl, pre-warmed (55° C.), Nuclease Free Water (Promega, P1195).

DNA was screened for toxin genes ($\alpha$, $\beta$, $\epsilon$, and $\iota$) specific to C. perfringens using polymerase chain reaction (PCR). Amplification of toxin genes was executed using a multiplex PCR containing four primer sets (Yoo et al., 1997) (Table 1.) The PCR mixture contained 2.5 µl 10×PCR Buffer, 2 µl of 50 mM $MgCl_2$, 0.5 µM of each primer (Table 1.), 0.1 µl of Invitrogen™ Platinum™ Taq DNA Polymerase, 2.5 µl of DNA, sterile water was added to achieve 25 µl for a total reaction volume. The mixture underwent 5 minutes at 94° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved. If one or multiple toxin genes were observed a toxin type identification was assigned to each isolate based on their toxin-gene profile (Songer, 1996). C. perfringens positive to total clostridia isolate ratio was used to calculate an estimated C. perfringens count based on the total clostridia count.

Unique strain-specific genetic fingerprints were generated using Random Amplification of Polymorphic DNA (RAPD) analysis on select isolates to determine diversity among fecal C. perfringens isolates. The PCR contained 5 µl of DNA, 2.5 µl RAPD primer 2 (10 µM) (Table 1.), and 17.5 µl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes finishing with a final elongation of 5 minutes at 72° C. PCR products observed on a Fragment Analyzer (Advanced Analytics) to determine amplification patterns and were imported into BioNumerics, bioinformatics software, for analysis. RAPD patterns were compared with a band based Dice correlation analysis method to determine the similarity between RAPD patterns as a way to monitor diversity between isolates. Cluster cut-off was at 75% similarity.

To identify clostridia that did not have at least one toxin gene specific to C. perfringens, a PCR reaction was performed on the isolate DNA to amplify the 16S region of rDNA using primers 27F-YM and 1492R-Y (Table 1). This was done on 20% of the isolates that did not contain a toxin gene specific to C. perfringens. The PCR mixture contained 5 µl of 10×PCR Buffer, 2 µl of 50 mM $MgCl_2$, 1 µl of 50 mM dNTPs, 0.4 µM of each primer (Table 1.), 0.2 µl of Invitrogen™ Platinum™ Taq DNA Polymerase, 5 µl of DNA, and sterile water was added to achieve 50 µl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to gene wiz to obtain the sequences for the 16S genes. Sequences were compared to known typed bacterial strains obtained from EZbiocloud online electronic database. Based on comparisons of these sequences a bacterial identification was assigned to the isolates.

Results:

Milk production increased during the treatment period on Farm BS as ECM increased 0.6 lbs per day.

Figure 89:
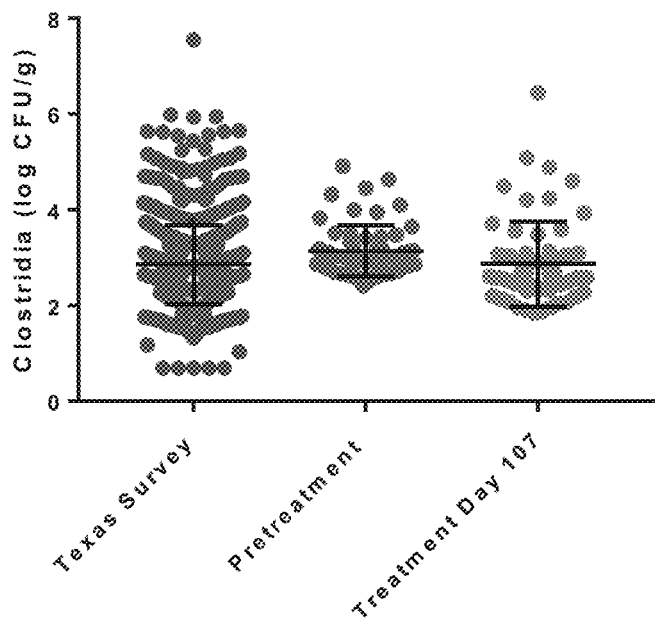
FIG. 89 is a chart showing enumeration results from Farm BS of total clostridia by individual fecal sample for all time points, including those of Example 6, where Time points that are significantly different from the Pretreatment samples are indicated by asterisks over the mean error bars in accordance with one embodiment of the present invention, pursuant to Example 14.
Figure 90:
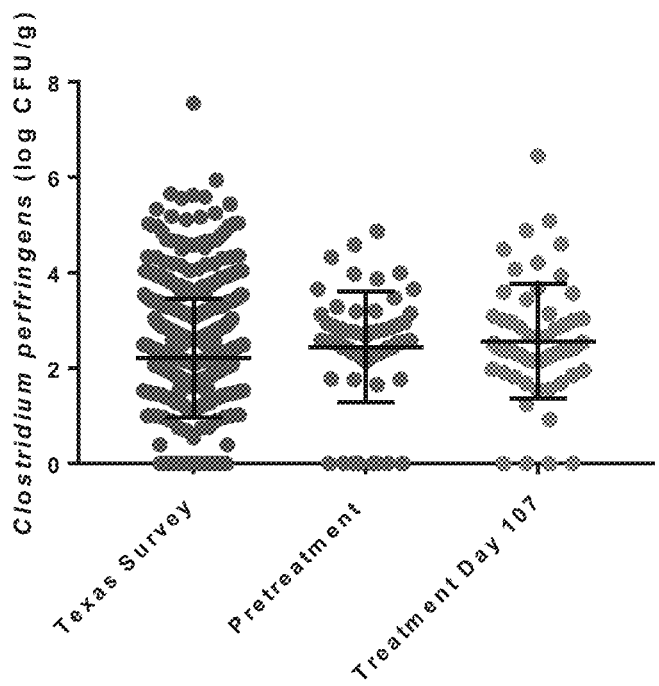
FIG. 90 is a chart showing calculated counts from Farm BS of *Clostridium perfringens* by individual fecal sample for all time points, including those of Example 6 in accordance with one embodiment of the present invention, pursuant to Example 14.
Figure 91:
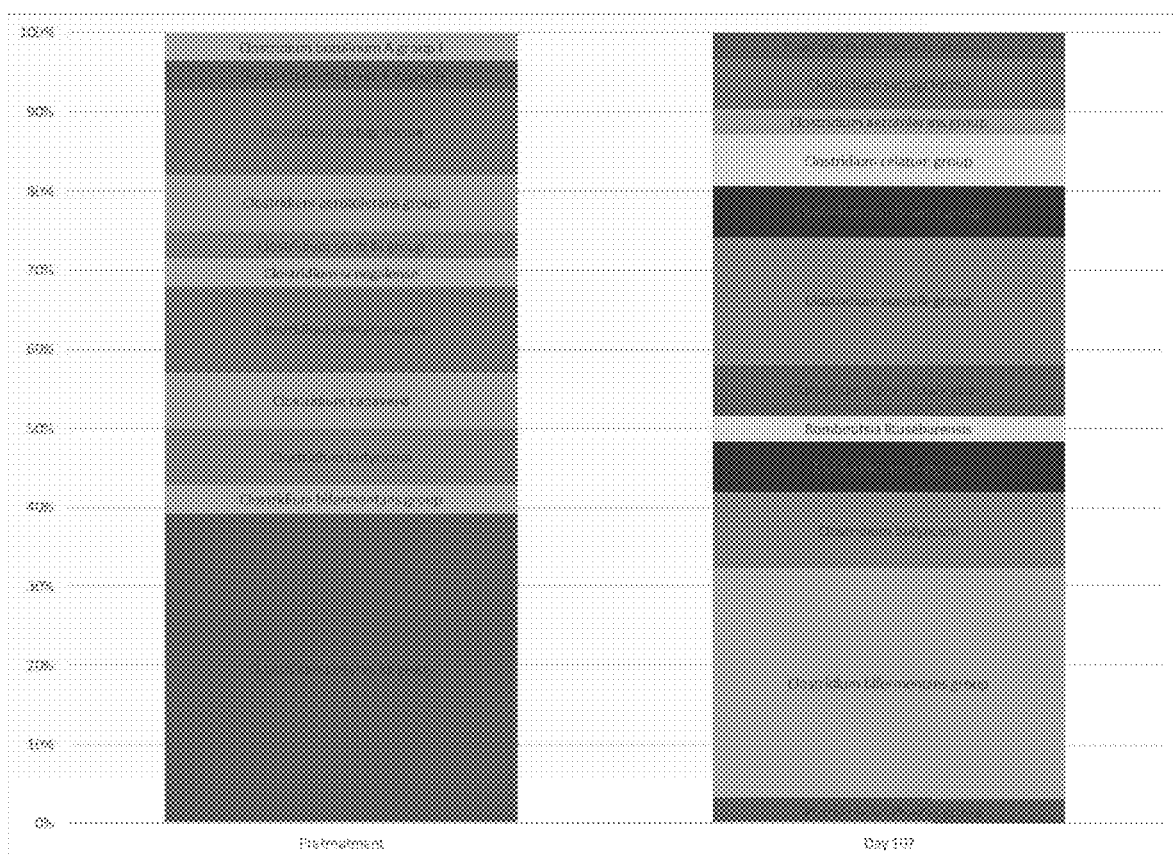
FIG. 91 is a graph showing proportions of non-toxigenic *Clostridium* species from the pretreatment compared to 107 days treated sampling points from Texas Farm BS in accordance with one embodiment of the present invention, pursuant to Example 14.
Figure 92:
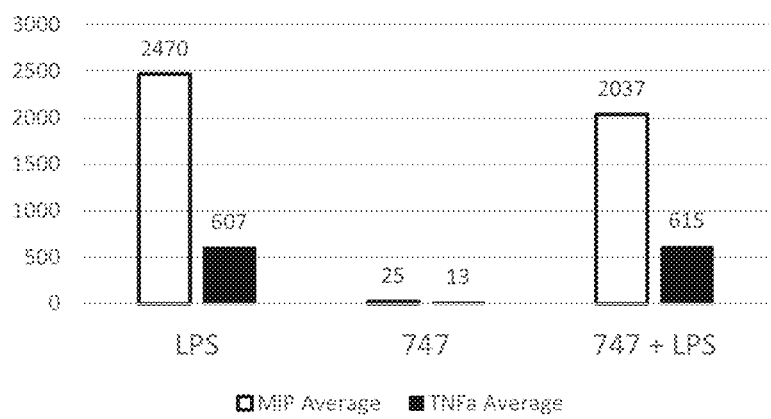
FIG. 92 is a graph showing fold-change in inflammatory cytokine (MIP-2 and TNF-$\alpha$) gene expression elicited by *Bacillus* strain 747 with and without LPS, in accordance with one embodiment of the present invention, pursuant to Example 15.

The average total clostridia counts on Farm BS (FIG. 89) were significantly higher (P>0.05) than those determined during the Texas survey (Example 6). There was no change in total clostridia or C. perfringens during treatment with the Bacillus blend (FIG. 90), however there was less strain diversity in the C. perfringens isolated during treatment as indicated by the Shannon-Wiever index of the C. perfringens RAPD patterns (Table 28). C. beijerincki group isolates were supplanted by C. bifermentans group isolates during treatment (FIG. 91 and Table 29).

Discussion:

Milk production improved during the treatment period, in addition the blend of Bacillus strains, in accordance with this embodiment of the present invention, decreased the diversity of C. perfringens strains in the cows. The Bacillus product also reduced the diversity of non-toxigenic clostridial species and caused the displacement of C. beijerinckii group strains by C. bifermentans. These data demonstrate that even when clostridial counts are not greatly reduced by the *Bacillus* strains the diversity of *C. perfringens* isolates and the types of *Clostridium* species are effected by the product. The reduction in the proportion of the *C. beijerinckii* group, which are known to produce high levels of butanol and acetone, most likely improved rumen fermentation and feed efficiency thereby increasing milk production as measured in these dairy cows.

TABLE 28

| RAPD fingerprint diversity of the *Clostridium perfringens* isolates over time from Texas Farm BS. | | | |
|---|---|---|---|
| | Isolates | Clusters | Shannon-Wiener Index of Diversity |
| Pretreatment | 190 | 39 | 2.94 |
| Treatment Day 107 | 358 | 26 | 2.14 |

TABLE 29

Diversity of non-toxigenic *Clostridium* species and change in proportions of the two most predominant groups over time from Texas Farm BS.

| Species Diversity | Isolates | Species | Shannon-Wiener Index of Diversity | *Clostridium beijerinckii* group | *Clostridium bifermentans* group |
|---|---|---|---|---|---|
| Pretreatment | 28 | 11 | 2.01 | 39% | 4% |
| Day 107 | 31 | 12 | 2.21 | 3% | 29% |

Example 15: Immune Gene Expression Response of *Bacillus* Strains to LPS Challenge in an Intestinal Epithelial Cell Line Introduction:

An in vitro cell culture screening study was conducted to determine the effects of *Bacillus* strains and a combination of strains on the inflammatory cytokine gene expression response in an intestinal epithelial cell line. *Bacillus* strains were screened in the IEC-6 rat intestinal epithelial cell line in an LPS challenge model to determine the effect of each *Bacillus* strain and combination on inflammatory cytokine gene expression response with and without LPS challenge. *Bacillus* strains and combinations tested in the model included:

*Bacillus* strain 747

*Bacillus* strain 1781

*Bacillus* strain 1104

*Bacillus* strain 1541

*Bacillus* strain 2018

*Bacillus* strain 747+1781

Materials and Methods:

Cell Culture Preparation: The IEC6 rat intestinal epithelial cell line (ATCC) was used in this study; cells were expanded in a 37° C. incubator at 5% $CO_2$ to passage 18 in tissue culture flasks to 80% confluence in CCM Complete Growth Medium (DMEM: Dulbecco's Modified Eagle's Medium containing 4 mM L-glutamine and 4.5 g/L glucose; 1.5 g/L sodium bicarbonate; 0.1 Unit/mL bovine insulin, 90%; 10% FBS: fetal bovine serum) with 1% antibiotic (penicillin, 10 U/mL/streptomycin, 10 mg/mL). Growth media was removed from flasks and cells were then washed twice with warmed Dulbecco's Phosphate-Buffered Saline (DPBS). Trypsin warmed to 37° C. was added to cover the cell monolayer in the flask and incubated at 37° C. until cells lifted off the surface of the flask. CCM Growth Media was immediately added to the trypsinized cells, mixed thoroughly by pipetting and removed to a 15 mL conical tube. Cells were pelleted by centrifuging at 1500 rpm for 10 min. After discarding the supernatant, cells were resuspended in 2-3 mL CCM Growth Medium and cell concentration and viability was determined by diluting a portion of the cell suspension in Trypan Blue and counting on a hemocytometer. Cells were diluted to $3\times10^5$ cells/mL, 1 mL of this cell suspension was added to each well of a 24-well plate, and incubated overnight in a 37° C. incubator at 5% $CO_2$ in order for cells to adhere to the bottom of the wells and form a monolayer. The following day, growth media was removed from each well, the cell monolayers were washed twice with DPBS, and treatments were administered to designated wells.

Cell Culture Treatment Administration:

Treatments were administered to wells in a 24-well. Antibiotic-free CCM media was used for this stage of the assay when treatments were administered. A 30 ng/mL LPS solution was prepared in CCM media without antibiotics and 500 uL of this solution was administered to each LPS treated well, resulting in 15 ng administered to each appropriate well. *Bacillus* strains were grown overnight in tryptic soy both and diluted in DPBS such that 250 uL of each respective treatment was administered to each well to deliver $1\times10^5$ cfu/well. A total volume of 1 mL was administered to each well with either DPBS or CCM media added as appropriate to bring each well to an equal 1 mL volume. Specific volumes administered to Unstimulated, LPS, *Bacillus*, and *Bacillus*+LPS designated wells are shown in Table 30.

Following treatment administration to designated wells, plates were incubated for 1 hour at 37° C. and 5% $CO_2$. After the one hour incubation, media was removed from the wells and cells were washed 2× with warm DPBS. Immediately after the second DPBS wash, 400 uL of Trizol was added to each well and allowed to incubate at room temperature for 5 minutes. Trizol was removed from each well, placed in a 1.5 mL microcentrifuge tube labelled with designated treatment and immediately snap-frozen in liquid nitrogen. Tubes were stored in −80° C. for future RNA extraction and qPCR gene expression analysis.

RNA Extraction and cDNA Synthesis:

Frozen Trizol tubes were removed from freezer storage and allowed to thaw on ice. RNA was extracted using the Direct-zol RNA MiniPrep kit (Zymo Research, Irvine, Calif.) according to manufacturer's instructions. RNA concentration was checked on the Qubit fluorometer (ThermoFisher Scientific, Inc.) and recorded to document RNA extraction from each well of the cell culture experimental template. The QuantiNova Reverse Transcription kit (Qiagen, Germantown, Md.) was used to prepare cDNA per manufacturer's instructions.

Real-Time Ouantitative PCR:

qPCR was performed on the Applied Biosystems StepOne Plus Real Time PCR system (Applied Biosystems, Foster City, Calif.) using Platinum Taq polymerase and the primers listed in Table 31. β-Actin was used as the housekeeping gene and ΔCt values were determined for each well treatment by subtracting the number of PCR cycles related to the target gene from the PCR cycles associated with the housekeeping gene. Fold change in gene expression was also calculated using the ΔΔCt method to calculate fold change in gene expression of each LPS and *Bacillus* treatment relative to the unstimulated cells.

Results:

All *Bacillus* strains tested elicited some inflammatory response when exposed to the intestinal epithelial cell line, as indicated by the increased fold-change in gene expression of the inflammatory cytokines, MIP-2 and TNF-α (FIGS. 92-96). Of the five *Bacillus* strains tested, *Bacillus* 747 (FIG. 92) exhibited substantially lower fold increase in expression of the inflammatory cytokine genes than the others. When combined with LPS, three of the *Bacillus* strains (*Bacillus*

Figure 93:
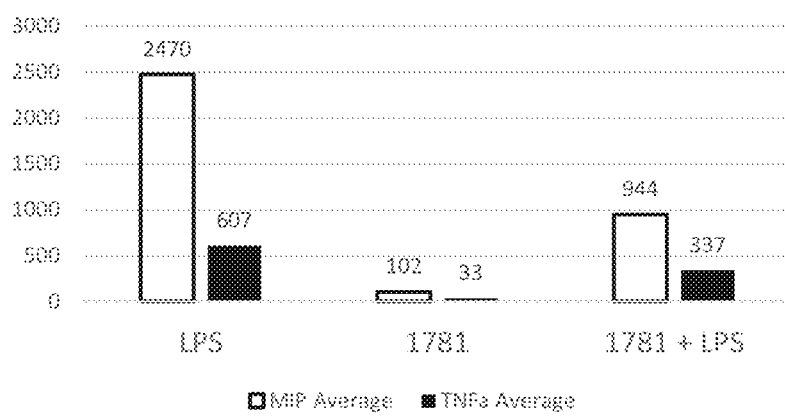
FIG. 93 is a graph showing fold-change in inflammatory cytokine (MIP-2 and TNF-$\alpha$) gene expression elicited by *Bacillus* strain 1781 with and without LPS, in accordance with one embodiment of the present invention, pursuant to Example 15.
Figure 94:
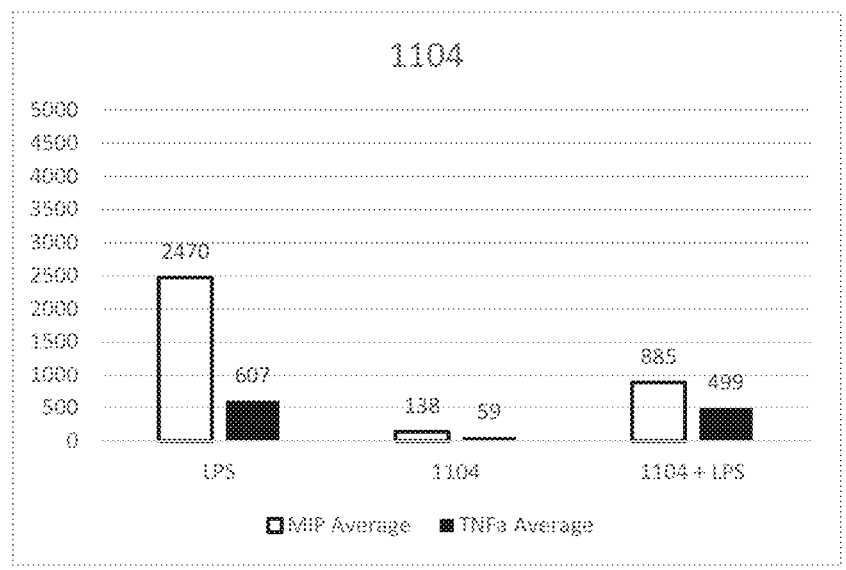
FIG. 94 is a graph showing fold-change in inflammatory cytokine (MIP-2 and TNF-$\alpha$) gene expression elicited by *Bacillus* strain 1104 with and without LPS, in accordance with one embodiment of the present invention, pursuant to Example 15.
Figure 95:
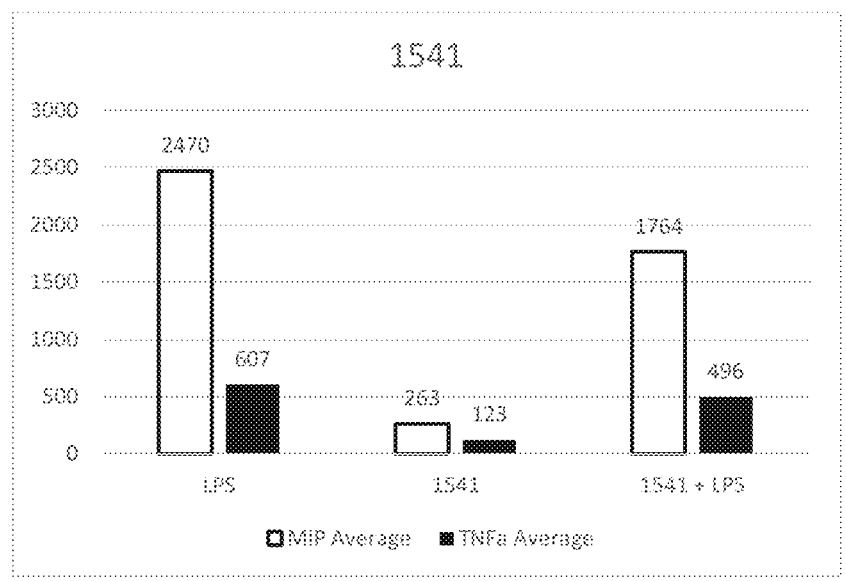
FIG. 95 is a graph showing fold-change in inflammatory cytokine (MIP-2 and TNF-$\alpha$) gene expression elicited by *Bacillus* strain 1541 with and without LPS, in accordance with one embodiment of the present invention, pursuant to Example 15.
Figure 96:
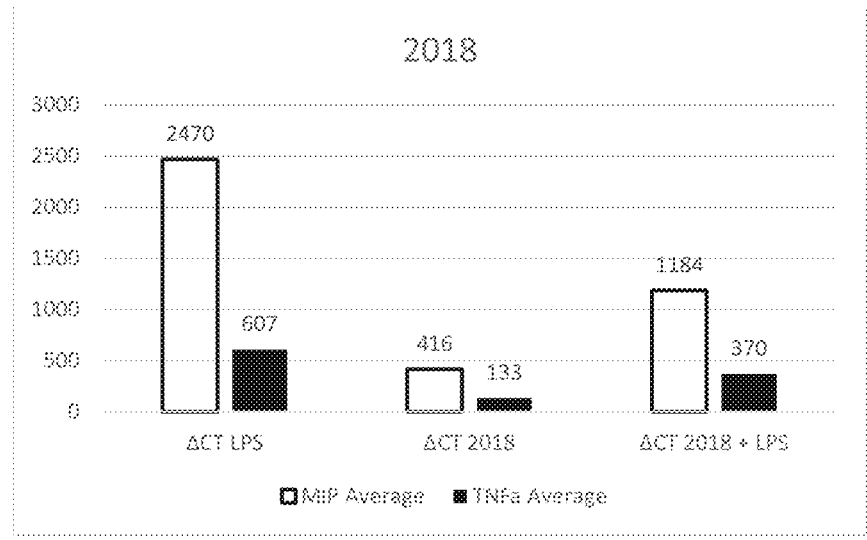
FIG. 96 is a graph showing fold-change in inflammatory cytokine (MIP-2 and TNF-$\alpha$) gene expression elicited by *Bacillus* strain 2018 with and without LPS, in accordance with one embodiment of the present invention, pursuant to Example 15.
Figure 97:
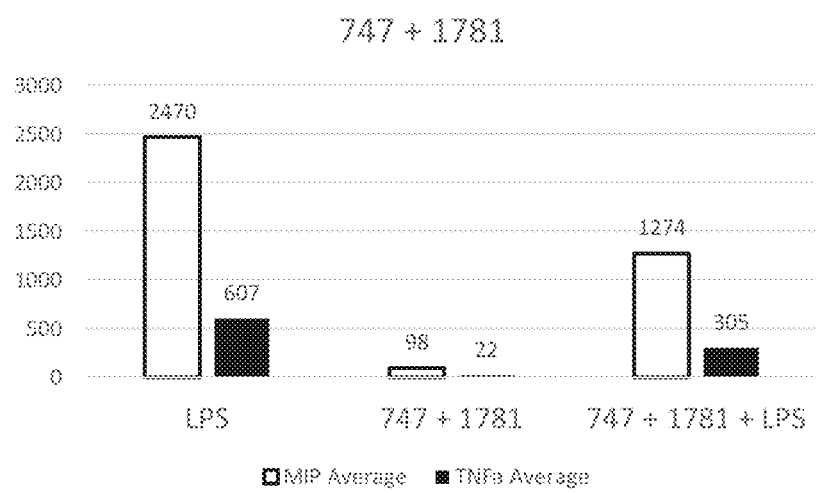
FIG. 97 is a graph showing fold-change in inflammatory cytokine (MIP-2 and TNF-$\alpha$) gene expression elicited by *Bacillus* strains 747 and 1781 with and without LPS, in accordance with one embodiment of the present invention, pursuant to Example 15.

1781, *Bacillus* 1104, and *Bacillus* 2018; FIGS. 93, 94, and 96, respectively) reduced the inflammatory cytokine gene expression compared to LPS inflammatory challenge alone, indicating these *Bacillus* strains have the ability to ameliorate responses to inflammatory challenge in the gastrointestinal tissue. The combination of *Bacillus* 747 and *Bacillus* 1781 administered to the IEC-6 epithelial cell line resulted in a fold-change in gene expression similar to *Bacillus* 747 administered alone, and exhibited a moderate propensity to reduce the inflammatory response induced by LPS challenge, similarly to *Bacillus* 1781 (FIG. 97).

Discussion:

These data illustrate the immunomodulatory potential of *Bacillus* strains in an inflammatory challenge model, simulating the effects of a gram-negative bacterial pathogenic infection. Furthermore, individual *Bacillus* strains elicit distinct immunomodulatory effects on inflammation, suggesting *Bacillus* strains should for the specific functions (inflammatory or anti-inflammatory) to meet the health needs of the host.

TABLE 30

Primer sequences used in the cell culture yeast products study.

| Name | Sequence |
|---|---|
| β-Actin-F | TGACGAGGCCCAGAGCAAGA (SEQ ID No. 18) |
| β-Actin-R | ATGGGCACAGTGTGGGTGAC (SEQ ID No. 19) |
| MIP2-3F | CCCCTTGGTTCAGAGGATCG (SEQ ID No. 20) |
| MIP2-3R | TTGATTCTGCCCGTTGAGGT (SEQ ID No. 21) |
| TNFα-3F | GGCCCGAGGCAACACAT (SEQ ID No. 22) |
| TNFα-3R | GGGCCATGGAACTGATGAGA (SEQ ID No. 23) |

TABLE 31

Volumes administered to each well based on treatment designation.

| | UNSTIM | LPS | *Bacillus* | *Bacillus* + LPS |
|---|---|---|---|---|
| CCM (w/o Ab) | 750 uL | 250 uL | 750 uL | 250 uL |
| DPBS | 250 uL | 250 uL | — | — |
| LPS | — | 500 uL | — | 500 uL |
| *Bacillus* | — | — | 250 uL | 250 uL |

Example 16: Administration of a Direct-Fed Microbial Containing *Bacillus* and *Lactobacillus* Strains to Calf Milk Replacer Introduction:

Pre- and post weaning performance and health of nursery dairy calves when fed direct-fed microbials (DFM) supplemented into the milk replacers Material and Methods:

A total of 100 Holstein heifer calves (39.2±0.65 kg body weight) were included in a trial to assess the effect of two different microbial combinations administered as a direct-fed microbial (DFM) added to calf milk replacer. The 56-day study included a 42-day pre-weaning portion in which calves were administered a 20/20 (20% fat/20% protein) milk replacer and a 14-day post-weaning period in which calves were fed completely on a dry diet. An all-milk protein, non-medicated milk replacer was fed at 0.28 kg in 2 L of water 2× daily from d 1 to d 35 and 1× daily from d 36 to weaning at d 42. The nutrient composition of milk replacer and dry feed used in the study are summarized in Table 32. Calves were randomly assigned to one of four treatments (25 calves/treatment) that were added to the daily mix of calf milk replacer administered individually to each calf on test:

1) Control—20/20 milk replacer
2) Antibiotic—Control supplemented with neomycin and oxytetracycline at a rate of 22 mg/kg BW for 14 days
3) *Bacillus* 747—Control supplemented with 5 g of DFM premix containing *Bacillus* strain 747 ($1 \times 10^9$ CFU/head/d) per feeding for 42 days
4) *Bacillus* 747+1781—Control supplemented with 5 g of DFM premix containing *Bacillus* strains 747+1781 ($1 \times 10^9$ CFU/head/d total CFU with each *Bacillus* strain representing 50% of the total) feeding for 42 days.

Body weight of calves was recorded on day 14, 28, 42, and 56 of the study and average daily gain (ADG) was calculated. Hip height was measured and recorded for each calf on day 1 and day 56 of the study. Intake of all feed was recorded daily and summarized every two weeks by treatment. Fecal scores were conducted on calves daily and summarized weekly through the first four weeks of the study, using a 1-4 scale defined as 1=normal, 2=loose, 3 very loose, but no watery separation, and 4=very watery. Health records including medication treatments, number of treatment days, medication treatment costs, and mortality were recorded throughout the study.

A 10 mL blood sample was obtained into EDTA tubes from each calf 14 days following the initial treatment administration. A 0.5 mL subsample was removed from the 10 mL sample and placed in RNA Protect tubes (Qiagen, Inc., Valencia, Calif.). Blood plasma was collected from the remaining whole blood sample and analyzed for the acute phase protein, haptoglobin. Haptoglobin was analyzed by ELISA kit per the manufacturer's instructions (MyBioSource, San Diego, Calif.). The blood from the RNA Protect tubes was used to extract RNA from blood cells and measure the gene expression analysis of various immune cytokines between the four treatments. Briefly, RNA extraction was performed on the blood sample stored in the RNA Protect tubes using the RNEasy Protect Animal Blood Kit per the manufacturer's instructions (Qiagen, Inc.). The QuantiNova Reverse Transcription kit (Qiagen, Germantown, Md.) was used to prepare cDNA per manufacturer's instructions. Real-time quantitative PCR (RT-qPCR) was performed on the Applied Biosystems StepOne Plus Real Time PCR system (Applied Biosystems, Foster City, Calif.) using Platinum Taq polymerase and the primers listed in Table 33. Glyceraldehyde 3-phosphate dehydrogenase (GAPDH) was used as the housekeeping gene and ΔCt values were determined for each well treatment by subtracting the number of PCR cycles related to the target gene from the PCR cycles associated with the housekeeping gene.

Growth performance and calf health data were analyzed using the PROC MIXED procedure of SAS and repeated measures analyses applied where appropriate. Serum acute phase proteins and cytokine gene expression data were analyzed using the General Linear Model procedure using JMP. Least squares means were used to differentiate treatment effects using Student's t-test. Initial body weight (BW)

was used as a covariate for BW, ADG and dry matter intake (DMI) data when significant. Initial hip heights were used as a covariate for day 56 hip height and hip height gain.

Results:

Calves fed the Antibiotic treatment (TRT2) and *Bacillus* 747 (TRT3) had greater (P=0.05) body weight on day 56 of the study and tended (P<0.10) to have greater ADG and total body weight gain compared to calves fed the Control (TRT1) milk replacer, whereas calves administered *Bacillus* 747+1781 (TRT4) was intermediate between the Control and the other treatments (Table 34). Milk replacer and calf starter feed intake were similar across all treatments (Table 35 and Table 36), and no differences were observed in serum proteins, fecal scores, scouring days, or treatment costs (Table 37).

Figure 98:
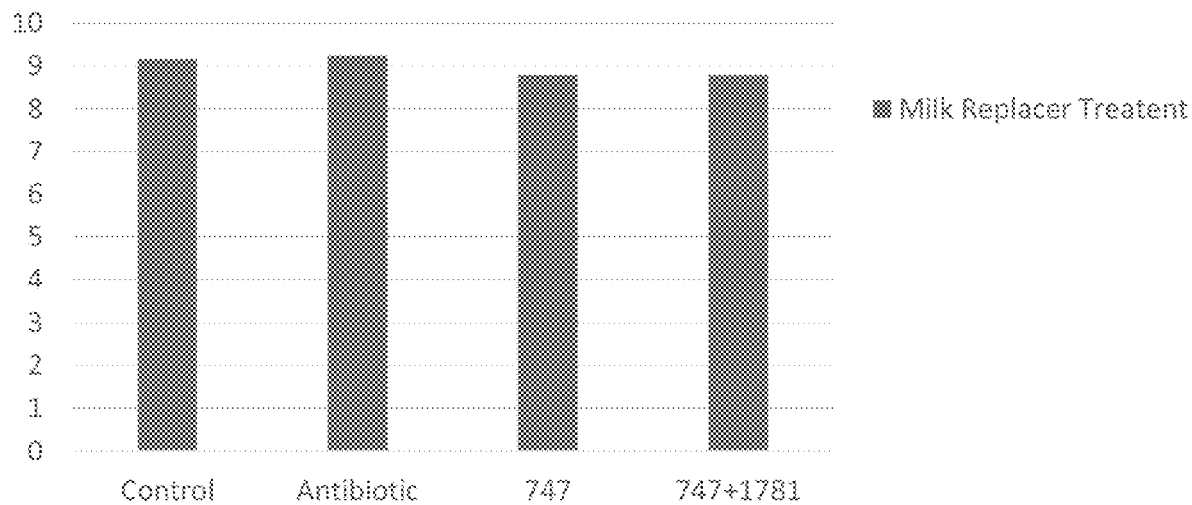
FIG. 98 is a graph showing plasma haptoglobin concentrations of calves 14 days following the initiation of milk replacer treatments, in accordance with one embodiment of the present invention, pursuant to Example 16.

Plasma haptoglobin concentrations were similar across all four treatments (FIG. 98). Gene expression of the reactive oxygen compound, iNOS, was greater (P<0.05) in the blood cells of calves administered the *Bacillus* 747+1781 treatment compared to all others (Table 38). Furthermore, gene expression of the inflammatory cytokine, IL-6, was greater (P<0.05) in calves fed the Antibiotic treatment compared to calves administered the Control and *Bacillus* 747 treatments, and calves administered the Control milk replacer and with *Bacillus* 747+1781 supplementation had greater (P<0.05) gene expression of the chemokine, CCL8, compared to calves fed the Antibiotic or *Bacillus* 747. The differences in cytokine gene expression observed in this study indicate that *Bacillus* 747 administered alone promotes a less inflammatory environment compared to the combination of *Bacillus* 747+178 1, as indicated by the greater gene expression of iNOS and CCL8 observed in calves fed *Bacillus* 747+1781.

Discussion:

Calves fed milk replacer with *Bacillus* supplementation had similar growth and health as calves offered milk replacers containing the antibiotics, neomycin sulfate:oxytetracycline for 14 days, indicating that *Bacillus* administered to calves has the potential to be used as alternatives to antibiotic administration to promote health and efficient growth. Furthermore, this study shows that specific *Bacillus* strains alone or in combination, elicit different immunomodulatory activities, promoting either an inflammatory or quiescent immunological environment in the young calf, potentially resulting in a divergence of immune development and function.

TABLE 32

Nutrient composition of basal milk replacer (MR) and basal calf starter (CS).

| Nutrient Analyses | MR | CS |
|---|---|---|
| Dry Matter, % | 96.14 | 86.31 |
| ADF[1], % | — | 10.22 |
| NDF[1], % | 0.25 | 16.97 |
| CP[1], % | 21.34 | 19.72 |
| Ash, % | 10.15 | 6.61 |
| Ether Extract, % | 20.35 | 3.95 |
| Starch, % | — | 35.98 |
| Calcium, % | 0.90 | 1.08 |
| Phosphorus, % | 0.91 | 0.63 |
| Potassium, % | 2.72 | 1.31 |
| Magnesium, % | 0.20 | 0.31 |
| TDN[1], % | — | 76.77 |
| NFC[1], % | 47.92 | 53.53 |

[1]ADF = acid detergent fiber; NDF = neutral detergent fiber; CP = crude protein; TDN = total digestible nutrients; NFC = non-fiber carbohydrates

TABLE 33

Bovine primer sequences for immune gene expression analysis using RT-qPCR.

| Gene | Forward | Reverse | Product Size |
|---|---|---|---|
| PTX3 | GGCAGACTCACAGGCTTCAATATC (SEQ. ID No. 24) | CCTTCTCCAGTCTCCCTTTCAACT | 343 |
| GAPDH | GGCGTGAACCACGAGAAGTATAA (SEQ. ID No. 25) | CCCTCCACGATGCCAAAGT | 194 |
| SOD | ACTTCGAGGCAAAGGGAGATAC (SEQ. ID No. 26) | TTTTGGCCCACCGTGTT | 164 |
| COX2 | TCCTGAAACCCACTCCCAACA (SEQ. ID No. 27) | TGGGCAGTCATCAGGCACAG | 242 |
| iNOS | GGCTACGGAACTGGACATCAAC (SEQ. ID No. 28) | CTCAGGGATTCTGGAGACG | 162 |
| IL6 | ATGACTTCTGCTTTCCCTACCC (SEQ. ID No. 29) | GCTGCTTTCACACTCATCATTC | 179 |
| IL-18 | CACGTTTCCTCTCCTAAGAAGC (SEQ. ID No. 30) | TACTTGTTCTGCAGCCATCTTT | 60 |
| CCL2 | CCAGATGCAATTAACTCCCAAG (SEQ. ID No. 31) | GCATGGAGATCTTCTTACTGTTGA | 64 |
| CCL8 | AAGCAGAAGTGGGTCCAGACT (SEQ. ID No. 32) | CTTCGGTGTTCGGGACTTT | 60 |
| TLR-2 | TCCACGGACTGTGGTACATGAAGA (SEQ. ID No. 33) | GCTTAAAGGGAGGGTTGAAGTGCT | 180 |
| TLR-4 | TCAGAGTTTCCTGCAGTGGGTCAA (SEQ. ID No. 34) | ACTAAGCACTGGCATGTCCTCCAT | 106 |

TABLE 34

Growth parameters of calves measured on day 1 to 56 of the study.

|  | TRT1[1] | TRT2[1] | TRT3[1] | TRT4[1] | SEM |
|---|---|---|---|---|---|
| Calves, n | 25 | 25 | 25 | 25 |  |
| Initial Body Weight[2], lb | 85.6 | 85.1 | 85.4 | 85.5 | 1.37 |
| Initial Hip Height[3], in | 31.48 | 31.79 | 31.66 | 31.47 | 0.18 |
| Body Weight (BW), Lb |  |  |  |  |  |
| d 14 | 93.0 | 95.1 | 93.8 | 93.2 | 0.72 |
| d 28 | 105.4 | 108.0 | 107.6 | 105.9 | 1.10 |
| d 42 | 123.5 | 126.8 | 127.4 | 124.3 | 1.75 |
| d 56 | 149.1[c] | 155.7[a] | 154.8[ab] | 151.5[a,b,c] | 2.43 |
| d 84 | 202.3 | 209.4 | 210.0 | 203.3 | 3.75 |
| Average Daily Gain (ADG), lb/d |  |  |  |  |  |
| d 1 to 14 | 0.54 | 0.69 | 0.59 | 0.55 | 0.04 |
| d 15 to 28 | 0.90 | 0.94 | 1.00 | 0.84 | 0.06 |
| d 29 to 42 | 1.30 | 1.36 | 1.43 | 1.40 | 0.09 |
| d 1 to 42 | 0.90 | 0.98 | 0.99 | 0.91 | 0.05 |
| d 43 to 56 | 1.85 | 2.07 | 1.97 | 1.96 | 0.09 |
| d 1 to 56 | 1.15[z] | 1.26[x] | 1.25[x,y] | 1.19[y,z] | 0.04 |
| d 57 to 84 | 1.89 | 1.90 | 1.95 | 1.84 | 0.07 |
| d 1 to 84 | 1.39 | 1.47 | 1.48 | 1.4 | 0.04 |
| Total BW Gain, lb |  |  |  |  |  |
| d 1 to 14 | 7.5 | 9.6 | 8.3 | 7.7 | 0.63 |
| d 15 to 28 | 12.6 | 13.1 | 14.0 | 11.8 | 0.89 |
| d 29 to 42 | 18.3 | 19.0 | 20.0 | 19.5 | 1.20 |
| d 1 to 42 | 37.8 | 41.1 | 41.7 | 38.3 | 1.97 |
| d 43 to 56 | 25.8 | 29.0 | 27.6 | 27.4 | 1.21 |
| d 1 to 56 | 64.2[z] | 70.7[x] | 69.8[xy] | 66.4[y,z] | 2.48 |
| Hip Height, in |  |  |  |  |  |
| d 56 | 35.18 | 35.4 | 35.3 | 35.43 | 0.14 |
| d 84 | 37.57 | 37.84 | 37.69 | 38.04 | 0.18 |
| Hip Height gain, in |  |  |  |  |  |
| d 1 to d 56 | 3.59 | 3.80 | 3.70 | 3.83 | 0.14 |
| d 57 to 84 | 2.41 | 2.44 | 2.39 | 2.61 | 0.14 |
| d 1 to 84 | 5.98 | 6.25 | 6.09 | 6.44 | 0.18 |

[1]TRT1 = Control; TRT2 = Antibiotic; TRT3 = *Bacillus* 747; TRT4 = *Bacillus* 747 + 1781.
[2]Initial body weight (BW) utilized as a covariate for body weight and average daily gain data.
[3]Initial hip height (HH) utilized as a covariate for hip height measurement on day 56 and HH gain.
[a,b,c]Means in the same row with different superscripts differ (P = 0.05).
[x,y,z]Means in the same row with different superscripts differ (P < 0.10).

TABLE 35

Milk replacer (MR) intake of calves measured on day 1 to 42 of the study.

|  | TRT1[1] | TRT2[1] | TRT3[1] | TRT4[1] | SEM |
|---|---|---|---|---|---|
| Total MR intake, lbs DM |  |  |  |  |  |
| d 1 to 14 | 16.27 | 16.49 | 16.38 | 16.31 | 0.08 |
| d 15 to 28 | 16.84 | 16.81 | 16.82 | 16.82 | 0.08 |
| d 29 to 42 | 12.61 | 12.62 | 12.62 | 12.60 | 0.08 |
| d 1 to 42 | 45.72 | 45.90 | 45.81 | 45.72 | 0.15 |
| Intake, lb/d DM |  |  |  |  |  |
| d 1 to 14 | 1.16 | 1.18 | 1.17 | 1.17 | 0.005 |
| d 15 to 28 | 1.20 | 1.20 | 1.20 | 1.20 | 0.005 |
| d 29 to 42 | 0.90 | 0.90 | 0.90 | 0.90 | 0.005 |
| d 1 to 42 | 1.09 | 1.09 | 1.09 | 1.09 | 0.003 |

[1]TRT1 = Control; TRT2 = Antibiotic; TRT3 = *Bacillus* 747; TRT4 = *Bacillus* 747 + 1781.

TABLE 36

Starter feed, dry matter (DM) intake, and feed efficiency of calves measured on day 1 to 56 of the study.

|  | TRT1[1] | TRT2[1] | TRT3[1] | TRT4[1] | SEM |
|---|---|---|---|---|---|
| Starter intake, lb/d |  |  |  |  |  |
| d 1 to 7 | 0.02 | 0.02 | 0.02 | 0.01 | 0.01 |
| d 8 to 14 | 0.03 | 0.05 | 0.04 | 0.04 | 0.01 |
| d 15 to 21 | 0.22 | 0.26 | 0.26 | 0.19 | 0.05 |
| d 22 to 28 | 0.43 | 0.52 | 0.62 | 0.44 | 0.07 |
| d 29 to 35 | 0.87 | 0.93 | 0.98 | 0.82 | 0.09 |
| d 36 to 42 | 1.83 | 1.96 | 2.12 | 1.86 | 0.12 |
| d 43 to 49 | 3.44 | 3.54 | 3.70 | 3.56 | 0.17 |
| d 50 to 56 | 4.12 | 4.48 | 4.46 | 4.30 | 0.14 |
| Total starter intake, lbs |  |  |  |  |  |
| d 1 to 42 | 23.75 | 26.35 | 28.32 | 23.47 | 2.45 |
| d 43 to 56 | 53.71 | 57.09 | 57.91 | 55.53 | 2.44 |
| d 1 to 56 | 76.62 | 82.34 | 85.36 | 78.57 | 4.00 |
| DM Intake, lbs/d |  |  |  |  |  |
| d 1 to 14 | 1.19 | 1.22 | 1.21 | 1.20 | 0.01 |
| d 15 to 28 | 1.53 | 1.59 | 1.65 | 1.52 | 0.06 |
| d 29 to 42 | 2.25 | 2.35 | 2.45 | 2.24 | 0.11 |
| d 1 to 42 | 1.65 | 1.72 | 1.77 | 1.65 | 0.06 |
| d 43 to 56 | 3.84 | 4.04 | 4.12 | 3.95 | 0.15 |
| d 1 to 56 | 2.20 | 2.30 | 2.36 | 2.23 | 0.07 |
| DM intake, lbs |  |  |  |  |  |
| d 1 to 14 | 16.68 | 17.03 | 16.88 | 16.75 | 0.19 |
| d 15 to 28 | 21.45 | 22.33 | 23.04 | 21.32 | 0.87 |
| d 29 to 42 | 31.55 | 32.91 | 34.36 | 31.40 | 1.53 |
| d 1 to 42 | 69.48 | 72.26 | 74.13 | 69.20 | 2.46 |
| d 43 to 56 | 53.71 | 56.60 | 57.72 | 55.30 | 2.04 |
| d 1 to 56 | 123.4 | 128.8 | 132.0 | 124.8 | 4.04 |
| Gain:Feed Ratio |  |  |  |  |  |
| d 1 to 14 | 0.44 | 0.55 | 0.48 | 0.45 | 0.03 |
| d 15 to 28 | 0.57 | 0.58 | 0.59 | 0.53 | 0.03 |
| d 29 to 42 | 0.57 | 0.57 | 0.57 | 0.62 | 0.02 |
| d 1 to 42 | 0.54 | 0.57 | 0.56 | 0.55 | 0.01 |
| d 43 to 56 | 0.49 | 0.52 | 0.47 | 0.50 | 0.02 |
| d 1 to 56 | 0.52 | 0.55 | 0.53 | 0.52 | 0.01 |

[1]TRT1 = Control; TRT2 = Antibiotic; TRT3 = *Bacillus* 747; TRT4 = *Bacillus* 747 + 1781.

TABLE 37

Serum protein and health measurements of calves from d 1 to 56 of the study.

|  | TRT1[1] | TRT2[1] | TRT3[1] | TRT4[1] | SEM |
|---|---|---|---|---|---|
| Serum Protein | 5.96 | 5.87 | 5.87 | 5.87 | 0.15 |
| Fecal Score[2] |  |  |  |  |  |
| d 1 to 14 | 1.74 | 1.98 | 1.82 | 1.77 | 0.06 |
| d 15 to 28 | 1.26 | 1.31 | 1.24 | 1.30 | 0.04 |
| d 29 to 42 | 1.07 | 1.06 | 1.09 | 1.03 | 0.02 |
| d 1 to 42 | 1.35 | 1.45 | 1.38 | 1.37 | 0.03 |
| d 43 to 56 | 1.10 | 1.05 | 1.08 | 1.03 | 0.03 |
| d 1 to 56 | 1.29 | 1.35 | 1.31 | 1.28 | 0.02 |

TABLE 37-continued

Serum protein and health measurements of calves from d 1 to 56 of the study.

|  | TRT1[1] | TRT2[1] | TRT3[1] | TRT4[1] | SEM |
|---|---|---|---|---|---|
| Scouring days[3] | | | | | |
| d 1 to 42 | 2.71 | 3.26 | 2.38 | 3.08 | 0.36 |
| d 43 to 56 | 0.00 | 0.06 | 0.00 | 0.03 | 0.03 |
| # Days = 4 | | | | | |
| d 1 to 42 Treatment cost, $ | 0.30 | 0.36 | 0.30 | 0.34 | 0.12 |
| d 1 to 42 | 0.41 | 0.43 | 0.70 | 0.62 | 0.19 |
| d 43 to 56 | 0.00 | 0.00 | 0.15 | 0.00 | 0.18 |
| d 1 to 56 | 0.34 | 0.37 | 0.85 | 0.56 | 0.29 |

[1]TRT1 = Control; TRT2 = Antibiotic; TRT3 = *Bacillus* 747; TRT4 = *Bacillus* 747 + 1781.
[2]Fecal score value from 1 to 4, with 1 = normal to 4 = watery.
[3]Scouring day = any day with a fecal score ≥3.

TABLE 38

Immune gene expression of calves 14 days after administration of milk replacer treatments.

| Immune Gene Expression, ΔCt[2] | TRT1[1] | TRT2[1] | TRT3[1] | TRT4[1] | SEM | P = |
|---|---|---|---|---|---|---|
| PTX3 | 11.00 | 11.00 | 11.38 | 10.83 | 0.65 | 0.946 |
| SOD | 10.90 | 10.88 | 11.00 | 11.12 | 0.42 | 0.994 |
| COX2 | 9.00 | 9.00 | 9.00 | 9.50 | 0.42 | 0.801 |
| iNOS | 13.20$^a$ | 11.56$^{a,b}$ | 13.12$^a$ | 11.00$^b$ | 0.71 | 0.094 |
| IL6 | 20.00$^a$ | 14.29$^c$ | 19.20$^{a,b}$ | 16.25$^{b,c}$ | 1.21 | 0.004 |
| IL-18 | 5.40 | 6.11 | 5.75 | 6.00 | 0.27 | 0.161 |
| CCL2 | 11.00 | 11.13 | 11.75 | 11.00 | 0.98 | 0.354 |
| CCL8 | 9.56$^b$ | 11.11$^a$ | 10.57$^{a,b}$ | 9.50$^b$ | 0.53 | 0.050 |
| TLR-2 | 5.40 | 5.11 | 5.00 | 4.75 | 0.25 | 0.429 |
| TLR-4 | 4.90 | 4.67 | 4.38 | 4.25 | 0.26 | 0.356 |

[1]TRT1 = Control; TRT2 = Antibiotic; TRT3 = *Bacillus* 747; TRT4 = *Bacillus* 747 + 1781.
[2]Note: ΔCt measures number of PCR cycles and is inversely proportional to gene expression; greater ΔCt = lower gene expression.
$^{a,b,c}$Means in the same row with different superscripts differ (P < 0.05).

Example 17: The Effect of a Combination of *Bacillus* Strains on the Herd Milk Production of Dairy Cows on Five Herds in Wisconsin Introduction:

Hemorrhagic bowel syndrome (HBS) was first reported in 1991 and observed in five high-producing Holstein cows from one dairy in Idaho (Sockett, 2004). Symptoms included point-source sub-mucosal hematomas, each affecting 10-20 cm of the jejunum. One of the five cows exhibited a ruptured hematoma with exsanguination into the lumen of the jejunum. Although *Aspergillus fumigatus* and *Clostridium perfringens* are known to be involved in the etiology of HBS, the syndrome is better described as being poly-microbial and multi-factorial in nature. Increased consumption of a high-energy diet seems to be the most plausible common pathway for all the risk factors that have been described (Berghaus et al., 2005).

HBS is characterized by sudden drop in milk production, abdominal pain due to obstructed bowel and anemia (Anderson, 2002). Clinical signs of the disease are decreased feed intake, depression, decreased milk production, dehydration, abdominal distension, and dark clotted blood in the feces. Death comes within 48 hours from the onset of the obstructing blood clot plug. Due to the sporadic, acute etiology few treatments are known to be effective.

In addition to *Clostridium* isolates of several species causing enteric disease, other *Clostridium* species produce high levels of acetone, butanol, 1,3 propanediol and butyric acid as end products of their metabolism. If produced in the rumen, these metabolic end products may affect rumen function and decrease efficiency.

The *Bacillus* strains selected by the inventors, to inhibit pathogens, produce multiple compounds with inhibitory activity against other microbes with many strains containing more than ten operons producing antifungal and antibacterial compounds. Multiple bacteriocins are being produced in vitro directly at the site of action by the *Bacillus* strains so a robust blend of bacteriocins are present at doses lower than would be needed if isolated bacteriocins were being added directly to the feed.

The purpose of this study was to measure milk production in dairy cows on five farms in Wisconsin treated with the product, in accordance with this embodiment of the present invention.

Materials and Methods:

Five Wisconsin dairy farms were selected to study the impact of *Bacillus*, in accordance with this embodiment of the present invention, on Energy Corrected Milk (ECM). ECM is a calculation to standardize volume of milk produced on a total energy basis considering fluid milk production (lbs), milk fat (lbs), and milk protein (lbs). The calculation adjusts actual milk fat (lbs) to a standardized 3.5 percent and actual milk protein (lbs) to a standardized 3.2 percent. This calculation allows producers to compare the volume of milk produced on a standardized basis.

The formula for ECM:

$$ECM = (0.327 \times \text{milk pounds}) + (12.95 \times \text{fat pounds}) + (7.65 \times \text{protein pounds})$$

Herd sizes in the study ranged from 185 head to 940 head. Farms selected for this summary are considered typical Wisconsin dairy farms. The five herds selected had no major management changes during the measured times.

The product, in accordance with this embodiment of the present invention was a combination product of three *Bacillus* strains; *Bacillus* 1104 (50%), *Bacillus* 1781 (45%) and *Bacillus* 1541 (5%) incorporated into the total mixed ration (TMR) at a dose of 2 billion CFU per head per day.

The average ECM production was calculated for the 4 months prior to feeding the *Bacillus* to the dairy cows. The *Bacillus* was included into the dairy cows feed ration on a daily basis (*Bacillus* Treatment Period). The ECM production was calculated for the 4 months after the inclusion of the *Bacillus* into the feed.

Results:

Herd responses (Table 39) ranged from an increase of 0.4 lbs ECM per day (Herd ID #2) to 2.8 lbs ECM per day (Herd ID #5). The average increase of ECM for all 5 herds is 1.82 lbs per day.

Discussion:

The blend of *Bacillus* strains, in accordance with this embodiment of the present invention, selected to inhibit clostridia, consistently improved milk production as measured by ECM across multiple farms of various sizes in Wisconsin.

TABLE 39

Improvement in Energy Corrected Milk (ECM) while on the *Bacillus* product from five herds in Wisconsin.

| Herd ID | Herd Size (cows) | Pretreatment | *Bacillus* Treatment | Change in ECM |
|---|---|---|---|---|
| #1 | 806 | Jan. 1, 2015 to Apr. 30, 2015 | May 5, 2015 to Sep.1, 2015 | +2.1 lbs |
| #2 | 185 | Feb. 15, 2015 to Jun. 4, 2015 | Jun. 5, 2015 to Oct. 5, 2015 | +0.4 lbs |
| #3 | 940 | May 5, 2015 to Sep. 14, 2015 | Sep. 15, 2015 to Jan. 15, 2016 | +2.6 lbs |
| #4 | 317 | Aug. 10 2015 to Dec. 9, 2015 | Dec. 10, 2015 to Apr. 6, 2016 | +1.2 lbs |
| #5 | 264 | Sep. 15, 2015 to Jan. 14, 2016 | Jan. 15, 2016 to May 15, 2016 | +2.8 lbs |
|  |  | Average Increase of ECM |  | +1.82 lbs |

Example 18: The Effect of a Combination of *Bacillus* Strains on the Herd Health, Milk Production and Clostridial Populations of Dairy Cows on Farm WB in Wisconsin Introduction:

Hemorrhagic bowel syndrome (HBS) was first reported in 1991 and observed in five high-producing Holstein cows from one dairy in Idaho (Sockett, 2004). Symptoms included point-source sub-mucosal hematomas, each affecting 10-20 cm of the jejunum. One of the five cows exhibited a ruptured hematoma with exsanguination into the lumen of the jejunum. Although *Aspergillus fumigatus* and *Clostridium perfringens* are known to be involved in the etiology of HBS, the syndrome is better described as being poly-microbial and multi-factorial in nature. Increased consumption of a high-energy diet seems to be the most plausible common pathway for all the risk factors that have been described (Berghaus et al., 2005).

HBS is characterized by sudden drop in milk production, abdominal pain due to obstructed bowel and anemia (Anderson, 2002). Clinical signs of the disease are decreased feed intake, depression, decreased milk production, dehydration, abdominal distension and dark clotted blood in the feces. Death comes within 48 hours from the onset of the obstructing blood clot plug. Due to the sporadic, acute etiology few treatments are known to be effective.

In addition to *Clostridium* isolates of several species causing enteric disease, other *Clostridium* species produce high levels of acetone, butanol, 1,3 propanediol and butyric acid as end products of their metabolism. If produced in the rumen, these metabolic end products may affect rumen function and decrease efficiency.

The *Bacillus* strains selected by the inventors, to inhibit pathogens, produce multiple compounds with inhibitory activity against other microbes with many strains containing more than ten operons producing antifungal and antibacterial compounds. Multiple bacteriocins are being produced in vitro directly at the site of action by the *Bacillus* strains so a robust blend of bacteriocins are present at doses lower than would be needed if isolated bacteriocins were being added directly to the feed.

The purpose of this study was to measure the herd health, milk production, clostridia levels and diversity in dairy cows on Farm WB treated with the product, in accordance with this embodiment of the present invention, (referred to herein as "treated"), over 86 days. Treatment was discontinued for 98 days and then recommenced for a second period.

Materials and Methods:

A dairy herd in Wisconsin (Farm WB) was selected to study the impact of a *Bacillus* product, in accordance with this embodiment of the present invention, on herd health and milk production. The herd consists of 900 milk cows housed in a free stall barn and the cows are bedded on sand. The herd is milked 3 times daily and has a rolling herd average of approximately 30,000 pounds per cow per year.

The product, in accordance with this embodiment of the present invention was a combination product of three *Bacillus* strains in equal proportions; *Bacillus* 747, *Bacillus* 1781 and *Bacillus* 2018 incorporated into the total mixed ration (TMR) at a dose of 2 billion CFU per head per day.

Herd health was determined by measuring cow deaths due to digestive issues.

Milk production on the farm was tracked using Energy Corrected Milk (ECM). ECM is a calculation to standardize volume of milk produced on a total energy basis considering fluid milk production (lbs), milk fat (lbs), and milk protein (lbs). The calculation adjusts actual milk fat (lbs) to a standardized 3.5 percent and actual milk protein (lbs) to a standardized 3.2 percent. This calculation allows producers to compare the volume of milk produced on a standardized basis.

The formula for ECM:

$$ECM = (0.327 \times \text{milk pounds}) + (12.95 \times \text{fat pounds}) + (7.65 \times \text{protein pounds})$$

Fecal samples were obtained from cows before, during and after treatment. Sample dates and number of animals sampled are indicated in Table 1.

Fecal samples from cows were diluted 1:10 with sterile peptone, heat shocked for 30 minutes at 60° C., enumerated in sterile peptone and pour plated on Tryptose Sulphite Cycloserine (TSC) agar with D-cycloserine (400 mg/L) to select for clostridial species. Agar plates were incubated at 37° C. anaerobically for 24 hours. If present, isolated sulphite-reducing colonies were counted for total clostridia counts (CFU/g) and representative isolates were picked into Reinforced Clostridia Medium (RCM) (Oxoid, CM0149) and incubated anaerobically for 24 hours at 37° C. After 24 hours of incubation the cultures were transferred (10%) to Brain Heart Infusion (BHI) broth (BD, 211059) and incubated anaerobically for 24 hours at 37° C.

DNA extractions were performed in 96-well blocks containing 500 µl presumptive clostridia culture per well. Cells were harvested by centrifugation at 4,700 rpm for 10 minutes, the supernatant was removed. Cells were re-suspended in 500 µl of 50 mM of EDTA-2Na (pH=8.0). Aliquots of 300 µl of the suspended cells were transferred to a new 96-well block and combined with 20 µl of lysozyme from chicken egg white (Sigma, L6876) solution (100 mg/ml in 50 mM EDTA) to lyse bacterial cells. The 96-well block was incubated for 1 hour at 37° C. to lyse bacterial cells. Following the incubation 220 µl of lysis buffer (6 M Guanidine, 20% Triton-X 100, 10 mM Tris-HCL, pH 7.5) was added, mixed then incubated at room temperature for 15 minutes. Following the incubation 20 µl of Proteinase K (NEB, 800 U/mL)

was added to each well, mixed and incubated at 55° C. for 30 minutes to degrade proteins. The cell lysate was then transferred to 96-well binding plate (Promega, A2278) and centrifuged at 4,700 rpms for 5 minutes. Flow through was discarded, three washes of the binding plate columns were executed centrifuging 750 µl of Column Wash Solution (Promega, A1318) at 4700 rpms for 1 minute and 30 seconds discarding flow through at the end of each spin. The binding plate was centrifuged for an additional 10 minutes at 4,700 rpm to remove any residual ethanol. A clean elution plate was then placed under the binding plate and DNA was eluted with 200 µl, pre-warmed (55° C.), Nuclease Free Water (Promega, P1195).

DNA was screened for toxin genes ($\alpha$, $\beta$, $\epsilon$, and $\iota$) specific to C. perfringens using polymerase chain reaction (PCR). Amplification of toxin genes was executed using a multiplex PCR containing four primer sets (Yoo et al., 1997) (Table 1.) The PCR mixture contained 2.5 µl 10×PCR Buffer, 2 µl of 50 mM $MgCl_2$, 0.5 µM of each primer (Table 1.), 0.1 µl of Invitrogen™ Platinum™ Taq DNA Polymerase, 2.5 µl of DNA, sterile water was added to achieve 25 µl for a total reaction volume. The mixture underwent 5 minutes at 94° C., followed by 30 cycles of 94° C. for 1 minute, 55° C. for 1 minute, 72° C. for 1 minute finishing with a final elongation of 3 minutes at 72° C. PCR products were observed using a Fragment Analyzer (Advanced Analytics) to determine if amplification was achieved. If one or multiple toxin genes were observed a toxin type identification was assigned to each isolate based on their toxin-gene profile (Songer, 1996). C. perfringens positive to total clostridia isolate ratio was used to calculate an estimated C. perfringens count based on the total clostridia count.

Unique strain-specific genetic fingerprints were generated using Random Amplification of Polymorphic DNA (RAPD) analysis on select isolates to determine diversity among fecal C. perfringens isolates. The PCR contained 5 µl of DNA, 2.5 µl RAPD primer 2 (10 µM) (Table 1.), and 17.5 µl of sterile water which was added to a Ready-To-Go RAPD Analysis Bead (Life Sciences, 27-9500-01). The mixture underwent 5 minutes at 95° C., followed by 45 cycles of 95° C. for 1 minute, 36° C. for 1 minute, 72° C. for 2 minutes finishing with a final elongation of 5 minutes at 72° C. PCR products observed on a Fragment Analyzer (Advanced Analytics) to determine amplification patterns and were imported into BioNumerics, bioinformatics software, for analysis. RAPD patterns were compared with a band based Dice correlation analysis method to determine the similarity between RAPD patterns as a way to monitor diversity between isolates. Cluster cut-off was at 75% similarity.

To identify clostridia that did not have at least one toxin gene specific to C. perfringens, a PCR reaction was performed on the isolate DNA to amplify the 16S region of rDNA using primers 27F-YM and 1492R-Y (Table 1). This was done on 20% of the isolates that did not contain a toxin gene specific to C. perfringens. The PCR mixture contained 5 µl of 10×PCR Buffer, 2 µl of 50 mM $MgCl_2$, 1 µl of 50 mM dNTPs, 0.4 µM of each primer (Table 1.), 0.2 µl of Invitrogen™ Platinum™ Taq DNA Polymerase, 5 µl of DNA, and sterile water was added to achieve 50 µl for a total reaction volume. The mixture underwent 4 minutes at 95° C., followed by 35 cycles of 95° C. for 30 seconds, 50° C. for 30 seconds, 72° C. for 2 minutes finishing with a final elongation of 7 minutes at 72° C. A quality check was done on the amplification and PCR product was sent to gene wiz to obtain the sequences for the 16S genes. Sequences were compared to known typed bacterial strains obtained from EZbiocloud online electronic database. Based on comparisons of these sequences a bacterial identification was assigned to the isolates.

Results:

The herd recorded 5 cow deaths due to digestive issues during the pretreatment period. The Bacillus product, in accordance with this embodiment of the present invention, was included into the dairy cows feed ration on a daily basis beginning 4-16-2016 and inclusion continued until 9-1-2016. During this Bacillus Treatment Period #1 the herd recorded one cow death due to digestive issues. The Bacillus was removed from the feed for a post-treatment period from 9-2-2016 to 12-8-2016. During this period the farm recorded 6 cow deaths due to digestive issues. The Bacillus Treatment Period #2 began on 12-9-2016 and the farm recorded zero cow deaths due to digestive issues thru 5-1-2017 (Table 41.).

Results indicate ECM increased 3.9 lbs/day and milk fat increased 0.3% during the Bacillus treatment period (Table 42.).

Average temperature was recorded from the time periods in 2015 and compared to the same time periods in 2016. This was done to ensure the positive milk response recorded during the Bacillus treatment Period was not simply due to a lower average temperature. The Bacillus treatment period in 2016 was an average of +2.6 F warmer on average in June and +2.7 F warmer in July (Table 43.).

Figure 99:
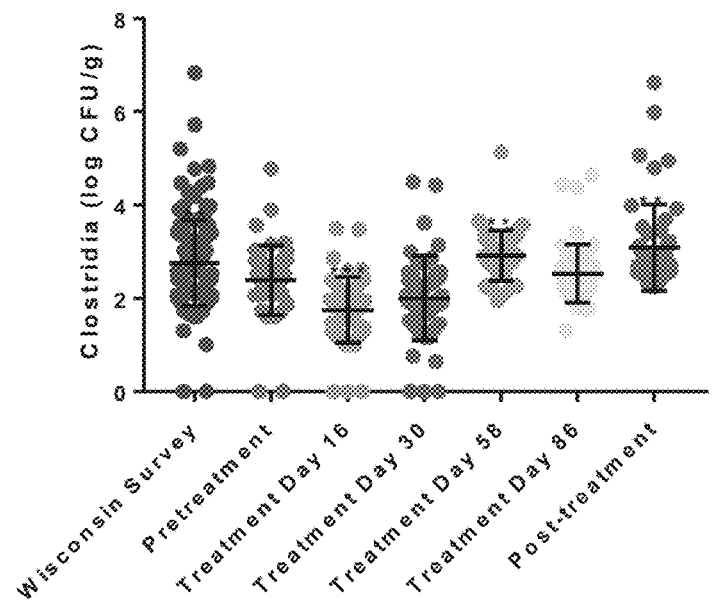
FIG. 99 is a chart showing enumeration results from Wisconsin Farm WB of total clostridia by individual fecal sample for all time points, including those of Example 5, where time points that are significantly different from the Pretreatment samples are indicated by asterisks over the mean error bars in accordance with one embodiment of the present invention, pursuant to Example 18.
Figure 100:
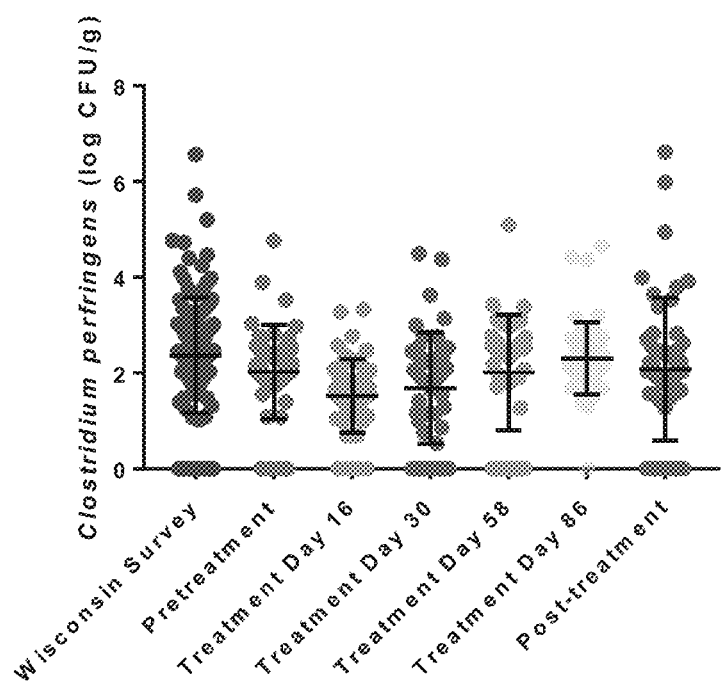
FIG. 100 is a chart showing calculated counts of *Clostridium perfringens* from Wisconsin Farm WB by individual fecal sample for all time points, including those of Example 5 in accordance with one embodiment of the present invention, pursuant to Example 18.
Figure 101:
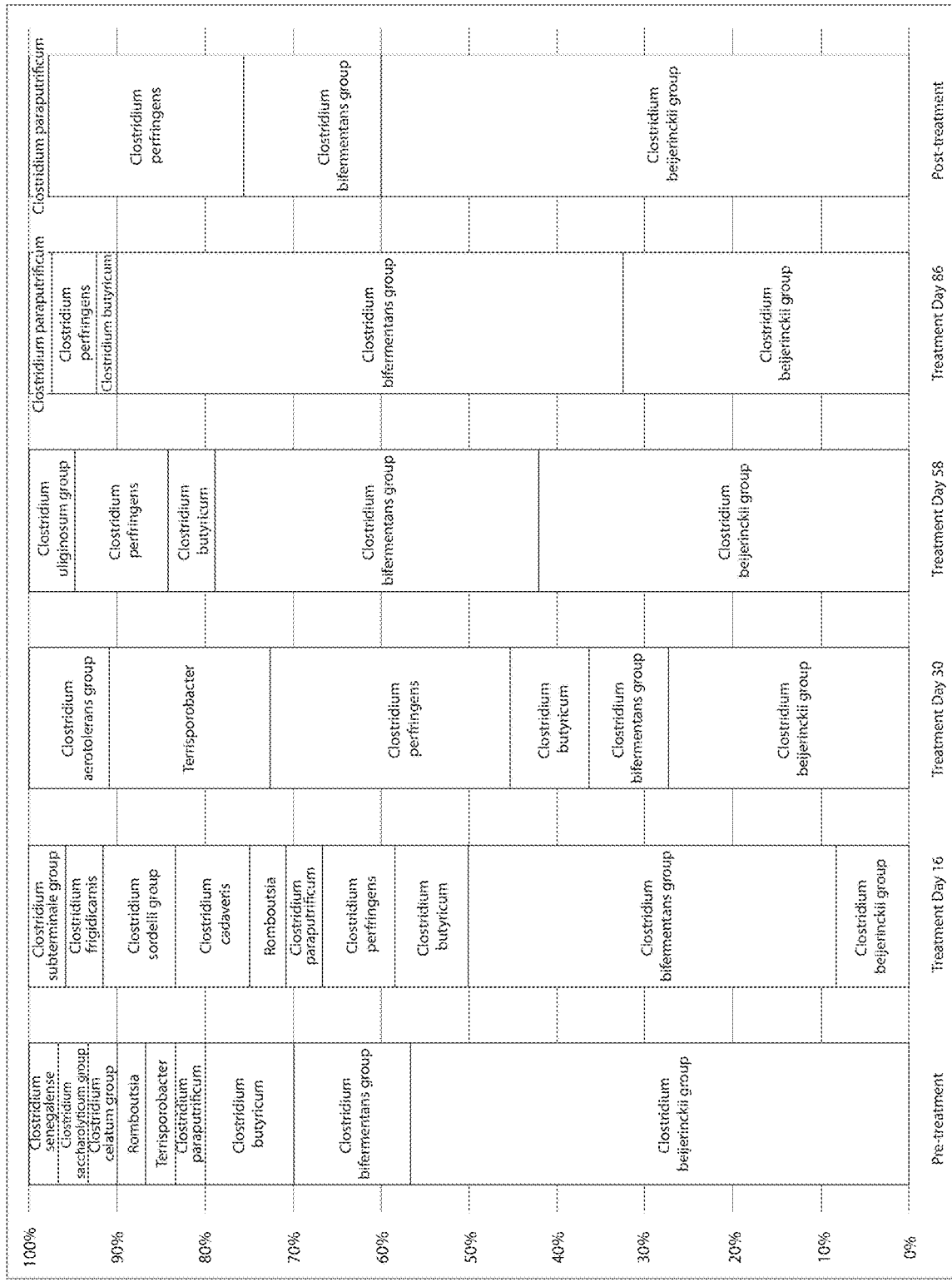
FIG. 101 is a chart showing proportions of non-toxigenic *Clostridium* species over time from Wisconsin Farm WB in accordance with one embodiment of the present invention, pursuant to Example 18.

Total clostridia counts on Farm WB (FIG. 99) were not significantly different than those determined during the Wisconsin survey (Example 5). During the first 16 days on the product total clostridia decreased significantly and then either were not different (days 30 and 86) or were higher (Day 58) compared to the Pretreatment. Clostridial counts for samples taken 98 days after the product was discontinued were significantly higher than before the product was started. Although there was no reduction in C. perfringens at any time during or after treatment with the Bacillus blend (FIG. 100), there was less strain diversity in the C. perfringens isolated during treatment and this was maintained post-treatment as indicated by the Shannon-Wiever index of the C. perfringens RAPD patterns (Table 44). Diversity of the non-toxigenic clostridia was also reduced during treatment and the predominant C. beijerinckii group isolates were supplanted by C. bifermentans group isolates during treatment (FIG. 101 and Table 45). When treatment was discontinued C. beijerinckii group strains became the predominant non-toxigenic clostridia again.

Discussion:

The blend of Bacillus strains, in accordance with this embodiment of the present invention, selected to inhibit clostridia, reduced the number of cow deaths due to digestive issues such as HBS. The number of digestive deaths increased again when the product was discontinued. Milk production as measured as ECM and milk fat was also improved. This production increase occurred even though more potential heat stress was present during the treatment period. The blend of Bacillus strains, in accordance with this embodiment of the present invention, selected to inhibit C. perfringens, initially caused a decrease in total clostridial counts and decreased the diversity of C. perfringens strains in the cows. There was also a reduction in the diversity of non-toxigenic clostridial species and the product caused the displacement of C. beijerinckii group strains by C. bifermentans. The proportions of C. beijerinckii group increased again when the treatment was discontinued. These data demonstrate that the product, in accordance with the embodiment of the present invention, improves herd health and milk production by reducing the levels and diversity of

*C. perfringens* isolates and the diversity and types of *Clostridium* species present. The reduction in the proportion of the *C. beijerinckii* group, which are known to produce high levels of butanol and acetone, likely improves rumen fermentation and improves feed efficiency resulting in increased milk production in dairy cows.

TABLE 41

Number of cow deaths due to digestive issues from Wisconsin Farm WB.

| Dates | Treatment Periods | Deaths |
|---|---|---|
| Jan. 15, 2016 to Apr. 15, 2016 | Pretreatment | 5 |
| Apr. 16, 2016 to Sep. 1, 2016 | *Bacillus* Treatment # 1 | 1 |
| Sep. 2, 2016 to Dec. 8, 2016 | Post-Treatment | 6 |
| Dec. 9, 2016 to May 1, 2017 | *Bacillus* Treatment #2 | 0 |

TABLE 42

ECM production levels were tracked during a pretreatment period (Apr. 1, 2015 to Aug. 1, 2015) and a *Bacillus* treatment period (Apr. 1, 2016 to Aug. 1, 2016) from Wisconsin Farm WB.

| Time Period | Treatment Period | ECM (lbs) | Milk Fat (%) |
|---|---|---|---|
| Apr. 1, 2015 to Aug. 1, 2015 | Pretreatment | 98.3 | 3.9% |
| Apr. 1, 2016 to Aug. 1, 2016 | *Bacillus* Treatment # 1 | 102.2 | 4.2% |
| | Difference | +3.9 | +0.3% |

TABLE 43

Weather Station Recordings- Temperature in Fahrenheit (F.) from Wisconsin Farm WB.

| | June Low | June High | June Average | July Low | July High | July Average |
|---|---|---|---|---|---|---|
| 2015 | 55.2 | 76.2 | 65.7 | 58.6 | 79.7 | 69.1 |
| 2016 | 57.2 | 79.4 | 68.3 | 62.1 | 81.6 | 71.8 |
| Difference | +2.0 | +3.2 | +2.6 | +3.5 | +1.9 | +2.7 |

TABLE 44

RAPD fingerprint diversity of the *Clostridium perfringens* isolates over time from Wisconsin Farm WB.

| | Isolates | Clusters | Shannon-Wiener |
|---|---|---|---|
| Pretreatment | 316 | 81 | 3.93 |
| Treatment Day 16 | 196 | 43 | 3.11 |
| Treatment Day 30 | 145 | 33 | 3.02 |
| Treatment Day 58 | 205 | 56 | 3.78 |
| Treatment Day 86 | 328 | 64 | 3.60 |
| Post-treatment | 180 | 31 | 2.59 |

TABLE 45

Diversity of non-toxigenic *Clostridium* species and change in proportions of the two predominant groups over time for Wisconsin Farm WB.

| Species Diversity | Iso-lates | Spe-cies | Shannon-Wiener Index of Diversity | *Clostridium beijerinckii* group | *Clostridium bifermentans* group |
|---|---|---|---|---|---|
| Pretreatment | 30 | 9 | 1.35 | 57% | 13% |
| Day 16 | 24 | 10 | 2.05 | 8% | 42% |
| Day 30 | 11 | 6 | 1.47 | 27% | 9% |
| Day 58 | 19 | 5 | 1.11 | 42% | 32% |
| Day 86 | 40 | 5 | 1.02 | 33% | 58% |
| Post-treatment Day 98 | 45 | 4 | 1.10 | 60% | 16% |

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

BIBLIOGRAPHY

Berghaus, R. D., McCluskey, B. J., and Callan, R. J. (2005). Risk factors associated with hemorrhagic bowel syndrome in dairy cattle. J. Am. Vet. Med. Assoc. 226, 1700-1706.

Ceci, L., Paradies, P., Sasanelli, M., De Caprariis, D., Guarda, F., Capucchio, M. t., and Carelli, G. (2006). Haemorrhagic Bowel Syndrome in Dairy Cattle: Possible Role of *Clostridium perfringens* Type A in the Disease Complex. J. Vet. Med. Ser. A 53, 518-523.

Dennison, A. C., VanMetre, D. C., Callan, R. J., Dinsmore, P., Mason, G. L., and Ellis, R. P. (2002). Hemorrhagic bowel syndrome in dairy cattle: 22 cases (1997-2000). J. Am. Vet. Med. Assoc. 221, 686-689.

Dennison, A. C., Van Metre, D. C., Morley, P. S., Callan, R. J., Plampin, E. C., and Ellis, R. P. (2005). Comparison of the odds of isolation, genotypes, and in vivo production of maj or toxins by *Clostridium perfringens* obtained from the gastrointestinal tract of dairy cows with hemorrhagic bowel syndrome or left-displaced abomasum. J. Am. Vet. Med. Assoc. 227, 132-138.

Duc, L. H., Hong, H. A., Fairweather, N., Ricca, E., and Cutting, S. M. (2003). Bacterial spores as vaccine vehicles. Infect. Immun. 71, 2810-2818.

Duc, L. H., Hong, H. A., Uyen, N. Q., and Cutting, S. M. (2004). Intracellular fate and immunogenicity ofB. *subtilis* spores. Vaccine 22, 1873-1885.

Hong, H. A., Duc, L. H., and Cutting, S. M. (2005). The use of bacterial spore formers as probiotics. FEMS Microbiol. Rev. 29, 813-835.

Hou, X., From, N., Angelidaki, I., Huijgen, W. J. J., and Bjerre, A.-B. (2017). Butanol fermentation of the brown seaweed *Laminaria digitata* by *Clostridium beijerinckii* DSM-6422. Bioresour. Technol. 238, 16-21.

Kosaka, T., Maeda, T., Nakada, Y., Yukawa, M., and Tanaka, S. (1998). Effect of *Bacillus subtilis* spore administration on activation of macrophages and natural killer cells in mice. Vet. Microbiol. 60, 215-225.

Lej a, K., Samul, D., Droździńska, A., Myszka, K., Juzwa, W., Pawlicka, J., and Czaczyk, K. (2014). Hypothetical glycerol pathways of newly isolated strains capable of 1,3-propanediol production. Acta Biochim. Pol. 61, 759-763.

Luo, C., Liu, X., Zhou, H., Wang, X., and Chen, Z. (2015a). Nonribosomal peptide synthase gene clusters for lipopeptide biosynthesis in *Bacillus subtilis* 916 and their phenotypic functions. Appl. Environ. Microbiol. 81, 422-431.

Luo, C., Liu, X., Zhou, X., Guo, J., Truong, J., Wang, X., Zhou, H., Li, X., and Chen, Z. (2015b). Unusual biosynthesis and structure of locillomycins from *Bacillus subtilis* 916. Appl. Environ. Microbiol. 81, 6601-6609.

McDonald, P., Henderson, A. R., and Heron, S. J. E. (1991). The biochemistry of silage (Chalcombe Publications).

Muck, R. E. (2010). Silage microbiology and its control through additives. Rev. Bras. Zootec. 39, 183-191.

Myszka, K., Leja, K., Olejnik-Schmidt, A. K., and Czaczyk, K. (2012). Isolation process of industrially useful *Clostridium bifermentans* from natural samples. J. Biosci. Bioeng. 113, 631-633.

Rajput, I. R., Ying, H., Yajing, S., Arain, M. A., Weifen, L., Ping, L., Bloch, D. M., and Wenhua, L. (2017). *Saccharomyces boulardii* and *Bacillus subtilis* B 10 modulate TLRs and cytokines expression patterns in jejunum and ileum of broilers. PLOS ONE 12, e0173917.

Seglar, B. (2003). Fermentation analysis and silage quality testing.

Sockett, D. C. (2004). Hemorrhagic bowel syndrome. In Proceedings of the 2 Mid-Atlantic Nutrition Conference., (College Park, Md.), pp. 139-145.

Songer, J. G. (1996). Clostridial enteric diseases of domestic animals. Clin. Microbiol. Rev. 9, 216-234.

Weng, H., Endo, K., Li, J., Kito, N., and Iwai, N. (2015). Induction of Peroxisomes by Butyrate-Producing Probiotics. PLoS ONE 10.

Yoo, H. S., Lee, S. U., Park, K. Y., and Park, Y. H. (1997). Molecular typing and epidemiological survey of prevalence of *Clostridium perfringens* types by multiplex PCR. J. Clin. Microbiol. 35, 228-232.

We claim:

1. A method of improving ruminant performance, comprising:
introducing into the digestive system of one or more ruminants an effective amount of a direct fed microbial composition comprising a *Bacillus* strain, wherein the *Bacillus* strain is selected from the group consisting of: *Bacillus subtilis* 1104, deposited as NRRL B-67258; *Bacillus subtilis* 1781, deposited as NRRL B-67259; *Bacillus subtilis* 747, deposited as NRRL B-67257; *Bacillus subtilis* 1541, deposited as NRRL B-67260; *Bacillus subtilis* 1999, deposited as NRRL B-67318; and *Bacillus subtilis* 2018, deposited as NRRL B-67261,
wherein the introduction of the direct fed microbial composition decreases the diversity of *Clostridia* species in the one or more ruminants and further provides at least one benefit chosen from:
inhibiting a pathogen chosen from at least one of *Clostridium perfringens*, *Clostridium bifermentans*, *Clostridium beijerinckii*, *Clostridium butyricum*, *Clostridium tertium*, and *Clostridium sordellii* in the one or more ruminants;
decreasing a mortality rate of the one or more ruminants;
improving the feed efficiency of the one or more ruminants;
reducing the occurrence of hemorrhagic bowel syndrome in the one or more ruminants;
improving rumen fermentation in the one or more ruminants;
improving milk production in the one or more ruminants; and
modulating immune responses of inflammatory cytokines in systemic and intestinal immune cells in the one or more ruminants.

2. The method of claim 1, wherein the *Bacillus* strains comprise *B. subtilis* 1781, deposited as NRRL B-67259 and *B. subtilis* 747, deposited as NRRL B-67257 and the introduction of the direct fed microbial composition provides the benefit of decreasing diversity of *Clostridium perfringens* strains in the one or more ruminants.

3. The method of claim 1, wherein the *Bacillus* strains comprise *B. subtilis* 1781, deposited as NRRL B-67259 and *B. subtilis* 747, deposited as NRRL B-67257 and the introduction of the direct fed microbial composition provides the benefit of decreasing diversity of non-toxigenic clostridial strains in the one or more ruminants.

4. The method of claim 1, wherein the *Bacillus* strains comprise *B. subtilis* 1781, deposited as NRRL B-67259 and *B. subtilis* 747, deposited as NRRL B-67257 and the introduction of the direct fed microbial composition provides the benefit of increasing average energy corrected milk production in the one or more ruminants when the one or more ruminants are dairy cows.

5. The method of claim 1, wherein the *Bacillus* strains comprise *B. subtilis* 1781, deposited as NRRL B-67259; *B. subtilis* 747, deposited as NRRL B-67257; and *B. subtilis* 2018, deposited as NRRL B-67261 and the introduction of the direct fed microbial composition provides the benefit of decreasing a digestive system related mortality rate of the one or more ruminants during a period of direct fed microbial administration.

6. The method of claim 1, wherein the introduction step includes adding the direct fed microbial composition to a ruminant feed and introducing said ruminant feed to said one or more ruminants.

* * * * *

SEQUENCE LISTING

```
<160> NUMBER OF SEQ ID NOS: 45

<210> SEQ ID NO 1
<211> LENGTH: 10
<212> TYPE: DNA
<213> ORGANISM: Artificial Sequence
<220> FEATURE:
<223> OTHER INFORMATION: Primer 1

<400> SEQUENCE: 1
ggtgcgggaa                                                          10

<210> SEQ ID NO 2
<211> LENGTH: 10
<212> TYPE: DNA
<213> ORGANISM: Artificial Sequence
<220> FEATURE:
<223> OTHER INFORMATION: Primer 2

<400> SEQUENCE: 2
gtttcgctcc                                                          10

<210> SEQ ID NO 3
<211> LENGTH: 10
<212> TYPE: DNA
<213> ORGANISM: Artificial Sequence
<220> FEATURE:
<223> OTHER INFORMATION: Primer 3

<400> SEQUENCE: 3
gtagacccgt                                                          10

<210> SEQ ID NO 4
<211> LENGTH: 10
<212> TYPE: DNA
<213> ORGANISM: Artificial Sequence
<220> FEATURE:
<223> OTHER INFORMATION: Priner 4

<400> SEQUENCE: 4
aagagcccgt                                                          10

<210> SEQ ID NO 5
<211> LENGTH: 10
```

```
<212> TYPE: DNA
<213> ORGANISM: Artificial Sequence
<220> FEATURE:
<223> OTHER INFORMATION: Primer 5

<400> SEQUENCE: 5
aacgcgcaac                                                          10

<210> SEQ ID NO 6
<211> LENGTH: 10
<212> TYPE: DNA
<213> ORGANISM: Artificial Sequence
<220> FEATURE:
<223> OTHER INFORMATION: Primer 6

<400> SEQUENCE: 6
cccgtcagca                                                          10

<210> SEQ ID NO 7
<211> LENGTH: 24
<212> TYPE: DNA
<213> ORGANISM: Artificial Sequence
<220> FEATURE:
<223> OTHER INFORMATION: Alpha Toxin Forward Primer

<400> SEQUENCE: 7
gttgatagcg caggacatgt taag                                          24

<210> SEQ ID NO 8
<211> LENGTH: 24
<212> TYPE: DNA
<213> ORGANISM: Artificial Sequence
<220> FEATURE:
<223> OTHER INFORMATION: Alpha Toxin Reverse Primer

<400> SEQUENCE: 8
catgtagtca tctgttccag catc                                          24

<210> SEQ ID NO 9
<211> LENGTH: 24
<212> TYPE: DNA
<213> ORGANISM: Artificial Sequence
<220> FEATURE:
<223> OTHER INFORMATION: Beta Toxin Forward Primer

<400> SEQUENCE: 9
actatacaga cagatcattc aacc                                          24

<210> SEQ ID NO 10
<211> LENGTH: 24
<212> TYPE: DNA
<213> ORGANISM: Artificial Sequence
<220> FEATURE:
<223> OTHER INFORMATION: Beta Toxin Reverse Primer

<400> SEQUENCE: 10
ttaggagcag ttagaactac agac                                          24

<210> SEQ ID NO 11
<211> LENGTH: 24
<212> TYPE: DNA
<213> ORGANISM: Artificial Sequence
<220> FEATURE:
<223> OTHER INFORMATION: Epsilon Toxin Forward Primer

<400> SEQUENCE: 11
```
actgcaacta ctactcatac tgtg                                          24

<210> SEQ ID NO 12
<211> LENGTH: 24
<212> TYPE: DNA
<213> ORGANISM: Artificial Sequence
<220> FEATURE:
<223> OTHER INFORMATION: Epsilon Toxin Reverse Primer

<400> SEQUENCE: 12
ctggtgcctt aatagaaaga ctcc                                          24

<210> SEQ ID NO 13
<211> LENGTH: 24
<212> TYPE: DNA
<213> ORGANISM: Artificial Sequence
<220> FEATURE:
<223> OTHER INFORMATION: Iota Toxin Forward Primer

<400> SEQUENCE: 13
gcgatgaaaa gcctacacca ctac                                          24

<210> SEQ ID NO 14
<211> LENGTH: 24
<212> TYPE: DNA
<213> ORGANISM: Artificial Sequence
<220> FEATURE:
<223> OTHER INFORMATION: Iota Toxin Reverse Primer

<400> SEQUENCE: 14
ggtatatcct ccacgcatat agtc                                          24

<210> SEQ ID NO 15
<211> LENGTH: 10
<212> TYPE: DNA
<213> ORGANISM: Artificial Sequence
<220> FEATURE:
<223> OTHER INFORMATION: RAPD primer 2

<400> SEQUENCE: 15
gtttcgctcc                                                          10

<210> SEQ ID NO 16
<211> LENGTH: 20
<212> TYPE: DNA
<213> ORGANISM: Artificial Sequence
<220> FEATURE:
<223> OTHER INFORMATION: 16S_27F-YM Primer

<400> SEQUENCE: 16
agagtttgat ymtggctcag                                               20

<210> SEQ ID NO 17
<211> LENGTH: 16
<212> TYPE: DNA
<213> ORGANISM: Artificial Sequence
<220> FEATURE:
<223> OTHER INFORMATION: 16S_1492R-Y Primer

<400> SEQUENCE: 17
taccttgtta ygactt                                                   16

<210> SEQ ID NO 18
<211> LENGTH: 20
<212> TYPE: DNA
<213> ORGANISM: Artificial Sequence

```
<220> FEATURE:
<223> OTHER INFORMATION: B-Actin-F Primer

<400> SEQUENCE: 18
tgacgaggcc cagagcaaga                                        20

<210> SEQ ID NO 19
<211> LENGTH: 20
<212> TYPE: DNA
<213> ORGANISM: Artificial Sequence
<220> FEATURE:
<223> OTHER INFORMATION: B-Actin-R

<400> SEQUENCE: 19
atgggcacag tgtgggtgac                                        20

<210> SEQ ID NO 20
<211> LENGTH: 20
<212> TYPE: DNA
<213> ORGANISM: Artificial Sequence
<220> FEATURE:
<223> OTHER INFORMATION: MIP2-3F Primer

<400> SEQUENCE: 20 cccccttggtt cagaggatcg                                       20

<210> SEQ ID NO 21
<211> LENGTH: 20
<212> TYPE: DNA
<213> ORGANISM: Artificial Sequence
<220> FEATURE:
<223> OTHER INFORMATION: MIP2-3R Primer

<400> SEQUENCE: 21
ttgattctgc ccgttgaggt                                        20

<210> SEQ ID NO 22
<211> LENGTH: 17
<212> TYPE: DNA
<213> ORGANISM: Artificial Sequence
<220> FEATURE:
<223> OTHER INFORMATION: TNFa -3F

<400> SEQUENCE: 22
ggcccgaggc aacacat                                           17

<210> SEQ ID NO 23
<211> LENGTH: 20
<212> TYPE: DNA
<213> ORGANISM: Artificial Sequence
<220> FEATURE:
<223> OTHER INFORMATION: TNFa -3R Primer

<400> SEQUENCE: 23
gggccatgga actgatgaga                                        20

<210> SEQ ID NO 24
<211> LENGTH: 24
<212> TYPE: DNA
<213> ORGANISM: Artificial Sequence
<220> FEATURE:
<223> OTHER INFORMATION: PTX3 Forward Primer

<400> SEQUENCE: 24
ggcagactca caggcttcaa tatc                                   24
```

```
<210> SEQ ID NO 25
<211> LENGTH: 23
<212> TYPE: DNA
<213> ORGANISM: Artificial Sequence
<220> FEATURE:
<223> OTHER INFORMATION: GAPDH Forward Primer

<400> SEQUENCE: 25
ggcgtgaacc acgagaagta taa                                                 23

<210> SEQ ID NO 26
<211> LENGTH: 22
<212> TYPE: DNA
<213> ORGANISM: Artificial Sequence
<220> FEATURE:
<223> OTHER INFORMATION: SOD Forward Primer

<400> SEQUENCE: 26
acttcgaggc aaagggagat ac                                                  22

<210> SEQ ID NO 27
<211> LENGTH: 21
<212> TYPE: DNA
<213> ORGANISM: Artificial Sequence
<220> FEATURE:
<223> OTHER INFORMATION: COX2 Primer

<400> SEQUENCE: 27
tcctgaaacc cactcccaac a                                                   21

<210> SEQ ID NO 28
<211> LENGTH: 22
<212> TYPE: DNA
<213> ORGANISM: Artificial Sequence
<220> FEATURE:
<223> OTHER INFORMATION: iNOS Forward Primer

<400> SEQUENCE: 28
ggctacggaa ctggacatca ac                                                  22

<210> SEQ ID NO 29
<211> LENGTH: 22
<212> TYPE: DNA
<213> ORGANISM: Artificial Sequence
<220> FEATURE:
<223> OTHER INFORMATION: IL6 Forward Primer

<400> SEQUENCE: 29
atgacttctg ctttccctac cc                                                  22

<210> SEQ ID NO 30
<211> LENGTH: 22
<212> TYPE: DNA
<213> ORGANISM: Artificial Sequence
<220> FEATURE:
<223> OTHER INFORMATION: IL-18 Forward Primer

<400> SEQUENCE: 30
cacgtttcct ctcctaagaa gc                                                  22

<210> SEQ ID NO 31
<211> LENGTH: 22
<212> TYPE: DNA
<213> ORGANISM: Artificial Sequence
<220> FEATURE:
<223> OTHER INFORMATION: CCL2 Forward Primer
```

```
<400> SEQUENCE: 31
ccagatgcaa ttaactccca ag                                              22

<210> SEQ ID NO 32
<211> LENGTH: 21
<212> TYPE: DNA
<213> ORGANISM: Artificial Sequence
<220> FEATURE:
<223> OTHER INFORMATION: CCL8 Forward Primer

<400> SEQUENCE: 32
aagcagaagt gggtccagac t                                               21

<210> SEQ ID NO 33
<211> LENGTH: 24
<212> TYPE: DNA
<213> ORGANISM: Artificial Sequence
<220> FEATURE:
<223> OTHER INFORMATION: TLR-2 Forward Primer

<400> SEQUENCE: 33
tccacggact gtggtacatg aaga                                            24

<210> SEQ ID NO 34
<211> LENGTH: 24
<212> TYPE: DNA
<213> ORGANISM: Artificial Sequence
<220> FEATURE:
<223> OTHER INFORMATION: TLR-4 Forward Primer

<400> SEQUENCE: 34
tcagagtttc ctgcagtggg tcaa                                            24

<210> SEQ ID NO 35
<211> LENGTH: 24
<212> TYPE: DNA
<213> ORGANISM: Artificial Sequence
<220> FEATURE:
<223> OTHER INFORMATION: PTX3 Reverse Primer

<400> SEQUENCE: 35
ccttctccag tctccctttc aact                                            24

<210> SEQ ID NO 36
<211> LENGTH: 19
<212> TYPE: DNA
<213> ORGANISM: Artificial Sequence
<220> FEATURE:
<223> OTHER INFORMATION: GAPDH Reverse Primer

<400> SEQUENCE: 36
ccctccacga tgccaaagt                                                  19

<210> SEQ ID NO 37
<211> LENGTH: 17
<212> TYPE: DNA
<213> ORGANISM: Artificial Sequence
<220> FEATURE:
<223> OTHER INFORMATION: SOD Reverse Primer

<400> SEQUENCE: 37
ttttggccca ccgtgtt                                                    17

<210> SEQ ID NO 38
```

```
<211> LENGTH: 20
<212> TYPE: DNA
<213> ORGANISM: Artificial Sequence
<220> FEATURE:
<223> OTHER INFORMATION: COX2 Reverse Primer

<400> SEQUENCE: 38
tgggcagtca tcaggcacag                                                   20

<210> SEQ ID NO 39
<211> LENGTH: 19
<212> TYPE: DNA
<213> ORGANISM: Artificial Sequence
<220> FEATURE:
<223> OTHER INFORMATION: iNOS Reverse Primer

<400> SEQUENCE: 39
ctcagggatt ctggagacg                                                    19

<210> SEQ ID NO 40
<211> LENGTH: 22
<212> TYPE: DNA
<213> ORGANISM: Artificial Sequence
<220> FEATURE:
<223> OTHER INFORMATION: IL6 Reverse Primer

<400> SEQUENCE: 40
gctgctttca cactcatcat tc                                                22

<210> SEQ ID NO 41
<211> LENGTH: 22
<212> TYPE: DNA
<213> ORGANISM: Artificial Sequence
<220> FEATURE:
<223> OTHER INFORMATION: IL-18 Reverse Primer

<400> SEQUENCE: 41
tacttgttct gcagccatct tt                                                22

<210> SEQ ID NO 42
<211> LENGTH: 24
<212> TYPE: DNA
<213> ORGANISM: Artificial Sequence
<220> FEATURE:
<223> OTHER INFORMATION: CCL2 Reverse Primer

<400> SEQUENCE: 42
gcatggagat cttcttactg ttga                                              24

<210> SEQ ID NO 43
<211> LENGTH: 19
<212> TYPE: DNA
<213> ORGANISM: Artificial Sequence
<220> FEATURE:
<223> OTHER INFORMATION: CCL8 Reverse Primer

<400> SEQUENCE: 43
cttcggtgtt cgggactttt                                                   19

<210> SEQ ID NO 44
<211> LENGTH: 24
<212> TYPE: DNA
<213> ORGANISM: Artificial Sequence
<220> FEATURE:
<223> OTHER INFORMATION: TLR-2 Reverse Primer

<400> SEQUENCE: 44
```

```
gcttaaaggg agggttgaag tgct                                          24

<210> SEQ ID NO 45
<211> LENGTH: 24
<212> TYPE: DNA
<213> ORGANISM: Artificial Sequence
<220> FEATURE:
<223> OTHER INFORMATION: TLR-4 Reverse Primer

<400> SEQUENCE: 45
actaagcact ggcatgtcct ccat                                          24
```